United States Patent
Blake et al.

(10) Patent No.: US 12,180,207 B2
(45) Date of Patent: Dec. 31, 2024

(54) SUBSTITUTED PYRAZOLO[1,5-A]PYRIDINE COMPOUNDS AS INHIBITORS OF FGFR TYROSINE KINASES

(71) Applicant: ARRAY BIOPHARMA INC., Boulder, CO (US)

(72) Inventors: James F. Blake, Boulder, CO (US); David A. Moreno, Boulder, CO (US); Li Ren, Boulder, CO (US); Tony P. Tang, Boulder, CO (US); Shane M. Walls, Boulder, CO (US)

(73) Assignee: Array Biopharma Inc., Boulder, CO (US)

( * ) Notice: Subject to any disclaimer, the term of this patent is extended or adjusted under 35 U.S.C. 154(b) by 783 days.

(21) Appl. No.: 17/416,117

(22) PCT Filed: Dec. 13, 2019

(86) PCT No.: PCT/US2019/066278
§ 371 (c)(1),
(2) Date: Jun. 18, 2021

(87) PCT Pub. No.: WO2020/131627
PCT Pub. Date: Jun. 25, 2020

(65) Prior Publication Data
US 2022/0081438 A1    Mar. 17, 2022

Related U.S. Application Data

(60) Provisional application No. 62/781,990, filed on Dec. 19, 2018.

(51) Int. Cl.
*C07D 471/04* (2006.01)
*A61P 35/00* (2006.01)
*C07D 519/00* (2006.01)

(52) U.S. Cl.
CPC ............ *C07D 471/04* (2013.01); *A61P 35/00* (2018.01); *C07D 519/00* (2013.01)

(58) Field of Classification Search
CPC .. C07D 471/04; C07D 471/06; C07D 231/56; C07D 231/10; A61P 35/00
See application file for complete search history.

(56) References Cited

U.S. PATENT DOCUMENTS

| | | | |
|---|---|---|---|
| 4,304,777 A | 12/1981 | Lesher et al. |
| 4,305,943 A | 12/1981 | Lesher et al. |
| 4,826,835 A | 5/1989 | Kuhla et al. |
| 5,455,348 A | 10/1995 | Austel et al. |
| 7,265,120 B2 | 9/2007 | Tsutsumi et al. |
| 7,696,352 B2 | 4/2010 | Zhu et al. |
| 7,718,662 B1 | 5/2010 | Chen et al. |
| 8,163,749 B2 | 4/2012 | Corte |
| 8,426,424 B2 | 4/2013 | Blomgren et al. |
| 8,445,489 B2 | 5/2013 | Stieber et al. |
| 8,598,174 B2 | 12/2013 | Barbosa, Jr. et al. |
| 8,669,251 B2 | 3/2014 | Crawford et al. |
| 8,673,925 B1 | 3/2014 | Goldstein |
| 8,716,274 B2 | 5/2014 | Crawford et al. |
| 8,889,682 B2 | 11/2014 | Brotherton-Pleiss et al. |
| 8,895,745 B2 | 11/2014 | Berdini et al. |
| 8,940,891 B2 | 1/2015 | Tran et al. |
| 9,242,969 B2 | 1/2016 | Barsanti et al. |
| 9,254,288 B2 | 2/2016 | Pollock |
| 9,260,415 B2 | 2/2016 | Crawford et al. |
| 9,267,176 B2 | 2/2016 | Futami et al. |

(Continued)

FOREIGN PATENT DOCUMENTS

| | | |
|---|---|---|
| CN | 101679408 A | 3/2010 |
| CN | 102741256 | 10/2012 |

(Continued)

OTHER PUBLICATIONS

Helsten et al. Clin Cancer Res; 22(1) Jan. 1, 2016, p. 259-67 (Year: 2016).*
International Search Report and Written Opinion, issued by the International Searching Authority (ISA/EP) in PCT Application No. PCT/US2019/066278 on Mar. 2, 2020. 10 pages.
Wang, Yuming, et al. "Discovery of potent irreversible pan-fibroblast growth factor receptor (FGFR) inhibitors." Journal of medicinal chemistry 61.20 (2018): 9085-9104.
Barf, Tjeerd, and Allard Kaptein. "Irreversible protein kinase inhibitors: balancing the benefits and risks." Journal of medicinal chemistry 55.14 (2012): 6243-6262.

(Continued)

*Primary Examiner* — Noble E Jarrell
*Assistant Examiner* — Richard Grant Peckham
(74) *Attorney, Agent, or Firm* — Meunier Carlin & Curfman LLC

(57) ABSTRACT

Provided herein are compounds of the general Formula I: and stereoisomers and pharmaceutically acceptable salts or solvates thereof, in which Ring A, Ring B, Ring C, $R^1$, $R^2$, L, Y, and W have the meanings given in the specification, which are inhibitors of FGFR1, FGFR2, FGFR3 and/or FGFR4 and are useful in the treatment and prevention of diseases which can be treated with an FGFR inhibitor, including diseases or disorders mediated by FGFR1, FGFR2, FGFR3 and/or FGFR4.

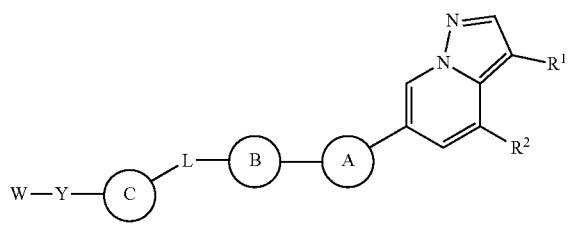

14 Claims, 3 Drawing Sheets
Specification includes a Sequence Listing.

(56) References Cited

U.S. PATENT DOCUMENTS

| | | | |
|---|---|---|---|
| 9,326,985 | B2 | 5/2016 | Crawford et al. |
| 9,447,098 | B2 | 9/2016 | Saxty et al. |
| 9,695,165 | B2 * | 7/2017 | Bifulco, Jr. .......... C07D 471/04 |
| 10,208,024 | B2 | 2/2019 | Andrews et al. |
| 2004/0067955 | A1 | 4/2004 | Tabuchi et al. |
| 2008/0090827 | A1 | 4/2008 | Taylor et al. |
| 2011/0008347 | A1 | 1/2011 | Ullrich et al. |
| 2011/0098269 | A1 | 4/2011 | Becknell et al. |
| 2011/0207711 | A1 * | 8/2011 | Katz ....................... A61P 19/02 514/210.16 |
| 2013/0012485 | A1 | 1/2013 | Baschlin et al. |
| 2015/0158873 | A1 | 6/2015 | Bogdan et al. |
| 2015/0366866 | A1 | 12/2015 | Ali et al. |
| 2015/0376167 | A1 | 12/2015 | Jorand-Lebrun et al. |
| 2016/0215350 | A1 | 7/2016 | Rabizadeh et al. |
| 2016/0235744 | A1 | 8/2016 | Berdini et al. |
| 2017/0066812 | A1 | 3/2017 | Bifulco, Jr. et al. |
| 2019/0209564 | A1 | 7/2019 | Wu |

FOREIGN PATENT DOCUMENTS

| | | |
|---|---|---|
| EP | 3023101 | 5/2016 |
| JP | 2010013369 | 1/2010 |
| JP | 2012180344 A | 9/2012 |
| WO | 1989/008108 | 9/1989 |
| WO | 2009/047522 | 4/2009 |
| WO | 2010017047 A1 | 2/2010 |
| WO | 2010/069504 | 6/2010 |
| WO | 2011/135376 | 11/2011 |
| WO | 2012/073017 | 6/2012 |
| WO | 2013/061081 | 5/2013 |
| WO | 2013/130976 | 9/2013 |
| WO | 2014/011900 | 1/2014 |
| WO | 2014/071419 | 5/2014 |
| WO | 2015027222 A2 | 2/2015 |
| WO | 2015/089333 | 6/2015 |
| WO | 2015/099127 | 7/2015 |
| WO | 2015/106717 | 7/2015 |
| WO | 2015108992 A1 | 7/2015 |
| WO | 2015/120094 | 8/2015 |
| WO | 2015/144804 | 10/2015 |
| WO | 2015/150900 | 10/2015 |
| WO | 2015/160634 | 10/2015 |
| WO | 2015/160636 | 10/2015 |
| WO | 2015144803 A1 | 10/2015 |
| WO | 2016/030509 | 3/2016 |
| WO | 2016/038582 | 3/2016 |
| WO | 2016/084883 | 6/2016 |
| WO | 2016/105503 | 6/2016 |
| WO | 2016/139227 | 9/2016 |
| WO | 2018/040885 A1 | 3/2018 |
| WO | 2018113584 A1 | 6/2018 |
| WO | 2018/141921 | 8/2018 |

OTHER PUBLICATIONS

"Certificate of Analysis Alexa Fluor® 647-Poly GT, 10 nmol," Life Technologies, Jun. 4, 2012, 1 page.
"Certificate of Analysis FGFR2, 100 µg: Recombinant Human Fibroblast Growth Factor Receptor 2, Histidine-tagged," Life Technologies, Feb. 24, 2012, 2 pages.
"Certificate of Analysis FGF-R3 wt, fibroblast growth factor receptor 3: Recombinant Active Protein Kinase," ProQinase, retrieved from https://www.proqinase.com/sites/default/files/public/FGFR3_wt_Lot005_V2.pdf on Jan. 31, 2017, 2 pages.
"Certificate of Analysis LanthaScreen® Eu-PY20 Antibody, 25 µg," Life Technologies, Apr. 4, 2014, 1 page.
"Certificate of Analysis FGFR1, 100µg: Recombinant Human Fibroblast Growth Factor Receptor1, Histidine-tagged," Life Technologies, Feb. 25, 2014, 2 pages.
Baroy et al., "Genome Analysis of Osteosarcoma Progression Samples Identifies FGFR1 Overexpression as a Potential Treatment Target and CHM as a Candidate Tumor Suppressor Gene," PLoS One. Sep. 29, 2016;11(9):e0163859. doi: 10.1371/journal.pone.0163859.
Becker et al., "KIAA1549: Braf Gene Fusion and FGFR1 Hotspot Mutations Are Prognostic Factors in Pilocytic Astrocytomas," J. Neuropathol. Exp. Neurol., Jul. 2015, 74(7):743-754.
Beenken et al. "The FGF family: biology, pathophysiology and therapy," Nat. Rev. Drug Discov., Mar. 2009, 8:235-253.
Bennett et al., "Mosaic Activating Mutations in FGFR1 Cause Encephalocraniocutaneous Lipomatosis," Am J Hum Genet. Mar. 3, 2016;98(3):579-87. doi: 10.1016/j.aihg.2016.02.006.
Birrer et al., "Whole Genome Oligonucleotide-Based Array Comparative Genomic Hybridization Analysis Identified Fibroblast Growth Factor 1 As a Prognostic Marker for Advanced-Stage Serous Ovarian Adenocarcinomas," J Clin Oncol. Jun. 1, 2007;25(16):2281-7.
Brooks et al., "Molecular Pathways: Fibroblast Growth Factor Signaling: A New Therapeutic Opportunity in Cancer," Clin Cancer Res. Apr. 1, 2012;18(7):1855-62. doi: 10.1158/1078-0432.CCR-11-0699. Epub Mar. 2, 2012.
Bunney et al., "The Effect of Mutations on Drug Sensitivity and Kinase Activity of Fibroblast Growth Factor Receptors: A Combined Experimental and Theoretical Study," EBioMedicine. Mar. 1, 2015;2(3):194-204.
Byron et al., "FGFR2 point mutations in 466 endometrioid endometrial tumors: relationship with MSI, KRAS, PIK3CA, CTNNBI mutations and clinicopathological features," PLoS One. 2012;7(2):e30801. doi: 10.1371/journal.pone.0030801. Epub Feb. 23, 2012.
Byron et al., "The N550K/H mutations in FGFR2 confer differential resistance to PD173074, dovitinib, and ponatinib ATP-competitive inhibitors," Neoplasia. Aug. 2013;15(8):975-88.
Cazier et al., "Whole-genome sequencing of bladder cancers reveals somatic CDKN1A mutations and clinicopathological associations with mutation burden," Nat Commun. Apr. 29, 2014;5:3756. doi: 10.1038/ncomms4756.
Chang et al., "Prognostic value of FGFR gene amplification in patients with different types of cancer: a systematic review and meta-analysis," PLoS One. Aug. 29, 2014;9(8):e105524. doi:10.1371/journal.pone.0105524.eCollection 2014.
Chang et al., "EGF Induced RET Inhibitor Resistance in CCDC6-RET Lung Cancer Cells," Yonsei Med J, Jan. 2017, 58(1):9-18.
Chellaiah et al., "Fibroblast growth factor receptor (FGFR) 3. Alternative splicing in immunoglobulin-like domain III creates a receptor highly specific for acidic FGF/FGF-1," J Biol Chem. Apr. 15, 1994;269(15):11620-7.
Cheon et al., "High-affinity binding sites for related fibroblast growth factor ligands reside within different receptor immunoglobulin-like domains," Proc Natl Acad Sci US A. Feb. 1, 1994;91(3):989-93.
Chesi M, et al., "Frequent translocation t(4;14)(pl6.3;q32.3) in multiple myeloma is associated with increased expression and activating mutations of fibroblast growth factor receptor 3," Nat Genet. Jul. 1997;16(3):260-4.
Davies et al., "Somatic mutations of the protein kinase gene family in human lung cancer," Cancer Res. Sep. 1, 2005;65(17):7591-5.
Dieci et al., "Fibroblast growth factor receptor inhibitors as a cancer treatment: from a biologic rationale to medical perspectives," Cancer Discov. Mar. 2013;3(3):264-79. doi: 10.1158/2159-8290.CD-12-0362. Epub Feb. 15, 2013.
Dienstmann et al., "Genomic aberrations in the FGFR pathway: opportunities for targeted therapies in solid tumors," Ann Oncol. Mar. 2014;25(3):552-63. doi: 10.1093/annonc/mdt419. Epub Nov. 20, 2013.
Dutt et al., "Drug-sensitive FGFR2 mutations in endometrial carcinoma," Proc Natl Acad Sci U S A. Jun. 24, 2008;105(25):8713-7. doi: 10.1073/pnas.0803379105. Epub Jun. 13, 2008.
Dutt et al., "Inhibitor-sensitive FGFR1 amplification in human non-small cell lung cancer," PLoS One. 2011;6(6):e20351. doi: 10.1371/journal.pone.0020351. Epub Jun. 7, 2011.
Gallo et al., "Functions of Fibroblast Growth Factor Receptors in cancer defined by novel translocations and mutations," Cytokine Growth Factor Rev. Aug. 2015;26(4):425-49. doi: 10.1016/j.cytogfr.2015.03.003. Epub Apr. 20, 2015.

(56) References Cited

OTHER PUBLICATIONS

Gauglhofer et al., "Up-regulation of the fibroblast growth factor 8 subfamily in human hepatocellular carcinoma for cell survival and neoangiogenesis," Hepatology. Mar. 2011;53(3):854-64. doi: 10.1002/hep.24099. Epub Feb. 11, 2011.
Goncalves et al., "Novel FGFR1 mutations in Kallmann syndrome and normosmic idiopathic hypogonadotropic hypogonadism: evidence for the involvement of an alternatively spliced isoform," Fertil Steril. Nov. 2015;I04(5):1261-7.el. doi: 10.1016/j.fertnstert. 2015.07.1142. Epub Aug. 12, 2015.
Hanada et al., "Identification of fibroblast growth factor-5 as an overexpressed antigen in multiple humanad enocarcinomas," Cancer Res. Jul. 15, 2001;61(14):5511-6.
Hart et al., "Transformation and Stat activation by derivatives of FGFR1, FGFR3, and FGFR4," Oncogene. Jul. 6, 2000;19(29):3309-20.
Helsten et al., "The FGFR Landscape in Cancer: Analysis of 4,853 Tumors by Next-Generation Sequencing," Clin Cancer Res. Jan. 1, 2016;22(1):259-67. doi: 10.1158/1078-0432.CCR-14-3212. Epub Sep. 15, 2015.
Hu MC, et al., "FGF-18, a novel member of the fibroblast growth factor family, stimulates hepatic and intestinal proliferation," Mol Cell Biol. Oct. 1998;18(10):6063-74.
International Preliminary Report on Patentability, issued in PCT Application No. PCT/US2019/066278 on Jul. 1, 2021. 8 pages.
International Preliminary Report on Patentability, issued in PCT Application No. PCT/US2019/066478 on Jul. 1, 2021. 8 pages.
International Search Report and Written Opinion, issued by the International Searching Authority (ISA/EP) in PCT Application No. PCT/US2019/066478 on Mar. 13, 2020. 11 pages.
International Preliminary Report on Patentability in the International Application No. PCT/US2016/058549, dated May 3, 2018, 7 pages.
International Search Report and Written Opinion in the International Application No. PCT/US2016/058549, dated Jan. 20, 2017, 11 pages.
Johnson et al., "The human fibroblast growth factor receptor genes: a common structural arrangement underlies the mechanisms for generating receptor forms that differ in their third immunoglobulin domain," Mol Cell Biol. Sep. 1991;II(9):4627-34.
Kasaian et al., "The genomic and transcriptomic landscape of anaplastic thyroid cancer: implications for therapy," BMC Cancer. Dec. 18, 2015;15:984. doi: 10.1186/sl2885-015-1955-9.
Kelleher et al., "Fibroblast growth factor receptors, developmental corruption and malignant disease," Carcinogenesis. Oct. 2013;34(10):2198-205. doi: 10.1093/carcin/bgt254. Epub Jul. 23, 2013.
Kore et al. "The role of fibroblast growth factors in tumor growth," Curr Cancer Drug Targets. Aug. 2009;9(5):639-51. Epub Aug. 1, 2009.
Krstevska-Konstantinova et al., "Favorable Growth Hormone Treatment Response in a Young Boy with Achondroplasia," Med Arch. Apr. 2016;70(2):148-50. doi: 10.5455/medarh.2016.70.148-150. Epub Apr. 1, 2016.
Kuentz et al., "Mosaic-activating FGFR2 mutation in two fetuses with papillomatous pedunculated sebaceous naevus," Br J Dermatol. Jan. 2017;176(1):204-208. doi: 10.1111/bjd.14681. Epub Oct. 2, 2016.
Kunii et al., "FGFR2-amplified gastric cancer cell lines require FGFR2 and Erbb3 signaling for growth and survival," Cancer Res. Apr. 1, 2008;68(7):2340-8. doi: 10.1158/0008-5472.CAN-07-5229.
Laitinen et al., "Reversible congenital hypogonadotropic hypogonadism in patients with CHD7, FGFR1 or GNRHR mutations," PLoS One. 2012;7(6):e39450. doi: 10.1371/journal.pone.0039450. Epub Jun. 19, 2012.
Lewin, et al., "Development of Fibroblast Growth Factor Receptor Inhibitors: Kissing Frogs to Find a Prince?," J Clin Oncol. Oct. 20, 2015;33(30):3372-4. doi: 10.1200/JCO.2015.62.7380. Epub Aug. 31, 2015.
Liao et al., "Inhibitor-sensitive FGFR2 and FGFR3 mutations in lung squamous cell carcinoma," Cancer Res. Aug. 15, 2013;73(16):5195-205. doi: 10.1158/0008-5472.CAN-12-3950. Epub Jun. 20, 2013.
Lin et al., "Modeling genomic diversity and tumor dependency in malignant melanoma," Cancer Res. Feb. 1, 2008;68(3):664-73. doi: 10.1158/0008-5472.CAN-07-2615.
Lin et al., "Molecular analysis of FGFR 2 and associated clinical observations in two Chinese families with Crouzon syndrome," Mol Med Rep. Sep. 2016;14(3): 1941-6. doi: 10.3892/mmr.2016.5497. Epub Jul. 11, 2016.
Liu et al., "Clinical significance of fibroblast growth factor receptor-3 mutations in bladder cancer: a systematic review and meta-analysis," Genet Mol Res. Feb. 20, 2014;13(1):1109-20. doi: 10.4238/2014.Febmary.20.12.
Liu et al. Org. Biomol. ChLiu, Jian, et al. "Design, synthesis and biological evaluation of novel FGFR inhibitors bearing an indazole scaffold." Organic & biomolecular chemistry 13.28 (2015): 7643-7654.em., 2015, 13, 7643-7654.
Lo Iacono et al., "Retrospective study testing next generation sequencing of selected cancer-associated genes in resected prostate cancer," Oncotarget. Mar. 22, 2016;7(12):14394-404. doi: 10.18632/oncotarget.7343.
Marchwicka et al., "Restored expression of vitamin D receptor and sensitivity to 1,25-dihydroxyvitamin D3 in response to disrupted fusion FOP2-FGFR1 gene in acute myeloid leukemia cells," Cell Biosci. Feb. 2, 2016;6:7. doi: 10.1186/s13578-016-0075-9. eCollection 2016.
Marek et al., "Fibroblast growth factor (FGF) and FGF receptor-mediated autocrine signaling in non-small-cell lung cancer cells," Mol Pharmacol. Jan. 2009;75(1):196-207. doi: 10.1124/mol.108.049544. Epub Oct. 10, 2008.
Martincorena et al., "Tumor evolution. High burden and pervasive positive selection of somatic mutations in normal human skin," Science. May 22, 2015;348(6237):880-6. doi: 10.I126/science.aaa6806.
Matsubara et al., "Identification of CCDC6-RET fusion in the human lung adenocarcinoma cell line, LC-2/ad," Journal of Thoracic Oncology, Dec. 2012;7(12):1872-1876.
Mazen et al., "Homozygous Mutation of the FGFRI Gene Associated with Congenital Heart Disease and 46,)CY Disorder of Sex Development," Sex Dev. 2016;10(1):16-22. doi: 10.1159/000444948. Epub Apr. 8, 2016.
Miki et al., "Determination of ligand-binding specificity by alternative splicing: two distinct growth factor receptors encoded by a single gene," Proc Natl Acad Sci US A. Jan. 1, 1992;89(1):246-50.
Moeini et al., "Molecular Pathogenesis and Targeted Therapies for Intrahepatic Cholangiocarcinoma," Clin Cancer Res. Jan. 15, 2016;22(2):291-300. doi: 10.1158/1078-0432.CCR-14-3296. Epub Sep. 24, 2015.
Nagahara et al., "A Japanese familial case of hypochondroplasia with a novel mutation in FGFR3," Clin PediatrEndocrinol. Jul. 2016;25(3):103-6. doi: 10.1297/cpe.25.103. Epub Jul. 20, 2016.
Nicholes et al., "A mouse model of hepatocellular carcinoma: ectopic expression of fibroblast growth factor 19 in skeletal muscle of transgenic mice," Am J Pathol. Jun. 2002;I60(6):2295-307.
Ohishi et al., "Mutation analysis ofFGFRI-3 in 11 Japanese patients with syndromic craniosynostoses," Am J Med Genet A. Jan. 2017;I73(1):157-162. doi: 10.1002/ajmg.a.37992. Epub Sep. 28, 2016.
Pardo et al., "FGF-2 protects small cell lung cancer cells from apoptosis through a complex involving PKCepsilon, B-Raf and S6K2," EMBO J. Jul. 12, 2006;25(13):3078-88. Epub Jun. 29, 2006.
Presta M, et al., "Fibroblast growth factor/fibroblast growth factor receptor system in angiogenesis," Cytokine Growth Factor Rev. Apr. 2005;I6(2):159-78. Epub Feb. 2, 2005.
Qian et al., "N-cadherin/FGFR promotes metastasis through epithelial-to-mesenchymal transition and stem/progenitor cell-like properties," Oncogene. Jun. 26, 2014;33(26):3411-21. doi: 10.1038/onc.2013.310. Epub Aug. 26, 2013.

(56) References Cited

OTHER PUBLICATIONS

Qing et al., "Antibody-based targeting of FGFR3 in bladder carcinoma and t(4;14)-positive multiple myeloma in mice," J Clin Invest. May 2009;119(5):1216-29. doi: 10.1172/JCI38017. Epub Apr. 20, 2009.

Rivera et al., "Germline and somatic FGFR1 abnormalities in dysembryoplastic neuroepithelial tumors," Acta Neuropathol. Jun. 2016;131(6):847-63. doi: 10.1007/s00401-016-1549-x. Epub Feb. 26, 2016.

Ron et al., "A Case of Beare-Stevenson Syndrome with Unusual Manifestations," Am J Case Rep. Apr. 15, 2016;17:254-8.

Rosseau et al., "Mutations in the gene encoding fibroblast growth factor receptor-3 in achondroplasia," Nature. Sep. 15, 1994;371(6494):252-4.

Ruotsalainen et al., "High pretreatment serum concentration of basic fibroblast growth factor is a predictor of poor prognosis in small cell lung cancer," Cancer Epidemiol Biomarkers Prev. Nov. 2002;11(11):1492-5.

Sawey et al., "Identification of a therapeutic strategy targeting amplified FGF19 in liver cancer by Oncogenomic screening," Cancer Cell. Mar. 8, 2011;19(3):347-58. doi: 10.1016/j.ccr.2011.01.040.

Shiang et al., "Mutations in the transmembrane domain of FGFR3 cause the most common genetic form of dwarfism, achondroplasia," Cell. Jul. 29, 1994;78(2):335-42.

Taylor et al., "Identification of FGFR4-activating mutations in human rhabdomyosarcomas that promote metastasis in xenotransplanted models," J Clin Invest. Nov. 2009;119(11):3395-407. doi: 10.1172/JCI39703. Epub Oct. 5, 2009.

Thussbas et al., "FGFR4 Arg388 allele is associated with resistance to adjuvant therapy in primary breast cancer," J Clin Oncol. Aug. 10, 2006;24(23):3747-55. Epub Jul. 5, 2006.

Ueda et al., "Deletion of the carboxyl-terminal exons of K-sam/FGFR2 by short homology-mediated recombination, generating preferential expression of specific messenger RNAs," Cancer Res. Dec. 15, 1999;59(24):6080-6.

Van Rhijn et al., "Novel fibroblast growth factor receptor 3 (FGFR3) mutations in bladder cancer previously identified in non-lethal skeletal disorders," Eur J Hum Genet. Dec. 2002;10(12): 819-24.

Weiss et al., "Frequent and focal FGFR1 amplification associates with therapeutically tractable FGFR1 dependency in squamous cell lung cancer," Sci Transl Med. Dec. 15, 2010;2(62):62ra93. doi: 10.1126/scitranslmed.3001451.

Welm et al., "Inducible dimerization of FGFR1: development of a mouse model to analyze progressive transformation of the mammary gland," J Cell Biol. May 13, 2002;157(4):703-14. Epub May 13, 2002.

Wesche et al., "Fibroblast growth factors and their receptors in cancer," Biochem J. Jul. 15, 2011;437(2):199-213. doi: 10.1042/BJ20101603.

Wilkie et al., "Functions of fibroblast growth factors and their receptors," Curr Biol. May 1, 1995;5(5):500-7.

Wu et al., "Identification of targetable FGFR gene fusions in diverse cancers," Cancer Discov. Jun. 2013;3(6):636-47. doi: 10.1158/2159-8290.CD-13-0050. Epub Apr. 4, 2013.

Zhang et al., "Receptor specificity of the fibroblast growth factor family. The complete mammalian FGF family," J Biol Chem. Jun. 9, 2006;281(23): 15694-700. Epub Apr. 4, 2006.

Zhao et al., "Monoclonal antibodies to fibroblast growth factor receptor 2 effectively inhibit growth of gastric tumor xenografts," Clin Cancer Res. Dec. 1, 2010;16(23):5750-8. doi: 10.1158/1078-0432.CCR-10-0531. Epub Jul. 29, 2010.

Zhao et al., "Whole-exome sequencing and whole genome re-sequencing for prenatal diagnosis of achondroplasia," Int J Clin EXP Med. Oct. 15, 2015;8(10):19241-9. eCollection 2015.

Zhao G, et al., "A novel, selective inhibitor of fibroblast growth factor receptors that shows a potent broad spectrum of antitumor activity in several tumor xenograft models," Mol Cancer Ther. Nov. 2011;10(11):2200-10. doi: 10.1158/1535-7163.MCT-11-0306. Epub Sep. 7, 2011.

Zhou et al., "A Pro250Arg substitution in mouse Fgfr1 causes increased expression of Cbfa1 and premature fusion of calvarial sutures," Hum Mol Genet. Aug. 12, 2000;9(13):2001-8.

Zimmer et al., "Multiple structural elements determine ligand binding of fibroblast growth factor receptors. Evidence that both Ig domain 2 and 3 define receptor specificity," J Biol Chem. Apr. 15, 1993;268(11):7899-903.

\* cited by examiner

Figure 1

SEQ ID NO: 1
Alpha A1 isoform of FGFR 1 (see UniParc entry UPI00000534B8)

MWSWKCLLFWAVLVTATLCTARPSPTLPEQAQPWGAPVEVESFLVHPGDLLQLRCRLRDDVQSINWLRDGVQLAESN
RTRITGEEVEVQDSVPADSGLYACVTSSPSGSDTTYFSVNVSDALPSSEDDDDDDSSSEEKETDNTKPNRMPVAPY
WTSPEKMEKKLHAVPAAKTVKFKCPSSGTPNPTLRWLKNGKEFKPDHRIGGYKVRYATWSIIMDSVVPSDKGNYTCI
VENEYGSINHTYQLDVVERSPHRPILQAGLPANKTVALGSNVEFMCKVYSDPQPHIQWLKHIEVNGSKIGPDNLPYV
QILKTAGVNTTDKEMEVLHLRNVSFEDAGEYTCLAGNSIGLSHHSAWLTVLEALEERPAVMTSPLYLEIIIYCTGAF
LISCMVGSVIVYKMKSGTKKSDFHSQMAVHKLAKSIPLRRQVTVSADSSASMNSGVLLVRPSRLSSSGTPMLAGVSE
YELPEDPRWELPRDRLVLGKPLGEGCFGQVVLAEAIGLDKDKPNRVTKVAVKMLKSDATEKDLSDLISEMEMMKMIG
KHKNIINLLGACTQDGPLYVIVEYASKGNLREYLQARRPPGLEYCYNPSHNPEEQLSSKDLVSCAYQVARGMEYLAS
KKCIHRDLAARNVLVTEDNVMKIADFGLARDIHHIDYYKKTTNGRLPVKWMAPEALFDRIYTHQSDVWSFGVLLWEI
FTLGGSPYPGVPVEELFKLLKEGHRMDKPSNCTNELYMMMRDCWHAVPSQRPTFKQLVEDLDRIVALTSNQEYLDLS
MPLDQYSPSFPDTRSSTCSSGEDSVFSHEPLPEEPCLPRHPAQLANGGLKRR

SEQ ID NO: 2
Alpha B1 isoform of FGFR1 (see UniParc entry UPI0000001C0F)

MWSWKCLLFWAVLVTATLCTARPSPTLPEQAQPWGAPVEVESFLVHPGDLLQLRCRLRDDVQSINWLRDGVQLAESN
RTRITGEEVEVQDSVPADSGLYACVTSSPSGSDTTYFSVNVSDALPSSEDDDDDDSSSEEKETDNTKPNRMPVAPY
WTSPEKMEKKLHAVPAAKTVKFKCPSSGTPNPTLRWLKNGKEFKPDHRIGGYKVRYATWSIIMDSVVPSDKGNYTCI
VENEYGSINHTYQLDVVERSPHRPILQAGLPANKTVALGSNVEFMCKVYSDPQPHIQWLKHIEVNGSKIGPDNLPYV
QILKTAGVNTTDKEMEVLHLRNVSFEDAGEYTCLAGNSIGLSHHSAWLTVLEALEERPAVMTSPLYLEIIIYCTGAF
LISCMVGSVIVYKMKSGTKKSDFHSQMAVHKLAKSIPLRRQVSADSSASMNSGVLLVRPSRLSSSGTPMLAGVSEYE
LPEDPRWELPRDRLVLGKPLGEGCFGQVVLAEAIGLDKDKPNRVTKVAVKMLKSDATEKDLSDLISEMEMMKMIGKH
KNIINLLGACTQDGPLYVIVEYASKGNLREYLQARRPPGLEYCYNPSHNPEEQLSSKDLVSCAYQVARGMEYLASKK
CIHRDLAARNVLVTEDNVMKIADFGLARDIHHIDYYKKTTNGRLPVKWMAPEALFDRIYTHQSDVWSFGVLLWEIFT
LGGSPYPGVPVEELFKLLKEGHRMDKPSNCTNELYMMMRDCWHAVPSQRPTFKQLVEDLDRIVALTSNQEYLDLSMP
LDQYSPSFPDTRSSTCSSGEDSVFSHEPLPEEPCLPRHPAQLANGGLKRR

SEQ ID NO: 3
IIIc isoform of FGFR2 (see UniParc entry UPI000012A72A)

MVSWGRFICLVVVTMATLSLARPSFSLVEDTTLEPEEPPTKYQISQPEVYVAAPGESLEVRCLLKDAAVISWTKDGV
HLGPNNRTVLIGEYLQIKGATPRDSGLYACTASRTVDSETWYFMVNVTDAISSGDDEDDTGAEDFVSENSNNKRAP
YWTNTEKMEKRLHAVPAANTVKFRCPAGGNPMPTMRWLKNGKEFKQEHRIGGYKVRNQHWSLIMESVVPSDKGNYTC
VVENEYGSINHTYHLDVVERSPHRPILQAGLPANASTVVGGDVEFVCKVYSDAQPHIQWIKHVEKNGSKYGPDGLPY
LKVLKAAGVNTTDKEIEVLYIRNVTFEDAGEYTCLAGNSIGISFHSAWLTVLPAPGREKEITASPDYLEIAIYCIGV
FLIACMVVTVILCRMKNTTKKPDFSSQPAVHKLTKRIPLRRQVTVSAESSSSMNSNTPLVRITTRLSSTADTPMLAG
VSEYELPEDPKWEFPRDKLTLGKPLGEGCFGQVVMAEAVGIDKDKPKEAVTVAVKMLKDDATEKDLSDLVSEMEMMK
MIGKHKNIINLLGACTQDGPLYVIVEYASKGNLREYLRARRPPGMEYSYDINRVPEEQMTFKDLVSCTYQLARGMEY
LASQKCIHRDLAARNVLVTENNVMKIADFGLARDINNIDYYKKTTNGRLPVKWMAPEALFDRVYTHQSDVWSFGVLM
WEIFTLGGSPYPGIPVEELFKLLKEGHRMDKPANCTNELYMMMRDCWHAVPSQRPTFKQLVEDLDRILTLTTNEEYL
DLSQPLEQYSPSYPDTRSSCSSGDDSVFSPDPMPYEPCLPQYPHINGSVKT

SEQ ID NO: 4
IIIb isoform of FGFR2 (see UniParc entry UPI000002A99A)

MVSWGRFICLVVVTMATLSLARPSFSLVEDTTLEPEEPPTKYQISQPEVYVAAPGESLEVRCLLKDAAVISWTKDGV
HLGPNNRTVLIGEYLQIKGATPRDSGLYACTASRTVDSETWYFMVNVTDAISSGDDEDDTGAEDFVSENSNNKRAP
YWTNTEKMEKRLHAVPAANTVKFRCPAGGNPMPTMRWLKNGKEFKQEHRIGGYKVRNQHWSLIMESVVPSDKGNYTC
VVENEYGSINHTYHLDVVERSPHRPILQAGLPANASTVVGGDVEFVCKVYSDAQPHIQWIKHVEKNGSKYGPDGLPY

Figure 1 – cont'd

LKVLKHSGINSSNAEVLALFNVTEADAGEYICKVSNYIGQANQSAWLTVLPKQQAPGREKEITASPDYLEIAIYCIG
VFLIACMVVTVILCRMKNTTKKPDFSSQPAVHKLTKRIPLRRQVTVSAESSSSMNSNTPLVRITTRLSSTADTPMLA
GVSEYELPEDPKWEFPRDKLTLGKPLGEGCFGQVVMAEAVGIDKDKPKEAVTVAVKMLKDDATEKDLSDLVSEMEMM
KMIGKHKNIINLLGACTQDGPLYVIVEYASKGNLREYLRARRPPGMEYSYDINRVPEEQMTFKDLVSCTYQLARGME
YLASQKCIHRDLAARNVLVTENNVMKIADFGLARDINNIDYYKKTTNGRLPVKWMAPEALFDRVYTHQSDVWSFGVL
MWEIFTLGGSPYPGIPVEELFKLLKEGHRMDKPANCTNELYMMMRDCWHAVPSQRPTFKQLVEDLDRILTLTTNEEY
LDLSQPLEQYSPSYPDTRSSCSSGDDSVFSPDPMPYEPCLPQYPHINGSVKT

SEQ ID NO: 5
IIIc isoform of FGFR3 (see Uniparc entry UPI000012A72C)

MGAPACALALCVAVAIVAGASSESLGTEQRVVGRAAEVPGPEPGQQEQLVFGSGDAVELSCPPPGGGPMGPTVWVKD
GTGLVPSERVLVGPQRLQVLNASHEDSGAYSCRQRLTQRVLCHFSVRVTDAPSSGDDEDGEDEAEDTGVDTGAPYWT
RPERMDKKLLAVPAANTVRFRCPAAGNPTPSISWLKNGREFRGEHRIGGIKLRHQQWSLVMESVVPSDRGNYTCVVE
NKFGSIRQTYTLDVLERSPHRPILQAGLPANQTAVLGSDVEFHCKVYSDAQPHIQWLKHVEVNGSKVGPDGTPYVTV
LKTAGANTTDKELEVLSLHNVTFEDAGEYTCLAGNSIGFSHHSAWLVVLPAEEELVEADEAGSVYAGILSYGVGFFL
FILVVAAVTLCRLRSPPKKGLGSPTVHKISRFPLKRQVSLESNASMSSNTPLVRIARLSSGEGPTLANVSELELPAD
PKWELSRARLTLGKPLGEGCFGQVVMAEAIGIDKDRAAKPVTVAVKMLKDDATDKDLSDLVSEMEMMKMIGKHKNII
NLLGACTQGGPLYVLVEYAAKGNLREFLRARRPPGLDYSFDTCKPPEEQLTFKDLVSCAYQVARGMEYLASQKCIHR
DLAARNVLVTEDNVMKIADFGLARDVHNLDYYKKTTNGRLPVKWMAPEALFDRVYTHQSDVWSFGVLLWEIFTLGGS
PYPGIPVEELFKLLKEGHRMDKPANCTHDLYMIMRECWHAAPSQRPTFKQLVEDLDRVLTVTSTDEYLDLSAPFEQY
SPGGQDTPSSSSSGDDSVFAHDLLPPAPPSSGGSRT

SEQ ID NO: 6
IIIb isoform of FGFR3 (see UniParc entry UPI000002A9AC)

MGAPACALALCVAVAIVAGASSESLGTEQRVVGRAAEVPGPEPGQQEQLVFGSGDAVELSCPPPGGGPMGPTVWVKD
GTGLVPSERVLVGPQRLQVLNASHEDSGAYSCRQRLTQRVLCHFSVRVTDAPSSGDDEDGEDEAEDTGVDTGAPYWT
RPERMDKKLLAVPAANTVRFRCPAAGNPTPSISWLKNGREFRGEHRIGGIKLRHQQWSLVMESVVPSDRGNYTCVVE
NKFGSIRQTYTLDVLERSPHRPILQAGLPANQTAVLGSDVEFHCKVYSDAQPHIQWLKHVEVNGSKVGPDGTPYVTV
LKSWISESVEADVRLRLANVSERDGGEYLCRATNFIGVAEKAFWLSVHGPRAAEEELVEADEAGSVYAGILSYGVGF
FLFILVVAAVTLCRLRSPPKKGLGSPTVHKISRFPLKRQVSLESNASMSSNTPLVRIARLSSGEGPTLANVSELELP
ADPKWELSRARLTLGKPLGEGCFGQVVMAEAIGIDKDRAAKPVTVAVKMLKDDATDKDLSDLVSEMEMMKMIGKHKN
IINLLGACTQGGPLYVLVEYAAKGNLREFLRARRPPGLDYSFDTCKPPEEQLTFKDLVSCAYQVARGMEYLASQKCI
HRDLAARNVLVTEDNVMKIADFGLARDVHNLDYYKKTTNGRLPVKWMAPEALFDRVYTHQSDVWSFGVLLWEIFTLG
GSPYPGIPVEELFKLLKEGHRMDKPANCTHDLYMIMRECWHAAPSQRPTFKQLVEDLDRVLTVTSTDEYLDLSAPFE
QYSPGGQDTPSSSSSGDDSVFAHDLLPPAPPSSGGSRT

SEQ ID NO: 7
Isoform 1 of FGFR4 (see Uniparc entry UPI000012A72D)

MRLLLALLGVLLSVPGPPVLSLEASEEVELEPCLAPSLEQQEQELTVALGQPVRLCCGRAERGGHWYKEGSRLAPAG
RVRGWRGRLEIASFLPEDAGRYLCLARGSMIVLQNLTLITGDSLTSSNDDEDPKSHRDPSNRHSYPQQAPYWTHPQR
MEKKLHAVPAGNTVKFRCPAAGNPTPTIRWLKDGQAFHGENRIGGIRLRHQHWSLVMESVVPSDRGTYTCLVENAVG
SIRYNYLLDVLERSPHRPILQAGLPANTTAVVGSDVELLCKVYSDAQPHIQWLKHIVINGSSFGADGFPYVQVLKTA
DINSSEVEVLYLRNVSAEDAGEYTCLAGNSIGLSYQSAWLTVLPEEDPTWTAAAPEARYTDIILYASGSLALAVLLL
LAGLYRGQALHGRHPRPPATVQKLSRFPLARQFSLESGSSGKSSSSLVRGVRLSSSGPALLAGLVSLDLPLDPLWEF
PRDRLVLGKPLGEGCFGQVVRAEAFGMDPARPDQASTVAVKMLKDNASDKDLADLVSEMEVMKLIGRHKNIINLLGV
CTQEGPLYVIVECAAKGNLREFLRARRPPGPDLSPDGPRSSEGPLSFPVLVSCAYQVARGMQYLESRKCIHRDLAAR
NVLVTEDNVMKIADFGLARGVHHIDYYKKTSNGRLPVKWMAPEALFDRVYTHQSDVWSFGILLWEIFTLGGSPYPGI
PVEELFSLLREGHRMDRPPHCPPELYGLMRECWHAAPSQRPTFKQLVEALDKVLLAVSEEYLDLRLTFGPYSPSGGD
ASSTCSSSDSVFSHDPLPLGSSSFPFGSGVQT

Figure 1 – cont'd

SEQ ID NO: 8
Isoform 2 of FGFR4 (see Uniparc entry UPI000013E0B8)

MRLLLALLGVLLSVPGPPVLSLEASEEVELEPCLAPSLEQQEQELTVALGQPVRLCCGRAERGGHWYKEGSRLAPAG
RVRGWRGRLEIASFLPEDAGRYLCLARGSMIVLQNLTLITGDSLTSSNDDEDPKSHRDPSNRHSYPQQAPYWTHPQR
MEKKLHAVPAGNTVKFRCPAAGNPTPTIRWLKDGQAFHGENRIGGIRLRHQHWSLVMESVVPSDRGTYTCLVENAVG
SIRYNYLLDVLERSPHRPILQAGLPANTTAVVGSDVELLCKVYSDAQPHIQWLKHIVINGSSFGADGFPYVQVLKTA
DINSSEVEVLYLRNVSAEDAGEYTCLAGNSIGLSYQSAWLTVLPGTGRIPHLTCDSLTPAGRTKSPTLQFSLESGSS
GKSSSSLVRGVRLSSSGPALLAGLVSLDLPLDPLWEFPRDRLVLGKPLGEGCFGQVVRAEAFGMDPARPDQASTVAV
KMLKDNASDKDLADLVSEMEVMKLIGRHKNIINLLGVCTQEGPLYVIVECAAKGNLREFLRARRPPGPDLSPDGPRS
SEGPLSFPVLVSCAYQVARGMQYLESRKCIHRDLAARNVLVTEDNVMKIADFGLARGVHHIDYYKKTSNGRLPVKWM
APEALFDRVYTHQSDVWSFGILLWEIFTLGGSPYPGIPVEELFSLLREGHRMDRPPHCPPELYGLMRECWHAAPSQR
PTFKQLVEALDKVLLAVSEEYLDLRLTFGPYSPSGGDASSTCSSSDSVFSHDPLPLGSSSFPFGSGVQT

SUBSTITUTED PYRAZOLO[1,5-A]PYRIDINE COMPOUNDS AS INHIBITORS OF FGFR TYROSINE KINASES

BACKGROUND

The present disclosure relates to novel compounds that exhibit inhibition of fibroblast growth factor receptor tyrosine kinases (FGFRs), in particular FGFR1, FGFR2, FGFR3 and/or FGFR4, pharmaceutical compositions comprising the compounds, to processes for making the compounds, and the use of the compounds in therapy. More particularly, it relates to substituted pyrazolo[1,5-a]pyridine compounds useful in the treatment or prevention of diseases which can be treated with an FGFR inhibitor, including diseases mediated by FGFR tyrosine kinases.

Fibroblast growth factors (FGFs) and their receptors (FGFRs) regulate a wide range of physiologic cellular processes, such as embryonic development, differentiation, proliferation, survival, migration, and angiogenesis.

The FGF family comprises 18 secreted ligands (FGFs) which are readily sequestered to the extracellular matrix by heparin sulfate proteoglycans (HPSGs). For signal propagation, FGFs are released from the extracellular matrix by proteases or specific FGF-binding proteins, with the liberated FGFs subsequently binding to a cell surface FGF-receptor (FGFR) in a ternary complex consisting of FGF, FGFR and HPSG (Been ken, A., Nat. Rev. Drug Discov. 2009; 8:235-253).

There are five FGFRs, of which four (FGFRs 1-4) are highly conserved single-pass transmembrane tyrosine kinase receptors (Eswarakumar, V. P., Cytokine Growth Factor Rev., 2005; 16:139-149). The binding of an FGF to an FGFR leads to receptor dimerization and transphosphorylation of tyrosine kinase domains (Dieci, M. V., et al., Cancer Discov. 2013; 3:264-279; Korc, N., and Friesel, R. E., Curr. Cancer Drug Targets 2009; 5:639-651). Activation of downstream signaling occurs via the intracellular receptor substrate FGFR substrate 2 (FRS2) and phospholipase Cγ (PLC-γ), leading to subsequent upregulation of RAS/mitogen-activated protein kinase (MAPK) and phosphoinositide 3-kinase (PI3K)/AKT signaling pathways. Other pathways can be activated, including STAT-dependent signaling (Turner, N., Grose, R., Nat. Ref. Cancer 2010; 10:116-129; Brooks, N. S., et al., Clin Cancer Res. 2012; 18:1855-1862; Dienstmann, R., et al., Ann. Oncol. 2014; 25:552-563).

FGFR signaling components are frequently altered in human cancer, and several preclinical models have provided compelling evidence for the oncogenic potential of aberrant FGFR signaling in carcinogenesis, thereby validating FGFR signaling as an attractive target for cancer treatment.

The mechanisms by which FGFR signaling is dysregulated and drive cancer are better understood in recent years, and include activating mutations, FGFR gene amplification, chromosomal translocations, autocrine and paracrine signaling, and altered FGFR splicing.

SUMMARY OF THE INVENTION

It has now been found that substituted pyrazolo[1,5-a] pyridine compounds are inhibitors of FGFR1, FGFR2, FGFR3 and/or FGFR4, which are useful in the treatment or prevention of diseases which can be treated with an inhibitor of FGFR1, FGFR2, FGFR3 and/or FGFR4, including diseases mediated by FGFR1, FGFR2, FGFR3 and/or FGFR4.

Accordingly, provided herein is a compound of the general Formula I:

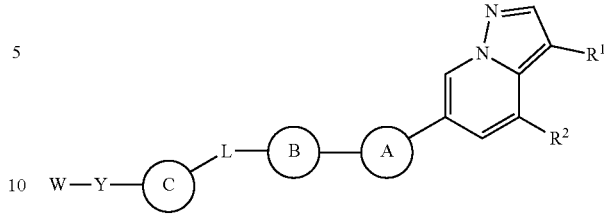

or pharmaceutically acceptable salt or solvate thereof, wherein Ring A, Ring B, Ring C, $R^1$, $R^2$, L, Y, and W are as defined herein.

Also provided herein is a pharmaceutical composition comprising a compound of Formula I or a pharmaceutically acceptable salt or solvate thereof, in admixture with a pharmaceutically acceptable diluent or carrier.

Also provided herein is a compound of Formula I, wherein the compound is at least about 3-fold more selective for FGFR3 than FGFR1.

Also provided herein is a compound of Formula I, wherein the compound is at least about 3-fold more selective for FGFR2 than FGFR1.

Also provided herein is a compound of Formula I, wherein the compound forms a covalent bond with a cysteine in a kinase insert domain in a FGFR3 protein.

Also provided herein is a compound of Formula I, wherein the compound forms a covalent bond with a cysteine in a c-terminal tail in a FGFR2 protein.

Also provided herein is a pharmaceutical composition, comprising a compound according to Formula I in admixture with a pharmaceutically acceptable diluent or carrier.

Also provided herein is a compound of Formula I covalently bonded to a cysteine.

Also provided herein is a FGFR3 inhibitor of Formula I that is at least about 3-fold more selective for FGFR3 than for FGFR1.

Also provided herein is a FGFR2 inhibitor of Formula I that is at least about 3-fold more selective for FGFR2 than for FGFR1.

Also provided herein is an inhibited FGFR3 protein covalently bound to a molecule via a cysteine in the kinase insert domain of the FGFR3 protein.

Also provided herein is an inhibited FGFR2 protein covalently bound to a molecule via a cysteine in the c-terminal tail of the FGFR2 protein.

Also provided herein is an inhibited FGFR protein covalently bonded via a cysteine to a compound of Formula I.

Also provided herein is a method for treating cancer in a subject in need thereof, the method comprising administering a pharmaceutical composition comprising a therapeutically effective amount of a compound according to Formula I or a pharmaceutically acceptable salt or solvate thereof.

Also provided herein is a method for treating cancer in a subject in need thereof, the method comprising determining if the cancer exhibits a dysregulation of a FGFR gene, a FGFR kinase, or expression or activity or level of any of the same, and if the cancer is determined to exhibit a dysregulation of a FGFR gene, a FGFR kinase, or expression or activity or level of any of the same, administering to the subject a therapeutically effective amount of a compound of Formula I or a pharmaceutically acceptable salt or solvate thereof.

Also provided herein is a method of treating a FGFR-associated cancer in a subject, the method comprising administering to a subject identified or diagnosed as having a FGFR-associated cancer a therapeutically effective amount of a compound of Formula I or a pharmaceutically acceptable salt or solvate thereof, to the subject.

Also provided herein is a method of treating cancer in a subject, the method comprising administering a therapeutically effective amount of a compound of Formula I or a pharmaceutically acceptable salt or solvate thereof, to a subject having a clinical record that indicates that the subject has a dysregulation of a FGFR gene, a FGFR kinase, or expression or activity or level of any of the same.

Also provided herein is a method of treating a FGFR-associated cancer in a subject, the method comprising determining that the cancer in the subject is a FGFR-associated cancer, and administering to a subject determined to have a FGFR-associated cancer a therapeutically effective amount of a compound of Formula I or a pharmaceutically acceptable salt or solvate thereof.

Also provided herein is a method of treating a subject having a cancer, wherein the method comprises administering one or more doses of a first FGFR inhibitor to the subject for a period of time, after administering the one or more doses of a first FGFR inhibitor to the subject for a period of time, determining whether a cancer cell in a sample obtained from the subject has at least one FGFR inhibitor resistance mutation that confers increased resistance to a cancer cell or tumor to treatment with the first FGFR inhibitor, and administering a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation that confers increased resistance to a cancer cell or tumor to treatment with the first FGFR inhibitor, or administering additional doses of the first FGFR inhibitor to the subject if the subject has a cancer cell that does not have a FGFR inhibitor resistance mutation that confers increased resistance to a cancer cell or tumor to treatment with the first FGFR inhibitor.

Also provided herein is a method of treating a subject having a cancer, wherein the method comprises determining whether a cancer cell in a sample obtained from a subject having a cancer and previously administered one or more doses of a first FGFR inhibitor has one or more FGFR inhibitor resistance mutations that confer increased resistance to a cancer cell or tumor to treatment with the first FGFR inhibitor that was previously administered to the subject, and administering a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation that confers increased resistance to a cancer cell or tumor to treatment with the first FGFR inhibitor that was previously administered to the subject, or administering additional doses of the first FGFR inhibitor to the subject if the subject has cancer cell that does not have a FGFR inhibitor resistance mutation that confers increased resistance to a cancer cell or tumor to treatment with the first FGFR inhibitor previously administered to the subject.

Also provided herein is a method of treating a subject having a cancer, wherein the method comprises administering one or more doses of a compound of Formula I or a pharmaceutically acceptable salt or solvate thereof for a period of time, after administering one or more doses of a compound of Formula I or a pharmaceutically acceptable salt or solvate thereof for a period of time, determining whether a cancer cell in a sample obtained from the subject has one or more FGFR inhibitor resistance mutations that confer increased resistance to a cancer cell or tumor to treatment with the compound of Formula I or a pharmaceutically acceptable salt or solvate thereof, and administering a second FGFR inhibitor or a second compound of Formula I or a pharmaceutically acceptable salt or solvate thereof as a monotherapy or in conjunction with an additional therapy or therapeutic agent to a subject having a cancer cell that has one or more FGFR inhibitor resistance mutations that confer increased resistance to a cancer cell or tumor to treatment with the compound of Formula I or a pharmaceutically acceptable salt or solvate thereof, or administering additional doses of the compound of Formula I or a pharmaceutically acceptable salt or solvate thereof to a subject having a cancer cell that does not have a FGFR inhibitor resistance mutation that confers increased resistance to a cancer cell or tumor to treatment with the compound of Formula I or a pharmaceutically acceptable salt or solvate thereof.

Also provided herein is a method of treating a subject having a cancer, wherein the method comprises determining whether a cancer cell in a sample obtained from a subject having a cancer and previously administered one or more doses of a compound of Formula I or a pharmaceutically acceptable salt or solvate thereof has one or more FGFR inhibitor resistance mutations that confer increased resistance to a cancer cell or tumor to treatment with the compound of Formula I or a pharmaceutically acceptable salt or solvate thereof that was previously administered to the subject, administering a second FGFR inhibitor or a second compound of Formula I or a pharmaceutically acceptable salt or solvate thereof as a monotherapy or in conjunction with an additional therapy or therapeutic agent to a subject having a cancer cell that has one or more FGFR inhibitor resistance mutations that confer increased resistance to a cancer cell or tumor to treatment the compound of Formula I or a pharmaceutically acceptable salt or solvate thereof that was previously administered to the subject, or administering additional doses of the compound of Formula I or a pharmaceutically acceptable salt or solvate thereof previously administered to a subject having a cancer cell that does not have a FGFR inhibitor resistance mutation that confers increased resistance to a cancer cell or tumor to treatment with the compound of Formula I or a pharmaceutically acceptable salt or solvate thereof that was previously administered to the subject.

Also provided herein is a method of treating a FGFR-associated cancer in a subject, the method comprising administering one or more doses of a compound of Formula I, or a pharmaceutically acceptable salt or solvate thereof, as a monotherapy to a subject identified or diagnosed as having a FGFR-associated cancer, after administering one or more doses of a compound of Formula I, or a pharmaceutically acceptable salt or solvate thereof, as a monotherapy to the subject identified or diagnosed as having a FGFR-associated cancer, determining a level of circulating tumor DNA in a biological sample obtained from the subject, administering a therapeutically effective amount of a compound of Formula I, or a pharmaceutically acceptable salt or solvate thereof, and an additional therapy or therapeutic agent to a subject identified as having about the same or an elevated level of circulating tumor DNA as compared to a reference level of circulating tumor DNA.

Also provided herein is a method of treating a FGFR-associated cancer in a subject, the method comprising administering a therapeutically effective amount of a compound of Formula I, or a pharmaceutically acceptable salt or solvate thereof, and an additional therapy or therapeutic agent to a subject (i) identified or diagnosed as having a FGFR-associated cancer, (ii) previously administered one or more doses of the compound of Formula I, or a pharmaceutically acceptable salt or solvate thereof, as a monotherapy, and (iii) after administration of the one or more doses of the compound of Formula I, or a pharmaceutically acceptable salt or solvate thereof, as a monotherapy, identified as having about the same or an elevated level of circulating tumor DNA as compared to a reference level of circulating tumor DNA.

Also provided herein is a method of treating a FGFR-associated cancer in a subject, the method comprising identifying a subject having a FGFR-associated cancer and an elevated serum phosphate level following administration of one or more doses of a first FGFR1 inhibitor, and administering to the identified subject a compound of Formula I or a pharmaceutically acceptable salt or solvate thereof.

Also provided herein is a method of treating a subject identified as having an elevated serum phosphate level and a FGFR-associated cancer, the method comprising administering to the subject a compound of Formula I or a pharmaceutically acceptable salt or solvate thereof.

Also provided herein is a method for treating a FGFR-associated cancer in a subject in need of such treatment, the method comprising detecting a dysregulation of a FGFR gene, a FGFR kinase, or the expression or activity or level of any of the same in a sample from the subject, administering to the subject a therapeutically effective amount of a first FGFR1 inhibitor, determining whether a sample from a subject exhibits an elevated serum phosphate level, and administering a compound of Formula I, or a pharmaceutically acceptable salt of solvate thereof as a monotherapy or in conjunction with an additional therapy or therapeutic agent to the subject if the sample from the subject exhibits an elevated serum phosphate level, or administering additional doses of the first FGFR1 inhibitor to the subject if the sample from the subject does not exhibit an elevated serum phosphate level.

Also provided herein is a method for treating a FGFR-associated cancer in a subject in need of such treatment, the method comprising determining whether a sample from a subject previously administered one or more doses of a first FGFR1 inhibitor exhibits an elevated serum phosphate level, and administering a compound of Formula I, or a pharmaceutically acceptable salt of solvate thereof as a monotherapy or in conjunction with an additional therapy or therapeutic agent to the subject if the sample from the subject exhibits an elevated serum phosphate level, or administering additional doses of the first FGFR1 inhibitor to the subject if the sample from the subject does not exhibit an elevated serum phosphate level.

Also provided herein is a method for treating a FGFR-associated cancer in a subject in need of such treatment, the method comprising identifying a subject having a FGFR-associated cancer and previously demonstrating an elevated serum phosphate level, and administering to the subject a compound of Formula I or a pharmaceutically acceptable salt or solvate thereof.

Also provided herein is a method for treating a FGFR-associated cancer in a subject in need of such treatment, the method comprising identifying a subject having a FGFR-associated cancer and previously administered one or more doses of a first FGFR1 inhibitor and previously demonstrating an elevated serum phosphate level, and administering to the subject a compound of Formula I or a pharmaceutically acceptable salt or solvate thereof.

Also provided herein is a method of treating a subject having a cancer, wherein the method comprises administering one or more doses of a compound of Formula I or a pharmaceutically acceptable salt or solvate thereof for a period of time, after administering one or more doses of a compound of Formula I or a pharmaceutically acceptable salt or solvate thereof for a period of time, determining whether a cancer cell in a sample obtained from the subject has a FGFR resistance mutation in a cysteine that confers increased resistance to a cancer cell or tumor to treatment with the compound of Formula I or a pharmaceutically acceptable salt or solvate thereof, and administering a second FGFR inhibitor as a monotherapy or in conjunction with an additional therapy or therapeutic agent to a subject having a cancer cell that has a FGFR resistance mutation in a cysteine that confers increased resistance to a cancer cell or tumor to treatment with the compound of Formula I or a pharmaceutically acceptable salt or solvate thereof, or administering additional doses of the compound of Formula I or a pharmaceutically acceptable salt or solvate thereof to a subject having a cancer cell that does not have a FGFR resistance mutation in a cysteine that confers increased resistance to a cancer cell or tumor to treatment with the compound of Formula I or a pharmaceutically acceptable salt or solvate thereof.

Also provided herein is a method for treating a FGFR-associated cancer in a subject in need of such treatment, the method comprising detecting a dysregulation of a FGFR gene, a FGFR kinase, or the expression or activity or level of any of the same in a sample from the subject, administering to the subject a therapeutically effective amount of a FGFR inhibitor, determining whether a sample from a subject exhibits a dysregulation of a second kinase gene, a second kinase, or the expression or activity or level of any of the same in a sample from the subject, and administering an inhibitor of the second kinase in conjunction with an additional therapy or therapeutic agent to the subject if the sample from the subject exhibits a dysregulation of a second kinase gene, a second kinase, or the expression or activity or level of any of the same, or administering additional doses of the FGFR inhibitor to the subject if the sample from the subject does not exhibit a dysregulation of a second kinase gene, a second kinase, or the expression or activity or level of any of the same.

Also provided herein is a method for treating a FGFR-associated cancer in a subject in need of such treatment, the method comprising detecting a dysregulation of a FGFR gene, a FGFR kinase, or the expression or activity or level of any of the same in a sample from the subject, administering to the subject a therapeutically effective amount of a compound of Formula I in conjunction with an inhibitor of a second kinase.

Also provided herein is a method for treating a FGFR-associated cancer in a subject in need of such treatment, the method comprising determining whether a sample from a subject previously administered one or more doses of a compound of Formula I exhibits a dysregulation of a second kinase gene, a second kinase, or the expression or activity or level of any of the same, and administering an inhibitor of the second kinase in conjunction with an additional therapy or therapeutic agent to the subject if the sample from the subject exhibits a dysregulation of a second kinase gene, a second kinase, or the expression or activity or level of any of the same, or administering additional doses of the compound of Formula I to the subject if the sample from the subject does not exhibit a dysregulation of a second kinase gene, a second kinase, or the expression or activity or level of any of the same.

Also provided herein is a method for treating a cancer in a subject in need of such treatment, the method comprising detecting a dysregulation of a first kinase gene, a first kinase, or the expression or activity or level of any of the same in a sample from the subject, administering to the subject a therapeutically effective amount of an inhibitor of the first kinase, determining whether a sample from a subject exhibits a dysregulation of a FGFR gene, a FGFR kinase, or the expression or activity or level of any of the same, and administering a FGFR inhibitor in conjunction with an additional therapy or therapeutic agent to the subject if the sample from the subject exhibits a dysregulation of a FGFR gene, a FGFR kinase, or the expression or activity or level of any of the same, or administering additional doses of the inhibitor of the first kinase to the subject if the sample from the subject does not exhibit a dysregulation of a FGFR gene, a FGFR kinase, or the expression or activity or level of any of the same.

Also provided herein is a method for treating a cancer in a subject in need of such treatment, the method comprising detecting a dysregulation of a first kinase gene, a first kinase, or the expression or activity or level of any of the same in a sample from the subject, and administering to the subject a therapeutically effective amount of an inhibitor of the first kinase in conjunction with a FGFR inhibitor to the subject if the sample from the subject exhibits a dysregulation of a FGFR gene, a FGFR kinase, or the expression or activity or level of any of the same.

Also provided herein is a method for treating a cancer in a subject in need of such treatment, the method comprising determining whether a sample from a subject exhibits a dysregulation of a FGFR gene, a FGFR kinase, or the expression or activity or level of any of the same in a subject previously administered an inhibitor of a first kinase, and administering a FGFR inhibitor in conjunction with an additional therapy or therapeutic agent to the subject if the sample from the subject exhibits a dysregulation of a FGFR gene, a FGFR kinase, or the expression or activity or level of any of the same, or administering additional doses of the inhibitor of the first kinase to the subject if the sample from the subject does not exhibit a dysregulation of a FGFR gene, a FGFR kinase, or the expression or activity or level of any of the same.

Also provided herein is a method of treating a subject having a cancer, wherein the method comprises administering one or more doses of a first therapeutic agent to the subject for a period of time, after administering one or more doses of the first therapeutic agent to the subject for a period of time, determining whether a cancer cell in a sample obtained from the subject has at least one FGFR inhibitor resistance mutation that confers increased resistance to a cancer cell or tumor to treatment with the first therapeutic agent, and administering a second FGFR inhibitor as a monotherapy or in conjunction with an additional therapy or therapeutic agent to the subject if the subject has a cancer cell that has at least one FGFR inhibitor resistance mutation that confers increased resistance to a cancer cell or tumor to treatment with the first therapeutic agent, or administering additional doses of the FGFR inhibitor to the subject if the subject has a cancer cell that does not have a FGFR inhibitor resistance mutation that confers increased resistance to a cancer cell or tumor to treatment with the first therapeutic agent, and wherein the mutation corresponds to (i) amino acid position 561 of SEQ ID NO: 1, (ii) amino acid position 564 of SEQ ID NO: 3, (iii) amino acid position 555 of SEQ ID NO: 5, or (iv) amino acid position 550 of SEQ ID NO: 7.

Also provided herein is a method of treating a subject having a cancer, wherein the method comprises determining whether a cancer cell in a sample obtained from a subject having a cancer and previously administered one or more doses of a first therapeutic agent has one or more FGFR inhibitor resistance mutations that confer increased resistance to a cancer cell or tumor to treatment with the first therapeutic agent previously administered to the subject, and administering a second FGFR inhibitor to the subject as a monotherapy or in conjunction with an additional therapy or therapeutic agent to the subject if the subject has a cancer cell that has at least one FGFR inhibitor resistance mutation that confers increased resistance to a cancer cell or tumor to treatment with the first therapeutic agent that was previously administered to the subject, or administering additional doses of the first therapeutic agent that was previously administered to the subject if the subject has cancer cell that does not have a FGFR inhibitor resistance mutation that confers increased resistance to a cancer cell or tumor to treatment with the first therapeutic agent that was previously administered to the subject.

Also provided herein is a method of treating a subject, the method comprising administering a therapeutically effective amount of a compound of Formula I or a pharmaceutically acceptable salt or solvate thereof, to a subject having a clinical record that indicates that the subject has a dysregulation of a FGFR gene, a FGFR kinase, or expression or activity or level of any of the same.

Also provided herein is a method of treating a subject, the method comprising administering a therapeutically effective amount of a compound of Formula I or a pharmaceutically acceptable salt or solvate thereof, to a subject having a dysregulation of a FGFR gene, a FGFR kinase, or expression or activity or level of any of the same.

Also provided herein a method of treating a subject with a FGFR-associated disease or disorder, the method comprising administering a therapeutically effective amount of a compound of Formula I or a pharmaceutically acceptable salt or solvate thereof to a subject with a FGFR-associated disease or disorder.

Also provided herein is a method of treating a subject, the method comprising detecting a dysregulation of a FGFR gene, a FGFR kinase, or expression or activity or level of any of the same, and administering to the subject a therapeutically effective amount of a compound of Formula I or a pharmaceutically acceptable salt or solvate thereof.

Also provided herein is a method of treating achondroplasia, hypochondroplasia, or thanatophoric dysplasia in a subject, the method comprising administering to a subject identified or diagnosed as having achondroplasia, hypochondroplasia, or thanatophoric dysplasia a therapeutically effective amount of a compound of Formula I or a pharmaceutically acceptable salt or solvate thereof, to the subject.

Also provided herein is a method for inhibiting angiogenesis in a subject in need thereof, the method comprising administering to the subject a therapeutically effective amount of a compound of Formula I, or a pharmaceutically acceptable salt or solvate thereof.

Also provided herein is a method of treating a FGFR-associated cancer in a subject in need thereof, the method comprising administering to the subject a compound of Formula I or a pharmaceutically acceptable salt or solvate thereof wherein following administration of the compound of Formula I or a pharmaceutically acceptable salt or solvate thereof, a sample from the subject has a phosphate level that is lower than the phosphate level of a sample from a second subject having a FGFR-associated cancer following administration of a compound that is not a compound of Formula I or a pharmaceutically acceptable salt or solvate thereof.

Also provided herein is a method of treating a FGFR-associated cancer in a subject in need thereof, the method comprising administering to the subject a compound of Formula I or a pharmaceutically acceptable salt or solvate thereof, wherein following administration of the compound of Formula I or a pharmaceutically acceptable salt or solvate thereof, a sample from the subject does not demonstrate an elevated serum phosphate level.

Also provided herein is a method of reducing the risk of hyperphosphatemia in a subject with an FGFR-associated cancer, the method comprising administering to the subject a compound of Formula I or a pharmaceutically acceptable salt or solvate thereof.

Also provided herein is a method of changing the adverse effects of treatment of a subject with a FGFR-associated cancer, the method comprising administering to the subject a compound of Formula I or a pharmaceutically acceptable salt or solvate thereof, and reducing a dose of a FGFR1 inhibitor administered to the subject, not administering a FGFR1 inhibitor to the subject, or ceasing to administer a FGFR1 inhibitor to the subject.

Also provided herein is a method of reversing an elevated serum phosphate level in a subject with a FGFR-associated cancer being treated with a FGFR1 inhibitor, the method comprising reducing the dose or ceasing administration of the FGFR1 inhibitor, and administering to the subject a compound of Formula I or a pharmaceutically acceptable salt or solvate thereof.

Also provided herein is use of a compound of Formula I or a pharmaceutically acceptable salt or solvate thereof for the manufacture of a medicament for treating a FGFR-associated cancer in a subject.

Also provided herein is a compound of Formula I or a pharmaceutically acceptable salt or solvate thereof for use in treating a subject identified or diagnosed as having a FGFR-associated cancer.

Also provided herein is a method for inhibiting FGFR kinase activity in a mammalian cell, the method comprising contacting the mammalian cell with a compound of Formula I or a pharmaceutically acceptable salt or solvate thereof.

Also provided herein is a method of selecting a treatment for a subject, the method comprising selecting a treatment comprising administration of a therapeutically effective amount of a compound of Formula I or a pharmaceutically acceptable salt or solvate thereof, for a subject identified or diagnosed as having a FGFR-associated cancer.

Also provided herein is a method of selecting a treatment for a subject having a cancer, the method comprising determining that the cancer in the subject is a FGFR-associated cancer, and selecting a treatment including administration of a therapeutically effective amount of a compound of Formula I or a pharmaceutically acceptable salt or solvate thereof, for a subject determined to have a FGFR-associated cancer.

Also provided herein is a method of selecting a subject for treatment including administration of a therapeutically effective amount of a compound of Formula I or a pharmaceutically acceptable salt or solvate thereof, the method comprising identifying a subject having a FGFR-associated cancer, and selecting the subject for treatment including administration of a therapeutically effective amount of a compound of Formula I or a pharmaceutically acceptable salt or solvate thereof.

Also provided herein is a method of selecting a subject having cancer for treatment including administration of a therapeutically effective amount of a compound of Formula I or a pharmaceutically acceptable salt or solvate thereof, the method comprising determining that the cancer in the subject is a FGFR-associated cancer, and selecting a subject determined to have a FGFR-associated cancer for treatment including administration of a therapeutically effective amount of a compound of Formula I or a pharmaceutically acceptable salt or solvate thereof.

Also provided herein is a method for inhibiting angiogenesis of a cancer in a subject in need thereof, the method comprising administering to the subject a therapeutically effective amount of a compound of Formula I, or a pharmaceutically acceptable salt or solvate thereof.

Also provided herein is a method for inhibiting metastasis of a cancer in a subject in need thereof, the method comprising administering to the subject a therapeutically effective amount of a compound of Formula I, or a pharmaceutically acceptable salt or solvate thereof.

Also provided herein is a method of selecting a treatment for a subject, the method comprising selecting a therapeutically effective amount of a compound of Formula I, or a pharmaceutically acceptable salt or solvate thereof, for a subject (i) identified or diagnosed as having a FGFR-associated cancer, (ii) previously administered one or more doses of a second FGFR inhibitor, and (iii) after administration of the one or more doses of the second FGFR inhibitor, identified as having about the same or an elevated level of circulating tumor DNA as compared to a reference level of circulating tumor DNA.

Also provided herein is a method of selecting a treatment for a subject, the method comprising selecting a therapeutically effective amount of a compound of Formula I, or a pharmaceutically acceptable salt or solvate thereof, and an additional therapy or therapeutic agent for a subject (i) identified or diagnosed as having a FGFR-associated cancer, (ii) previously administered one or more doses of the compound of Formula I, or a pharmaceutically acceptable salt or solvate thereof, as a monotherapy, and (iii) after administration of the one or more doses of the compound of Formula I, or a pharmaceutically acceptable salt or solvate thereof, identified as having about the same or an elevated level of circulating tumor DNA as compared to a reference level of circulating tumor DNA.

Also provided herein is a method of determining efficacy of a treatment in a subject, the method comprising determining a first level of circulating tumor DNA in a biological sample obtained from a subject identified or diagnosed as having a FGFR-associated cancer at a first time point, administering a treatment comprising one or more doses of a compound of Formula I, or a pharmaceutically acceptable salt or solvate thereof to the subject, after the first time point and before a second time point, determining a second level of circulating tumor DNA in a biological sample obtained from the subject at the second time point, and identifying that the treatment is effective in a subject determined to have a decreased second level of circulating tumor DNA as compared to the first level of circulating tumor DNA, or identifying the treatment is not effective in a subject determined to have about the same or an elevated second level of circulating tumor DNA as compared to the first level of circulating tumor DNA.

Also provided herein is a method of determining whether a subject has developed resistance to a treatment, the method comprising determining a first level of circulating tumor DNA in a biological sample obtained from a subject identified or diagnosed as having a FGFR-associated cancer at a first time point, administering a treatment comprising one or more doses of a compound of Formula I, or a pharmaceutically acceptable salt or solvate thereof to the subject, after the first time point and before a second time point, determining a second level of circulating tumor DNA in a biological sample obtained from the subject at the second time point, and determining that a subject having a decreased second level of circulating tumor DNA as compared to the first level of circulating tumor DNA has not developed resistance to the treatment, or determining that a subject having about the same or an elevated second level of circulating tumor DNA as compared to the first level of circulating tumor DNA has developed resistance to the treatment.

Also provided herein is a process for preparing a compound of Formula I or a pharmaceutically acceptable salt or solvate thereof.

Also provided herein is a compound of Formula I or a pharmaceutically acceptable salt or solvate thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description, and from the claims.

DESCRIPTION OF DRAWINGS

FIG. 1 contains amino acid sequences of SEQ ID NOs: 1-8

DETAILED DESCRIPTION OF THE INVENTION

In one aspect, provided herein is a compound of Formula I

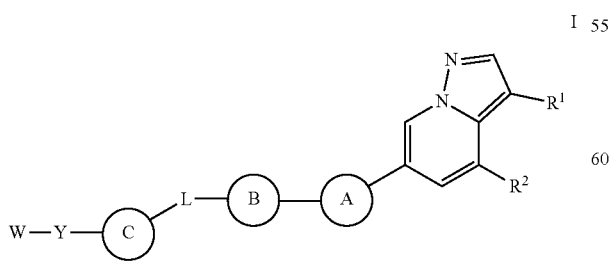

and pharmaceutically acceptable salts and solvates thereof, wherein:

$R^1$ is CN or Cl;

$R^2$ is C1-C6 alkoxy, C1-C6 alkyl, C3-C6 cycloalkoxy, or phenyl optionally substituted with 1-2 groups independently selected from halogen and (C3-C6 cycloalkyl)C(=O)NH—;

Ring A is $Ar^1$ or $hetAr^1$;

$Ar^1$ is phenyl optionally substituted with 1-2 groups independently selected from halogen, C1-C6 alkyl, fluoroC1-C6 alkyl, and C1-C6 alkoxy;

$hetAr^1$ is a 5-6 membered heteroaryl ring having 1-3 ring nitrogen atoms and optionally substituted with 1-2 independently selected halogen, C1-C6 alkyl, fluoroC1-C6 alkyl, or C1-C6 alkoxy substituents;

Ring B is a $Ar^2$, a 4-8 membered monocyclic heterocyclic ring having 1-2 ring nitrogen atoms and 0-1 ring oxygen atoms, a 7-11 membered bridged heterocyclic ring having 1-2 ring nitrogen atoms, a 7-12 membered spiroheterocyclic ring having 2 ring nitrogen atoms, or absent;

$Ar^2$ is phenyl optionally substituted with 1-2 groups independently selected from halogen, C1-C6 alkyl, fluoroC1-C6 alkyl, and C1-C6 alkoxy;

L is —C(=O)—, —CH$_2$—, —SO$_2$—, O, *—NHC(=O)—, *C(=O)NH—, *—NHS(O)$_2$—, *—S(O)$_2$NH— or absent, wherein the asterisk indicates the point of attachment to Ring C;

Ring C is $Cyc^1$, $Cyc^2$, $hetCyc^1$, $hetCyc^2$, $hetCyc^3$, $hetCyc^4$, $Ar^3$, or absent;

$Cyc^1$ is 4-8 membered cycloalkyl ring optionally substituted with halo, CN, OH, C1-C6 alkyl, fluoroC1-C6 alkyl, and C1-C6 alkoxy;

$Cyc^2$ is a 5-11 membered bridged cycloalkyl ring;

$hetCyc^1$ is a 4-6 membered heterocyclic ring having 1-2 ring nitrogen atoms and optionally substituted with 1-4 substituents independently selected from halogen, CN, OH, C1-C6 alkyl, C1-C6 alkoxy, and cyanoC1-C6 alkyl;

$hetCyc^2$ is a 7-11 membered bridged heterocyclic ring having 1-3 ring heteroatoms independently selected from N and O;

$hetCyc^3$ is a 7-12 membered spiroheterocyclic ring having 1-2 ring nitrogen atoms;

$hetCyc^4$ is a 7-10 membered fused bicyclic heterocyclic ring having 2 ring nitrogen atoms;

$Ar^3$ is phenyl optionally substituted with C1-C6 alkyl or C1-C6 alkoxy;

Y is —NH—, —N(C1-C3 alkyl)-, or absent; and

W is a warhead.

In another aspect, provided herein is a compound of Formula I

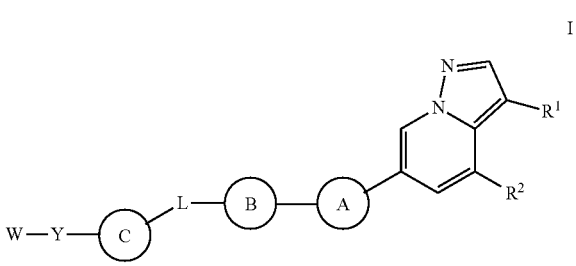

and pharmaceutically acceptable salts and solvates thereof, wherein:

$R^1$ is CN or Cl;

$R^2$ is C1-C6 alkoxy, C1-C6 alkyl, C3-C6 cycloalkoxy, or phenyl optionally substituted with 1-2 groups independently selected from halogen and (C3-C6 cycloalkyl)C(=O)NH—;

Ring A is $Ar^1$ or $hetAr^1$;

$Ar^1$ is phenyl optionally substituted with 1-2 groups independently selected from halogen, C1-C6 alkyl, fluoroC1-C6 alkyl, and C1-C6 alkoxy;

$hetAr^1$ is a 5-6 membered heteroaryl ring having 1-3 ring nitrogen atoms and optionally substituted with 1-2 independently selected halogen, C1-C6 alkyl, fluoroC1-C6 alkyl, or C1-C6 alkoxy substituents;

Ring B is a $Ar^2$, a 4-8 membered monocyclic heterocyclic ring having 1-2 ring nitrogen atoms and 0-1 ring oxygen atoms, a 7-11 membered bridged heterocyclic ring having 1-2 ring nitrogen atoms, a 7-12 membered spiroheterocyclic ring having 2 ring nitrogen atoms, or absent;

$Ar^2$ is phenyl optionally substituted with 1-2 groups independently selected from halogen, C1-C6 alkyl, fluoroC1-C6 alkyl, and C1-C6 alkoxy;

L is —C(=O)—, —CH$_2$—, —SO$_2$—, O, *—NHC(=O)—, *C(=O)NH—, *—NHS(O)$_2$—, *—S(O)$_2$NH— or absent, wherein the asterisk indicates the point of attachment to Ring C;

Ring C is $Cyc^1$, $Cyc^2$, $hetCyc^1$, $hetCyc^2$, $hetCyc^3$, $hetCyc^4$, $Ar^3$, or absent;

$Cyc^1$ is 4-8 membered cycloalkyl ring optionally substituted with halo, CN, OH, C1-C6 alkyl, fluoroC1-C6 alkyl, and C1-C6 alkoxy;

$Cyc^2$ is a 5-11 membered bridged cycloalkyl ring;

$hetCyc^1$ is a 4-6 membered heterocyclic ring having 1-2 ring nitrogen atoms and optionally substituted with 1-4 substituents independently selected from halogen, CN, OH, C1-C6 alkyl, C1-C6 alkoxy, and cyanoC1-C6 alkyl;

$hetCyc^2$ is a 7-11 membered bridged heterocyclic ring having 1-3 ring heteroatoms independently selected from N and O;

$hetCyc^3$ is a 7-12 membered spiroheterocyclic ring having 1-2 ring nitrogen atoms;

$hetCyc^4$ is a 7-10 membered fused bicyclic heterocyclic ring having 2 ring nitrogen atoms;

$Ar^3$ is phenyl optionally substituted with C1-C6 alkyl or C1-C6 alkoxy;

Y is —NH—, —N(C1-C3 alkyl)-, or absent;

W is $R^3R^4C=CR^5C(=O)$—, $R^6R^7NCH_2CH=CHC(=O)$—, $H_2C=CHSO_2$— or $R^8C\equiv CC(=O)$—;

$R^3$ is hydrogen;

$R^4$ is hydrogen, CF$_3$ or Z(C1-C6 alkyl)- wherein Z is H, F, Cl, Br, HO—, C1-C6 alkoxy, or fluoroC1-C6 alkoxy, and $R^5$ is hydrogen, C1-C3 alkyl, fluoroC1-C3 alkyl or halogen, or $R^4$ and $R^5$ together with the carbon atoms to which they are attached form a 4-8-membered carbocyclic ring;

each of $R^6$ and $R^7$ is independently C1-C6 alkyl, or $R^6$ and $R^7$ together with the nitrogen atom to which they are attached form a 5-6 membered heterocyclic ring optionally having an additional ring heteroatom which is O, wherein said ring is optionally substituted with halogen;

$R^8$ is hydrogen, C1-C3 alkyl, HO—C1-C3 alkyl or R'R"NCH$_2$—; and

R' and R" are each independently hydrogen or C1-C6 alkyl.

For complex chemical names employed herein, a substituent group is typically named before the group to which it attaches. For example, methoxyethyl comprises an ethyl backbone with a methoxy substituent.

The term "halogen" or "halo" means —F (sometimes referred to herein as "fluoro" or "fluoros"), —Cl, —Br and —I.

The term "alkyl" refers to a hydrocarbon chain that may be a straight chain or branched chain, containing the indicated number of carbon atoms. For example, the term "C1-C6 alkyl" as used herein refers to saturated linear or branched-chain monovalent hydrocarbon radicals of one to six carbon atoms. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "haloalkyl" refers to an alkyl, in which one or more hydrogen atoms is/are replaced with an independently selected halo.

The term "fluoroC1-C6 alkyl" as used herein refers to a C1-C6 alkyl radical as defined herein, wherein one to three hydrogen atoms is replaced with one to three fluoro atoms, respectively. Examples include, but are not limited to, fluoromethyl, difluoromethyl, trifluoromethyl, 2-fluoroethyl, 2,2-difluoroethyl, 2,2,2- and trifluoroethyl.

The term "alkenyl" as used herein refers to a hydrocarbon chain that may be a straight chain or branched chain having one or more carbon-carbon double bonds. The alkenyl moiety contains the indicated number of carbon atoms. For example, $C_{2-6}$ or C2-C6 indicates that the group may have from 2 to 6 (inclusive) carbon atoms in it.

The term "alkynyl" as used herein refers to a hydrocarbon chain that may be a straight chain or branched chain having one or more carbon-carbon triple bonds. The alkynyl moiety contains the indicated number of carbon atoms. For example, $C_{2-6}$ or C2-C6 indicates that the group may have from 2 to 6 (inclusive) carbon atoms in it.

The term "alkoxy" refers to an —O-alkyl radical (e.g., —OCH$_3$). For example, the term "C1-C6 alkoxy" as used herein refers to saturated linear or branched-chain monovalent alkoxy radicals of one to six carbon atoms, wherein the radical is on the oxygen atom. Examples include methoxy, ethoxy, propoxy, isopropoxy, butoxy and tert-butoxy.

The term "haloalkoxy" refers to an —O-haloalkyl radical (e.g., —OCH$_3$).

The term "cyanoC1-C6 alkyl", as used herein refers to saturated linear or branched-chain monovalent alkyl radicals of one to six or two to six carbon atoms, respectively, wherein one of the carbon atoms is substituted with a cyano group.

The term "cycloalkyl" as used herein includes saturated cyclic hydrocarbon groups having 3 to 20 ring carbons, preferably 3 to 16 ring carbons, and more preferably 3 to 12 ring carbons or 3-10 ring carbons or 4-8 ring carbons or 3-6 ring carbons, wherein the cycloalkyl group may be optionally substituted. Examples of cycloalkyl groups include, without limitation, cyclopropyl, cyclobutyl, cyclopentyl, cyclohexyl, cycloheptyl, and cyclooctyl. Cycloalkyl may include multiple fused and/or bridged rings. Non-limiting examples of fused/bridged cycloalkyl includes: bicyclo[1.1.0]butane, bicyclo[2.1.0]pentane, bicyclo[1.1.1]pentane, bicyclo[3.1.0]hexane, bicyclo[2.1.1]hexane, bicyclo[3.2.0]heptane, bicyclo[4.1.0]heptane, bicyclo[2.2.1]heptane, bicyclo[3.1.1]heptane, bicyclo[4.2.0]octane, bicyclo[3.2.1]octane, bicyclo[2.2.2]octane, and the like. Cycloalkyl also includes spirocyclic rings (e.g., spirocyclic bicycle wherein two rings are connected through just one atom). Non-limiting examples of spirocyclic cycloalkyls include spiro [2.2]pentane, spiro[2.5]octane, spiro[3.5]nonane, spiro[3.5] nonane, spiro[3.5]nonane, spiro[4.4]nonane, spiro[2.6] nonane, spiro[4.5]decane, spiro[3.6]decane, spiro[5.5] undecane, and the like. The term "C3-C6 cycloalkyl" as used herein refers to cyclopropyl, cyclobutyl, cyclopentyl or cyclohexyl. The term "4-8 membered cycloalkyl ring" as used herein refers to cyclobutyl, cyclopentyl, cyclohexyl, cycloheptyl, and cyclooctyl.

The term "cycloalkenyl" as used herein includes partially unsaturated non-aromatic cyclic hydrocarbon groups having 3 to 20 ring carbons, preferably 3 to 16 ring carbons, and more preferably 3 to 12 ring carbons or 3-10 ring carbons or 3-6 ring carbons, wherein the cycloalkenyl group may be optionally substituted. Examples of cycloalkenyl groups include, without limitation, cyclopentenyl, cyclohexenyl, cycloheptenyl, and cyclooctenyl. Cycloalkenyl groups may have any degree of saturation provided that none of the rings in the ring system are aromatic; and the cycloalkenyl group is not fully saturated overall. Cycloalkenyl may include multiple fused and/or bridged and/or spirocyclic rings. The term "heterocycloalkenyl" as used herein refers to a "cycloalkenyl" wherein from 1-4 ring sp$^3$ carbon atoms are replaced by heteroatoms.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, and the like.

The term "heteroaryl", as used herein, means a mono-, bi-, tri- or polycyclic group having 5 to 20 ring atoms, alternatively 5, 6, 9, 10, or 14 ring atoms; and having 6, 10, or 14 pi electrons shared in a cyclic array; wherein at least one ring in the system is aromatic (but does not have to be a ring which contains a heteroatom, e.g. tetrahydroisoquinolinyl, e.g., tetrahydroquinolinyl), and at least one ring in the system contains one or more heteroatoms independently selected from the group consisting of N, O, and S(O)$_{0-2}$. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3] dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

The term "heterocyclyl" refers to a mon-, bi-, tri-, or polycyclic nonaromatic saturated ring system with 3-16 ring atoms (e.g., 4-8 (e.g., 4-6) membered monocyclic, 7-12 (e.g., 7-11 or 7-10) membered bicyclic, or 11-14 membered tricyclic ring system) having 1-3 heteroatoms if monocyclic, 1-6 heteroatoms if bicyclic, or 1-9 heteroatoms if tricyclic or polycyclic, said heteroatoms selected from O, N, or S (e.g., carbon atoms and 1-3, 1-6, or 1-9 heteroatoms of N, O, or S(O)$_{0-2}$ if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. Heterocyclyl may include multiple fused and bridged rings. Non-limiting examples of fused/bridged heteorocyclyl includes: 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, 3-azabicyclo[3.2.1]octane, 2-oxabicyclo[1.1.0]butane, 2-oxabicyclo[2.1.0]pentane, 2-oxabicyclo[1.1.1]pentane, 3-oxabicyclo[3.1.0]hexane, 5-oxabicyclo[2.1.1]hexane, 3-oxabicyclo[3.2.0]heptane, 3-oxabicyclo [4.1.0]heptane, 7-oxabicyclo[2.2.1]heptane, 6-oxabicyclo [3.1.1]heptane, 7-oxabicyclo[4.2.0]octane, 2-oxabicyclo [2.2.2]octane, 3-oxabicyclo[3.2.1]octane, and the like. Heterocyclyl also includes spirocyclic rings (e.g., spirocyclic bicycle wherein two rings are connected through just one atom). Non-limiting examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro [3.5]nonane, 2-azaspiro[4.4]nonane, 6-azaspiro[2.6]nonane, 1,7-diazaspiro[4.5]decane, 7-azaspiro[4.5]decane 2,5-diazaspiro[3.6]decane, 3-azaspiro[5.5]undecane, 2-oxaspiro [2.2]pentane, 4-oxaspiro[2.5]octane, 1-oxaspiro[3.5] nonane, 2-oxaspiro[3.5]nonane, 7-oxaspiro[3.5]nonane, 2-oxaspiro[4.4]nonane, 6-oxaspiro[2.6]nonane, 1,7-dioxaspiro[4.5]decane, 2,5-dioxaspiro[3.6]decane, 1-oxaspiro[5.5] undecane, 3-oxaspiro[5.5]undecane, 3-oxa-9-azaspiro[5.5] undecane and the like.

The term "alkylene" refers to a branched or unbranched divalent alkyl (e.g., —CH$_2$—).

The term "heterocyclylene" and the like refer to divalent forms of the ring system, here divalent heterocyclyl.

The term "oxo" as used herein means an oxygen that is double bonded to a carbon atom or heteroatom, i.e., =O. For example, a 4-6 membered heterocyclic ring having 1-2 ring heteroatoms independently selected from N and O and substituted with an oxo may be, for example, a pyrrolidinyl ring substituted with oxo (e.g., a pyrrolidinonyl ring), which may be represented by the structure:

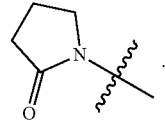 [SMILES: *N1CCCC1=O]

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer. An example of a tautomeric forms includes the following example:

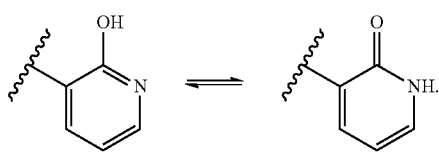 [SMILES: *c1cccnc1O ; *c1ccc[nH]c1=O]

It will be appreciated that certain compounds provided herein may contain one or more centers of asymmetry and may therefore be prepared and isolated in a mixture of isomers such as a racemic mixture, or in an enantiomerically pure form.

Embodiments can include any one or more of the features delineated below and/or in the claims.

Ring A

In some embodiments, Ring A is hetAr$^1$.

In certain embodiments (when Ring A is hetAr$^1$), Ring A is 5 membered heteroaryl ring having 1-3 ring nitrogen atoms and substituted with 1-2 independently selected halogen, C1-C6 alkyl, fluoroC1-C6 alkyl, or C1-C6 alkoxy substituents (e.g., optionally substituted with 1-2 independently selected C1-C6 alkyl substituents).

In certain embodiments, Ring A is selected from pyrazolyl, triazolyl, and imidazolyl, each of which is optionally substituted with 1-2 independently selected halogen, C1-C6 alkyl, fluoroC1-C6 alkyl, or C1-C6 alkoxy substituents (e.g., optionally substituted with 1-2 independently selected C1-C6 alkyl substituents).

In certain embodiments of the foregoing, Ring A is pyrazolyl optionally substituted with 1-2 independently selected halogen, C1-C6 alkyl, fluoroC1-C6 alkyl, or C1-C6 alkoxy substituents (e.g., optionally substituted with 1-2 independently selected C1-C6 alkyl substituents).

As non-limiting examples of the foregoing embodiments, Ring A can be selected from the following:

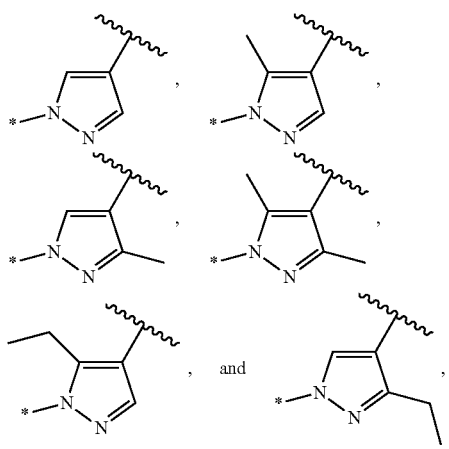

wherein the asterisk indicates point of attachment to Ring B.

For example, Ring A can be

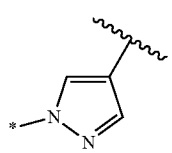

wherein the asterisk indicates point of attachment to Ring B.

In certain embodiments (when Ring A is selected from pyrazolyl, triazolyl, and imidazolyl, each of which is optionally substituted with 1-2 independently selected halogen, C1-C6 alkyl, fluoroC1-C6 alkyl, or C1-C6 alkoxy substituents (e.g., optionally substituted with 1-2 independently selected C1-C6 alkyl substituents)), Ring A is triazolyl (e.g., 1,2,3-triazolyl) optionally substituted with one C1-C6 alkyl substituent.

As non-limiting examples of the foregoing embodiments, Ring A can be selected from the following:

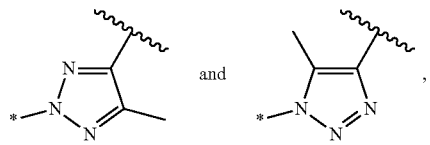

wherein the asterisk indicates point of attachment to Ring B.

In certain embodiments (when Ring A is selected from pyrazolyl, triazolyl, and imidazolyl, each of which is optionally substituted with 1-2 independently selected halogen, C1-C6 alkyl, fluoroC1-C6 alkyl, or C1-C6 alkoxy substituents (e.g., optionally substituted with 1-2 independently selected C1-C6 alkyl substituents)), Ring A is imidazolyl.

As a non-limiting example of the foregoing embodiments, Ring A can be:

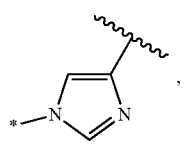 [SMILES: *c1cn(*)cn1]

wherein the asterisk indicates point of attachment to Ring B.

In certain embodiments (when Ring A is hetAr$^1$), Ring A is a 6-membered heteroaryl ring having 1-3 ring nitrogen atoms and optionally substituted with 1-2 independently selected halogen, C1-C6 alkyl, fluoroC1-C6 alkyl, or C1-C6 alkoxy substituents (e.g., optionally substituted with 1-2 independently selected C1-C6 alkyl substituents).

In certain embodiments, Ring A is selected from pyridinyl, pyrimidinyl, pyrazinyl, and pyridazinyl, each of which is optionally substituted with 1-2 independently selected halogen, C1-C6 alkyl, fluoroC1-C6 alkyl, or C1-C6 alkoxy substituents.

In certain embodiments, Ring A is selected from pyridinyl, pyrimidinyl, pyrazinyl, and pyridazinyl, each of which is optionally substituted with 1-2 independently selected halogen, C1-C6 alkyl, or fluoroC1-C6 alkyl substituents.

In certain embodiments, Ring A is selected from pyridinyl, pyrimidinyl, pyrazinyl, and pyridazinyl, each of which is optionally substituted with 1-2 independently selected C1-C6 alkyl substituents.

In certain embodiments of the foregoing, Ring A is pyridinyl optionally substituted with 1-2 independently selected C1-C6 alkyl substituents.

As non-limiting examples of the foregoing embodiments, Ring A can be selected from the following:

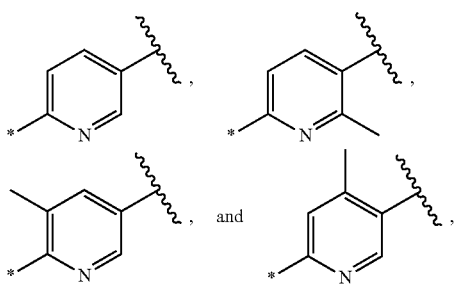

wherein the asterisk indicates point of attachment to Ring B.

In certain embodiments (when Ring A is selected from pyridinyl, pyrimidinyl, pyrazinyl, and pyridazinyl, each of which is optionally substituted with 1-2 independently selected C1-C6 alkyl substituents), Ring A is pyrimidinyl optionally substituted with 1-2 independently selected C1-C6 alkyl substituents.

As a non-limiting example of the foregoing embodiments, Ring A can be:

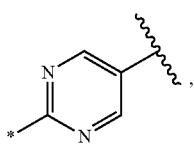 [SMILES: *c1cnc(*)nc1]

wherein the asterisk indicates point of attachment to Ring B.

In certain embodiments (when Ring A is selected from pyridinyl, pyrimidinyl, pyrazinyl, and pyridazinyl, each of which is optionally substituted with 1-2 independently selected C1-C6 alkyl substituents), Ring A is pyrazinyl optionally substituted with 1-2 independently selected C1-C6 alkyl substituents.

As a non-limiting example of the foregoing embodiments, Ring A can be:

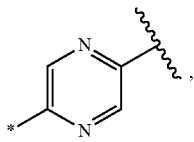 [SMILES: *c1cnc(*)cn1]

wherein the asterisk indicates point of attachment to Ring B.

In certain embodiments (when Ring A is selected from pyridinyl, pyrimidinyl, pyrazinyl, and pyridazinyl, each of which is optionally substituted with 1-2 independently selected C1-C6 alkyl substituents), Ring A is pyridazinyl optionally substituted with 1-2 independently selected C1-C6 alkyl substituents.

As a non-limiting example of the foregoing embodiments, Ring A can be:

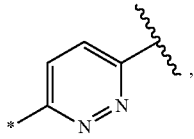 [SMILES: *c1ccc(*)nn1]

wherein the asterisk indicates point of attachment to Ring B.

In some embodiments, Ring A is Ar¹.

In certain embodiments of foregoing, Ring A is unsubstituted phenyl.

Ring B

In some embodiments, Ring B is a 4-8 membered monocyclic heterocyclic ring having 1-2 ring nitrogen atoms and 0-1 ring oxygen atoms.

In certain embodiments (when Ring B is a 4-8 membered monocyclic heterocyclic ring having 1-2 ring nitrogen atoms and 0-1 ring oxygen atoms), Ring B is a 4-6 membered monocyclic heterocyclic ring having 1-2 ring nitrogen atoms.

In certain embodiments of the foregoing, Ring B is azetidinyl.

As a non-limiting example of the foregoing embodiments, Ring B can be:

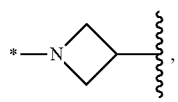

wherein the asterisk indicates point of attachment to L.

In certain embodiments (when Ring B is a 4-6 membered monocyclic heterocyclic ring having 1-2 ring nitrogen atoms), Ring B is pyrrolidinyl.

As a non-limiting example of the foregoing embodiments, Ring B can be:

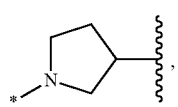

wherein the asterisk indicates point of attachment to L.

In certain embodiments (when Ring B is a 4-6 membered monocyclic heterocyclic ring having 1-2 ring nitrogen atoms), Ring B is a 6 membered monocyclic heterocyclic ring having 1-2 ring nitrogen atoms.

In certain embodiments of the foregoing, Ring B is piperidinyl.

As non-limiting examples of the foregoing embodiments, Ring B can be:

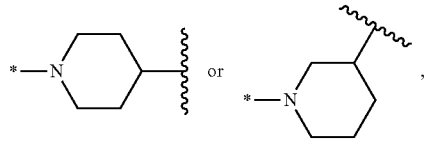 [SMILES: *C1CCN(*)CC1 ; *C1CCCN(*)C1]

wherein the asterisk indicates point of attachment to L.

In certain embodiments (when Ring B is a 6 membered monocyclic heterocyclic ring having 1-2 ring nitrogen atoms), Ring B is piperazinyl.

As a non-limiting example of the foregoing embodiments, Ring B can be:

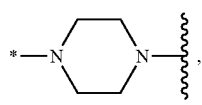

wherein the asterisk indicates point of attachment to L.

In some embodiments, Ring B is 7-11 membered bridged heterocyclic ring having 1-2 ring nitrogen atoms.

In certain embodiments of the foregoing, Ring B is a 7-8 membered bridged heterocyclic ring having 2 ring nitrogen atoms.

As non-limiting examples of the foregoing embodiments, Ring B can be selected from the following:

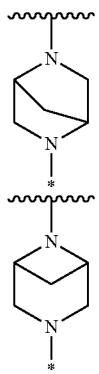 ,  , 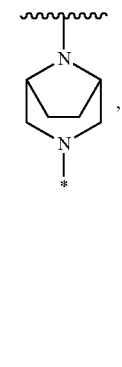 , 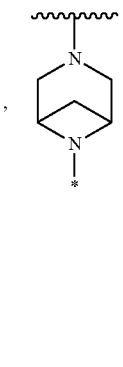 , and wherein the asterisk indicates the point of attachment to L.

In some embodiments, Ring B is a 7-12 membered spiroheterocyclic ring having 2 ring nitrogen atoms.

In certain embodiments of the foregoing, Ring B is a 7-9 membered spiroheterocyclic ring having 2 ring nitrogen atoms.

As non-limiting examples of the foregoing embodiments, Ring B can be selected from the following:

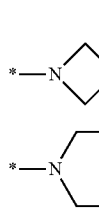 , 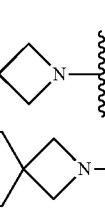 , and 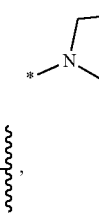 , wherein the asterisk indicates the point of attachment to L.

In some embodiments, Ring B is $Ar^2$.

In some embodiments, Ring B is absent.

The Variable L

In some embodiments, L is —C(=O)—.

In some embodiments, L is —CH$_2$—.

In some embodiments, L is —SO$_2$—.

In some embodiments, L is O.

In some embodiments, L is *—NHC(=O)—, wherein the asterisk indicates the point of attachment to Ring C.

In some embodiments, L is absent.

Ring C

In some embodiments, Ring C is $Cyc^1$.

In certain embodiments (when Ring C is $Cyc^1$), Ring C is 4-6 membered cycloalkyl ring optionally substituted with halo, CN, OH, C1-C6 alkyl, fluoroC1-C6 alkyl, and C1-C6 alkoxy.

In certain embodiments of the foregoing, Ring C is 4-6 membered cycloalkyl ring.

As non-limiting examples to the foregoing embodiments, Ring C can be selected from the following:

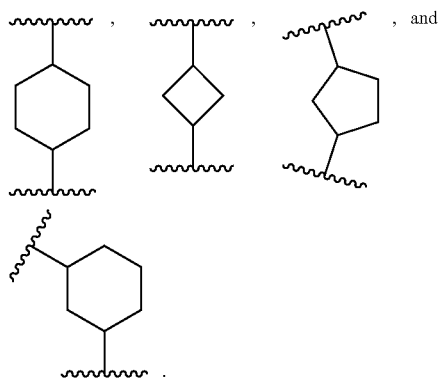

In some embodiments, Ring C is $Cyc^2$.

In certain embodiments (when Ring C is $Cyc^2$), Ring C is

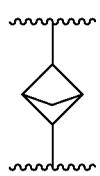 .

In some embodiments, Ring C is $hetCyc^1$.

In certain embodiments (when Ring C is $hetCyc^1$), Ring C is piperidinyl optionally substituted with 1-2 substituents independently selected from halogen and CN.

As non-limiting examples of the foregoing embodiments, Ring C can be selected from the following:

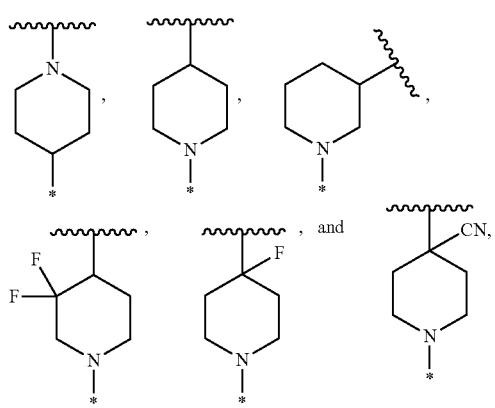

wherein the asterisk indicates the point of attachment to —Y—W.

In certain embodiments (when Ring C is $hetCyc^1$), Ring C is azetidinyl optionally substituted with 1-2 substituents independently selected from halogen, CN, OH, C1-C6 alkyl, and C1-C6 alkoxy.

As non-limiting examples of the foregoing embodiments, Ring C can be selected from the following:

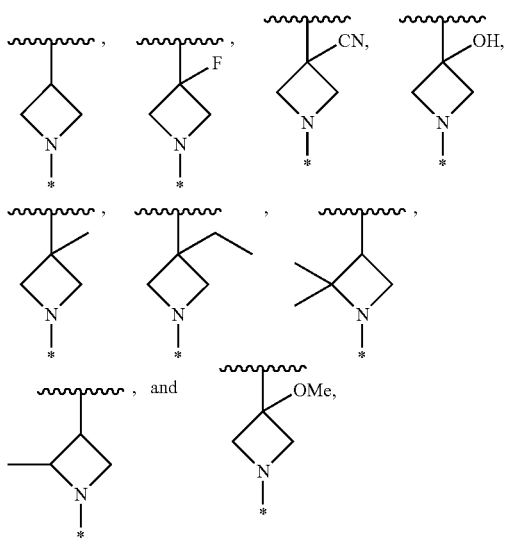

wherein the asterisk indicates the point of attachment to —Y—W.

In certain embodiments (when Ring C is hetCyc¹), C is piperazinyl optionally substituted with 1-2 substituents independently selected from cyanoC1-C6 alkyl.

As non-limiting examples of the foregoing embodiments, Ring C can be selected from the following:

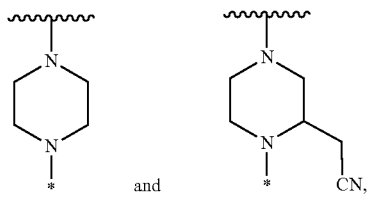

wherein the asterisk indicates the point of attachment to —Y—W.

In certain embodiments (when Ring C is hetCyc¹), Ring C is pyrrolidinyl optionally substituted with 1-2 substituents independently selected from halogen and CN.

As non-limiting examples of the foregoing embodiments, Ring C can be selected from the following:

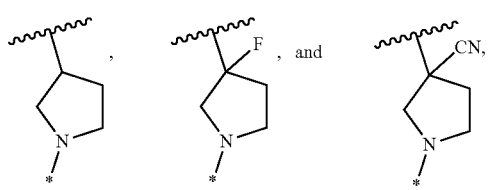 [SMILES: *C1CCN(*)C1 ; *N1CCC(*)(F)C1 ; *N1CCC(*)(C#N)C1]

wherein the asterisk indicates the point of attachment to —Y—W.

In some embodiments, Ring C is hetCyc².

In certain embodiments (when Ring C is hetCyc²), Ring C is a 7-9 membered bridged heterocyclic ring having 1-3 ring heteroatoms independently selected from N and O.

As non-limiting examples of the foregoing embodiments, Ring C can be selected from the following:

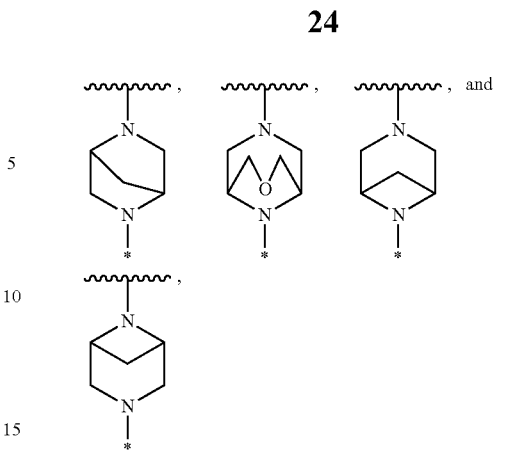

wherein the asterisk indicates the point of attachment to —Y—W.

In some embodiments, Ring C is hetCyc³.

In certain embodiments (when Ring C is hetCyc³), Ring C is a 7-9 membered spiroheterocyclic ring having 1-2 ring nitrogen atoms.

As non-limiting examples of the foregoing embodiments, Ring C can be selected from the following:

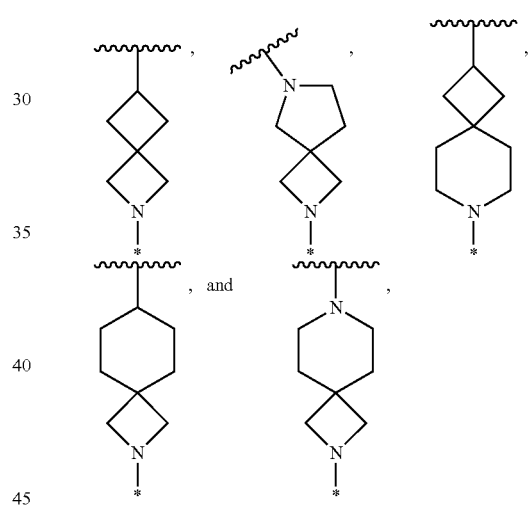

wherein the asterisk indicates the point of attachment to —Y—W.

In some embodiments, Ring C is hetCyc⁴.

As non-limiting examples of the foregoing embodiments, Ring C can be:

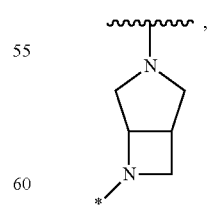

wherein the asterisk indicates the point of attachment to —Y—W.

In some embodiments, Ring C is Ar³.

As non-limiting examples of the foregoing embodiments, Ring C can be selected from the following:

wherein the asterisk indicates the point of attachment to —Y—W.

In some embodiments, Ring C is absent.

Variable Y

In some embodiments, Y is —NH—.

In some embodiments, Y is —N(CH$_3$)—.

In some embodiments, Y is absent.

In certain embodiments (when Ring C is hetCyc$^1$, hetCyc$^2$, hetCyc$^3$, hetCyc$^4$, or absent), Y is absent.

Variable R$^1$

In some embodiments, R$^1$ is CN.

In some embodiments, R$^1$ is Cl.

Variable R$^2$

In some embodiments, R$^2$ is C1-C6 alkoxy.

In certain embodiments (when R$^2$ is C1-C6 alkoxy), R$^2$ is methoxy.

In certain embodiments (when R$^2$ is C1-C6 alkoxy), R$^2$ is selected from ethoxy, isopropoxy, and isobutoxy (i.e., 2-methylprop-1-oxy).

In some embodiments, R$^2$ is C1-C6 alkyl.

In certain embodiments (when R$^2$ is C1-C6 alkyl), R$^2$ is isopropyl.

In some embodiments, R$^2$ is C3-C6 cycloalkoxy.

In certain embodiments (when R$^2$ is C3-C6 cycloalkoxy), R$^2$ is cyclobutoxy.

In some embodiments, R$^2$ is phenyl optionally substituted with 1-2 groups independently selected from halogen and (C3-C6 cycloalkyl)C(=O)NH—.

In certain embodiments of the foregoing, R$^2$ is phenyl optionally substituted with 1-2 groups independently selected from fluoro and cyclopropylC(=O)NH—.

Non-Limiting Combinations of Ring A, Ring B, Ring C, L, Y, R$^1$, and R$^2$

In some embodiments, zero, one, or two of Ring B, Ring C, and L are absent.

In certain embodiments of the foregoing, from 0-1 of Ring B, Ring C, and L are absent.

In certain embodiments, from 1-2 of Ring B, Ring C, and L are absent.

[A]

In some embodiments, Ring A is hetAr$^1$; and Ring B is a 4-6 membered monocyclic heterocyclic ring having 1-2 ring nitrogen atoms.

In certain embodiments of the foregoing, Ring B is selected from the group consisting of azetidinyl, piperidinyl, pyrrolidinyl, and piperazinyl.

In some embodiments, Ring A is hetAr$^1$; and Ring B is a 7-8 membered bridged heterocyclic ring having 2 ring nitrogen atoms.

In some embodiments, Ring A is hetAr$^1$; and Ring B is a 7-9 membered spiroheterocyclic ring having 2 ring nitrogen atoms.

In certain embodiments of [A], Ring A is a 5 membered heteroaryl ring having 1-3 ring nitrogen atoms and optionally substituted with 1-2 independently selected C1-C6 alkyl substituents.

As a non-limiting example of the foregoing embodiments, Ring A can be pyrazolyl optionally substituted with 1-2 independently selected C1-C6 alkyl substituents.

In certain embodiments of [A], Ring A is a 6-membered heteroaryl ring having 1-3 ring nitrogen atoms and optionally substituted with 1-2 independently selected C1-C6 alkyl substituents.

As a non-limiting example of the foregoing embodiments, Ring A can be pyridinyl optionally substituted with 1-2 independently selected C1-C6 alkyl substituents.

[B]

In some embodiments, Ring A is Ar$^1$; and Ring B is a 4-6 membered monocyclic heterocyclic ring having 1-2 ring nitrogen atoms.

As a non-limiting example of the foregoing embodiments, Ring A can be phenyl.

In certain embodiments of [B] (when Ring A is Ar$^1$; and Ring B is a 4-6 membered monocyclic heterocyclic ring having 1-2 ring nitrogen atoms), Ring B is a 6 membered monocyclic heterocyclic ring having 1-2 ring nitrogen atoms.

In some embodiments, Ring A is Ar$^1$; and Ring B is absent.

In some embodiments of [A] or [B], L is selected from C(=O) and CH$_2$.

In some embodiments of [A] or [B], Ring C is selected from Cyc$^1$ and Cyc$^2$.

In some embodiments of [A] or [B], Ring C is hetCyc$^1$.

In certain embodiments of [A] or [B] (when Ring C is hetCyc$^1$), Ring C is a 4-6 membered heterocyclic ring having 1-2 ring nitrogen atoms and optionally substituted with 1-2 substituents independently selected from halogen, CN, OH, C1-C6 alkyl, C1-C6 alkoxy, and cyanoC1-C6 alkyl.

In certain embodiments of the foregoing, Ring C is selected from:
(i) azetidinyl optionally substituted with 1-2 substituents independently selected from halogen, CN, OH, C1-C6 alkyl, and C1-C6 alkoxy;
(ii) piperidinyl optionally substituted with 1-2 substituents independently selected from halogen and CN;
(iii) pyrrolidinyl optionally substituted with 1-4 substituents independently selected from halogen and CN; and
(iv) piperazinyl optionally substituted with 1-2 substituents independently selected from cyanoC1-C6 alkyl.

In some embodiments of [A] or [B], Ring C is hetCyc$^2$.

In certain embodiments of [A] or [B] (when Ring C is hetCyc$^2$), Ring C is a 7-9 membered bridged heterocyclic ring having 2-3 ring heteroatoms independently selected from N and O.

In some embodiments of [A] or [B], Ring C is hetCyc$^3$.

In certain embodiments of [A] or [B] (when Ring C is hetCyc$^3$), Ring C is a 7-9 membered spiroheterocyclic ring having 1-2 ring nitrogen atoms.

In some embodiments of [A] or [B], Ring C is Ar$^a$.

[C]

In some embodiments, the compound of Formula I has Formula I-A:

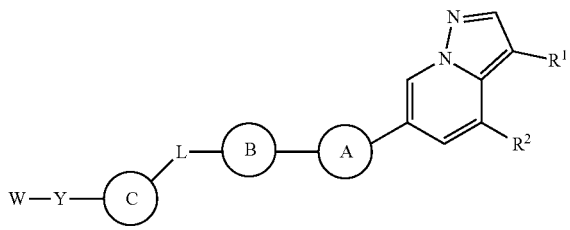

I-A and pharmaceutically acceptable salts and solvates thereof, wherein:
each of B, C, and L is present.

In some embodiments of Formula I-A, Ring B is a 4-6 membered monocyclic heterocyclic ring having 1-2 ring nitrogen atoms, a 7-8 membered bridged heterocyclic ring having 2 ring nitrogen atoms, or a 7-9 membered spiroheterocyclic ring having 2 ring nitrogen atoms, wherein Ring B is attached to L via a ring nitrogen atom;
L is —C(=O)—, —CH$_2$—, or —SO$_2$—; and
Ring C is Cyc$^1$, Cyc$^2$, hetCyc$^1$, hetCyc$^2$, hetCyc$^3$, hetCyc$^4$, or Ar$^3$.

In some embodiments of Formula I-A, Ring A is hetAr$^1$.

In some embodiments of Formula I-A, Ring B is a 4-6 membered monocyclic heterocyclic ring having 1-2 ring nitrogen atoms.

In some embodiments of Formula I-A, Ring B is a 7-8 membered bridged heterocyclic ring having 2 ring nitrogen atoms.

In some embodiments of Formula I-A, Ring B is a 7-9 membered spiroheterocyclic ring having 2 ring nitrogen atoms.

In some embodiments of Formula I-A, L is —C(=O)—.
In some embodiments of Formula I-A, L is —CH$_2$—.
In some embodiments of Formula I-A, L is —SO$_2$—.
In some embodiments of Formula I-A, Ring C is Cyc$^1$, Cyc$^2$, or Ar$^3$.
In some embodiments of Formula I-A, Ring C is hetCyc$^1$.
In some embodiments of Formula I-A, Ring C is hetCyc$^2$, hetCyc$^3$, or hetCyc$^4$.

[D]

In some embodiments, the compound of Formula I has Formula I-B:

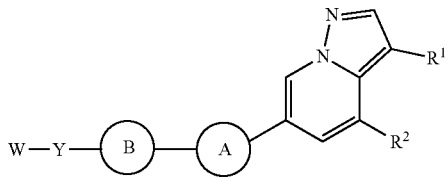

I-B and pharmaceutically acceptable salts and solvates thereof, wherein:
Ring B is present.

In some embodiments of Formula I-B, Ring A is hetAr$^1$.
In some embodiments of Formula I-B, Ring A is Ar$^1$.

In some embodiments of Formula I-B, Ring B is a 4-6 membered monocyclic heterocyclic ring having 1-2 ring nitrogen atoms.

In some embodiments of Formula I-B, Y is absent.

[E]

In some embodiments, the compound of Formula I has Formula I-C:

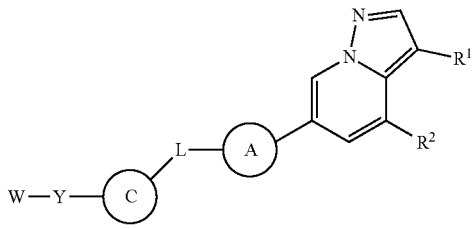

I-C and pharmaceutically acceptable salts and solvates thereof, wherein:
Ring C is present; and
L is present.

In some embodiments of Formula I-C, Ring A is Ar$^1$.
In some embodiments of Formula I-C, L is selected from —C(=O)— and *—NH(C(=O)—, wherein the asterisk indicates the point of attachment to Ring C.
In some embodiments of Formula I-C, Ring C is hetCyc$^1$.
In some embodiments of Formula I-C, Ring C is Cyc$^1$.
In some embodiments of [A]-[E], R$^1$ is CN.
In some embodiments of [A]-[E], R$^1$ is Cl.
In some embodiments of [A]-[E], R$^2$ is C1-C6 alkoxy.
In certain embodiments of the foregoing, R$^2$ is methoxy.

Variable W

In some embodiments, W is a warhead as defined elsewhere herein.
In some embodiments, W is R$^3$R$^4$C=CR$^5$C(=O)—.
In certain embodiments (when W is R$^3$R$^4$C=CR$^5$C(=O)—), R$^3$ is hydrogen.
In certain embodiments (when W is R$^3$R$^4$C=CR$^5$C(=O)—), R$^4$ is hydrogen.
In certain embodiments (when W is R$^3$R$^4$C=CR$^5$C(=O)—), R$^4$ is CF$_3$.
In certain embodiments (when W is R$^3$R$^4$C=CR$^5$C(=O)—), R$^4$ is ZCH$_2$—, wherein Z is F, Cl, Br, HO— or CH$_3$O—.
In certain embodiments (when W is R$^3$R$^4$C=CR$^5$C(=O)—), R$^5$ is H.
In certain embodiments (when W is R$^3$R$^4$C=CR$^5$C(=O)—), R$^5$ is F.
In certain embodiments (when W is R$^3$R$^4$C=CR$^5$C(=O)—), R$^4$ and R$^5$ together with the carbon atoms to which they are attached form a 4-membered carbocyclic ring.
In some embodiments, W is R$^6$R$^7$NCH$_2$CH=CHC(=O)—.
In certain embodiments (when W is R$^6$R$^7$NCH$_2$CH=CHC(=O)—), each of R$^6$ and R$^7$ is independently C1-C6 alkyl.
In certain embodiments (when W is R$^6$R$^7$NCH$_2$CH=CHC(=O)—), each of R$^6$ and R$^7$ is independently C1-C3 alkyl.
In certain embodiments (when W is R$^6$R$^7$NCH$_2$CH=CHC(=O)—), R$^6$ and R$^7$ are both methyl.
In certain embodiments (when W is R$^6$R$^7$NCH$_2$CH=CHC(=O)—), R$^6$ and R$^7$ together with the nitrogen atom to which they are attached form a 5-6 membered heterocyclic ring optionally having an additional ring heteroatom which is O, wherein said ring is optionally substituted with halogen.

In certain embodiments of the foregoing, $R^6$ and $R^7$ together with the nitrogen atom to which they are attached form a 5-6 membered heterocyclic ring selected from the group consisting of piperidine, morpholine, and pyrrolidine, wherein said ring is optionally substituted with halogen.

In some embodiments, W is $R^8C\equiv CC(=O)$—.

In certain embodiments (when W is $R^8C\equiv CC(=O)$—), $R^8$ is hydrogen or methyl.

In certain embodiments (when W is $R^8C\equiv CC(=O)$—), $R^8$ is $HOCH_2$—.

In certain embodiments (when W is $R^8C\equiv CC(=O)$—), $R^8$ is R'R"NCH$_2$—.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid salts. In one embodiment, compounds of Formula I include trifluoroacetic acid and dihydrochloride salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

In some embodiments, the compounds of Formula I include the compounds of Examples 1-135, 137-146, and 148-196 and stereoisomers and pharmaceutically acceptable salts and solvates thereof. In one embodiment, the compounds of Examples 1-135, 137-146, and 148-196 are in the free base form. In one embodiment, the compounds of Examples 1-135, 137-146, and 148-196 are trifluoroacetate salts.

The term "pharmaceutically acceptable" indicates that the compound, or salt or composition thereof is compatible chemically and/or toxicologically with the other ingredients comprising a formulation and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds provided herein therefore also comprise compounds with one or more isotopes of one or more atoms, and mixtures thereof, including radioactive compounds, wherein one or more non-radioactive atoms has been replaced by one of its radioactive enriched isotopes.

Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

The compounds described herein include one or more "warheads" as part of their chemical structure. In Formula I, variable "W" represents a warhead. As used herein, the term "warhead" refers to a moiety having one or more reactive functional groups that are capable of covalently binding (e.g., irreversibly or reversibly; e.g., irreversibly) to one or more cysteine residues present in an FGFR protein (e.g., FGFR2 or FGFR3), thereby irreversibly or reversibly forming a covalent bond between the warhead and the one or more cysteine residues. Without wishing to be bound by theory, it is believed that the formation of said covalent bond between the warhead and the one or more cysteine residues can alter one or more properties associated with an FGFR protein; e.g., can inhibit one or more functions or activities associated with the FGFR protein.

In some embodiments, the "warhead" is a chemical moiety that is capable of irreversibly forming a covalent bond to one or more cysteine residues present in an FGFR protein.

In some embodiments, the "warhead" is a chemical moiety that is capable of reversibly forming a covalent bond to one or more cysteine residues present in an FGFR protein.

In some embodiments, the warhead is suitable for covalently binding to a key cysteine residue in the binding domain of a FGFR protein. One of ordinary skill in the art will appreciate that FGFR receptors, mutants thereof, and fusion proteins thereof have a cysteine residue in the binding domain. It is believed that proximity of a warhead to the cysteine of interest facilitates covalent modification of that cysteine by the warhead.

In some embodiments, the compounds described herein include one or more warheads that covalently modify (e.g., reversibly or irreversibly; e.g., irreversibly) one or more cysteine residues in a kinase insert domain in a FGFR protein (e.g., an FGFR3 protein). In certain embodiments, the compounds described herein include one or more warheads that covalently modify Cys582 in SEQ ID NO: 5.

In some embodiments, the compounds described herein include one or more warheads that covalently modify (e.g., reversibly or irreversibly; e.g., irreversibly) one or more cysteine residues in a c-terminal tail of a FGFR protein (e.g., an FGFR2 protein). In certain embodiments, the compounds described herein include one or more warheads that covalently modify Cys808 in SEQ ID NO: 3.

Non-limiting examples of warheads include:
1) α,β unsaturated systems (e.g., $L^{W1}$-EWG, wherein $L^{W1}$ is alkenyl or alkynyl; and EWG is an electron withdrawing group; e.g., Michael acceptors, e.g., acrylamides, acrylates, vinylsulfones, α,β-unsaturated ketones)
2) Strained non-aromatic heterocycles (e.g., heterocycles having from 3-4 ring atoms wherein 1 ring atom is a heteroatom selected from oxygen, nitrogen, and sulfur; e.g., epoxide, aziridine, beta-lactam, and other strained systems);
3) Strained carbocyclic systems (e.g., cyclopropyl substituted with one or more electron-withdrawing groups);
4) Activated ketone (e.g., halomethylketone);
5) Acylating agents (e.g., carbamates, aza-peptides, acyl hydroxamates), phosphonylating agents (e.g., phosphonyl fluorides), or sulfonylation agents (e.g., sulfonyl fluoride);
6) Boronic acids or boronic esters; and 7) Aliphatic organonitrile compounds (e.g., alkyl nitrile, cyanamide, or acyl cyanamide).

Non-limiting examples of "warhead" include W which is a moiety of Formula $A^W$-W', wherein W' is selected from the group consisting of:

a) $L^{W1}$-EWG, wherein $L^{W1}$ is $C_{2-8}$ alkenyl, $C_{4-10}$ cycloalkenyl, 5-10 membered heterocycloalkenyl, or $C_{2-8}$ alkynyl, wherein –EWG is attached to a $sp^2$ or sp hybridized carbon of $L^{W1}$, thereby providing an α,β-unsaturated system;

$L^{W1}$ is optionally substituted with one halo (e.g., F) at the carbon atom attached to –EWG;

the $sp^2$ or sp hybridized carbons of $L^{W1}$ which are not attached to EWG are optionally substituted with 1 $R^{L1}$; and each spa hybridized carbon of $L^{W1}$ is optionally substituted with from 1-3 substituents each independently selected from halo, OH, $C_{1-6}$ alkoxy, $C_{1-6}$ haloalkoxy, $NH_2$, $NH(R^N)$, $N(R^N)_2$, and $R^{L1}$; and EWG is a divalent group selected from: —C(O)—, —S(O)$_2$—, —C(O)O—, —C(O)NH—, —C(O)NR$^N$—, —S(O)$_2$NH—, and —S(O)$_2$NR$^N$—;

b) $C_{4-10}$cycloalkenyl substituted with from 1-4 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, provided that the cycloalkenyl comprises from 1-4 $R^e$;

c) heterocycloalkenyl having from 5-10 ring atoms including from 2-7 ring carbon atoms each optionally substituted with 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, $N(R^N)$, $N(R^e)$, O, and $S(O)_{0-2}$, provided that the heterocycloalkenyl comprises one or more $R^e$;

d) heterocyclyl having from 3-4 ring atoms wherein one ring atom is a heteroatom selected from N, NH, $N(R^N)$, $NC(O)R^N$, $NC(O)OR^N$, $NS(O)_2R^N$, O, and S; and 2-3 ring atoms are ring carbon atoms each optionally substituted with from 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, wherein the heterocyclyl is optionally fused to a ring having from 3-8 ring atoms, including from 1-8 ring carbon atoms each of which optionally substituted 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, and from 0-2 heteroatoms each independently selected from N, NH, $N(R^N)$, O, and $S(O)_{0-2}$;

e) $C_{3-4}$ (e.g., $C_3$) cycloalkyl substituted with from 1-4 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, provided that the cycloalkyl comprises one or more $R^e$;

f) —C(=O)(CH$_2$)$_{n1}$X$^{w1}$ wherein X$^{w1}$ is selected from —C(O)R$^c$, —S(O)$_2$R$^c$, —C(O)OR$^c$, —C(O)NHR$^c$, —C(O)NR$^N$R$^c$, —S(O)$_2$NHR$^c$, and —S(O)$_2$NR$^N$R$^c$; and n1 is 0, or 1;

g) —C(=O)(CH$_2$)$_{n2}$X$^{w2}$ or —C(=O)CH(X$^{w2}$)—R$^c$, wherein X$^{w2}$ is selected from OR$^c$, SR$^c$, S(R$^c$)$_2$, —OP(O)(R$^c$)$_2$, OC(O)R$^c$, OC(O)OR$^c$, O—NHC(O)R$^c$, —OS(O)$_2$R$^c$, —N$_2$, halo (e.g., F), —CN, and —NO$_2$; and n2 is 1 or 2;

h) —C(O)NH—N(R$^N$)C(O)OR$^c$, —C(O)NH—NHC(O)OR$^c$, —C(O)NH—N(R$^N$)C(O)SR$^c$, —C(O)NH—NHC(O)SR$^c$, —NHC(O)OR$^c$, —N(R$^N$)C(O)OR$^c$, —NHC(O)SR$^c$, —N(R$^N$)C(O)SR$^c$, —C(O)NH—OC(O)OR$^c$, —C(O)N(R$^N$)—OC(O)OR$^c$, —C(O)NH—OC(O)SR$^c$, and —C(O)N(R$^N$)—OC(O)SR$^c$;

i) —P(O)(OR$^c$(OR$^c$), —P(O)(NH$_2$)(OR$^c$), —P(O)(NHR$^N$)(OR$^c$), —P(O)(NR$^N$R$^N$)(OR$^c$), —P(O)(OR$^c$)F, —S(O)$_2$OR$^c$ and —S(O)$_2$F;

j) $C_{2-4}$ alkenyl or $C_{2-4}$ alkynyl optionally substituted with from 1-2 substituents selected from nitro and —CN;

k) —B(OR$^c$)$_2$;

l) $L^{w2}$–EWG, wherein $L^{w2}$ is $C_{2-6}$ alkenyl, wherein

–EWG is attached to a $sp^2$ hybridized carbon of $L^{w2}$, thereby providing an α,β-unsaturated system;

$L^{w2}$ is substituted with one $R^R$ at the carbon atom attached to –EWG; and $L^{w2}$ is further optionally substituted with from 1-3 substituents each independently selected from halo, OH, $C_{1-6}$ alkoxy, $C_{1-6}$ haloalkoxy, $NH_2$, $NH(R^N)$, $N(R^N)_2$, and $R^{L2}$; and EWG is a divalent group selected from: —C(O)—, —S(O)$_2$—, —C(O)O—, —C(O)NH—, —C(O)NR$^N$—, —S(O)$_2$NH—, and —S(O)$_2$NR$^N$—;

m) $C_{1-6}$ alkyl substituted with one or more CN or —(H)N—CN; and n) heterocyclyl having from 5-10 ring atoms including from 2-7 ring carbon atoms, and from 1-3 heteroatoms each independently selected from N, NH, $N(R^N)$, $N(R^e)$, O, and $S(O)_{0-2}$, wherein the heterocyclyl is substituted with one or more CN or —(H)N—CN; and the heterocyclyl is further optionally substituted with from 1-2 independently selected $R^e$;

$A^W$ is a bond or $C_{1-8}$ alkylene optionally substituted with from 1-2 substituents independently selected from OH, $C_{1-4}$ haloalkyl, $C_{1-4}$ alkoxy, and $C_{1-4}$ haloalkyl, wherein from 1-4 CH$_2$ units of the $C_{1-8}$ alkylene are optionally replaced by a group independently selected from:

1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, $N(R^N)$, O, and $S(O)_{0-2}$; and
6) $C_{3-8}$ cycloalkylene optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy;

wherein:

each occurrence of $R^{L1}$ and $R^{L2}$ is independently selected from:

$C_{3-8}$ cycloalkyl, wherein the $C_{3-8}$ cycloalkyl is optionally substituted with from 1-4 substituents independently selected from the group consisting of halo, $C_{1-4}$ alkyl, $C_{1-4}$ haloalkyl, $C_{1-4}$ alkoxy, $C_{1-4}$ haloalkoxy, $C_{1-4}$ thioalkoxy, $NO_2$, $C(O)OH$, $C(O)OC_{1-4}$ alkyl, $C(O)NH_2$, $C(O)NHR^N$, $C(O)NR^N_2$, and CN; and heterocyclyl, wherein the heterocyclyl includes from 3-16 ring atoms, wherein from 1-3 ring atoms are heteroatoms, each independently selected from the group consisting of N, NH, $N(R^N)$, $NC(O)R^N$, $NC(O)OR^N$, $NS(O)_2R^N$, O, and $S(O)_{0-2}$ wherein the heterocyclyl is optionally substituted with from 1-4 substituents independently selected from the group consisting of halo, $C_{1-4}$ alkyl, $C_{1-4}$ haloalkyl, $C_{1-4}$ alkoxy, $C_{1-4}$ haloalkoxy, $C_{1-4}$ thioalkoxy, $NO_2$, $C(O)OH$, $C(O)OC_{1-4}$ alkyl, $C(O)NH_2$, $C(O)NHR^N$, $C(O)NR^N_2$, and CN, provided that the heterocyclyl is attached to $L^{W1}$ or $L^{W2}$ via a carbon atom;

each occurrence of $R^c$ is independently selected from:
- $C_{1-6}$ alkyl optionally substituted with from 1-4 substituents independently selected from halo and $C_{1-4}$ alkoxy;
- $(C_{0-3}$ alkylene)-$C_{3-8}$ cycloalkyl, wherein the $C_{3-8}$ cycloalkyl is optionally substituted with from 1-4 substituents independently selected from the group consisting of halo, $C_{1-4}$ alkyl, $C_{1-4}$ haloalkyl, $C_{1-4}$ alkoxy, $C_{1-4}$ haloalkoxy, $C_{1-4}$ thioalkoxy, $NO_2$, $C(O)OH$, $C(O)OC_{1-4}$ alkyl, $C(O)NH_2$, $C(O)NHR^N$, $C(O)NR^N_2$, and CN; and
- $(C_{0-3}$ alkylene)-heterocyclyl, wherein the heterocyclyl includes from 3-16 ring atoms, wherein from 1-3 ring atoms are heteroatoms, each independently selected from the group consisting of N, NH, $N(R^N)$, $NC(O)R^N$, $NC(O)OR^N$, $NS(O)_2R^N$, O, and $S(O)_{0-2}$ wherein the heterocyclyl is optionally substituted with from 1-4 substituents independently selected from the group consisting of halo, $C_{1-4}$ alkyl, $C_{1-4}$ haloalkyl, $C_{1-4}$ alkoxy, $C_{1-4}$ haloalkoxy, $C_{1-4}$ thioalkoxy, $NO_2$, $C(O)OH$, $C(O)OC_{1-4}$ alkyl, $C(O)NH_2$, $C(O)NHR^N$, $C(O)NR^N_2$, and CN;

each occurrence of $R^{c'}$ is an independently selected $R^c$ or H;

each occurrence of $R^e$ is independently selected from oxo, $NO_2$, halo, CN, a suitable leaving group, and $-Q^1-Q^2$, wherein $-Q^1$ is a bond or a group selected from:
- $C_{1-6}$ alkylene, $C_{2-6}$ alkenylene, $C_{2-6}$ alkynylene wherein from one to two $CH_2$ units are optionally replaced by a group independently selected from:
—$N(R^N)$—, —$S(O)_{0-2}$—, —O—, —$C(O)$—, —$C(O)O$—, —$C(O)N(R^N)$—, —$C(O)NH$—, —$S(O)_2N(R^N)$—, and —$S(O)_2N(H)$—;

$Q^2$ is hydrogen or $C_{1-6}$ alkyl optionally substituted with from 1-2 independently selected oxo, halo, $NO_2$, CN, or a suitable leaving group, provided that when $Q^1$ is a bond, $Q^2$ is not hydrogen or unsubstituted $C_{1-6}$ alkyl;

$R^R$ is independently selected from the group consisting of: CN, $NO_2$, —$C(O)R^c$, —$S(O)_2R^c$, —$C(O)OR^c$, —$C(O)NHR^c$, —$C(O)NR^NR^c$, —$S(O)_2NHR^c$, and —$S(O)_2NR^NR^c$;

each $R^N$ is independently selected from the group consisting of: $C_{1-4}$ alkyl, $C_{3-10}$ cycloalkyl, and 4-8 membered heterocyclyl, each of which is optionally substituted with from 1-2 substituents selected from halo, $C_{1-4}$ alkyl, and $C_{1-4}$ haloalkyl; or a pair of $R^N$ together with the nitrogen atom to which each is attached forms a ring having from 3-8 ring atoms, wherein the ring includes: (a) from 1-7 ring carbon atoms, each of which is substituted with from 1-2 substituents independently selected from the group consisting of halo and $C_{1-3}$ alkyl; and (b) from 0-3 ring heteroatoms (in addition to the nitrogen atom attached to $R^N$), which are each independently selected from the group consisting of N, N(H), O, and $S(O)_{0-2}$.

In certain embodiments, $R^e$ comprises a suitable leaving group (i.e., a group that is capable of undergoing nucleophilic displacement). A "suitable leaving group" is a chemical moiety that is readily displaced by an incoming nucleophilic moiety such as the —SH moiety of a cysteine. Suitable leaving groups are well-known in the art (e.g., see, "Advanced Organic Chemistry," Jerry March, 5$^{th}$ Ed., pp. 351-357, John Wiley and Sons, N.Y.). Non-limiting examples of such groups include: halo, alkoxy (e.g., $OR^c$), thioalkoxy (e.g., $SR^c$), sulfonyloxy (e.g., $OS(O)_2R^c$, acyloxy (e.g., $OC(O)R^c$), and diazonium moieties. Examples of suitable leaving groups include, but are not limited to: —Cl, —Br, —I, —$OR^c$, —$SR^c$, —$S(R^c)_2$, $OC(O)R^c$, $OC(O)OR^c$, $OS(O)_2R^c$, and $OP(O)(OR^c)_2$.

Exemplary Embodiments of Warhead "W"

[1]

In some embodiments of W, W' is:
$L^{W1}$-EWG, wherein
$L^{W1}$ is $C_{2-8}$ alkenyl, $C_{4-10}$ cycloalkenyl, 5-10 membered heterocycloalkenyl, or $C_{2-8}$ alkynyl, wherein
-EWG is attached to a sp$^2$ or sp hybridized carbon of $L^{W1}$, thereby providing an α,β-unsaturated system;
$L^{W1}$ is optionally substituted with one halo (e.g., F) at the carbon atom attached to -EWG;
the sp$^2$ or sp hybridized carbons of $L^{W1}$ which are not attached to EWG are optionally substituted with 1 $R^{L1}$; and
each sp$^3$ hybridized carbon of $L^{W1}$ is optionally substituted with from 1-3 substituents each independently selected from halo, OH, $C_{1-6}$ alkoxy, $C_{1-6}$ haloalkoxy, $NH_2$, $NH(R^N)$, $N(R^N)_2$, and $R^{L1}$; and
EWG is a divalent group selected from: —$C(O)$—, —$S(O)_2$—, —$C(O)O$—, —$C(O)NH$—, —$C(O)NR^N$—, —$S(O)_2NH$—, and —$S(O)_2NR^N$—.

In some embodiments of [1], EWG is a divalent group selected from: —$C(O)$—, —$S(O)_2$—, $C(O)O$—, —$C(O)NH$—, and —$S(O)_2NH$—. As non-limiting examples of the foregoing, EWG can be —$C(O)$— or —$S(O)_2$.

In some embodiments of [1], $L^{W1}$ is $C_{2-3}$ alkenyl (e.g., $C_2$ alkenyl) optionally substituted with one halo.

In certain embodiments, $L^{W1}$ is $C_{2-3}$ alkenyl (e.g., $C_2$ alkenyl). As a non-limiting example, $L^{W1}$ can be

In certain embodiments, $L^{W1}$ is $C_{2-3}$ alkenyl (e.g., $C_2$ alkenyl) substituted with one halo at the carbon atom attached to -EWG. As a non-limiting example, $L^{W1}$ can be

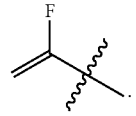 [SMILES: *C(=C)F]

In some embodiments of [1], $L^{W1}$ is $C_{3-8}$ alkenyl (e.g., C3 alkenyl) optionally substituted with from 1-3 halo, OH, $C_{1-6}$ alkoxy, $C_{1-6}$ haloalkoxy, or $N(R^N)_2$ at the sp$^3$ hybridized carbons.

In certain embodiments of [1], $L^{W1}$ is $C_{3-8}$ alkenyl (e.g., C3 alkenyl) optionally substituted with from 1-3 halo at a sp$^3$ hybridized carbon.

In some embodiments of [1], $L^{W1}$ is $C_{3-8}$ alkenyl (e.g., C3 alkenyl) optionally substituted with one OH, $C_{1-6}$ alkoxy, or $C_{1-6}$ haloalkoxy at a sp$^3$ hybridized carbon.

In some embodiments of [1], $L^{W1}$ is $C_{3-8}$ alkenyl (e.g., C3 alkenyl) substituted with one OH, $C_{1-6}$ alkoxy, or $C_{1-6}$ haloalkoxy at a sp$^3$ hybridized carbon.

In some embodiments of [1], $L^{W1}$ is $C_{3-8}$ alkenyl (e.g., $C_3$ alkenyl) optionally substituted with from one $N(R^N)_2$ at a sp$^3$ hybridized carbon.

In some embodiments of [1], $L^{W1}$ is $C_{3-8}$ alkenyl (e.g., C3 alkenyl) substituted with from one $N(R^N)_2$ at a $sp^3$ hybridized carbon.

In some embodiments of [1], $L^{W1}$ is $C_{3-8}$ alkenyl (e.g., $C_3$ alkenyl) optionally substituted with 1 $R^{L1}$ at a $sp^2$ hybridized carbon that is not attached to EWG.

In some embodiments of [1], $L^{W1}$ is $C_{4-10}$ (e.g., $C_{4-6}$, e.g., $C_4$) cycloalkenyl. As a non-limiting example, $L^{W1}$ can be

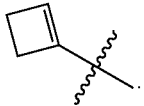 [SMILES: *C1=CCC1]

In some embodiments of [1], $L^{W1}$ is $C_{2-8}$ alkynyl (e.g., $C_{3-8}$) optionally substituted with from 1-3 halo, OH, $C_{1-6}$ alkoxy, $C_{1-6}$ haloalkoxy, OH, or $N(R^N)_2$ at the spa carbons.

In some embodiments of [1], $A^W$ is a bond.

In some embodiments of [1], $A^W$ is $C_{1-8}$ alkylene optionally substituted with from 1-2 substituents independently selected from OH, $C_{1-4}$ haloalkyl, $C_{1-4}$ alkoxy, and $C_{1-4}$ haloalkyl, wherein from 1-4 $CH_2$ units of the $C_{1-8}$ alkylene are optionally replaced by a group independently selected from:

2) $-S(O)_{0-2}$;
3) $-NH-$, $-NR^N-$;
4) $-O-$;
5) heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, $N(R^N)$, O, and $S(O)_{0-2}$; and
6) $C_{3-8}$ cycloalkylene optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy.

[1-1]

In some embodiments of [1], $A^W$ is a bond (i.e., W is W').

In some embodiments of [1-1], W or W' is $R^3R^4C=CR^5C(=O)-$, $R^6R^7NCH_2CH=CHC(=O)-$, $H_2C=CHSO_2-$ or $R^8C\equiv CC(=O)-$; wherein:

$R^3$ is hydrogen;

$R^4$ is hydrogen, $CF_3$ or Z(C1-C6 alkyl)- wherein Z is H, F, Cl, Br, HO—, C1-C6 alkoxy, or fluoroC1-C6 alkoxy, and $R^5$ is hydrogen, C1-C3 alkyl, fluoroC1-C3 alkyl or halogen, or $R^4$ and $R^5$ together with the carbon atoms to which they are attached form a 4-8-membered carbocyclic ring;

each of $R^6$ and $R^7$ is independently C1-C6 alkyl, or $R^6$ and $R^7$ together with the nitrogen atom to which they are attached form a 5-6 membered heterocyclic ring optionally having an additional ring heteroatom which is O, wherein said ring is optionally substituted with halogen;

$R^8$ is hydrogen, C1-C3 alkyl, HO—C1-C3 alkyl or R'R"NCH$_2$—; and

R' and R" are each independently hydrogen or C1-C6 alkyl.

In some embodiments of [1-1], W or W' is $R^3R^4C=CR^5C(=O)-$.

In certain embodiments, $R^3$ is hydrogen.
In certain embodiments, $R^4$ is hydrogen.
In certain embodiments, $R^4$ is $CF_3$.
In certain embodiments, $R^4$ is $ZCH_2-$, wherein Z is F, Cl, Br, HO— or $CH_3O-$.
In certain embodiments, $R^5$ is H.
In certain embodiments, $R^5$ is F.
In certain embodiments, $R^4$ and $R^5$ together with the carbon atoms to which they are attached form a 4-membered carbocyclic ring.

As non-limiting examples to any of the foregoing embodiments (when W is $R^3R^4C=CR^5C(=O)-$), W or W' can be:

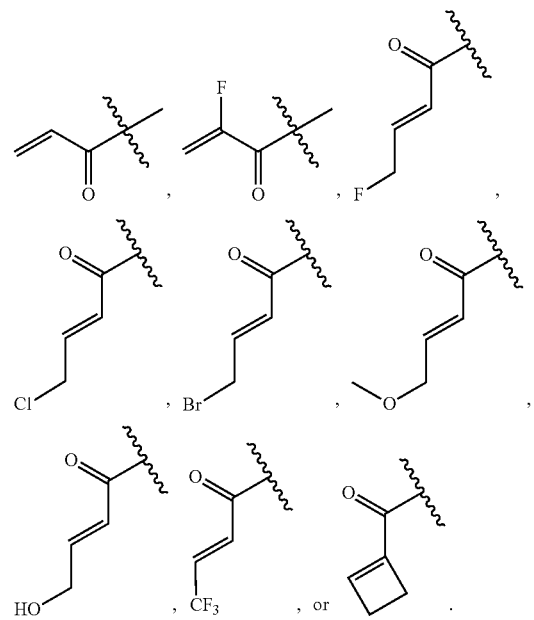

In some embodiments of [1-1], W or W' is $R^6R^7NCH_2CH=CHC(=O)-$.

In certain embodiments, each of $R^6$ and $R^7$ is independently selected C1-C6 alkyl.

In certain embodiments, each of $R^6$ and $R^7$ is independently selected C1-C3 alkyl.

In certain embodiments, $R^6$ and $R^7$ are both methyl.

In certain embodiments, $R^6$ and $R^7$ together with the nitrogen atom to which they are attached form a 5-6 membered heterocyclic ring optionally having an additional ring heteroatom which is O, wherein said ring is optionally substituted with halogen.

In certain embodiments, $R^6$ and $R^7$ together with the nitrogen atom to which they are attached form a 5-6 membered heterocyclic ring selected from the group consisting of piperidine, morpholine, and pyrrolidine, wherein said ring is optionally substituted with halogen.

As non-limiting examples to any of the foregoing embodiments (when W is $R^6R^7NH_2CH=CHC(=O)-$), W or W' can be:

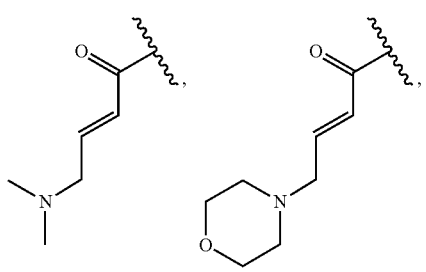

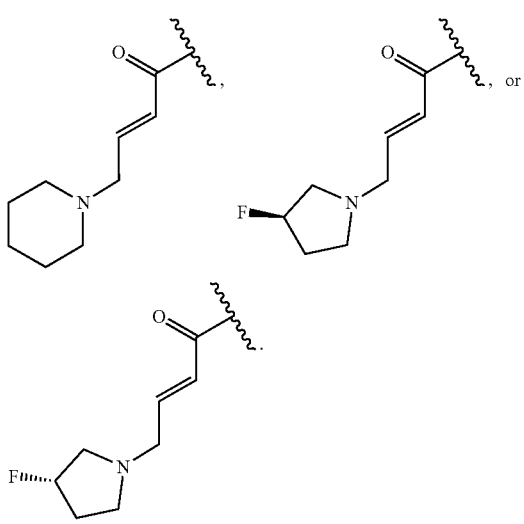

In some embodiments of [1-1], W or W' is $R^8C\equiv CC(=O)-$.

In certain embodiments, $R^8$ is hydrogen or methyl.
In certain embodiments, $R^8$ is $HOCH_2-$.
In certain embodiments, $R^8$ is $R'R''NCH_2-$.

As non-limiting examples to any of the foregoing embodiments (when W is $R^8C\equiv CC(=O)-$), W or W' can be:

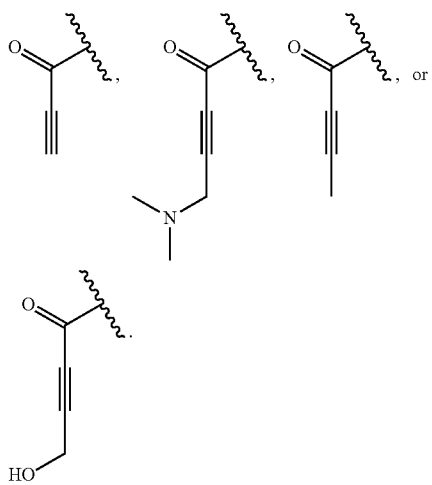

In some embodiments of [1-1], W or W' is $H_2C=CHSO_2-$.

Non-limiting examples of W when W is defined according to [1-1] include:

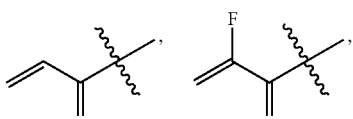

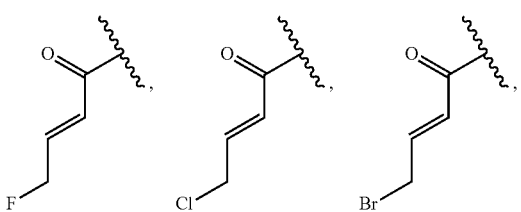

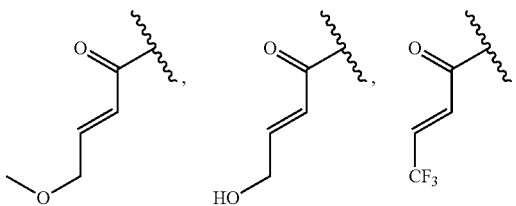

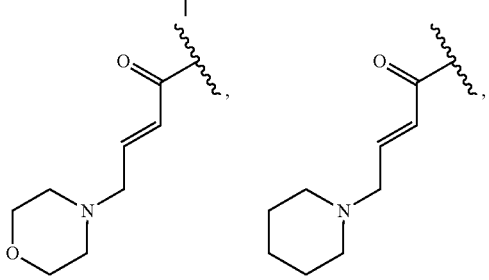

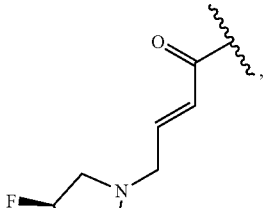

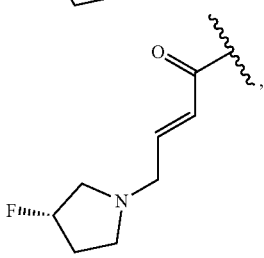

-continued

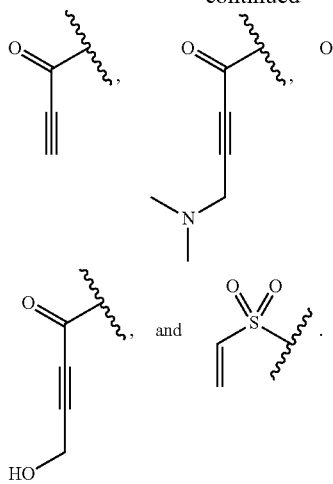

[1-2]

In some embodiments of [1], $A^W$ is $C_{1-8}$ alkylene optionally substituted with from 1-2 substituents independently selected from OH, $C_{1-4}$ haloalkyl, $C_{1-4}$ alkoxy, and $C_{1-4}$ haloalkyl, wherein from 1-4 $CH_2$ units of the $C_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, N(R$^N$), O, and S(O)$_{0-2}$; and
6) $C_{3-8}$ cycloalkylene optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy.

In some embodiments of [1-2], one $CH_2$ unit of $A^W$ is replaced by C(O).

In some embodiments of [1-2], one $CH_2$ unit of $A^W$ is replaced by —NH—.

In certain embodiments of the foregoing, one $CH_2$ unit of $A^W$ is replaced by C(O); and one $CH_2$ unit of $A^W$ is replaced by —NH—.

In some embodiments of [1-2], one $CH_2$ unit of $A^W$ is replaced by S(O)$_2$.

In some embodiments of [1-2], one $CH_2$ unit of $A^W$ is replaced by —NH—.

In certain embodiments of the foregoing, one $CH_2$ unit of $A^W$ is replaced by S(O)$_2$; and one $CH_2$ unit of $A^W$ is replaced by —NH—.

In some embodiments of [1-2], one $CH_2$ unit of $A^W$ is replaced by heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, N(R$^N$), O, and S(O)$_{0-2}$.

In some embodiments of [1-2], W is

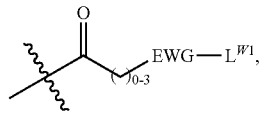

wherein EWG and $L^{W1}$ are as defined elsewhere herein.
Non-limiting examples of the foregoing include:

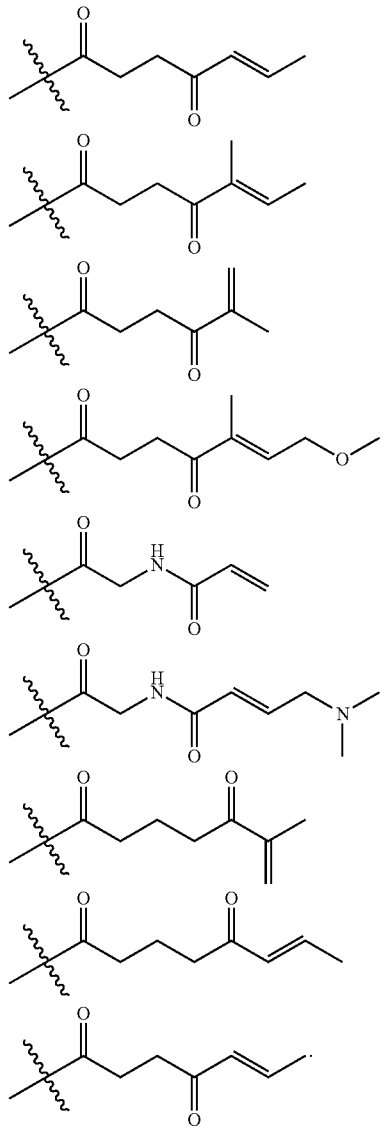

In some embodiments of [1-2], W is

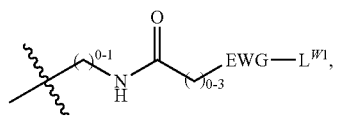

wherein EWG and $L^{W1}$ are as defined elsewhere herein.

Non-limiting examples of the foregoing include:

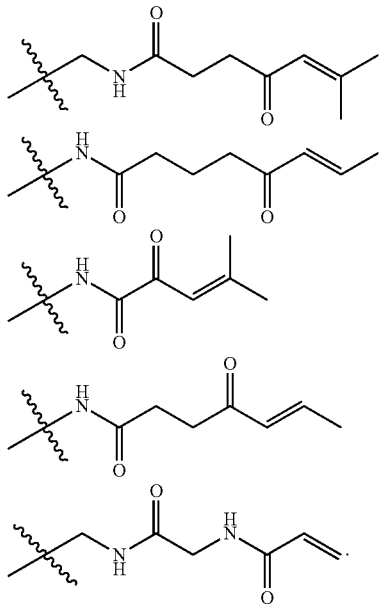

[2]
In some embodiments of W, W' is selected from the group consisting of:
- $C_{4-10}$ cycloalkenyl substituted with from 1-4 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, provided that the cycloalkenyl comprises one or more $R^e$; and
- heterocycloalkenyl having from 5-10 ring atoms including from 2-7 ring carbon atoms each optionally substituted with 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, $N(R^N)$, $N(R^e)$, O, and $S(O)_{0-2}$, provided that the heterocycloalkenyl comprises one or more $R^e$, and the heterocycloalkenyl ring does not include an N—S bond.

In some embodiments of W, W' is selected from:
- $C_{4-10}$ cycloalkenyl (e.g., $C_{4-6}$) substituted with from 1-4 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, provided that the cycloalkenyl comprises one or more $R^e$.

In certain embodiments of the foregoing, one or more $R^e$ is oxo.

Non-limiting examples of the foregoing include:

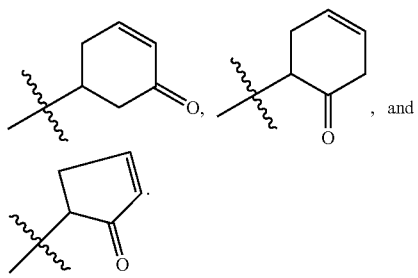

In some embodiments of W, W' is selected from:
- heterocycloalkenyl having from 5-10 ring atoms including from 2-7 ring carbon atoms each optionally substituted with 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, $N(R^N)$, $N(R^e)$, O, and $S(O)_{0-2}$, provided that the heterocycloalkenyl comprises one or more $R^e$, and the heterocycloalkenyl ring does not include an N—S bond.

In certain embodiments of the foregoing, one or more $R^e$ is oxo, wherein one or more oxo is conjugated to a C=C double bond.

Non-limiting examples of the foregoing include:

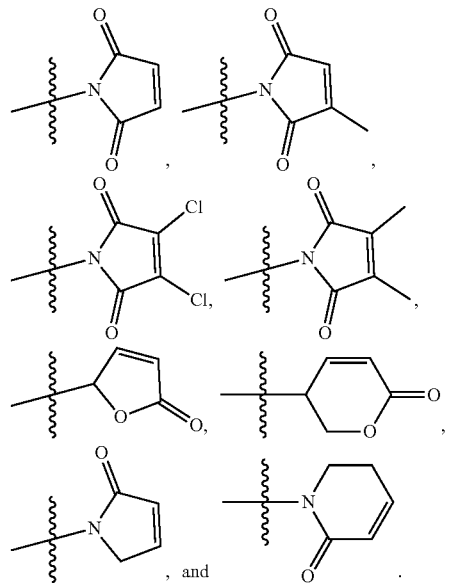

In some embodiments of [2], $A^W$ is a bond.
In some embodiments of [2], $A^W$ is $C_{1-8}$ alkylene optionally substituted with from 1-2 substituents independently selected from OH, $C_{1-4}$ haloalkyl, $C_{1-4}$ alkoxy, and $C_{1-4}$ haloalkyl, wherein from 1-4 $CH_2$ units of the $C_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, $N(R^N)$, O, and $S(O)_{0-2}$; and
6) $C_{3-8}$ cycloalkylene optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy.

In certain embodiments of the foregoing, $A^W$ is $C_{1-6}$ alkylene wherein from 1-2 $CH_2$ are optionally replaced by a group independently selected from:
3) —NH—, —NR$^N$—; and
4) —O—.

In certain embodiments, $A^W$ is a $C_{1-6}$ alkylene.

Non-limiting examples of W when W is as defined for [2] include:

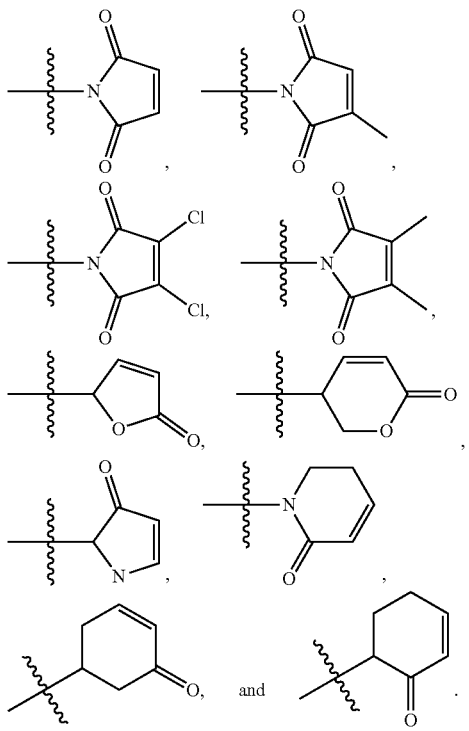

[3]

In some embodiments of W, W' is selected from:
heterocyclyl having from 3-4 ring atoms wherein one ring atom is a heteroatom selected from N, NH, N($R^N$), NC(O)$R^N$, NC(O)O$R^N$, NS(O)$_2R^N$, O, and S; and 2-3 ring atoms are ring carbon atoms each optionally substituted with from 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, wherein the heterocyclyl is optionally fused to a ring having from 3-8 ring atoms including from 1-8 ring carbon atoms each of which optionally substituted 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, and from 0-2 heteroatoms each independently selected from N, NH, N($R^N$), O, and S(O)$_{0-2}$.

In some embodiments of W, W' is selected from:
heterocyclyl having from 3-4 ring atoms wherein one ring atom is a heteroatom selected from N, NH, N($R^N$), NC(O)$R^N$, NC(O)O$R^N$, NS(O)$_2R^N$, O, and S; and 2-3 ring atoms are ring carbon atoms each optionally substituted with from 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy.

In some embodiments of W, W' is selected from:
heterocyclyl having from 3-4 ring atoms wherein one ring atom is a heteroatom selected from N, NH, N($R^N$), NC(O)$R^N$, NC(O)O$R^N$, and O (e.g., O); and 2-3 ring atoms are ring carbon atoms each optionally substituted with from 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy.

In some embodiments of W, W' is selected from:
heterocyclyl having from 3 ring atoms wherein one ring atom is a heteroatom selected O; and 2 ring atoms are ring carbon atoms each optionally substituted with from 1-2 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy.

Non-limiting examples of the foregoing include:

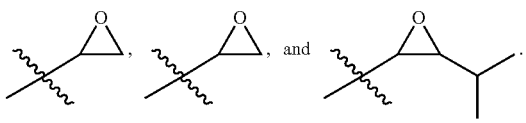

In some embodiments of [3], $A^W$ is a bond.

In some embodiments of [3], $A^W$ is $C_{1-8}$ alkylene optionally substituted with from 1-2 substituents independently selected from OH, $C_{1-4}$ haloalkyl, $C_{1-4}$ alkoxy, and $C_{1-4}$ haloalkyl, wherein from 1-4 CH$_2$ units of the $C_{1-8}$ alkylene are optionally replaced by a group independently selected from:
1) —C(O)—;
2) —S(O)$_{0-2}$;
3) —NH—, —N$R^N$—;
4) —O—;
5) heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, N($R^N$), O, and S(O)$_{0-2}$; and
6) $C_{3-8}$ cycloalkylene optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy.

In certain embodiments of the foregoing, $A^W$ is $C_{1-6}$ alkylene wherein from 1-2 CH$_2$ are optionally replaced by a group independently selected from:
1) —C(O)—;
2) —S(O)$_{0-2}$;
3) —NH—, —N$R^N$—; and
4) —O—.

In certain embodiments of the foregoing, $A^W$ is $C_{1-6}$ alkylene wherein from 1-2 CH$_2$ are optionally replaced by a group independently selected from:
3) —NH—, —N$R^N$—; and
4) —O—.

In certain embodiments, $A^W$ is a $C_{1-6}$ alkylene.

Non-limiting examples of W when W is defined according to [3] include:

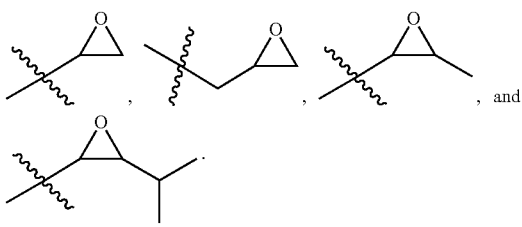

[4]

In some embodiments of W, W' is selected from:

$C_{3-4}$ (e.g., $C_3$) cycloalkyl substituted with from 1-4 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, provided that the cycloalkyl comprises one or more $R^e$.

In certain embodiments of the foregoing, W' is selected from:

cyclopropyl substituted with from 1-4 substituents independently selected from $R^e$, $C_{1-4}$ alkyl, $C_{1-4}$ haloalkyl, $C_{1-4}$ alkoxy, $C_{1-4}$ haloalkoxy, and $C_{1-4}$ thioalkoxy, provided that the cyclopropyl comprises one or more $R^e$.

In certain embodiments of the foregoing, one $R^e$ is —CN.

In certain embodiments, one $R^e$ is -$Q^1$-$Q^2$, wherein $Q^1$ is $C_{1-3}$ alkylene wherein one $CH_2$ unit is replaced by C(O), C(O)NH, or C(O)O.

Non-limiting examples of the foregoing include:

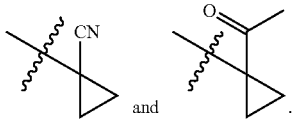

In some embodiments of [4], $A^W$ is a bond.

In some embodiments of [4], $A^W$ is $C_{1-8}$ alkylene optionally substituted with from 1-2 substituents independently selected from OH, $C_{1-4}$ haloalkyl, $C_{1-4}$ alkoxy, and $C_{1-4}$ haloalkyl, wherein from 1-4 $CH_2$ units of the $C_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, N(R$^N$), O, and S(O)$_{0-2}$; and
6) $C_{3-8}$ cycloalkylene optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy.

In certain embodiments of the foregoing, $A^W$ is $C_{1-6}$ alkylene wherein from 1-2 $CH_2$ are optionally replaced by a group independently selected from:
1) —C(O)—;
2) —S(O)$_{0-2}$;
3) —NH—, —NR$^N$—; and
4) —O—.

In certain embodiments, $A^W$ is a $C_{1-6}$ alkylene.

Non-limiting examples of W when W is as defined according to [4] include:

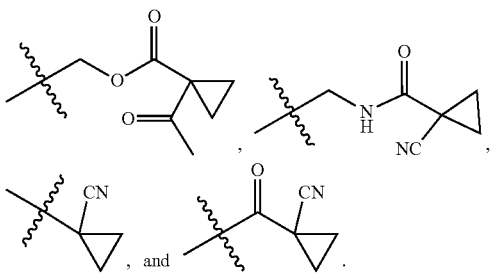

[5]

In some embodiments of W, W' is selected from:

—C(=O)(CH$_2$)$_{n1}$X$^{w1}$ wherein X$^{w1}$ is selected from —C(O)R$^c$, —S(O)$_2$R$^c$, —C(O)OR$^c$, —C(O)NHR$^c$, —C(O)NR$^N$R$^c$, —S(O)$_2$NHR$^c$, and —S(O)$_2$NR$^N$R$^c$; and n1 is 0, or 1 (e.g., 0); and —C(=O)(CH$_2$)$_{n2}$X$^{w2}$ or —C(=O)CH(X$^{w2}$)—R$^c$, wherein X$^{w2}$ is selected from OR$^c$, SR$^c$, S(R$^c$)$_2$, —OP(O)(R$^c$)$_2$, OC(O)R$^c$, OC(O)OR$^c$, O—NHC(O)R$^c$, —OS(O)$_2$R$^c$, —N$_2$, halo (e.g., F), —CN, and —NO$_2$; and n2 is 1 or 2 (e.g., 1).

In some embodiments of [5], $A^W$ is a bond.

In some embodiments of [5], $A^W$ is $C_{1-8}$ alkylene optionally substituted with from 1-2 substituents independently selected from OH, $C_{1-4}$ haloalkyl, $C_{1-4}$ alkoxy, and $C_{1-4}$ haloalkyl, wherein from 1-4 $CH_2$ units of the $C_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy, and from 1-3 heteroatoms each independently selected from N, NH, N(R$^N$), O, and S(O)$_{0-2}$; and
6) $C_{3-8}$ cycloalkylene optionally substituted with from 1-2 substituents each independently selected from halo, $C_{1-4}$ alkyl, $C_{1-4}$ haloalkyl, $C_{1-4}$ alkoxy, $C_{1-4}$ haloalkoxy, and $C_{1-4}$ thioalkoxy.

In certain embodiments of the foregoing, $A^W$ is $C_{1-6}$ alkylene wherein from 1-2 $CH_2$ are optionally replaced by a group independently selected from:
1) —C(O)—;
2) —S(O)$_{0-2}$;
3) —NH—, —NR$^N$—; and
4) —O—.

In certain embodiments of the foregoing, $A^W$ is $C_{1-6}$ alkylene.

Non-limiting examples of W (when W is as defined according to [5]) include:

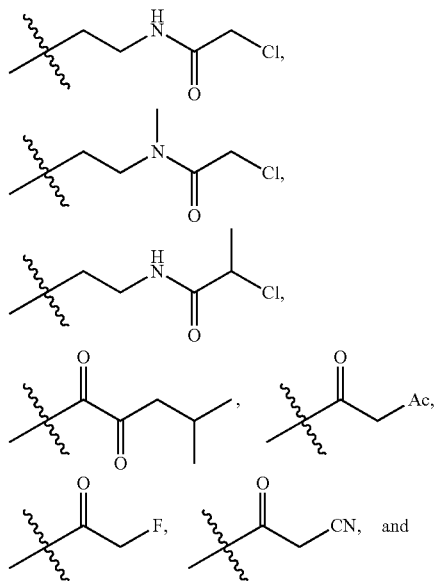

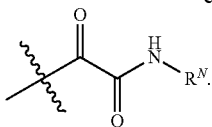

[6]

In some embodiments of W, W' is selected from:
—C(O)NH—N(R$^N$)C(O)OR$^c$, —C(O)NH—NHC(O)OR$^c$, —C(O)NH—N(R$^N$)C(O)SR$^c$, —C(O)NH—NHC(O)SR$^c$, —NHC(O)OR$^c$, —N(R$^N$)C(O)OR$^c$, —NHC(O)SR$^c$, —N(R$^N$)C(O)SR$^c$, —C(O)NH—OC(O)OR$^c$, —C(O)N(R$^N$)—OC(O)OR$^c$, —C(O)NH—OC(O)SR$^c$, and —C(O)N(R$^N$)—OC(O)SR$^c$; and
—P(O)(OR$^c$)(OR$^c$), —P(O)(NH$_2$)(OR$^c$), —P(O)(NHR$^N$)(OR$^c$), —P(O)(NR$^N$R$^N$)(OR$^c$), —P(O)(OR$^c$)F, —S(O)$_2$OR$^c$ and —S(O)$_2$F.

In some embodiments of [6], A$^W$ is a bond.

In some embodiments of [6], A$^W$ is C$_{1-8}$ alkylene optionally substituted with from 1-2 substituents independently selected from OH, C$_{1-4}$ haloalkyl, C$_{1-4}$ alkoxy, and C$_{1-4}$ haloalkyl, wherein from 1-4 CH$_2$ units of the C$_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy, and from 1-3 heteroatoms each independently selected from N, NH, N(R$^N$), O, and S(O)$_{0-2}$; and
6) C$_{3-8}$ cycloalkylene optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy.

In certain embodiments of the foregoing, A$^W$ is C$_{1-6}$ alkylene wherein from 1-2 CH$_2$ are optionally replaced by a group independently selected from:
1) —C(O)—;
2) —S(O)$_{0-2}$;
3) —NH—, —NR$^N$—; and
4) —O—.

In certain embodiments, A$^W$ is a C$_{1-6}$ alkylene (e.g., CH$_2$).

[7]

In some embodiments of W, W' is selected from:
C$_{2-4}$ alkenyl or C$_{2-4}$ alkynyl optionally substituted with from 1-2 substituents selected from nitro and —CN;

In certain embodiments of W, W' is selected from:
C$_2$ alkenyl and C$_2$ alkynyl.

In some embodiments of W, W' is selected from:
C$_2$ alkenyl substituted with from 1 substituent selected from nitro and —CN;

Non-limiting examples of the foregoing include:

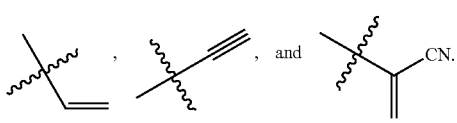

In some embodiments of [7], A$^W$ is a bond.

In some embodiments of [7], A$^W$ is C$_{1-8}$ alkylene optionally substituted with from 1-2 substituents independently selected from OH, C$_{1-4}$ haloalkyl, C$_{1-4}$ alkoxy, and C$_{1-4}$ haloalkyl, wherein from 1-4 CH$_2$ units of the C$_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy, and from 1-3 heteroatoms each independently selected from N, NH, N(R$^N$), O, and S(O)$_{0-2}$; and
6) C$_{3-8}$ cycloalkylene optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy;

In certain embodiments of the foregoing, A$^W$ is C$_{1-6}$ alkylene wherein from 1-2 CH$_2$ are optionally replaced by a group independently selected from:
1) —C(O)—;
2) —S(O)$_{0-2}$;
3) —NH—, —NR$^N$—; and
4) —O—.

In certain embodiments of the foregoing, A$^W$ is C$_{1-6}$ alkylene wherein from 1-2 CH$_2$ are optionally replaced by a group independently selected from:
3) —NH—, —NR$^N$—; and
4) —O—.

In certain embodiments, A$^W$ is a C$_{1-6}$ alkylene optionally substituted with one OH.

In certain embodiments, A$^W$ is a C$_{1-6}$ alkylene (e.g., CH$_2$).

Non-limiting examples of W when W is as defined for [7] include:

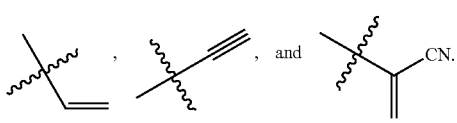

[8]

In some embodiments of W, W' is selected from:
—B(OH)$_2$.

Non-limiting examples of the foregoing include:
—B(OH)$_2$.

In some embodiments of [8], A$^W$ is a bond.

In some embodiments of [8], A$^W$ is alkylene optionally substituted with from 1-2 substituents independently selected from OH, C$_{1-4}$ haloalkyl, C$_{1-4}$ alkoxy, and C$_{1-4}$ haloalkyl, wherein from 1-4 CH$_2$ units of the C$_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy, and from 1-3 heteroatoms each independently selected from N, NH, N(R$^N$), O, and S(O)$_{0-2}$; and 6) C$_{3-8}$ cycloalkylene optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy.

In certain embodiments of the foregoing, A$^W$ is C$_{1-8}$ alkylene optionally substituted with from 1-2 substituents independently selected from OH, C$_{1-4}$ haloalkyl, C$_{1-4}$ alkoxy, and C$_{1-4}$ haloalkyl, wherein from 1-4 CH$_2$ units of the C$_{1-8}$ alkylene are optionally replaced by a group independently selected from:
1) —C(O)—;
2) —S(O)$_{0-2}$;
3) —NH—, —NR$^N$—; and
4) —O—.

In certain embodiments of the foregoing, A$^W$ is C$_{1-8}$ alkylene, wherein from 1-2 CH$_2$ units of the C$_{1-8}$ alkylene are optionally replaced by a group independently selected from:
1) C(=O)
3) —NH—, —NR$^N$—; and
4) —O—.

In certain embodiments, A$^W$ is a C$_{1-6}$ alkylene (e.g., CH$_2$).

Non-limiting examples of W when W is as defined for [8] include:

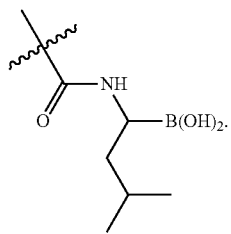 [SMILES: *C(=O)NC(CC(C)C)B(O)O]

[9]
In some embodiments of W, W' is selected from:
L$^{W2}$-EWG, wherein
L$^{W2}$ is Cm alkenyl, wherein
-EWG is attached to a sp$^2$ hybridized carbon of L$^{w2}$, thereby providing an α,β-unsaturated system;
L$^{W2}$ is substituted with one R$^R$ at the carbon atom attached -EWG; and
L$^{W2}$ is further optionally substituted with from 1-3 substituents each independently selected from halo, OH, C$_{1-6}$ alkoxy, C$_{1-6}$ haloalkoxy, NH$_2$, NH(R$^N$), N(R$^N$)$_2$, and R$^{L2}$; and
EWG is a divalent group selected from: —C(O)—, —S(O)$_2$—, —C(O)O—, —C(O)NH—, —C(O)NR$^N$—, —S(O)$_2$NH—, and —S(O)$_2$NR$^N$—.

In certain embodiments of the foregoing, L$^{W2}$ is C$_{2-3}$ alkenyl, wherein L$^{W2}$ is substituted with one R$^R$ at a carbon adjacent to EWG.

In certain embodiments of the foregoing, R$^R$ is independently selected from the group consisting of:
CN, NO$_2$, —C(O)R$^c$, —S(O)$_2$R$^c$, —C(O)OR$^c$, —C(O)NHR$^c$, —C(O)NR$^N$R$^c$, —S(O)$_2$NR$^N$R$^c$, and —S(O)$_2$NR$^N$R$^c$.

As a non-limiting example of the foregoing, R$^R$ can be —CN.

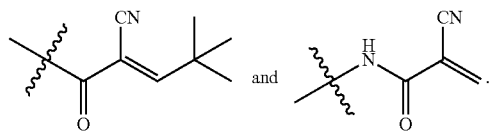

Non-limiting examples of the foregoing include:
In some embodiments of [9], A$^W$ is a bond.
In some embodiments of [9], A$^W$ is C$_{1-8}$ alkylene optionally substituted with from 1-2 substituents independently selected from OH, C$_{1-4}$ haloalkyl, C$_{1-4}$ alkoxy, and C$_{1-4}$ haloalkyl, wherein from 1-4 CH$_2$ units of the C$_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy, and from 1-3 heteroatoms each independently selected from N, NH, N(R$^N$), O, and S(O)$_{0-2}$; and
6) C$_{3-8}$ cycloalkylene optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy.

In certain embodiments of the foregoing, A$^W$ is C$_{1-6}$ alkylene wherein from 1-2 CH$_2$ are optionally replaced by a group independently selected from:
1) —C(O)—;
2) —S(O)$_{0-2}$;
3) —NH—, —NR$^N$—; and
4) —O—.

In certain embodiments of the foregoing, A$^W$ is C$_{1-6}$ alkylene wherein from 1-2 CH$_2$ are optionally replaced by a group independently selected from:
3) —NH—, —NR$^N$—; and
4) —O—.

In certain embodiments, A$^W$ is a C$_{1-6}$ alkylene (e.g., CH$_2$).

Non-limiting examples of W when W is as defined according to [9] include:

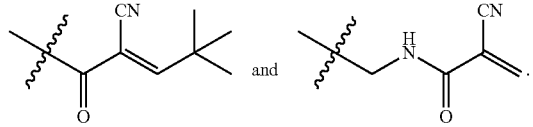

[10]
In some embodiments of W, W' is selected from:
C$_{1-6}$ alkyl substituted with one or more CN or —(H)N—CN; and
heterocyclyl having from 5-10 ring atoms including from 2-7 ring carbon atoms, and from 1-3 heteroatoms each independently selected from N, NH, N(R$^N$), N(R$^e$), O, and S(O)$_{0-2}$, wherein the heterocyclyl is substituted with one or more CN or —(H)N—CN; and the heterocyclyl is further optionally substituted with from 1-2 R$^e$.

In some embodiments of W, W' is selected from:
C$_{1-6}$ alkyl substituted with one CN or —(H)N—CN; and
heterocyclyl having from 5-10 ring atoms including from 2-7 ring carbon atoms, and from 1-3 heteroatoms each independently selected from N, NH, N(R$^N$), N(R$^e$), O, and S(O)$_{0-2}$, wherein the heterocyclyl is substituted with one CN or —(H)N—CN; and the heterocyclyl is further optionally substituted with from 1-2 R$^e$.

In some embodiments of [10], A$^W$ is a bond.

In some embodiments of [10], A$^W$ is C$_{1-8}$ alkylene optionally substituted with from 1-2 substituents independently selected from OH, C$_{1-4}$ haloalkyl, C$_{1-4}$ alkoxy, and C$_{1-4}$ haloalkyl, wherein from 1-4 CH$_2$ units of the C$_{1-8}$ alkylene are optionally replaced by a group independently selected from:
1) —C(O)—;
2) —S(O)$_{0-2}$;
3) —NH—, —NR$^N$—;
4) —O—;
5) heterocyclylene having from 5-10 ring atoms, including from 2-7 ring carbon atoms each optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy, and from 1-3 heteroatoms each independently selected from N, NH, N(R$^N$), O, and S(O)$_{0-2}$; and
6) C$_{3-8}$ cycloalkylene optionally substituted with from 1-2 substituents each independently selected from halo, C$_{1-4}$ alkyl, C$_{1-4}$ haloalkyl, C$_{1-4}$ alkoxy, C$_{1-4}$ haloalkoxy, and C$_{1-4}$ thioalkoxy.

In certain embodiments of the foregoing, A$^W$ is C$_{1-6}$ alkylene wherein from 1-2 CH$_2$ are optionally replaced by a group independently selected from:
1) —C(O)—;
2) —S(O)$_{0-2}$;
3) —NH—, —NR$^N$—; and
4) —O—.

In certain embodiments of [10], one CH$_2$ unit of A$^W$ is replaced by a C(O).

In certain embodiments of [10], one CH$_2$ unit of A$^W$ is replaced by —NH— or —NR$^N$.

In some embodiments of [10], A$^W$ is a C$_{1-6}$ alkylene (e.g., CH$_2$).

Non-limiting examples of W when W is as defined according to [10] include the following:

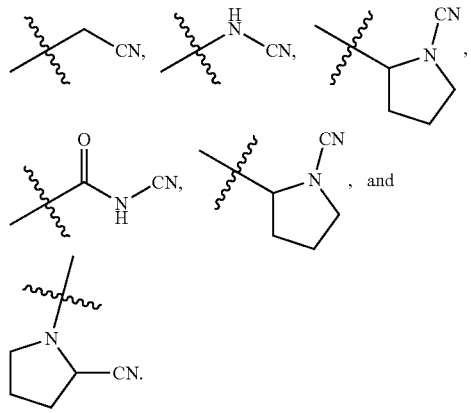

Further non-limiting examples of "warheads" include those described in U.S. Patent Application Publication No. 2011/0230476 and those described in *Chem. Rev.* 2002, 102, 4639, each of which is incorporated by reference herein in its entirety.

Other non-limiting examples of "warhead" include those described in *Curr. Opin. Chem. Biol.* 2016, 34, 110-116, which is incorporated by reference herein in its entirety.

For illustrative purposes, Schemes 1-9 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

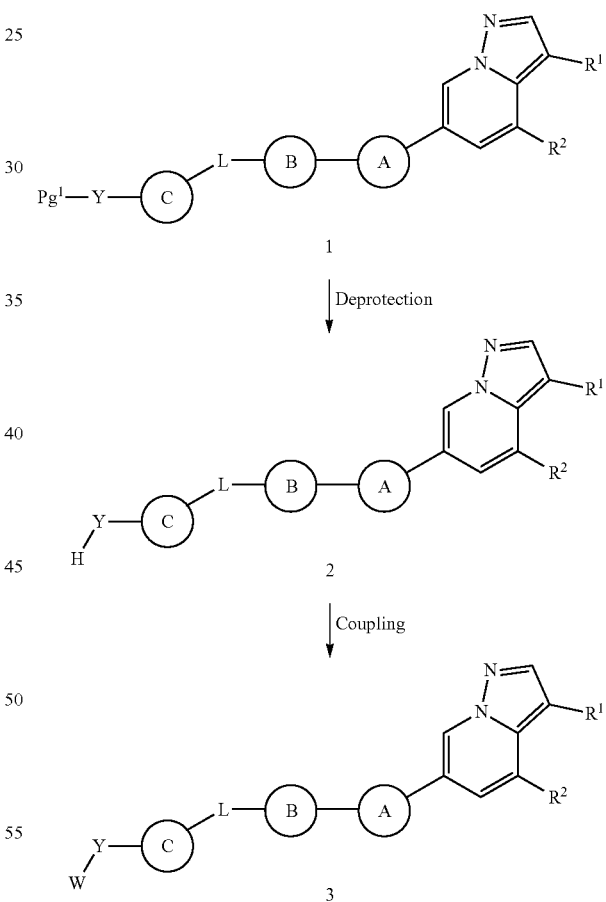

Scheme 1

Scheme 1 shows a general scheme for the synthesis of a compound of Formula I (shown as compound 3 in Scheme 1), wherein R$^1$, R$^2$, Ring A, Ring B, L, Ring C, Y, and W are as defined for Formula I. Compound 1, wherein R$^1$, R$^2$, Ring A, Ring B, L, Ring C, and Y are as defined for Formula I; and Pg$^1$ is an amino protecting group (e.g., Boc), can be subjected to deprotection conditions (e.g., acidic conditions such as trifluoroacetic acid) to afford compound 2 which can then be converted into compound 3, a compound of Formula I. Optionally, compound 1 can be subjected to additional functionalizations (e.g., on Ring C) prior to conversion to 2 and 3.

As a non-limiting example of the transformation from 2 to 3, when W is $R^3R^4C=CR^5C(=O)$— wherein $R^3$, $R^4$, and $R^5$ are as defined for Formula I, 2 may be coupled with a reagent of formula: $R^3R^4C=CR^5C(=O)Lg$ (e.g., acroyl chloride) wherein $R^3$, $R^4$, and $R^5$ are as defined for Formula I; and Lg is a leaving atom such as halo (Cl) or leaving group (e.g., OAc, OPiv, or OBz). Alternatively, 2 may be reacted with a reagent of formula: $R^3R^4C=CR^5C(=O)OH$ wherein $R^3$, $R^4$, and $R^5$ are as defined for Formula I, in the presence of one or more amide coupling reagents (e.g., HATU) to provide compound 3.

As another non-limiting example of the transformation between 2 and 3, when W is $R^6R^7NCH_2CH=CHC(=O)$— wherein $R^6$ and $R^7$ are as defined for Formula I, compound 2 may be reacted with a compound of formula $R^6R^7NCH_2CH=CHC(=O)OH$ wherein $R^6$ and $R^7$ are as defined for Formula I in the presence of one or more amide coupling reagents (e.g., HATU) to provide compound 3.

As another non-limiting example of the transformation between 2 and 3, when W is $H_2C=CHSO_2$—, compound 2 may be reacted with a compound of formula $H_2C=CHSO_2Lg$ wherein Lg is a leaving atom (e.g., halo (e.g., Cl)) or leaving group (e.g., OTf) to provide compound 3.

As yet another non-limiting example of the transformation between 2 and 3, when W is $R^8C\equiv CC(=O)$— wherein $R^8$ is as defined for Formula I, compound 2 may be coupled with a compound of formula $R^8C\equiv CC(=O)OH$ in the presence of one or more amide coupling reagents (e.g., HATU) to provide compound 3.

Non-limiting examples for the preparation of compound 1 are described in Schemes 2-7 below.

Scheme 2 shows a general example for the synthesis of compound 1 (shown as compound 8 in Scheme 2), wherein $R^1$=CN or Cl; Ring A, L, and Ring C are as defined for Formula I provided that L and Ring C are present; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; and $Pg^1$ is an amino protecting group. Compound 4-1 wherein $R^1$=CN or Cl; and each $R^B$ is independently H or (1-6C)alkyl, or each $R^B$ together with the atoms to which they are connected form a 5-6 membered ring optionally substituted with 1-4 substituents selected from (C1-C3 alkyl), may be coupled (e.g., Suzuki coupling using a palladium catalyst) with a compound of formula 5-1, wherein Ring A is defined for Formula I; and Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; X is halo (e.g., Br); and $Pg^1$ is an amino protecting group, to provide compound 6. Alternatively, compound 6 can be prepared through the coupling (e.g., Suzuki coupling using a palladium catalyst) between 4-2 wherein X is halo (e.g., Br); and $R^1$=CN or Cl with 5-2 wherein Ring A is as defined for Formula I; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; each $R^B$ is independently H or (1-6C)alkyl, or each $R^B$ together with the atoms to which they are connected form a 5-6 membered ring optionally substituted with 1-4 substituents selected from (C1-C3 alkyl); and $Pg^1$ is an amino protecting group. Compound 6 can be subjected

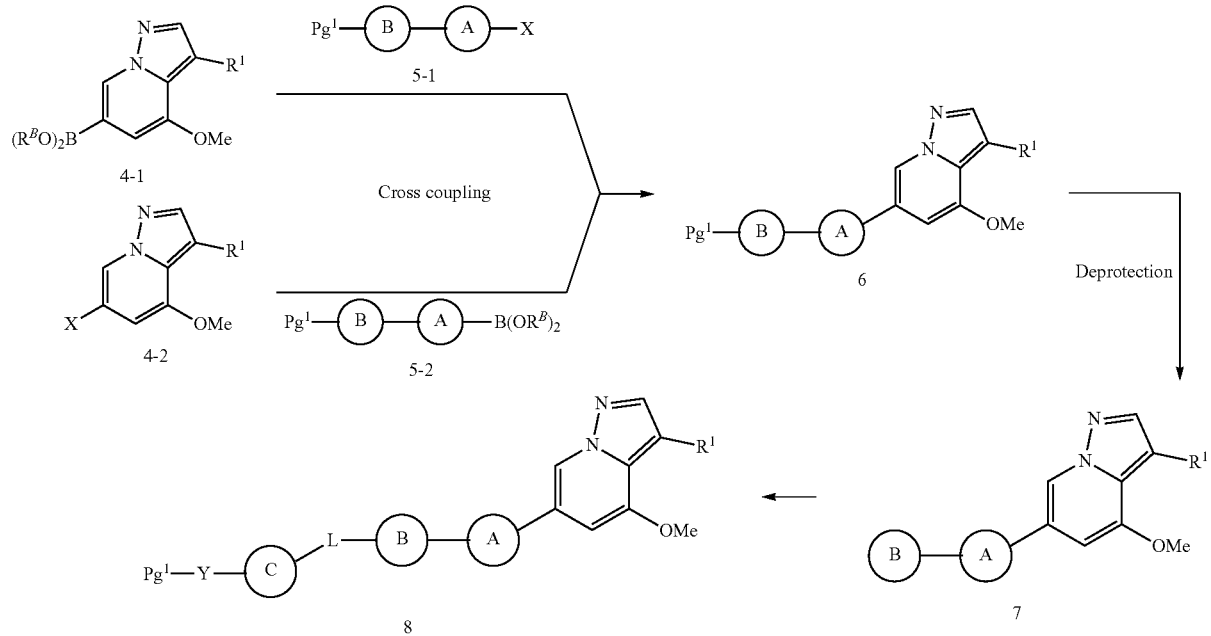

Scheme 2 to deprotection (e.g., under acidic conditions, e.g., trifluoroacetic acid), whereupon the resulting compound 7 can be converted into compound 8.

As a non-limiting example for the conversion between 7 and 8, when L is CH$_2$; and Ring B is attached to L via a nitrogen atom, 7 can be coupled with a reagent of formula

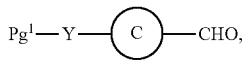

wherein Ring C and Y are as defined for Formula I provided that Ring C is present; and Pg$^1$ is an amino protecting group, under reductive amination conditions to provide compound 8 wherein L is CH$_2$.

As another non-limiting example for the conversion between 7 and 8, when L is C(=O); Ring B is attached to L via a nitrogen atom; and Ring C is attached to L via a nitrogen atom, 7 can be reacted with a urea coupling reagent (e.g., 4-nitrophenyl-chloroformate) and a compound of formula

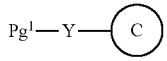

wherein Y is as defined for Formula I; and Ring C is selected from hetCyc$^1$, hetCyc$^2$, hetCyc$^3$, and hetCyc$^4$; and Pg$^1$ is an amino protecting group, to provide compound 8 wherein L is C(=O).

As another non-limiting example for the conversion between 7 and 8, when L is C(=O); and Ring B is attached to L via a nitrogen atom, compound 7 may be coupled to a compound of formula

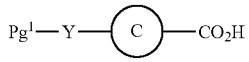

wherein Ring C and Y are as defined for Formula I provided that Ring C is present; and Pg$^1$ is an amino protecting group, to provide compound 8 wherein L is C(=O).

As yet another example of the compound the conversion between 7 and 8, when L is S(O)$_2$, compound 7 may be coupled to a compound of formula

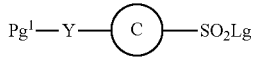

wherein Lg is a leaving atom (e.g., halo (e.g., Cl)) or leaving group (e.g., OTf); Ring C and Y are as defined for Formula I provided that Ring C is present; and Pg$^1$ is an amino protecting group, to provide compound 8 wherein L is S(O)$_2$.

In any of the foregoing examples, when Y is not absent, —Y-Pg$^1$, taken together, may be NO$_2$, which can be reduced and converted into —NH$_2$ or —NHMe under standard conditions. For example,

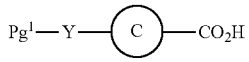

can be

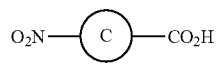

(e.g., Ring C is Ar$^3$).

Scheme 3

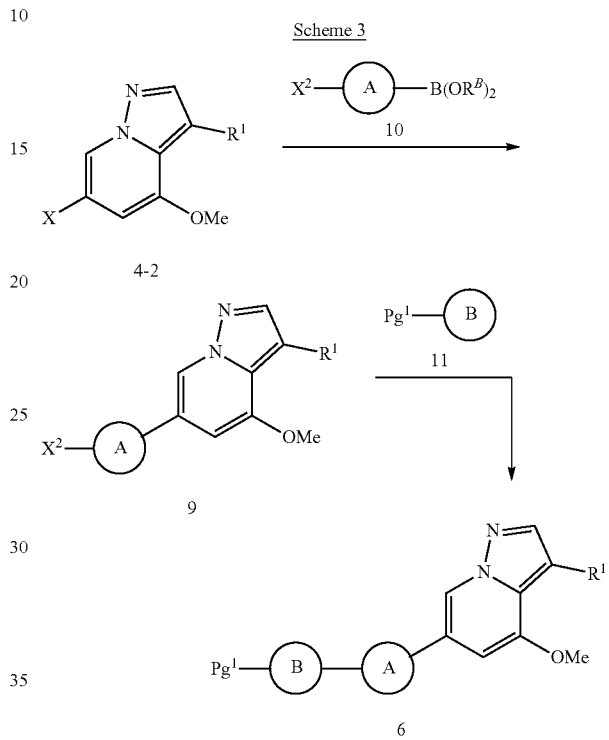

Scheme 3 shows an alternative method to prepare compound 6 wherein R$^1$=CN or Cl; Ring A and Ring B are as defined for Formula I and Scheme 2 (e.g., Ring B is a 4-8 membered monocyclic heterocyclic ring having 2 ring nitrogen atoms and 0-1 ring oxygen atoms, a 7-11 membered bridged heterocyclic ring having 2 ring nitrogen atoms, or a 7-12 membered spiroheterocyclic ring having 2 ring nitrogen atoms); and Pg$^1$ is an amino protecting group. Compound 4-2 wherein R$^1$=CN or Cl; and X is halo (e.g., Br) can be coupled (e.g., Suzuki coupling with a palladium catalyst) with compound 10 wherein Ring A is as defined for Formula I; X$^2$ is a leaving atom (e.g., halo (e.g., F)) or leaving group (e.g., OTf); and each R$^B$ is independently H or (1-6C)alkyl, or each R$^B$ together with the atoms to which they are connected form a 5-6 membered ring optionally substituted with 1-4 substituents selected from (C1-C3 alkyl) to afford compound 9. A non-limiting example of 10 can be:

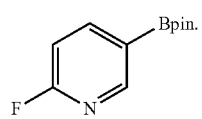

Compound 9 may in turn be coupled (e.g., under S$_N$Ar) with compound 11, wherein Ring B is as defined for Formula I and Scheme 2 (e.g., Ring B is a 4-8 membered monocyclic heterocyclic ring having 2 ring nitrogen atoms and 0-1 ring oxygen atoms, a 7-11 membered bridged heterocyclic ring having 2 ring nitrogen atoms, or a 7-12 membered spiro-heterocyclic ring having 2 ring nitrogen atoms); and Pg¹ is an amino protecting group to provide compound 6.

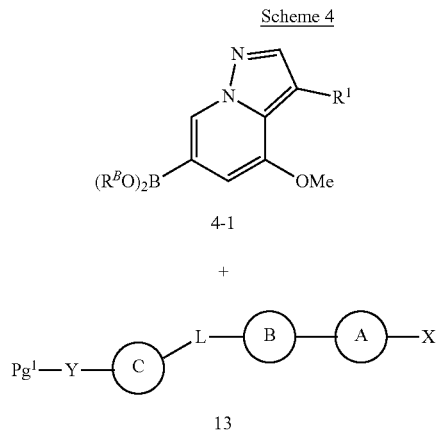

Scheme 4

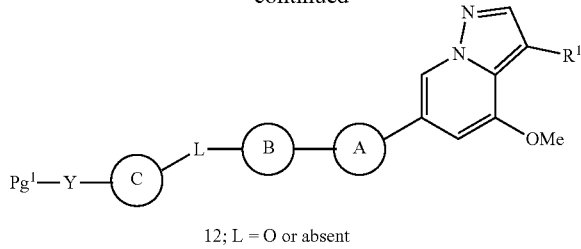

12; L = O or absent

Scheme 4 shows another general example for the synthesis of compound 1 (shown as compound 12 in Scheme 4), wherein $R^1$=CN or Cl; Ring A, Ring B, Ring C, and Y are as defined form Formula I provided that Ring B and Ring C are present; L is as defined for Formula I (e.g., L is absent or —O—); and Pg¹ is an amino protecting group. Compound 4-1 wherein $R^1$=CN or Cl; and each $R^B$ is independently H or (1-6C)alkyl, or each $R^B$ together with the atoms to which they are connected form a 5-6 membered ring optionally substituted with 1-4 substituents selected from (C1-C3 alkyl) can be coupled (e.g., Suzuki coupling with a palladium catalyst) with compound 13 wherein Ring A, Ring B, Ring C, and Y are as defined for Formula I provided that Ring B and Ring C are present; L is as defined for Formula I (e.g., L is —O— or absent); X is halo (e.g., Br); and Pg¹ is an amino protecting group to provide compound 12.

Scheme 5

Scheme 5 shows another general example for the synthesis of compound 1 (shown as compound 19 in Scheme 5), wherein $R^1$ and $R^2$ are as defined for Formula I; Ring A, Ring C, Y, and L are as defined for Formula I, provided that Ring C is present; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; and $Pg^1$ is an amino protecting group. Compound 14 (which may be prepared from compound 4-2 via removal of the methyl group) wherein $R^1$ is as defined for Formula I; and X is halo (e.g., Br) can be coupled (e.g., Suzuki coupling with a palladium catalyst) with compound 15 wherein Ring A is as defined for Formula I; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; each $R^B$ of compound 18 can be functionalized to provide compound 19 wherein $R^2$ is as defined for Formula I.

As a non-limiting example for the transformation of 18 into 19, the hydroxy group may be reacted with a reagent of Formula $R^{2'}$-Lg wherein $R^{2'}$ is C1-C6 alkyl or C3-C6 cycloalkyl; and Lg is a leaving atom (e.g., halo) or leaving group (e.g., OTf) to provide compound 19 wherein $R^2$ is C1-C6 alkoxy or C3-C6 cycloalkoxy.

As another non-limiting example for the transformation of 18 into 19, the hydroxy group may be sulfonylated (e.g., trifluoromethylsulfonylated into an OTf group). The resulting intermediate can be coupled (e.g., palladium-catalyzed cross coupling) with appropriate nucleophiles (e.g., boronic acids, boronic esters, or boronate salts) optionally followed by additional functional group transformations to provide compound 19 wherein $R^2$ is C1-C6 alkyl or phenyl optionally substituted with 1-2 groups independently selected from halogen and (C3-C6 cycloalkyl)C(═O)NH—.

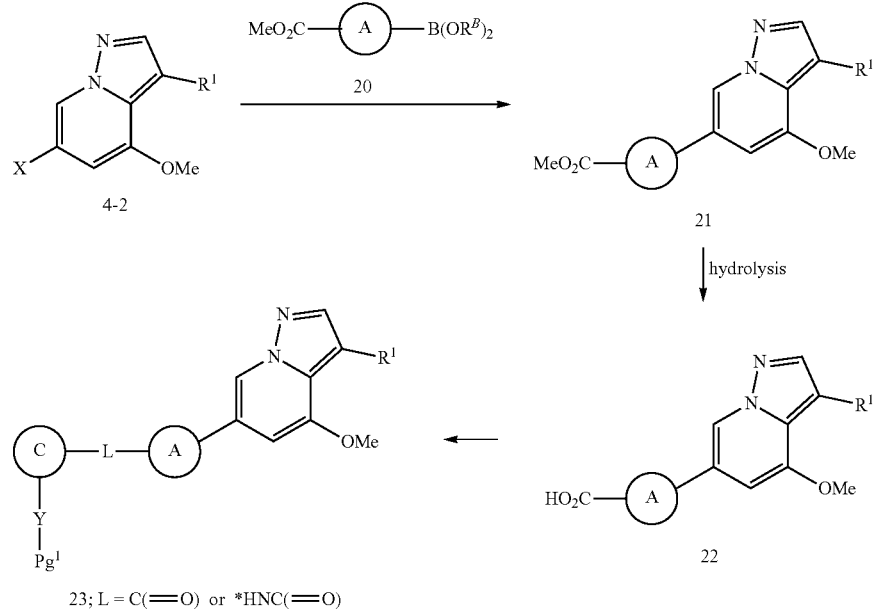

Scheme 6 is independently H or (1-6C)alkyl, or each $R^B$ together with the atoms to which they are connected form a 5-6 membered ring optionally substituted with 1-4 substituents selected from (C1-C3 alkyl); and $Pg^1$ is an amino protecting group. The nitrogen protecting group on the resulting compound 16 can be removed to provide compound 17 which can then be converted into 18 using a method similar to the transformation of 7 into 8 as described for Scheme 2 above. For example, when L is C(═O), 17 can be coupled with a reagent of formula

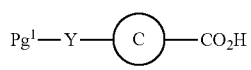

wherein Ring C is as defined for Formula I provided that Ring C is present; Y is as defined for Formula I; and $Pg^1$ is an amino protecting group to afford 18. The hydroxy group Scheme 6 shows another general method for the synthesis of compound 1 (shown as compound 23 in Scheme 6) wherein $R^1$, Ring A, Ring C, and Y are as defined for Formula I provided that Ring C is present; $Pg^1$ is an amino protecting group; and L is C(═O) that is attached to Ring C via a nitrogen atom, or L is *HNC(═O) as defined for Formula I. Compound 4-2 wherein $R^1$ is as defined for Formula I; and X is halo (e.g., Br) can be coupled (e.g., Suzuki coupling with a palladium catalyst) with compound 20 wherein Ring A is as defined for Formula I to provide compound 21; and each $R^B$ is independently H or (1-6C) alkyl, or each $R^B$ together with the atoms to which they are connected form a 5-6 membered ring optionally substituted with 1-4 substituents selected from (C1-C3 alkyl). The methyl ester in compound 21 can be hydrolyzed (e.g., under basic conditions such as NaOH) to afford compound 22. Compound 22 can be converted into compound 23. For example, when L is C(═O) that is attached to Ring C via a nitrogen atom, 22 can be converted into 23 through coupling with a reagent of formula

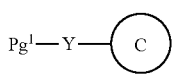

wherein Y is as defined for Formula I; and Ring C is hetCyc¹, hetCyc², hetCyc³, or hetCyc⁴; and Pg¹ is an amino protecting group. In another example when L is *HNC(=O), 22 can be converted into 23 through coupling with a reagent of formula:

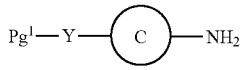

wherein Y and Ring C are as defined for Formula I provided that Ring C is present; and Pg¹ is an amino protecting group.

substituted with 1-4 substituents selected from (C1-C3 alkyl); and Pg¹ is an amino protecting group.

Scheme 8

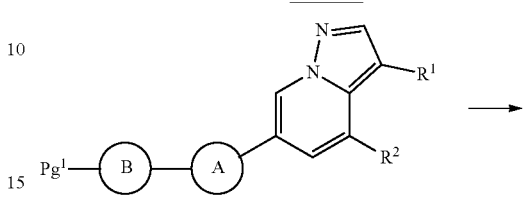

26

Scheme 7

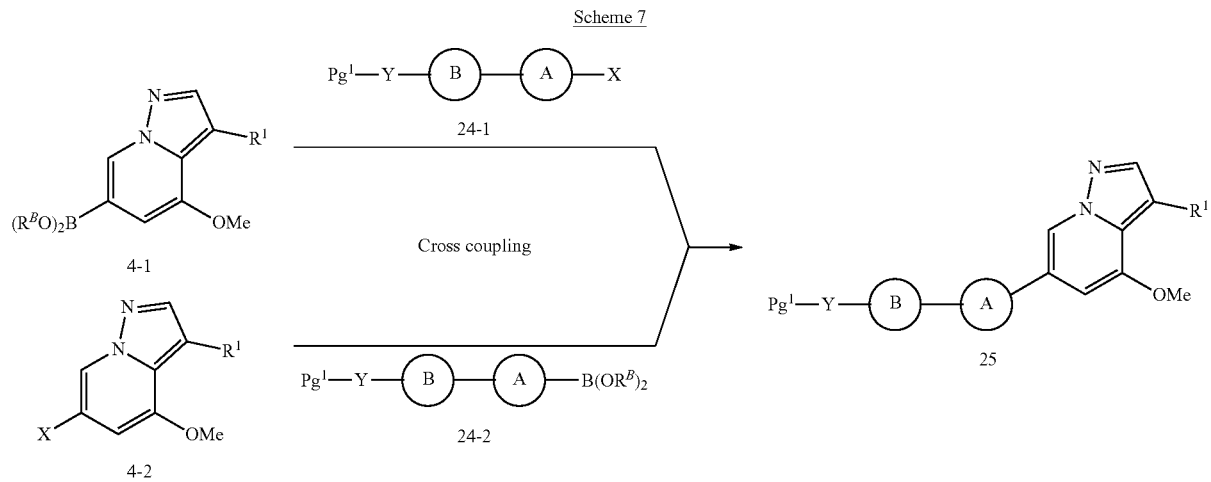

Scheme 7 shows another general method for the synthesis of compound 1 (shown as compound 25 in Scheme 7) wherein R¹, Ring A, Ring B, and Y are as defined for Formula I; and Pg¹ is an amino protecting group. Compound 4-1 wherein R¹=CN or Cl; and each $R^B$ is independently H or (1-6C)alkyl, or each $R^B$ together with the atoms to which they are connected form a 5-6 membered ring optionally substituted with 1-4 substituents selected from (C1-C3 alkyl) may be coupled (e.g., Suzuki coupling using a palladium catalyst) with a compound of formula 24-1, wherein Ring A, Ring B, and Y are as defined for Formula I; X is halo (e.g., Br); and Pg¹ is an amino protecting group, to provide compound 25. Alternatively, compound 25 can be prepared through the coupling (e.g., Suzuki coupling using a palladium catalyst) between 4-2 wherein X is halo (e.g., Br); and R¹=CN or Cl with 24-2 wherein Ring A, Ring B, and Y are as defined for Formula I; each $R^B$ is independently H or (1-6C)alkyl, or each $R^B$ together with the atoms to which they are connected form a 5-6 membered ring optionally -continued

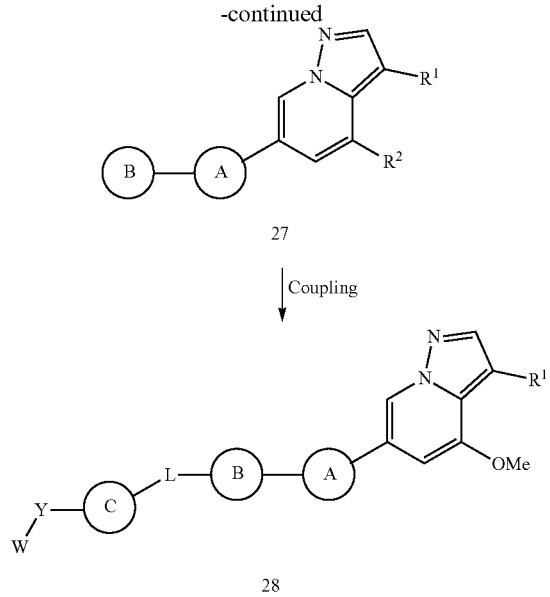

Scheme 8 shows another general method for the synthesis of a compound of Formula I shown as (compound 28 in Scheme 7) wherein R¹, R², Ring A, Ring C, Y, and W are as defined for Formula I, provided that Ring C is present; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; and L is —C(=O)—, —CH₂—, —SO₂—, *—NHC(=O)—, *—NHS(O)₂—, or absent. Compound 26 wherein R¹, R², and Ring A are as defined for Formula I; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; and Pg¹ is an amino protecting group can be deprotected to afford compound 27. Compound 27 can be converted into compound 28. As a non-limiting example, when L is C(=O), compound 27 may be reacted with a compound of formula:

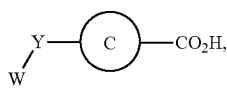

wherein Ring C is as defined for Formula I provided that Ring C is present; and Y and W are as defined for Formula I, in the presence of an mide coupling reagent (such as HATU).

I. Compound 29 wherein R¹ and R² are as defined for Formula I; and X is halo (e.g., Br) can be coupled (e.g., Suzuki coupling with a palladium catalyst) with compound 30 wherein Ring A is as defined for Formula I; and each R$^B$ is independently H or (1-6C)alkyl, or each R$^B$ together with the atoms to which they are connected form a 5-6 membered ring optionally substituted with 1-4 substituents selected from (C1-C3 alkyl) to provide compound 31. The methyl ester in compound 31 can be hydrolyzed (e.g., under basic conditions such as NaOH) to afford compound 32. Compound 32 can be converted into compound 33.

For example, when L is C(=O) that is attached to Ring C via a nitrogen atom, 22 can be converted into 23 through coupling with a reagent of formula

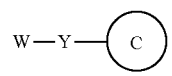

wherein Y and W are as defined for Formula I; and Ring C is hetCyc¹, hetCyc², hetCyc³, or hetCyc⁴. In another example when L is *HNC(=O), 22 can be converted into 23 through coupling with a reagent of formula:

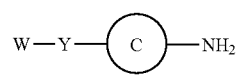

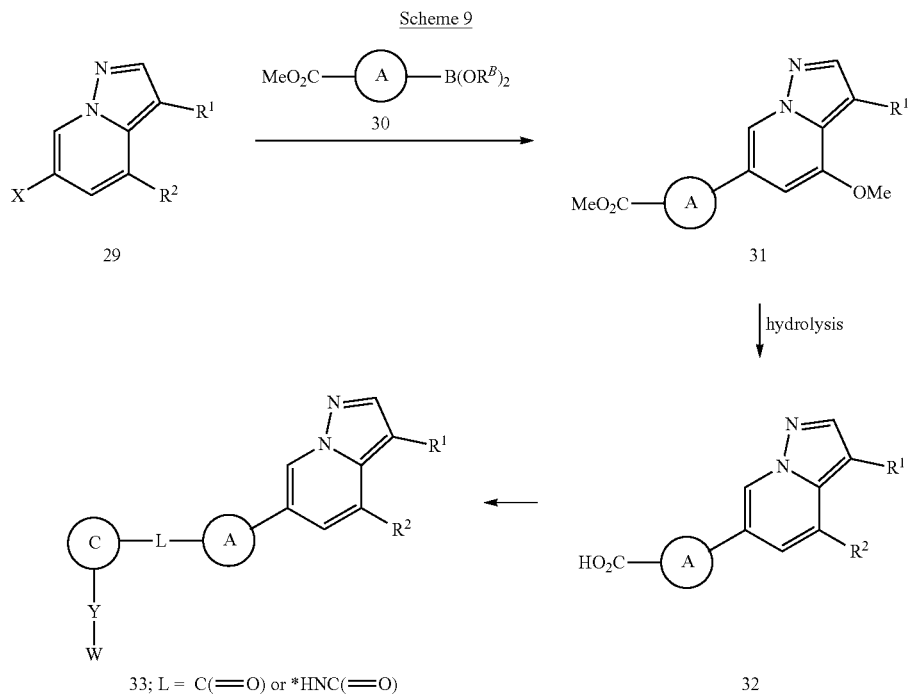

Scheme 9

Scheme 9 shows another general method for the synthesis of a compound of Formula I (shown as compound 33 in Scheme 6) wherein R¹, R² (e.g., R² is OMe), Ring A, Ring C, Y, and W are as defined for Formula I provided that Ring C is present; and L is C(=O) that is attached to Ring C via a nitrogen atom, or L is *HNC(=O) as defined for Formula wherein Y, W, and Ring C are as defined for Formula I provided that Ring C is present (e.g., C is Ar³).

Additionally, a compound of Formula I wherein Y=NMe may be obtained from a compound of Formula I wherein Y=NH upon reaction with a methylation agent (e.g., methyl iodide; e.g., in the presence of a base).

Accordingly, further provided herein is a process for preparing a compound of Formula I, comprising:

(a) for a compound of Formula I wherein $R^1$, $R^2$, Ring A, Ring B, L, Ring C, Y, and W are as defined for Formula I, functionalizing a compound having the formula:

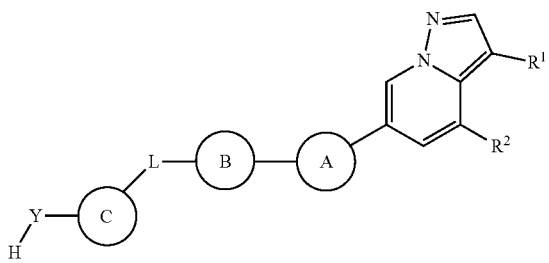

wherein $R^1$, $R^2$, Ring A, Ring B, L, Ring C, and Y are as defined for Formula I; or (b) for a compound of Formula I, wherein $R^1$, $R^2$, Ring A, Ring C, Y, and W are as defined for Formula I, provided that Ring C is present; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms; and L is —C(=O)—, —CH$_2$—, —SO$_2$—, *—NHC(=O)—, *—NHS(O)$_2$—, or absent, functionalizing a compound having the following formula:

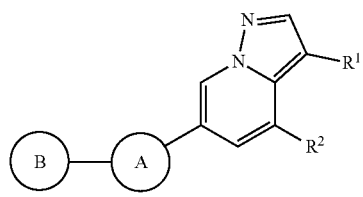

wherein $R^1$, $R^2$, and Ring A are as defined for Formula I; Ring B is a 4-8 membered monocyclic heterocyclic ring having 1-2 ring nitrogen atoms and 0-1 ring oxygen atoms, a 7-11 membered bridged heterocyclic ring having 1-2 ring nitrogen atoms, or a 7-12 membered spiroheterocyclic ring having 2 ring nitrogen atoms, at Ring B; or (c) for a compound of Formula I, wherein Ring B is absent; $R^1$, $R^2$, Ring A, C, Y, and W are as defined for Formula I provided that C is present; and L is C(=O) that is attached to Ring C via a nitrogen atom, or L is *HNC(=O) as defined for Formula I, reacting a compound of the following formula:

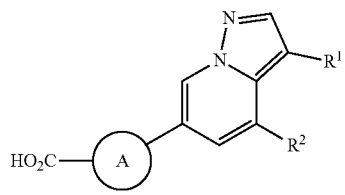

with a compound having the following formula:

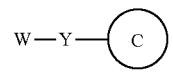

wherein Ring C is hetCyc$^1$, hetCyc$^2$, hetCyc$^3$, or hetCyc$^4$; and W and Y are as defined for Formula I; or
a compound having the following formula:

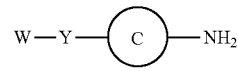

wherein Ring C, Y, and W are as defined for Formula I provided that Ring C is present; or (d) for a compound of Formula I, wherein $R^1$, $R^2$, Ring A, Ring B, Ring C, L, and W are as defined for Formula I; and Y is NMe, reacting a compound of Formula I wherein $R^1$, $R^2$, Ring A, Ring B, Ring C, L, and W are as defined for Formula I; and Y is NH with a methylating agent; and removing any additional protecting groups if present and optionally preparing a pharmaceutically acceptable salt thereof.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, imines, as well as many N-heteroatom derivatives that can be removed to regenerate the desired amine group. Non-limiting examples of amino protecting groups are acetyl, trifluoroacetyl, t-butyloxycarbonyl ("Boc"), benzyloxycarbonyl ("CBz") and 9-fluorenylmethyleneoxycarbonyl ("Fmoc"). Further examples of these groups, and other protecting groups, are found in T. W. Greene, et al., Greene's Protective Groups in Organic Synthesis. New York: Wiley Interscience, 2006.

In general, the FGFR receptors (FGFR1, FGFR2, FGFR3, and FGFR4) share several structural features in common, including three extracellular immunoglobulin-like (Ig) domains, a hydrophobic transmembrane domain, and an intracellular tyrosine kinase domain split by a kinase insert domain, followed by a cytoplasmic c-terminal tail (Johnson et al., Adv. Cancer Res. 60:1-40, 1993; and Wilkie et al., Curr. Biol. 5:500-507, 1995). In FGFR1, the kinase insert domain spans positions 582 to 595 of the alpha A1 isoform of FGFR1 (SEQ ID NO:1). In FGFR2, the kinase insert domain spans positions 585 to 598 of the FGFR2 IIIc isoform (SEQ ID NO:3). In FGFR3, the kinase insert domain spans positions 576 to 589 of the FGFR3 IIIc isoform (SEQ ID NO:5). In FGFR4, the kinase insert domain spans positions 571 to 584 of FGFR4 isoform 1 (SEQ ID NO: 7). The c-terminal tail of FGFRs begins following the end of the tyrosine kinase domain and extends to the c-terminus of the protein. Several isoforms of each FGFR have been identified and are the result of alternative splicing of their mRNAs (Johnson et al., Mol. Cell. Biol. 11:4627-4634, 1995; and Chellaiah et al., J. Biol. Chem. 269:11620-11627, 1994). Exemplary amino acid sequences for exemplary wildtype isoforms of FGFR1 are SEQ ID NO: 1 (also called the αA1 isoform of FGFR1) and SEQ ID NO: 2 (also called the αB1 isoform of FGFR1). Exemplary amino acid sequences for exemplary wildtype isoforms of FGFR2 are SEQ ID NO: 3 (also called the IIIc isoform of FGFR2) and SEQ ID NO: 4 (also called the IIIb isoform of FGFR2). Exemplary amino acid sequences for exemplary wildtype isoforms of FGFR3 are SEQ ID NO: 5 (also called the IIIc isoform of FGFR3) and SEQ ID NO: 6 (also called the IIIb isoform of FGFR3). Exemplary amino acid sequences for exemplary wildtype isoforms of FGFR4 are SEQ ID NO: 7 (also called isoform 1 of FGFR4) and SEQ ID NO: 8 (also called isoform 2 of FGFR4). These amino acid sequences are shown in FIG. 1.

As defined herein, the "c-terminal tail" of a FGFR protein begins at an amino acid corresponding to amino acid 756 in SEQ ID NO: 1, amino acid 759 in SEQ ID NO:3, 750 in SEQ ID NO: 5, or 745 in SEQ ID NO:7 and ends at the c-terminus of the protein.

A few of the receptor variants that result from this alternative splicing have different ligand binding specificities and affinities (Zimmer et al., J. Biol. Chem. 268:7899-7903, 1993; Cheon et al., Proc. Natl. Acad. Sci. U.S.A. 91:989-993, 1994; and Miki et al., Proc. Natl. Acad. Sci. U.S.A. 89:246-250, 1992). Protein sequences for FGFR proteins and nucleic acids encoding FGFR proteins are known in the art.

The amino acid positions used to describe the FGFR substitutions herein are generally specified to correspond to a particular SEQ ID NO. When a particular SEQ ID NO is not specified, it is to be understood that the amino acid position referred to is from the first SEQ ID of the specified FGFR (i.e., SEQ ID NO:1 for FGFR1, SEQ ID NO:3 for FGFR2, SEQ ID NO:5 for FGFR3, or SEQ ID NO:7 for FGFR4). A "corresponding" amino acid position (or substitution) in a different isoform of the same FGFR (e.g., in SEQ ID NO:2, when SEQ ID NO:1 is specified) or in a different FGFR (e.g., FGFR2 when FGFR1 is specified) can be identified by performing a sequence alignment between the protein sequences of interest. In some cases, there is no corresponding amino acid position identified by an alignment. Some non-limiting corresponding amino acid positions are provided in Tables BA, BD, and BE. A lack of a corresponding amino acid position in any of these Tables does not necessarily mean that no corresponding amino acid position exists.

Signaling by FGFRs regulates key biological processes including cell proliferation, survival, migration, and differentiation. Dysregulation of a FGFR gene, a FGFR protein, or expression or activity, or level of the same, has been associated with many types of cancer. For example, dysregulation of FGFRs can occur by multiple mechanisms, such as FGFR gene overexpression, FGFR gene amplification, activating mutations (e.g., point mutations or truncations), and chromosomal rearrangements that lead to FGFR fusion proteins. Dysregulation of a FGFR gene, a FGFR protein, or expression or activity, or level of the same, can result in (or cause in part) the development of a variety of different FGFR-associated cancers. Non-limiting examples of the types of FGFR-associated cancers and the dysregulation of a FGFR gene, a FGFR protein, or expression or activity, or level of the same, that causes (or causes in part) the development of the FGFR-associated cancers are listed in Tables BA-BD.

The term "FGFR" or "FGFR protein" includes any of the FGFR proteins described herein (e.g., a FGFR1, a FGFR2, a FGFR3 or a FGFR4 protein, or isoforms thereof).

The term "FGFR gene" includes any of the FGFR genes described herein (e.g., a FGFR1, a FGFR2, a FGFR3 gene, or a FGFR4 gene).

The ability of test compounds to act as inhibitors of FGFR1, FGFR2 and/or FGFR3 may be demonstrated by the assays described in Examples A-E. Functional parameters (e.g., $IC_{50}$ values, $k_{obs}$ values) are shown in Tables EA-EE.

Compounds of Formula I have been found to inhibit FGFR1, FGFR2 and/or FGFR3, and are therefore believed to be useful for treating diseases and disorders which can be treated with an inhibitor of FGFR1, FGFR2, FGFR3 and/or FGFR4, such as FGFR-associated diseases and disorders, e.g., proliferative disorders such as cancers, including hematological cancers and solid tumors.

In certain embodiments, compounds of Formula I are useful for preventing diseases and disorders as defined herein (for example cancer).

In some embodiments, compounds of Formula I are covalent inhibitors of FGFR1, FGFR2 and/or FGFR3. Covalent inhibitors in general are known in the medical arts (see, e.g., Singh et al, Nat. Rev. Drug. Disc., 10(4):307-317, 2011; Zhao et al, Drug Discov. Today 23(3):727-735, 2018). In some cases, a covalent inhibitor includes a binding moiety that can bind reversibly to a target protein and a warhead that reacts with a cysteine in the target protein to form a covalent bond between the inhibitor and a cysteine residue in a target protein. The covalent bond can be reversible or irreversible. In some cases, a warhead can be exposed through metabolic activation of an inhibitor by a subject.

Accordingly, in some aspects, this disclosure provides FGFR inhibitors that are compounds that can form a covalent bond with a cysteine residue in a FGFR protein. Examples of such compounds include compounds of Formula I. In some embodiments, this disclosure provides compounds that can form a covalent bond with a cysteine residue in a kinase insert domain in a FGFR protein. In some embodiments, the FGFR protein is a FGFR3 protein. In some embodiments, the cysteine residue corresponds to Cys582 in SEQ ID NO: 5. For example, in some embodiments of any of the methods described herein, a compound that can form a covalent bond with a cysteine residue in a FGFR protein can be a compound that can form a covalent bond with a cysteine residue in a kinase insert domain in a FGFR protein. In some embodiments, this disclosure provides compounds that can form a covalent bond with a cysteine residue in a c-terminal tail of a FGFR protein. In some embodiments, the FGFR protein is a FGFR2 protein. In some embodiments, the cysteine residue corresponds to Cys790 in SEQ ID NO: 3. For example, in some embodiments of any of the methods herein, a compound that can form a covalent bond with a cysteine residue in a FGFR protein can be a compound that can form a covalent bond with a cysteine residue in a c-terminal tail in a FGFR protein. In some embodiments of any of the methods described herein, a compound that can form a covalent bond with a cysteine residue in a FGFR protein can be a compound that can form a covalent bond with a cysteine residue in a kinase insert domain in a FGFR protein or a cysteine residue in a c-terminal tail of a FGFR protein. A covalent bond between a protein and a compound (e.g., a compound of Formula I) can be determined by any method known in the art. For example, washout experiments can show that removal of excess compound (e.g, by dialysis or gel filtration) from a protein does not result in a recovery of activity in the protein. As another example, intact mass of a protein can be measured by mass spectrometry and the mass of a protein and covalently bound compound can be determined using this technique. The mass of a protein bound to a covalent compound will be greater than the mass of the protein without the compound. As another example, the mass of peptides from a target protein can be determined using mass spectrometry, and the mass of a peptide which is covalently bound by a compound will be greater than the mass of the peptide without the covalently attached compound. As another example, a covalent bond can be visualized using x-ray crystallography.

Accordingly, in some aspects, this disclosure provides FGFR inhibitors that are compounds that form a covalent bond with a cysteine residue in a FGFR protein. Examples of such compounds include compounds of Formula I. In some embodiments, this disclosure provides compounds that form a covalent bond with a cysteine residue in a kinase insert domain in a FGFR protein. In some embodiments, the FGFR protein is a FGFR3 protein. In some embodiments, the cysteine residue corresponds to Cys582 in SEQ ID NO: 5. For example, in some embodiments of any of the methods described herein, a compound that forms a covalent bond with a cysteine residue in a FGFR protein can be a compound that forms a covalent bond with a cysteine residue in a kinase insert domain in a FGFR protein. In some embodiments, this disclosure provides compounds that form a covalent bond with a cysteine residue in a c-terminal tail of a FGFR protein. In some embodiments, the FGFR protein is a FGFR2 protein. In some embodiments, the cysteine residue corresponds to Cys790 in SEQ ID NO: 3. For example, in some embodiments of any of the methods herein, a compound that forms a covalent bond with a cysteine residue in a FGFR protein can be a compound that forms a covalent bond with a cysteine residue in a c-terminal tail in a FGFR protein. In some embodiments of any of the methods described herein, a compound that forms a covalent bond with a cysteine residue in a FGFR protein can be a compound that forms a covalent bond with a cysteine residue in a kinase insert domain in a FGFR protein or a cysteine residue in a c-terminal tail of a FGFR protein.

In one aspect, this disclosure provides FGFR3 inhibitors of Formula I that are at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR3 than for FGFR1. In some embodiments, such an inhibitor can form a covalent bond with a cysteine in a kinase insert domain in a FGFR3 protein. In some embodiments, such an inhibitor forms a covalent bond with a cysteine in a kinase insert domain in a FGFR3 protein. In some embodiments, the cysteine corresponds to Cys582 of SEQ ID NO: 5.

In one aspect, this disclosure provides FGFR2 inhibitors of Formula I that are at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR2 than for FGFR1. In some embodiments, such an inhibitor can form a covalent bond with a cysteine in a c-terminal tail in a FGFR2 protein. In some embodiments, such an inhibitor forms a covalent bond with a cysteine in a c-terminal tail in a FGFR2 protein. In some embodiments, the cysteine corresponds to Cys790 of SEQ ID NO: 3.

In another aspect, this disclosure provides an inhibited FGFR3 protein covalently bound to a molecule via a cysteine in the kinase insert domain of the FGFR3 protein. In some embodiments, the cysteine corresponds to Cys582 of SEQ ID NO: 5. In some embodiments, the molecule is a compound of Formula I. In some embodiments, the molecule is at least about 3-fold (e.g., 4-, 5-, at least about 6-, 7-, 8-, 9-, 10-, 15-, 20-, 30-, 40-, 50-, 75-, 100-, 200-, 500-, 1000-fold, or more) more selective for FGFR3 than for FGFR1.

In another aspect, this disclosure provides an inhibited FGFR2 protein covalently bound to a molecule via a cysteine in the c-terminal tail of the FGFR2 protein. In some embodiments, the cysteine corresponds to Cys790 of SEQ ID NO: 3. In some embodiments, the molecule is a compound of Formula I. In some embodiments, the molecule is at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR2 than for FGFR1.

In another aspect, this disclosure also provides a compound of Formula I covalently bonded to a cysteine. In some embodiments, the cysteine is in a kinase insert domain of a protein. In some embodiments, the cysteine is in a c-terminal tail of a protein. In some embodiments, the protein is a FGFR protein. In some embodiments, the protein is a FGFR3 protein. In some embodiments, the cysteine corresponds to Cys582 of SEQ ID NO: 5. In some embodiments, the cysteine is in a kinase insert domain of a FGFR3 protein. In some embodiments, the compound is at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR3 than for FGFR1. In some embodiments, the protein is a FGFR2 protein. In some embodiments, the cysteine is in a c-terminal tail of a FGFR2 protein. In some embodiments, the cysteine corresponds to Cys790 of SEQ ID NO: 3. In some embodiments, the compound is at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR2 than for FGFR1.

In another aspect, this disclosure provides an inhibited kinase protein covalently bonded to a compound of Formula I. In some embodiments, the inhibited kinase protein is covalently bonded to a compound of Formula I via a cysteine in the kinase protein. In some embodiments, the kinase protein is a tyrosine kinase. In some embodiments, the kinase protein is a FGFR protein. In some embodiments, the kinase protein is a FGFR3 protein. In some embodiments, the cysteine is a cysteine in a kinase insert domain of a FGFR3 protein. In some embodiments, the cysteine corresponds to Cys582 of SEQ ID NO: 5. In some embodiments, the kinase protein is a FGFR2 protein. In some embodiments, the cysteine is a cysteine in a c-terminal tail of a FGFR2 protein. In some embodiments, the cysteine corresponds to Cys790 of SEQ ID NO: 3.

In another aspect, this disclosure provides a compound of Formula I, wherein the compound forms a covalent bond with a cysteine in a FGFR protein. This disclosure also provides a compound of Formula I, wherein the compound can form a covalent bond with a cysteine in a FGFR protein. In some embodiments, the cysteine is a cysteine in a kinase insert domain of a FGFR protein or a cysteine in a c-terminal tail of a FGFR protein. In some embodiments, the compound is at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR3 than for FGFR1. In some embodiments, the cysteine corresponds to Cys582 of SEQ ID NO: 5. In some embodiments, the compound is at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR2 than for FGFR1. In some embodiments, the cysteine corresponds to Cys790 of SEQ ID NO: 3.

In another aspect, this disclosure provides a compound of Formula I, wherein the compound forms a covalent bond with a cysteine in a kinase insert domain in a FGFR3 protein. This disclosure also provides a compound of Formula I, wherein the compound can form a covalent bond with a cysteine in a kinase insert domain in a FGFR3 protein. In some embodiments, the compound is at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR3 than for FGFR1. In some embodiments, the cysteine corresponds to Cys582 of SEQ ID NO: 5.

In another aspect, this disclosure provides a compound of Formula I, wherein the compound forms a covalent bond with a cysteine in a c-terminal tail in a FGFR2 protein. This disclosure also provides a compound of Formula I, wherein the compound can form a covalent bond with a cysteine in a c-terminal tail in a FGFR2 protein. In some embodiments, the compound is at least about 3-fold (e.g., at least about 4-, 5-, 6-, 7-, 8-, 9-, 10-, 15-, 20-, 30-, 40-, 50-, 75-, 100-, 200-, 500-, 1000-fold, or more) more selective for FGFR2 than for FGFR1. In some embodiments, the cysteine corresponds to Cys790 of SEQ ID NO: 3.

In certain embodiments, compounds that can form a covalent bond with a cysteine residue in a FGFR protein are useful for preventing diseases or disorders as defined herein (for example cancer). In certain embodiments, compounds that form a covalent bond with a cysteine residue in a FGFR protein are useful for preventing diseases or disorders as defined herein (for example cancer).

As used herein, "an inhibited FGFR protein covalently bound to a molecule via a cysteine" means that the molecule has an $IC_{50}$ value of less than about 500 nM, as determined by any of the assays described in Examples A, B, D, or E.

In some embodiments, the compounds provided herein (e.g., compounds of Formula I) exhibit potent and selective FGFR inhibition. For example, the compounds provided herein can exhibit nanomolar potency against wild type FGFR and a FGFR kinase encoded by a FGFR gene including an activating mutation or a FGFR kinase inhibitor resistance mutation, including, for example, the FGFR3-TACC3 fusion, and gatekeeper mutations (corresponding to V561M in SEQ ID NO:1, V564F or V564I in SEQ ID NO:3, V555M in SEQ ID NO:5, or V550L, V550M, or V550E in SEQ ID NO:7), with minimal activity against related kinases.

In some embodiments, the compounds provided herein (e.g., compounds of Formula I) exhibit nanomolar potency against an altered FGFR fusion protein encoded by a FGFR gene encoding the FGFR fusion protein (e.g. any of the FGFR fusion proteins described herein including, without limitation, FGFR3-TACC3 or FGFR2-BICC1) which FGFR gene includes a FGFR kinase inhibitor resistance mutation (e.g., any of the FGFR mutations described herein including, without limitation, mutations corresponding to V561M in SEQ ID NO:1, V564F in SEQ ID NO:3, V555M in SEQ ID NO:5, or V550L, V550M, or V550E in SEQ ID NO:7) such that the altered FGFR protein is a FGFR fusion protein that exhibits FGFR kinase resistance due to the presence of a FGFR kinase inhibitor resistance amino acid substitution or deletion. Non-limiting examples include FGFR3-TACC3-V555M and FGFR2-BICC1-V564F. In some embodiments, the compounds provided herein exhibit nanomolar potency against an altered FGFR protein encoded by a FGFR gene that that includes a FGFR mutation (e.g. any of the FGFR mutations described herein including, without limitation, FGFR2 N549K or FGFR3 N540K) and that includes a FGFR kinase inhibitor resistance mutation (e.g., any of the FGFR kinase inhibitor resistance mutations described herein including, without limitation, FGFR1 N546K, FGFR2 K659E, or FGFR3 V555M) such that the altered FGFR protein includes a FGFR substitution caused by the FGFR mutation (e.g., a FGFR primary mutation) and the altered FGFR protein exhibits FGFR kinase resistance due to the presence of a FGFR kinase inhibitor resistance amino acid substitution or deletion.

In some embodiments, the compounds of Formula I or a pharmaceutically acceptable salt or solvate thereof, selectively target a FGFR kinase. For example, a compound of Formula I or a pharmaceutically acceptable salt or solvate thereof, can selectively target a FGFR kinase over another kinase or non-kinase target.

As used herein, the "selectivity" of a compound for a first target over a second target means that the compound has more potent activity at the first target than the second target. A fold selectivity can be calculated by any method known in the art. For example, a fold selectivity can be calculated by dividing the $IC_{50}$ value of a compound for the second target (e.g., FGFR1) by the $IC_{50}$ value of the same compound for the first target (e.g., FGFR2 or FGFR3). An $IC_{50}$ value can be determined by any method known in the art. For example, an $IC_{50}$ value can be determined by any of the methods described in Examples A, B, D, or E. As another example, a fold selectivity can be calculated by dividing the observed rate of covalent modification (e.g., a $k_{obs}$ value) for the first target (e.g., FGFR2 or FGFR3) by the $k_{obs}$ value for the second target (e.g., FGFR1). A $k_{obs}$ value can be determined by any method known in the art. For example, a $k_{obs}$ value can be determined by the method described in Example C. In some embodiments, a compound is first determined to have an activity of less than 500 nM for the first target. In some embodiments, a compound is first determined to have an activity of less than 500 nM for the second target.

As another example, a $k_{obs}$ value can be determined as follows. A LCMS assay is used to determine of the extent of covalent modification of the intact FGFR1 or FGFR3 protein over time. The proteins are first diluted to 2× concentration in partial assay buffer [25.0 mM HEPES (4-(2-hydroxyethyl)-1-piperazineethanesulfonic acid) pH 7.5, 150.0 mM NaCl, 5.0 mM $MgCl_2$, 0.5 mM tris(2-carboxyethyl) phosphine (TCEP), and 10.0 mM octyl β-D-glucopyranoside (β-OG)]. Compound dilutions are performed in 3 steps. All are initially diluted in dimethyl sulfoxide (DMSO) to a concentration equal to 25× the final assay concentration. The initial stocks are then diluted 12.5× in partial assay buffer such that the final concentration is 2× the assay concentration and 8% (v:v) DMSO. The assay is initiated by a final dilution of 10 μL of 2× compound into 10 μL of 2× protein. Final assay buffer conditions are 25.0 mM HEPES pH 7.5, 150.0 mM NaCl, 5.0 mM $MgCl_2$, 0.5 mM TCEP, and 10.0 mM β-OG,0 4% DMSO. Final protein and compound concentrations are 0.5 μM protein and either 0.0 or 3.0 μM compound. The 0.0 μM compound (DMSO Control) samples are used as a tool to assess the protein stability during the assay, and to normalize the mass spec signals across samples during the data processing stage. Protein and compound reactions are allowed to proceed for varying lengths of time and upon reaching an appropriate incubation, the reactions are quenched by the addition of 20 μL of 0.4% formic acid. Quenched reactions are then analyzed on either an Agilent 6520A or Agilent 6545XT ESI-QTOF mass spectrometer in positive ion mode.

The reactions are injected onto an Agilent Poroshell C3 column running a solvent system of 0.1% formic acid: acetonitrile+0.1% formic acid (85:15%). A gradient is developed by running 15% to 95% acetonitrile+0.1% formic acid over 1 minute. Mass spec data are collected throughout the entire gradient. Protein signals are then automatically deconvoluted using Agilent Masshunter software. Deconvoluted mass signals are exported to Tibco Spotfire data analysis program for further processing and normalization.

Data analysis includes five steps. First, the signals for the "DMSO Controls" are analyzed to determine the percent of signal associated with unmodified FGFR1 or FGFR3 at each timepoint. Next, the percent of the signal associated with the covalent modification is determined. Third, the average nonmodified "DMSO Control" signal is used to normalize the modified protein signals at each timepoint. This normalized value is coined "Normalized Percent of Control" or POC. A POC value that increases over time is consistent with a protein showing increasing modification over time.

$$POC = \frac{\%_{Modified}}{\%_{UnmodifiedControl}} \times 100$$

The POC values are refit to a standard exponential growth model resulting in an observed rate ($k_{obs.}$) of modification of the protein.

$$POC = [\% \text{ Modified}]_o \times e^{-k_{obs.}t}$$

Where:
POC=Normalized POC value
[% Modified]$_o$=Initial amount of modified protein (%)
$k_{obs.}$=Observed rate (min$^{-1}$)
t=time (min)

In some embodiments, a compound of Formula I or a pharmaceutically acceptable salt or solvate thereof exhibits at least a 30-fold selectivity for a FGFR kinase over another kinase. For example, a compound of Formula I or a pharmaceutically acceptable salt or solvate thereof, exhibits at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 200-fold selectivity; at least 300-fold selectivity; at least 400-fold selectivity; at least 500-fold selectivity; at least 600-fold selectivity; at least 700-fold selectivity; at least 800-fold selectivity; at least 900-fold selectivity; or at least 1000-fold selectivity for a FGFR kinase over another kinase. In some embodiments, selectivity for a FGFR kinase over another kinase is measured in a cellular assay (e.g., a cellular assay as provided herein).

In some embodiments, the compounds provided herein (e.g., compounds of Formula I) can exhibit selectivity for a FGFR kinase over a KDR kinase (e.g., VEGFR2). In some embodiments, the selectivity for a FGFR kinase over a KDR kinase is observed without loss of potency for a FGFR kinase encoded by a FGFR gene including an activating mutation or a FGFR kinase inhibitor resistance mutation (e.g., a gatekeeper mutant). In some embodiments, the selectivity over a KDR kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of FGFR3-TACC3 (e.g., the compounds are more potent against FGFR3-TACC3 than KDR). In some embodiments, the selectivity for a FGFR kinase over a KDR kinase is about 30-fold. In some embodiments, the selectivity for a FGFR kinase over a KDR kinase is at least 100-fold. In some embodiments, the selectivity for a FGFR kinase over a KDR kinase is at least 150-fold. In some embodiments, the selectivity for a FGFR kinase over a KDR kinase is at least 400-fold. Without being bound by any theory, potent KDR kinase inhibition is believed to be a common feature among multikinase inhibitors (MKIs) that target FGFR and may be the source of the dose-limiting toxicities observed with such compounds.

In some embodiments, the compounds provided herein (e.g., compounds of Formula I) can exhibit selectivity for a FGFR kinase over an Aurora B kinase (e.g., VEGFR2). In some embodiments, the selectivity for a FGFR kinase over an Aurora B kinase is observed without loss of potency for a FGFR kinase encoded by a FGFR gene including an activating mutation or a FGFR kinase inhibitor resistance mutation (e.g., a gatekeeper mutant). In some embodiments, the selectivity over an Aurora B kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of FGFR3-TACC3 (e.g., the compounds are more potent against FGFR3-TACC3 than KDR). In some embodiments, the selectivity for a FGFR kinase over an Aurora B kinase is about 30-fold. In some embodiments, the selectivity for a FGFR kinase over an Aurora B kinase is at least 100-fold. In some embodiments, the selectivity for a FGFR kinase over an Aurora B kinase is at least 150-fold. In some embodiments, the selectivity for a FGFR kinase over an Aurora B kinase is at least 400-fold. Without being bound by any theory, potent KDR kinase inhibition is believed to be a common feature among multikinase inhibitors (MKIs) that target FGFR and may be the source of the dose-limiting toxicities observed with such compounds.

In some embodiments, the compounds provided herein (e.g., compounds of Formula I) can exhibit selectivity for a first FGFR family member (e.g., FGFR2 or FGFR3) over a second FGFR family member (e.g., FGFR1 or FGFR4). In some embodiments, the selectivity for a first FGFR family member over a second FGFR family member is observed without loss of potency for the first FGFR family member, or activating or resistance mutations thereof. In some embodiments, the selectivity over a second FGFR family member is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of the first FGFR family member (e.g., the compounds are more potent against FGFR3 than FGFR1). In some embodiments, the selectivity for a first FGFR family member over a second FGFR family member is about 30-fold. In some embodiments, the selectivity for a first FGFR family member over a second FGFR family member is at least 100-fold. In some embodiments, the selectivity for a first FGFR family member over a second FGFR family member is at least 150-fold. In some embodiments, the selectivity for a first FGFR family member over a second FGFR family member is at least 400-fold. Without being bound by any theory, it is believed that selectivity over FGFR1 can reduce side effects associated with its inhibition (e.g., elevated phosphate level (e.g., hyperphosphatemia)).

In some embodiments, inhibition of FGFR1 V561M is similar to that observed for wild-type FGFR1. For example, inhibition of V561M is within about 2-fold (e.g., about 5-fold, about 7-fold, about 10-fold) of inhibition of wild-type FGFR1 (e.g., the compounds are similarly potent against wild-type FGFR1 and V561M). In some embodiments, selectivity for a wildtype or V561M FGFR1 kinase over another kinase is measured in an enzyme assay (e.g., an enzyme assay as provided herein). In some embodiments, the compounds provided herein (e.g., compounds of Formula I) exhibit selective cytotoxicity to FGFR1-mutant cells.

In some embodiments, inhibition of FGFR2 V564I or V564F is similar to that observed for wild-type FGFR2. For example, inhibition of V565I or V565F is within about 2-fold (e.g., about 5-fold, about 7-fold, about 10-fold) of inhibition of wild-type FGFR2 (e.g., the compounds are similarly potent against wild-type FGFR2 and V565I or V565F). In some embodiments, selectivity for a wildtype or V565I or V565F FGFR2 kinase over another kinase is measured in an enzyme assay (e.g., an enzyme assay as provided herein). In some embodiments, the compounds provided herein (e.g., compounds of Formula I) exhibit selective cytotoxicity to FGFR2-mutant cells.

In some embodiments, inhibition of FGFR3 V555M is similar to that observed for wild-type FGFR3. For example, inhibition of V555M is within about 2-fold (e.g., about 5-fold, about 7-fold, about 10-fold) of inhibition of wild-type FGFR3 (e.g., the compounds are similarly potent against wild-type FGFR3 and V555M). In some embodiments, selectivity for a wildtype or V555M FGFR 3kinase over another kinase is measured in an enzyme assay (e.g., an enzyme assay as provided herein). In some embodiments, the compounds provided herein (e.g., compounds of Formula I) exhibit selective cytotoxicity to FGFR3-mutant cells.

In some embodiments, the compounds provided herein (e.g., compounds of Formula I) exhibit brain and/or central nervous system (CNS) penetrance. Such compounds are capable of crossing the blood brain barrier and inhibiting a FGFR kinase in the brain and/or other CNS structures. In some embodiments, the compounds provided herein are capable of crossing the blood brain barrier in a therapeutically effective amount. For example, treatment of a subject with cancer (e.g., a FGFR-associated cancer such as a FGFR-associated brain or CNS cancer) can include administration (e.g., oral administration) of the compound to the subject. In some such embodiments, the compounds provided herein are useful for treating a primary brain tumor or metastatic brain tumor. For example, a FGFR-associated primary brain tumor or metastatic brain tumor.

In some embodiments, the compounds of Formula I or a pharmaceutically acceptable salt or solvate thereof, exhibit one or more of high GI absorption, low clearance, and low potential for drug-drug interactions.

Compounds of Formula I are useful for treating diseases and disorders which can be treated with a FGFR kinase inhibitor, such as FGFR-associated diseases and disorders, e.g., proliferative disorders such as cancers, including hematological cancers and solid tumors, angiogenesis-related disorders, and developmental disorders such as achondroplasia, hypochondroplasia, or thanatophoric dysplasia.

The term "preventing" as used herein means the prevention of the recurrence or spread, in whole or in part, of the disease or condition as described herein, or a symptom thereof.

As used herein, the word "a" before a noun represents one or more of the particular noun. For example, the phrase "a cell" represents "one or more cells."

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with a dysregulation of a FGFR gene, a FGFR protein, or expression or activity, or level of any of the same (a FGFR-associated cancer) (e.g., as determined using a regulatory agency-approved, e.g., FDA-approved, assay or kit). In some embodiments, the subject has a tumor that is positive for a dysregulation of a FGFR gene, a FGFR protein, or expression or activity, or level of any of the same (e.g., as determined using a regulatory agency-approved assay or kit). The subject can be a subject with a tumor(s) that is positive for a dysregulation of a FGFR gene, a FGFR protein, or expression or activity, or level of any of the same (e.g., identified as positive using a regulatory agency-approved, e.g., FDA-approved, assay or kit). The subject can be a subject whose tumors have a dysregulation of a FGFR gene, a FGFR protein, or expression or activity, or a level of the same (e.g., where the tumor is identified as such using a regulatory agency-approved, e.g., FDA-approved, kit or assay). In some embodiments, the subject is suspected of having a FGFR-associated cancer. In some embodiments, the subject has a clinical record indicating that the subject has a tumor that has a dysregulation of a FGFR gene, a FGFR protein, or expression or activity, or level of any of the same (and optionally the clinical record indicates that the subject should be treated with any of the compositions provided herein). In some embodiments, the patient is a pediatric patient. In some embodiments, the patient is in utero.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds disclosed herein (e.g., compounds of Formula I) are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "FGFR-associated disease or disorder" as used herein refers to diseases or disorders associated with or having a dysregulation of a FGFR gene, a FGFR kinase (also called herein FGFR kinase protein or FGFR protein), or the expression or activity or level of any (e.g., one or more) of the same (e.g., any of the types of dysregulation of a FGFR gene, a FGFR kinase, a FGFR kinase domain, or the expression or activity or level of any of the same described herein). Non-limiting examples of a FGFR-associated disease or disorder include, for example, cancer, angiogenesis-related disorders, and developmental disorders such as achondroplasia, hypochondroplasia, or thanatophoric dysplasia. In some embodiments of any of the methods described herein, a FGFR-associated disease or disorder can be a FGFR1-associated disorder. In some embodiments of any of the methods described herein, a FGFR-associated disease or disorder can be a FGFR2-associated disease or disorder. In some embodiments of any of the methods described herein, a FGFR-associated disease or disorder can be a FGFR3-associated disease or disorder. In some embodiments of any of the methods described herein, a FGFR-associated disease or disorder can be a FGFR4-associated disease or disorder.

The term "FGFR-associated cancer" as used herein refers to cancers associated with or having a dysregulation of a FGFR gene, a FGFR kinase (also called herein FGFR kinase protein), or expression or activity, or level of any of the same. Non-limiting examples of a FGFR-associated cancer are described herein. In some embodiments of any of the methods described herein, a FGFR-associated cancer can be a FGFR1-associated cancer. In some embodiments of any of the methods described herein, a FGFR-associated cancer can be a FGFR2-associated cancer. In some embodiments of any of the methods described herein, a FGFR-associated cancer can be a FGFR3-associated cancer. In some embodiments of any of the methods described herein, a FGFR-associated cancer can be a FGFR4-associated cancer.

The phrase "dysregulation of a FGFR gene, a FGFR kinase, or the expression or activity or level of any of the same" refers to a genetic mutation (e.g., a chromosomal translocation that results in the expression of a fusion protein including a FGFR kinase domain and a fusion partner, a mutation in a FGFR gene that results in the expression of a FGFR protein that includes a deletion of at least one amino acid as compared to a wildtype FGFR protein, a mutation in a FGFR gene that results in the expression of a FGFR protein with one or more point mutations as compared to a wildtype FGFR protein, a mutation in a FGFR gene that results in the expression of a FGFR protein with at least one inserted amino acid as compared to a wildtype FGFR protein, a gene duplication that results in an increased level of FGFR protein in a cell, or a mutation in a regulatory sequence (e.g., a promoter and/or enhancer) that results in an increased level of FGFR protein in a cell), an alternative spliced version of a FGFR mRNA that results in a FGFR protein having a deletion of at least one amino acid in the FGFR protein as compared to the wild-type FGFR protein), or increased expression (e.g., increased levels) of a wildtype FGFR kinase in a mammalian cell due to aberrant cell signaling and/or dysregulated autocrine/paracrine signaling (e.g., as compared to a control non-cancerous cell). As another example, a dysregulation of a FGFR gene, a FGFR protein, or expression or activity, or level of any of the same, can be a mutation in a FGFR gene that encodes a FGFR protein that is constitutively active or has increased activity as compared to a protein encoded by a FGFR gene that does not include the mutation. For example, a dysregulation of a FGFR gene, a FGFR protein, or expression or activity, or level of any of the same, can be the result of a gene or chromosome translocation which results in the expression of a fusion protein that contains a first portion of FGFR that includes a functional kinase domain, and a second portion of a partner protein (i.e., that is not FGFR). In some examples, dysregulation of a FGFR gene, a FGFR protein, or expression or activity or level of any of the same can be a result of a gene translocation of one FGFR gene with another non-FGFR gene. Non-limiting examples of fusion proteins are described in Table BA. Non-limiting examples of FGFR kinase protein point mutations/insertions/deletions are described in Table BC. Additional examples of FGFR kinase protein mutations (e.g., point mutations) are FGFR inhibitor resistance mutations. Non-limiting examples of FGFR inhibitor resistance mutations are described in Table BE.

In some embodiments, dysregulation of a FGFR gene, a FGFR kinase, or the expression or activity or level of any of the same can be caused by an activating mutation in a FGFR gene (see, e.g., chromosome translocations that result in the expression of any of the fusion proteins listed in Table BA). In some embodiments, dysregulation of a FGFR gene, a FGFR kinase, or the expression or activity or level of any of the same can be caused by a genetic mutation that results in the expression of a FGFR kinase that has increased resistance to inhibition by a FGFR kinase inhibitor and/or a multi-kinase inhibitor (MKI), e.g., as compared to a wild-type FGFR kinase (see, e.g., the amino acid substitutions in Table BC). In some embodiments, dysregulation of a FGFR gene, a FGFR kinase, or the expression or activity or level of any of the same can be caused by a mutation in a nucleic acid encoding an altered FGFR protein (e.g., a FGFR fusion protein or a FGFR protein having a mutation (e.g., a primary mutation)) that results in the expression of an altered FGFR protein that has increased resistance to inhibition by a FGFR kinase inhibitor and/or a multi-kinase inhibitor (MKI), e.g., as compared to a wildtype FGFR kinase (see, e.g., the amino acid substitutions in Table BC). The exemplary FGFR kinase point mutations, insertions, and deletions shown in Table BC can be caused by an activating mutation and/or can result in the expression of a FGFR kinase that has increased resistance to inhibition by a FGFR kinase inhibitor and/or a multi-kinase inhibitor (MKI).

For example, dysregulation of a FGFR1 gene, a FGFR1 protein, or expression or activity, or level of the same, can include FGFR1 gene amplification, a FGFR1 gene fusion from those listed in Table BA, and/or one or more point mutations selected from those listed in Table BC (e.g., one of more of T141R, R445W, N546K, V561M, K656E, and G818R). Dysregulation of a FGFR2 gene, a FGFR2 protein, or expression or activity, or level of the same, can, e.g., include FGFR2 gene amplification, a FGFR2 gene fusion from those listed in Table BA, and/or one or more point mutations selected from those listed in Table BC (e.g., one or more of S252W, P253R, A315T, D336N, Y375C, C382R, V395D, D471N, I547V, N549K, N549Y, V565I, V565F, and K659E). Dysregulation of a FGFR3 gene, a FGFR3 protein, or expression or activity, or level of the same can, e.g., include FGFR3 gene amplification, a FGFR3 gene fusion from those listed in Table BA, and/or one or more point mutations selected from those listed in Table BC (e.g., one or more of S131L, R248C, S249C, G370C, S371C, Y373C, G380R, R399C, E627K, K650E, K650M, V555M, V554L, V677I, and D785Y). Dysregulation of a FGFR4 gene, a FGFR4 protein, or expression or activity, or level of the same can, e.g., include FGFR4 gene amplification and/or one or more point mutations selected from those listed in Table BC (e.g., one or more of R183S, R434Q, D425N in FGFR4 isoform 2, V550L, and R610H).

Additional examples of FGFR fusion proteins, FGFR point mutations, FGFR gene overexpression, or FGFR gene amplification that cause (or cause in part) the development of a FGFR-associated cancer are described in: Wu et al., Cancer Discovery 3:636, 2013; Wesche et al., Biochem. J. 437:199-213, 2011; Gallo et al., Cytokine Growth Factor Rev. 26:425-449, 2015; Parker et al., J. Pathol. 232:4-15, 2014; Katoh et al., Expert Rev. Anticancer Res. 10:1375-1379, 2010; Chang et al., PLoS One 9:e105524, 2014; Kelleher et al., Carcinogenesis 34:2198-2205, 2013; Katoh et al., Med. Res. Rev. 34:280-300, 2014; Knights et al., Pharmacol. Therapeutics 125:105-117, 2010; Turner et al., Sci. Transl. Med. 2:62p556, 2010; Dutt et al., PLoS One 6(6):e20351, 2011; Weiss et al., Sci. Transl. Med. 2:62ra93, 2010; Becker et al., J. Neuropathol. Exp. Neurol. 74:743-754, 2015; Byron et al., PLoS One 7(2):e30801, 2012; van Rhihn et al., Eur. J. Human Genetics 10:819-824, 2002; Hart et al., Oncogene 19(29):3309-3320, 2000; Lin et al., Cancer Res. 68:664-673, 2008; and Helsten et al., Clin. Cancer Res., e-publication dated Sep. 15, 2015 (each of which is incorporated herein by reference). Additional non-limiting aspects and examples of FGFR fusion proteins, FGFR point mutations, FGFR gene overexpression, or FGFR gene amplification are described below.

The term "activating mutation" describes a mutation in a FGFR kinase gene that results in the expression of a FGFR kinase that has an increased kinase activity, e.g., as compared to a wildtype FGFR kinase, e.g., when assayed under identical conditions. For example, an activating mutation can result in the expression of a fusion protein that includes a FGFR kinase domain and a fusion partner. In another example, an activating mutation can be a mutation in a FGFR kinase gene that results in the expression of a FGFR kinase that has one or more (e.g., two, three, four, five, six, seven, eight, nine, or ten) amino acid substitutions (e.g., any combination of any of the amino acid substitutions described herein) that has increased kinase activity, e.g., as compared to a wildtype FGFR kinase, e.g., when assayed under identical conditions. In another example, an activating mutation can be a mutation in a FGFR kinase gene that results in the expression of a FGFR kinase that has one or more (e.g., two, three, four, five, six, seven, eight, nine, or ten) amino acids deleted, e.g., as compared to a wildtype FGFR kinase, e.g., when assayed under identical conditions. In another example, an activating mutation can be a mutation in a FGFR kinase gene that results in the expression of a FGFR kinase that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to a wildtype FGFR kinase, e.g., the exemplary wildtype FGFR kinase described herein, e.g., when assayed under identical conditions. Additional examples of activating mutations are known in the art.

The term "wildtype" or "wild-type" describes a nucleic acid (e.g., a FGFR gene or a FGFR mRNA) or protein (e.g., a FGFR protein) that is found in a subject that does not have a FGFR-associated disease, e.g., a FGFR-associated cancer (and optionally also does not have an increased risk of developing a FGFR-associated disease and/or is not suspected of having a FGFR-associated disease), or is found in a cell or tissue from a subject that does not have a FGFR-associated disease, e.g., a FGFR-associated cancer (and optionally also does not have an increased risk of developing a FGFR-associated disease and/or is not suspected of having a FGFR-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a FGFR-associated cancer) in a subject in need of such treatment, the method comprising administering to the subject a therapeutically effective amount of a compound of Formula I or pharmaceutically acceptable salt or solvate thereof. For example, provided herein are methods for treating a FGFR-associated cancer in a subject in need of such treatment, the method comprising a) detecting a dysregulation of a FGFR gene, a FGFR kinase, or the expression or activity or level of any of the same in a sample from the subject; and b) administering a therapeutically effective amount of a compound of Formula I or a pharmaceutically acceptable salt or solvate thereof. In some embodiments, the dysregulation of a FGFR gene, a FGFR kinase, or the expression or activity or level of any of the same includes one or more fusion proteins. Non-limiting examples of FGFR gene fusion proteins are described in Table BA. In some embodiments, the fusion protein is FGFR3-TACC3. In some embodiments, the dysregulation of a FGFR gene, a FGFR kinase, or the expression or activity or level of any of the same includes one or more FGFR kinase protein point mutations/insertions. Non-limiting examples of FGFR kinase protein point mutations/insertions/deletions are described in Table BC. In some embodiments, the FGFR1 kinase protein point mutations/insertions/deletions are selected from the group consisting of T141R, R445W, N546K, V561M, K656E, and G818R. In some embodiments, the FGFR2 kinase protein point mutations/insertions/deletions are selected from the group consisting of S252W, P253R, A315T, D336N, Y375C, C382R, V395D, D471N, I547V, N549K, N549Y, V565I, V565F, and K659E. In some embodiments, the FGFR3 kinase protein point mutations/insertions/deletions are selected from the group consisting of S131L, R248C, S249C, G370C, S371C, Y373C, G380R, R399C, E627K, K650E, K650M, V555M, V554L, V677I, and D785Y. In some embodiments, the FGFR4 kinase protein point mutations/insertions/deletions are selected from the group consisting of R183S, R434Q, D425N in FGFR4 isoform 2, V550L, and R610H. In some embodiments, the FGFR kinase protein point mutations/insertions/deletions occur in a FGFR fusion protein (e.g., any of the FGFR gene fusion proteins described in Table BA).

A dysregulation of a FGFR gene, a FGFR protein, or expression or activity, or level of the same, can, e.g., include a mutation(s) in a FGFR1, FGFR2, FGFR3, or FGFR4 gene that results in a FGFR1, FGFR2, FGFR3, or FGFR4 protein containing at least one (e.g., two, three, four, or five) point mutations (e.g., one of more of the point mutations listed in Table BC or Table BD).

A dysregulation of a FGFR gene, a FGFR protein, or expression or activity, or level of the same, can be a mutation in a FGFR1, FGFR2, FGFR3, or FGFR4 gene that results in a deletion of one or more contiguous amino acids (e.g., at least two, at least three, at least four, at least 5, at least 6, at least 7, at least 8, at least 9, at least 10, at least 15, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, at least 390, or at least 400 amino acids) in the FGFR1, FGFR2, FGFR3, or FGFR4 protein (except for the deletion of amino acids in the kinase domain of FGFR1, FGFR2, FGFR3, or FGFR4 that would result in inactivation of the kinase domain).

In some examples, a dysregulation of a FGFR gene, a FGFR protein, or expression or activity, or level of the same, can include an alternate spliced form of a FGFR mRNA. In some examples, a dysregulation of a FGFR gene, a FGFR protein, or expression or activity, or level of the same, includes an amplification of a FGFR gene (e.g., one, two, three, or four additional copies of a FGFR1, FGFR2, FGFR3, and/or FGFR4 gene) that can result, e.g., in an autocrine expression of a FGFR gene in a cell.

In some embodiments of any of the methods or uses described herein, the cancer (e.g., FGFR-associated cancer) is a hematological cancer. In some embodiments of any of the methods or uses described herein, the cancer (e.g., FGFR-associated cancer) is a solid tumor. In some embodiments of any of the methods or uses described herein, the cancer (e.g., FGFR-associated cancer) is a lung cancer (e.g., small cell lung carcinoma, non-small cell lung carcinoma, squamous cell carcinoma, lung adenocarcinoma, large cell carcinoma, mesothelioma, lung neuroendocrine carcinoma, smoking-associated lung cancer), prostate cancer, colorectal cancer (e.g., rectal adenocarcinoma), endometrial cancer (e.g., endometrioid endometrial cancer, endometrial adenocarcinoma), breast cancer (e.g., hormone-receptor-positive breast cancer, triple-negative breast cancer, neuroendodrine carcinoma of the breast), skin cancer (e.g., melanoma, cutaneous squamous cell carcinoma, basal cell carcinoma, large squamous cell carcinoma), gallbladder cancer, liposarcoma (e.g., dedifferentiated liposarcoma, myxoid liposarcoma), pheochromocytoma, myoepithelial carcinoma, urothelial carcinoma, spermatocytic seminoma, stomach cancer, head and neck cancer (e.g., head and neck (squamous) carcinoma, head and neck adenoid cystic adenocarcinoma), brain cancer (e.g., glialneural tumors, glioma, neuroblastoma, glioblastoma, pilocytic astrocytoma, Rosette forming glioneural tumor, dysembryoplastic neuroepithelial tumor, anaplastic astrocytoma, medulloblastoma, ganglioglioma, oligodendroglioma), malignant peripheral nerve sheath tumor, sarcoma (e.g., soft tissue sarcoma (e.g., leiomyosarcoma), osteosarcoma), esophageal cancer (e.g., esophageal adenocarcinoma), lymphoma, bladder cancer (e.g., bladder urothelial (transition cell) carcinoma), cervical cancer (e.g., cervical squamous cell carcinoma, cervical adenocarcinoma), fallopian tube cancer (e.g., fallopian tube carcinoma), ovarian cancer (e.g., ovarian serous cancer, ovarian mucinous carcinoma), cholangiocarcinoma, adenoid cystic carcinoma, pancreatic cancer (e.g., pancreatic exocrine carcinoma, pancreatic ductal adenocarcinoma, pancreatic cancer intraepithelial neoplasia), salivary gland cancer (e.g., pleomorphic salivary gland adenocarcinoma, salivary adenoid cystic cancer), oral cancer (e.g., oral squamous cell carcinoma), uterine cancer, gastric or stomach cancer (e.g., gastric adenocarcinoma), gastrointestinal stromal tumors, myeloma (e.g., multiple myeloma), lymphoepithelioma, anal cancer (e.g., anal squamous cell carcinoma), prostate cancer (e.g., prostate adenocarcinoma), renal cell carcinoma, thymic cancer, gastroesophogeal junction adenocarcinoma, testicular cancer, rhabdomyosarcoma (e.g., alveolar rhabdomyosarcoma, embryonic rhabomyosarcoma), renal papillary carcinoma, liver cancer (e.g., hepatocellular carcinoma, intrahepatic cholangiocarcinoma), carcinoid, myeloid proliferative disorders (also called myeloid proliferative neoplasms (MPN); e.g., 8p11 myeloproliferative syndrome (EMS, also called stem cell leukemia/lymphoma), acute myeloid leukemia (AML), chronic myeloid leukemia (CML)), lymphoma (e.g., T-cell lymphoma, T-lymphoblastic lymphoma, acute lymphoblastic leukemia (ALL), B-cell lymphoma), myeloid and lymphoid neoplasms, chronic neutrophilic leukemia, phosphaturic mesenchymal tumor, thyroid cancer (e.g. anaplastic thyroid carcinoma), or biliary duct cancer. Additional examples of FGFR-associated cancer are listed in Tables BA, BB, and BC.

In some embodiments of any of the methods or uses described herein, the cancer (e.g., FGFR-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are FGFR-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a FGFR-associated cancer) is AML or CMML.

In some embodiments, the cancer (e.g., the FGFR-associated cancer) is a solid tumor. Examples of solid tumors (e.g., solid tumors that are FGFR-associated cancers) include, for example, lung cancer (e.g., lung adenocarcinoma, non-small-cell lung carcinoma, squamous cell lung cancer), bladder cancer, colorectal cancer, brain cancer, testicular cancer, bile duct cancer cervical cancer, prostate cancer, and sparmatocytic seminomas. See, for example, Turner and Grose, *Nat. Rev. Cancer,* 10(2):116-129, 2010.

In some embodiments, the cancer is selected from the group consisting of bladder cancer, brain cancer, breast cancer, cholangiocarcinoma, head and neck cancer, lung cancer, multiple myeloma, rhabdomyosarcoma, urethral cancer, and uterine cancer. In some embodiments the cancer is selected from the group consisting of FGFR fusion lung cancer, FGFR fusion breast cancer, FGFR fusion bladder cancer, FGFR fusion biliary tract cancer, FGFR fusion urethral cancer, FGFR fusion head and neck cancer, or FGFR fusion multiple myeloma. In some embodiments, the cancer is selected from the group consisting of lung cancer, breast cancer, and brain cancer. In some embodiments, a FGFR1-associated cancer is selected from the group consisting of lung cancer, breast cancer, and brain cancer. In some embodiments, the cancer is selected from the group consisting of breast cancer, uterine cancer, cholangiocarcinoma, and lung cancer. In some embodiments, a FGFR2-associated cancer is selected from the group consisting of breast cancer, uterine cancer, cholangiocarcinoma, and lung cancer. In some embodiments, the cancer is selected from the group consisting of lung cancer, bladder cancer, urethral cancer, multiple myeloma, and head and neck cancer. In some embodiments, a FGFR3-associated cancer is selected from the group consisting of lung cancer, bladder cancer, urethral cancer, multiple myeloma, and head and neck cancer. In some embodiments, the cancer is selected from lung cancer, rhabdomyosarcoma, and breast cancer. In some embodiments, a FGFR4-associated cancer is selected from lung cancer, rhabdomyosarcoma, and breast cancer.

In some embodiments, the patient is a human.

Compounds of Formula I and pharmaceutically acceptable salts and solvates thereof are also useful for treating a FGFR-associated cancer.

Accordingly, also provided herein is a method for treating a subject diagnosed with or identified as having a FGFR-associated disease or disorder (e.g., a FGFR-associated cancer, e.g., any of the exemplary FGFR-associated cancers disclosed herein), comprising administering to the subject a therapeutically effective amount of a compound of Formula I or a pharmaceutically acceptable salt or solvate thereof, or a pharmaceutical composition thereof as defined herein.

Dysregulation of a FGFR kinase, a FGFR gene, or the expression or activity or level of any (e.g., one or more) of the same can contribute to tumorigenesis. For example, a dysregulation of a FGFR kinase, a FGFR gene, or expression or activity or level of any of the same can be a translocation, overexpression, activation, amplification, or mutation of a FGFR kinase, a FGFR gene, or a FGFR kinase domain. Translocation can include a gene translocation resulting in the expression of a fusion protein that includes a FGFR kinase domain and a fusion partner. For example, a fusion protein can have increased kinase activity as compared to a wildtype FGFR protein. In some embodiments, a mutation in a FGFR gene can involve mutations in the FGFR ligand-binding site, extracellular domains, kinase domain, and in regions involved in protein:protein interactions and downstream signaling. In some embodiments, a mutation (e.g., an activating mutation) in a FGFR gene can result in the expression of a FGFR kinase having one or more (e.g., two, three, four, five, six, seven, eight, nine, or ten) amino acid substitutions (e.g., one or more amino acid substitutions in the kinase domain (e.g., corresponding to amino acid positions 477-761 in SEQ ID NO. 1, amino acid positions 480-764 in SEQ ID NO. 3, or amino acid positions 471-755 in SEQ ID NO. 5); a gatekeeper amino acid (e.g., corresponding to amino acid position 561 in SEQ ID NO. 1, amino acid position 564 in SEQ ID NO. 3, or amino acid position 555 in SEQ ID NO. 5); the P-loop (e.g., corresponding to amino acid positions 484-491 in SEQ ID NO. 1, amino acid positions 487-494 in SEQ ID NO. 3, or amino acid positions 478-485 in SEQ ID NO. 5); the DFG motif (e.g., corresponding to amino acid positions 641-643 in SEQ ID NO. 1, amino acid positions 644-646 in SEQ ID NO. 3, or amino acid positions 635-637 in SEQ ID NO. 5); the activation loop (e.g., corresponding to amino acid positions 640-665 in SEQ ID NO. 1, amino acid positions 643-668 in SEQ ID NO. 3, or amino acid positions 634-659 in SEQ ID NO. 5); the C-helix and loop preceeding the C-helix (e.g., corresponding to amino acid positions 524-545 in SEQ ID NO. 1, amino acid positions 527-548 in SEQ ID NO. 3, or amino acid positions 518-539 in SEQ ID NO. 5); and/or the ATP binding site (e.g., corresponding to amino acid positions 487-489, 562-565, 627, 628, 630, and 641 in SEQ ID NO. 1, amino acid positions 490-492, 565-568, 630, 631, 633, and 644 in SEQ ID NO. 3, or amino acid positions 481-483, 556-559, 621, 622, 624, and 635 in SEQ ID NO. 5). In some embodiments, a mutation can be a gene amplification of a FGFR gene. In some embodiments, a mutation (e.g., an activating mutation) in a FGFR gene can result in the expression of a FGFR kinase that lacks at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) as compared to a wildtype FGFR protein. In some embodiments, dysregulation of a FGFR kinase can be increased expression (e.g., increased levels) of a wildtype FGFR kinase in a mammalian cell due to aberrant cell signaling and/or dysregulated autocrine/paracrine signaling (e.g., as compared to a control non-cancerous cell). In some embodiments, a mutation (e.g., an activating mutation) in a FGFR gene can result in the expression of a FGFR kinase that has at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) inserted as compared to a wildtype FGFR protein. In some embodiments, dysregulation of a FGFR kinase can be increased expression (e.g., increased levels) of a wildtype FGFR kinase in a mammalian cell (e.g., as compared to a control non-cancerous cell), e.g., due to aberrant cell signaling and/or dysregulated autocrine/paracrine signaling. Other dysregulations can include FGFR mRNA splice variants. In some embodiments, the wildtype FGFR protein is the exemplary wildtype FGFR protein described herein.

In some embodiments, the dysregulation of a FGFR gene, a FGFR kinase, or expression or activity or level of any of the same, includes overexpression of wild-type FGFR kinase (e.g., leading to autocrine activation). In some embodiments, the dysregulation of a FGFR gene, a FGFR kinase protein, or expression or activity or level of any of the same, includes overexpression, activation, amplification, or mutation in a chromosomal segment comprising the FGFR gene or a portion thereof, including, for example, the kinase domain portion, or a portion capable of exhibiting kinase activity.

Several FGFR translocations have been identified to play a role in defects in development and in a wide range of malignancies, whereby chromosomal rearrangement results in a nucleic acid sequence encoding a fusion protein that includes a kinase domain of a FGFR protein and an amino acid sequence from a partner protein. In some examples, fusion proteins are located in the cytosol, do not undergo lysosomal degradation, are not susceptible to feedback inhibition, and are permanently dimerized in the absence of ligand. Such translocations can lead to FGFR overexpression, permanent dimerization of the fusion protein-FGFR complex, and continuous signaling. The mechanism of proliferation is dependent on the type of fusion protein and seems to be disease specific (Jackson C C, et al., Hum Pathol 2010; 41:461-476). For example, a t(4;14) intergenic translocation, bringing FGFR3 and the adjacent Multiple Myeloma SET domain (MMSET) gene under the control of the Ig heavy chain (IGH) promoter, has been identified in 10% to 20% of multiple myelomas and is associated with poor prognosis and dependence upon FGFR signaling (Chesi M, et al., Nat Genet 1997; 16:260-264; Qing J, et al., J Clin Invest 2009; 119:1216-1229). FGFR3 translocations are rarely found in prodromal conditions of multiple myeloma, implicating these translocations in the conversion to full multiple myeloma. Additional examples of FGFR fusion proteins and the specific FGFR-associated cancers that they cause (or cause in part) are listed in Table BA. The expression of FGFR fusion proteins can, e.g., cause (or cause in part) cholangiocarcinoma, bladder cancer, lung cancer, and breast cancer. Additional examples of FGFR fusion proteins are known in the art.

In some embodiments, the dysregulation of a FGFR gene, a FGFR kinase protein, or expression or activity or level of any of the same, includes one or more chromosome translocations or inversions resulting in a FGFR gene fusion. In some embodiments, the dysregulation of a FGFR gene, a FGFR kinase protein, or expression or activity or level of any of the same, is a result of genetic translocations in which the expressed protein is a fusion protein containing residues from a non-FGFR partner protein, and includes a minimum of a functional FGFR kinase domain.

Non-limiting examples of FGFR fusion proteins are shown in Table BA.

TABLE BA

FGFR Fusion Proteins

| FGFR | Fusion partner | Non-limiting Exemplary FGFR-Associated Cancer(s) |
|---|---|---|
| FGFR1 | TACC1 | Glioblastoma multiforme, Gastrointestinal stromal tumors[13] |
| FGFR1 | FGFR1 | Urothelial carcinoma |
| FGFR1 | CNTRL | Stem cell myeloproliferative disorders, EMS, AML, CML, T-cell lymphoma |
| FGFR1 | FGFR1OP2 | Myeloproliferative disorders, myeloproliferative disorder stem cell leukemia/lymphoma syndrome, acute myeloid leukemia, 8p11 myeloproliferative disorder[32], AML, MPN |
| FGFR1 | FGFR1OP (also called FOP) | Myeloproliferative disorders, e.g., acute myeloid leukemia, T-cell lymphoma, B-cell lymphoma, 8p11 myeloproliferative disorder, myeloproliferative disorder stem cell leukemia/lymphoma syndrome and |

TABLE BA-continued

FGFR Fusion Proteins

| FGFR | Fusion partner | Non-limiting Exemplary FGFR-Associated Cancer(s) |
|---|---|---|
| FGFR1 | ZMYM2 (also called RAMP, FIM, or ZNF198) | lung cancer, myeloid and lymphoid neoplasms Myeloproliferative disorder stem cell leukemia/lymphoma syndrome myeloid and lymphoid neoplasms, 8p11 myeloproliferative disorder, Chronic neutrophilic leukemia[22], ALL, CMD, T-lymphoblastic lymphoma, AML[2] |
| FGFR1 | CEP110 (also called CEP1 or centriolin) | Myeloid and lymphoid neoplasms; 8p11 myeloproliferative disorder, Myeloproliferative disorder stem cell leukemia/lymphoma syndrome |
| FGFR1 | BCR | Myeloproliferative disorder stem cell leukemia/lymphoma syndrome, 8p11 myeloproliferative disorder, AML, CML, ALL (e.g., B-ALL) |
| FGFR1 | LRRFIP1 | Myeloproliferative disorder stem cell leukemia/lymphoma syndrome, 8p11 myeloproliferative disorder, ALL, CMD, AML |
| FGFR1 | CPSF6 | Hematological Malignancies; 8p11 myeloproliferative disorder, CMD, MPN, AML, Myeloproliferative disorder stem cell leukemia/lymphoma syndrome |
| FGFR1 | BAG4 | Lung squamous cell carcinoma, non-small cell lung cancer |
| FGFR1 | ERLIN2 | Breast cancer |
| FGFR1 | TRIM24 (also called TIF1) | Myeloproliferative disorder stem cell leukemia/lymphoma syndrome, 8p11 myeloproliferative disorder, AML, MPN |
| FGFR1 | MYO18A | Myeloproliferative disorder stem cell leukemia/lymphoma syndrome, 8p11 myeloproliferative disorder, MPN, AML |
| FGFR1 | HERV-K | Myeloproliferative disorder stem cell leukemia/lymphoma syndrome, 8p11 myeloproliferative disorder, CMD, MPD, AML |
| FGFR1 | PLAG1 | Head and neck cancer, pleomorphic salivary gland adenocarcinoma |
| FGFR1 | CUX1 | Leukemia, lymphoma, 8p11 myeloproliferative disorder, AML, MPN |
| FGFR1 | FOXO1 | Rhabdomyosarcoma, alveolar rhabdomyosarcoma |
| FGFR1 | SQSTM1 | Leukemia |
| FGFR1 | FN1 | Phosphaturic mesenchymal tumor |
| FGFR1 | NUP98 | 8p11 myeloproliferative disorder |
| FGFR1 | RANBP2 (also called NUP358) | 8p11 myeloproliferative disorder, MPN, AML |
| FGFR1 | TPR | 8p11 myeloproliferative disorder, MPN, T-lymphoblastic lymphoma, MPN T-lymphoblastic lymphoma |
| FGFR1 | ZNF703 | Breast cancer |
| FGFR1 | NTM | Bladder cancer, bladder urothelial (transition cell) carcinoma |
| FGFR1[1] | ZNF343 | Osteosarcoma |
| FGFR1[3] | FOP2 | AML |
| FGFR1[7] | OP2 | AML |
| FGFR1[11] | TKD | Glioma |
| FGFR1[15] | ADAM32 | Embryonal Rhabdomyosarcoma |
| FGFR1[17] | EGFR | Non-small cell lung carcinoma |
| FGFR1[27] | ZNF577 | Breast cancer |
| FGFR1[28] | ZNF791 | |
| FGFR1[28] | NDS3 (also called as WHSC1L1) | Breast cancer[29] |
| FGFR1[28] | ADGRA2 (also called GPR124) | |
| FGFR1[28] | RHOT1 | Bladder cancer[29] |
| FGFR1[29] | ADAM18 | Bladder cancer |
| FGFR1[29] | SLC20A2 | Lung adenocarcinoma |
| FGFR1[31] | RUNX1 | Myeloproliferative neoplasm[31] |
| FGFR1[37] | USP6 | Aneurysmal bone cyst |
| FGFR1[38] | HOOK3 | Gastrointestinal stromal tumor[38] |

TABLE BA-continued

FGFR Fusion Proteins

| FGFR | Fusion partner | Non-limiting Exemplary FGFR-Associated Cancer(s) |
|---|---|---|
| FGFR2 | CCAR2 | Lung squamous cell carcinoma |
| FGFR2 | CD44 | Gastric cancer |
| FGFR2 | BICC1 | Metastatic cholangiocarcinoma, cholangiocarcinoma, colorectal cancer, hepatocellular carcinoma, carcinoma of unknown primary |
| FGFR2 | SLC45A3 | Prostate cancer |
| FGFR2 | AFF3 | Breast cancer |
| FGFR2 | CASP7 | Breast cancer |
| FGFR2 | CCDC6 | Breast cancer, cholangiocarcinoma |
| FGFR2[16] | KIAA1598 (also called SHOOTIN1) | Cholangiocarcinoma, intrahepatic cholangiocarcinoma |
| FGFR2 | KIAA1967 | Lung squamous cell cancer |
| FGFR2 | OFD1 | Thyroid cancer |
| FGFR2 | CIT | Lung adenocarcinoma |
| FGFR2 | AHCYL1 | Cholangiocarcinoma |
| FGFR2 | PPHLN1 | Cholangiocarcinoma |
| FGFR2 | TACC3 | Cholangiocarcinoma, intrahepatic cholangiocarcinoma |
| FGFR2 | MGEA5 | Cholangiocarcinoma, intrahepatic cholangiocarcinoma |
| FGFR2 | FAM76A | Ovarian cancer |
| FGFR2 | FRAG1 | Osteosarcoma |
| FGFR2 | NPM1 | Colorectal carcinoma (e.g., colorectal adenocarcinoma), large cell lung carcinoma |
| FGFR2 | TACC2 | Cancer of unknown primary, gastric cancer, gastoesophageal junction adenocarcinoma |
| FGFR2 | C10orf68 | Gastric cancer, gastroesophageal junction adenocarcinoma |
| FGFR2 | NCALD | Breast carcinoma |
| FGFR2 | NOL4 | Cholangiocarcinoma |
| FGFR2 | PPAPDC1A | Prostate carcinoma |
| FGFR2[5] | PARK2 | Cholangiocarcinoma |
| FGFR2[5] | ZDHHC6 | Cholangiocarcinoma |
| FGFR2[6] | TXLNA | Biliary tract cancer |
| FGFR2[6] | KCTD1 | Biliary tract cancer |
| FGFR2[6] | BICC1 type 2 | Biliary tract cancer |
| FGFR2[8] | CCDC147 | Cholangiocarcinoma |
| FGFR2[8] | VCL | Cholangiocarcinoma |
| FGFR2[9] | BUB1 | Cholangiocarcinoma |
| FGFR2[9] | CDCA8 | Cholangiocarcinoma |
| FGFR2[9] | DNAH5 | Cholangiocarcinoma |
| FGFR2[10] | OGDH | Anaplastic thyroid carcinoma |
| FGFR2[12] | CCDC3 | Breast carcinoma |
| FGFR2[14] | KIAA1217 | Cholangiocarcinoma |
| FGFR2[18] | INA | Ganglioma |
| FGFR2[19] | IDH1 | Cholangiocarcinoma |
| FGFR2[23] | WAC | Hepatobiliary cancer |
| FGFR2[23] | OPTN | Hepatobiliary cancer |
| FGFR2[23] | ZMYM4 | Hepatobiliary cancer |
| FGFR2[23] | TBC1D1 | Hepatobiliary cancer |
| FGFR2[23] | FRK | Hepatobiliary cancer |
| FGFR2[23] | CREB5 | Hepatobiliary cancer |
| FGFR2[23] | STK26 | Hepatobiliary cancer |
| FGFR2[24] | TACC1 | Intrahepatic cholangiocarcinoma |
| FGFR2[25] | PDHX | Gastric carcinoma |
| FGFR2[25] | COL14A1 | Colorectal adenocarcinoma |
| FGFR2[26] | PASD1 | Oligodendrogliomaa |
| FGFR2[28] | ATE1 | |
| FGFR2[28] | NSMCE4A | |
| FGFR2[29] | USP10 | Ovarian cancer |
| FGFR2[33] | KLK2 | Prostate cancer |
| FGFR2[34] | CEP55 | Pancreatic intraductal tubulopapillary neoplasm |
| FGFR2[34] | SASS6 | Pancreatic intraductal tubulopapillary neoplasm |
| FGFR2[34] | DISP1 | Pancreatic intraductal tubulopapillary neoplasm |
| FGFR2[35] | GAB2 | Esophageal adenocarcinoma |
| FGFR2[36] | ACSL5 | Gastric cancer |
| FGFR3 | ELAVL3 | Glioblastoma multiforme |
| FGFR3 | TACC3 | Bladder cancer, oral cancer, head and neck squamous cell carcinoma, lung |

TABLE BA-continued

FGFR Fusion Proteins

| FGFR | Fusion partner | Non-limiting Exemplary FGFR-Associated Cancer(s) |
|---|---|---|
| | | squamous cell carcinoma, cervical carcinoma or cancer, cervical adenocarcinoma, gallbladder cancer or carcinoma, lung adenocarcinoma, non-small cell lung cancer, glioma, glioblastoma multiforme, carcinoma of unknown primary, endometrial adenocarcinoma, glioma, renal cell carcinoma, urothelial carcinoma, pancreatic exocrine carcinoma, urothelial carcinoma |
| FGFR3 | BAIAP2L1 | Bladder cancer, lung adenocarcinoma, lung squamous cell carcinoma |
| FGFR3 | IGH | Multiple myeloma |
| FGFR3 | MMSET | Multiple myeloma |
| FGFR3 | TEL/ETV6 | T-cell lymphoma |
| FGFR3 | JAKMIP1 | Bladder cancer, bladder urothelial (transition cell) carcinoma, urothelial carcinoma |
| FGFR3 | TNIP2 | Bladder urothelial (transition cell) carcinoma, urothelial carcinoma |
| FGFR3 | WHSC1 (also called NSD2) | Breas carcinoma, multiple myeloma[30] |
| FGFR3 | ADD1 | Urothelial carcinoma |
| FGFR3[4] | RANBP17 | Breast carcinoma |
| FGFR3[20] | TET2 | Multiple myeloma |
| FGFR3[21] | NBR1 | Anaplastic astrocytoma |
| FGFR3[21] | BRAP | Glioblastoma multiforme |
| FGFR3[29] | AES | Prostate adenocarcinoma |
| FGFR3[29] | TPRG1 | Head and neck squamous cell carcinoma |
| FGFR3[30] | TET | Multiple myeloma |

[1] Baroy et al., *PloS One*; 11(9): e0163859. doi: 10.1371/journal.pone.0163859, 2016.
[2] Ren et al., *Int. J. Cancer*, 139(4): 836-40, 2016.
[3] Marchwicka et al., *Cell Biosci.*, 6: 7. doi: 10.1186/s13578-016-0075-9, 2016.
[4] PCT Patent Application Publication No. WO 2014/071419A2.
[5] U.S. Patent Application Publication No. 2015/0366866A1.
[6] PCT Patent Application Publication No. WO 2016/084883A1.
[7] PCT Patent Application Publication No. WO 2016/030509A1.
[8] PCT Patent Application Publication No. WO 2015/150900A2.
[9] PCT Patent Application Publication No. WO 2015/120094A2.
[10] Kasaian et al., *BMC Cancer.*, 15: 984, 2015.
[11] Vakil et al., *Neuro-Oncology*, 18: Supp. Supplement 3, pp. iii93. Abstract Number: LG-64, 17th International Symposium on Pediatric Neuro-Oncology, Liverpool, United Kingdom, 2016.
[12] Astsaturov et al., *Journal of Clinical Oncology*, 34: Supp. Supplement 15, Abstract Number: 11504, 2016 Annual Meeting of the American Society of Clinical Oncology, Chicago, IL.
[13] Heinrich et al., *Journal of Clinical Oncology*, 34: Supp. Supplement 15, Abstract Number: 11012, 2016 Annual Meeting of the American Society of Clinical Oncology, Chicago, IL.
[14] Hall et al., *Molecular Cancer Therapeutics*, Vol. 14, No. 12, Supp.2, Abstract Number: B151, AACR-NCI-EORTC International Conference: Molecular Targets and Cancer Therapeutics, 2015.
[15] Reuther et al., *Journal of Molecular Diagnostics*, Vol. 17, No. 6, pp. 813, Abstract Number: ST02, 2015 Annual Meeting of the Association for Molecular Pathology, Austin, TX.
[16] Moeini et al., *Clin. Cancer. Res.*, 22(2):291-300, 2016.
[17] Schrock et al, *J Thorac. Oncol.* pii S1556-0864(18)30674-9, 2018. doi: 10.1016/j.jtho.2018.05.027
[18] Pekmezci et al, *Acta Nurotaphol. Commun.* 6(1): 47. doi: 10.1186/540478-018-0551-z
[19] Lowery et al. *Clin Cancer Res.* pii: clincanres.0078.2018. doi: 10.1158/1078-0432.CCR-18-0078
[20] Ryland et al. *J Clin Pathol* pii: jclinpath-2018-205195, 2018. doi: 10.1136/jclinpath-2018-205195.
[21] Ferguson et al. *J Neuropathol Exp Neurol* 77(6): 437-442, 2018. doi: 10.1093/jnen/nly022
[22] Wu et al, *BMC Cancer* 18(1): 343, 2018. doi: 10.1186/512885-018-4236-6
[23] Shibata et al, *Cancer Sci* 109(5): 1282-1291, 2018. doi: 10.1111/cas.13582
[24] Papdopoulos et al, *Br J Cancer*, 1117(11): 1592-1599, 2017. doi: 10.1038/bjc.2017.330
[25] Hall et al, *PLoS One*, 11(9): e1062594, 2016. doi: 10.1371/journal.pone.0162594
[26] Johnson et al, *Oncologist*, 22(12): 1478-1490, 2017. doi: 10.1634/theoncologist.2017-0242
[27] Yang et al, *Am J Hum Genet*, 98(5): 843-856, 2016. doi: 10.1016/j.ajhg.2016.03.017
[28] U.S. Patent Application Publication No. 2013/009621
[29] Babina and Turner, *Nat Rev Cancer* 17(5): 318-332, 2017. doi: 10.1038/nrc.2017.8
[30] Ryland et al, *J Clin Pathol.*, 2018 May 14. pii: jclinpath-2018-205195. doi: 10.1136/jclinpath-2018-205195. [Epub ahead of print]
[31] Kumar et al, *Am J Clin Pathol.* 143(5): 738-748, 2015. doi: 10.1309/AJCPUD6W1JLQQMNA
[32] Grand et al, *Genes Chromosomes Cancer* 40(1): 78-83, 2004. doi: 10.1002/gcc.20023
[33] Reeser, et al, *J Mol Diagn*, 19(5): 682-696, 2017. doi: 10.1016/j.jmoldx.2017.05.006
[34] Basturk, et al, *Mod Pathol*, 30(12): 1760-1772, 2017. doi: 10.1038/modpathol.2017.60
[35] Wang, et al, *Cancer* 123(20): 3916-3924, 2017. doi: 10.1002/cncr.30837
[36] Kim, et al, *Oncotarget*, 8(9): 15014-15022, 2017. doi: 10.18632/oncotarget.14788
[37] Busse, et al, *Genes Chromosomes Cancer*, 56(10): 730-749, 2017. doi: 10.1002/gcc.22477
[38] Shi, et al, *J Transl Med.*, 14(1): 339, 2016. doi: 10.1186/512967-016-1075-6

FGFR gene amplification often leads to FGFR overexpression, which can provoke ligand-independent signaling. In breast cancer, amplification of the genomic locus of FGFR1 (8p11-12) occurs in approximately 10% of predominantly estrogen receptor (ER)-positive patients (Taylor J G, et al., J Clin Invest 2009; 119:3395-4307). In vitro studies support the potential oncogenic nature of FGFR1 amplification (Welm B E, et al., J Cell Biol 2002; 157:703-14); however, due to the gene-dense nature of the 8p11-12 amplicon in breast cancer, there is continuing debate about the identity of the driving oncogene. More recently, FGFR1 has been found to be amplified in 22% of squamous NSCLC (Weiss J, et al., Sci Transl Med 2010; 2:62ra93), and these amplifications seem to confer dependence upon FGFR signaling. Unlike the broad amplicon containing FGFR1 found in breast cancers, the amplicon in lung is more focal; it remains to be seen if these differences influence the degree of oncogenic addiction to FGFR1. FGFR2 amplifications have been reported in up to 10% of gastric cancers, most of which are diffuse-type with relatively poor prognosis (Kunii K, et al., Cancer Res 2008; 68:2340-2348). Further, in a FGFR2-amplified gastric cancer cell line, Snu-16, FGFR2 downregulation led to significant inhibition of cell growth and survival that further translated into tumor growth regression in vivo (Xie L, et al., AZD4547, a potent and selective inhibitor of FGF-receptor tyrosine kinases 1, 2 and 3, inhibits the growth of FGF-receptor 2 driven gastric cancer models in vitro and in vivo. In: Proceedings of the American Association of Cancer Research Annual Meeting; 2011 Apr. 2-6; Orlando (Fla.). Philadelphia (Pa.): AACR; 2011. Abstract nr 1643). In some gastric cancer cell lines, FGFR2 amplification is accompanied by deletion of the coding exon located proximal to the C-terminus (Ueda T, et al., Cancer Res 1999; 59:6080-6086). This deletion impedes receptor internalization, thereby contributing to constitutive activation of the receptor. The presence of FGFR2 gene amplifications in gastric cancer is associated with sensitivity to inhibition of FGFR signaling by tyrosine kinase inhibitors and monoclonal antibodies in preclinical models (Zhao G, et al., Mol Cancer Ther 2011; 10:2200-2210; Zhao W M, et al., Clin Cancer Res 2010; 16:5750-5758). Non-limiting examples of FGFR-associated cancers that are caused (or caused in-part) by the amplification and/or overexpression of the FGFR1 gene, the FGFR2 gene, the FGFR3 gene, or the FGFR4 gene are listed in Table BB.

TABLE BB

Overexpression or Amplification of FGFR Genes and FGFR-Associated Cancer

| Type of Dysregulation | FGFR-Associated Cancer |
|---|---|
| FGFR1 | |
| Amplification or Overexpression | Breast cancer or carcinoma (e.g., hormone receptor-positive breast cancer, ductal carcinoma in situ (breast)), pancreatic ductal adenocarcinoma, pancreatic exocrine carcinoma, smoking-associated lung cancer, small cell lung cancer, lung adenocarcinoma, non-small cell lung cancer, squamous cell lung cancer or carcinoma, prostate cancer or carcinoma, ovarian cancer, fallopian tube carcinoma, bladder cancer, rhabdomyosarcoma, head and neck carcinoma (e.g., head and neck squamous cell carcinoma), esophageal cancer (e.g., esophageal squamous cell carcinoma), sarcoma (e.g., osteosarcoma), hepatocellular carcinoma, renal cell carcinoma, colorectal cancer (e.g., colorectal adenocarcinoma), prostate cancer, salivary gland tumors, glioblastoma multiforme, urinary bladder cancer, urothelial carcinoma, carcinoma of unknown primary, squamous non-lung tumors, gastric cancer, gastroesophageal junction carcinoma, adenoid cystic carcinoma, anal squamous cell carcinoma, oral squamous cell carcinoma, cholangiocarcinoma, hemangioendothelioma, leiomyosarcoma, melanoma, neuroendocrine carcinoma, squamous cell carcinoma, uterine carcinosarcoma |
| FGFR2 | |
| Amplification | Gastric cancer, gastroesophageal junction adenocarcinoma, breast cancer (e.g., triple-negative breast cancer), colon cancer, colorectal cancer (e.g., colorectal adenocarcinoma), urothelial cancer, bladder adenocarcinoma, carcinoma of unknown primary, cholangiocarcinoma, endometrial adenocarcinoma, esophageal adenocarcinoma, gallbladder carcinoma, ovarian cancer, fallopian tube carcinoma, pancreatic exocrine carcinoma, sarcoma, squamous cell carcinoma |
| Overexpression | Myxoid lipocarcinoma, rectal cancer, renal cell carcinoma, breast cancer |
| FGFR3 | |
| Upregulation of Activity | Colorectal cancer, hepatocellular carcinoma, pancreatic exocrine carcinoma |
| Overexpression | Multiple myeloma, thyroid carcinoma, |
| Amplification | Bladder cancer and salivary adenoid cystic cancer, urothelial cancer, breast cancer, carcinoid, carcinoma of unknown primary, colorectal cancer (e.g., colorectal adenocarcinoma), gallbladder carcinoma, gastric cancer, gastroesophageal junction adenocarcinoma, glioma, mesothelioma, non-small cell lung carcinoma, small cell lung cancer, ovarian cancer, fallopian tube carcinoma, pancreatic exocrine carcinoma |
| FGFR4 | |
| Amplification | Rhabdomyosarcoma, prostate cancer or carcinoma, breast cancer, urothelial cancer, carcinoid, carcinoma of unknown primary, esophageal adenocarcinoma, head and neck carcinoma, hepatocellular carcinoma, non-small cell lung carcinoma, ovarian cancer, fallopian tube carcinoma, peritoneal carcinoma, renal cell carcinoma |
| Upregulation of Activity | Colorectal cancer, hepatocellular carcinoma, adrenal carcinoma, breast cancer |
| Overexpression | Pancreatic intraepithelial neoplasia, and pancreatic ductal adenocarcinoma |

FGFR mutations that confer constitutive activation have been described in a number of congenital skeletal disorders (Turner N, Grose R., Nat Rev Cancer 2010; 10:116-129). FGFRs have been identified as among the most commonly mutated kinase genes in human cancers, with mutations in FGFR2 and FGFR3 being most prevalent (Turner N., Grose R., Nat Rev Cancer 2010; 10:116-129). For example, approximately 50% to 60% of non-muscle invasive and 17% of high-grade bladder cancers possess FGFR3 mutations that cause constitutive FGFR dimerization and activation (Cappellen D. et al., Nat Genet 1999; 23:18-20). Activating and oncogenic FGFR2 mutations located in the extracellular and kinase domains of the receptor have been described in 12% of endometrial carcinomas (Dutt A. et al., Proc Natl Acad Sci USA 2008; 105:8713-8717). Importantly, the FGFR2 mutations found in endometrial cancer confer sensitivity to FGFR inhibition (Dutt A. et al., Proc Natl Acad Sci USA 2008; 105:8713-8717).

More recently, FGFR2 mutations have been described in 5% of squamous non-small cell lung cancers (NSCLC; Hammerman P. et al., Genomic characterization and targeted therapeutics in squamous cell lung cancer [abstract]. In: Proceedings of the 14th World Conference on Lung Cancer; 2011 3-7 Jul.; Aurora (Colo.): International Association for the Study of Lung Cancer; 2011). FGFR3 mutations in bladder cancer and FGFR2 mutations in endometrial cancer are mutually exclusive with mutations in HRAS and KRAS, respectively. In addition, mutations in the FGFR4 kinase domain have been found in the childhood soft tissue sarcoma rhabdomyosarcoma, causing autophosphorylation and constitutive signaling (Taylor J G, et al., J Clin Invest 2009; 119:3395-407). FGFR1, FGFR2, FGFR3, and/or FGFR4 can include one, two, three, four, five, six, seven, eight, nine, ten, eleven, twelve, thirteen, fourteen, fifteen, sixteen, seventeen, eighteen, nineteen, or twenty different point mutations (as compared to an appropriate corresponding wildtype FGFR1, FGFR2, FGFR3, or FGFR4 amino acid sequence, respectively). Non-limiting examples of point mutations in FGFR1, FGFR2, FGFR3, or FGFR4 that are thought to cause (or cause in-part) a FGFR-associated cancer are listed in Table BC.

In some embodiments, the dysregulation of a FGFR gene, a FGFR kinase, or expression or activity or level of any of the same, includes one or more deletions (e.g., deletion of corresponding to amino acids 795-808 in SEQ ID NO:5), insertions, or point mutation(s) in a FGFR kinase. In some embodiments, the dysregulation of a FGFR gene, a FGFR kinase, or expression or activity or level of any of the same, includes a deletion of one or more residues from the FGFR kinase, resulting in constitutive activity of the FGFR kinase domain. In some embodiments, the dysregulation of a FGFR gene, a FGFR kinase, or expression or activity or level of any of the same, includes at least one point mutation in a FGFR gene that results in the production of a FGFR kinase that has one or more amino acid substitutions, insertions, or deletions as compared to the wild-type FGFR kinase (see, for example, the point mutations listed in Table BC or Table BD).

TABLE BC

FGFR Point Mutations

FGFR1

| Amino acid position (αA1 isoform)[1,A] | Amino acid position (αB1 isoform)[1,B] | Amino acid position (other isoform) | Non-limiting Exemplary mutation(s) | Non-limiting Exemplary FGFR-Associated Cancer(s) |
|---|---|---|---|---|
| 25 | 25 | | P25Q | Lung cancer |
| 70 | 70 | | G70R | Lung cancer, Lung squamous cell carcinoma |
| 78 | 78 | | R78H | Prostate cancer |
| 79 | 79 | | T79N[48] | Colorectal cancer[48] |
| | | 87[J] | R87C[66] | Cholangiocarcinoma[66] |
| | | 93[J] | D93Y[68] | Squamous cell lung cancer[68] |
| 97 | 97 | | A97T | Endometrioid endometrial cancer or endometrial cancer |
| 107 | 107 | | S107L[48] | Colorectal cancer[48] |
| | | 109[J] | S109N[66] | Cholangiocarcinoma[66] |
| 125 | 125 | | S125L, c.373_374insTCA/ p.S125-E126insS[40] | Breast cancer, skin cancer, Gallbladder cancer, Dedifferentiated liposarcoma[24], Non-small cell lung carcinoma[40] |
| 126 | 126 | | P126S[2] | Neuroendocrine carcinoma of the breast |
| 127 | 127 | | D127E[49] | Pheochromocytoma[49] |
| | | 140[J] | S140L[51] | Myoepithelial carcinoma[51] |
| 141 | 141 | | T141R | Lung cancer, Non-small cell lung carcinoma, Lung squamous cell carcinoma, Endometrial adenocarcinoma, Urothelial carcinoma |
| 150 | 150 | | P150S | Colorectal cancer |
| 249 | 249 | | E249V[71] | Exposure to nephrotoxin aristolochic acid[71] |
| 252 | 252 | | P252R, P252S, P252T | Skin cancer, melanoma, lung cancer, Lung adenocarcinoma, Spermatocytic seminoma |
| 268 | 268 | | A268S | Colorectal cancer, Stomach cancer |
| | | 294[J] | A294T[66] | Cholangiocarcinoma[66] |
| 330 | 330 | | N330I | Spermatocytic seminoma |
| 334 | 334 | | E334Q | Head and neck squamous cell carcinoma |

TABLE BC-continued

FGFR Point Mutations

| | | | | |
|---|---|---|---|---|
| 340 | 340 | | T340M[45] | Colon adenocarcinoma[45] |
| 366 | 366 | | P366P[55] | Lung adenocarcinoma[55] |
| 374 | 374 | | Y374C | Spermatocytic seminoma |
| 381 | 381 | | C381R | Spermatocytic seminoma |
| | | 397[J] | P397L[66] | Cholangiocarcinoma[66] |
| 430 | 428 | | S430F | Colorectal cancer |
| 431 | 429 | | A431S | Colorectal cancer |
| 445 | 443 | | R445W | Cutaneous squamous cell carcinoma |
| | | 455[J] | R455C[66] | Cholangiocarcinoma[66] |
| 471 | 469 | | W471L | Lung cancer |
| 546 | 544 | | N546K | Brain cancer or glioneural tumors, glioma, neuroblastoma, Malignant peripheral nerve sheath tumor, paraganglioma, glioblastoma, Pilocytic astrocytoma, Rosette forming glioneural tumor, Pineal tumor, Sarcoma, Dysembryoplastic neuroepithelial tumor[19], (in vitro study) |
| 561 | 559 | | V561M[25,26,30-32] | (In vitro study) |
| 563 | 561 | | Y563C[32] | (In vitro study) |
| 569 | 567 | | L567T[41] | Glioneuronal tumor[41] |
| 576 | 574 | | R576W | Brain cancer or glioneural tumors, glioblastoma, Spermatocytic seminoma |
| 598 | 596 | | K598N | Esophageal adenocarcinoma |
| 610 | 608 | | G610D | Colorectal cancer |
| | | 614[J] | R614*[66] | Cholangiocarcinoma[66] |
| 654 | 652 | | Y654Y[65] | Intraheptatic cholangiocarcinoma[65] |
| 655 | 653 | | K655I | Pilocytic astrocytoma |
| 656 | 654 | | K656D, K656E, K656M, K656N | Brain cancer or glioneural tumors, glioma, glioblastoma, Pilocytic astrocytoma, Rosette forming glioneural tumor, Dysembryoplastic neuroepithelial tumor[19] |
| 661 | 659 | | R661P | Dysembryoplastic neuroepithelial tumor[19] |
| 658 | 656 | | T658P | Pilocytic astrocytoma |
| 664 | 662 | | V664L | Lung cancer, Lung large cell carcinoma |
| | | 668[J] | M668T[66] | Cholangiocarcinoma[66] |
| | | 686[J] | K668N[66] | Cholangiocarcinoma[66] |
| 772 | 770 | | P772S[59] | Neurofibromatosis type 1[59] |
| 788 | 786 | | C788Y[48] | Colorectal cancer[48] |
| 818 | 816 | | G818R | Urothelial carcinoma |
| | | 841[J] | H841Y[68] | Squamous cell lung cancer[68] |
| | Exon 18[41] | | Exon 18 inversion[41] | Glioneuronal tumor[41] |

FGFR2

| Amino acid position (IIIb isoform)[1,C] | Amino acid position (IIIc isoform)[1,D] | Amino acid position (other isoform) | Non-limiting Exemplary mutation(s) | Non-limiting Exemplary FGFR-Associated Cancer(s) |
|---|---|---|---|---|
| 24 | 24 | | S24F | Skin cancer, melanoma |
| 57 | 57 | | S57L[55] | Ulcerative colitis patients at high risk of colorectal carcinoma (UCHR)[70] |
| | | 71[E] | M71T[3] | Lymphoma, Bladder cancer |
| 73 | 73 | | T73N[72] | Squamous cell carcinoma[72] |
| 77 | 77 | | V77M | Skin cancer, melanoma |
| 97 | 97 | | A97T | Cervical cancer or cervical squamous cell carcinoma |
| 98 | 98 | | T98T[55] | Lung adenocarcinoma[55] |
| 101 | 101 | | D101Y | Endometrioid endometrial cancer or endometrial cancer |
| 104 | 104 | | L104P[44] | Colon cancer[44] |
| 116 | 116 | | E116K | Lung cancer, Lung adenocarcinoma |
| 138 | 138 | | D138N | Lung cancer, Squamous cell lung cancer |
| 142 | 142 | | D142V[45] | Rectal adenocarcinoma[45] |
| 156 | 156 | | W156* | Melanoma |
| 160 | 160 | | E160A | Skin cancer, melanoma |
| 161 | 161 | | K161N[66] | Cholangiocarcinoma[66] |
| 186 | 186 | | M186T | Lymphoma, Bladder cancer |
| 190 | 190 | | R190G | Lung cancer |
| 203 | 203 | | R203H, R203C | Colorectal cancer (e.g., colorectal adenocarcinoma), Breast cancer |

TABLE BC-continued

FGFR Point Mutations

| | | | |
|---|---|---|---|
| 210 | 210 | R210Q | Colorectal cancer (e.g., colorectal adenocarcinoma) |
| 211 | 211 | N211I | Lung cancer, Squamous cell lung cancer, Endometrioid endometrial cancer or endometrial cancer |
| 212 | 212 | Q212K | Brain Cancer, Gallbladder cancer |
| 213 | 213 | H213Y | Skin cancer, melanoma |
| 219 | 219 | E219K | Skin cancer, melanoma |
| 227 | 227 | G227E | Skin cancer, melanoma |
| 232 | 232 | V232V[55] | |
| 247 | 247 | D247Y | Lung cancer, Squamous cell lung cancer |
| 248 | 248 | V248D | Skin cancer, melanoma |
| 251 | 251 | R251Q | Skin cancer, melanoma |
| 252 | 252 | S252W, S252L, S252F | Basal cell carcinoma, Breast Cancer, Ovarian cancer, Fallopian tube carcinoma, Cervical cancer or cervical squamous cell carcinoma, Squamous cell lung cancer, Endometrioid endometrial cancer or endometrial cancer, Spermatocytic seminoma |
| 253 | 253 | P253L, P253R, P253S | Lung cancer, Lung adenocarcinoma, Squamous cell lung cancer, Non-small cell lung cancer, Endometrioid endometrial cancer or endometrial cancer, Spermatocytic seminoma, Oral squamous cell carcinoma |
| 256 | 256 | P256S | Cervical cancer or cervical squamous cell carcinoma |
| 266 | 266 | A266_S267insSTVVGGD[38] | Non-small cell lung cancer[38] |
| 267 | 267 | S267P | Stomach cancer, Spermatocytic seminoma |
| 271 | 271 | G271E, G271G[46] | Skin cancer, melanoma, hepatocellular carcinoma[46] |
| 272 | 272 | G272V | Ovarian cancer or ovarian serous cancer |
| 276 | 276 | F276V, F276C[65] | Spermatocytic seminoma, intrahepatic cholangiocarcinoma[65] |
| 278 | 278 | C278F | Spermatocytic seminoma |
| 281 | 281 | Y281C | Spermatocytic seminoma |
| 283 | 283 | D283N | Lung cancer, Squamous cell lung cancer |
| 288 | 288 | I288S[62] | (tumor induced in mice)[62] |
| 289 | 289 | Q289P | Spermatocytic seminoma |
| 290 | 290 | W290C, W290R[62] | Lung cancer, Squamous cell lung cancer, Endometrioid endometrial cancer or endometrial cancer, Spermatocytic seminoma, (tumor induced in mice)[62] |
| 290-291 | 290-291 | 290_291W1 > C (i.e., W290 and I291 replaced with C)[38,54] | Cholangiocarcinoma[38] |
| 292 | 292 | K292M | Exposure to nephrotoxin aristolochic acid[71] |
| 302 | 302 | G302W[4], G302K[44] | Lung cancer, Squamous cell lung cancer, colon cancer[44] |
| 305 | 305 | G305R | Skin cancer, melanoma |
| 310 | 310 | K310R | Endometrioid endometrial cancer or endometrial cancer |
| | 314 | A314D | Endometrioid endometrial cancer or endometrial cancer |
| | 315 | A315T, A315S | Colorectal cancer (e.g., colorectal adenocarcinoma), Lung cancer, Non-small cell lung cancer, Endometrioid endometrial cancer or endometrial cancer, Spermatocytic seminoma |
| 320 | | S320C[4] | Lung cancer, Squamous cell lung cancer |
| 332 | | E332K[66] | Cholangiocarcinoma[66] |
| 334 | 336 | D336N | Colorectal cancer (e.g., colorectal adenocarcinoma) |
| 336 | 338 | G338R | Spermatocytic seminoma |
| 338 | 340 | Y340C, Y340H | Spermatocytic seminoma |
| | 341 | T341P | Spermatocytic seminoma |

TABLE BC-continued

| | | FGFR Point Mutations | |
|---|---|---|---|
| 340 | 342 | C342F, C342R, C342S, C342W, C342Y | Spermatocytic seminoma |
| | 344 | A344G, A344P | Spermatocytic seminoma |
| 344 | 346 | N346K[62] | (tumor induced in mice)[62] |
| | 347 | S347C | Spermatocytic seminoma |
| 352 | 354 | S354C | Spermatocytic seminoma |
| 361 | | Q361R | Colorectal cancer (e.g., colorectal adenocarcinoma) |
| 371 | 370 | T370R | Melanoma |
| 373 | 372 | S372C | Endometrioid endometrial cancer or endometrial cancer |
| 376 | 375 | Y375C | Adenoid cystic carcinoma, Ovarian cancer or ovarian serous cancer, Endometrioid endometrial cancer or endometrial cancer, Pancreatic exocrine carcinoma, Spermatocytic seminoma |
| 381 | 380 | I380V | Lung cancer, Lung adenocarcinoma |
| 383 | 382 | C382R | Esophageal cancer, Lung cancer, Squamous cell lung cancer, Endometrioid endometrial cancer or endometrial cancer, Cholangiocarcinoma |
| 390 | 389 | A389T | Endometrioid endometrial cancer or endometrial cancer |
| 392 | 391 | M391R | Endometrioid endometrial cancer or endometrial cancer |
| 393 | 392 | V392A | Oral squamous cell carcinoma |
| 396 | 395 | V395D | Salivary gland carcinoma, Endometrioid endometrial cancer or endometrial cancer |
| 398 | 397 | L397M | Endometrioid endometrial cancer or endometrial cancer |
| 400 | 399 | R399Q[68] | Squamous cell lung cancer[68] |
| 406 | 405 | K405E | Cervical cancer or cervical squamous cell carcinoma |
| 421 | 420 | K420I | Lung cancer, Lung adenocarcinoma |
| 436 | 435 | S435I[70] | Ulcerative colitis patients at high risk of colorectal carcinoma (UCHR)[70] |
| 451 | 450 | R450Q[68] | Squamous cell lung cancer[68] |
| 459 | 458 | P459fs[45] | Colon adenocarcinoma[45] |
| 463 | 462 | G462E | Brain cancer, Spermatocytic seminoma |
| 471 | 470 | E470Q | Lung cancer, Squamous cell lung cancer |
| 472 | 471 | D471N | Gallbladder cancer |
| 475 | 474 | W474X | Skin cancer, melanoma |
| 476 | 475 | E475K | Skin cancer, melanoma |
| 480 | 479 | D479N | Lung cancer, Lung adenocarcinoma |
| 506 | 505 | K505E[70] | Ulcerative colitis patients at high risk of colorectal carcinoma (UCHR)[70] |
| 527 | 526 | K526E | Spermatocytic seminoma |
| 531 | 530 | D530N | Skin cancer, melanoma |
| 536 | 535 | M535I[14,33] | Endometrial cancer[14], (in vitro study)[33] |
| 538 | 537 | M535I[14,33] | Lung cancer, Squamous cell lung cancer, Endometrial cancer[14], (in vitro study)[33] |
| 545 | 544 | H544Q | Lung cancer, Lung adenocarcinoma |
| 548 | 547 | I547V[33], I547D | Anaplastic astrocytoma, Endometrioid endometrial cancer or endometrial cancer, (in vitro study)[33] |
| 549 | 548 | I548S[62] | (tumor induced in mice)[62] |
| 549/290 | 548/290 | I548S/W290R | (tumor induced in mice)[62] |
| 550 | 549 | N549D, N549K[14,33], N549Y, N549H[14,28,33,34], N549S[14,33], N549T[62] | Head and neck squamous cell carcinoma, Adenoid cystic carcinoma, basal cell carcinoma, breast cancer, Endometrioid endometrial cancer or endometrial cancer, Uterine carcinosarcoma, Spermatocytic seminoma, (in vitro study)[33,34], uterine cancer[28], (tumor induced in mice)[62] |
| 550/310 | 549/310 | K310R/N550K[52] | Endometrial carcinoma[52] |
| 552 | 551 | L551I | Colorectal cancer (e.g., colorectal adenocarcinoma) |
| 563 | 562 | V562L[29] | (in vitro study)[29] |
| 565 | 564 | V564I[14,28,33,34], V564F[29] | Endometrial cancer[14], (in vitro study)[29,33,34], uterine cancer[28] |

TABLE BC-continued

| | | FGFR Point Mutations | |
|---|---|---|---|
| 566 | 565 | E565G[14,28,33,34], E565A[58], E565L[62] | Endometrial cancer[14], (in vitro study)[33,34], uterine cancer[28], cholangiocarcinoma[58], (tumor induced in mice)[62] |
| 569 | 568 | S568L[62] | (tumor induced in mice)[62] |
| 569/563 | 568/562 | S568L/V562L[62] | (tumor induced in mice)[62] |
| 575 | 574 | E574K | Skin cancer, melanoma |
| 583 | 582 | P582L | Colorectal cancer (e.g., colorectal adenocarcinoma) |
| 584 | 583 | G583W[4], G583V | Lung cancer, Lung adenocarcinoma, Squamous cell lung cancer |
| 585 | 584 | M584V | Cervical cancer or cervical squamous cell carcinoma |
| 588 | 587 | 5587C | Breast cancer |
| 589 | 588 | Y588D | Cervical cancer or cervical squamous cell carcinoma |
| 591 | 590 | I590M | Lung cancer, Lung adenocarcinoma |
| 603 | 602 | D602E | Lung cancer, Squamous cell lung cancer |
| 613 | 612 | R612T | Lung cancer, adenocarcinoma |
| 618 | 617 | L617M[14,33], L617V[58] | Endometrial cancer[14], (in vitro study)[33], cholangiocarcinoma[58] |
| 621 | 620 | Q620K | Lung cancer, Lung adenocarcinoma |
| 626 | 625 | R625T | Lung cancer, Lung adenocarcinoma |
| 637 | 636 | E636K | Skin cancer, melanoma |
| 641 | 640 | M640I | Skin cancer, melanoma |
| 642 | 641 | K641R, K641N[14] | Adenoid cystic carcinoma, Spermatocytic seminoma, Endometrial cancer[14] |
| 643 | 642 | I642V | Skin cancer, melanoma |
| 649 | 648 | A648T | Skin cancer, melanoma |
| 660 | 659 | K659E[1,21,23], K659N[34], K659M[17,28,34] | Salivary gland carcinoma, Brain cancer, Medulloblastoma, Pilocytic astrocytoma, Breast cancer, Cervical cancer or cervical squamous cell carcinoma, Lung cancer, Squamous cell lung cancer, Endometrioid endometrial cancer or endometrial cancer, Spermatocytic seminoma, uterine cancer, Head and neck adenoid cystic carcinoma, (in vitro study)[34], uterine cancer[28] |
| 665 | 664 | R664W | Colorectal cancer (e.g., colorectal adenocarcinoma) |
| 689 | 688 | S688F | Skin cancer, melanoma |
| 702 | 701 | G701S | Skin cancer, melanoma |
| 709 | 708 | P708S | Skin cancer, melanoma |
| 719 | 718 | E718G[14,33] | Endometrial cancer[14], (in vitro study)[33] |
| 728 | 727 | N72S5[70] | Ulcerative colitis patients at high risk of colorectal carcinoma (UCHR)[70] |
| 759 | 758 | D758H[43] | |
| 760 | 759 | R759X, R759Q | Skin cancer, melanoma |
| 771 | 770 | L770V | Skin cancer, melanoma |
| 770 | | Y770IfsX14[14,33] | Endometrial cancer[14], (in vitro study)[33] |
| 773 | 772 | L772F | Lung cancer, Squamous cell lung cancer |
| 778 | 777 | E777K | Colorectal cancer (e.g., colorectal adenocarcinoma) |
| 779 | 778 | Q778A[41] | Glioneuronal tumor[41] |
| 787 | 786 | T786K | Lung cancer, Squamous cell lung cancer |
| Exon 17 | Exon 17 | Exon 17 splice site mutation[42] | Ganglioglioma[42] |
| | Splice site mutation 940-2A > G[13] | | Gastric cancer[13] |
| | Intron 17 | Intron 17 truncation[56] | Urothelial cancer |
| g.chr10:123237608_123237610delGAT[65] | | | Intrahepatic cholangiocarcinoma[65] |

TABLE BC-continued

FGFR Point Mutations

FGFR3

| Amino acid position (IIIb isoform)[1,F] | Amino acid position (IIIC isoform)[1,G] | Amino acid position (other isoform) | Non-limiting Exemplary mutation(s) | Non-limiting Exemplary FGFR-Associated Cancer(s) |
|---|---|---|---|---|
| 53 | 53 | | S53S[65] | Intrahepatic cholangiocarcinoma[65] |
| 64 | 64 | | P64P[65] | Intrahepatic cholangiocarcinoma[65] |
| 79 | 79 | | T79S | Lung cancer, Lung adenocarcinoma |
| 116 | 116 | | R116R[55] | |
| 121 | 121 | | F121Y[45] | Gastric adenocarinoma[45] |
| 131 | 131 | | S131L, S131S[55] | Urothelial carcinoma, testicular cancer[55] |
| 139 | 139 | | D139D[55] | |
| 192 | 192 | | G192D[66] | Cholangiocarncinoma[66] |
| 196 | 196 | | R196R[55] | Testicular cancer[55] |
| 197 | 197 | | G197S | Multiple myeloma |
| 201 | 201 | | I201I[55] | |
| 209 | 209 | | Q209H | Head and neck cancer |
| 216 | 216 | | E216K | Bladder cancer |
| 222 | 222 | | D222N | Bladder cancer |
| 228 | 228 | | C228R | Colorectal cancer |
| 235 | 235 | | G235D | Bladder cancer |
| 241 | 241 | | Y241C | Multiple myeloma |
| 248 | 248 | | R248C[18], R248H | Carcinoma of unknown primary, Gallbladder cancer, Cervical cancer, Head and neck cancer, Lung cancer, Non-small cell lung carcinoma, Squamous cell lung cancer, Urothelial carcinoma, Lymphoepithelioma, Multiple myeloma, Bladder cancer, Spermatocytic seminoma, Sarcoma, Seborrheic keratosis, Bladder cancer[18] |
| 249 | 249 | | S249C[16] | Carcinoma of unknown primary, Anal squamous cell carcinoma, Gallbladder cancer, Cervical cancer, Head and neck cancer, Lung cancer, Non-small cell lung carcinoma, Squamous cell lung cancer, Urothelial carcinoma, Cervical cancer, Multiple myeloma, Bladder cancer, Prostate cancer, Spermatocytic seminoma, Renal cell carcinoma, Pancreatic exocrine carcinoma, Seborrheic keratosis, Breast cancer[16], Exposure to nephrotoxin aristolochic acid[71] |
| 248/249 | 248/249 | | R248C/S249C[60] | Bladder cancer[60] |
| 250 | 250 | | P250R | Multiple myeloma, Spermatocytic seminoma |
| 270 | 270 | | D270N[69] | Bladder cancer[69] |
| 283 | 283 | | P283S | Bladder cancer |
| 286 | 286 | | Q286R[64] | Gastric cancer[64] |
| 299 | 299 | | G299S[39] | Bladder cancer[39] |
| 306 | 306 | | V306I | Bladder cancer |
| 320 | | | D320N[44] | Colon cancer[44] |
| | 320 | | E320*[64] | Gastric cancer[64] |
| | 322 | | E322K | Colorectal cancer |
| | 330 | | T330T[55] | |
| | 338 | | T338M[55] | |
| | 341 | | A341T | Esophageal cancer or esophageal adenocarcinoma |
| | 349 | | H349Y | Bladder cancer |
| | 352 | | A352E[44] | Colon cancer[44] |
| 370 | 368 | | E368K | Spermatocytic seminoma |
| 372 | 370 | | G370C | Gallbladder cancer, Cervical cancer, Lung cancer, Non-small cell lung carcinoma, Squamous cell lung cancer, Urothelial carcinoma, Multiple myeloma, Bladder cancer, Spermatocytic seminoma, Cutaneous squamous cell carcinoma, Seborrheic keratosis |
| 373 | 371 | | S371C | Multiple myeloma, Bladder cancer, Spermatocytic seminoma, Cutaneous squamous cell carcinoma, Seborrheic keratosis |

TABLE BC-continued

| | | FGFR Point Mutations | |
|---|---|---|---|
| 374 | 372 | V372C[39] | Bladder cancer[39] |
| 375 | 373 | Y373C | Gallbladder cancer, Urothelial carcinoma, Multiple myeloma, Bladder cancer, Spermatocytic seminoma, Thymic cancer |
| 377 | 375 | G375C | Spermatocytic seminoma |
| 381 | 379 | Y379C | Bladder cancer |
| 382 | 380 | G380R, G380E | Anal squamous cell carcinoma, Gallbladder cancer, Multiple myeloma, Bladder cancer, Spermatocytic seminoma, Urothelial carcinoma |
| 248/382 | 248/380 | R248C/G380R[60] | Bladder cancer[60] |
| 384 | 382 | G382D | Multiple myeloma |
| 386 | 384 | F384L[20] | Multiple myeloma, Bladder cancer, Prostate cancer[20], Pheochromocytoma[49] |
| 388 | 386 | F386L[20] | Head and neck cancer, Prostate cancer[20] |
| 378 | 376 | I376C | Bladder cancer |
| 392 | 390 | V390L[67] | Lung adenocarcinoma[67] |
| 393 | 391 | A393E | Urothelial carcinoma, Bladder cancer, Prostate cancer, Spermatocytic seminoma, Seborrheic keratosis |
| 401 | 399 | R399C, R399H[64] | Gastric cancer, gastroesophageal junction adenocarcinoma, Carcinoma of unknown primary, Colorectal cancer, gastric cancer[64] |
| | 400 | S400fs[48] | Colorectal cancer[48] |
| 413 | 411 | V411M[39] | Bladder cancer[39] |
| 415 | 413 | K413N | Head and neck cancer |
| 416 | 414 | I414I[55] | Lung cancer[55] |
| 422 | 420 | K420R[66] | Cholangiocarcinoma[66] |
| 431 | 429 | A431T[45] | Colon adenocarcinoma[45] |
| 435 | 433 | S433C | Lung cancer, Squamous cell lung cancer, Multiple myeloma |
| 443 | 441 | A441T | Multiple myeloma |
| 447 | 445 | S445L[48] | Colorectal cancer[48] |
| 454 | 452 | A452S | Multiple myeloma |
| 468 | 466 | E466K | Brain cancer, Glioblastoma |
| 542 | 540 | N540S, N540K, N540T, N540V | Bladder cancer, Spermatocytic seminoma |
| 557 | 555 | V555M[37] | KMS-11 myeloma cell line derivative[37] |
| 571 | 569 | A569V[44] | Colon cancer[44] |
| 587 | 585 | P585T[70] | Ulcerative colitis patients at high risk of colorectal carcinoma (UCHR)[70] |
| 605 | 603 | R603Q | Glioblastoma |
| 619 | 617 | D617G | Head and neck cancer |
| 629 | 627 | E627K | Sarcoma |
| 632 | 630 | V630M | Head and neck cancer |
| 636 | 634 | A634T[70] | Ulcerative colitis patients at high risk of colorectal carcinoma (UCHR)[70] |
| 646 | 644 | N644D[53] | Melanoma[53] |
| 648 | 646 | D646Y, D646N[55] | Mesothelioma, Bladder cancer, Lung squamous cell carcinoma[55] |
| 652 | 650 | K650M[24], K650E, K650Q, K650N, K650T | Gallbladder cancer, Cervical cancer, Testicular cancer, Glioma, Head and neck cancer, Colorectal cancer, Lung cancer, Non-small cell lung carcinoma, Squamous cell lung cancer, Urothelial carcinoma, Cervical cancer, Multiple myeloma, Bladder cancer, Lymphoma, Spermatocytic seminoma, Seborrheic keratosis, Dedifferentiated liposarcoma[24] |
| 382/652 | 380/650 | G380R/K650N[60] | Bladder cancer[60] |
| 653 | 651 | T651I[44] | Colon cancer[44] |
| 677 | 675 | S675S | Urothelial carcinoma[57] |
| 679 | 677 | V677I | Endometrial adenocarcinoma |
| 684 | 682 | V682I[70] | Ulcerative colitis patients at high risk of colorectal carcinoma (UCHR)[70] |
| 688 | 686 | E686C | Head and neck cancer |
| 693 | 691 | G691R[50] | Lung adenocarcinoma[50] |
| 699 | 697 | G697C | Gallbladder cancer, Head and neck cancer, Spermatocytic seminoma, Oral squamous cell cancer |
| 717 | 715 | K715M | Lung cancer, Squamous cell lung cancer |
| 719 | 717 | A717T | Multiple myeloma, Colorectal cancer[48] |

TABLE BC-continued

| | | FGFR Point Mutations | | |
|---|---|---|---|---|
| 723 | 721 | | H721R[70] | Ulcerative colitis patients at high risk of colorectal carcinoma (UCHR)[70] |
| 728 | 726 | | I726F | Multiple myeloma |
| | 746 | | 746_747insG | Urothelial carcinoma[57] |
| 769 | 767 | | F767L[66] | Cholangiocarcinoma[66] |
| 787 | 785 | | D785Y, c.2349_2350delAG/ p.D785fs*31[40] | Carcinoma of unknown primary, Non-small cell lung carcinoma[40] |
| 796 | 794 | | L794R | Multiple myeloma |
| 797 | 795 | | P795A[4] | Multiple myeloma[4] |
| Deletion of amino acids 797-810[63] | Deletion of amino acids 795-808[63] | | | Multiple myeloma[63] |
| 799 | 797 | | A797P | Urothelial carcinoma[57] |
| 809 (stop) | 807 (stop) | | 807R[9,10], 807C, 807G, 807T | Multiple myeloma, Spermatocytic seminoma |

| | | FGFR4 | | |
|---|---|---|---|---|
| Amino acid position (P22455-1)[1,H] | Amino acid position (P22455-2)[1,J] | Amino acid position (other isoform) | Non-limiting Exemplary mutation(s) | Non-limiting Exemplary FGFR-Associated Cancer(s) |
| 10 | 10 | | V10L[47], V10I[55] | Colorectal cancer[47] |
| 54 | 54 | | R54R[55] | |
| 56 | 56 | | C56S | Rhabdomyosarcoma |
| 59 | 59 | | R59W[22] | Lung cancer[22] |
| 72 | 72 | | R72L | Rhabdomyosarcoma |
| 122 | 122 | | T122A | Rhabdomyosarcoma |
| 136 | 136 | | P136L[47] | Colorectal cancer[47] |
| 137 | 137 | | S137S[55] | Ovarian mucinous carcinoma[55] |
| 144 | 144 | | Q144E | Brain cancer, Glioblastoma, Lung cancer, Lung squamous cell carcinoma |
| 163 | 163 | | P163P[55] | Renal papillary carcinoma[55] |
| 175 | 175 | | A175T | Rhabdomyosarcoma |
| 179 | 179 | | T179A[55] | Colorectal adenocarcinoma[55] |
| 183 | 183 | | R183S | Lung cancer, Non-small cell lung carcinoma, Lung adenocarcinoma |
| 197 | 197 | | I197T[48] | Colorectal cancer[48] |
| 202 | 202 | | L202L[55] | Melanoma[55] |
| 228 | 228 | | N228N[55] | Renal chromophobe[55] |
| 232 | 232 | | S232I | Lung cancer, Lung adenocarcinoma |
| 234 | 234 | | R234H, R234R[55] | Rhabdomyosarcoma |
| | | 240[K] | R240S[71] | Exposure to nephrotoxin aristolochic acid[71] |
| | | 241[K] | R241W[71] | Exposure to nephrotoxin aristolochic acid[71] |
| 257 | 257 | | A257T[66] | Cholangiocarcinoma[66] |
| 326 | 326 | | E326K | Breast cancer |
| 334 | 334 | | L334L[55] | Lung squamous cell carcinoma[55] |
| 352 | 352 | | P352P[55] | Colorectal adenocarcinoma[55] |
| 367 | | | Y367C | Breast cancer |
| | 386 | | G386S[55] | Lung adenocarcinoma[55] |
| 388 | | | G388R[36], G388A[61] | Bladder cancer, Stomach cancer, Skin cancer, Prostate cancer, Head and neck squamous cell carcinoma, Liver cancer, Colorectal cancer (e.g., colorectal adenocarcinoma), Breast cancer[36], Mammary carcinoma, Lung cancer, Sarcoma (e.g., soft tissue sarcoma, Ewing sarcoma[61]), Rhabdomyosarcoma |
| 434 | 394 | | R394Q | Brain cancer, Glioblastoma, Liver cancer, Lung cancer, Lung squamous cell carcinoma |
| | 425 | | D425N | Carcinoid |
| 484 | 444 | | A484T | Breast cancer |
| 516 | 476 | | D516N[55] | Lung adenocarcinoma[55] |
| 535 | 495 | | N535D, N535K | Rhabdomyosarcoma |
| 550 | 510 | | V550M, V550E, V550L | Breast cancer, Rhabdomyosarcoma, Neuroendocrine carcinoma of the breast |
| 553 | 513 | | A553A[55] | |
| 554 | 514 | | A554V | Rhabdomyosarcoma |
| 568 | 528 | | P568Q[22] | Lung cancer[22] |
| 576 | 536 | | G576D | Rhabdomyosarcoma |
| 583 | 543 | | P583Q | Colorectal cancer (e.g., colorectal adenocarcinoma) |

TABLE BC-continued

| | | FGFR Point Mutations | |
|---|---|---|---|
| 610 | 570 | R610H | Prostate cancer |
| 614 | 574 | A614S | Colorectal cancer (e.g., colorectal adenocarcinoma) |
| 616 | 576 | R616G, R616C[45] | Lung cancer, Lung adenocarcinoma, cecum adenocarcinoma[45] |
| 636 | 596 | G636C[15] | Stomach cancer[15] |
| 671 | 631 | D671N | Head and neck squamous cell carcinoma |
| 681 | 641 | E681K | Lung cancer, Lung adenocarcinoma |
| 712 | 672 | P712T | Lung cancer, Lung adenocarcinoma |
| 716 | 676 | P716R | Skin cancer |
| 729 | 689 | A729G | Lung cancer, Lung adenocarcinoma |
| 738 | 698 | Q738K | Lung cancer |
| 772 | 732 | S772N | Lung cancer, Lung neuroendocrine carcinoma |

[A] See UniParc entry UPI100000534B8
[B] See UniParc entry UPI0000001C0F
[C] See UniParc entry UPI000002A99A
[D] See UniParc entry UPI000012A72A
[E] See UniParc entry UPI000059D1C2
[F] See UniParc entry UPI000002A9AC
[G] See Uniparc entry UPI000012A72C
[H] See Uniparc entry UPI000012A72D
[I] See Uniparc entry UPI000013E0B8
[J] See Uniparc entry UPI0001CE06A3
[K] See Genbank entry BAD92868.1

[1] Each isoform of FGFR1, FGFR2, FGFR3, and FGFR4 has a different length, and thus, the corresponding amino acid position in one isoform of FGFR1, FGFR2, FGFR3, and FGFR4 may be different in another isoform of FGFR1, FGFR2, FGFR3, and FGFR4. The position of each point mutation listed above in each isoform of FGFR1, FGFR2, FGFR3, and FGFR4 can be identified by first identifying the isoform(s) of FGFR1, FGFR2, FGFR3, or FGFR4 which correspond to the specific point mutation listed above (by amino acid position and starting amino acid), and then aligning the amino acid sequence of identified isoform(s) of FGFR1, FGFR2, FGFR3, or FGFR4 with the amino acid sequences of the other isoforms of FGFR1, FGFR2, FGFR3, or FGFR4.
[2] Ang et al., Diagn. Mol. Pathol. Feb. 24, 2014 (Epub ahead of print).
[3] U.S. Patent Application Publication No. 2011/0008347.
[4] Gallo et al., Cytokine Growth Factor Rev. 26: 425-449, 2015.
[5] Davies et al., J. Cancer Res. 65: 7591, 2005.
[6] Kelleher et al., Carcinogenesis 34: 2198, 2013.
[7] Cazier et al., Nat. Commun. 5: 3756, 2014.
[8] Liu et al., Genet. Mol. Res. 13: 1109, 2014.
[9] Trudel et al., Blood 107: 4039, 2006.
[10] Gallo et al., Cytokine Growth Factor Rev. 26: 425, 2015.
[11] Liao et al., Cancer Res. 73: 5195-5205, 2013.
[12] Martincorena et al., Science 348: 880 (2015).
[13] U.S. Patent Application Publication No. US2016/0235744A1.
[14] U.S. Pat. No. 9,254,288B2.
[15] U.S. Pat. No. 9,267,176B2.
[16] U.S. Patent Application Publication No. S2016/0215350A1.
[17] European Patent Application Publication No. EP3023101A1.
[18] PCT Patent Application Publication No. WO2016105503A1.
[19] Rivera et al., Acta. Neuropathol., 131(6): 847-63, 2016.
[20] Lo Iacono et al., Oncotarget., 7(12): 14394-404, 2016.
[21] Deeken et al., Journal of Clinical Oncology, 34: Supp. Supplement 15, pp. iii93. Abstract Number: e17520, 2016 Annual Meeting of the American Society of Clinical Oncology, Chicago, IL.
[22] Sullivan et al., Journal of Clinical Oncology, 34: Supp. Supplement 15, pp. iii93. Abstract Number: 11596, 2016 Annual Meeting of the American Society of Clinical Oncology, Chicago,
[23] Nguyen et al., Molecular Cancer Therapeutics, Vol. 14, No. 12, Supp.2, Abstract Number: C199, AACR-NCI-EORTC International Conference: Molecular Targets and Cancer Therapeutics, 2015.
[24] Li et al., Hum. Pathol., 55: 143-50, 2016.
[25] European Patent No. EP2203449B1.
[26] Yoza et al., Genes Cells., (10): 1049-1058, 2016.
[27] U.S. Pat. No. 9,254,288B2.
[28] European Patent Application Publication No. 3023101A1.
[29] PCT Application Publication No. WO 2015/099127A1.
[30] European Patent No. EP2203449B1.
[31] Yoza et al., Genes Cells., (10): 1049-1058, 2016.
[32] Bunney et al., EbioMedicine, 2(3): 194-204, 2015.
[33] Byron et al., Neoplasia, 15(8): 975-88, 2013.
[34] European Patent Application Publication No. EP3023101A1.
[35] PCT Application Publication No. WO 2015/099127A1.
[36] Thussbas et al., J. Clin. Oncol., 24(23): 3747-55, 2006.
[32] Chell et al., Oncogene, 32(25): 3059-70, 2013.
[38] Tanizaki et al, Cancer Res. 75(15): 3149-3146 doi: 10.1158/0008-5472.CAN-14-3771
[39] Yang et al, EBioMedicine pii S2352-3964(18)30218-4. doi: 10.1016/j.ebiom.2018.06.011
[40] Jakobsen, et al Oncotarget 9(40): 26195-26208, 2018. doi: 10.18632/oncotarget.25490
[41] Stone, et al Acta Neuropathol 135(1): 115-129, 2017. doi: 10.1007/s00401-017-1773-z
[42] Pekmezci et al, Acta Nurotaphol. Commun. 6(1): 47. doi: 10.1186/s40478-018-0551-z
[43] De Mattos-Arruda et al, Oncotarget 9(29): 20617-20630, 2018. doi: 10.18632/oncotarget.25041
[44] Oliveira et al, J Exp Clin Cancer Res 37(1): 84, 2018. doi: 10.1186/s13046-018-0746-y
[45] Cha et al, Mol Oncol 12(7): 993-1003, 2018. doi: 10.1002/1878-0261.12194
[46] Iked a et al, Oncologist, 23(5): 586-593, 2018. doi: 10.1634/theoncologist.2017-0479

TABLE BC-continued

FGFR Point Mutations

[47]Pelaez-Garcia et al, *PLoS One*, 8(5): e63695, 2013. doi: 10.1371/journal.pone.0063695
[48]Shimada et al, *Oncotarget*, 8(55): 93567-93579, 2017. doi: 10.18632/oncotarget.20510
[49]Welander et al, *World J Surg*, 42(2): 482-489, 2018. doi: 10.1007/s00268-017-4320-0
[50]Chandrani et al, *Ann Oncol*, 28(3): 597-603, 2017. doi: 10.1093/annonc/mdw636
[51]Dalin et al, *Nat Commun*, 8(1): 1197, 2017. doi: 10.1038/s41467-017-01178-z
[52]Taurin et al, *Int J Gynecol Cancer*, 28(1): 152-160, 2018. doi: 10.1097/IGC.0000000000001129
[53]Haugh et al, *J Invest Dermatol* 138(2): 384-393, 2018. doi: 10.1016/j.jid.2017.08.022
[54]Babina and Turner, *Nat Rev Cancer* 17(5): 318-332, 2017. doi: 10.1038/nrc.2017.8
[55]Greenman et al, *Nature* 446(7132): 153-158, 2007. doi: 10.1038/nature05610
[56]Helsten et al, *Clin Cancer Res*, 22(1): 259-267, 2016. doi: 10.1158/1078-0432.CCR-14-3212
[57]Kim et al, *BMC Urol*, 18: 68, 2018. doi: 10.1186/s12894-018-0380-1
[58]Goyal et al, *Cancer Discov*, 7(3): 252-263, 2017. doi: 10.1158/2159-8290.CD-16-1000
[59]Premov et al, *Oncogene*, 36(22): 3168-3177, 2017. doi: 10.1038/onc.2016.464
[60]Geelvink et al, *Intl Mol Sci*. 19(9): pii: E2548, 2018. doi: 10.3390/ijms19092548
[61]Lee et al, *Exp Ther Med*. 16(2): 1343-1349, 2018. doi: 10.3892/etm.2018.6323
[62]Kas et al, *Cancer Res*, 78(19): 5668-5679, 2018. doi: 10.1158/0008-5472.CAN-18-0757
[63]Chesi et al, *Blood*, 97(3): 729-736, 2001. PMID: 11157491. Note that the deletion of FGFR3 isoform IIIc residues 795-808 also deletes the stop codon, elongating the protein by 99 amino acids (ATGPQQCEGSLAAHPAAGAQPLPGMRLSADGET-ATQSFGLCVCVCVCVCVCTSACACVRAHLASRCRGTLGVPAAVQRSPDWCCSTEG-PLFWGDPVQNVSGPTRWDPVGQGAGPDMARPLPLHHGTSQGALGPSHTQS).
[64]Ge, et al, *Am J Cancer Res*. 7(7): 1540-1553, 2017. PMID: 28744403
[65]Jiao et al, *Nat Genet*, 45(12): 1470-1473, 2013. doi: 10.1038/ng.2813
[66]Jusakul et al, *Cancer Discov*. 7(10): 1116-1135, 2017. doi: 10.1158/2159-8290.CD-17-0368
[67]Guyard et al, *Respir Res*., 18(1): 120, 2018. doi: 10.1186/s12931-017-0605-y
[68]Paik et al, *Clin Cancer Res*., 23(18): 5366-5373, 2017. doi: 10.1158/1078-0432.CCR-17-0645
[69]Roy et al, *Mod Pathol*., 30(8): 1133-1143, 2017. doi: 10.1038/modpathol.2017.33
[70]Chakrabarty et al, *Br J Cancer*, 117(1): 136-143, 2017. doi: 10.1038/bjc.2017.148
[71]Hoang et al, *Sci Transl Med*., 5(197): 197ra102. doi: 10.1126/scitranslmed.3006200
[72]Kim et al, *Ann Oncol*., 28(6): 1250-1259. doi: 10.1093/annonc/mdx098

Point mutations in FGFR1, FGFR2, FGFR3, and FGFR4 have been identified to result in resistance of a cancer cell to a FGFR inhibitor. Non-limiting examples of these mutations are depicted in Table BC. In some embodiments, a FGFR-associated disorder (e.g., any of the cancers described herein) can have one or more of the point mutations listed in Table BC. Also provided herein are methods of treating a subject that include identifying a subject having one or more of the point mutations listed in Table BC, and administering to the identified subject a therapeutically effective amount of a compound of Formula I (e.g., any of the exemplary compounds described herein), or a pharmaceutically acceptable salt or solvate thereof. Also provided are methods of treating a subject that include administering to a subject identified as having one or more of the point mutations listed in Table BC a therapeutically effective amount of a compound of Formula I (e.g., any of the exemplary compounds described herein).

The term "mammal" as used herein, refers to a warm-blooded animal that has or is at risk of developing a disease described herein and includes, but is not limited to, guinea pigs, dogs, cats, rats, mice, hamsters, and primates, including humans.

The phrase "time of survival" means the length of time between the identification or diagnosis of cancer (e.g., any of the cancers described herein) in a subject or patient by a medical professional and the time of death of the subject or patient (caused by the cancer). Methods of increasing the time of survival in a subject or patient having a cancer are described herein.

In some embodiments, the dysregulation of a FGFR gene, a FGFR kinase, or expression or activity or level of any of the same, includes a splice variation in a FGFR mRNA which results in an expressed protein that is an alternatively spliced variant of FGFR having at least one residue deleted (as compared to the wild-type FGFR kinase) resulting in a constitutive activity of a FGFR kinase domain.

A "FGFR kinase inhibitor" as defined herein includes any compound exhibiting FGFR inhibition activity. In some embodiments, a FGFR kinase inhibitor is selective for a FGFR kinase. Exemplary FGFR kinase inhibitors can exhibit inhibition activity (ICA against a FGFR kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a FGFR kinase inhibitor can exhibit inhibition activity (ICA against a FGFR kinase of less than about 25 nM, less than about 10 nM, less than about 5 nM, or less than about 1 nM as measured in an assay as provided herein.

As used herein, a "first FGFR kinase inhibitor" or "first FGFR inhibitor" is a FGFR kinase inhibitor as defined herein, but which does not include a compound of Formula I or a pharmaceutically acceptable salt or solvate thereof as defined herein. As used herein, a "second FGFR kinase inhibitor" or a "second FGFR inhibitor" is a FGFR kinase inhibitor as defined herein, but which does not include a compound of Formula I or a pharmaceutically acceptable salt or solvate thereof as defined herein. When both a first and a second FGFR inhibitor are present in a method provided herein, the first and second FGFR kinase inhibitor are different.

In some embodiments, the dysregulation of a FGFR gene, a FGFR kinase, or expression or activity or level of any of the same, includes at least one point mutation in a FGFR gene that results in the production of a FGFR kinase that has one or more amino acid substitutions or insertions or deletions in a FGFR gene that results in the production of a FGFR kinase that has one or more amino acids inserted or removed, as compared to the wild-type FGFR kinase. In some cases, the resulting FGFR kinase is more resistant to inhibition of its phosphotransferase activity by one or more first FGFR kinase inhibitor(s), as compared to a wildtype FGFR kinase or a FGFR kinase not including the same mutation. Such mutations, optionally, do not decrease the sensitivity of the cancer cell or tumor having the FGFR kinase to treatment with a compound of Formula I or a pharmaceutically acceptable salt or solvate thereof (e.g., as compared to a cancer cell or a tumor that does not include the particular FGFR inhibitor resistance mutation). In addition, such mutations, optionally, do not decrease the sensitivity of the cancer cell or tumor having the FGFR kinase to treatment with a compound that can form a covalent bond with a cysteine residue in a FGFR protein or a pharmaceutically acceptable salt or solvate thereof (e.g., as compared to a cancer cell or a tumor that does not include the particular FGFR inhibitor resistance mutation). In such embodiments, a FGFR inhibitor resistance mutation can result in a FGFR kinase that has one or more of an increased $V_{max}$, a decreased $K_m$ for ATP, and an increased $K_D$ for a first FGFR kinase inhibitor, when in the presence of a first FGFR kinase inhibitor, as compared to a wildtype FGFR kinase or a FGFR kinase not having the same mutation in the presence of the same first FGFR kinase inhibitor.

In other embodiments, the dysregulation of a FGFR gene, a FGFR kinase, or expression or activity or level of any of the same, includes at least one point mutation in a FGFR gene that results in the production of a FGFR kinase that has one or more amino acid substitutions as compared to the wild-type FGFR kinase, and which has increased resistance to a compound of Formula I or a pharmaceutically acceptable salt or solvate thereof, as compared to a wildtype FGFR kinase or a FGFR kinase not including the same mutation. In such embodiments, a FGFR inhibitor resistance mutation can result in a FGFR kinase that has one or more of an increased $V_{max}$, a decreased $K_m$, and a decreased $K_D$ in the presence of a compound of Formula I or a pharmaceutically acceptable salt or solvate thereof, as compared to a wildtype FGFR kinase or a FGFR kinase not having the same mutation in the presence of the same compound of Formula I or a pharmaceutically acceptable salt or solvate thereof.

Examples of FGFR inhibitor resistance mutations can, e.g., include point mutations, insertions, or deletions in and near the ATP binding site in the tertiary structure of a FGFR kinase (e.g., corresponding to amino acid positions 487-489, 562-565, 627, 628, 630, and 641 in SEQ ID NO. 1, amino acid positions 490-492, 565-568, 630, 631, 633, and 644 in SEQ ID NO. 3, or amino acid positions 481-483, 556-559, 621, 622, 624, and 635 in SEQ ID NO. 5) including but not limited to a gatekeeper residue (e.g., e.g., corresponding to amino acid position 561 in SEQ ID NO. 1, amino acid position 564 in SEQ ID NO. 3, or amino acid position 555 in SEQ ID NO. 5), P-loop residues (e.g., corresponding to amino acid positions 484-491 in SEQ ID NO. 1, amino acid positions 487-494 in SEQ ID NO. 3, or amino acid positions 478-485 in SEQ ID NO. 5), residues in or near the DFG motif (e.g., corresponding to amino acid positions 641-643 in SEQ ID NO. 1, amino acid positions 644-646 in SEQ ID NO. 3, or amino acid positions 635-637 in SEQ ID NO. 5).

Additional examples of these types of mutations include changes in residues that may affect enzyme activity and/or drug binding including but are not limited to residues in the activation loop (e.g., corresponding to amino acid positions 640-665 in SEQ ID NO. 1, amino acid positions 643-668 in SEQ ID NO. 3, or amino acid positions 634-659 in SEQ ID NO. 5), residues near or interacting with the activation loop, residues contributing to active or inactive enzyme conformations, changes including mutations, deletions, and insertions in the loop proceeding the C-helix and in the C-helix (e.g., corresponding to amino acid positions 524-545 in SEQ ID NO. 1, amino acid positions 527-548 in SEQ ID NO. 3, or amino acid positions 518-539 in SEQ ID NO. 5). In some embodiments, the wildtype FGFR protein is the exemplary wildtype FGFR kinase described herein (e.g., any of SEQ ID NOs: 1-8). Specific residues or residue regions that may be changed (and are FGFR inhibitor resistance mutations) include but are not limited to those listed in Table BC and Table BD. In some embodiments, a FGFR inhibitor resistance mutation can be a mutation in a cysteine. In some embodiments, a FGFR inhibitor resistance mutation in a cysteine is a FGFR inhibitor resistance mutation in a cysteine that corresponds to Cys582 of SEQ ID NO: 5. In some embodiments, a FGFR inhibitor resistance mutation in a cysteine is a FGFR inhibitor resistance mutation in a cysteine that corresponds to Cys790 of SEQ ID NO:3. As can be appreciated by those skilled in the art, an amino acid position in a reference protein sequence that corresponds to a specific amino acid position in, e.g., SEQ ID NO: 1, can be determined by aligning the reference protein sequence with SEQ ID NO: 1 (e.g., using a software program, such as ClustalW2). A corresponding residue can be in a different isoform of the same FGFR (e.g., isoform IIIb of FGFR2 compared to isoform IIIc of FGFR2), or in a different FGFR (e.g., in any isoform of FGFR3 compared to isoform IIIc of FGFR2). Additional examples of FGFR inhibitor resistance mutation positions are shown in Table BE. Changes to these residues may include single or multiple amino acid changes, insertions within or flanking the sequences, and deletions within or flanking the sequences. See also J. Kooistra, G. K. Kanev, O. P. J. Van Linden, R. Leurs, I. J. P. De Esch, and C. De Graaf, "KLIFS: A structural kinase-ligand interaction database," Nucleic Acids Res., vol. 44, no. D1, pp. D365-D371, 2016, which is incorporated by reference in its entirety herein.

Non-limiting examples of additional FGFR-associated diseases that are caused by dysregulation of FGFR are listed in Table BD. A subject having any of the additional FGFR-associated diseases described herein or known in the art can be treated by administering to the subject a therapeutically effective amount of a compound of Formula I (e.g., any of the exemplary compounds described herein).

TABLE BD

Additional FGFR-associated diseases caused or caused in part by deregulation of a FGFR

| FGFR1 | | | | |
|---|---|---|---|---|
| Amino acid position (αA1 isoform)[Z,A] | Amino acid position (αB1 isoform)[Z,B] | Amino acid position (other isoform) | Non-limiting Exemplary alteration(s) | Non-limiting Exemplary FGFR-Associated Condition(s) |
| 4 P33Afs*17[37] | 4 P33Afs*17[37] | | W4C | Kallman syndrome[37] Kallman syndrome[37] |
| | | | Splice-site mutation (c.91 + 2T > A) | Hypogonadotropic Hypogonadism[2] |

TABLE BD-continued

Additional FGFR-associated diseases caused or caused in part by deregulation of a FGFR

| | | | | |
|---|---|---|---|---|
| 48 | 48 | | G48S | Hypogonadotropic Hypogonadism 2 with or without anosmia |
| 58 | 58 | | R58Q[42] | Ichthyosis vulgaris and/or atopic dermatitis[42] |
| 70 | 70 | | G70R | Hypogonadotropic Hypogonadism 2 with or without anosmia |
| 77 | 77 | | N77K | Hypogonadotropic Hypogonadism 2 with or without anosmia |
| 78 | 78 | | R78C | Hypogonadotropic Hypogonadism 2 with or without anosmia |
| 96 | 96 | | S96C | Kallman syndrome[37] |
| 97 | 97 | | G97D | Hypogonadotropic Hypogonadism 2 with or without anosmia, Kallman syndrome[50] |
| 99 | 99 | | Y99C | Hypogonadotropic Hypogonadism 2 with or without anosmia, Kallman syndrome[50] |
| 101 | 101 | | C101F | Hypogonadotropic Hypogonadism 2 with or without anosmia |
| 102 | 102 | | V102I | Hypogonadotropic Hypogonadism 2 with or without anosmia |
| 116 | 116 | | V116I | Hypogonadotropic Hypogonadism 2 with or without anosmia |
| 117 | 117 | | N117S | Hypogonadotropic Hypogonadism 2 with or without anosmia |
| 129 | 129 | | D129A | Hypogonadotropic Hypogonadism 2 with or without anosmia |
| 165 | 165 | | L165H | Hartsfield Syndrome |
| 167 | 167 | | A167S | Hypogonadotropic Hypogonadism 2 with or without anosmia, Kallman syndrome[50] |
| 174 | 174 | | V174A | Hypogonadotropic Hypogonadism 2 with or without anosmia |
| 178 | 178 | | C178S | Hypogonadotropic Hypogonadism 2 with or without anosmia, Kallman syndrome[39] |
| 191 | 191 | | L191S | Hartsfield Syndrome |
| 224 | 224 | | D224H | Hypogonadotropic Hypogonadism 2 with or without anosmia |
| 228 | 228 | | Y228D | Hypogonadotropic Hypogonadism 2 with or without anosmia |
| 237 | 237 | | G237D, G237S | Hypogonadotropic Hypogonadism 2 with or without anosmia |
| 239 | 239 | | I239T | Hypogonadotropic Hypogonadism 2 with or without anosmia |
| | | 244[H] | c.730_731insG | Craniosynostosis[14] |
| 245 | 245 | | L245P | Hypogonadotropic Hypogonadism 2 with or without anosmia |
| 250 | 250 | | R250Q, R250W | Hypogonadotropic Hypogonadism 2 with or without anosmia |
| 252 | 252 | | P252R | Pfeiffer Syndrome[1,8] |
| 254 | 254 | | R254Q | Hypogonadotropic Hypogonadism 2 with or without anosmia |
| | | 261[H] | T261M | Craniosynostosis[14] |
| 270 | 270 | | G270D | Hypogonadotropic Hypogonadism 2 with or without anosmia |
| 273 | 273 | | V273M | Hypogonadotropic Hypogonadism 2 with or without anosmia |
| 274 | 274 | | E274G | Hypogonadotropic Hypogonadism 2 with or without anosmia |
| 277 | 277 | | C277Y | Hypogonadotropic Hypogonadism 2 with or without anosmia |
| 283 | 283 | | P283R | Hypogonadotropic Hypogonadism 2 with or without anosmia |
| 300 | 300 | | I300T | Trigonocephaly 1 |
| 330 | 330 | | N330I | Osteoglophonic Dysplasia |
| 332 | 332 | | S332C | Hypogonadotropic Hypogonadism 2 with or without anosmia |
| 339 | 339 | | Y339C | Hypogonadotropic Hypogonadism 2 with or without anosmia |
| 342 | 342 | | L342S | Hypogonadotropic Hypogonadism 2 with or without anosmia |
| 343 | 343 | | A343V | Hypogonadotropic Hypogonadism 2 with or without anosmia |
| 346 | 346 | | S346C | Hypogonadotropic Hypogonadism 2 with or without anosmia |
| 348 | 348 | | G348R | Hypogonadotropic Hypogonadism 2 with or without anosmia |
| | | 353[E] | A353T in alternatively spliced exon 8A[37] | Kallman syndrome[37] |

TABLE BD-continued

Additional FGFR-associated diseases caused or caused in part by deregulation of a FGFR

| | | | |
|---|---|---|---|
| 366 | 366 | P366L | Hypogonadotropic Hypogonadism 2 with or without anosmia |
| 374 | 374 | Y374C | Osteoglophonic Dysplasia |
| 381 | 381 | C381R | Osteoglophonic Dysplasia |
| 470 | 468 | R470L | Hypogonadotropic Hypogonadism 2 with or without anosmia |
| 475 | 473 | R473Q[41] | Congenital heart disease associated with ambiguous genitalia[41] |
| 483 | 481 | P483T | Hypogonadotropic Hypogonadism 2 with or without anosmia |
| 490 | 488 | G480R | Hartsfield Syndrome |
| 520 | 518 | A520T | Hypogonadotropic Hypogonadism 2 with or without anosmia |
| 538 | 536 | I538V | Hypogonadotropic Hypogonadism 2 with or without anosmia |
| 546 | 544 | N546K[31] | Encephalocraniocutaneous lipomatosis[31] |
| 607 | 605 | V607M | Hypogonadotropic Hypogonadism 2 with or without anosmia, Kallman syndrome[50] |
| 618 | 616 | K618N | Hypogonadotropic Hypogonadism 2 with or without anosmia |
| 621 | 619 | H621R | Hypogonadotropic Hypogonadism 2 with or without anosmia |
| 622 | 620 | R622G, R622Q, R622*[50] | Hypogonadotropic Hypogonadism 2 with or without anosmia, Kallman syndrome[50] |
| 623 | 621 | D623Y | Hartsfield Syndrome |
| 627 | 625 | R627T | Hartsfield Syndrome |
| 628 | 626 | N628K | Hartsfield Syndrome |
| 654 | 652 | Y654* | Kallman syndrome[37] |
| 656 | 654 | K656E[31] | Encephalocraniocutaneous lipomatosis[31] |
| 666 | 664 | W666R | Hypogonadotropic Hypogonadism 2 with or without anosmia |
| 670 | 668 | E670K | Hypogonadotropic Hypogonadism 2 with or without anosmia, Kallman syndrome[50] |
| 671 | 669 | A671P | Hypogonadotropic Hypogonadism 2 with or without anosmia |
| 685 | 683 | S685F | Hypogonadotropic Hypogonadism 2 with or without anosmia |
| 687 | 685 | G687R | Hypogonadotropic Hypogonadism 2 with or without anosmia |
| 692 | 690 | E692G | Hypogonadotropic Hypogonadism 2 with or without anosmia |
| 693 | 691 | I693F | Hypogonadotropic Hypogonadism 2 with or without anosmia |
| 703 | 701 | G703R, G703S | Hypogonadotropic Hypogonadism 2 with or without anosmia |
| 719 | 717 | M719R, M719V[37] | Hypogonadotropic Hypogonadism 2 with or without anosmia, Kallman syndrome[37] |
| 722 | 720 | P722H, P722S | Hypogonadotropic Hypogonadism 2 with or without anosmia, Kallman syndrome[50] |
| 724 | 722 | N724K | Hypogonadotropic Hypogonadism 2 with or without anosmia |
| 725 | 723 | C725Y | Hartsfield Syndrome |
| 745 | 743 | P745S | Hypogonadotropic Hypogonadism 2 with or without anosmia |
| 768 | 766 | D768Y | Hypogonadotropic Hypogonadism 2 with or without anosmia |
| 772 | 770 | P772S | Hypogonadotropic Hypogonadism 2 with or without anosmia, Ichthyosis vulgaris and/or atopic dermatitis[42] |
| 795 | 793 | V795I[49] | Hypogonadotropic hypogonadism[49] |
| | | FN1 fusion | Tumor-induced osteomalacia (TIO)[38] |

FGFR2

| Amino acid position (IIIb isoform)[Z,C] | Amino acid position (IIIc isoform)[Z,D] | Amino acid position (other isoform) | Non-limiting Exemplary alteration(s) | Non-limiting Exemplary FGFR-Associated Condition(s) |
|---|---|---|---|---|
| 105 | 105 | | Y105C[45] | Crouzon Syndrome[45] |
| 172 | 172 | | A172F[45] | Pfeiffer syndrome[45] |
| 186 | 186 | | M186T[45] | Apert Syndrome[45] |
| 252 | 252 | | S252W, S252L | Apert Syndrome[11], Crouzon syndrome[20] |
| 253 | 253 | | P253R, P253L[45] | Apert Syndrome[11,45] |

TABLE BD-continued

| Additional FGFR-associated diseases caused or caused in part by deregulation of a FGFR | | | | |
|---|---|---|---|---|
| 255 | 255 | | R255Q | Ectrodactyly[25], Lethal Pulmonary Acinar Dysplasia[25] |
| 267 | 267 | | S267P, S267F[46] | Crouzon Syndrome[10,46] |
| 273 | 273 | | p.273insE | Crouzon syndrome[24] |
| 276 | 276 | | F276V[45] | Crouzon syndrome[45] |
| 278 | 278 | | C278F, C278Y[46] | Crouzon Syndrome[10,46] |
| 281 | 281 | | Y281C | Crouzon syndrome[24] |
| 288 | 288 | | I288N[46] | Crouzon syndrome[46] |
| 289 | 289 | | Q289P | Crouzon Syndrome[10] |
| 290 | 290 | | W290C, W290R, W290G[46] | Craniosynostosis[13], Crouzon syndrome[22,46] |
| 308 | 308 | | Y308C[46] | Crouzon syndrome[46] |
| | 314 | | A314D[45] | Pfeiffer syndrome[45] |
| | 315 | | A315S, A315T | Crouzon syndrome[45] |
| | 315/252 | | A252L/A315S[48] | Syndactyly[48] |
| | Nucleotides 958-959 | | 958-959delAC[46] | Jackson-Weiss syndrome[46] |
| | 321 | | D321A | Pfeiffer Syndrome[9], Craniosynostosis[13] |
| | 328 | | Y328C | Crouzon Syndrome[10] |
| | 337 | | A337P[46] | Crouzon syndrome[46] |
| | 338 | | G338R[45] | Crouzon syndrome[45] |
| | 340 | | Y340H, Y340C, Y340S[46] | Crouzon Syndrome[10,46], Craniosynostosis[13] |
| | 341 | | T341P | Pfeiffer Syndrome[9] |
| | 342 | | C342R, C342Y, C342S, C342F, C342W | Pfeiffer Syndrome[9], Crouzon Syndrome[10], Craniosynostosis[13] |
| | 344 | | A344G, A344A[46] | Jackson-Weiss Syndrome[12], Crouzon syndrome[46] |
| | 347 | | S347C | Crouzon Syndrome[10], Jackson-Weiss syndrome[20] |
| | 354 | | S354C, S354F[46] | Crouzon Syndrome[10,46] |
| 358 | 357 | | L357S[46] | Crouzon syndrome[46] |
| 373 | 372 | | S372C | Beare-Stevenson syndrome (BSS)[28] |
| 376 | 375 | | Y375C | Beare-Stevenson syndrome (BSS)[28] |
| 383 | 382 | | C382R | Papillomatous pedunculated sebaceous naevus (PPSN)[27] |
| 385 | 384 | | G384R | Craniosynostosis[47] |
| 527 | 526 | | K526E[45] | Crouzon syndrome[45] |
| 550 | 549 | | N549H, N549T, N549D[45] N549K[45] | Craniosynostosis[13], Crouzon syndrome[20,45], Pfeiffer syndrome[45] |
| 642 | 641 | | K641R | Craniosynostosis[13] |
| 660 | 659 | | K695N[46] | Crouzon syndrome[46] |
| | Atypical splice mutation (940-2A →G) | | | Apert syndrome[29] |

| FGFR3 | | | | |
|---|---|---|---|---|
| Amino acid position (IIIb isoform)[Z,F] | Amino acid position (IIIc isoform)[Z,G] | Amino acid position (other isoform) | Non-limiting Exemplary alteration(s) | Non-limiting Exemplary FGFR-Associated Condition(s) |
| 84 | 84 | | S84L | Hypochondroplasia[17] |
| 200 | 200 | | R200C | Hypochondroplasia[17] |
| 248 | 248 | | R248C | Thanatophoric dysplasia type I[17], Seborrheic keratosis[19] |
| 248 | 248 | | R248delinsLC | Thanatophoric dysplasia[30] |
| 250 | 250 | | P250R, P250L | Muenke Coronal Craniosynostosis |
| 262 | 262 | | N262H | Hypochondroplasia[17] |
| 268 | 268 | | G268C | Hypochondroplasia[17] |
| 278 | 278 | | Y278C | Hypochondroplasia[17] |
| 279 | 279 | | S279C | Hypochondroplasia[17] |
| | 324 | | L324H | Hypochondroplasia[21] |
| | 329 | | V329I[44] | Cleft lip and palate and microphthalmia[44] |

TABLE BD-continued

Additional FGFR-associated diseases caused or caused in part by deregulation of a FGFR

|  |  |  |  |
|---|---|---|---|
|  | 328 | N328I | Hypochondroplasia[7] |
|  | 334 | A334T[44] | Craniosynostosis[44] |
|  | 344 | S344C | Achondroplasia[36] |
|  | 346 | G346E[47] | Achondroplasia[47] |
|  | 348 | S348C | Achondroplasia[34] |
| 372 | 370 | G370C | Thanatophoric dysplasia type I[17] |
| 373 | 371 | S371C | Thanatophoric dysplasia type I[17] |
| 375 | 373 | Y373C | Thanatophoric dysplasia type I[17] |
| 377 | 375 | G375C, G375R[47] | Achondroplasia |
| 382 | 380 | G380R | Achondroplasia, Achondroplasia[4,5] |
| 383 | 381 | V381E | Hypochondroplasia[17] |
| 393 | 391 | A391G, A391E | Crouzon syndrome[17], Seborrheic keratosis[19] |
| 528 | 526 | M528I[43] | Proportionate short stature[43] |
| 542 | 540 | N540S, N540T, N540K | Hypochondroplasia[17,18] |
| 623 | 621 | R623H | CATSHL syndrome[40] |
| 652 | 650 | K650E, K650M, K650T, K650N, K650Q | Thanatophoric Dysplasia[3], Skeletal Dysplasia[16], Thanatophoric dysplasia type I[17], Thanatophoric dysplasia type II[17], Acanthosis nigricans[32], Hypochondroplasia[17] |
| 809 (stop) | 807 (stop) | X807R, X807C, X807G, X807S, X807W | Thanatophoric dysplasia type I[17] |
|  | c.1959 + 19G > A |  | Achondroplasia[33] |

[A] See UniParc entry UPI00000534B8
[B] See UniParc entry UPI0000001C0F
[C] See UniParc entry UPI000002A99A
[D] See UniParc entry UPI000012A72A
[E] See Uniparc entry UPI0001BE80CD
[F] See UniParc entry UPI000002A9AC
[G] See Uniparc entry UPI000012A72C
[H] See Uniparc entry UPI000007296F
[Z] Each isoform of FGFR1, FGFR2, FGFR3, and FGFR4 has a different length, and thus, the corresponding amino acid position in one isoform of FGFR1, FGFR2, FGFR3, and FGFR4 may be different in another isoform of FGFR1, FGFR2, FGFR3, and FGFR4. The position of each point mutation listed above in each isoform of FGFR1, FGFR2, FGFR3, and FGFR4 can be identified by first identifying the isoform(s) of FGFR1, FGFR2, FGFR3, or FGFR4 which correspond to the specific point mutation listed above (by amino acid position and starting amino acid), and then aligning the amino acid sequence of identified isoform(s) of FGFR1, FGFR2, FGFR3, or FGFR4 with the amino acid sequences of the other isoforms of FGFR1, FGFR2, FGFR3, or FGFR4.
[1] Yong-Xing et al., Hum. Mol. Genet. 9(13): 2001-2008, 2000.
[2] Eeva-Maria Laitinen et al., PLoS One 7(6): e39450, 2012.
[3] Hart et al., Oncogene 19(29): 3309-3320, 2000.
[4] Shiang et al., Cell 76: 335-342, 1994.
[5] Rosseau et al., Nature 371: 252-254, 1994.
[6] Tavormina et al., Nature Genet. 9: 321-328, 1995.
[7] Bellus et al., Nature Genet. 10: 357-359, 1995.
[8] Muenke et al., Nature Genet. 8: 269-274, 1994.
[9] Rutland et al., Nature Genet. 9: 173-176, 1995.
[10] Reardon et al., Nature Genet. 8: 98-103, 1994.
[11] Wilkie et al., Nature Genet. 9: 165-172, 1995.
[12] Jabs et al., Nature Genet. 8: 275-279, 1994.
[13] Japanese Patent No. JP05868992B2.
[14] Ye et al., Plast. Reconstr. Surg., 137(3): 952-61, 2016.
[15] U.S. Pat. No. 9,447,098B2.
[16] Bellus et al., Am. J. Med. Genet. 85(1): 53-65, 1999.
[17] PCT Patent Application Publication No. WO2016139227A1.
[18] Australian Patent Application Publication No. AU2014362227A1.
[19] Chinese Patent No. CN102741256B.
[20] Ohishi et al., Am. J. Med. Genet. A., doi: 10.1002/ajmg.a.37992, 2016.
[21] Nagahara et al., Clin. Pediatr. Endocrinol., 25(3): 103-106, 2016.
[22] Hibberd et al., Am. J. Med. Genet. A., doi: 10.1002/ajmg.a.37862, 2016.
[23] Dias et al., Exp. Mol. Pathol., 101(1): 116-23, 2016.
[24] Lin et al., Mol. Med. Rep., 14(3): 1941-6, 2016.
[25] Barnett et al., Hum. Mutat., 37(9): 955-63, 2016.
[26] Krstevska-Konstantinova et al., Med. Arch., 70(2): 148-50, 2016.
[27] Kuentz et al., Br. J. Dermatol., doi: 10.1111/bjd.14681, 2016.
[28] Ron et al., Am. J. Case Rep., 15; 17: 254-8, 2016.
[29] Fernandes et al., Am. J. Med. Genet. A., 170(6): 1532-7, 2016.
[30] Lindy et al., Am. J. Med. Genet. A., 170(6): 1573-9, 2016.
[31] Bennett et al., Am. J. Hum. Genet., 98(3): 579-87, 2016.
[32] Ichiyama et al., J. Eur. Acad. Dermatol. Venereol., 30(3): 442-5, 2016.
[33] Zhao et al., Int. J. Clin. Exp. Med., 8(10): 19241-9, 2015.
[34] Hasegawa et al., Am. J. Med. Genet. A., 170A(5): 1370-2, 2016.

TABLE BD-continued

Additional FGFR-associated diseases caused or caused in part by deregulation of a FGFR

[35]Legeai-Mallet, Endocr. Dev., 30: 98-105, 2016.
[36]Takagi, Am. J. Med. Genet. A., 167A(11): 2851-4, 2015.
[37]Goncalves, Fertil. Steril., 104(5): 1261-7.e1, 2015.
[38]Miller et al., Journal of Clinical Oncology, 34: Supp. Supplement 15, pp. iii93. Abstract Number: e22500, 2016 Annual Meeting of the American Society of Clinical Oncology, Chicago, IL.
[39]Sarabipour et al., J. Mol. Biol., 428(20): 3903-3910, 2016.
[40]Escobar et al., Am. J. Med. Genet. A., 170(7): 1908-11, 2016.
[41]Mazen et al., Sex Dev., 10(1): 16-22, 2016.
[42]Taylan et al., J Allergy Clin Immunol, 136(2): 507-9, 2015. doi: 10.1016/j.jaci.2015.02.010
[43]Kant et al, Euro Journ Endocrinol, 172(6): 763-770, 2015. doi: 10.1530/EJE-14-0945
[44]González-Del Angel et al, Am J med Genet A, 176(1): 161-166, 2018. doi: 10.1002/ajmg.a.38526
[45]Lei and Deng, Int J Biol Sci 13(9): 1163:1171, 2017. doi: 10.7150/ijbs.20792
[46]Lajeunie et al, Eur J Hum Genet, 14(3): 289-298, 2006. doi: 10.1038/sj.ejhg.5201558
[47]Karadimas et al, Prenat Diagn, 26(3): 258-261, 2006. doi: 10.1002/pd.1392
[48]Ibrahimi et al, Hum Mol Genet 13(19): 2313-2324, 2004. doi: 10.1093/hmg/ddh235
[49]Trarbach et al, J Clin Endocrinol Metab., 91(10): 4006-4012, 2006. doi: 10.1210/jc.2005-2793
[50]Dode et al, Nat Genet, 33(4): 463-465, 2003. doi: 10.1038/ng1122

Additional point mutations in FGFR1, FGFR2, FGFR3, and FGFR4 have been identified to result in resistance of a cancer cell to a FGFR inhibitor. Non-limiting examples of these mutations are depicted in Table BE. In some embodiments, a FGFR-associated disorder (e.g., any of the cancers described herein) can have one or more of the point mutations listed in Table BE. Also provided herein are methods of treating a subject that include identifying a subject having one or more of the point mutations listed in Table BE, and administering to the identified subject a therapeutically effective amount of a compound of Formula I (e.g., any of the exemplary compounds described herein), or a pharmaceutically acceptable salt or solvate thereof. Also provided are methods of treating a subject that include administering to a subject identified as having one or more of the point mutations listed in Table BE a therapeutically effective amount of a compound of Formula I (e.g., any of the exemplary compounds described herein).

TABLE BE

FGFR Resistance Mutations

| Amino acid position (αA1 isoform)[Z,A] | Amino acid position (αB1 isoform)[Z,B] | Amino acid position (other isoform) | Non-limiting Exemplary mutations(s) | Non-limiting Exemplary FGFR-Associated Cancer(s) |
|---|---|---|---|---|
| 546 | 544 | | N546K[5] | (In vitro study) |
| 561 | 559 | | V561M[3,5,7] | (In vitro study) |
| 563 | 561 | | Y563C[7] | (In vitro study) |

FGFR2

| Amino acid position (IIIb isoform)[Z,C] | Amino acid position (IIIc isoform)[Z,D] | Amino acid position (other isoform) | Non-limiting Exemplary mutation(s) | Non-limiting Exemplary FGFR-Associated Cancer(s) |
|---|---|---|---|---|
| 288 | 288 | | I288S[11] | (tumor induced in mice)[11] |
| 290 | 290 | | W290R[11] | (tumor induced in mice)[11] |
| 338 | 340 | | Y340C[11] | (tumor induced in mice)[11] |
| 344 | 346 | | N346K[11] | (tumor induced in mice)[11] |
| 536 | 535 | | M536I[1] | (In vitro study) |
| 538 | 537 | | M538I[1] | (In vitro study) |
| 548 | 547 | | I548V[1] | (In vitro study) |
| 549 | 548 | | I548S[11] | (tumor induced in mice)[11] |
| 549/290 | 548/290 | | I548S/W290R[11] | (tumor induced in mice)[11] |
| 550 | 549 | | N550H[1,2,9], N550K[1], N550S[1], N549T[11] | (In vitro study), cholangiocarcinoma[9], (tumor induced in mice)[11] |
| 563 | 562 | | V562L[4,11] | (In vitro study), (tumor induced in mice)[11] |
| 565 | 564 | | V565I[1,2], V565F[4,9] | (In vitro study), cholangiocarcinoma[9] |
| 566 | 565 | | E566G[1,2], E565L[11] | (In vitro study), (tumor induced in mice)[11] |
| 569 | 568 | | S568L[11] | (tumor induced in mice)[11] |
| 569/563 | 568/562 | | S568L/V562[11] | (tumor induced in mice)[11] |
| 618 | 617 | | L618M[1] | (In vitro study) |
| 642 | 641 | | K642N[1], K641R[9,11] | (In vitro study), cholangiocarcinoma[9], (tumor induced in mice)[11] |
| 660 | 659 | | K660E[1], K660M[2,11], K660N[2] | (In vitro study), (tumor induced in mice)[11] |

TABLE BE-continued

| 719 | 718 | | E719G[1] | (In vitro study) |
| 770 | | | Y770IfsX14[1] | (In vitro study) |

FGFR3

| Amino acid position (IIIb isoform)[Z,E] | Amino acid position (IIIc isoform)[Z,F] | Amino acid position (other isoform) | Non-limiting Exemplary mutation(s) | Non-limiting Exemplary FGFR-Associated Cancer(s) |
|---|---|---|---|---|
| 542 | 540 | | N540K[9], N540D[10] | (In vitro study)[9,10] |
| 557 | 555 | | V555M[6,9], V555L[9] | (KMS-11 myeloma cell line derivative), (in vitro study)[9] |
| 610 | 608 | | L608V[9] | (In vitro study)[9] |
| 652 | 650 | | K650E[9] | (In vitro study)[9] |

FGFR4

| Amino acid position (P22455-1)[Z,G] | Amino acid position (P22455-2)[Z,H] | Amino acid position (other isoform) | Non-limiting Exemplary mutation(s) | Non-limiting Exemplary FGFR-Associated Cancer(s) |
|---|---|---|---|---|
| 388 | | | G388R[8] | Breast cancer |

[A]See UniParc entry UPI00000534B8
[B]See UniParc entry UPI0000001C0F
[C]See UniParc entry UPI000002A99A
[D]See UniParc entry UPI000012A72A
[E]See UniParc entry UPI000002A9AC
[F]See Uniparc entry UPI000012A72C
[G]See Uniparc entry UPI000012A72D
[H]See Uniparc entry UPI000013E0B8
[Z]Each isoform of FGFR1, FGFR2, FGFR3, and FGFR4 has a different length, and thus, the corresponding amino acid position in one isoform of FGFR1, FGFR2, FGFR3, and FGFR4 may be different in another isoform of FGFR1, FGFR2, FGFR3, and FGFR4. The position of each point mutation listed above in each isoform of FGFR1, FGFR2, FGFR3, and FGFR4 can be identified by first identifying the isoform(s) of FGFR1, FGFR2, FGFR3, or FGFR4 which correspond to the specific point mutation listed above (by amino acid position and starting amino acid), and then aligning the amino acid sequence of identified isoform(s) of FGFR1, FGFR2, FGFR3, or FGFR4 with the amino acid sequences of the other isoforms of FGFR1, FGFR2, FGFR3, or FGFR4.
[1]Byron et al., *Neoplasia*, 15(8): 975-88, 2013.
[2]European Patent Application Publication No. EP3023101A1.
[3]European Patent No. EP2203449B1.
[4]PCT Application Publication No. WO 2015/099127A1.
[5]Yoza et al., *Genes Cells.*, (10): 1049-1058, 2016.
[6]Chell et al., *Oncogene*, 32(25): 3059-70, 2013.
[7]Bunney et al., *EbioMedicine*, 2(3): 194-204, 2015.
[8]Thussbas et al., *J. Clin. Oncol.*, 24(23): 3747-55, 2006.
[9]Goyal et al, *Cancer Discov*, 7(3): 252-263, 2017. doi: 10.1158/2159-8290.CD-16-1000
[10]Chen et al, *Oncogene*, 24(56): 8259-8267, 2005. doi: 10.1038/sj.onc.1208989
[11]Kas et al, *Cancer Res*, 78(19): 5668-5679, 2018. doi: 10.1158/0008-5472.CAN-18-0757

The term "angiogenesis-related disorder" means a disease characterized in part by an increased number or size of blood vessels in a tissue in a subject or patient, as compared to a similar tissue from a subject not having the disease. Non-limiting examples of angiogenesis-related disorders include: cancer (e.g., any of the exemplary cancers described herein, such as prostate cancer, lung cancer, breast cancer, bladder cancer, renal cancer, colon cancer, gastric cancer, pancreatic cancer, ovarian cancer, melanoma, hepatoma, sarcoma, and lymphoma), exudative macular degeneration, proliferative diabetic retinopathy, ischemic retinopathy, retinopathy of prematurity, neovascular glaucoma, iritis rubeosis, corneal neovascularization, cyclitis, sickle cell retinopathy, and pterygium.

The term "resistant cancer cell to an anti-cancer drug" means a cancer cell that demonstrates an increased rate of growth and/or proliferation in the presence of an anti-cancer drug as compared to the rate of growth and/or proliferation of a similar cancer cell (or an average rate of growth and/or proliferation of a population of a similar cancer cells). For example, a cancer cell that demonstrates an increased rate of growth and/or proliferation in the presence of an anti-cancer drug (as compared to the rate of growth and/or proliferation of a similar cancer cell) can be present in a patient or a subject (e.g., a patient or a subject having a FGFR-associated cancer).

The term "increasing sensitivity to an anti-cancer drug" means a decrease in the rate of growth and/or proliferation of a resistant cancer cell (to an anti-cancer drug) when contacted with the anti-cancer drug and at least one of the compounds described herein, as compared to the rate of growth and/or proliferation of a resistant cancer cell when contacted with the anti-cancer drug alone. Although many of the mechanisms discussed so far are the result of genetic dysregulation of the FGF/FGFR signaling axis, ligand-dependent signaling is also likely to play a key role in cancer development (e.g., described as "Upregulation of Activity" in Table BB). Autocrine FGF overproduction has been reported in many tumor types (Turner N, Grose R., Nat Rev Cancer 2010; 10:116-129). In vitro studies have shown that FGFS overexpression has been associated with a number of tumor cell lines (lung, esophagus, melanoma, colon, and prostate; Hanada K, et al., Cancer Res 2001; 61:5511-5516), and in hepatocellular carcinomas (HCC), the upregulation of FGF2, 8, 17, and 18 initiates autocrine growth stimulation, cell survival, and neoangiogenesis (Uematsu S, et al., J Gastroenterol Hepatol 2005; 20:583-588; Hu M C, et al., Mol Cell Biol 1998; 18:6063-6074; Kin M, et al., J Hepatol 1997; 27:677-687; Gauglhofer C, et al., Hepatology 2011; 53:854-864). Further, HCC has been found to develop in transgenic mice overexpressing the hormonal FGF19 (Nicholes K, et al., Am J Pathol 2002; 160:2295-2307), and FGF19 is found on an amplicon on chromosome 11q that also invariably contains the adjacent FGF3, FGF4, and Cyclin D1 (CCND1) genes. This amplicon is found in various diseases, including head and neck squamous cell carcinoma, breast cancer, and squamous NSCLC. Although there is uncertainty about the key oncogenic gene on this amplicon or a presumption that it is CCND1, genetic knockdown of FGF19 inhibits the growth of HCC cell lines carrying the amplicon (Sawey E T, et al., Cancer Cell 2011; 19:347-358). Autocrine FGF2-FGFR1 feedback loops have also been reported in NSCLC cell lines and in human melanomas grown as subcutaneous tumors in nude mice (Marek L, et al., Mol Pharmacol 2009; 75:196-207; Wang Y, Becker D., Nat Med 1997; 3:887-893).

Paracrine production of FGFs has also been reported in multiple tumor types. High levels of serum FGF2 have been observed in small cell lung cancer and are associated with a poor prognosis (Ruotsalainen T, et al., Cancer Epidemiol Biomarkers Prev 2002; 11:1492-1495), possibly because of an FGF2-mediated cytoprotective effect, whereby the expression of antiapoptotic proteins are upregulated, promoting resistance to current anticancer treatments (Pardo O E, et al., EMBO J 2006; 25:3078-3088). Increased paracrine expression of one or more of FGF1, 2, 4, 5, 8, and 18 has been found to promote tumor neoangiogenesis in preclinical models via the main endothelial FGFRs, FGFR1 and 2 (Presta M, et al., Cytokine Growth Factor Rev 2005; 16:159-178). Poor prognosis has been associated with neoangiogenesis in ovarian cancer and melanomas (Birrer M J, et al., J Clin Oncol 2007; 25:2281-2287).

In addition to overexpression of FGFs, altered splicing of FGFR mRNAs is another mechanism by which ligand-dependent signaling is upregulated. Altered FGFR mRNA splicing can allow tumor cells to be stimulated by a broader range of FGFs than would be capable under normal physiologic conditions (Zhang X, et al., J Biol Chem 2006; 281:15694-15700). Altered splicing of the IgIII domains in FGFRs 1,2, and 3 can switch receptor binding affinity in cancer cells towards FGFs found in the healthy stroma, creating an aberrant paracrine signaling loop (Wesche J, Haglund K, Haugsten E M. et al., Biochem J 2011; 437: 199-213). In bladder and prostate cancer cell lines, a switch from the FGFR2-IIIb isoform to the IIIc isoform has been associated with tumor progression, epithelial-mesenchymal transition, and increased invasiveness (Wesche J, et al., Biochem J 2011; 437:199-213).

Accordingly, provided herein are methods for treating a subject diagnosed with (or identified as having) a FGFR-associated disease or disorder (e.g., a FGFR-associated cancer) that include administering to the subject a therapeutically effective amount of a compound of Formula I or a pharmaceutically acceptable salt or solvate thereof. Also provided herein are methods for treating a subject identified or diagnosed as having a FGFR-associated disease or disorder (e.g., a FGFR-associated cancer) that include administering to the subject a therapeutically effective amount of a compound of Formula I or pharmaceutically acceptable salt or solvate thereof. In some embodiments, the subject that has been identified or diagnosed as having a FGFR-associated disease or disorder (e.g., a FGFR-associated cancer) through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the FGFR-associated disease or disorder is a FGFR-associated cancer. For example, the FGFR-associated cancer can be a cancer that includes one or more FGFR inhibitor resistance mutations.

Also provided are methods for treating a disease or disorder in a subject in need thereof, the method comprising: (a) detecting a FGFR-associated disease or disorder in the subject; and (b) administering to the subject a therapeutically effective amount of a compound of Formula I or pharmaceutically acceptable salt or solvate thereof. Some embodiments of these methods further include administering to the subject an additional therapy or therapeutic agent (e.g., a second FGFR inhibitor, a second compound of Formula I or a pharmaceutically acceptable salt or solvate thereof, or an immunotherapy. In some embodiments, the subject was previously treated with a first FGFR inhibitor or previously treated with another treatment. In some embodiments, the subject is determined to have a FGFR-associated disease or disorder through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a FGFR-associated cancer in the subject; and (b) administering to the subject a therapeutically effective amount of a compound of Formula I or pharmaceutically acceptable salt or solvate thereof. Some embodiments of these methods further include administering to the subject an additional therapy or therapeutic agent (e.g., a second FGFR inhibitor, a second compound of Formula I or a pharmaceutically acceptable salt or solvate thereof, or an immunotherapy). In some embodiments, the subject was previously treated with a first FGFR inhibitor or previously treated with another anticancer treatment, e.g., at least partial resection of the tumor or radiation therapy. In some embodiments, the subject is determined to have a FGFR-associated cancer through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the cancer is a FGFR-associated cancer. For example, the FGFR-associated cancer can be a cancer that includes one or more FGFR inhibitor resistance mutations.

Also provided are methods of treating a subject that include performing an assay on a sample obtained from the subject to determine whether the subject has a dysregulation of a FGFR gene, a FGFR kinase, or expression or activity or level of any of the same, and administering (e.g., specifically or selectively administering) a therapeutically effective amount of a compound of Formula I or pharmaceutically acceptable salt or solvate thereof to the subject determined to have a dysregulation of a FGFR gene, a FGFR kinase, or expression or activity or level of any of the same. Some embodiments of these methods further include administering to the subject an additional therapy or therapeutic agent (e.g., a second FGFR inhibitor, a second compound of Formula I or a pharmaceutically acceptable salt or solvate thereof, or immunotherapy). In some embodiments of these methods, the subject was previously treated with a first FGFR inhibitor or previously treated with another anticancer treatment, e.g., at least partial resection of a tumor or radiation therapy. In some embodiments, the subject is a subject suspected of having a FGFR-associated disease or disorder (e.g., a FGFR-associated cancer), a subject presenting with one or more symptoms of a FGFR-associated disease or disorder (e.g., a FGFR-associated cancer), or a subject having an elevated risk of developing a FGFR-associated disease or disorder (e.g., a FGFR-associated cancer). In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a FGFR gene, a FGFR kinase, or expression or activity or level of any of the same includes one or more FGFR inhibitor resistance mutations.

Also provided is a compound of Formula I or pharmaceutically acceptable salt or solvate thereof for use in treating a FGFR-associated disease or disorder (e.g., a FGFR-associated cancer) in a subject identified or diagnosed as having a FGFR-associated disease or disorder (e.g., a FGFR-associated cancer) through a step of performing an assay (e.g., an in vitro assay) on a sample obtained from the subject to determine whether the subject has a dysregulation of a FGFR gene, a FGFR kinase, or expression or activity or level of any of the same, where the presence of a dysregulation of a FGFR gene, a FGFR kinase, or expression or activity or level of any of the same, identifies that the subject has a FGFR-associated disease or disorder (e.g., a FGFR-associated cancer). Also provided is the use of a compound of Formula I or a pharmaceutically acceptable salt or solvate thereof for the manufacture of a medicament for treating a FGFR-associated disease or disorder (e.g., a FGFR-associated cancer) in a subject identified or diagnosed as having a FGFR-associated disease or disorder (e.g., a FGFR-associated cancer) through a step of performing an assay on a sample obtained from the subject to determine whether the subject has a dysregulation of a FGFR gene, a FGFR kinase, or expression or activity or level of any of the same where the presence of dysregulation of a FGFR gene, a FGFR kinase, or expression or activity or level of any of the same, identifies that the subject has a FGFR-associated disease or disorder (e.g., a FGFR-associated cancer). Some embodiments of any of the methods or uses described herein further include recording in the subject's clinical record (e.g., a computer readable medium) that the subject is determined to have a dysregulation of a FGFR gene, a FGFR kinase, or expression or activity or level of any of the same, through the performance of the assay, should be administered a compound of Formula I or pharmaceutically acceptable salt or solvate thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the dysregulation of a FGFR gene, a FGFR kinase, or expression or activity or level of any of the same includes one or more FGFR inhibitor resistance mutations.

Also provided is a compound of Formula I or a pharmaceutically acceptable salt or solvate thereof, for use in the treatment of a disease or disorder in a subject in need thereof or a subject identified or diagnosed as having a FGFR-associated disease or disorder. Also provided is the use of a compound of Formula I or a pharmaceutically acceptable salt or solvate thereof for the manufacture of a medicament for treating a disease or disorder in a subject identified or diagnosed as having a FGFR-associated disease or disorder. In some embodiments, the cancer is a FGFR-associated cancer, for example, a FGFR-associated cancer having one or more FGFR inhibitor resistance mutations. In some embodiments, a subject is identified or diagnosed as having a FGFR-associated disease or disorder through the use of a regulatory agency-approved, e.g., FDA-approved, kit for identifying dysregulation of a FGFR gene, a FGFR kinase, or expression or activity or level of any of the same, in a subject or a biopsy sample from the sample. As provided herein, a FGFR-associated disease or disorder includes those described herein and known in the art.

Also provided is a compound of Formula I or a pharmaceutically acceptable salt or solvate thereof, for use in the treatment of a cancer in a subject in need thereof or a subject identified or diagnosed as having a FGFR-associated cancer. Also provided is the use of a compound of Formula I or a pharmaceutically acceptable salt or solvate thereof for the manufacture of a medicament for treating a cancer in a subject identified or diagnosed as having a FGFR-associated cancer. In some embodiments, the cancer is a FGFR-associated cancer, for example, a FGFR-associated cancer having one or more FGFR inhibitor resistance mutations. In some embodiments, a subject is identified or diagnosed as having a FGFR-associated cancer through the use of a regulatory agency-approved, e.g., FDA-approved, kit for identifying dysregulation of a FGFR gene, a FGFR kinase, or expression or activity or level of any of the same, in a subject or a biopsy sample from the sample. As provided herein, a FGFR-associated cancer includes those described herein and known in the art.

In some embodiments of any of the methods or uses described herein, the subject has been identified or diagnosed as having a cancer with a dysregulation of a FGFR gene, a FGFR kinase, or expression or activity or level of any of the same. In some embodiments of any of the methods or uses described herein, the subject has a tumor that is positive for a dysregulation of a FGFR gene, a FGFR kinase, or expression or activity or level of any of the same. In some embodiments of any of the methods or uses described herein, the subject can be a subject with a tumor(s) that is positive for a dysregulation of a FGFR gene, a FGFR kinase, or expression or activity or level of any of the same. In some embodiments of any of the methods or uses described herein, the subject can be a subject whose tumors have a dysregulation of a FGFR gene, a FGFR kinase, or expression or activity or level of any of the same. In some embodiments of any of the methods or uses described herein, the subject is suspected of having a FGFR-associated cancer (e.g., a cancer having one or more FGFR inhibitor resistance mutations). In some embodiments, provided herein are methods for treating a FGFR-associated cancer in a subject in need of such treatment, the method comprising a) detecting a dysregulation of a FGFR gene, a FGFR kinase, or the expression or activity or level of any of the same in a sample from the subject; and b) administering a therapeutically effective amount of a compound of Formula I or a pharmaceutically acceptable salt or solvate thereof. In some embodiments, the dysregulation of a FGFR gene, a FGFR kinase, or the expression or activity or level of any of the same includes one or more fusion proteins. In some embodiments of any of the methods or uses described herein, the subject is suspected of having a FGFR-associated cancer (e.g., a cancer having one or more FGFR inhibitor resistance mutations). Non-limiting examples of FGFR gene fusion proteins are described in Table BA. In some embodiments, the fusion protein is FGFR3-TACC3. In some embodiments, the dysregulation of a FGFR gene, a FGFR kinase, or the expression or activity or level of any of the same includes one or more FGFR kinase protein point mutations/insertions/deletions. Non-limiting examples of FGFR kinase protein point mutations/insertions/deletions are described in Table BC. In some embodiments, the FGFR kinase protein point mutations/insertions/deletions are selected from the group consisting of point mutations/insertions/deletions corresponding to V561M in SEQ ID NO. 1, V564I or V564F in SEQ ID NO. 3, or V555M in SEQ ID NO. 5. In some embodiments, the dysregulation of a FGFR gene, a FGFR kinase, or the expression or activity or level of any of the same includes one or more FGFR inhibitor resistance mutations. Non-limiting examples of FGFR inhibitor resistance mutations are described in Table BE. In some embodiments, the FGFR inhibitor resistance mutation corresponds to V561M in SEQ ID NO. 1, V564I or V564F in SEQ ID NO. 3, or V555M in SEQ ID NO. 5. In some embodiments, the cancer with a dysregulation of a FGFR gene, a FGFR kinase, or expression or activity or level of any of the same is determined using a regulatory agency-approved, e.g., FDA-approved, assay or kit. In some embodiments, the tumor that is positive for a dysregulation of a FGFR gene, a FGFR kinase, or expression or activity or level of any of the same is a tumor positive for one or more FGFR inhibitor resistance mutations. In some embodiments, the tumor with a dysregulation of a FGFR gene, a FGFR kinase, or expression or activity or level of any of the same is determined using a regulatory agency-approved, e.g., FDA-approved, assay or kit.

In some embodiments of any of the methods or uses described herein, the subject has a clinical record indicating that the subject has a tumor that has a dysregulation of a FGFR gene, a FGFR kinase, or expression or activity or level of any of the same (e.g., a tumor having one or more FGFR inhibitor resistance mutations). In some embodiments, the clinical record indicates that the subject should be treated with one or more of the compounds of Formula I or a pharmaceutically acceptable salts or solvates thereof or compositions provided herein. In some embodiments, the cancer with a dysregulation of a FGFR gene, a FGFR kinase, or expression or activity or level of any of the same is a cancer having one or more FGFR inhibitor resistance mutations. In some embodiments, the cancer with a dysregulation of a FGFR gene, a FGFR kinase, or expression or activity or level of any of the same is determined using a regulatory agency-approved, e.g., FDA-approved, assay or kit. In some embodiments, the tumor that is positive for a dysregulation of a FGFR gene, a FGFR kinase, or expression or activity or level of any of the same is a tumor positive for one or more FGFR inhibitor resistance mutations. In some embodiments, the tumor with a dysregulation of a FGFR gene, a FGFR kinase, or expression or activity or level of any of the same is determined using a regulatory agency-approved, e.g., FDA-approved, assay or kit.

Also provided are methods of treating a subject that include administering a therapeutically effective amount of a compound of Formula I or a pharmaceutically acceptable salt or solvate thereof to a subject having a clinical record that indicates that the subject has a dysregulation of a FGFR gene, a FGFR kinase, or expression or activity or level of any of the same. Also provided is the use of a compound of Formula I or a pharmaceutically acceptable salt or solvate thereof for the manufacture of a medicament for treating a FGFR-associated cancer in a subject having a clinical record that indicates that the subject has a dysregulation of a FGFR gene, a FGFR kinase, or expression or activity or level of any of the same. Some embodiments of these methods and uses can further include: a step of performing an assay (e.g., an in vitro assay) on a sample obtained from the subject to determine whether the subject has a dysregulation of a FGFR gene, a FGFR kinase, or expression or activity or level of any of the same, and recording the information in a subject's clinical file (e.g., a computer readable medium) that the subject has been identified to have a dysregulation of a FGFR gene, a FGFR kinase, or expression or activity or level of any of the same. In some embodiments, the assay is an in vitro assay. For example, an assay that utilizes next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of a FGFR gene, FGFR kinase, or expression or activity or level of any of the same includes one or more FGFR inhibitor resistance mutations.

Also provided herein is a method of treating a subject. In some embodiments, the method includes performing an assay on a sample obtained from the subject to determine whether the subject has a dysregulation of a FGFR gene, a FGFR protein, or expression or level of any of the same. In some such embodiments, the method also includes administering to a subject determined to have a dysregulation of a FGFR gene, a FGFR protein, or expression or activity, or level of any of the same a therapeutically effective amount of a compound of Formula I or a pharmaceutically acceptable salt or solvate thereof. In some embodiments, the method includes determining that a subject has a dysregulation of a FGFR gene, a FGFR protein, or expression or level of any of the same via an assay performed on a sample obtained from the subject. In some such embodiments, the method also includes administering to a subject a therapeutically effective amount of a compound of Formula I or a pharmaceutically acceptable salt or solvate thereof. In some embodiments, the dysregulation in a FGFR gene, a FGFR kinase protein, or expression or activity of the same is a gene or chromosome translocation that results in the expression of a FGFR fusion protein (e.g., any of the FGFR fusion proteins described herein). In some embodiments, the FGFR fusion can be selected from a FGFR3-TACC3 fusion and a FGFR2-BICC1 fusion. In some embodiments, the dysregulation in a FGFR gene, a FGFR kinase protein, or expression or activity or level of any of the same is one or more point mutation in the FGFR gene (e.g., any of the one or more of the FGFR point mutations described herein). The one or more point mutations in a FGFR gene can result, e.g., in the translation of a FGFR protein having an amino acid substitution that corresponds to one or more of the following: V561M in SEQ ID NO. 1, V564I or V564F in SEQ ID NO. 3, or V555M in SEQ ID NO. 5. In some embodiments, the dysregulation in a FGFR gene, a FGFR kinase protein, or expression or activity or level of any of the same is one or more FGFR inhibitor resistance mutations (e.g., any combination of the one or more FGFR inhibitor resistance mutations described herein). Some embodiments of these methods further include administering to the subject an additional therapy or therapeutic agent (e.g., a second FGFR inhibitor, a second compound of Formula I, or immunotherapy).

In some embodiments, the compounds provided herein exhibit brain and/or central nervous system (CNS) penetrance. Such compounds are capable of crossing the blood brain barrier and inhibiting a FGFR kinase in the brain and/or other CNS structures. In some embodiments, the compounds provided herein are capable of crossing the blood brain barrier in a therapeutically effective amount. For example, treatment of a subject with cancer (e.g., a FGFR-associated cancer such as a FGFR-associated brain or CNS cancer) can include administration (e.g., oral administration) of the compound to the subject. In some such embodiments, the compounds provided herein (e.g., compounds of Formula) are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the subject has previously been treated with another anticancer agent, e.g., another FGFR inhibitor (e.g., a compound that is not a compound of Formula I) or a multi-kinase inhibitor. In some embodiments, the brain tumor is a metastatic brain tumor. In some embodiments, the subject has previously been treated with another anticancer agent, e.g., another FGFR inhibitor (e.g., a compound that is not a compound of Formula I) or a multi-kinase inhibitor.

Also provided are methods (e.g., in vitro methods) of selecting a treatment for a subject identified or diagnosed as having a FGFR-associated cancer. Some embodiments can further include administering the selected treatment to the subject identified or diagnosed as having a FGFR-associated cancer. For example, the selected treatment can include administration of a therapeutically effective amount of a compound of Formula I or a pharmaceutically acceptable salt or solvate thereof. Some embodiments can further include a step of performing an assay on a sample obtained from the subject to determine whether the subject has a dysregulation of a FGFR gene, a FGFR kinase, or expression or activity or level of any of the same, and identifying and diagnosing a subject determined to have a dysregulation of a FGFR gene, a FGFR kinase, or expression or activity or level of any of the same, as having a FGFR-associated cancer. In some embodiments, the cancer is a FGFR-associated cancer having one or more FGFR inhibitor resistance mutations. In some embodiments, the subject has been identified or diagnosed as having a FGFR-associated cancer through the use of a regulatory agency-approved, e.g., FDA-approved, kit for identifying dysregulation of a FGFR gene, a FGFR kinase, or expression or activity or level of any of the same, in a subject or a biopsy sample from the subject. In some embodiments, the FGFR-associated cancers is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided herein are methods of selecting a treatment for a subject, wherein the methods include a step of performing an assay on a sample obtained from the subject to determine whether the subject has a dysregulation of a FGFR gene, a FGFR kinase, or expression or activity or level of any of the same (e.g., one or more FGFR inhibitor resistance mutations), and identifying or diagnosing a subject determined to have a dysregulation of a FGFR gene, a FGFR kinase, or expression or activity or level of any of the same, as having a FGFR-associated cancer. Some embodiments further include administering the selected treatment to the subject identified or diagnosed as having a FGFR-associated cancer. For example, in some embodiments, the selected treatment can include administration of a therapeutically effective amount of a compound of Formula I or a pharmaceutically acceptable salt or solvate thereof to the subject identified or diagnosed as having a FGFR-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided are methods of selecting a subject for treatment, wherein the methods include selecting, identifying, or diagnosing a subject having a FGFR-associated cancer, and selecting the subject for treatment including administration of a therapeutically effective amount of a compound of Formula I or a pharmaceutically acceptable salt or solvate thereof. In some embodiments, identifying or diagnosing a subject as having a FGFR-associated cancer can include a step of performing an assay on a sample obtained from the subject to determine whether the subject has a dysregulation of a FGFR gene, a FGFR kinase, or expression or activity or level of any of the same, and identifying or diagnosing a subject determined to have a dysregulation of a FGFR gene, a FGFR kinase, or expression or activity or level of any of the same, as having a FGFR-associated cancer. In some embodiments, the method of selecting a subject for treatment can be used as a part of a clinical study that includes administration of various treatments of a FGFR-associated cancer. In some embodiments, a FGFR-associated cancer is a cancer having one or more FGFR inhibitor resistance mutations. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of the FGFR gene, the FGFR kinase, or expression or activity or level of any of the same includes one or more FGFR inhibitor resistance mutations.

In some embodiments of any of the methods or uses described herein, an assay used to determine whether the subject has a dysregulation of a FGFR gene, or a FGFR kinase, or expression or activity or level of any of the same, using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a FGFR gene, a FGFR kinase, or expression or activity or levels of any of the same (see, e.g., the references cited herein). In some embodiments, the dysregulation of the FGFR gene, the FGFR kinase, or expression or activity or level of any of the same includes one or more FGFR inhibitor resistance mutations. In some embodiments, the sample is a biological sample or a biopsy sample (e.g., a paraffin-embedded biopsy sample) from the subject. In some embodiments, the subject is a subject suspected of having a FGFR-associated cancer, a subject having one or more symptoms of a FGFR-associated cancer, and/or a subject that has an increased risk of developing a FGFR-associated cancer).

Exemplary assays for detecting dysregulation of a FGFR gene, a FGFR protein, or expression or activity, or levels of the same are commercially available, e.g., FGFR Pathway Mutation PCR Array (Qiagen), HTG Edge FGFR Expression Assay (HTG Molecular Diagnostics), HTScan® FGF Receptor 1 Kinase Assay Kit (Cell Signaling Technology), Vysis LSI IGH/FGFR3 Dual Color, Dual Fusion Translocation Probe (Abbott Molecular), FGFR1 FISH Probe (Empire Genomics), FGFR1 FISH (Sonic Genomics), FISH IGH/FGFR3 (Quest Diagnostics), FGFR1 (8p11) [RUO] (Leica Biosystems), FGFR1 Break Apart FISH Probe (Empire Genomics), FGFR2/CEN10p FISH Probe (Abnova Corporation), FGFR2 (10q26) [ASR] (Leica Biosystems), Anti-FGFR-4 (IN), Z-FISH (AnaSpec), ZytoLight® SPEC FGFR2 Break Apart Probe (Bio-Optica), FGFR3 (4p16.3) (ZytoVision), and ZytoLight® SPEC FGFR3/CEN4 Dual Color Probe (ZytoVision). Additional assays for detecting dysregulation of a FGFR gene, a FGFR protein, or expression or activity or levels of the same are known in the art.

In some embodiments, dysregulation of a FGFR gene, a FGFR kinase, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.*, 3(3):36, 2016. Liquid biopsy methods can be used to detect total tumor burden and/or the dysregulation of a FGFR gene, a FGFR kinase, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a FGFR gene, a FGFR kinase, or the expression or activity or level of any of the same. In some embodiments, liquid biopsies can be used to detect the presence of dysregulation of a FGFR gene, a FGFR kinase, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect circulating free DNA (cfDNA). In some embodiments, circulating free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a FGFR gene, a FGFR kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a FGFR gene, a FGFR kinase, or the expression or activity or level of any of the same). Liquid biopsies can be used to detect dysregulation of a FGFR gene, a FGFR kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a liquid biopsy can be used to detect a genetic mutation that develops after development of the primary genetic mutation (e.g., a resistance mutation that arises in response to a treatment administered to a subject). In some embodiments, a dysregulation of a FGFR gene, a FGFR kinase, or the expression or activity or level of any of the same identified using a liquid biopsy is also present in a cancer cell that is present in the subject (e.g., in a tumor). In some embodiments, any of the types of dysregulation of a FGFR gene, a FGFR kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a FGFR gene, a FGFR kinase, or the expression or activity or level of any of the same in the subject can indicate that the subject will be responsive to a treatment that includes administration of a compound of Formula I or a pharmaceutically acceptable salt thereof.

Liquid biopsies can be performed at multiple times during a course of diagnosis, a course of monitoring, and/or a course of treatment to determine one or more clinically relevant parameters including, without limitation, progression of the disease, efficacy of a treatment, or development of resistance mutations after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable) or to determine the presence of a resistance mutation that has arisen as a result of the treatment. In some embodiments, a treatment to be administered to a subject can include a compound of Formula I or a pharmaceutically acceptable salt thereof.

In some embodiments, the efficacy of a compound of Formula I or a pharmaceutically acceptable salt or solvate thereof, can be determined by assessing the allele frequency of a dysregulation of a FGFR gene in cfDNA obtained from a subject at different time points, e.g., cfDNA obtained from the subject at a first time point and cfDNA obtained from the subject at a second time point, where at least one dose of a compound of Formula I or a pharmaceutically acceptable salt or solvate thereof is administered to the subject between the first and second time points. Some embodiments of these methods can further include administering to the subject the at least one dose of the compound of Formula I or a pharmaceutically acceptable salt or solvate thereof, between the first and second time points. For example, a reduction (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction) in the allele frequency (AF) of the dysregulation of a FGFR gene in the cfDNA obtained from the subject at the second time point as compared to the allele frequency (AF) of the dysregulation of a FGFR gene in the cfDNA obtained from the subject at the first time point indicates that the treatment (e.g., a compound of Formula I or a pharmaceutically acceptable salt thereof), was effective in the subject. In some embodiments, the AF is reduced such that the level is below the detection limit of the instrument. Alternatively, an increase in the allele frequency (AF) of the dysregulation of a FGFR gene in the cfDNA obtained from the subject at the second time point as compared to the allele frequency (AF) of the dysregulation of a FGFR gene in the cfDNA obtained from the subject at the first time point indicates that the treatment (e.g., a compound of Formula I or a pharmaceutically acceptable salt thereof) was not effective in the subject (e.g., the subject has developed a resistance mutation to the treatment (e.g., a compound of Formula I or a pharmaceutically acceptable salt thereof). Some embodiments of these methods can further include, administering additional doses of a compound of Formula I or a pharmaceutically acceptable salt thereof, to a subject in which a compound of Formula I or a pharmaceutically acceptable salt thereof, was determined to be effective. Some embodiments of these methods can further include, administering a different treatment (e.g., a treatment that does not include the administration of compound of Formula I or a pharmaceutically acceptable salt thereof, as a monotherapy) to a subject in which a compound of Formula I or a pharmaceutically acceptable salt thereof, was determined not to be effective.

In some examples of these methods, the time difference between the first and second time points can be about 1 day to about 1 year, about 1 day to about 11 months, about 1 day to about 10 months, about 1 day to about 9 months, about 1 day to about 8 months, about 1 day to about 7 months, about 1 day to about 6 months, about 1 day to about 5 months, about 1 day to about 4 months, about 1 day to about 3 months, about 1 day to about 10 weeks, about 1 day to about 2 months, about 1 day to about 6 weeks, about 1 day to about 1 month, about 1 day to about 25 days, about 1 day to about 20 days, about 1 day to about 15 days, about 1 day to about 10 days, about 1 day to about 5 days, about 2 days to about 1 year, about 5 days to about 1 year, about 10 days to about 1 year, about 15 days to about 1 year, about 20 days to about 1 year, about 25 days to about 1 year, about 1 month to about 1 year, about 6 weeks to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year, about 11 months to about 1 year, about 1 day to about 7 days, about 1 day to about 14 days, about 5 days to about 10 days, about 5 day to about 20 days, about 10 days to about 20 days, about 15 days to about 1 month, about 15 days to about 2 months, about 1 week to about 1 month, about 2 weeks to about 1 month, about 1 month to about 3 months, about 3 months to about 6 months, about 4 months to about 6 months, about 5 months to about 8 months, or about 7 months to about 9 months. In some embodiments of these methods, the subject can be previously identified as having a cancer having a dysregulated FGFR gene (e.g., any of the examples of a dysregulated FGFR gene described herein). In some embodiments of these methods, a subject can have been previously diagnosed as having any of the types of cancer described herein. In some embodiments of these methods, the subject can have one or more metastases (e.g., one or more brain metastases).

In some of the above embodiments, the cfDNA comprises ctDNA such as FGFR-associated ctDNA. For example, the cfDNA is ctDNA such as FGFR-associated ctDNA. In some embodiments, at least some portion of cfDNA is determined to be FGFR-associated ctDNA, for example, a sequenced and/or quantified amount of the total cfDNA is determined to have a FGFR fusion and/or a FGFR resistance mutation. In some embodiments provided herein, circulating tumor DNA can be used to monitor the responsiveness of a subject to a particular therapy (e.g., a first FGFR inhibitor, a second FGFR inhibitor, or a compound of Formula I or a pharmaceutically acceptable salt or solvate thereof). For example, prior to starting treatment with a therapy as described herein (e.g., a first FGFR inhibitor, a second FGFR inhibitor, or a compound of Formula I or a pharmaceutically acceptable salt or solvate thereof), a biological sample can be obtained from the subject and the level of circulating tumor DNA determined in the biological sample. This sample can be considered a base-line sample. The subject can then be administered one or more doses of a therapy as described herein (e.g., a first FGFR inhibitor, a second FGFR inhibitor, or a compound of Formula I or a pharmaceutically acceptable salt or solvate thereof) and the levels of circulating tumor DNA can be monitored (e.g., after the first dose, second dose, third dose, etc. or after one week, two weeks, three weeks, four weeks, etc.). If the level of circulating tumor DNA is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In some embodiments, the level of circulating tumor DNA is reduced such that it is below the detection limit of the instrument. In some embodiments, the level of circulating tumor DNA in a biological sample obtained from the subject (n) is compared to the sample taken just previous (n−1). If the level of circulating tumor DNA in the n sample is lower than the n−1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In some embodiments, the level of circulating tumor DNA is reduced such that it is below the detection limit of the instrument. In the case of responsiveness to therapy, the subject can to be administered one or more doses of the therapy and the circulating tumor DNA can be continued to be monitored.

If the level of circulating tumor DNA in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. If the level of circulating tumor DNA in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. When resistance to therapy is suspected, the subject can undergo one or more of imaging, biopsy, surgery, or other diagnostic tests. In some embodiments, when resistance to the therapy is suspected, the subject can be administered (either as a monotherapy or in combination with the previous therapy) a compound capable of treating a FGFR inhibitor resistance (e.g., a compound of Formula I or a pharmaceutically acceptable salt or solvate thereof). See, for example, Cancer Discov; 7(12); 1368-70 (2017); and Cancer Discov; 7(12); 1394-403 (2017).

In some embodiments provided herein, a protein biomarker can be used to monitor the responsiveness of a subject to a particular therapy (e.g., a first FGFR inhibitor, a second FGFR inhibitor, or a compound of Formula I or a pharmaceutically acceptable salt or solvate thereof). For example, prior to starting treatment with a therapy as described herein (e.g., a first FGFR inhibitor, a second FGFR inhibitor, or a compound of Formula I or a pharmaceutically acceptable salt or solvate thereof), a biological sample can be obtained from the subject and the level of a protein biomarker can be determined in the biological sample. This sample can be considered a base-line sample. The subject can then be administered one or more doses of a therapy as described herein (e.g., a first FGFR inhibitor, a second FGFR inhibitor, or a compound of Formula I or a pharmaceutically acceptable salt or solvate thereof) and the levels of the protein biomarker can be monitored (e.g., after the first dose, second dose, third dose, etc. or after one week, two weeks, three weeks, four weeks, etc.). If the level of the protein biomarker is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to the therapy. In some embodiments, the level of the protein biomarker is reduced such that it is below the detection limit of the instrument. In some embodiments, the level of the protein biomarker in a biological sample obtained from the subject (n) is compared to the sample taken just previous (n−1). If the level of the protein biomarker in the n sample is lower than the n−1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In some embodiments, the level of the protein biomarker is reduced such that it is below the detection limit of the instrument. In the case of responsiveness to therapy, the subject can to be administered one or more doses of the therapy and the protein biomarker can continue to be monitored.

If the level of the protein biomarker in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. If the level of the protein biomarker in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of resistance to the therapy. When resistance to therapy is suspected, the subject can undergo one or more of imaging, biopsy, surgery, or other diagnostic tests. In some embodiments, when resistance to the therapy is suspected, the subject can be administered (either as a monotherapy or in combination with the previous therapy) a compound capable of treating a FGFR inhibitor resistance (e.g., a compound of Formula I or a pharmaceutically acceptable salt or solvate thereof).

In some embodiments, one or more biomarkers are monitored. In some embodiments, the one or more biomarkers include one or more protein biomarkers. The particular biomarkers to be monitored can depend on the type of cancer and can be readily identified by one having ordinary skill in the art. Non-limiting examples of protein biomarkers include: CA 125, carcinoembryonic antigen (CEA), calcitonin, CA 19-9, prolactin, hepatocyte growth factor, osteopontin, myeloperoxidase, tissue inhibitor of metalloproteinases 1, angiopoietin-1 (Ang-1), cytokeratin 19 (CK-19), tissue inhibitor of metalloproteinase-1 (TIMP-1), chitinase 3 like-1 (YKL-40), galectin-3 (GAL-3), CYFRA 21-1 (cytokeratins), EPCAM (epithelial cell adhesion molecule), Pro-GRP (pro-gastrin-releasing peptide), and CEACAM (carcinoembryonic antigen). See, for example, Cohen J D, Li L, Wang Y, et al. Detection and localization of surgically resectable cancers with a multi-analyte blood test. Science; Published online 18 Jan. 2018. pii: eaar3247. DOI: 10.1126/science.aar3247; Fawaz M Makki et al. Serum biomarkers of papillary thyroid cancer. *J Otolaryngol Head Neck Surg.* 2013; 42(1): 16; Tatiana N. Zamay et al. Current and Prospective Protein Biomarkers of Lung Cancer. *Cancers* (Basel). 2017 November; 9(11): 155; Leiblich, Recent Developments in the Search for Urinary Biomarkers in Bladder Cancer *Curr. Urol. Rep.* 2017; 18(12): 100; and Santoni et al, Urinary Markers in Bladder Cancer: An Update *Front. Oncol.* 2018; 8: 362. In some embodiments, the cancer is bladder cancer and the biomarkers are urinary extracellular vesicles. In some embodiments, the cancer is bladder cancer, and the protein biomarkers are urinary protein biomarkers. In some embodiments, the cancer is bladder cancer and the protein biomarkers include alpha-1-anti-trypsin. In some embodiments, the cancer is bladder cancer and the protein biomarkers include H2B1K. In some embodiments, the cancer is bladder cancer and the protein biomarkers include BcLA-1 or BCLA-4. In some embodiments, the cancer is bladder cancer, and the protein biomarkers include aurora A kinase. In some embodiments, the cancer is bladder cancer, and the protein biomarkers include leukocyte cell adhesion molecule (ALCAM). In some embodiments, the cancer is bladder cancer and the protein biomarkers include nicotinamide N-methyltransferase. In some embodiments, the cancer is bladder cancer and the protein biomarkers include apurinic/apyrimidinic endonuclease 1/redox factor-1 (APE/Ref-1). In some embodiments, the cancer is bladder cancer, and the protein biomarkers include cytokeratin-20 (CK20). In some embodiments, the cancer is bladder cancer and the protein biomarkers include one or more of apolipoproteins A1, A2, B, C2, C3, and E. In some embodiments, the cancer is bladder cancer and the protein biomarkers include one or more of uromodulin, collagen α-1 (I), collagen α-1 (III), and membrane-associated progesterone receptor component 1. In some embodiments, the cancer is bladder cancer and the protein biomarkers include one or more of IL-8, MMP-9/10, ANG, APOE, SDC-1, α1AT, PAI-1, VEGFA, and CA9. In some embodiments, cancer is bladder cancer and the protein biomarkers include one or more of midkine (MDK) and synuclein G or MDK, ZAG2 and CEACAM1, angiogenin, and clusterin. In some embodiments, the cancer is bladder cancer and the protein biomarkers include one or more of CK20 and Insulin Like Growth Factor II (IGFII). In some embodiments, the cancer is bladder cancer and the protein biomarkers include one or more of HAI-1 and Epcam. In some embodiments, the cancer is bladder cancer and the protein biomarkers include survivin. In some embodiments, the cancer is bladder cancer and the protein biomarkers include Snail. In some embodiments, the cancer is bladder cancer and the protein biomarkers include CD44.

Also provided herein are methods of treating a FGFR-associated cancer in a subject that include (a) administering one or more (e.g., two or more, three or more, four or more, five or more, or ten or more) doses of a first FGFR kinase inhibitor to a subject identified or diagnosed as having a FGFR-associated cancer (e.g., any of the types of FGFR-associated cancers described herein)(e.g., identified or diagnosed as having a FGFR-associated cancer using any of the exemplary methods described herein or known in the art); (b) after step (a), determining a level of circulating tumor DNA in a biological sample (e.g., a biological sample comprising blood, serum, or plasma) obtained from the subject; (c) administering a therapeutically effective amount of a second FGFR inhibitor or a compound of Formula I, or a pharmaceutically acceptable salt or solvate thereof as a monotherapy or in conjunction with an additional therapy or therapeutic agent to a subject identified as having about the same or an elevated level of circulating tumor DNA as compared to a reference level of circulating tumor DNA (e.g., any of the reference levels of circulating tumor DNA described herein). In some examples of these methods, the reference level of circulating tumor DNA is a level of circulating tumor DNA in a biological sample obtained from the subject prior to step (a). Some embodiments of these methods further include determining the level of circulating tumor DNA in the biological sample obtained from the subject prior to step (a). In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some examples of these methods, the first FGFR inhibitor is selected from the group of: ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Also provided herein are methods of treating a FGFR-associated cancer in a subject that include administering a therapeutically effective amount of a compound of Formula I, or a pharmaceutically acceptable salt or solvate thereof, to a subject (i) identified or diagnosed as having a FGFR-associated cancer (e.g., any of the types of FGFR-associated cancers described herein) (e.g., identified or diagnosed as having a FGFR-associated cancer using any of the exemplary methods described herein or known in the art), (ii) previously administered one or more (e.g., two or more, three or more, four or more, five or more, or ten or more) doses of a second FGFR kinase inhibitor, and (ii) after the prior administration of the one or more doses of the second FGFR kinase inhibitor, identified as having about the same or an elevated level of circulating tumor DNA as compared to a reference level of circulating tumor DNA (e.g., any of the reference levels of circulating tumor DNA described herein or known in the art). In some embodiments of these methods, the reference level of circulating tumor DNA is a level of circulating tumor DNA in a biological sample (e.g., a biological sample comprising blood, plasma, or serum) obtained from the subject prior to the administration of the one or more doses of the second FGFR kinase inhibitor. Some embodiments of these methods further include determining the level of circulating tumor DNA in the biological sample obtained from the subject prior to administration of the one or more doses of the second FGFR kinase inhibitor. In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some embodiments of these methods, the second FGFR kinase inhibitor is selected from the group consisting of: ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Also provided herein are methods of treating a FGFR-associated cancer in a subject that include: (a) administering one or more doses of a compound of Formula I, or a pharmaceutically acceptable salt or solvate thereof, as a monotherapy to a subject identified or diagnosed as having a FGFR-associated cancer (e.g., any of the types of FGFR-associated cancer described herein) (e.g., a subject identified or diagnosed as having a FGFR-associated cancer using any of the methods described herein or known in the art); (b) after step (a), determining a level of circulating tumor DNA in a biological sample (e.g., a biological sample comprising blood, serum, or plasma) obtained from the subject; (c) administering a therapeutically effective amount of a compound of Formula I, or a pharmaceutically acceptable salt or solvate thereof, and an additional therapy or therapeutic agent (e.g., any of the additional therapies or therapeutic agents of a FGFR-associated cancer described herein or known in the art) to a subject identified as having about the same or an elevated level of circulating tumor DNA as compared to a reference level of circulating tumor DNA (e.g., any of the exemplary reference levels of circulating tumor DNA described herein or known in the art). In some embodiments of these methods, the additional therapeutic agent is a second FGFR kinase inhibitor (e.g., a FGFR kinase inhibitor selected from the group of: ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some examples of any of these methods, the additional therapy or therapeutic agent comprises one or more of: radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor) and one or more other kinase inhibitors (e.g., any of the exemplary kinase inhibitors described herein or known in the art). In some examples of these methods, the reference level of circulating tumor DNA is a level of circulating tumor DNA in a biological sample (e.g., a biological sample comprising blood, serum, or plasma) obtained from the subject prior to step (a). In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment).

Also provided herein are methods of treating a FGFR-associated cancer in a subject that include: administering a therapeutically effective amount of a compound of Formula I, or a pharmaceutically acceptable salt or solvate thereof, and an additional therapy or therapeutic agent to a subject (i) identified or diagnosed as having a FGFR-associated cancer (e.g., any of the types of FGFR-associated cancer described herein) (e.g., a subject identified or diagnosed as having a FGFR-associated cancer using any of the methods described herein or known in the art), (ii) previously administered one or more doses of the compound of Formula I, or the therapeutically acceptable salt or solvate thereof, as a monotherapy, and (ii) after administration of the one or more (e.g., two or more, three or more, four or more, five or more, or ten or more) doses of the compound of Formula I, or the therapeutically acceptable salt or solvate thereof, as a monotherapy, identified as having about the same or an elevated level of circulating tumor DNA as compared to a reference level of circulating tumor DNA (e.g., any of the exemplary reference levels of circulating tumor DNA described herein). In some embodiments of these methods, the reference level of circulating tumor DNA is a level of circulating tumor DNA in a biological sample obtained from the subject prior to administration of the one or more (e.g., two or more, three or more, four or more, five or more, or ten or more) doses of the compound of Formula I, or the pharmaceutically acceptable salt or solvate thereof, as a monotherapy. Some embodiments of these methods further include determining the level of circulating tumor DNA in the biological sample obtained from the subject prior to administration of the one or more doses of the compound of Formula I, or the pharmaceutically acceptable salt or solvate thereof, as a monotherapy. In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some embodiments of this method, the additional therapeutic agent is a second FGFR kinase inhibitor (e.g., a second FGFR kinase inhibitor selected from the group of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments of these methods, the additional therapy or therapeutic agent includes one or more of radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor), and one or more other kinase inhibitors (e.g., any of the kinase inhibitors described herein or known in the art).

Also provided herein are methods of selecting a treatment for a subject that include: selecting a therapeutically effective amount of a compound of Formula I, or a pharmaceutically acceptable salt or solvate thereof, for a subject (i) identified or diagnosed as having a FGFR-associated cancer (e.g., any of the FGFR-associated cancers described herein) (e.g., a subject identified or diagnosed as having a FGFR-associated cancer using any of the methods described herein or known in the art), (ii) previously administered one or more (e.g., two or more, three or more, four or more, five or more, or ten or more) doses of a second FGFR kinase inhibitor (e.g., any of the FGFR kinase inhibitors described herein or known in the art), and (ii) after administration of the one or more doses of the second FGFR kinase inhibitor, identified as having about the same or an elevated level of circulating tumor DNA as compared to a reference level of circulating tumor DNA. In some embodiments of any of these methods, the reference level of circulating tumor DNA is a level of circulating tumor DNA in a biological sample (e.g., a biological sample comprising blood, serum, or plasma) obtained from the subject prior to administration of the one or more doses of the second FGFR kinase inhibitor. Some embodiments of these methods further include determining the level of circulating tumor DNA in the biological sample obtained from the subject prior to administration of the one or more doses of the second FGFR kinase inhibitor. In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some embodiments of any these methods, the second FGFR kinase inhibitor is selected from the group of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Also provided herein are methods of selecting a treatment for a subject that include selecting a therapeutically effective amount of a compound of Formula I, or a pharmaceutically acceptable salt or solvate thereof, and an additional therapy or therapeutic agent for a subject (i) identified or diagnosed as having a FGFR-associated cancer (e.g., any of the FGFR-associated cancers described herein or known in the art) (e.g., a subject diagnosed or identified as having a FGFR-associated cancer using any of the methods described herein or known in the art), (ii) previously administered one or more doses (e.g., two or more, three or more, four or more, five or more, or ten or more) of the compound of Formula I, or the therapeutically acceptable salt or solvate thereof, as a monotherapy, and (ii) after administration of the one or more doses of the compound of Formula I, or the therapeutically acceptable salt or solvate thereof, identified as having about the same or an elevated level of circulating tumor DNA as compared to a reference level of circulating tumor DNA. Some embodiments further include determining the level of circulating tumor DNA in the biological sample obtained from the subject prior to administration of the one or more doses of the compound of Formula I, or the pharmaceutically acceptable salt or solvate thereof, as a monotherapy. Some embodiments further include determining the level of circulating tumor DNA in the biological sample obtained from the subject prior to administration of the one or more doses of the compound of Formula I, or the pharmaceutically acceptable salt or solvate thereof, as a monotherapy. In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some embodiments of any of these methods, the additional therapeutic agent is a second FGFR kinase inhibitor (e.g., a second FGFR kinase inhibitor selected from the group of: ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120). In some embodiments of any of the methods described herein, the additional therapy or therapeutic agent includes one or more of radiation therapy, a chemotherapeutic agent (e.g., any of the examples of a chemotherapeutic agent described herein or known in the art), a checkpoint inhibitor (e.g., any of the checkpoint inhibitors described herein or known in the art), surgery (e.g., at least partial resection of the tumor), and one or more other kinase inhibitors (e.g., any of the other kinase inhibitors described herein or known in the art).

Also provided herein are methods of determining the efficacy of a treatment in a subject that include: (a) determining a first level of circulating tumor DNA in a biological sample (e.g., a biological sample including blood, serum, or plasma) obtained from a subject identified or diagnosed as having a FGFR-associated cancer at a first time point; (b) administering a treatment including one or more doses of a compound of Formula I, or a pharmaceutically acceptable salt or solvate thereof to the subject, after the first time point and before a second time point; (c) determining a second level of circulating tumor DNA in a biological sample (e.g., a biological sample comprising blood, serum, or plasma) obtained from the subject at the second time point; and (d) identifying that the treatment is effective in a subject determined to have a decreased second level of circulating tumor DNA as compared to the first level of circulating tumor DNA; or identifying the treatment is not effective in a subject determined to have about the same or an elevated second level of circulating tumor DNA as compared to the first level of circulating tumor DNA. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Also provided herein are methods of determining whether a subject has developed resistance to a treatment that include: (a) determining a first level of circulating tumor DNA in a biological sample (e.g., a biological sample comprising blood, serum, or plasma) obtained from a subject identified or diagnosed as having a FGFR-associated cancer at a first time point; (b) administering a treatment including one or more (e.g., two or more, three or more, four or more, five or more, or ten or more) doses of a compound of Formula I, or a pharmaceutically acceptable salt or solvate thereof to the subject, after the first time point and before a second time point; (c) determining a second level of circulating tumor DNA in a biological sample obtained from the subject at the second time point; and (d) determining that a subject having a decreased second level of circulating tumor DNA as compared to the first level of circulating tumor DNA has not developed resistance to the treatment; or determining that a subject having about the same or an elevated second level of circulating tumor DNA as compared to the first level of circulating tumor DNA has developed resistance to the treatment. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Exemplary methods for detecting circulating tumor DNA are described in Moati et al., *Clin. Res. Hepatol. Gastroenterol.* Apr. 4, 2018; Oussalah et al., *EBioMedicine* Mar. 28, 2018; Moon et al., *Adv. Drug Deliv. Rev.* Apr. 4, 2018; Solassaol et al., *Clin. Chem. Lab. Med.* Apr. 7, 2018; Arriola et al., *Clin. Transl. Oncol.* Apr. 5, 2018; Song et al., *J. Circ. Biomark.* Mar. 25, 2018; Aslibekyan et al., *JAMA Cardiol.* Apr. 4, 2018; Isbell et al., *J. Thorac. Cardiovasc. Surg.* Mar. 13, 2018; Boeckx et al., *Clin. Colorectal Cancer* Feb. 22, 2018; Anunobi et al., *J. Surg. Res. Mar.* 28, 2018; Tan et al., *Medicine* 97(13):e0197, 2018; Reithdorf et al., *Transl. Androl. Urol.* 6(6):1090-1110, 2017; Volckmar et al., *Genes Chromosomes Cancer* 57(3):123-139, 2018; and Lu et al., *Chronic Dis. Transl. Med.* 2(4):223-230, 2016. Additional methods for detecting circulating tumor DNA are known in the art.

In the field of medical oncology, it is normal practice to use a combination of different forms of treatment to treat each subject with cancer. In medical oncology, the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery.

In some embodiments, an additional therapeutic agent(s) is selected from agents active against the downstream FGFR pathway, including, e.g., Ras, MEK, JNK, and p38 kinase inhibitor.

Compounds of Formula I therefore may also be useful as adjuvants to cancer treatment, that is, they can be used in combination with one or more additional therapies or therapeutic agents, for example a chemotherapeutic agent that works by the same or by a different mechanism of action. In some embodiments, a compound of Formula I, or a pharmaceutically acceptable salt thereof, can be used prior to administration of an additional therapeutic agent or additional therapy. For example, a subject in need thereof can be administered one or more doses of a compound of Formula I or a pharmaceutically acceptable salt thereof for a period of time and then under go at least partial resection of the tumor. In some embodiments, the treatment with one or more doses of a compound of Formula I or a pharmaceutically acceptable salt thereof reduces the size of the tumor (e.g., the tumor burden) prior to the at least partial resection of the tumor. In some embodiments, a subject has a cancer (e.g., a locally advanced or metastatic tumor) that is refractory or intolerant to standard therapy (e.g., administration of a chemotherapeutic agent, such as a first FGFR inhibitor or a multikinase inhibitor, immunotherapy, radiation, or a platinum-based agent (e.g., cisplatin)). In some embodiments, a subject has a cancer (e.g., a locally advanced or metastatic tumor) that is refractory or intolerant to prior therapy (e.g., administration of a chemotherapeutic agent, such as a first FGFR inhibitor or a multikinase inhibitor, immunotherapy, radiation, or a platinum-based agent (e.g., cisplatin)).

In some embodiments of any the methods described herein, the compound of Formula I (or a pharmaceutically acceptable salt or solvate thereof) is administered in combination with a therapeutically effective amount of at least one additional therapeutic agent selected from one or more additional therapies or therapeutic (e.g., chemotherapeutic) agents.

Non-limiting examples of additional therapeutic agents include: other FGFR-targeted therapeutic agents (i.e. a first or second FGFR kinase inhibitor), other kinase inhibitors (e.g., receptor tyrosine kinase-targeted therapeutic agents (e.g., Trk inhibitors or EGFR inhibitors)), signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

In some embodiments, an additional therapy or therapeutic agent can include a platinum coordination compound, for example, cisplatin optionally combined with amifostine, carboplatin, or oxaliplatin. In some embodiments, an additional therapy or therapeutic agent can include taxane compounds for example paclitaxel, paclitaxel protein bound particles (Abraxane™), or docetaxel. In some embodiments, an additional therapy or therapeutic agent can include topoisomerase I inhibitors such as camptothecin compounds, for example, irinotecan, SN-38, topotecan, topotecan HCl. In some embodiments, an additional therapy or therapeutic agent can include topoisomerase II inhibitors such as antitumour epipodophyllotoxins or podophyllotoxin derivatives, for example, etoposide, etoposide phosphate, or teniposide. In some embodiments, an additional therapy or therapeutic agent can include anti-tumour *vinca* alkaloids, for example, vinblastine, vincristine, vindesine, or vinorelbine. In some embodiments, an additional therapy or therapeutic agent can include anti-tumour nucleoside derivatives, for example, 5-fluorouracil, leucovorin, gemcitabine, gemcitabine HCl, capecitabine, cladribine, fludarabine, or nelarabine. In some embodiments, an additional therapy or therapeutic agent can include alkylating agents such as nitrogen mustard or nitrosourea, for example, cyclophosphamide, chlorambucil, carmustine, thiotepa, mephalan (melphalan), lomustine, semustine, altretamine, busulfan, dacarbazine, estramustine, ifosfamide optionally in combination with mesna, pipobroman, procarbazine, streptozocin, telozolomide, or uracil. In some embodiments, an additional therapy or therapeutic agent can include anti-tumour anthracycline derivatives, for example, daunorubicin, doxorubicin optionally in combination with dexrazoxane, doxil, idarubicin, mitoxantrone, epirubicin, epirubicin HCl, or valrubicin. In some embodiments, an additional therapy or therapeutic agent can include tetrocarcin derivatives, for example, tetrocarcin A. In some embodiments, an additional therapy or therapeutic agent can include glucocorticoids, for example, prednisone or prednisolone. In some embodiments, an additional therapy or therapeutic agent can include estrogen receptor antagonists or selective estrogen receptor modulators or inhibitors of estrogen synthesis, for example, tamoxifen, fulvestrant, toremifene, droloxifene, faslodex, raloxifene, or letrozole. In some embodiments, an additional therapy or therapeutic agent can include differentiating agents such as retinoids, vitamin D, or retinoic acid and retinoic acid metabolism blocking agents (RAMBA), for example, accutane. In some embodiments, an additional therapy or therapeutic agent can include DNA methyl transferase inhibitors, for example, azacytidine or decitabine. In some embodiments, an additional therapy or therapeutic agent can include antifolates, for example, premetrexed disodium. In some embodiments, an additional therapy or therapeutic agent can include antibiotics, for example, antinomycin D, bleomycin, deoxycoformycin, mitomycin C, dactinomycin, carminomycin, daunomycin, levamisole, plicamycin, mithramycin. In some embodiments, an additional therapy or therapeutic agent can include antimetabolites, for example, clofarabine, aminopterin, cytosine arabinoside, methotrexate, azacitidine, cytarabine, floxuridine, pentostatin, or thioguanine. In some embodiments, an additional therapy or therapeutic agent can include apoptosis inducing agents and antiangiogenic agents such as Bcl-2 inhibitors, for example, YC 137, BH 312, ABT 737, gossypol, HA 14-1, TW 37, or decanoic acid. In some embodiments, an additional therapy or therapeutic agent can include tubulin-binding agents, for example, combrestatin, colchicines. or nocodazole. In some embodiments, an additional therapy or therapeutic agent can include farnesyltransferase inhibitors, for example, tipifarnib. In some embodiments, an additional therapy or therapeutic agent can include histone deacetylase (HDAC) inhibitors, for example, sodium butyrate, suberoylanilide hydroxamide acid (SAHA), depsipeptide (FR 901228), panobinostat, NVP-LAQ824, R306465, JNJ-26481585, trichostatin A, or vorinostat. In some embodiments, an additional therapy or therapeutic agent can include inhibitors of the ubiquitin-proteasome pathway for example PS-341, MLN 0.41, bortezomib, or carfilzomib. In some embodiments, an additional therapy or therapeutic agent can include Yondelis. In some embodiments, an additional therapy or therapeutic agent can include telomerase inhibitors, for example, telomestatin. In some embodiments, an additional therapy or therapeutic agent can include matrix metalloproteinase inhibitors, for example, batimastat, marimastat, prinostat, or metastat. In some embodiments, an additional therapy or therapeutic agent can include recombinant interleukins, for example, aldesleukin, denileukin diftitox, interferon alfa 2a, interferon alfa 2b, or peginterferon alfa 2b. In some embodiments, an additional therapy or therapeutic agent can include retinoids, for example, alitretinoin, bexarotene, or tretinoin. In some embodiments, an additional therapy or therapeutic agent can include arsenic trioxide. In some embodiments, an additional therapy or therapeutic agent can include asparaginase, pegaspargase. In some embodiments, an additional therapy or therapeutic can include steroids, for example, dromostanolone propionate, megestrol acetate, nandrolone (decanoate, phenpropionate), or dexamethasone. In some embodiments, an additional therapy or therapeutic agent can include gonadotropin releasing hormone agonists or antagonists, for example, abarelix, goserelin acetate, histrelin acetate, or leuprolide acetate. In some embodiments, an additional therapy or therapeutic agent can include thalidomide, lenalidomide, CC-5013, or CC-4047). In some embodiments, an additional or therapeutic agent can include mercaptopurine. In some embodiments, an additional therapy or therapeutic agent can include mitotane. In some embodiments, an additional therapy or therapeutic agent can include pamidronate. In some embodiments, an additional therapy or therapeutic agent can include pegademase. In some embodiments, an additional therapy or therapeutic agent can include rasburicase. In some embodiments, an additional therapy or therapeutic agent can include BH3 mimetics, for example, ABT-737. In some embodiments, an additional therapy or therapeutic agent can include colony-stimulating factor analogs, for example, filgrastim, pegfilgrastim, or sargramostim. In some embodiments, an additional therapy or therapeutic agent can include erythropoietin or analogues thereof (e.g. darbepoetin alfa). In some embodiments, an additional therapy or therapeutic agent can include interleukin 11. In some embodiments, an additional therapy or therapeutic agent can include oprelvekin. In some embodiments, an additional therapy or therapeutic agent can include zoledronate or zoledronic acid. In some embodiments, an additional therapy or therapeutic agent can include fentanyl. In some embodiments, an additional therapy or therapeutic agent can include bisphosphonate. In some embodiments, an additional therapy or therapeutic agent can include palifermin. In some embodiments, an additional therapy or therapeutic agent can include a steroidal cytochrome P450 17alpha-hydroxylase-17,20-lyase inhibitor (CYP17), for example, abiraterone, or abiraterone acetate. In some embodiments, an additional therapy or therapeutic agent can include a CDK9 inhibitor, for example, flavoperidol. In some embodiments, an additional therapy or therapeutic agent can include anti-androgens, for example, flutamide, bicalutamide, or nilutamide. In some embodiments, an additional therapy or therapeutic agent can include luteinizing hormone-releasing hormone (LHRH) analogs, for example, leuprolide, goserelin, triptorelin, and histrelin. In some embodiments, an additional therapy or therapeutic agent can include LHRH antagonists (e.g., degarelix), androgen receptor blockers (e.g., enzalutamide), or agents that inhibit androgen production (e.g., abiraterone). In some embodiments, an additional therapy or therapeutic agent can include an anti-viral agent, for example, nucleoside and nucleotide reverse transcriptase inhibitors (NRTIs), non-nucleoside reverse transcriptase inhibitors (NNRTIs), protease inhibitors, or other antiviral drugs.

Non-limiting examples NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2′,3′-dicleoxy-5-fluoro-cytidene); DAPD, ((−)-beta-D-2,6,-diamino-purine dioxolane); and lodenosine (FddA/); nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B. Non-limiting examples of protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Non-limiting examples of other antiviral drugs include hydroxyurea, ribavirin, IL-2, IL-12, pentafuside and Yissum Project No. 11607. In some embodiments, an additional therapy or therapeutic agent can include a protein chaperone inhibitor, for example an inhibitor of Hsp90 (e.g., tanespimycin). In some embodiments, an additional therapy or therapeutic agent can include a PARP inhibitor, for example, olaparib. In some embodiments, an additional therapy or therapeutic agent can include pemetrexed. In some embodiments, an additional therapy or therapeutic agent can include an antimetabolite (e.g., folic acid antagonists, pyrimidine analogs, purine analogs and adenosine deaminase inhibitors), for example, 6-mercaptopurine, 6-thioguanine, fludarabine phosphate, pentostatine, ara-C, ara-A, gemcitabine, or N-phosphonoacetyl-L-aspartate. In some embodiments, an additional therapy or therapeutic agent can include a cytotoxic agent, for example, navelbene, CPT-11, anastrazole, letrazole, capecitabine, reloxafine, ifosamide, or droloxafine. In some embodiments, an additional therapy or therapeutic agent can include a histidyl-tRNA synthetase (HRS) polypeptide or an expressible nucleotide that encodes the HRS polypeptide. In some embodiments, an additional therapy or therapeutic agent can include erythrohydroxynonyladenine. In some embodiments, an additional therapy or therapeutic agent can include ethinyl estradiol, fluoxymesterone, hydroxyprogesterone caproate, medroxyprogesterone acetate, or testosterone propionate. In some embodiments, an additional therapy or therapeutic agent can include an inhibitor of transcription, for example, an inhibitor of a cyclin-dependent kinase (e.g., dinaciclib, palbociclib, olomoucine, AT7519M, P1446A-05, AG-024322, (R)-roscovitine, P276-00, SNS-032, LEE011, PD 0332991, GT28-01, NSC 638850, aminopurvalanol A, arcyriaflavin A, AZD 5438, (R)—CR8, (R)-DRF053, dihydrochloride, E9, flavopiridol, 10Z-hymenialdisine, irdirubin-3'-oxime, kenpaullone, NSC 625987, NSC 663284, NSC 693868, NU 2058, NU 6140, olomoucine, PHA 767491, purvalanol A, purvalanol B, RO 3306, ryuvidine, senexin A, SNS 032, SU 9516, THZ1 ((E)-N-(3-(5-chloro-4-(1H-indol-3-yl)pyrimidin-2-ylamino)phenyl)-4-(4-(dimethylamino)but-2-enamido)benzamide), THZ5-31-1 ((E)-N-(4-((3R)-3-(5-chloro-4-(1H-indol-3-yl)pyrimidin-2-ylamino)piperidine-1-carbonyl)phenyl)-4-(dimethylamino)but-2-enamide), p16 protein, p15 protein, p18 protein, p19 protein, p21/WAF1 protein, p27 protein, or p57 protein), N-(4-(2-((1s, 4s)-4-(dimethylamino)cyclohexylamino)-9-isopropyl-9H-purin-6-ylamino)phenyl)acrylamide, N-(3-(3-ethyl-5-(2-(2-hydroxyethyl)piperidin-1-yl)pyrazolo[1,5-a]pyrimidin-7-ylamino)phenyl)acrylamide, tert-butyl 2-((6S, Z)-4-(4-chlorophenyl)-2,3,9-trimethyl-6a, 7-dihydro-6H-thieno[3,2-f][1,2,4]triazolo[4,3-a][1,4]diazepin-6-yl)acetate, an inhibitor of a bromodomain-containing protein (e.g., I-BET 151, I-BET 762, JQ1, OTX-015, TEN-010, CPI-203, CPI-0610, RVX-208, LY294002, BMS-986158, GSK525762), a TBP (TATA box binding protein)-associated factor protein (TAF) inhibitor, a CREB-binding protein (CBP) inhibitor, or an E1A binding protein p300 (EP300) inhibitor. In some embodiments, an additional therapy or therapeutic agent can include a therapy for focal segmental glomerulosclerosis, for example, any of the compounds disclosed in U.S. Patent Application Publication No. 2018/0141587, incorporated herein by reference. In some embodiments, an additional therapy or therapeutic agent can include a bile acid sequesterant, e.g., cholestyramine, colesevelam, colesevalam hydrochloride, colestipol, or selevamer. In some embodiments, an additional therapy or therapeutic can include a mast cell stabilizer, for example, cromolyn sodium. In some embodiments, an additional therapy or therapeutic agent can include a PD-1 antagonist, for example, AMP-224 (B7-DCIg), AMP-514, an immunoadhesin that specifically binds to PD-1, BAP049-Clone-B, BAP049-Clone-E, h409A11, h409A16, h409A17, nivolumab (BMS-936558), PDR001, pembrolizumab (also known as MK-3475), or pidilizumab. In some embodiments, an additional therapy or therapeutic agent can include a PD-L1 antagonist, for example, an immunoadhesin that specifically binds to PD-L1, BMS-936559, MEDI4736, MPDL3280A, or MSB0010718C. In some embodiments, an additional therapy or therapeutic agent can include an apoptosis modulator or a signal transduction inhibitor, for example, everolimus, perifosine, rapamycin, sorafenib, temsirolimus, trametinib, or vemurafenib.

Treatment of a subject having a cancer with a FGFR inhibitor in combination with an additional therapy or therapeutic agent including an immunomodulatory or anti-inflammatory agent can have increased therapeutic efficacy as compared to treatment of the same subject or a similar subject with the FGFR inhibitor as a monotherapy. Accordingly, provided are methods of treating a subject in need thereof including administering to the subject a compound of Formula I an additional therapy or therapeutic agent comprising an immunomodulatory or anti-inflammatory agent.

Exemplary immunomodulatory or anti-inflammatory agents include, without limitation, cyclosporin, rapamycin, or ascomycin, or immunosuppressant analogues thereof, for example, cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, such as monoclonal antibodies for leukocyte receptors, for example MHC, CD2, CD3, CD4, CD7, CD25, CD28, B7, CD45, CD58 or their ligands, or other immunomodulatory compounds, such as CTLA41g.

Treatment of a subject having a cancer with a FGFR inhibitor in combination with an additional therapy or therapeutic agent including an inhibitor of the interaction between a FGFR and FGFR substrate 2 (FRS2) can have increased therapeutic efficacy as compared to treatment of the same subject or a similar subject with the FGFR inhibitor as a monotherapy. Accordingly, provided are methods of treating a subject in need thereof including administering to the subject a compound of Formula I an additional therapy or therapeutic agent comprising inhibitor of the interaction between a FGFR and FRS2.

Non-limiting exemplary inhibitors of the interaction between a FGFR and FRS2 are described in U.S. Pat. No. 9,957,236, incorporated herein by reference.

In some embodiments, the other FGFR-targeted therapeutic is a multikinase inhibitor exhibiting FGFR inhibition activity. In some embodiments, the other FGFR-targeted therapeutic inhibitor is selective for a FGFR kinase. Exemplary FGFR kinase inhibitors can exhibit inhibition activity (ICA against a FGFR kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a FGFR kinase inhibitors can exhibit inhibition activity (ICA against a FGFR kinase of less than about 25 nM, less than about 10 nM, less than about 5 nM, or less than about 1 nM as measured in an assay as provided herein.

Non-limiting examples of FGFR-targeted therapeutics (e.g., a first FGFR inhibitor or a second FGFR inhibitor) include masitinib (AB1010, 4-[(4-methylpiperazin-1-yl)methyl]-N-[4-methyl-3-[(4-pyridin-3-yl-1,3-thiazol-2-yl)amino]phenyl]benzamide), EOC317 (ACTB 1003, 1-[4-[4-amino-6-(methoxymethyl)-7-(morpholin-4-ylmethyl)pyrrolo[2,1-f][1,2,4]triazin-5-yl]-2-fluorophenyl]-3-[2-fluoro-5-(trifluoromethyl)phenyl]urea), Anlotinib (AL3818, 1-[[4-[(4-fluoro-2-methyl-1H-indol-5-yl)oxy]-6-methoxyquinolin-7-yl]oxymethyl]cyclopropan-1-amine), Ponatinib (AP24535, 3-(2-imidazo[1,2-b]pyridazin-3-ylethynyl)-4-methyl-N-[4-[(4-methylpiperazin-1-yl)methyl]-3-(trifluoromethyl)phenyl]benzamide), Regorafenib (BAY 73-4506, 4-[4-[[4-chloro-3-(trifluoromethyl)phenyl]carbamoylamino]-3-fluorophenoxy]-N-methylpyridine-2-carboxamide), Rogaratinib (BAY1163877, 4-[[4-amino-6-(methoxymethyl)-5-(7-methoxy-5-methyl-1-benzothiophen-2-yl)pyrrolo[2,1-f][1,2,4]triazin-7-yl]methyl]piperazin-2-one), Dasatinib (BMS 354825, N-(2-chloro-6-methylphenyl)-2-[[6-[4-(2-hydroxyethyl)piperazin-1-yl]-2-methylpyrimidin-4-yl]amino]-1,3-thiazole-5-carboxamide), Brivanib (BMS-540215, (2R)-1-[4-[(4-fluoro-2-methyl-1H-indol-5-yl)oxy]-5-methylpyrrolo[2,1-f][1,2,4]triazin-6-yl]oxypropan-2-ol), Debio 1347 (CH5183284, (5-amino-1-(2-methyl-1H-benzo[d]imidazol-6-yl)-1H-pyrazol-4-yl)(1H-indol-2-yl)methanone), ARQ-087 (derazantinib, (6R)-6-(2-fluorophenyl)-N-[3-[2-(2-methoxyethylamino)ethyl]phenyl]-5,6-dihydrobenzo[h]quinazolin-2-amine), Lucitanib (E3810, 6-[7-[(1-aminocyclopropyl)methoxy]-6-methoxyquinolin-4-yl]oxy-N-methylnaphthalene-1-carboxamide), Lenvatinib (E-7080, Lenvima®, 4-[3-chloro-4-(cyclopropylcarbamoylamino)phenoxy]-7-methoxyquinoline-6-carboxamide), Erdafitinib (JNJ42756493, N'-(3,5-dimethoxyphenyl)-N'-[3-(1-methylpyrazol-4-yl)quinoxalin-6-yl]-N-propan-2-ylethane-1,2-diamine), BIBF1120 (nintedanib, methyl (3Z)-3-[[4-[methyl-[2-(4-methylpiperazin-1-yl)acetyl]amino]anilino]phenylmethylidene]-2-oxo-1H-indole-6-carboxylate), BGJ398 (NVP-BGJ398, infigratinib, 3-(2,6-dichloro-3,5-dimethoxyphenyl)-1-[6-[4-(4-ethylpiperazin-1-yl)anilino]pyrimidin-4-yl]-1-methylurea), nintedanib (Ofev®, Vargatef®, Methyl (3Z)-3-{[(4-{methyl[(4-methylpiperazin-1-yl)acetyl]amino}phenyl)amino](phenyl)methylidene}-2-oxo-2,3-dihydro-1H-indole-6-carboxylate), Dovitinib (TKI 258, CHIR 258, (3Z)-4-amino-5-fluoro-3-[5-(4-methylpiperazin-1-yl)-1,3-dihydrobenzimidazol-2-ylidene]quinolin-2-one), Orantinib (TSU-68, 3-[2,4-dimethyl-5-[(Z)-(2-oxo-1H-indol-3-ylidene)methyl]-1H-pyrrol-3-yl]propanoic acid), ASP5878 (2-(4-((5-((2,6-difluoro-3,5-dimethoxybenzyl)oxy)pyrimidin-2-yl)amino)-1H-pyrazol-1-yl)ethan-1-ol), TAS-120 (1-[(3S)-3-[4-amino-3-[2-(3,5-dimethoxyphenyl)ethynyl]pyrazolo[3,4-d]pyrimidin-1-yl]pyrrolidin-1-yl]prop-2-en-1-one), pazopanib (5-[[4-[(2,3-dimethylindazol-6-yl)-methylamino]pyrimidin-2-yl]amino]-2-methylbenzenesulfonamide), pemigatinib (3-(2,6-difluoro-3,5-dimethoxyphenyl)-1-ethyl-8-(morpholin-4-ylmethyl)-4,7-dihydropyrrolo[4,5]pyrido[1,2-d]pyrimidin-2-one), E7090 (5-[2-[[4-[1-(2-hydroxyethyl)piperidin-4-yl]benzoyl]amino]pyridin-4-yl]oxy-6-(2-methoxyethoxy)-N-methylindole-1-carboxamide), PRN1371 (6-(2,6-dichloro-3,5-dimethoxyphenyl)-2-(methylamino)-8-[3-(4-prop-2-enoylpiperazin-1-yl)propyl]pyrido[2,3-d]pyrimidin-7-one), BLU-554 (N-[(3S,4S)-3-[[6-(2,6-dichloro-3,5-dimethoxyphenyl)quinazolin-2-yl]amino]oxan-4-yl]prop-2-enamide), Sulfatinib (N-[2-(dimethylamino)ethyl]-1-[3-[[4-[(2-methyl-1H-indol-5-yl)oxy]pyrimidin-2-yl]amino]phenyl]methanesulfonamide), H3B-6527 (N-[2-[[6-[(2,6-dichloro-3,5-dimethoxyphenyl)carbamoyl-methylamino]pyrimidin-4-yl]amino]-5-(4-ethylpiperazin-1-yl)phenyl]prop-2-enamide), AZD4547 (N-[5-[2-(3,5-Dimethoxyphenyl)ethyl]-2H-pyrazol-3-yl]-4-(3,5-diemthylpiperazin-1-yl)benzamide), FGF401 (N-[5-cyano-4-(2-methoxyethylamino)pyridin-2-yl]-7-formyl-6-[(4-methyl-2-oxopiperazin-1-yl)methyl]-3,4-dihydro-2H-1,8-naphthyridine-1-carboxamide), XL228, HMPL-453, INCB054828, MAX-40279, XL999, INCB062079, B-701, BAY1179470, FPA144 (Bemarituzumab), BAY1187982, ISIS-FGFR4RX, and LY3076226.

Additional FGFR-targeted agents include those described in U.S. Pat. Nos. 9,931,401 and 9,925,240; U.S. Patent Application Publication Nos. 2018/0237424, 2018/0194844, 2018/0161327, 2018/0155340, 2018/0065960; and PCT Publication Nos. 2018/149382 and 2018/049781, each of which is herein incorporated by reference.

Non-limiting examples of receptor tyrosine kinase (e.g., Trk) targeted therapeutic agents include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, VM-902A, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in Cancer Chemother. Pharmacol. 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in ACS Med. Chem. Lett. 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in Cancer 117(6):1321-1391, 2011; AZD6918, described in Cancer Biol. Ther. 16(3):477-483, 2015; AZ64, described in Cancer Chemother. Pharmacol. 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in Mol. Cancer Ther. 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in Int. J. Cancer 72:672-679, 1997; CT327, described in Acta Derm. Venereol. 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in PLoS One 9:e95628, 2014; compounds described in International Publication No. WO 2011/133637; compounds described in U.S. Pat. No. 8,637,256; compounds described in Expert. Opin. Ther. Pat. 24(7):731-744, 2014; compounds described in Expert Opin. Ther. Pat. 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol as described in ACS Med. Chem. Lett. 6(5):562-567, 2015; GTx-186 and others, as described in PLoS One 8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in Mol. Cell Biochem. 339(1-2):201-213, 2010; 4-aminopyrazolylpyrimidines, e.g., AZ-23 U(S)-5-chloro-N2-(1-(5-fluoropyridin-2-yl)ethyl)-N4-(5-isopropoxy-1H-pyrazol-3-yl)pyrimidine-2,4-diamine)), as described in J. Med. Chem. 51(15):4672-4684, 2008; PHA-739358 (danusertib), as described in Mol. Cancer Ther. 6:3158, 2007; Gö 6976 (5,6,7,13-tetrahydro-13-methyl-5-oxo-12H-indolo[2,3-a]pyrrolo[3,4-c]carbazole-12-propanenitrile), as described in J. Neurochem. 72:919-924, 1999; GW441756 ((3Z)-3-[(1-methylindol-3-yl)methylidene]-1H-pyrrolo[3,2-b]pyridin-2-one), as described in IJAE 115:117, 2010; milciclib (PHA-848125AC), described in J. Carcinog. 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5S,6S,8R)-6-Hydroxy-6-(hydroxymethyl)-5-methyl-7,8,14,15-tetrahydro-5H-16-oxa-4b,8a,14-triaza-5, 8-methanodibenzo[b,h]cycloocta[jkl]cyclopenta[e]-as-indacen-13(6H)-one); dovitinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl) pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl) phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, the receptor tyrosine kinase inhibitor is an epidermal growth factor receptor typrosine kinase inhibitor (EGFR). For example, EGFR inhibitors can include osimertinib (merelectinib, Tagrisso), erlotinib (Tarceva), gefitinib (Iressa), cetuximab (Erbitux), necitumumab (Portrazza), neratinib (Nerlynx), lapatinib (Tykerb), panitumumab (Vectibix), and vandetanib (Caprelsa). In some embodiments, the EGFR inhibitor is osimertinib.

In some embodiments, signal transduction pathway inhibitors include Ras-Raf-MEK-ERK pathway inhibitors (e.g., binimetinib, selumetinib, encorafenib, sorafenib, trametinib, and vemurafenib), PI3K-Akt-mTOR-56K pathway inhibitors (e.g. everolimus, rapamycin, perifosine, temsirolimus), JAK-STAT pathway inhibitors (e.g., methotrexate, ruxolitinib, tofacitinib, oclacitinib, baricitinib) and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MED14736, MSB0010718C, BMS-936559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine.

In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is bacillus Calmette-Guerin (BCG) therapy. In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S(E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Further examples of kinase inhibitors include luminespib (AUY-922, NVP-AUY922) (5-(2,4-dihydroxy-5-isopropylphenyl)-N-ethyl-4-(4-(morpholinomethyl)phenyl)isoxazole-3-carboxamide) and doramapimod (BIRB-796) (1-[5-tert-butyl-2-(4-methylphenyl)pyrazol-3-yl]-3-[4-(2-morpholin-4-ylethoxy)naphthalen-1-yl]urea).

Accordingly, also provided herein is a method of treating cancer, comprising administering to a subject in need thereof a pharmaceutical combination for treating cancer which comprises (a) a compound of Formula I or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or a pharmaceutically acceptable salt or solvate thereof and the additional therapeutic agent are together effective in treating the cancer.

These additional therapeutic agents may be administered with one or more doses of the compound of Formula I, or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

In some embodiments of any of the methods disclosed herein, the additional therapeutic agent(s) includes any one of the above listed therapies or therapeutic agents which are standards of care in cancers wherein the cancer has a dysregulation of a FGFR gene, a FGFR protein, or expression or activity, or level of any of the same.

Also provided herein is (i) a pharmaceutical combination for treating a cancer in a subject in need thereof, which comprises (a) a compound of Formula I or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a subject in need thereof. In some embodiments, the subject is a human. In some embodiments, the cancer is a FGFR-associated cancer. For example, a FGFR-associated cancer having one or more FGFR inhibitor resistance mutations.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., a chemotherapeutic agent), are both administered to a subject simultaneously in the form of a single composition or dosage. The term "non-fixed combination" means that a compound of Formula I or a pharmaceutically acceptable salt or solvate thereof and at least one additional therapeutic agent (e.g., chemotherapeutic agent) are formulated as separate compositions or dosages such that they may be administered to a subject in need thereof simultaneously, concurrently or sequentially with variable intervening time limits, wherein such administration provides effective levels of the two or more compounds in the body of the subject. These also apply to cocktail therapies, e.g. the administration of three or more active ingredients.

Accordingly, also provided herein is a method of treating a disease or disorder, comprising administering to a subject in need thereof a pharmaceutical combination for treating the disease or disorder which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of the disease or disorder, wherein the amounts of the compound of Formula I or pharmaceutically acceptable salt or solvate thereof and the additional therapeutic agent are together effective in treating the disease or disorder. In some embodiments, the compound of Formula I or pharmaceutically acceptable salt or solvate thereof, and the additional therapeutic agent are administered simultaneously as separate dosages. In some embodiments, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In some embodiments, the compound of Formula I or pharmaceutically acceptable salt or solvate thereof, and the additional therapeutic agent are administered simultaneously as a combined dosage. In some embodiments, the disease or disorder is a FGFR-associated disease or disorder. In some embodiments, the subject has been administered one or more doses of a compound of Formula I, or a pharmaceutically acceptable salt thereof, prior to administration of the pharmaceutical composition.

Also provided herein is a compound of Formula I or a pharmaceutically acceptable salt or solvate thereof, for use in the treatment of a FGFR-associated disease or disorder as defined hereinabove.

In certain embodiments of these methods, the treatment period can be from about 1 day to about 30 days (e.g., from about 1 day to about 15 days; e.g. about 7 days; e.g., from about 16 days to about 30 days, e.g., about 21 days). In other embodiments of these methods, the treatment period can be from 30 days to about 12 months (e.g., from about 30 days to about 9 months, from about 30 days to about 6 months, from about 30 days to about 120 days, from about 30 days to about 90 days, from about 30 days to about 60 days). In still other embodiments, the treatment period is 7 days or more or 21 days or more (e.g., more than 7 days or more than 21 days to about 12 months, more than 7 days or more than 21 days to about 9 months, more than 7 days or more than 21 days to about 6 months, more than 7 days or more than 21 days to about 120 days, more than 7 days or more than 21 days to about 90 days, more than 7 days or more than 21 days to about 60 days, more than 7 days or more than 21 days to about 30 days).

In some embodiments of these methods, the treatment period is at least or about 1 day, at least or about 2 days, at least or about 3 days, at least or about 4 days, at least or about 5 days, at least or about 6 days, at least or about 7 days, at least or about 8 days, at least or about 9 days, at least or about 10 days, at least or about 11 days, at least or about 12 days, at least or about 13 days, at least or about 14 days, at least or about 15 days, at least or about 16 days, at least or about 17 days, at least or about 18 days, at least or about 19 days, at least or about 20 days, at least or about 21 days, at least or about 22 days, at least or about 23 days, at least or about 24 days, at least or about 25 days, at least or about 26 days, at least or about 27 days, at least or about 28 days, at least or about 29 days, at least or about 30 days, at least or about 31 days, at least or about 45 days, at least or about 60 days, at least or about 90 days, at least or about 120 days, at least or about 6 months, at least or about 9 months, at least or about 12 months.

Accordingly, also provided herein is a method of treating a cancer, comprising administering to a subject in need thereof a pharmaceutical combination for treating cancer which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or pharmaceutically acceptable salt or solvate thereof and the additional therapeutic agent are together effective in treating the cancer. In some embodiments, the compound of Formula I or pharmaceutically acceptable salt or solvate thereof, and the additional therapeutic agent are administered simultaneously as separate dosages. In some embodiments, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In some embodiments, the compound of Formula I or pharmaceutically acceptable salt or solvate thereof, and the additional therapeutic agent are administered simultaneously as a combined dosage. In some embodiments, the cancer is a FGFR-associated cancer. For example, a FGFR-associated cancer having one or more FGFR inhibitor resistance mutations. In some embodiments, the additional therapeutic agent is crizotinib. In some embodiments, the additional therapeutic agent is osimertinib. In some embodiments, the subject has been administered one or more doses of a compound of Formula I, or a pharmaceutically acceptable salt thereof, prior to administration of the pharmaceutical composition. In some embodiments, the cancer is a bladder cancer (e.g., a FGFR-associated bladder cancer).

Also provided herein is a method of treating a disease or disorder mediated by FGFR in a subject in need of such treatment, the method comprising administering to the subject a therapeutically effective amount of a compound of Formula I or pharmaceutically acceptable salt or solvate thereof. In some embodiments, the disease or disorder mediated by FGFR is a dysregulation of FGFR gene, a FGFR kinase, or expression or activity or level of any of the same. For example, the dysregulation of a FGFR gene, a FGFR kinase, or expression or activity or level of any of the same includes one or more FGFR inhibitor resistance mutations. A disease or disorder mediated by FGFR can include any disease, disorder or condition that is directly or indirectly linked to expression or activity of a FGFR, including overexpression and/or abnormal activity levels. In some embodiments, the disease is cancer (e.g., a FGFR-associated cancer). In some embodiments, the cancer is any of the cancers or FGFR-associated cancers described herein. In some embodiments, the additional therapeutic agent is crizotinib. In some embodiments, the additional therapeutic agent is osimertinib. In some embodiments, the subject has been administered one or more doses of a compound of Formula I, or a pharmaceutically acceptable salt thereof, prior to administration of the pharmaceutical composition. In some embodiments, the cancer is a bladder cancer (e.g., a FGFR-associated bladder cancer).

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. FGFR proteins have been implicated for a role in metastasis (Qian et al., Oncogene 33:3411-3421, 2014).

Accordingly, also provided herein are methods for inhibiting, preventing, aiding in the prevention, or decreasing the symptoms of metastasis of a cancer in a subject in need thereof, the method comprising administering to the subject a therapeutically effective amount of a compound of Formula I or pharmaceutically acceptable salt or solvate thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., *Rev Neurosci* 2018 Jan. 26; 29:93-98; Gao L, et al., *Pancreas* 2015 January; 44:134-143; Ding K et al., *J Biol Chem* 2014 Jun. 6; 289:16057-71; and Amit M et al., *Oncogene* 2017 Jun. 8; 36:3232-3239. In some embodiments, the cancer is a FGFR-associated cancer. In some embodiments, the compound of Formula I or a pharmaceutically acceptable salt or solvate thereof is used in combination with an additional therapy or another therapeutic agent, including a chemotherapeutic agent, such as a kinase inhibitor. For example, a first or second FGFR kinase inhibitor. In some embodiments, the additional therapeutic agent is crizotinib. In some embodiments, the additional therapeutic agent is osimertinib. In some embodiments, the subject has been administered one or more doses of a compound of Formula I, or a pharmaceutically acceptable salt thereof, prior to administration of the pharmaceutical composition. In some embodiments, the cancer is a bladder cancer (e.g., a FGFR-associated bladder cancer).

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a subject having a FGFR-associated cancer that include: selecting, identifying, or diagnosing a subject as having a FGFR-associated cancer, and administering a therapeutically effective amount of a compound of Formula I or a pharmaceutically acceptable salt or solvate thereof to the subject selected, identified, or diagnosed as having a FGFR-associated cancer. Also provided are methods of decreasing the risk of developing a metastasis or an additional metastasis in a subject having a FGFR-associated cancer that includes administering a therapeutically effective amount of a compound of Formula I or a pharmaceutically acceptable salt or solvent thereof to a subject having a FGFR-associated cancer. The decrease in the risk of developing a metastasis or an additional metastasis in a subject having a FGFR-associated cancer can be compared to the risk of developing a metastasis or an additional metastasis in the subject prior to treatment, or as compared to a subject or a population of subjects having a similar or the same FGFR-associated cancer that has received no treatment or a different treatment. The decrease in the risk of developing a metastasis or an additional metastasis can be about 1% to about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5%; about 5% to about 99%, about 95%, about 90%, about 85%, about 80%, about 75%, about 70%, about 65%, about 60%, about 55%, about 50%, about 45%, about 40%, about 35%, about 30%, about 25%, about 20%, about 15%, or about 10%; about 10% to about 99%, about 95%, about 90%, about 85%, about 80%, about 75%, about 70%, about 65%, about 60%, about 55%, about 50%, about 45%, about 40%, about 35%, about 30%, about 25%, about 20%, or about 15%; about 15% to about 99%, about 95%, about 90%, about 85%, about 80%, about 75%, about 70%, about 65%, about 60%, about 55%, about 50%, about 45%, about 40%, about 35%, about 30%, about 25%, or about 20%; about 20% to about 99%, about 95%, about 90%, about 85%, about 80%, about 75%, about 70%, about 65%, about 60%, about 55%, about 50%, about 45%, about 40%, about 35%, about 30%, or about 25%; about 25% to about 99%, about 95%, about 90%, about 85%, about 80%, about 75%, about 70%, about 65%, about 60%, about 55%, about 50%, about 45%, about 40%, about 35%, or about 30%; about 30% to about 99%, about 95%, about 90%, about 85%, about 80%, about 75%, about 70%, about 65%, about 60%, about 55%, about 50%, about 45%, about 40%, or about 35%; about 35% to about 99%, about 95%, about 90%, about 85%, about 80%, about 75%, about 70%, about 65%, about 60%, about 55%, about 50%, about 45%, or about 40%; about 40% to about 99%, about 95%, about 90%, about 85%, about 80%, about 75%, about 70%, about 65%, about 60%, about 55%, about 50%, or about 45%; about 45% to about 99%, about 95%, about 90%, about 85%, about 80%, about 75%, about 70%, about 65%, about 60%, about 55%, or about 50%; about 50% to about 99%, about 95%, about 90%, about 85%, about 80%, about 75%, about 70%, about 65%, about 60%, or about 55%; about 55% to about 99%, about 95%, about 90%, about 85%, about 80%, about 75%, about 70%, about 65%, or about 60%; about 60% to about 99%, about 95%, about 90%, about 85%, about 80%, about 75%, about 70%, or about 65%; about 65% to about 99%, about 95%, about 90%, about 85%, about 80%, about 75%, or about 70%; about 70% to about 99%, about 95%, about 90%, about 85%, about 80%, or about 75%; about 75% to about 99%, about 95%, about 90%, about 85%, or about 80%; about 80% to about 99%, about 95%, about 90%, or about 85%; about 85% to about 99%, about 95%, or about 90%; about 90% to about 99% or about 90%; or about 95% to about 99% as compared to the risk of developing a metastasis or an additional metastasis in the patient prior to treatment, or as compared to a patient or a population of patients having a similar or the same FGFR-associated cancer that has received no treatment or a different treatment.

In some examples, the risk of developing a metastasis or an additional metastasis is over about 2 weeks, 1 month, 1.5 months, 2 months, 2.5 months, 3 months, 3.5 months, 4 months, 4.5 months, 5 months, 5.5 months, 6 months, 6.5 months, 7 months, 7.5 months, 8 months, 8.5 months, 9 months, 9.5 months, 10 months, 10.5 months, 11 months, 11.5 months, 12 months, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, or 10 years.

Also provided is the use of a compound of Formula I or a pharmaceutically acceptable salt or solvate thereof for decreasing the risk of developing a metastasis or an additional metastasis in a patient having a FGFR-associated cancer. Also provided is the use of a compound of Formula I or a pharmaceutically acceptable salt or solvate thereof for the manufacture of a medicament for decreasing the risk of developing a metastasis or an additional metastasis in a patient having a FGFR-associated cancer.

In some embodiments, the FGFR-associated cancer is a FGFR-associated cancer having one or more FGFR inhibitor resistance mutations. In some embodiments, the additional therapeutic agent is crizotinib. In some embodiments, the additional therapeutic agent is osimertinib. In some embodiments, the subject has been administered one or more doses of a compound of Formula I, or a pharmaceutically acceptable salt thereof, prior to administration of the pharmaceutical composition. In some embodiments, the cancer is a bladder cancer (e.g., a FGFR-associated bladder cancer).

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a multikinase inhibitor (MKI) or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering a compound of Formula I, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the multikinase inhibitor of step (b) to the subject if the subject has a cancer cell that does not have a FGFR inhibitor resistance mutation. In some embodiments of any of the methods disclosed herein, a multikinase inhibitor can be selected from the group consisting of brivanib, dovitinib, erdafitinib, lenvatinib, lucitanib, nintedanib, orantinib, pemigatinib, ponatinib, rogaratinib, and sulfatinib.

In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first multikinase inhibitor or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the multikinase inhibitor of step (b) to the subject if the subject has a cancer cell that does not have a FGFR inhibitor resistance mutation. In some embodiments of any of the methods disclosed herein, a multikinase inhibitor can be selected from the group consisting of brivanib, dovitinib, erdafitinib, lenvatinib, lucitanib, nintedanib, orantinib, pemigatinib, ponatinib, rogaratinib, and sulfatinib.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC a sample from the subject; and (b) administering to the subject a therapeutically effective amount of a multikinase inhibitor or a pharmaceutically acceptable salt or solvate thereof. In some embodiments, the methods further comprise (after (b)) (c) determining whether a cancer cell in a sample obtained from the subject has at least one FGFR inhibitor resistance mutation of Table BE; and (d) administering a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the multikinase inhibitor of step (b) to the subject if the subject has a cancer cell that does not have a FGFR inhibitor resistance mutation. In some embodiments of any of the methods disclosed herein, a multikinase inhibitor can be selected from the group consisting of brivanib, dovitinib, erdafitinib, lenvatinib, lucitanib, nintedanib, orantinib, pemigatinib, ponatinib, rogaratinib, and sulfatinib.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC a sample from the subject; and (b) administering to the subject a therapeutically effective amount of a multikinase inhibitor or a pharmaceutically acceptable salt or solvate thereof. In some embodiments, the methods further comprise (after (b)) (c) determining whether a cancer cell in a sample obtained from the subject has at least one FGFR inhibitor resistance mutation of Table BE; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the multikinase inhibitor of step (b) to the subject if the subject has a cancer cell that does not have a FGFR inhibitor resistance mutation. In some embodiments of any of the methods disclosed herein, a multikinase inhibitor can be selected from the group consisting of brivanib, dovitinib, erdafitinib, lenvatinib, lucitanib, nintedanib, orantinib, pemigatinib, ponatinib, rogaratinib, and sulfatinib.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a multikinase inhibitor or a pharmaceutically acceptable salt or solvate thereof. In some embodiments, the methods further comprise (after (b)) (c) determining whether a cancer cell in a sample obtained from the subject has a FGFR inhibitor resistance mutation corresponding to V561M in SEQ ID NO. 1, V564I or V564F in SEQ ID NO. 3, or V555M in SEQ ID NO. 5; and (d) administering a compound of Formula I or a pharmaceutically acceptable salt or solvate thereof selected from the group consisting of a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the multikinase inhibitor of step (b) to the subject if the subject has a cancer cell that does not have a FGFR inhibitor resistance mutation. In some embodiments of any of the methods disclosed herein, a multikinase inhibitor can be selected from the group consisting of brivanib, dovitinib, erdafitinib, lenvatinib, lucitanib, nintedanib, orantinib, pemigatinib, ponatinib, rogaratinib, and sulfatinib.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a multikinase inhibitor or a pharmaceutically acceptable salt or solvate thereof. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the multikinase inhibitor of step (b) to the subject if the subject has a cancer cell that does not have a FGFR inhibitor resistance mutation. In some embodiments of any of the methods disclosed herein, a multikinase inhibitor can be selected from the group consisting of brivanib, dovitinib, erdafitinib, lenvatinib, lucitanib, nintedanib, orantinib, pemigatinib, ponatinib, rogaratinib, and sulfatinib.

In some embodiments, the presence of one or more FGFR inhibitor resistance mutations in a tumor causes the tumor to be more resistant to treatment with a first FGFR inhibitor. Methods useful when a FGFR inhibitor resistance mutation causes the tumor to be more resistant to treatment with a first FGFR inhibitor are described below. For example, provided herein are methods of treating a subject having a cancer that include: identifying a subject having a cancer cell that has one or more FGFR inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first FGFR inhibitor. Also provided are methods of treating a subject identified as having a cancer cell that has one or more FGFR inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first FGFR inhibitor. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M).

For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR inhibitor, wherein the first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the methods further comprise (after (b)) (c) determining whether a cancer cell in a sample obtained from the subject has at least one FGFR inhibitor resistance mutation; and (d) administering a compound of Formula I, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the first FGFR inhibitor of step (b) to the subject if the subject has a cancer cell that does not have a FGFR inhibitor resistance mutation.

In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR inhibitor, wherein the first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the methods further comprise (after (b)) (c) determining whether a cancer cell in a sample obtained from the subject has at least one FGFR inhibitor resistance mutation; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the first FGFR inhibitor of step (b) to the subject if the subject has a cancer cell that does not have a FGFR inhibitor resistance mutation.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR inhibitor, wherein the first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the methods further comprise (after (b)) (c) determining whether a cancer cell in a sample obtained from the subject has at least one FGFR inhibitor resistance mutation of Table BE; and (d) administering a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the first FGFR inhibitor of step (b) to the subject if the subject has a cancer cell that does not have a FGFR inhibitor resistance mutation.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR inhibitor, wherein the first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the methods further comprise (after (b)) (c) determining whether a cancer cell in a sample obtained from the subject has at least one FGFR inhibitor resistance mutation of Table BE; and (d) administering a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the first FGFR inhibitor of step (b) to the subject if the subject has a cancer cell that does not have a FGFR inhibitor resistance mutation.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR inhibitor, wherein the first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the methods further comprise (after (b)) (c) determining whether a cancer cell in a sample obtained from the subject has at least one FGFR inhibitor resistance mutation of Table BE; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the first FGFR inhibitor of step (b) to the subject if the subject has a cancer cell that does not have a FGFR inhibitor resistance mutation.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR inhibitor, wherein the first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering a compound of Formula I or a pharmaceutically acceptable salt or solvate thereof selected from the group consisting of a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the first FGFR inhibitor of step (b) to the subject if the subject has a cancer cell that does not have a FGFR inhibitor resistance mutation.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR inhibitor, wherein the first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering a compound of Formula I or a pharmaceutically acceptable salt or solvate thereof selected from the group consisting of a compound of Formula I selected from Examples 1-135, 137-146, and 148-

196, or a pharmaceutically acceptable salt or solvate thereof as a monotherapy or in conjunction with an additional therapy or therapeutic agent to the subject if the subject has a cancer cell that has at least one FGFR inhibitor resistance mutation; or (e) administering additional doses of the first FGFR inhibitor of step (b) to the subject if the subject has a cancer cell that does not have a FGFR inhibitor resistance mutation.

Also provided are methods of treating a subject having a cancer that include: (a) administering one or more doses of a first FGFR inhibitor to the subject for a period of time; (b) after (a), determining whether a cancer cell in a sample obtained from the subject has at least one FGFR inhibitor resistance mutation; and (c) administering a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation; or (d) administering additional doses of the first FGFR inhibitor of step (a) to the subject if the subject has a cancer cell that does not have a FGFR inhibitor resistance mutation. In some embodiments, where the subject is administered additional doses of the first FGFR inhibitor of step (a), the subject can also be administered an additional therapy or therapeutic agent (e.g., a second FGFR inhibitor or a compound of Formula I or a pharmaceutically acceptable salt or solvate thereof, or immunotherapy). In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments of step (c), another FGFR inhibitor can be the first FGFR inhibitor administered in step (a). In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M).

Also provided are methods of treating a subject having a cancer that include: (a) administering one or more doses of a first FGFR inhibitor to the subject for a period of time; (b) after (a), determining whether a cancer cell in a sample obtained from the subject has at least one FGFR inhibitor resistance mutation; and (c) administering a second FGFR inhibitor as a monotherapy or in conjunction with an additional therapy or therapeutic agent to the subject if the subject has a cancer cell that has at least one FGFR inhibitor resistance mutation; or (d) administering additional doses of the first FGFR inhibitor step (a) to the subject if the subject has a cancer cell that does not have a FGFR inhibitor resistance mutation. In some embodiments, where the subject is administered additional doses of the first FGFR inhibitor of step (a), the subject can also be administered an additional therapy or therapeutic agent. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M). In some embodiments, the additional therapy or therapeutic agent is any anticancer agent known in the art. For example, the additional therapy or therapeutic agent is another FGFR inhibitor (e.g., a compound of Formula I or a pharmaceutically acceptable salt or solvate thereof). In some embodiments, the additional therapy or therapeutic agent is an immunotherapy. In some embodiments, a compound of Formula I is at least about 3-fold more selective for FGFR3 over FGFR1. In some embodiments, a compound of Formula I is at least about 3-fold more selective for FGFR2 over FGFR1.

Also provided are methods of treating a subject having a cancer (e.g., a FGFR-associated cancer) that include: (a) determining whether a cancer cell in a sample obtained from a subject having a cancer and previously administered one or more doses of a first FGFR inhibitor, has one or more FGFR inhibitor resistance mutations; and (b) administering a compound of Formula I or a pharmaceutically acceptable salt or solvate thereof as a monotherapy or in conjunction with an additional therapy or therapeutic agent to the subject if the subject has a cancer cell that has at least one FGFR inhibitor resistance mutation; or (c) administering additional doses of the first FGFR inhibitor previously administered to the subject if the subject has cancer cell that does not have a FGFR inhibitor resistance mutation. In some embodiments, where the subject is administered additional doses of the first FGFR inhibitor previously administered to the subject, the subject can also be administered an additional therapy or therapeutic agent (e.g., a compound of Formula I or a pharmaceutically acceptable salt or solvate thereof, or immunotherapy). In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M). In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments of step (b), the additional therapy or therapeutic agent can be the first FGFR inhibitor administered in step (a).

Also provided are methods of treating a subject having a cancer that include: (a) determining whether a cancer cell in a sample obtained from a subject having a cancer and previously administered one or more doses of a first FGFR inhibitor has one or more FGFR inhibitor resistance mutations; and (b) administering a second FGFR inhibitor as a monotherapy or in conjunction with an additional therapy or therapeutic agent to the subject if the subject has a cancer cell that has at least one FGFR inhibitor resistance mutation; or (c) administering additional doses of the first FGFR inhibitor previously administered to the subject if the subject has a cancer cell that does not have a FGFR inhibitor resistance mutation. In some embodiments, where the subject is administered additional doses of the first FGFR inhibitor previously administered to the subject, the subject can also be administered an additional therapy or therapeutic agent. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M). In some embodiments, the additional therapy or therapeutic agent is any anticancer agent known in the art. For example, the additional therapy or therapeutic agent is another FGFR inhibitor (e.g., a compound of Formula I or a pharmaceutically acceptable salt or solvate thereof). In some embodiments, the additional therapy or therapeutic agent is an immunotherapy. In some embodiments of (b), the additional therapy or therapeutic agent can be the first FGFR inhibitor administered in step (a).

In some embodiments of any of the methods described herein, a FGFR inhibitor resistance mutation that confers increased resistance to a cancer cell or tumor to treatment with a first FGFR inhibitor can be any of the FGFR inhibitor resistance mutations listed in Table BE (e.g., a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M)).

Methods of determining the level of resistance of a cancer cell or a tumor to a FGFR inhibitor (e.g., any of the FGFR inhibitors described herein or known in the art) can be determined using methods known in the art. For example, the level of resistance of a cancer cell to a FGFR inhibitor can be assessed by determining the $IC_{50}$ of a FGFR inhibitor (e.g., any of the FGFR inhibitors described herein or known in the art) on the viability of a cancer cell. In other examples, the level of resistance of a cancer cell to a FGFR inhibitor can be assessed by determining the growth rate of the cancer cell in the presence of a FGFR inhibitor (e.g., any of the FGFR inhibitors described herein). In other examples, the level of resistance of a tumor to a FGFR inhibitor can be assessed by determining the mass or size of one or more tumors in a subject over time during treatment with a FGFR inhibitor (e.g., any of the FGFR inhibitors described herein). In other examples, the level of resistance of a cancer cell or a tumor to a FGFR inhibitor can be indirectly assessed by determining the activity of a FGFR kinase including one or more of the FGFR inhibitor resistance mutations (i.e., the same FGFR kinase expressed in a cancer cell or a tumor in a subject). The level of resistance of a cancer cell or tumor having one or more FGFR inhibitor resistance mutations to a FGFR inhibitor is relative to the level of resistance in a cancer cell or tumor that does not have a FGFR inhibitor resistance mutation (e.g., a cancer cell or tumor that does not have the same FGFR inhibitor resistance mutations, a cancer cell or a tumor that does not have any FGFR inhibitor resistance mutations, or a cancer cell or a tumor that expresses a wildtype FGFR protein). For example, the determined level of resistance of a cancer cell or a tumor having one or more FGFR inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a FGFR inhibitor resistance mutation (e.g., a cancer cell or tumor that does not have the same FGFR inhibitor resistance mutations, a cancer cell or a tumor that does not have any FGFR inhibitor resistance mutations, or a cancer cell or a tumor that expresses a wildtype FGFR protein).

In some embodiments, the presence of one or more FGFR inhibitor resistance mutations in a tumor causes the tumor to be more resistant to treatment with a compound of Formula I or a pharmaceutically acceptable salt or solvate thereof. Methods useful when a FGFR inhibitor resistance mutation causes the tumor to be more resistant to treatment with a compound of Formula I or a pharmaceutically acceptable salt or solvate thereof are described below. For example, provided herein are methods of treating a subject having a cancer that include: identifying a subject having a cancer cell that has one or more FGFR inhibitor resistance mutations; and administering to the identified subject a treatment that does not include a compound of Formula I or a pharmaceutically acceptable salt or solvate thereof as a monotherapy or in conjunction with an additional therapy or therapeutic agent (e.g., a second FGFR kinase inhibitor). Also provided are methods of treating a subject identified as having a cancer cell that has one or more FGFR inhibitor resistance mutations that include administering to the subject a treatment that does not include a compound of Formula I or a pharmaceutically acceptable salt or solvate thereof as a monotherapy or in conjunction with an additional therapy or therapeutic agent (e.g., a second FGFR kinase inhibitor). In some embodiments, the one or more FGFR inhibitor resistance mutations confer increased resistance to a cancer cell or tumor to treatment with a compound of Formula I or a pharmaceutically acceptable salt or solvate thereof.

Also provided are methods of treating a subject having a cancer that include: (a) administering one or more doses of a compound of Formula I or a pharmaceutically acceptable salt or solvate thereof for a period of time; (b) after (a), determining whether a cancer cell in a sample obtained from the subject has one or more FGFR inhibitor resistance mutations; and (c) administering a second FGFR inhibitor or a second compound of Formula I or a pharmaceutically acceptable salt or solvate thereof as a monotherapy or in conjunction with an additional therapy or therapeutic agent to a subject having a cancer cell that has one or more FGFR inhibitor resistance mutations; or (d) administering additional doses of the compound of Formula I or a pharmaceutically acceptable salt or solvate thereof of step (a) to a subject having a cancer cell that does not have a FGFR inhibitor resistance mutation. In some embodiments, where the subject is administered additional doses of the compound of Formula I or a pharmaceutically acceptable salt or solvate thereof of step (a), the subject can also be administered an additional therapy or therapeutic agent or a second compound of Formula I or a pharmaceutically acceptable salt or solvate thereof. In some embodiments, the one or more FGFR inhibitor resistance mutations confer increased resistance to a cancer cell or tumor to treatment with a compound of Formula I or a pharmaceutically acceptable salt or solvate thereof. In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments, another FGFR inhibitor can be the compound of Formula I or a pharmaceutically acceptable salt or solvate thereof administered in step (a).

Also provided are methods of treating a subject having a cancer that include: (a) determining whether a cancer cell in a sample obtained from a subject having a cancer and previously administered one or more doses of a compound of Formula I or a pharmaceutically acceptable salt or solvate thereof, has one or more FGFR inhibitor resistance mutations; (b) administering a second FGFR inhibitor or a second compound of Formula I or a pharmaceutically acceptable salt or solvate thereof as a monotherapy or in conjunction with an additional therapy or therapeutic agent to a subject having a cancer cell that has one or more FGFR inhibitor resistance mutations; or (c) administering additional doses of the compound of Formula I or a pharmaceutically acceptable salt or solvate thereof previously administered to a subject having a cancer cell that does not have a FGFR inhibitor resistance mutation. In some embodiments, where the subject is administered additional doses of the compound of Formula I or a pharmaceutically acceptable salt or solvate thereof of step (a), the subject can also be administered an additional therapy or therapeutic agent. In some embodiments, the one or more FGFR inhibitor resistance mutations confer increased resistance to a cancer cell or tumor to treatment with a compound of Formula I or a pharmaceutically acceptable salt or solvate thereof. In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments, another FGFR inhibitor can be the compound of Formula I or a pharmaceutically acceptable salt or solvate thereof administered in step (a).

In some embodiments of any of the methods described herein, a FGFR inhibitor resistance mutation that confers increased resistance to a cancer cell or tumor to treatment with a compound of Formula I or a pharmaceutically acceptable salt or solvate thereof, can be any of the FGFR inhibitor resistance mutations listed in Table BE.

Also, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation. Also, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I selected from the group consisting of Examples 1-135, 137-146, and 148-196 or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I or a pharmaceutically acceptable salt or solvate thereof. In some embodiments, the methods further comprise (after (b)) (c) determining whether a cancer cell in a sample obtained from the subject has at least one FGFR inhibitor resistance mutation of Table BE; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has at least one FGFR inhibitor resistance mutation of Table BE; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d).

Also, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) detecting at least one FGFR inhibitor resistance mutation in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) detecting at least one FGFR inhibitor resistance mutation in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I or a pharmaceutically acceptable salt or solvate thereof. In some embodiments, the methods further comprise (after (b)) (c) detecting at least one FGFR inhibitor resistance mutation of Table BE in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof. In some embodiments, the methods further comprise (after (b)) (c) detecting at least one FGFR inhibitor resistance mutation of Table BE in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I or a pharmaceutically acceptable salt or solvate thereof. In some embodiments, the methods further comprise (after (b)) (c) detecting the FGFR inhibitor resistance mutation corresponding to V561M in SEQ ID NO. 1, V564I or V564F in SEQ ID NO. 3, or V555M in SEQ ID NO. 5 in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) detecting the FGFR inhibitor resistance mutation corresponding to V561M in SEQ ID NO. 1, V564I or V564F in SEQ ID NO. 3, or V555M in SEQ ID NO. 5 in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d).

Further provided herein is a method for treating bladder cancer in a subject in need thereof, the method comprising administering to the subject a therapeutically effective amount of a compound of Formula I or a pharmaceutically acceptable salt thereof, crizotinib, osimertinib, or any combination thereof.

As another example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation of Table BE; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some of the embodiments of any of the methods described herein, a compound of Formula I can be selected from the group consisting of Examples 1-135, 137-146, and 148-196.

As another example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I or a pharmaceutically acceptable salt thereof. In some embodiments, the methods further comprise (after (b)) (c) determining whether a cancer cell in a sample obtained from the subject has at least one FGFR inhibitor resistance mutation; and (d) administering a second therapeutic agent, wherein the second therapeutic agent is selected from the group consisting of crizotinib and osimertinib, as a monotherapy or in conjunction with a compound of Formula I or a pharmaceutically acceptable salt thereof to the subject if the subject has a cancer cell that has at least one FGFR inhibitor resistance mutation; or (e) administering additional doses of the compound of Formula I or a pharmaceutically acceptable salt thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting one or more fusion proteins of Table BA and/or one or more FGFR kinase protein point mutations/insertions of Table BC in a sample from the subject; and (b) administering to the subject a therapeutically effective amount of a compound of Formula I or a pharmaceutically acceptable salt thereof. In some embodiments, the methods further comprise (after (b)) (c) determining whether a cancer cell in a sample obtained from the subject has at least one FGFR inhibitor resistance mutation of Table BE; and (d) administering a second therapeutic agent, wherein the second therapeutic agent is selected from the group consisting of crizotinib and osimertinib, as a monotherapy or in conjunction with a compound of Formula I or a pharmaceutically acceptable salt thereof to the subject if the subject has a cancer cell that has at least one FGFR inhibitor resistance mutation; or (e) administering additional doses of the compound of Formula I or a pharmaceutically acceptable salt thereof of step (b) to the subject if the subject has a cancer cell that does not have a FGFR inhibitor resistance mutation. In some embodiments of the above, the FGFR-associated cancer is a bladder cancer.

As another example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has at least one FGFR inhibitor resistance mutation; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has at least one FGFR inhibitor resistance mutation of Table BE; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has at least one FGFR inhibitor resistance mutation of Table BE; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering a multikinase inhibitor (e.g., brivanib, dasatinib, erdafitinib, lenvatinib, lucitanib, nintedanib, orantinib, ponatinib, or sulfatinib) as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation. In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has the FGFR inhibitor resistance mutation corresponding to V561M in SEQ ID NO. 1, V564I or V564F in SEQ ID NO. 3, or V555M in SEQ ID NO. 5; and (d) administering a multikinase inhibitor (e.g., brivanib, dasatinib, erdafitinib, lenvatinib, lucitanib, nintedanib, orantinib, ponatinib, or sulfatinib) as a monotherapy or in conjunction with an additional therapy or therapeutic agent to the subject if the subject has a cancer cell that has at least one FGFR inhibitor resistance mutation; or (e) administering additional doses of the compound of Formula I or a pharmaceutically acceptable salt or solvate thereof of step (b) to the subject if the subject has a cancer cell that does not have a FGFR inhibitor resistance mutation.

In some embodiments, the presence of one or more FGFR inhibitor resistance mutations in a cysteine in a tumor causes the tumor to be more resistant to treatment with a compound of Formula I or a pharmaceutically acceptable salt or solvate thereof. Methods useful when a FGFR inhibitor resistance mutation in a cysteine causes the tumor to be more resistant to treatment with a compound of Formula I or a pharmaceutically acceptable salt or solvate thereof are described below. For example, provided herein are methods of treating a subject having a cancer that include: identifying a subject having a cancer cell that has one or more FGFR inhibitor resistance mutations in a cysteine; and administering to the identified subject a treatment that does not include a compound of Formula I or a pharmaceutically acceptable salt or solvate thereof as a monotherapy or in conjunction with an additional therapy or therapeutic agent (e.g., a second FGFR kinase inhibitor). Also provided are methods of treating a subject identified as having a cancer cell that has one or more FGFR inhibitor resistance mutations in a cysteine that include administering to the subject a treatment that does not include a compound of Formula I or a pharmaceutically acceptable salt or solvate thereof as a monotherapy or in conjunction with an additional therapy or therapeutic agent (e.g., a second FGFR kinase inhibitor). In some embodiments, the one or more FGFR inhibitor resistance mutations in a cysteine confer increased resistance to a cancer cell or tumor to treatment with a compound of Formula I or a pharmaceutically acceptable salt or solvate thereof.

Also provided are methods of treating a subject having a cancer that include: (a) administering one or more doses of a compound of Formula I or a pharmaceutically acceptable salt or solvate thereof for a period of time; (b) after (a), determining whether a cancer cell in a sample obtained from the subject has one or more FGFR inhibitor resistance mutations in a cysteine; and (c) administering a second FGFR inhibitor or a second compound of Formula I or a pharmaceutically acceptable salt or solvate thereof as a monotherapy or in conjunction with an additional therapy or therapeutic agent to a subject having a cancer cell that has one or more FGFR inhibitor resistance mutations in a cysteine; or (d) administering additional doses of the compound of Formula I or a pharmaceutically acceptable salt or solvate thereof of step (a) to a subject having a cancer cell that does not have a FGFR inhibitor resistance mutation in a cysteine. In some embodiments, where the subject is administered additional doses of the compound of Formula I or a pharmaceutically acceptable salt or solvate thereof of step (a), the subject can also be administered an additional therapy or therapeutic agent or a second compound of Formula I or a pharmaceutically acceptable salt or solvate thereof. In some embodiments, the one or more FGFR inhibitor resistance mutations in a cysteine confer increased resistance to a cancer cell or tumor to treatment with a compound of Formula I or a pharmaceutically acceptable salt or solvate thereof. In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments, another FGFR inhibitor can be the compound of Formula I or a pharmaceutically acceptable salt or solvate thereof administered in step (a).

Also provided are methods of treating a subject having a cancer that include: (a) determining whether a cancer cell in a sample obtained from a subject having a cancer and previously administered one or more doses of a compound of Formula I or a pharmaceutically acceptable salt or solvate thereof, has one or more FGFR inhibitor resistance mutations in a cysteine; (b) administering a second FGFR inhibitor or a second compound of Formula I or a pharmaceutically acceptable salt or solvate thereof as a monotherapy or in conjunction with an additional therapy or therapeutic agent to a subject having a cancer cell that has one or more FGFR inhibitor resistance mutations in a cysteine; or (c) administering additional doses of the compound of Formula I or a pharmaceutically acceptable salt or solvate thereof previously administered to a subject having a cancer cell that does not have a FGFR inhibitor resistance mutation in a cysteine. In some embodiments, where the subject is administered additional doses of the compound of Formula I or a pharmaceutically acceptable salt or solvate thereof of step (a), the subject can also be administered an additional therapy or therapeutic agent. In some embodiments, the one or more FGFR inhibitor resistance mutations in a cysteine confer increased resistance to a cancer cell or tumor to treatment with a compound of Formula I or a pharmaceutically acceptable salt or solvate thereof. In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments, another FGFR inhibitor can be the compound of Formula I or a pharmaceutically acceptable salt or solvate thereof administered in step (a).

In some embodiments of any of the methods described herein, a FGFR inhibitor resistance mutation in a cysteine that confers increased resistance to a cancer cell or tumor to treatment with a compound of Formula I or a pharmaceutically acceptable salt or solvate thereof, can be a mutation in a cysteine corresponding to Cys582 in SEQ ID NO: 5. In some embodiments of any of the methods described herein, a FGFR inhibitor resistance mutation in a cysteine that confers increased resistance to a cancer cell or tumor to treatment with a compound of Formula I or a pharmaceutically acceptable salt or solvate thereof, can be a mutation in a cysteine corresponding to Cys790 in SEQ ID NO: 3.

Also, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation in a cysteine. Also, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I selected from the group consisting of Examples 1-135, 137-146, and 148-196 or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation in a cysteine. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation in a cysteine. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation in a cysteine. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has the FGFR inhibitor resistance mutation in a cysteine corresponding to Cys582 of SEQ ID NO: 5 or a cysteine corresponding to Cys790 of SEQ ID NO:3; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation in a cysteine. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has the FGFR inhibitor resistance mutation in a cysteine corresponding to Cys582 of SEQ ID NO: 5 or a cysteine corresponding to Cys790 of SEQ ID NO:3; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation) if the subject has a cancer cell that has at least one FGFR inhibitor resistance mutation in a cysteine. In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d).

Also, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) detecting at least one FGFR inhibitor resistance mutation in a cysteine in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) detecting at least one FGFR inhibitor resistance mutation in a cysteine in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I or a pharmaceutically acceptable salt or solvate thereof. In some embodiments, the methods further comprise (after (b)) (c) detecting at least one FGFR inhibitor resistance mutation in a cysteine in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof. In some embodiments, the methods further comprise (after (b)) (c) detecting at least one FGFR inhibitor resistance mutation in a cysteine in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I or a pharmaceutically acceptable salt or solvate thereof. In some embodiments, the methods further comprise (after (b)) (c) detecting the FGFR inhibitor resistance mutation in a cysteine corresponding to Cys582 of SEQ ID NO: 5 or a cysteine corresponding to Cys790 of SEQ ID NO:3 in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d). In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) detecting the FGFR inhibitor resistance mutation in a cysteine corresponding to Cys582 of SEQ ID NO: 5 or a cysteine corresponding to Cys790 of SEQ ID NO:3 in a cancer cell in a sample obtained from the subject; and (d) administering additional doses of the compound of Formula I or a pharmaceutically acceptable salt or solvate thereof of step (b) to the subject as a monotherapy or in conjunction with an additional therapy or therapeutic agent (e.g., a second FGFR inhibitor, a second compound of Formula I or a pharmaceutically acceptable salt thereof, or immunotherapy) or anticancer therapy (e.g., surgery or radiation). In some embodiments, a second FGFR inhibitor selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120 is administered in step (d).

As another example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has the FGFR inhibitor resistance mutation in a cysteine corresponding to Cys582 of SEQ ID NO: 5 or a cysteine corresponding to Cys790 of SEQ ID NO:3; and (d) administering a second FGFR inhibitor, wherein the second FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120, as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some of the embodiments of any of the methods described herein, a compound of Formula I can be selected from the group consisting of Examples 1-135, 137-146, and 148-196.

As another example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I or a pharmaceutically acceptable salt thereof. In some embodiments, the methods further comprise (after (b)) (c) determining whether a cancer cell in a sample obtained from the subject has at least one FGFR inhibitor resistance mutation in a cysteine; and (d) administering a second therapeutic agent, wherein the second therapeutic agent is selected from the group consisting of crizotinib and osimertinib, as a monotherapy or in conjunction with a compound of Formula I or a pharmaceutically acceptable salt thereof to the subject if the subject has a cancer cell that has at least one FGFR inhibitor resistance mutation in a cysteine; or (e) administering additional doses of the compound of Formula I or a pharmaceutically acceptable salt thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting one or more fusion proteins of Table BA and/or one or more FGFR kinase protein point mutations/insertions of Table BC in a sample from the subject; and (b) administering to the subject a therapeutically effective amount of a compound of Formula I or a pharmaceutically acceptable salt thereof. In some embodiments, the methods further comprise (after (b)) (c) determining whether a cancer cell in a sample obtained from the subject has at least one FGFR inhibitor resistance mutation in a cysteine; and (d) administering a second therapeutic agent, wherein the second therapeutic agent is selected from the group consisting of crizotinib and osimertinib, as a monotherapy or in conjunction with a compound of Formula I or a pharmaceutically acceptable salt thereof to the subject if the subject has a cancer cell that has at least one FGFR inhibitor resistance mutation in a cysteine; or (e) administering additional doses of the compound of Formula I or a pharmaceutically acceptable salt thereof of step (b) to the subject if the subject has a cancer cell that does not have a FGFR inhibitor resistance mutation in a cysteine. In some embodiments of the above, the FGFR-associated cancer is a bladder cancer.

As another example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has at least one FGFR inhibitor resistance mutation in a cysteine; and (d) administering a multikinase inhibitor (e.g., brivanib, dasatinib, erdafitinib, lenvatinib, lucitanib, nintedanib, orantinib, ponatinib, or sulfatinib), as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has the FGFR inhibitor resistance mutation in a cysteine corresponding to Cys582 of SEQ ID NO: 5 or a cysteine corresponding to Cys790 of SEQ ID NO:3; and (d) administering a multikinase inhibitor (e.g., brivanib, dasatinib, erdafitinib, lenvatinib, lucitanib, nintedanib, orantinib, ponatinib, or sulfatinib) as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine. In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a compound of Formula I selected from Examples 1-135, 137-146, and 148-196, or a pharmaceutically acceptable salt or solvate thereof. In some embodiments, the methods further comprise (after (b)) (c) determining whether a cancer cell in a sample obtained from the subject has the FGFR inhibitor resistance mutation in a cysteine corresponding to Cys582 of SEQ ID NO: 5 or a cysteine corresponding to Cys790 of SEQ ID NO:3; and (d) administering a multikinase inhibitor (e.g., brivanib, dasatinib, erdafitinib, lenvatinib, lucitanib, nintedanib, orantinib, ponatinib, or sulfatinib) as a monotherapy or in conjunction with an additional therapy or therapeutic agent to the subject if the subject has a cancer cell that has at least one FGFR inhibitor resistance mutation in a cysteine; or (e) administering additional doses of the compound of Formula I or a pharmaceutically acceptable salt or solvate thereof of step (b) to the subject if the subject has a cancer cell that does not have a FGFR inhibitor resistance mutation in a cysteine.

Also provided are methods of selecting a treatment for a subject having a cancer that include: identifying a subject having a cancer cell that has one or more FGFR inhibitor resistance mutations; and selecting a treatment that includes administration of a compound of Formula I or a pharmaceutically acceptable salt or solvate thereof. In some embodiments, the one or more FGFR inhibitor resistance mutations confer increased resistance to a cancer cell or tumor to treatment with a first FGFR inhibitor. In some embodiments, the compound of Formula I or a pharmaceutically acceptable salt or solvate thereof is administered in combination with the first FGFR inhibitor. Also provided are methods of selecting a treatment for a subject having a cancer that include: selecting a treatment that includes administration of a compound of Formula I or a pharmaceutically acceptable salt or solvate thereof for a subject identified as having a cancer cell that has one or more FGFR inhibitor resistance mutations. Also provided are methods of selecting a subject having a cancer for a treatment that does not include a first FGFR inhibitor as a monotherapy that include: identifying a subject having a cancer cell that has one or more FGFR inhibitor resistance mutations; and selecting the identified subject for a treatment that includes a compound of Formula I or a pharmaceutically acceptable salt or solvate thereof. Also provided are methods of selecting a subject having a cancer for a treatment that does not include a first FGFR inhibitor as a monotherapy that include: selecting a subject identified as having a cancer cell that has one or more FGFR inhibitor resistance mutations for a treatment that includes administration of a compound of Formula I or a pharmaceutically acceptable salt or solvate thereof. In some embodiments, the one or more FGFR inhibitor resistance mutations include one or more FGFR inhibitor resistance mutations listed in Table BE. In some embodiments, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M).

Also provided are methods of determining the likelihood that a subject having a cancer (e.g., a FGFR-associated cancer) will have a positive response to treatment with a first FGFR inhibitor as a monotherapy that include: determining whether a cancer cell in a sample obtained from the subject has one or more FGFR inhibitor resistance mutations; and determining that a subject having a cancer cell that has one or more FGFR inhibitor resistance mutations has a decreased likelihood of having a positive response (i.e. an increased likelihood of having a negative response) to treatment with a first FGFR inhibitor as a monotherapy. Also provided are methods of determining the likelihood that a subject having a cancer (e.g., a FGFR-associated cancer) will have a positive response to treatment with a first FGFR inhibitor as a monotherapy that include: determining whether a cancer cell in a sample obtained from the subject has one or more FGFR inhibitor resistance mutations; and determining that a subject not having a cancer cell that has one or more FGFR inhibitor resistance mutations has an increased likelihood of having a positive response to treatment with a first FGFR inhibitor as a monotherapy as compared to a subject having a cancer cell that has one or more FGFR inhibitor resistance mutations. Also provided are methods of predicting the efficacy of treatment with a first FGFR inhibitor as a monotherapy in a subject having cancer that include: determining whether a cancer cell in a sample obtained from the subject has one or more FGFR inhibitor resistance mutations; and determining that treatment with a first FGFR inhibitor as a monotherapy is less likely to be effective in a subject having a cancer cell in a sample obtained from the subject that has one or more FGFR inhibitor resistance mutations. Also provided are methods of predicting the efficacy of treatment with a first FGFR inhibitor as a monotherapy in a subject having cancer that include: determining that treatment with a first FGFR inhibitor as a monotherapy is less likely to be effective in a subject having a cancer cell in a sample obtained from the subject that has one or more FGFR inhibitor resistance mutations. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M).

Also provided are methods of selecting a treatment for a subject having a cancer that include (a) administering one or more doses of a first FGFR inhibitor to the subject for a period of time; (b) after (a), determining whether a cancer cell in a sample obtained from the subject has at least one FGFR inhibitor resistance mutation; and (c) selecting a compound of Formula I or a pharmaceutically acceptable salt or solvate thereof as a monotherapy or in conjunction with an additional therapy or therapeutic agent for the subject if the subject has a cancer cell that has one or more FGFR inhibitor resistance mutations; or (d) selecting additional doses of the first FGFR inhibitor of step (a) for the subject if the subject has a cancer cell that does not have a FGFR inhibitor resistance mutation. In some embodiments, when additional doses of the first FGFR inhibitor of step (a) are selected for the subject, the method can further include selecting doses of an additional therapy or therapeutic agent for the subject. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M). In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments of step (c), another FGFR inhibitor can be the first FGFR inhibitor administered in step (a).

Also provided are methods of selecting a treatment for a subject having a cancer that include (a) administering one or more doses of a first FGFR inhibitor to the subject for a period of time; (b) after (a), determining whether a cancer cell in a sample obtained from the subject has at least one FGFR inhibitor resistance mutation; and (c) selecting a second FGFR inhibitor as a monotherapy or in conjunction with an additional therapy or therapeutic agent if the subject has a cancer cell that has one or more FGFR inhibitor resistance mutations; or (d) selecting additional doses of the first FGFR inhibitor of step (a) for the subject if the subject has a cancer cell that does not have a FGFR inhibitor resistance mutation. In some embodiments, when additional doses of the first FGFR inhibitor of step (a) are selected for the subject, the method can further include selecting doses of an additional therapy or therapeutic agent for the subject. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M). In some embodiments, the additional therapy or therapeutic agent is any anticancer agent known in the art. For example, the additional therapy or therapeutic agent is another FGFR inhibitor (e.g., a compound of Formula I or a pharmaceutically acceptable salt or solvate thereof). In some embodiments, the additional therapy or therapeutic agent is an immunotherapy. In some embodiments, another FGFR inhibitor can be the first FGFR inhibitor administered in step (a).

Also provided are methods of selecting a treatment for a subject having a cancer that include (a) determining whether a cancer cell in a sample obtained from a subject having a cancer and previously administered one or more doses of a first FGFR inhibitor has one or more FGFR inhibitor resistance mutations; (b) selecting a compound of Formula I or a pharmaceutically acceptable salt or solvate thereof as a monotherapy or in conjunction with an additional therapy or therapeutic agent for the subject if the subject has a cancer cell that has at least one FGFR inhibitor resistance mutation; or (c) selecting additional doses of the first FGFR inhibitor previously administered to the subject if the subject has a cancer cell that does not have a FGFR inhibitor resistance mutation. In some embodiments, when additional doses of the first FGFR inhibitor previously administered to the subject are selected for the subject, the method can further include selecting doses of an additional therapy or therapeutic agent (e.g., a compound of Formula I or a pharmaceutically acceptable salt or solvate thereof or immunotherapy) for the subject. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M). In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments of step (c), another FGFR inhibitor can be the first FGFR inhibitor administered in step (a).

Also provided are methods of selecting a treatment for a subject having a cancer that include (a) determining whether a cancer cell in a sample obtained from a subject having a cancer and previously administered one or more doses of a first FGFR inhibitor has one or more FGFR inhibitor resistance mutations; (b) selecting a second FGFR inhibitor as a monotherapy or in conjunction with an additional therapy or therapeutic agent for the subject if the subject has a cancer cell that has at least one FGFR inhibitor resistance mutation; or (c) selecting additional doses of the first FGFR inhibitor previously administered to the subject if the subject has a cancer cell that does not have a FGFR inhibitor resistance mutation. In some embodiments, when additional doses of the first FGFR inhibitor previously administered to the subject are selected for the subject, the method can further include selecting doses of an additional therapy or therapeutic agent (e.g., a compound of Formula I or a pharmaceutically acceptable salt or solvate thereof, or an immunotherapy) for the subject. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M). In some embodiments, the additional therapy or therapeutic agent is any anticancer agent known in the art. For example, the additional therapy or therapeutic agent is another FGFR inhibitor (e.g., a compound of Formula I or a pharmaceutically acceptable salt or solvate thereof). In some embodiments, the additional therapy or therapeutic agent is an immunotherapy. In some embodiments, another FGFR can be the first FGFR inhibitor administered in step (a).

Also provided are methods of determining a subject's risk for developing a cancer that has some resistance to a first FGFR inhibitor that include: determining whether a cell in a sample obtained from the subject has one or more FGFR inhibitor resistance mutations; and identifying a subject having a cell that has one or more FGFR inhibitor resistance mutations, as having an increased likelihood of developing a cancer that has some resistance to the first FGFR inhibitor. Also provided are methods of determining a subject's risk for developing a cancer that has some resistance to a first FGFR inhibitor that include: identifying a subject having a cell that has one or more FGFR inhibitor resistance mutations, as having an increased likelihood of developing a cancer that has some resistance to the first FGFR inhibitor.

Also provided are methods of determining the presence of a cancer that has some resistance to a first FGFR inhibitor that include: determining whether a cancer cell in a sample obtained from the subject has one or more FGFR inhibitor resistance mutations; and determining that the subject having a cancer cell that has one or more FGFR inhibitor resistance mutations has a cancer that has some resistance to the first FGFR inhibitor. Also provided are methods of determining the presence of a cancer that has some resistance to a first FGFR inhibitor in a subject that include: determining that a subject having a cancer cell that has one or more FGFR inhibitor resistance mutations, has a cancer that has some resistance to the first FGFR inhibitor. In some embodiments, the one or more FGFR inhibitor resistance mutations confer increased resistance to a cancer cell or tumor to treatment with the first FGFR inhibitor. In some embodiments, the one or more FGFR inhibitor resistance mutations include one or more FGFR inhibitor resistance mutations listed in Table BE. For example, the one or more FGFR inhibitor resistance mutations can include a substitution at an amino acid position corresponding to amino acid position 561 in SEQ ID NO. 1 (e.g., V561M), amino acid position 564 in SEQ ID NO. 3 (e.g., V564I or V564F), or amino acid position 555 in SEQ ID NO. 5 (e.g., V555M).

Also provided are methods of selecting a treatment for a subject having a cancer that include: identifying a subject having a cancer cell that has one or more FGFR inhibitor resistance mutations; and selecting a treatment that does not include a compound of Formula I or a pharmaceutically acceptable salt or solvate thereof as a monotherapy for the identified subject (e.g., a second FGFR kinase inhibitor). Also provided are methods of selecting a treatment for a subject having a cancer that include: selecting a treatment that does not include a compound of Formula I or a pharmaceutically acceptable salt or solvate thereof as a monotherapy (e.g., a second FGFR kinase inhibitor) for a subject identified as having a cancer cell that has one or more FGFR inhibitor resistance mutations. Also provided are methods of selecting a subject having a cancer for a treatment that does not include a compound of Formula I or a pharmaceutically acceptable salt or solvate thereof as a monotherapy (e.g., a second FGFR kinase inhibitor) that include: identifying a subject having a cancer cell that has one or more FGFR inhibitor resistance mutations; and selecting the identified subject for a treatment that does not include a compound of Formula I or a pharmaceutically acceptable salt or solvate thereof as a monotherapy (e.g., a second FGFR kinase inhibitor). Also provided are methods of selecting a subject having a cancer for a treatment that does not include a compound of Formula I or a pharmaceutically acceptable salt or solvate thereof as a monotherapy (e.g., a second FGFR kinase inhibitor) that include: selecting a subject identified as having a cancer cell that has one or more FGFR inhibitor resistance mutations for a treatment that does not include a compound of Formula I or a pharmaceutically acceptable salt or solvate thereof as a monotherapy. In some embodiments, the one or more FGFR inhibitor resistance mutations confer increased resistance to a cancer cell or tumor to treatment with a compound of Formula I or a pharmaceutically acceptable salt or solvate thereof. In some embodiments, the one or more FGFR inhibitor resistance mutations include one or more FGFR inhibitor resistance mutations listed in Table BE. In some embodiments, the one or more FGFR inhibitor resistance mutations include one or more FGFR inhibitor resistance mutations in a cysteine. In some embodiments, the one or more FGFR inhibitor resistance mutations include a mutation in a cysteine that corresponds to Cys582 of SEQ ID NO: 5. In some embodiments, the one or more FGFR inhibitor resistance mutations include a mutation in a cysteine that corresponds to Cys790 of SEQ ID NO: 3.

Also provided are methods of determining the likelihood that a subject having a cancer will have a positive response to treatment with a compound of Formula I or a pharmaceutically acceptable salt or solvate thereof as a monotherapy that include: determining whether a cancer cell in a sample obtained from the subject has one or more FGFR inhibitor resistance mutations; and determining that the subject having the cancer cell that has one or more FGFR inhibitor resistance mutations has a decreased likelihood of having a positive response to treatment with a compound of Formula I or a pharmaceutically acceptable salt or solvate thereof as a monotherapy. Also provided are methods of determining the likelihood that a subject having cancer will have a positive response to treatment with a compound of Formula I or a pharmaceutically acceptable salt or solvate thereof as a monotherapy that include: determining that a subject having a cancer cell that has one or more FGFR inhibitor resistance mutations has a decreased likelihood of having a positive response to treatment with a compound of Formula I or a pharmaceutically acceptable salt or solvate thereof as a monotherapy. Also provided are methods of predicting the efficacy of treatment with a compound of Formula I or a pharmaceutically acceptable salt or solvate thereof as a monotherapy in a subject having cancer that include: determining whether a cancer cell in a sample obtained from the subject has one or more FGFR inhibitor resistance mutations; and determining that treatment with a compound of Formula I or a pharmaceutically acceptable salt or solvate thereof as a monotherapy is less likely to be effective in a subject having a cancer cell in a sample obtained from the subject that has one or more FGFR inhibitor resistance mutations. Also provided are methods of predicting the efficacy of treatment with a compound of Formula I or a pharmaceutically acceptable salt or solvate thereof as a monotherapy in a subject having cancer that include: determining that treatment with a compound of Formula I or a pharmaceutically acceptable salt or solvate thereof as a monotherapy is less likely to be effective in a subject having a cancer cell in a sample obtained from the subject that has one or more FGFR inhibitor resistance mutations. In some embodiments, the one or more FGFR inhibitor resistance mutations confer increased resistance to a cancer cell or tumor to treatment with a compound of Formula I or a pharmaceutically acceptable salt or solvate thereof.

Also provided are methods of selecting a treatment for a subject having a cancer that include: (a) administering one or more doses of a compound of Formula I or a pharmaceutically acceptable salt or solvate thereof to the subject for a period of time; (b) after (a), determining whether a cancer cell in a sample obtained from the subject has one or more FGFR inhibitor resistance mutations; and (c) selecting a second FGFR inhibitor or a second compound of Formula I or a pharmaceutically acceptable salt or solvate thereof as a monotherapy or in conjunction with an additional therapy or therapeutic agent for the subject if the subject has a cancer cell that has a FGFR inhibitor resistance mutation; or (d) selecting additional doses of the compound of Formula I or a pharmaceutically acceptable salt or solvate thereof of step (a) for the subject if the subject has a cancer cell that does not have a FGFR inhibitor resistance mutation. In some embodiments, where additional doses of a compound of Formula I or a pharmaceutically acceptable salt or solvate thereof of step (a) are selected for the subject, the method can also include further selecting an additional therapy or therapeutic agent. In some embodiments, the one or more FGFR inhibitor resistance mutations confer increased resistance to a cancer cell or tumor to treatment with a compound of Formula I or a pharmaceutically acceptable salt or solvate thereof. In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments, another FGFR inhibitor can be the compound of Formula I or a pharmaceutically acceptable salt or solvate thereof administered in step (a).

Also provided are methods of selecting a treatment for a subject having a cancer that include: (a) determining whether a cancer cell in a sample obtained from a subject having a cancer and previously administered one or more doses of a compound of Formula I or a pharmaceutically acceptable salt or solvate thereof, has one or more FGFR inhibitor resistance mutations; (b) selecting a second FGFR inhibitor or a second compound of Formula I or a pharmaceutically acceptable salt or solvate thereof as a monotherapy or in conjunction with an additional therapy or therapeutic agent for the subject if the subject has a cancer cell that has a FGFR inhibitor resistance mutation; or (c) selecting additional doses of the compound of Formula I or a pharmaceutically acceptable salt or solvate thereof previously administered to the subject if the subject has a cancer cell that does not have a FGFR inhibitor resistance mutation. In some embodiments, where additional doses of the compound of Formula I or a pharmaceutically acceptable salt or solvate thereof of step (a) are selected for the subject, the method can also include further selecting an additional therapy or therapeutic agent. In some embodiments, the one or more FGFR inhibitor resistance mutations confer increased resistance to a cancer cell or tumor to treatment with a compound of Formula I or a pharmaceutically acceptable salt or solvate thereof. In some embodiments, the additional therapy or therapeutic agent is any anticancer agent known in the art. For example, the additional therapy or therapeutic agent is another FGFR inhibitor (e.g., a second FGFR inhibitor). In some embodiments, the additional therapy or therapeutic agent is an immunotherapy. In some embodiments, another FGFR inhibitor can be the compound of Formula I or a pharmaceutically acceptable salt or solvate thereof administered in step (a).

Also provided are methods of determining a subject's risk for developing a cancer that has some resistance to a compound of Formula I or a pharmaceutically acceptable salt or solvate thereof that include: determining whether a cell in a sample obtained from the subject has one or more FGFR inhibitor resistance mutations; and identifying the subject if the subject has a cell that has one or more FGFR inhibitor resistance mutations as having an increased likelihood of developing a cancer that has some resistance to a compound of Formula I or a pharmaceutically acceptable salt or solvate thereof. Also provided are methods of determining a subject's risk for developing a cancer that has some resistance to a compound of Formula I or a pharmaceutically acceptable salt or solvate thereof that include: identifying a subject having a cell that has one or more FGFR inhibitor resistance mutations as having an increased likelihood of developing a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof that includes: determining whether a cancer cell in a sample obtained from the subject has one or more FGFR inhibitor resistance mutations; and determining that the subject having the cancer cell that has one or more FGFR inhibitor resistance mutations has a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof in a subject that include: determining that a subject having a cancer cell that has one or more FGFR inhibitor resistance mutations has a cancer that has some resistance to a compound of Formula I or a pharmaceutically acceptable salt or solvate thereof. In some embodiments, the one or more FGFR inhibitor resistance mutations confer increased resistance to a cancer cell or tumor to treatment with a compound of Formula I or a pharmaceutically acceptable salt or solvate thereof.

In some embodiments of any of the methods described herein, a FGFR inhibitor resistance mutation that confers increased resistance to a cancer cell or tumor to treatment with a compound of Formula I or a pharmaceutically acceptable salt or solvate thereof, can be any of the FGFR inhibitor resistance mutations listed in Table BE. In some embodiments of any of the methods described herein, a FGFR inhibitor resistance mutation that confers increased resistance to a cancer cell or tumor to treatment with a compound of Formula I or a pharmaceutically acceptable salt or solvate thereof, can be a FGFR inhibitor resistance mutations in a cysteine. In some embodiments, a FGFR inhibitor resistance mutation can be a mutation in a cysteine that corresponds to Cys582 of SEQ ID NO: 5. In some embodiments, a FGFR inhibitor resistance mutation can be a mutation in a cysteine that corresponds to Cys790 of SEQ ID NO: 3.

In some embodiments, dysregulation of a second protein can be present in a subject. In some embodiments, a second protein can be dysregulated before a FGFR protein is dysregulated. In some embodiments, a second protein can be dysregulated after a FGFR protein is dysregulated. Provided herein are methods useful when a second protein is dysregulated.

In some embodiments, a second protein can be MET. For example, a method can include: (a) detecting a dysregulation of a FGFR gene, a FGFR kinase, or the expression or activity or level of any of the same in a sample from the subject; and (b) administering to the subject a therapeutically effective amount of a compound of Formula I or a pharmaceutically acceptable salt thereof. In some embodiments, the methods further comprises (after (b)) (c) determining whether a cancer cell in a sample obtained from the subject has at least one FGFR inhibitor resistance mutation (e.g., a MET dysregulation such as a MET gene amplification); and (d) administering a second therapeutic agent, wherein the second therapeutic agent is crizotinib, as a monotherapy or in conjunction with a compound of Formula I or pharmaceutically acceptable salt thereof to the subject if the subject has a cancer cell that has at least one FGFR inhibitor resistance mutation; or (e) administering additional doses of the compound of Formula I or pharmaceutically acceptable salt thereof of step (b) to the subject if the subject has a cancer cell that does not have a FGFR inhibitor resistance mutation. In some such embodiments, the method comprises (a) detecting one or more fusion proteins of Table BA and/or one or more FGFR kinase protein point mutations/insertions of Table BC in a sample from the subject;

and (b) administering to the subject a therapeutically effective amount of a compound of Formula I or pharmaceutically acceptable salt thereof. In further embodiments, the methods further comprise (after (b)) (c) determining whether a cancer cell in a sample obtained from the subject has at least one FGFR inhibitor resistance mutation (e.g., a MET dysregulation such as a MET gene amplification); and (d) administering a second therapeutic agent, wherein the second therapeutic agent is crizotinib, as a monotherapy or in conjunction with a compound of Formula I or pharmaceutically acceptable salt thereof to the subject if the subject has a cancer cell that has at least one FGFR inhibitor resistance mutation; or (e) administering additional doses of the compound of Formula I or pharmaceutically acceptable salt thereof of step (b) to the subject if the subject has a cancer cell that does not have a FGFR inhibitor resistance mutation.

In some embodiments, a second protein can be EGFR. In some embodiments, a cancer is an EGFR-associated cancer. For example, the method can include: (a) detecting a dysregulation of an EGFR gene, an EGFR kinase, or the expression or activity or level of any of the same in a sample from the subject; and (b) administering to the subject a therapeutically effective amount of an EGFR inhibitor (e.g., osimertinib). In some embodiments, the methods further comprises (after (b)) (c) determining whether a cancer cell in a sample obtained from the subject has at least one dysregulation of a FGFR gene, a FGFR kinase, or the expression or activity or level of any of the same (e.g., a FGFR gene fusion); and (d) administering a compound of Formula I or pharmaceutically acceptable salt thereof, as a monotherapy or in conjunction with the EGFR inhibitor (e.g., osimertinib) to the subject if the subject has a cancer cell that has at least one dysregulation of a FGFR gene, a FGFR kinase, or the expression or activity or level of any of the same (e.g., a FGFR gene fusion); or (e) administering additional doses of the EGFR inhibitor (e.g., osimertinib) of step (b) to the subject if the subject has a cancer cell that does not have a dysregulation of a FGFR gene, a FGFR kinase, or the expression or activity or level of any of the same (e.g., a FGFR gene fusion). In some such embodiments, the method comprises (a) detecting a dysregulation of an EGFR gene, an EGFR kinase, or the expression or activity or level of any of the same in a sample from the subject; and (b) administering to the subject a therapeutically effective amount of osimertinib. In further embodiments, the methods further comprise (after (b)) (c) determining whether a cancer cell in a sample obtained from the subject has one or more fusion proteins of Table BA and/or one or more FGFR kinase protein point mutations/insertions of Table BC; and (d) administering a compound of Formula I or pharmaceutically acceptable salt thereof, as a monotherapy or in conjunction with osimertinib to the subject if the subject has a cancer cell that has one or more fusion proteins of Table BA and/or one or more FGFR kinase protein point mutations/insertions of Table BC; or (e) administering additional doses of the osimertinib of step (b) to the subject if the subject has a cancer cell that does not have one or more fusion proteins of Table BA and/or one or more FGFR kinase protein point mutations/insertions of Table BC.

In some embodiments, a FGFR-associated cancer as described herein can occur in a subject along with a dysregulation of another gene, another protein, or the expression or activity or level of any of the same. In some embodiments, a dysregulation of another gene, another protein, or the expression or activity or level of the same can occur before a dysregulation of a FGFR gene, FGFR protein, or the expression or activity or level of any of the same. In some embodiments, a dysregulation of another gene, another protein, or the expression or activity or level of any of the same can occur after a dysregulation of a FGFR gene, FGFR protein, or the expression or activity or level of any of the same.

The term "EGFR-associated cancer" as used herein refers to cancers associated with or having a dysregulation of an EGFR gene, an EGFR kinase, or expression or activity, or level of any of the same.

The phrase "dysregulation of an EGFR gene, an EGFR kinase, or the expression or activity or level of any of the same" refers to a genetic mutation (e.g., an EGFR gene translocation that results in the expression of a fusion protein, a deletion in an EGFR gene that results in the expression of an EGFR protein that includes a deletion of at least one amino acid as compared to the wild-type EGFR protein, or a mutation in an EGFR gene that results in the expression of a EGFR protein with one or more point mutations, or an alternative spliced version of an EGFR mRNA that results in an EGFR protein that results in the deletion of at least one amino acid in the EGFR protein as compared to the wild-type EGFR protein), or an EGFR gene amplification that results in overexpression of an EGFR protein or an autocrine activity resulting from the overexpression of an EGFR gene a cell, that results in a pathogenic increase in the activity of a kinase domain of an EGFR protein (e.g., a constitutively active kinase domain of an EGFR protein) in a cell. As another example, a dysregulation of an EGFR gene, an EGFR protein, or expression or activity, or level of any of the same, can be a mutation in an EGFR gene that encodes an EGFR protein that is constitutively active or has increased activity as compared to a protein encoded by a EGFR gene that does not include the mutation. For example, a dysregulation of an EGFR gene, a EGFR protein, or expression or activity, or level of any of the same, can be the result of a gene or chromosome translocation which results in the expression of a fusion protein that contains a first portion of EGFR that includes a functional kinase domain, and a second portion of a partner protein (i.e., that is not EGFR). In some examples, dysregulation of an EGFR gene, an EGFR protein, or expression or activity, can be a result of a gene translocation of one EGFR gene with another non-EGFR gene.

The term "wildtype EGFR" or "wild-type EGFR" describes a nucleic acid (e.g., an EGFR gene or an EGFR mRNA) or protein (e.g., an EGFR protein) that is found in a subject that does not have an EGFR-associated cancer (and optionally also does not have an increased risk of developing an EGFR-associated cancer and/or is not suspected of having an EGFR-associated cancer), or is found in a cell or tissue from a subject that does not have an EGFR-associated cancer (and optionally also does not have an increased risk of developing an EGFR-associated cancer and/or is not suspected of having an EGFR-associated cancer).

For example, a FGFR-associated cancer that exhibits a FGFR fusion can occur in a subject along with one or more of: a dysregulation of a MET gene, a MET protein, or the expression or activity or level of any of the same; a dysregulation of a PIK3CA gene, a PIK3CA protein, or the expression or activity or level of any of the same; a dysregulation of a KRAS gene, a KRAS protein, or the expression or activity or level of any of the same; a dysregulation of a EGFR gene, a EGFR protein, or the expression or activity or level of any of the same (e.g., an amplification of a EGFR gene); a dysregulation of a RET gene, a RET protein, or the expression or activity or level of any of the same (e.g., a fusion of an RET gene or an RET protein); a dysregulation of a CDK4 gene, a CDK4 protein, or the expression or activity or level of any of the same (e.g., an amplification of a CDK4 gene); a dysregulation of a mTOR gene, a mTOR protein, or the expression or activity or level of any of the same; a dysregulation of a CDKN2A gene, a CDKN2A protein, or the expression or activity or level of any of the same (e.g., a deletion in a CDKN2A gene or a CDKN2A protein); a dysregulation of a CDKN2B gene, a CDKN2B protein, or the expression or activity or level of any of the same (e.g., a deletion in a CDKN2B gene or a CDKN2B protein); a dysregulation of a NF1 gene, a NF1 protein, or the expression or activity or level of any of the same; a dysregulation of a MYC gene, a MYC protein, or the expression or activity or level of any of the same (e.g., an amplification in a MYC gene); a dysregulation of a MDM2 gene, a MDM2 protein, or the expression or activity or level of any of the same (e.g., an amplification in a MDM2 gene); a dysregulation of a GNAS gene, a GNAS protein, or the expression or activity or level of any of the same; a dysregulation of a BRCA2 gene, a BRCA2 protein, or the expression or activity or level of any of the same.

For example, a FGFR-associated cancer that exhibits a FGFR fusion can occur in a subject along with one or more of: a dysregulation of a ALK gene, a ALK protein, or the expression or activity or level of any of the same; a dysregulation of a AKT gene, a AKT protein, or the expression or activity or level of any of the same; a dysregulation of a aurora gene, a aurora protein, or the expression or activity or level of any of the same; a dysregulation of a AXL gene, a AXL protein, or the expression or activity or level of any of the same; a dysregulation of a BRAF gene, a BRAF protein, or the expression or activity or level of any of the same; a dysregulation of a CDK gene, a CDK protein, or the expression or activity or level of any of the same; a dysregulation of a EGFR gene, a EGFR protein, or the expression or activity or level of any of the same; a dysregulation of a EHMT2 gene, a EHMT2 protein, or the expression or activity or level of any of the same; a dysregulation of a ERK gene, a ERK protein, or the expression or activity or level of any of the same; a dysregulation of a FGFR1 gene, a FGFR1 protein, or the expression or activity or level of any of the same; a dysregulation of a FGFR2 gene, a FGFR2 protein, or the expression or activity or level of any of the same; a dysregulation of a FGFR3 gene, a FGFR3 protein, or the expression or activity or level of any of the same; a dysregulation of a FGFR4 gene, a FGFR4 protein, or the expression or activity or level of any of the same; a dysregulation of a FLT3 gene, a FLT3 protein, or the expression or activity or level of any of the same; a dysregulation of a HER2 (also called erbB-2) gene, a HER2 (also called erbB-2) protein, or the expression or activity or level of any of the same; a dysregulation of a HER3 (also called erbB-3) gene, a HER3 (also called erbB-3) protein, or the expression or activity or level of any of the same; a dysregulation of a HER4 (also called erbB-4) gene, a HER4 (also called erbB-4) protein, or the expression or activity or level of any of the same; a dysregulation of a IGFR gene, a IGFR protein, or the expression or activity or level of any of the same; a dysregulation of a JAK1 gene, a JAK1 protein, or the expression or activity or level of any of the same; a dysregulation of a JAK2 gene, a JAK2 protein, or the expression or activity or level of any of the same; a dysregulation of a JAK3 gene, a JAK3 protein, or the expression or activity or level of any of the same; a dysregulation of a Kit gene, a Kit protein, or the expression or activity or level of any of the same; a dysregulation of a MEK gene, a MEK protein, or the expression or activity or level of any of the same; a dysregulation of a MET gene, a MET protein, or the expression or activity or level of any of the same; a dysregulation of a mTOR gene, a mTOR protein, or the expression or activity or level of any of the same; a dysregulation of a PDGFRα gene, a PDGFRα protein, or the expression or activity or level of any of the same; a dysregulation of a PDGFRβ gene, a PDGFRβ protein, or the expression or activity or level of any of the same; a dysregulation of a PI3K gene, a PI3K protein, or the expression or activity or level of any of the same; a dysregulation of a RAC1 gene, a RAC1 protein, or the expression or activity or level of any of the same; a dysregulation of a RAF gene, a RAF protein, or the expression or activity or level of any of the same; a dysregulation of a RAS gene, a RAS protein, or the expression or activity or level of any of the same; a dysregulation of a RET gene, a RET protein, or the expression or activity or level of any of the same; a dysregulation of a ROS1 gene, a ROS1 protein, or the expression or activity or level of any of the same; a dysregulation of a SOS1 gene, a SOS1 protein, or the expression or activity or level of any of the same; a dysregulation of a trkA gene, a trkA protein, or the expression or activity or level of any of the same; a dysregulation of a trkB gene, a trkB protein, or the expression or activity or level of any of the same; a dysregulation of a trkC gene, a trkC protein, or the expression or activity or level of any of the same; a dysregulation of a VEGFR-1 gene, a VEGFR-1 protein, or the expression or activity or level of any of the same; a dysregulation of a VEGFR-2 gene, a VEGFR-2 protein, or the expression or activity or level of any of the same; or a dysregulation of a VEGFR-3 gene, a VEGFR-3 protein, or the expression or activity or level of any of the same.

In some embodiments, a FGFR-associated cancer that exhibits a mutation of a FGFR gene and/or a FGFR protein can occur in a subject along with one or more of: a dysregulation of a PIK3CA gene, a PIK3CA protein, or the expression or activity or level of any of the same; a dysregulation of a KRAS gene, a KRAS protein, or the expression or activity or level of any of the same; a dysregulation of a EGFR gene, a EGFR protein, or the expression or activity or level of any of the same; a dysregulation of a gene in the MAPK signaling pathway, a protein in the MAPK signaling pathway, or the expression or activity or level of any of the same; a dysregulation of a MEK gene, a MEK protein, or the expression or activity or level of any of the same; a dysregulation of a HER2 gene, a HER2 protein, or the expression or activity or level of any of the same (e.g., an amplification of HER2 gene); and a dysregulation of a KIT gene, a KIT protein, or the expression or activity or level of any of the same.

In some embodiments, a FGFR-associated cancer that exhibits a mutation of a FGFR gene and/or a FGFR protein can occur in a subject along with one or more of: a dysregulation of a ALK gene, a ALK protein, or the expression or activity or level of any of the same; a dysregulation of a AKT gene, a AKT protein, or the expression or activity or level of any of the same; a dysregulation of a aurora gene, a aurora protein, or the expression or activity or level of any of the same; a dysregulation of a AXL gene, a AXL protein, or the expression or activity or level of any of the same; a dysregulation of a BRAF gene, a BRAF protein, or the expression or activity or level of any of the same; a dysregulation of a CDK gene, a CDK protein, or the expression or activity or level of any of the same; a dysregulation of a EGFR gene, a EGFR protein, or the expression or activity or level of any of the same; a dysregulation of a EHMT2 gene, a EHMT2 protein, or the expression or activity or level of any of the same; a dysregulation of a ERK gene, a ERK protein, or the expression or activity or level of any of the same; a dysregulation of a FGFR1 gene, a FGFR1 protein, or the expression or activity or level of any of the same; a dysregulation of a FGFR2 gene, a FGFR2 protein, or the expression or activity or level of any of the same; a dysregulation of a FGFR3 gene, a FGFR3 protein, or the expression or activity or level of any of the same; a dysregulation of a FGFR4 gene, a FGFR4 protein, or the expression or activity or level of any of the same; a dysregulation of a FLT3 gene, a FLT3 protein, or the expression or activity or level of any of the same; a dysregulation of a HER2 (also called erbB-2) gene, a HER2 (also called erbB-2) protein, or the expression or activity or level of any of the same; a dysregulation of a HER3 (also called erbB-3) gene, a HER3 (also called erbB-3) protein, or the expression or activity or level of any of the same; a dysregulation of a HER4 (also called erbB-4) gene, a HER4 (also called erbB-4) protein, or the expression or activity or level of any of the same; a dysregulation of a IGFR gene, a IGFR protein, or the expression or activity or level of any of the same; a dysregulation of a JAK1 gene, a JAK1 protein, or the expression or activity or level of any of the same; a dysregulation of a JAK2 gene, a JAK2 protein, or the expression or activity or level of any of the same; a dysregulation of a JAK3 gene, a JAK3 protein, or the expression or activity or level of any of the same; a dysregulation of a Kit gene, a Kit protein, or the expression or activity or level of any of the same; a dysregulation of a MEK gene, a MEK protein, or the expression or activity or level of any of the same; a dysregulation of a MET gene, a MET protein, or the expression or activity or level of any of the same; a dysregulation of a mTOR gene, a mTOR protein, or the expression or activity or level of any of the same; a dysregulation of a PDGFRα gene, a PDGFRα protein, or the expression or activity or level of any of the same; a dysregulation of a PDGFRβ gene, a PDGFRβ protein, or the expression or activity or level of any of the same; a dysregulation of a PI3K gene, a PI3K protein, or the expression or activity or level of any of the same; a dysregulation of a RAC1 gene, a RAC1 protein, or the expression or activity or level of any of the same; a dysregulation of a RAF gene, a RAF protein, or the expression or activity or level of any of the same; a dysregulation of a RAS gene, a RAS protein, or the expression or activity or level of any of the same; a dysregulation of a RET gene, a RET protein, or the expression or activity or level of any of the same; a dysregulation of a ROS1 gene, a ROS1 protein, or the expression or activity or level of any of the same; a dysregulation of a SOS1 gene, a SOS1 protein, or the expression or activity or level of any of the same; a dysregulation of a trkA gene, a trkA protein, or the expression or activity or level of any of the same; a dysregulation of a trkB gene, a trkB protein, or the expression or activity or level of any of the same; a dysregulation of a trkC gene, a trkC protein, or the expression or activity or level of any of the same; a dysregulation of a VEGFR-1 gene, a VEGFR-1 protein, or the expression or activity or level of any of the same; a dysregulation of a VEGFR-2 gene, a VEGFR-2 protein, or the expression or activity or level of any of the same; or a dysregulation of a VEGFR-3 gene, a VEGFR-3 protein, or the expression or activity or level of any of the same.

In some embodiments, a FGFR-associated cancer that exhibits an amplification of a FGFR gene can occur in a subject along with one or more additional kinase amplifications. For example, an amplification in a gene in the MAPK signaling pathway; an amplification in a MEK gene; an amplification of a CDK4 gene; and an amplification in a CDK6 gene.

In some embodiments, wherein a FGFR-associated cancer as described herein can occur in a subject along with a dysregulation in another kinase, the methods described herein can further comprise administration of an additional therapeutic agent that targets and/or treats the dysregulation in the other kinase. For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a compound of Formula I, or a pharmaceutically acceptable salt or solvate thereof. In some embodiments, the method further comprises (c) detecting a dysregulation in another kinase in a sample from the subject; and (d) administering to the subject a therapeutic agent that targets and/or treats the dysregulation in the other kinase. In some embodiments, the administration of a compound of Formula I, or a pharmaceutically acceptable salt or solvate thereof is done concurrently, sequentially, or serially. In some embodiments, the detecting steps (a) and (c) can be done simultaneously or sequentially in any order.

Additional therapeutic agents that target and/or treat the dysregulation of an other kinase can include any known inhibitor of the other kinase. Examples of such agents are as follows:

Exemplary PARP inhibitors include: 3-aminobenzamide (INO-1001), 5-aminoisoquinoline, ABT472, ABT767, AG140361, AG14032, ANG2864, ANG3186, AZD2281, AZD2461, BGP-15, BSI101, BSI401, CEP6800, CEP8983, CK102, CEP9722 (prodrug of CEP8983), CPH101 with CPH102, DR2313, E7016 (GPI-21016), E7449, GP16150, IMP4297, IMP04149, INO1002, INO1003, JP1283, JP1289, KU0687, KU58948, niraparib (MK-4827), NT125, olaparib (AZD2281), ONO-1924H, ONO2231, pamiparib (BGB-290), PJ-34, rucaparib (AG014699), SC10914, SOMCL9112, talazoparib (BMN-673), and veliparib (ABT-888).

Exemplary CDK 4/6 inhibitors include: palbociclib (PD0332991), abemaciclib (LY2835219), ribociclib (LEE011), trilaciclib (G1T28), voruciclib, and G1T38.

Exemplary ERBB2 (HER2/neu) inhibitors include: afatinib, afatinib, dacomitinib (PF-00299804), DS8201-a, erlontinib, gefitinib, KU004, lapatinib, laptinib ditosylate, MM-111, mubritinib (TAK-165), neratinib, pyrotinib (HTI-1001), tucatinib (ONT-380, ARRY-380), 7C3, cetuximab, HER2-BsAb, hersintuzumab, margetuximab, M1130004, NeuVax, paitumumab, pertuzumab, SYD985, trastuzumab, and trastuzumab emtansine.

Exemplary inhibitors of amplified ERBB2 (HER2/neu) include dacomitinib (PF-00299804), lapatinib, neratinib, pertuzumab, trastuzumab, and trastuzumab emtansine.

Exemplary EGFR inhibitors include: AC0010, AEE788, afatinib, AP26113, ASP8273, avitinib, AZD3759, BIBX-1382 (N8-(3-chloro-4-fluoro-phenyl)-N2-(1-methyl-piperidin-4-yl)-pyrimido[5,4-d]pyrimidine-2,8-diamine), BMS-690514, brigatinib, canertinib, Cap-701, CHMFL-EGFR-202, CL-387785, CUDC-101, dacomitinib, EA1045, EGF816, erlontinib, erlotinib, gefitinib, GNS-1481, GNS-1486, Gö6976, HS-10296, icotinib, KU004, lapatinib, nazartinib, neratinib, olmutinib (HM61713, BI 1482694), osimertinib (AZD9291), pelitinib (EKB-569; (E)-N-[4-(3-chloro-4-fluoroanilino)-3-cyano-7-ethoxyquinolin-6-yl]-4-

(dimethylamino)but-2-enamide), PD 183805 (CI 1033, N-[4-(3-chloro-4-fluoroanilino)-7-(3-morpholin-4-yl-propoxy)quinazolin-6-yl]prop-2-enamide), PF-06747775, PKC412, PKI-166 ((R)-4-[4-[(1-phenylethyl)amino]-1H-pyrrolo[2,3-d]pyrimidin-6-yl]-phenol); (R)-6-(4-hydroxy-phenyl)-4-[(1-phenylethyl)amino]-7H-pyrrolo[2,3-d]pyrimidine), poziotinib (HM781-36), pyrotinib (HTI-1001), rocilentinib, sapitinib, vandetanib, varlitinib, XL647, ZM 105180 ((6-amino-4-(3-methylphenyl-amino)-quinazoline), 7C3, ABX-EGF, cetuximab, depatuxizumab mafodotin (ABT-414), EMD55900, GA201 (RG7160), IMC-11F8, MAb 225 (ATCC CRL 8508), MAb 455 (ATCC CRL HB8507), MAb 528 (ATCC CRL 8509), MAb 579 (ATCC CRL HB 8506), mAb806, mAb806 (humanized), matuzumab (EMD7200), MDX-447, nimotuzumab, panitumumab, Pertuzumab, reshaped human 225 (H225), and zalutumumab.

Exemplary wild-type EGFR inhibitors include: afatinib, BMS-690514, canertinib, CUDC-101, dacomitinib, erlotinib, gefitinib, lapatinib, neratinib, pelitinib, vandetanib, varlitinib, XL647, cetuximab, matuzumab, nimotuzumab, panitumumab, and zalutumumab.

Exemplary inhibitors of mutated EGFR include: AC0010, afatinib, AP26113, ASP8273, avatinib, avitinib, AZD3759, BMS-690514, brigatinib, canertinib, Cap-701, CHMFL-EGFR-202, CUDC-101, dacomitinib, EAI045, EGF816, GNS-1481, GNS-1486, Gö6976, HS-10296, icotinib, nazartinib, neratinib, olmutinib (HM61713, BI 1482694), osimertinib (AZD9291), PF-06747775, PKC412, rocilentinib, vandetanib, varlitinib, and cetuximab.

Additional exemplary EGFR inhibitors are described in U.S. Pat. Nos. 4,943,533; 5,212,290; 5,457,105; 5,475,001; 5,616,582; 5,654,307; 5,679,683; 5,747,498; 5,760,041; 5,770,599; 5,824,782; 5,866,572; 5,891,996; 6,002,008; 6,084,095; 6,140,332; 6,235,883; 6,265,410; 6,344,455; 6,344,459; 6,391,874; 6,399,602; 6,455,534; 6,521,620; 6,596,726; 6,602,863; 6,713,484; and 6,727,256; and PCT Publication Nos. 1996/040210; 1998/014451; 1998/050038; and 1999/009016, each of which is herein incorporated by reference.

An exemplary inhibitor of amplified EGFR is depatuxizumab mafodotin (ABT-414).

Exemplary inhibitors of FGFR include: ASP5878, AZD4547, BGJ398, BLU9931, brivanib, cediranib, danusertib, DEBIO 1347, derazantinib (ARQ-087), dovitinib (CHIR258), E-3810, E7090, ENMD-2076, erdafitinib (JNJ-42756493), FGF 401, FIIN-1, FIIN-2, FIIN-3, FRIN-1, INCB054828, L16H50, lenvatinib, lucitanib, LY2874455, masitinib (AB1010), nintedanib, NP603, orantinib (SU6668), pazopanib, PB105204, PD089828, PD161570, PD166866, PD173074, ponatinib, PRN1371, regorafenib, rogaratinib (BAY-1163877), 549076, SOMCL-085, SPP86, SSR128129E, SU4984, SU5402, sunitinib, TAS-120, Tyrophostin AG 1296, FP-1039, GAL-F2, GAL-FR21, GAL-FR22, GAL-FR23, GP369, hLD1.vb, HMPL-453, LD1, MFGR1877S, MK-2461, MM-161, PRO-001, and R3Mab.

Exemplary inhibitors of FGFR fusions include: BGJ398, DEBIO 1347, derazantinib (ARQ-087), E7090, erdafitinib (JNJ-42756293), lucitanib, and TAS-120.

Exemplary inhibitors of FGFR1, FGFR2, and FGFR3 include: AZD4547, BGJ398, DEBIO 1347, E7090, INCB054828, 549076, SOMCL-085, and TAS-120.

Exemplary inhibitors of FGFR4 include: BLU-554, BLU9931, NVP-FGF401, and hLD1.vb.

Exemplary inhibitors of amplified FGFR1 include: AZD4547, BGJ398, DEBIO 1347, derazantinib (ARQ-087), erdafitinib (JNJ-42756293), INCB054828, and lucitanib.

Exemplary inhibitors of amplified FGFR2 include: AZD4547, DEBIO 1347, derazantinib (ARQ-087), lucitanib, regorafenib, and TAS-120.

An exemplary inhibitor of amplified FGFR3 is AZD4547.

Exemplary MEK inhibitors include: AZD8330 (ARRY-424704), AZD6244 (ARRY-142866), BI-847325, binimetinib, B1X02188, B1X02189, CH4987655, CH5126766, CI-1040, cobemetinib (GDC-0973), EBI-1051, G-573, G8935, GDC-0623, Myricetin, nobiletin, PD0325901, PD184161, PD318088, PD98059, PD334581, pimasertib (AS-703026), refametinib (RDEA119, BAY 869766), selumetinib (AZD6244), SL-327, TAK-733, trametinib, and U0126.

Exemplary KRAS inhibitors include: 0375-0604, a covalent quinazoline-based switch II pocket (SIIP) compound, ARS-1620, AZD4785, and LP1.

Exemplary PI3K inhibitors include: 3-methyladenine, A66, alpelisib (BYL719), AMG319, apitolisib (GDC-0980, RG7422), AS-252424, AS-604850, AS-605240, AZD6842, AZD8186, AZD8835, BGT226 (NVP-BGT226), buparlisib (BKM120), CAY10505, CH5132799, copanlisib (BAY 80-6946), CUDC-907, CZC24832, dactolisib (BEZ235, NVP-BEZ235), DS7423, duvelisib (IPI-145, INK1197), GDC-0032, GDC-0084, GDC-0326, gedatolisib (PF-05212384, PKI-5587), GNE-317, GS-9820, GSK1059615, GSK2292767, GSK2636771, HS-173, IC-87114, Idelalisib (CAL-101, GS-1101), IPI-145, IPI-3063, IPI-549, LY294002, LY3023414, nemiralisib (GSK2269557), omipalisib (GSK2126458, GSK458), PF-04691502, PF-4989216, PI-103, PI-3065, pictilisib (GDC-0941), PIK-293, PIK-294, PIK-75, PIK-90, PIK-93, PIK-III, pilaralisib (XL147), PKI-587, PP-110, PQR309, PQR309, PW-12, PX-866, quercetin, S14161, SAR245409 (XL765), SAR260301, SAR405, serabelisib (INK-1117, MLN-1117, TAK-1117), SF-1126, SF-2523, SN32976, taselisib (GDC-0032), TB101110, TG100-115, TG100-713, TGR-1202, TGX-221, umbralisib (TGR-1202), voxtalisib (XL765, SAR245409), VPS34-IN1, VS-5584 (SB2343), WJD008, wortmannin, and ZSTK474.

Exemplary KIT inhibitors include: AMG 706, amuvatinib (MP-470), APcK110, axitinib (AG-013736), AZD2932, dasatinib (BMS-354825), dovitinib (TKI-258, CHIR-258), EXEL-0862, imatinib, KI-328, masitinib (AB1010), midostaurin, MLN518, motesanib, N3-(6-aminopyridin-3-yl)-N1-(2-cyclopentylethyl)-4-methylisophthalamide, nilotinib, OSI-930, pazopanib (GW786034), pexidartinib (PLX3397), PKC412, PLX647, PP1, quizartinib (AC220), regorafenib (BAY 73-4506), semaxinib (SU 5416), sitravatinib (MGCD516), sorafenib, STI571, SU11248, SU9529, sunitinib, telatinib, tivozanib (AV-951), tyrphostin AG 1296, VX-322, and WBZ_4.

Exemplary MDM2 inhibitors include: (−)-parthenolide, ALRN6924, AM-8553, AMG232, CGM-097, DS-3032b, GEM240, HDM201, HL198, idasanutlin (RG-7338), JapA, MI-219, MI-219, MI-319, MI-77301 (SAR405838), MK4828, MK-8242, MX69, NSC 207895 (XI-006), Nutlin-3, Nutlin-3a, Nutlin-3b, NVP-CFC218, NVP-CGM097, PXn727/822, RG7112, RO2468, RO5353, RO5503781, serdemetan (JNJ-26854165), SP-141, and YH239-EE.

Exemplary inhibitors of amplified MDM2 include: AM-8553, AMG232, DS-3032b, MI-77301 (SAR405838), NSC 207895 (XI-006), Nutlin-3a, NVP-CFC218, NVP-CGM097, and RG7112.

Exemplary inhibitors of MET include: (−)-Oleocanthal, ABBV-399, AMG-208, AMG-337, AMG-458, amuvatinib (MP740, N-(1,3-benzodioxol-5-ylmethyl)-4-([1]benzofuro[3,2-d]pyrimidin-4-yl)piperazine-1-carbothioamide), ASLAN002, ASP-08001, ASP-08126, BAY-853474, BMS-754807, BMS-777607, BMS-794833, BMS-817378 (prodrug of BMS-794833), cabozantinib (XL184, BMS-907351), capmatinib (INCB28060, 2-fluoro-N-methyl-4-{7-[(quinolin-6-yl)methyl]imidazo[1,2-b][1,2,4]triazin-2-yl}benzamide), crizotinib (PF-02341066), DE605, DP-3590, EMD-1204831, foretinib (GSK1363089, XL880), glesatinib (MGCD265), golvatinib (E7050), HM-5016504, INCB028060, JNJ-38877605, KRC-408, merestinib (LY2801653), MK-2461, MK8033, NPS-1034, NVP-BVU972, PF-04217903, PHA-665752, S49076, savolitinib (AZD6094, HMPL-504), SGX-523, SU11274, TAS-115, tivantinib (ARQ 197, (3R,4R)-3-(5,6-Dihydro-4H-pyrrolo[3,2,1-ij]quinolin-1-yl)-4-(1H-indol-3-yl)-2,5-pyrrolidinedione), tepotinib (EMD 1214063, MSC2156119J), volitinib, 6-[di-fluoro(6-pyridin-4-yl[1,2,4]triazolo[4,3-b]pyridazin-3-yl)methyl]quinoline, (E)-2-(1-(3-((7-fluoroquinolin-6-yl)methyl)imidazo[1,2-b]pyridazin-6-yl)ethylidene) hydrazinecarboxamide, CE-355621, emibetuzumab, ficlatuzumab, LY2875358 (LA-480), onartuzumab, rilotuzumab, and Tak-701. Other exemplary MET inhibitors can be found in, e.g., U.S. Pat. Nos. 10,085,982; 8,629,144; 8,497,368; and 8,030,305, each of which is incorporated herein by reference.

Exemplary inhibitors of mTOR include: anthracimycin, apitolisib (GDC-0980, RG7422), AZD-8055, BGT226 (NVP-BGT226), CC-223, CZ415, dactolisib (BEZ235, NVP-BEZ235), DS7423, everolimus (RAD001), GDC-0084, GDC-0349, gedatolisib (PF-05212384, PKI-5587), GSK1059615, INK128, KU-0063794, LY3023414, MLN0128, omipalisib (GSK2126458, GSK458), OSI-027, OSU-53, Palomid 529 (P529), PF-04691502, PI-103, PKI-587, PP242, PQR309, ridafarolimus (AP-23573), sapanisertib (INK 128, MLN0128), SAR245409 (XL765), SF-1126, SF2523, sirolimus (rapamycin), SN32976, TAK228, temsirolimus (CCI-779, NSC 683864), Torin 1, Torin 2, torkinib (PP242), umirolimus, vistusertib (AZD2014), voxtalisib (XL765, SAR245409), VS-5584, VS-5584 (5B2343), WAY-600, WYE-125132 (WYE-132), WYE-354, WYE-687, XL388, and zotarolimus (ABT-578).

Exemplary inhibitors of MYC include: 10058-F4, 10074-G5, and KSI-3716.

The phrase "dysregulation of a gene, a protein, or the expression or activity or level of any of the same" refers to a genetic mutation (e.g., a chromosomal translocation that results in the expression of a fusion protein including a kinase domain and a fusion partner, a mutation in a gene that results in the expression of a protein that includes a deletion of at least one amino acid as compared to a wildtype protein, a mutation in a gene that results in the expression of a protein with one or more point mutations as compared to a wildtype protein, a mutation in a gene that results in the expression of a protein with at least one inserted amino acid as compared to a wildtype protein, a gene duplication that results in an increased level of protein in a cell, or a mutation in a regulatory sequence (e.g., a promoter and/or enhancer) that results in an increased level of protein in a cell), an alternative spliced version of a mRNA that results in a protein having a deletion of at least one amino acid in the protein as compared to the wild-type protein), or increased expression (e.g., increased levels) of a wildtype protein in a mammalian cell due to aberrant cell signaling and/or dysregulated autocrine/paracrine signaling (e.g., as compared to a control non-cancerous cell). As another example, a dysregulation of a gene, a protein, or expression or activity, or level of any of the same, can be a mutation in a gene that encodes a protein that is constitutively active or has increased activity as compared to a protein encoded by a gene that does not include the mutation. For example, a dysregulation of a gene, a protein, or expression or activity, or level of any of the same, can be the result of a gene or chromosome translocation which results in the expression of a fusion protein that contains a first portion of a protein that includes a functional kinase domain, and a second portion of a partner protein (i.e., that is not the primary protein). In some examples, dysregulation of a gene, a protein, or expression or activity or level of any of the same can be a result of a gene translocation of one gene with a different gene.

Treatment of a subject having a cancer with a multi-kinase inhibitor (MKI) or target-specific kinase inhibitor (e.g., an ALK inhibitor, an AKT inhibitor, an aurora inhibitor, an AXL inhibitor, a BRAF inhibitor, an EGFR inhibitor, an ERK inhibitor, a FGFR1 inhibitor, a FGFR2 inhibitor, a FGFR3 inhibitor, a FGFR4 inhibitor, a FLT3 inhibitor, a HER2 (also called erbB-2) inhibitor, a HER3 (also called erbB-3) inhibitor, a HER4 (also called erbB-4) inhibitor, an IGFR inhibitor, a JAK1 inhibitor, a JAK2 inhibitor, a JAK 3 inhibitor, a Kit inhibitor, a MEK inhibitor, a MET inhibitor, a mTOR inhibitor, a PDGFRα inhibitor, a PDGFRβ inhibitor, a PI3K inhibitor, a RAF inhibitor, a RAS inhibitor, a RET inhibitor, a ROS inhibitor, a ROS1 inhibitor, a trkA inhibitor, a trkB inhibitor, a trkC inhibitor, a VEGFR-1 inhibitor, a VEGFR-2 inhibitor, or a VEGFR-3 inhibitor) can result in dysregulation of a FGFR gene, a FGFR kinase, or the expression or activity or level of the same in the cancer, and/or resistance to a FGFR inhibitor. Such dysregulation is sometimes called bypass resistance, as, without being bound by theory, it is believed that the dysregulation of a second protein (e.g., a FGFR) causes resistance to a MKI or a target-specific inhibitor. See, e.g., Yang et al., *J Biol Chem.*, 287(33):28087-98, 2012; and Huang et al., *Acta Pharm Sin B.*, 5(5):390-401, 2015.

Treatment of a subject having a FGFR-associated cancer with a FGFR inhibitor (e.g., a compound of Formula I) can result in dysregulation of a second kinase gene, a second kinase, or the expression or activity or level of the same in the cancer, and/or resistance to the FGFR inhibitor. Such dysregulation is sometimes called bypass resistance, as, without being bound by theory, it is believed that the dysregulation of a second kinase (e.g., ALK, AKT, aurora, AXL, BRAF, CDK, EGFR, ERK, FGFR1, FGFR2, FGFR3, FGFR4, FLT3, HER2 (also called erbB-2), HER3 (also called erbB-3), HER4 (also called erbB-4), IGFR, JAK1, JAK2, JAK3, Kit, MEK, MET, mTOR, PDGFRα, PDGFRβ, PI3K, RAF, RAS, RET, ROS1, trkA, trkB, trkC, VEGFR-1, VEGFR-2, or VEGFR-3) causes resistance to a FGFR inhibitor (e.g., a compound of Formula I). See, e.g., Wang et al., *Oncogene* 34(17):2167-2177, 2015; and Kim et al., *Oncogenesis* 5(5):e241, 2016.

Treatment of a subject having a cancer with target-specific kinase inhibitor (e.g., an aromatase inhibitor, a EHMT2 inhibitor, a RAC1 inhibitor, or a SOS1 inhibitor) can result in dysregulation of a FGFR gene, a FGFR kinase, or the expression or activity or level of the same in the cancer, and/or resistance to a FGFR inhibitor. Such dysregulation is sometimes called bypass resistance, as, without being bound by theory, it is believed that the dysregulation of a second protein (e.g., a FGFR) causes resistance a target-specific inhibitor. See, e.g., Yang et al., J Biol Chem., 287(33): 28087-98, 2012; and Huang et al., Acta Pharm Sin B., 5(5):390-401, 2015.

Treatment of a subject having a FGFR-associated cancer with a FGFR inhibitor (e.g., a compound of Formula I) can result in dysregulation of a second gene, a second protein, or the expression or activity or level of the same in the cancer, and/or resistance to the FGFR inhibitor. Such dysregulation is sometimes called bypass resistance, as, without being bound by theory, it is believed that the dysregulation of a second protein (e.g., aromatase, EHMT2, RAC1, or SOS1) causes resistance to a FGFR inhibitor (e.g., a compound of Formula I). See, e.g., Wang et al., Oncogene 34(17):2167-2177, 2015; and Kim et al., Oncogenesis 5(5):e241, 2016.

Treatment of a subject having a cancer with a FGFR inhibitor in combination with a multi-kinase inhibitor or a target-specific kinase inhibitor (e.g., an ALK inhibitor, an AKT inhibitor, an aurora inhibitor, an AXL inhibitor, a BRAF inhibitor, an EGFR inhibitor, an ERK inhibitor, a FGFR1 inhibitor, a FGFR2 inhibitor, a FGFR3 inhibitor, a FGFR4 inhibitor, a FLT3 inhibitor, a HER2 (also called erbB-2) inhibitor, a HER3 (also called erbB-3) inhibitor, a HER4 (also called erbB-4) inhibitor, an IGFR inhibitor, a JAK1 inhibitor, a JAK2 inhibitor, a JAK 3 inhibitor, a Kit inhibitor, a MEK inhibitor, a MET inhibitor, a mTOR inhibitor, a PDGFRα inhibitor, a PDGFRβ inhibitor, a PI3K inhibitor, a RAF inhibitor, a RAS inhibitor, a RET inhibitor, a ROS1 inhibitor, a trkA inhibitor, a trkB inhibitor, a trkC inhibitor, a VEGFR-1 inhibitor, a VEGFR-2 inhibitor, or a VEGFR-3 inhibitor) can have increased therapeutic efficacy as compared to treatment of the same subject or a similar subject with the FGFR inhibitor as a monotherapy, or the multi-kinase inhibitor or the target-specific kinase inhibitor as a monotherapy.

Treatment of a subject having a cancer with a FGFR inhibitor in combination with a target-specific inhibitor (e.g., an aromatase inhibitor, a EHMT2 inhibitor, a RAC1 inhibitor, or a SOS1 inhibitor) can have increased therapeutic efficacy as compared to treatment of the same subject or a similar subject with the FGFR inhibitor as a monotherapy, or the multi-kinase inhibitor or the target-specific kinase inhibitor as a monotherapy. Accordingly, in some embodiments, an additional therapy or therapeutic agent can include an aromatase inhibitor (e.g., any aromatase inhibitor provided herein or known in the art), a EHMT2 inhibitor (e.g., any EHMT2 inhibitor provided herein or known in the art), a RAC1 inhibitor (e.g., any RAC1 inhibitor provided herein or known in the art), or a SOS1 inhibitor (e.g., any SOS1 inhibitor provided herein or known in the art).

Provided herein are methods of treating a subject having a cancer (e.g., any of the cancers described herein that include: (a) detecting a dysregulation of a FGFR gene, a FGFR kinase, or the expression or activity or level of any of the same in a sample from the subject, (b) administering to the subject a therapeutically effective amount of a first FGFR inhibitor, (c) determining whether a sample from a subject exhibits a dysregulation of a second kinase gene, a second kinase, or the expression or activity or level of any of the same in a sample from the subject; and (d) administering an inhibitor of the second kinase in conjunction with an additional therapy or therapeutic agent to the subject if the sample from the subject exhibits a dysregulation of a second kinase gene, a second kinase, or the expression or activity or level of any of the same; or (e) administering additional doses of the first FGFR inhibitor of step (b) to the subject if the sample from the subject does not exhibit a dysregulation of a second kinase gene, a second kinase, or the expression or activity or level of any of the same. In some embodiments, a second kinase is selected from the group consisting of ALK, AKT, aurora, AXL, BRAF, CDK, EGFR, ERK, FGFR1, FGFR2, FGFR3, FGFR4, FLT3, HER2 (also called erbB-2), HER3 (also called erbB-3), HER4 (also called erbB-4), IGFR, JAK1, JAK2, JAK3, Kit, MEK, MET, mTOR, PDGFRα, PDGFRβ, PI3K, RAF, RAS, RET, ROS1, trkA, trkB, trkC, VEGFR-1, VEGFR-2, and VEGFR-3. In some embodiments, the inhibitor of the second kinase is selected from the group consisting of axitinib, cabozantinib, cetuximab, crizotinib, dasatinib, erlotinib, gefitinib, ibrutinib, imatinib, lapatinib, nilotinib, panitumumab, pazopanib, pertuzumab, regorafenib, ruxolitinib, sorafenib, sunitinib, trastuzumab, vandetanib, and vemurafenib. In some embodiments, the second kinase is a tyrosine kinase. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA). In some embodiments, a first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Provided herein are methods of treating a subject having a cancer (e.g., any of the cancers described herein that include: (a) detecting a dysregulation of a FGFR gene, a FGFR kinase, or the expression or activity or level of any of the same in a sample from the subject, (b) administering to the subject a therapeutically effective amount of a compound of Formula I, or a pharmaceutically acceptable salt or solvate thereof, (c) determining whether a sample from a subject exhibits a dysregulation of a second kinase gene, a second kinase, or the expression or activity or level of any of the same in a sample from the subject; and (d) administering an inhibitor of the second kinase in conjunction with an additional therapy or therapeutic agent to the subject if the sample from the subject exhibits a dysregulation of a second kinase gene, a second kinase, or the expression or activity or level of any of the same; or (e) administering additional doses of the compound of Formula I, or a pharmaceutically acceptable salt or solvate thereof of step (b) to the subject if the sample from the subject does not exhibit a dysregulation of a second kinase gene, a second kinase, or the expression or activity or level of any of the same. In some embodiments, a second kinase is selected from the group consisting of ALK, AKT, aurora, AXL, BRAF, CDK, EGFR, ERK, FGFR1, FGFR2, FGFR3, FGFR4, FLT3, HER2 (also called erbB-2), HER3 (also called erbB-3), HER4 (also called erbB-4), IGFR, JAK1, JAK2, JAK3, Kit, MEK, MET, mTOR, PDGFRα, PDGFRβ, PI3K, RAF, RAS, RET, ROS1, trkA, trkB, trkC, VEGFR-1, VEGFR-2, and VEGFR-3. In some embodiments, the inhibitor of the second kinase is selected from the group consisting of axitinib, cabozantinib, cetuximab, crizotinib, dasatinib, erlotinib, gefitinib, ibrutinib, imatinib, lapatinib, nilotinib, panitumumab, pazopanib, pertuzumab, regorafenib, ruxolitinib, sorafenib, sunitinib, trastuzumab, vandetanib, and vemurafenib. In some embodiments, the second kinase is a tyrosine kinase. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA). In some embodiments, a first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Provided herein are methods of treating a subject having a cancer (e.g., any of the cancers described herein that include: (a) determining whether a sample from a subject previously administered one or more doses of a first FGFR inhibitor exhibits a dysregulation of a second kinase gene, a second kinase, or the expression or activity or level of any of the same in a sample from the subject; and (b) administering an inhibitor of the second kinase in conjunction with an additional therapy or therapeutic agent to the subject if the sample from the subject exhibits a dysregulation of a second kinase gene, a second kinase, or the expression or activity or level of any of the same; or (c) administering additional doses of the first FGFR inhibitor of step (b) to the subject if the sample from the subject does not exhibit a dysregulation of a second kinase gene, a second kinase, or the expression or activity or level of any of the same. In some embodiments, a second kinase is selected from the group consisting of ALK, AKT, aurora, AXL, BRAF, CDK, EGFR, ERK, FGFR1, FGFR2, FGFR3, FGFR4, FLT3, HER2 (also called erbB-2), HER3 (also called erbB-3), HER4 (also called erbB-4), IGFR, JAK1, JAK2, JAK3, Kit, MEK, MET, mTOR, PDGFRα, PDGFRβ, PI3K, RAF, RAS, RET, ROS1, trkA, trkB, trkC, VEGFR-1, VEGFR-2, and VEGFR-3. In some embodiments, the inhibitor of the second kinase is selected from the group consisting of axitinib, cabozantinib, cetuximab, crizotinib, dasatinib, erlotinib, gefitinib, ibrutinib, imatinib, lapatinib, nilotinib, panitumumab, pazopanib, pertuzumab, regorafenib, ruxolitinib, sorafenib, sunitinib, trastuzumab, vandetanib, and vemurafenib. In some embodiments, the second kinase is a tyrosine kinase. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA). In some embodiments, a first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Provided herein are methods of treating a subject having a cancer (e.g., any of the cancers described herein) that include: (a) determining whether a sample from a subject previously administered one or more doses of a compound of Formula I, or a pharmaceutically acceptable salt or solvate thereof, exhibits a dysregulation of a second kinase gene, a second kinase, or the expression or activity or level of any of the same in a sample from the subject; and (b) administering an inhibitor of the second kinase in conjunction with an additional therapy or therapeutic agent to the subject if the sample from the subject exhibits a dysregulation of a second kinase gene, a second kinase, or the expression or activity or level of any of the same; or (c) administering additional doses of the compound of Formula I, or a pharmaceutically acceptable salt or solvate thereof, of step (b) to the subject if the sample from the subject does not exhibit a dysregulation of a second kinase gene, a second kinase, or the expression or activity or level of any of the same. In some embodiments, a second kinase is selected from the group consisting of ALK, AKT, aurora, AXL, BRAF, CDK, EGFR, ERK, FGFR1, FGFR2, FGFR3, FGFR4, FLT3, HER2 (also called erbB-2), HER3 (also called erbB-3), HER4 (also called erbB-4), IGFR, JAK1, JAK2, JAK3, Kit, MEK, MET, mTOR, PDGFRα, PDGFRβ, PI3K, RAF, RAS, RET, ROS1, trkA, trkB, trkC, VEGFR-1, VEGFR-2, and VEGFR-3. In some embodiments, the inhibitor of the second kinase is selected from the group consisting of axitinib, cabozantinib, cetuximab, crizotinib, dasatinib, erlotinib, gefitinib, ibrutinib, imatinib, lapatinib, nilotinib, panitumumab, pazopanib, pertuzumab, regorafenib, ruxolitinib, sorafenib, sunitinib, trastuzumab, vandetanib, and vemurafenib. In some embodiments, the second kinase is a tyrosine kinase. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA).

Also provided herein are methods of treating a subject in need of such treatment, including: (a) detecting a dysregulation of a first kinase gene, a first kinase, or the expression or activity or level of any of the same in a sample from the subject, (b) administering to the subject a therapeutically effective amount of an inhibitor of the first kinase, (c) determining whether a sample from a subject exhibits a dysregulation of a FGFR gene, a FGFR kinase, or the expression or activity or level of any of the same, and (d) administering a FGFR inhibitor in conjunction with an additional therapy or therapeutic agent to the subject if the sample from the subject exhibits a dysregulation of a FGFR gene, a FGFR kinase, or the expression or activity or level of any of the same, or (e) administering additional doses of the inhibitor of the first kinase of step (b) to the subject if the sample from the subject does not exhibit a dysregulation of a FGFR gene, a FGFR kinase, or the expression or activity or level of any of the same. In some embodiments, a first kinase is selected from the group consisting of ALK, AKT, aurora, AXL, BRAF, CDK, EGFR, ERK, FGFR1, FGFR2, FGFR3, FGFR4, FLT3, HER2 (also called erbB-2), HER3 (also called erbB-3), HER4 (also called erbB-4), IGFR, JAK1, JAK2, JAK3, Kit, MEK, MET, mTOR, PDGFRα, PDGFRβ, PI3K, RAF, RAS, RET, ROS1, trkA, trkB, trkC, VEGFR-1, VEGFR-2, and VEGFR-3. In some embodiments, the first kinase is a tyrosine kinase. In some embodiments, the inhibitor of the first kinase is selected from the group consisting of axitinib, cabozantinib, cetuximab, crizotinib, dasatinib, erlotinib, gefitinib, ibrutinib, imatinib, lapatinib, nilotinib, panitumumab, pazopanib, pertuzumab, regorafenib, ruxolitinib, sorafenib, sunitinib, trastuzumab, vandetanib, and vemurafenib. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA). In some embodiments, the FGFR inhibitor is a compound of Formula I or a pharmaceutically acceptable salt or solvate thereof. In some embodiments, the FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Provided herein are methods of treating a subject having a cancer (e.g., any of the cancers described herein that include: (a) detecting a dysregulation of a FGFR gene, a FGFR kinase, or the expression or activity or level of any of the same in a sample from the subject, (b) administering to the subject a therapeutically effective amount of a first FGFR inhibitor, (c) determining whether a sample from a subject exhibits a dysregulation of a second gene, a second protein, or the expression or activity or level of any of the same in a sample from the subject; and (d) administering an inhibitor of the second protein in conjunction with an additional therapy or therapeutic agent to the subject if the sample from the subject exhibits a dysregulation of a second kinase gene, a second kinase, or the expression or activity or level of any of the same; or (e) administering additional doses of the first FGFR inhibitor of step (b) to the subject if the sample from the subject does not exhibit a dysregulation of a second gene, a second protein, or the expression or activity or level of any of the same. In some embodiments, a second protein is selected from the group consisting of aromatase, EHMT2, RAC1, and SOS. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA). In some embodiments, a first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Provided herein are methods of treating a subject having a cancer (e.g., any of the cancers described herein that include: (a) detecting a dysregulation of a FGFR gene, a FGFR kinase, or the expression or activity or level of any of the same in a sample from the subject, (b) administering to the subject a therapeutically effective amount of a compound of Formula I, or a pharmaceutically acceptable salt or solvate thereof, (c) determining whether a sample from a subject exhibits a dysregulation of a second gene, a second protein, or the expression or activity or level of any of the same in a sample from the subject; and (d) administering an inhibitor of the second protein in conjunction with an additional therapy or therapeutic agent to the subject if the sample from the subject exhibits a dysregulation of a second gene, a second protein, or the expression or activity or level of any of the same; or (e) administering additional doses of the compound of Formula I, or a pharmaceutically acceptable salt or solvate thereof of step (b) to the subject if the sample from the subject does not exhibit a dysregulation of a second gene, a second protein, or the expression or activity or level of any of the same. In some embodiments, a second protein is selected from the group consisting of aromatase, EHMT2, RAC1, and SOS1. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA).

Provided herein are methods of treating a subject having a cancer (e.g., any of the cancers described herein that include: (a) determining whether a sample from a subject previously administered one or more doses of a first FGFR inhibitor exhibits a dysregulation of a second gene, a second protein, or the expression or activity or level of any of the same in a sample from the subject; and (b) administering an inhibitor of the second protein in conjunction with an additional therapy or therapeutic agent to the subject if the sample from the subject exhibits a dysregulation of a second gene, a second protein, or the expression or activity or level of any of the same; or (c) administering additional doses of the first FGFR inhibitor of step (b) to the subject if the sample from the subject does not exhibit a dysregulation of a second gene, a second protein, or the expression or activity or level of any of the same. In some embodiments, a second protein is selected from the group consisting of aromatase, EHMT2, RAC1, and SOS1. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA). In some embodiments, a first FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Provided herein are methods of treating a subject having a cancer (e.g., any of the cancers described herein) that include: (a) determining whether a sample from a subject previously administered one or more doses of a compound of Formula I, or a pharmaceutically acceptable salt or solvate thereof, exhibits a dysregulation of a second gene, a second protein, or the expression or activity or level of any of the same in a sample from the subject; and (b) administering an inhibitor of the second protein in conjunction with an additional therapy or therapeutic agent to the subject if the sample from the subject exhibits a dysregulation of a second gene, a second protein, or the expression or activity or level of any of the same; or (c) administering additional doses of the compound of Formula I, or a pharmaceutically acceptable salt or solvate thereof, of step (b) to the subject if the sample from the subject does not exhibit a dysregulation of a second gene, a second protein, or the expression or activity or level of any of the same. In some embodiments, a second protein is selected from the group consisting of aromatase, EHMT2, RAC1, and SOS1. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA).

Also provided herein are methods of treating a subject in need of such treatment, including: (a) detecting a dysregulation of a first gene, a first protein, or the expression or activity or level of any of the same in a sample from the subject, (b) administering to the subject a therapeutically effective amount of an inhibitor of the first protein, (c) determining whether a sample from a subject exhibits a dysregulation of a FGFR gene, a FGFR kinase, or the expression or activity or level of any of the same, and (d) administering a FGFR inhibitor in conjunction with an additional therapy or therapeutic agent to the subject if the sample from the subject exhibits a dysregulation of a FGFR gene, a FGFR kinase, or the expression or activity or level of any of the same, or (e) administering additional doses of the inhibitor of the first protein of step (b) to the subject if the sample from the subject does not exhibit a dysregulation of a FGFR gene, a FGFR kinase, or the expression or activity or level of any of the same. In some embodiments, a first protein is selected from the group consisting of aromatase, EHMT2, RAC1, or SOS1. In some embodiments, the dysregulation of a FGFR gene, a FGFR kinase, or the expression or activity or level of any of the same is a point mutation (e.g., any of the point mutations in Table BC). In some embodiments, the dysregulation of a FGFR gene, a FGFR kinase, or the expression or activity or level of any of the same is a fusion (e.g., any of the fusions in Table BA). In some embodiments, the FGFR inhibitor is a compound of Formula I or a pharmaceutically acceptable salt or solvate thereof. In some embodiments, the FGFR inhibitor is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120.

Provided herein are methods of treating a subject having a cancer (e.g., any of the cancers described herein) and previously administered a multi-kinase inhibitor (MKI) or a target-specific kinase inhibitor (e.g., an ALK inhibitor, an AXL inhibitor, a BRAF inhibitor, an EGFR inhibitor, an ERK inhibitor, a FGFR1 inhibitor, a FGFR2 inhibitor, a FGFR3 inhibitor, a FGFR4 inhibitor, a FLT3 inhibitor, a HER2 (also called erbB-2) inhibitor, a HER3 (also called erbB-3) inhibitor, a HER4 (also called erbB-4) inhibitor, an IGFR inhibitor, a JAK1 inhibitor, a JAK2 inhibitor, a JAK 3 inhibitor, a Kit inhibitor, a MEK inhibitor, a MET inhibitor, a mTOR inhibitor, a PDGFRα inhibitor, a PDGFRβ inhibitor, a PI3K inhibitor, a RAF inhibitor, a RAS inhibitor, a RET inhibitor, a ROS1 inhibitor, a trkA inhibitor, a trkB inhibitor, a trkC inhibitor, a VEGFR-1 inhibitor, a VEGFR-2 inhibitor, or a VEGFR-3 inhibitor) (e.g., as a monotherapy) that include: administering to the subject (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered MKI or the previously administered target-specific kinase inhibitor.

Provided herein are methods of treating a subject having a cancer (e.g., any of the cancers described herein) previously administered a MKI or a target specific kinase inhibitor (e.g., an ALK inhibitor, an AXL inhibitor, a BRAF inhibitor, an EGFR inhibitor, an ERK inhibitor, a FGFR1 inhibitor, a FGFR2 inhibitor, a FGFR3 inhibitor, a FGFR4 inhibitor, a FLT3 inhibitor, a HER2 (also called erbB-2) inhibitor, a HER3 (also called erbB-3) inhibitor, a HER4 (also called erbB-4) inhibitor, an IGFR inhibitor, a JAK1 inhibitor, a JAK2 inhibitor, a JAK 3 inhibitor, a Kit inhibitor, a MEK inhibitor, a MET inhibitor, a mTOR inhibitor, a PDGFRα inhibitor, a PDGFRβ inhibitor, a PI3K inhibitor, a RAF inhibitor, a RAS inhibitor, a RET inhibitor, a ROS1 inhibitor, a trkA inhibitor, a trkB inhibitor, a trkC inhibitor, a VEGFR-1 inhibitor, a VEGFR-2 inhibitor, or a VEGFR-3 inhibitor) (e.g., as a monotherapy) that include: identifying a subject having a cancer cell that has a dysregulation of a FGFR gene, a FGFR kinase, or the expression or activity or level of the same; and administering to the identified subject (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered MKI or the previously administered target-specific kinase inhibitor.

Provided herein are methods of treating a subject having a cancer (e.g., any of the cancers described herein) that include: administering to a subject a therapeutically effective amount of a MKI or a target-specific kinase inhibitor (e.g., an ALK inhibitor, an AKT inhibitor, an aurora inhibitor, an AXL inhibitor, a BRAF inhibitor, an EGFR inhibitor, an ERK inhibitor, a FGFR1 inhibitor, a FGFR2 inhibitor, a FGFR3 inhibitor, a FGFR4 inhibitor, a FLT3 inhibitor, a HER2 (also called erbB-2) inhibitor, a HER3 (also called erbB-3) inhibitor, a HER4 (also called erbB-4) inhibitor, an IGFR inhibitor, a JAK1 inhibitor, a JAK2 inhibitor, a JAK 3 inhibitor, a Kit inhibitor, a MEK inhibitor, a MET inhibitor, a mTOR inhibitor, a PDGFRα inhibitor, a PDGFRβ inhibitor, a PI3K inhibitor, a RAF inhibitor, a RAS inhibitor, a RET inhibitor, a ROS1 inhibitor, a trkA inhibitor, a trkB inhibitor, a trkC inhibitor, a VEGFR-1 inhibitor, a VEGFR-2 inhibitor, or a VEGFR-3 inhibitor) (e.g., as a monotherapy) for a first period of time; after the period of time, identifying a subject having a cancer cell that has a dysregulation of a FGFR gene, a FGFR kinase, or the expression or activity or level of the same; and administering to the identified subject (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered MKI or the previously administered target-specific kinase inhibitor.

Provided herein are methods of treating a subject having a cancer (e.g., any of the cancers described herein) and previously administered target-specific inhibitor (e.g., an aromatase inhibitor, a EHMT2 inhibitor, a RAC1 inhibitor, or a SOS1 inhibitor) (e.g., as a monotherapy) that include: administering to the subject (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered target-specific inhibitor.

Provided herein are methods of treating a subject having a cancer (e.g., any of the cancers described herein) previously a target specific inhibitor (e.g., an aromatase inhibitor, a EHMT2 inhibitor, a RAC1 inhibitor, or a SOS1 inhibitor) (e.g., as a monotherapy) that include: identifying a subject having a cancer cell that has a dysregulation of a FGFR gene, a FGFR kinase, or the expression or activity or level of the same; and administering to the identified subject (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered target-specific inhibitor.

Provided herein are methods of treating a subject having a cancer (e.g., any of the cancers described herein) that include: administering to a subject a therapeutically effective amount of a target-specific inhibitor (e.g., an aromatase inhibitor, a EHMT2 inhibitor, a RAC1 inhibitor, or a SOS1 inhibitor) for a first period of time; after the period of time, identifying a subject having a cancer cell that has a dysregulation of a FGFR gene, a FGFR kinase, or the expression or activity or level of the same; and administering to the identified subject (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered target-specific inhibitor.

Provided herein are methods of treating a subject having a cancer (e.g., any of the cancers described herein) that has dysregulation of an ALK gene, an ALK protein, or the expression or activity or level of the same that include administering to the subject (i) a therapeutically effective amount of a compound of Formula I or a pharmaceutically acceptable salt or solvate thereof and (ii) a therapeutically effective amount of an ALK inhibitor (e.g., any of the ALK inhibitors described herein or known in the art).

Provided herein are methods of treating a subject having a cancer (e.g., any of the cancers described herein) that include: identifying a subject having a cancer cell that has dysregulation of an ALK gene, an ALK protein, or the expression or activity or level of the same; and administering to the identified subject (i) a therapeutically effective amount of a compound of Formula I or a pharmaceutically acceptable salt or solvate thereof and (ii) a therapeutically effective amount of an ALK inhibitor (e.g., any of the ALK inhibitors described herein or known in the art).

Provided herein are methods of treating a subject having a cancer (e.g., any of the cancers described herein) that has dysregulation of an AKT gene, an AKT protein, or the expression or activity or level of the same that include administering to the subject (i) a therapeutically effective amount of a compound of Formula I or a pharmaceutically acceptable salt or solvate thereof and (ii) a therapeutically effective amount of an AKT inhibitor (e.g., any of the AKT inhibitors described herein or known in the art).

Provided herein are methods of treating a subject having a cancer (e.g., any of the cancers described herein) that include: identifying a subject having a cancer cell that has dysregulation of an AKT gene, an AKT protein, or the expression or activity or level of the same; and administering to the identified subject (i) a therapeutically effective amount of a compound of Formula I or a pharmaceutically acceptable salt or solvate thereof and (ii) a therapeutically effective amount of an AKT inhibitor (e.g., any of the AKT inhibitors described herein or known in the art).

Provided herein are methods of treating a subject having a cancer (e.g., any of the cancers described herein) that has dysregulation of an aurora gene, an aurora protein, or the expression or activity or level of the same that include administering to the subject (i) a therapeutically effective amount of a compound of Formula I or a pharmaceutically acceptable salt or solvate thereof and (ii) a therapeutically effective amount of an aurora inhibitor (e.g., any of the aurora inhibitors described herein or known in the art).

Provided herein are methods of treating a subject having a cancer (e.g., any of the cancers described herein) that include: identifying a subject having a cancer cell that has dysregulation of an aurora gene, an aurora protein, or the expression or activity or level of the same; and administering to the identified subject (i) a therapeutically effective amount of a compound of Formula I or a pharmaceutically acceptable salt or solvate thereof and (ii) a therapeutically effective amount of an aurora inhibitor (e.g., any of the aurora inhibitors described herein or known in the art).

Provided herein are methods of treating a subject having a cancer (e.g., any of the cancers described herein) that has dysregulation of an AXL gene, an AXL protein, or the expression or activity or level of the same that include administering to the subject (i) a therapeutically effective amount of a compound of Formula I or a pharmaceutically acceptable salt or solvate thereof and (ii) a therapeutically effective amount of an AXL inhibitor (e.g., any of the AXL inhibitors described herein or known in the art).

Provided herein are methods of treating a subject having a cancer (e.g., any of the cancers described herein) that include: identifying a subject having a cancer cell that has dysregulation of an AXL gene, an AXL protein, or the expression or activity or level of the same; and administering to the identified subject (i) a therapeutically effective amount of a compound of Formula I or a pharmaceutically acceptable salt or solvate thereof and (ii) a therapeutically effective amount of an AXL inhibitor (e.g., any of the AXL inhibitors described herein or known in the art).

Provided herein are methods of treating a subject having a cancer (e.g., any of the cancers described herein) that has dysregulation of a BRAF gene, a BRAF kinase, or the expression or activity or level of the same that include administering to the subject (i) a therapeutically effective amount of a compound of Formula I or a pharmaceutically acceptable salt or solvate thereof and (ii) a therapeutically effective amount of a BRAF inhibitor (e.g., any of the BRAF inhibitors described herein or known in the art).

Provided herein are methods of treating a subject having a cancer (e.g., any of the cancers described herein) that include: identifying a subject having a cancer cell that has dysregulation of a BRAF gene, a BRAF kinase, or the expression or activity or level of the same; and administering to the identified subject (i) a therapeutically effective amount of a compound of Formula I or a pharmaceutically acceptable salt or solvate thereof and (ii) a therapeutically effective amount of a BRAF inhibitor (e.g., any of the BRAF inhibitors described herein or known in the art).

Provided herein are methods of treating a subject having a cancer (e.g., any of the cancers described herein) that has dysregulation of an CDK gene, an CDK protein, or the expression or activity or level of the same that include administering to the subject (i) a therapeutically effective amount of a compound of Formula I or a pharmaceutically acceptable salt or solvate thereof and (ii) a therapeutically effective amount of an CDK inhibitor (e.g., any of the CDK inhibitors described herein or known in the art).

Provided herein are methods of treating a subject having a cancer (e.g., any of the cancers described herein) that include: identifying a subject having a cancer cell that has dysregulation of an CDK gene, an CDK protein, or the expression or activity or level of the same; and administering to the identified subject (i) a therapeutically effective amount of a compound of Formula I or a pharmaceutically acceptable salt or solvate thereof and (ii) a therapeutically effective amount of an CDK inhibitor (e.g., any of the CDK inhibitors described herein or known in the art).

Provided herein are methods of treating a subject having a cancer (e.g., any of the cancers described herein) that has dysregulation of an EGFR gene, an EGFR protein, or the expression or activity or level of the same that include administering to the subject (i) a therapeutically effective amount of a compound of Formula I or a pharmaceutically acceptable salt or solvate thereof and (ii) a therapeutically effective amount of an EGFR inhibitor (e.g., any of the EGFR inhibitors described herein or known in the art).

Provided herein are methods of treating a subject having a cancer (e.g., any of the cancers described herein) that include: identifying a subject having a cancer cell that has dysregulation of an EGFR gene, an EGFR protein, or the expression or activity or level of the same; and administering to the identified subject (i) a therapeutically effective amount of a compound of Formula I or a pharmaceutically acceptable salt or solvate thereof and (ii) a therapeutically effective amount of an EGFR inhibitor (e.g., any of the EGFR inhibitors described herein or known in the art).

Provided herein are methods of treating a subject having a cancer (e.g., any of the cancers described herein) that has dysregulation of an ERK gene, an ERK protein, or the expression or activity or level of the same that include administering to the subject (i) a therapeutically effective amount of a compound of Formula I or a pharmaceutically acceptable salt or solvate thereof and (ii) a therapeutically effective amount of an ERK inhibitor (e.g., any of the ERK inhibitors described herein or known in the art).

Provided herein are methods of treating a subject having a cancer (e.g., any of the cancers described herein) that include: identifying a subject having a cancer cell that has dysregulation of an ERK gene, an ERK protein, or the expression or activity or level of the same; and administering to the identified subject (i) a therapeutically effective amount of a compound of Formula I or a pharmaceutically acceptable salt or solvate thereof and (ii) a therapeutically effective amount of an ERK inhibitor (e.g., any of the ERK inhibitors described herein or known in the art).

Provided herein are methods of treating a subject having a cancer (e.g., any of the cancers described herein) that has dysregulation of an FLT3 gene, an FLT3 protein, or the expression or activity or level of the same that include administering to the subject (i) a therapeutically effective amount of a compound of Formula I or a pharmaceutically acceptable salt or solvate thereof and (ii) a therapeutically effective amount of an FLT3 inhibitor (e.g., any of the FLT3 inhibitors described herein or known in the art).

Provided herein are methods of treating a subject having a cancer (e.g., any of the cancers described herein) that include: identifying a subject having a cancer cell that has dysregulation of an FLT3 gene, an FLT3 protein, or the expression or activity or level of the same; and administering to the identified subject (i) a therapeutically effective amount of a compound of Formula I or a pharmaceutically acceptable salt or solvate thereof and (ii) a therapeutically effective amount of an FLT3 inhibitor (e.g., any of the FLT3 inhibitors described herein or known in the art).

Provided herein are methods of treating a subject having a cancer (e.g., any of the cancers described herein) that has dysregulation of an HER2 gene, an HER2 protein, or the expression or activity or level of the same that include administering to the subject (i) a therapeutically effective amount of a compound of Formula I or a pharmaceutically acceptable salt or solvate thereof and (ii) a therapeutically effective amount of an HER2 inhibitor (e.g., any of the HER2 inhibitors described herein or known in the art).

Provided herein are methods of treating a subject having a cancer (e.g., any of the cancers described herein) that include: identifying a subject having a cancer cell that has dysregulation of an HER2 gene, an HER2 protein, or the expression or activity or level of the same; and administering to the identified subject (i) a therapeutically effective amount of a compound of Formula I or a pharmaceutically acceptable salt or solvate thereof and (ii) a therapeutically effective amount of an HER2 inhibitor (e.g., any of the HER2 inhibitors described herein or known in the art).

Provided herein are methods of treating a subject having a cancer (e.g., any of the cancers described herein) that has dysregulation of an HER3 gene, an HER3 protein, or the expression or activity or level of the same that include administering to the subject (i) a therapeutically effective amount of a compound of Formula I or a pharmaceutically acceptable salt or solvate thereof and (ii) a therapeutically effective amount of an HER3 inhibitor (e.g., any of the HER3 inhibitors described herein or known in the art).

Provided herein are methods of treating a subject having a cancer (e.g., any of the cancers described herein) that include: identifying a subject having a cancer cell that has dysregulation of an HER3 gene, an HER3 protein, or the expression or activity or level of the same; and administering to the identified subject (i) a therapeutically effective amount of a compound of Formula I or a pharmaceutically acceptable salt or solvate thereof and (ii) a therapeutically effective amount of an HER3 inhibitor (e.g., any of the HER3 inhibitors described herein or known in the art).

Provided herein are methods of treating a subject having a cancer (e.g., any of the cancers described herein) that has dysregulation of an IGFR gene, an IGFR protein, or the expression or activity or level of the same that include administering to the subject (i) a therapeutically effective amount of a compound of Formula I or a pharmaceutically acceptable salt or solvate thereof and (ii) a therapeutically effective amount of an IGFR inhibitor (e.g., any of the IGFR inhibitors described herein or known in the art).

Provided herein are methods of treating a subject having a cancer (e.g., any of the cancers described herein) that include: identifying a subject having a cancer cell that has dysregulation of an IGFR gene, an IGFR protein, or the expression or activity or level of the same; and administering to the identified subject (i) a therapeutically effective amount of a compound of Formula I or a pharmaceutically acceptable salt or solvate thereof and (ii) a therapeutically effective amount of an IGFR inhibitor (e.g., any of the IGFR inhibitors described herein or known in the art).

Provided herein are methods of treating a subject having a cancer (e.g., any of the cancers described herein) that has dysregulation of an JAK1 gene, an JAK1 protein, or the expression or activity or level of the same that include administering to the subject (i) a therapeutically effective amount of a compound of Formula I or a pharmaceutically acceptable salt or solvate thereof and (ii) a therapeutically effective amount of an JAK1 inhibitor (e.g., any of the JAK1 inhibitors described herein or known in the art).

Provided herein are methods of treating a subject having a cancer (e.g., any of the cancers described herein) that include: identifying a subject having a cancer cell that has dysregulation of an JAK1 gene, an JAK1 protein, or the expression or activity or level of the same; and administering to the identified subject (i) a therapeutically effective amount of a compound of Formula I or a pharmaceutically acceptable salt or solvate thereof and (ii) a therapeutically effective amount of an JAK1 inhibitor (e.g., any of the JAK1 inhibitors described herein or known in the art).

Provided herein are methods of treating a subject having a cancer (e.g., any of the cancers described herein) that has dysregulation of an JAK2 gene, an JAK2 protein, or the expression or activity or level of the same that include administering to the subject (i) a therapeutically effective amount of a compound of Formula I or a pharmaceutically acceptable salt or solvate thereof and (ii) a therapeutically effective amount of an JAK2 inhibitor (e.g., any of the JAK2 inhibitors described herein or known in the art).

Provided herein are methods of treating a subject having a cancer (e.g., any of the cancers described herein) that include: identifying a subject having a cancer cell that has dysregulation of an JAK2 gene, an JAK2 protein, or the expression or activity or level of the same; and administering to the identified subject (i) a therapeutically effective amount of a compound of Formula I or a pharmaceutically acceptable salt or solvate thereof and (ii) a therapeutically effective amount of an JAK2 inhibitor (e.g., any of the JAK2 inhibitors described herein or known in the art).

Provided herein are methods of treating a subject having a cancer (e.g., any of the cancers described herein) that has dysregulation of an JAK3 gene, an JAK3 protein, or the expression or activity or level of the same that include administering to the subject (i) a therapeutically effective amount of a compound of Formula I or a pharmaceutically acceptable salt or solvate thereof and (ii) a therapeutically effective amount of an JAK3 inhibitor (e.g., any of the JAK3 inhibitors described herein or known in the art).

Provided herein are methods of treating a subject having a cancer (e.g., any of the cancers described herein) that include: identifying a subject having a cancer cell that has dysregulation of an JAK3 gene, an JAK3 protein, or the expression or activity or level of the same; and administering to the identified subject (i) a therapeutically effective amount of a compound of Formula I or a pharmaceutically acceptable salt or solvate thereof and (ii) a therapeutically effective amount of an JAK3 inhibitor (e.g., any of the JAK3 inhibitors described herein or known in the art).

Provided herein are methods of treating a subject having a cancer (e.g., any of the cancers described herein) that has dysregulation of a Kit gene, a Kit protein, or the expression or activity or level of the same that include administering to the subject (i) a therapeutically effective amount of a compound of Formula I or a pharmaceutically acceptable salt or solvate thereof and (ii) a therapeutically effective amount of a Kit inhibitor (e.g., any of the EGFR inhibitors described herein or known in the art).

Provided herein are methods of treating a subject having a cancer (e.g., any of the cancers described herein) that include: identifying a subject having a cancer cell that has dysregulation of a Kit gene, a Kit protein, or the expression or activity or level of the same; and administering to the identified subject (i) a therapeutically effective amount of a compound of Formula I or a pharmaceutically acceptable salt or solvate thereof and (ii) a therapeutically effective amount of a Kit inhibitor (e.g., any of the EGFR inhibitors described herein or known in the art).

Provided herein are methods of treating a subject having a cancer (e.g., any of the cancers described herein) that has dysregulation of a MEK gene, a MEK protein, or the expression or activity or level of the same that include administering to the subject (i) a therapeutically effective amount of a compound of Formula I or a pharmaceutically acceptable salt or solvate thereof and (ii) a therapeutically effective amount of a MEK inhibitor (e.g., any of the MEK inhibitors described herein or known in the art).

Provided herein are methods of treating a subject having a cancer (e.g., any of the cancers described herein) that include: identifying a subject having a cancer cell that has dysregulation of a MEK gene, a MEK protein, or the expression or activity or level of the same; and administering to the identified subject (i) a therapeutically effective amount of a compound of Formula I or a pharmaceutically acceptable salt or solvate thereof and (ii) a therapeutically effective amount of a MEK inhibitor (e.g., any of the MEK inhibitors described herein or known in the art).

Provided herein are methods of treating a subject having a cancer (e.g., any of the cancers described herein) that has dysregulation of a MET gene, a MET protein, or the expression or activity or level of the same that include administering to the subject (i) a therapeutically effective amount of a compound of Formula I or a pharmaceutically acceptable salt or solvate thereof and (ii) a therapeutically effective amount of a MET inhibitor (e.g., any of the MET inhibitors described herein or known in the art).

Provided herein are methods of treating a subject having a cancer (e.g., any of the cancers described herein) that include: identifying a subject having a cancer cell that has dysregulation of a MET gene, a MET protein, or the expression or activity or level of the same; and administering to the identified subject (i) a therapeutically effective amount of a compound of Formula I or a pharmaceutically acceptable salt or solvate thereof and (ii) a therapeutically effective amount of a MET inhibitor (e.g., any of the MET inhibitors described herein or known in the art).

Provided herein are methods of treating a subject having a cancer (e.g., any of the cancers described herein) that has dysregulation of a mTOR gene, a mTOR protein, or the expression or activity or level of the same that include administering to the subject (i) a therapeutically effective amount of a compound of Formula I or a pharmaceutically acceptable salt or solvate thereof and (ii) a therapeutically effective amount of a mTOR inhibitor (e.g., any of the mTOR inhibitors described herein or known in the art).

Provided herein are methods of treating a subject having a cancer (e.g., any of the cancers described herein) that include: identifying a subject having a cancer cell that has dysregulation of a mTOR gene, a mTOR protein, or the expression or activity or level of the same; and administering to the identified subject (i) a therapeutically effective amount of a compound of Formula I or a pharmaceutically acceptable salt or solvate thereof and (ii) a therapeutically effective amount of a mTOR inhibitor (e.g., any of the mTOR inhibitors described herein or known in the art).

Provided herein are methods of treating a subject having a cancer (e.g., any of the cancers described herein) that has dysregulation of a PDGFRα gene, a PDGFRα protein, or the expression or activity or level of the same that include administering to the subject (i) a therapeutically effective amount of a compound of Formula I or a pharmaceutically acceptable salt or solvate thereof and (ii) a therapeutically effective amount of a PDGFRα inhibitor (e.g., any of the PDGFRα inhibitors described herein or known in the art).

Provided herein are methods of treating a subject having a cancer (e.g., any of the cancers described herein) that include: identifying a subject having a cancer cell that has dysregulation of a PDGFRα gene, a PDGFRα protein, or the expression or activity or level of the same; and administering to the identified subject (i) a therapeutically effective amount of a compound of Formula I or a pharmaceutically acceptable salt or solvate thereof and (ii) a therapeutically effective amount of a PDGFRα inhibitor (e.g., any of the PDGFRα inhibitors described herein or known in the art).

Provided herein are methods of treating a subject having a cancer (e.g., any of the cancers described herein) that has dysregulation of a PDGFRβ gene, a PDGFRβ protein, or the expression or activity or level of the same that include administering to the subject (i) a therapeutically effective amount of a compound of Formula I or a pharmaceutically acceptable salt or solvate thereof and (ii) a therapeutically effective amount of a PDGFRβ inhibitor (e.g., any of the PDGFRβ inhibitors described herein or known in the art).

Provided herein are methods of treating a subject having a cancer (e.g., any of the cancers described herein) that include: identifying a subject having a cancer cell that has dysregulation of a PDGFRβ gene, a PDGFRβ protein, or the expression or activity or level of the same; and administering to the identified subject (i) a therapeutically effective amount of a compound of Formula I or a pharmaceutically acceptable salt or solvate thereof and (ii) a therapeutically effective amount of a PDGFRβ inhibitor (e.g., any of the PDGFRβ inhibitors described herein or known in the art).

Provided herein are methods of treating a subject having a cancer (e.g., any of the cancers described herein) that has dysregulation of a PI3K gene, a PI3K protein, or the expression or activity or level of the same that include administering to the subject (i) a therapeutically effective amount of a compound of Formula I or a pharmaceutically acceptable salt or solvate thereof and (ii) a therapeutically effective amount of a PI3K inhibitor (e.g., any of the PI3K inhibitors described herein or known in the art).

Provided herein are methods of treating a subject having a cancer (e.g., any of the cancers described herein) that include: identifying a subject having a cancer cell that has dysregulation of a PI3K gene, a PI3K protein, or the expression or activity or level of the same; and administering to the identified subject (i) a therapeutically effective amount of a compound of Formula I or a pharmaceutically acceptable salt or solvate thereof and (ii) a therapeutically effective amount of a PI3K inhibitor (e.g., any of the PI3K inhibitors described herein or known in the art).

Provided herein are methods of treating a subject having a cancer (e.g., any of the cancers described herein) that has dysregulation of a RAF gene, a RAF protein, or the expression or activity or level of the same that include administering to the subject (i) a therapeutically effective amount of a compound of Formula I or a pharmaceutically acceptable salt or solvate thereof and (ii) a therapeutically effective amount of a RAF inhibitor (e.g., any of the RAF inhibitors described herein or known in the art).

Provided herein are methods of treating a subject having a cancer (e.g., any of the cancers described herein) that include: identifying a subject having a cancer cell that has dysregulation of a RAF gene, a RAF protein, or the expression or activity or level of the same; and administering to the identified subject (i) a therapeutically effective amount of a compound of Formula I or a pharmaceutically acceptable salt or solvate thereof and (ii) a therapeutically effective amount of a RAF inhibitor (e.g., any of the RAF inhibitors described herein or known in the art).

Provided herein are methods of treating a subject having a cancer (e.g., any of the cancers described herein) that has dysregulation of a RAS gene, a RAS protein, or the expression or activity or level of the same that include administering to the subject (i) a therapeutically effective amount of a compound of Formula I or a pharmaceutically acceptable salt or solvate thereof and (ii) a therapeutically effective amount of a RAS inhibitor (e.g., any of the RAS inhibitors described herein or known in the art).

Provided herein are methods of treating a subject having a cancer (e.g., any of the cancers described herein) that include: identifying a subject having a cancer cell that has dysregulation of a RAS gene, a RAS protein, or the expression or activity or level of the same; and administering to the identified subject (i) a therapeutically effective amount of a compound of Formula I or a pharmaceutically acceptable salt or solvate thereof and (ii) a therapeutically effective amount of a RAS inhibitor (e.g., any of the RAS inhibitors described herein or known in the art).

Provided herein are methods of treating a subject having a cancer (e.g., any of the cancers described herein) that has dysregulation of a RET gene, a RET protein, or the expression or activity or level of the same that include administering to the subject (i) a therapeutically effective amount of a compound of Formula I or a pharmaceutically acceptable salt or solvate thereof and (ii) a therapeutically effective amount of a RET inhibitor (e.g., any of the RET inhibitors described herein or known in the art).

Provided herein are methods of treating a subject having a cancer (e.g., any of the cancers described herein) that include: identifying a subject having a cancer cell that has dysregulation of a RET gene, a RET protein, or the expression or activity or level of the same; and administering to the identified subject (i) a therapeutically effective amount of a compound of Formula I or a pharmaceutically acceptable salt or solvate thereof and (ii) a therapeutically effective amount of a RET inhibitor (e.g., any of the RET inhibitors described herein or known in the art).

Provided herein are methods of treating a subject having a cancer (e.g., any of the cancers described herein) that has dysregulation of a ROS1 gene, a ROS1 protein, or the expression or activity or level of the same that include administering to the subject (i) a therapeutically effective amount of a compound of Formula I or a pharmaceutically acceptable salt or solvate thereof and (ii) a therapeutically effective amount of a ROS1 inhibitor (e.g., any of the ROS1 inhibitors described herein or known in the art).

Provided herein are methods of treating a subject having a cancer (e.g., any of the cancers described herein) that include: identifying a subject having a cancer cell that has dysregulation of a ROS1 gene, a ROS1 protein, or the expression or activity or level of the same; and administering to the identified subject (i) a therapeutically effective amount of a compound of Formula I or a pharmaceutically acceptable salt or solvate thereof and (ii) a therapeutically effective amount of a ROS1 inhibitor (e.g., any of the ROS1 inhibitors described herein or known in the art).

Provided herein are methods of treating a subject having a cancer (e.g., any of the cancers described herein) that has dysregulation of a trkA gene, a trkA protein, or the expression or activity or level of the same that include administering to the subject (i) a therapeutically effective amount of a compound of Formula I or a pharmaceutically acceptable salt or solvate thereof and (ii) a therapeutically effective amount of a trkA inhibitor (e.g., any of the trkA inhibitors described herein or known in the art).

Provided herein are methods of treating a subject having a cancer (e.g., any of the cancers described herein) that include: identifying a subject having a cancer cell that has dysregulation of a trkA gene, a trkA protein, or the expression or activity or level of the same; and administering to the identified subject (i) a therapeutically effective amount of a compound of Formula I or a pharmaceutically acceptable salt or solvate thereof and (ii) a therapeutically effective amount of a trkA inhibitor (e.g., any of the trkA inhibitors described herein or known in the art).

Provided herein are methods of treating a subject having a cancer (e.g., any of the cancers described herein) that has dysregulation of a trkB gene, a trkB protein, or the expression or activity or level of the same that include administering to the subject (i) a therapeutically effective amount of a compound of Formula I or a pharmaceutically acceptable salt or solvate thereof and (ii) a therapeutically effective amount of a trkB inhibitor (e.g., any of the trkB inhibitors described herein or known in the art).

Provided herein are methods of treating a subject having a cancer (e.g., any of the cancers described herein) that include: identifying a subject having a cancer cell that has dysregulation of a trkB gene, a trkB protein, or the expression or activity or level of the same; and administering to the identified subject (i) a therapeutically effective amount of a compound of Formula I or a pharmaceutically acceptable salt or solvate thereof and (ii) a therapeutically effective amount of a trkB inhibitor (e.g., any of the trkB inhibitors described herein or known in the art).

Provided herein are methods of treating a subject having a cancer (e.g., any of the cancers described herein) that has dysregulation of a trkC gene, a trkC protein, or the expression or activity or level of the same that include administering to the subject (i) a therapeutically effective amount of a compound of Formula I or a pharmaceutically acceptable salt or solvate thereof and (ii) a therapeutically effective amount of a trkC inhibitor (e.g., any of the trkC inhibitors described herein or known in the art).

Provided herein are methods of treating a subject having a cancer (e.g., any of the cancers described herein) that include: identifying a subject having a cancer cell that has dysregulation of a trkC gene, a trkC protein, or the expression or activity or level of the same; and administering to the identified subject (i) a therapeutically effective amount of a compound of Formula I or a pharmaceutically acceptable salt or solvate thereof and (ii) a therapeutically effective amount of a trkC inhibitor (e.g., any of the trkC inhibitors described herein or known in the art).

Provided herein are methods of treating a subject having a cancer (e.g., any of the cancers described herein) that has dysregulation of a VEGFR-1 gene, a VEGFR-1 protein, or the expression or activity or level of the same that include administering to the subject (i) a therapeutically effective amount of a compound of Formula I or a pharmaceutically acceptable salt or solvate thereof and (ii) a therapeutically effective amount of a VEGFR-1 inhibitor (e.g., any of the VEGFR-1 inhibitors described herein or known in the art).

Provided herein are methods of treating a subject having a cancer (e.g., any of the cancers described herein) that include: identifying a subject having a cancer cell that has dysregulation of a VEGFR-1 gene, a VEGFR-1 protein, or the expression or activity or level of the same; and administering to the identified subject (i) a therapeutically effective amount of a compound of Formula I or a pharmaceutically acceptable salt or solvate thereof and (ii) a therapeutically effective amount of a VEGFR-1 inhibitor (e.g., any of the VEGFR-1 inhibitors described herein or known in the art).

Provided herein are methods of treating a subject having a cancer (e.g., any of the cancers described herein) that has dysregulation of a VEGFR-2 gene, a VEGFR-2 protein, or the expression or activity or level of the same that include administering to the subject (i) a therapeutically effective amount of a compound of Formula I or a pharmaceutically acceptable salt or solvate thereof and (ii) a therapeutically effective amount of a VEGFR-2 inhibitor (e.g., any of the VEGFR-2 inhibitors described herein or known in the art).

Provided herein are methods of treating a subject having a cancer (e.g., any of the cancers described herein) that include: identifying a subject having a cancer cell that has dysregulation of a VEGFR-2 gene, a VEGFR-2 protein, or the expression or activity or level of the same; and administering to the identified subject (i) a therapeutically effective amount of a compound of Formula I or a pharmaceutically acceptable salt or solvate thereof and (ii) a therapeutically effective amount of a VEGFR-2 inhibitor (e.g., any of the VEGFR-2 inhibitors described herein or known in the art).

Provided herein are methods of treating a subject having a cancer (e.g., any of the cancers described herein) that has dysregulation of a VEGFR-3 gene, a VEGFR-3 protein, or the expression or activity or level of the same that include administering to the subject (i) a therapeutically effective amount of a compound of Formula I or a pharmaceutically acceptable salt or solvate thereof and (ii) a therapeutically effective amount of a VEGFR-3 inhibitor (e.g., any of the VEGFR-3 inhibitors described herein or known in the art).

Provided herein are methods of treating a subject having a cancer (e.g., any of the cancers described herein) that include: identifying a subject having a cancer cell that has dysregulation of a VEGFR-3 gene, a VEGFR-3 protein, or the expression or activity or level of the same; and administering to the identified subject (i) a therapeutically effective amount of a compound of Formula I or a pharmaceutically acceptable salt or solvate thereof and (ii) a therapeutically effective amount of a VEGFR-3 inhibitor (e.g., any of the VEGFR-3 inhibitors described herein or known in the art).

Provided herein are methods of treating a subject having a cancer (e.g., any of the cancers described herein) that has dysregulation of an aromatase gene, an aromatase protein, or the expression or activity or level of the same that include administering to the subject (i) a therapeutically effective amount of a compound of Formula I or a pharmaceutically acceptable salt or solvate thereof and (ii) a therapeutically effective amount of an aromatase inhibitor (e.g., any of the aromatase inhibitors described herein or known in the art).

Provided herein are methods of treating a subject having a cancer (e.g., any of the cancers described herein) that include: identifying a subject having a cancer cell that has dysregulation of an aromatase gene, an aromatase protein, or the expression or activity or level of the same; and administering to the identified subject (i) a therapeutically effective amount of a compound of Formula I or a pharmaceutically acceptable salt or solvate thereof and (ii) a therapeutically effective amount of an aromatase inhibitor (e.g., any of the aromatase inhibitors described herein or known in the art).

Provided herein are methods of treating a subject having a cancer (e.g., any of the cancers described herein) that has dysregulation of an EHMT2 gene, an EHMT2 protein, or the expression or activity or level of the same that include administering to the subject (i) a therapeutically effective amount of a compound of Formula I or a pharmaceutically acceptable salt or solvate thereof and (ii) a therapeutically effective amount of an EHMT2 inhibitor (e.g., any of the EHMT2 inhibitors described herein or known in the art).

Provided herein are methods of treating a subject having a cancer (e.g., any of the cancers described herein) that include: identifying a subject having a cancer cell that has dysregulation of an EHMT2 gene, an EHMT2 protein, or the expression or activity or level of the same; and administering to the identified subject (i) a therapeutically effective amount of a compound of Formula I or a pharmaceutically acceptable salt or solvate thereof and (ii) a therapeutically effective amount of an EHMT2 inhibitor (e.g., any of the EHMT2 inhibitors described herein or known in the art).

Provided herein are methods of treating a subject having a cancer (e.g., any of the cancers described herein) that has dysregulation of an RAC1 gene, an RAC1 protein, or the expression or activity or level of the same that include administering to the subject (i) a therapeutically effective amount of a compound of Formula I or a pharmaceutically acceptable salt or solvate thereof and (ii) a therapeutically effective amount of an RAC1 inhibitor (e.g., any of the RAC1 inhibitors described herein or known in the art).

Provided herein are methods of treating a subject having a cancer (e.g., any of the cancers described herein) that include: identifying a subject having a cancer cell that has dysregulation of an RAC1 gene, an RAC1 protein, or the expression or activity or level of the same; and administering to the identified subject (i) a therapeutically effective amount of a compound of Formula I or a pharmaceutically acceptable salt or solvate thereof and (ii) a therapeutically effective amount of an RAC1 inhibitor (e.g., any of the RAC1 inhibitors described herein or known in the art).

Provided herein are methods of treating a subject having a cancer (e.g., any of the cancers described herein) that has dysregulation of an SOS1 gene, an SOS1 protein, or the expression or activity or level of the same that include administering to the subject (i) a therapeutically effective amount of a compound of Formula I or a pharmaceutically acceptable salt or solvate thereof and (ii) a therapeutically effective amount of an SOS1 inhibitor (e.g., any of the SOS1 inhibitors described herein or known in the art).

Provided herein are methods of treating a subject having a cancer (e.g., any of the cancers described herein) that include: identifying a subject having a cancer cell that has dysregulation of an SOS1 gene, an SOS1 protein, or the expression or activity or level of the same; and administering to the identified subject (i) a therapeutically effective amount of a compound of Formula I or a pharmaceutically acceptable salt or solvate thereof and (ii) a therapeutically effective amount of an SOS1 inhibitor (e.g., any of the SOS1 inhibitors described herein or known in the art).

The phrase "dysregulation of a second kinase gene, a second kinase protein, or the expression or activity or level of any of the same" refers to a genetic mutation (e.g., a chromosomal translocation that results in the expression of a fusion protein including a second kinase kinase domain and a fusion partner, a mutation in a second kinase gene that results in the expression of a second kinase protein that includes a deletion of at least one amino acid as compared to a wildtype second kinase protein, a mutation in a second kinase gene that results in the expression of a second kinase protein with one or more point mutations as compared to a wildtype second kinase protein, a mutation in a second kinase gene that results in the expression of a second kinase protein with at least one inserted amino acid as compared to a wildtype second kinase protein, a gene duplication that results in an increased level of second kinase protein in a cell, or a mutation in a regulatory sequence (e.g., a promoter and/or enhancer) that results in an increased level of second kinase protein in a cell), an alternative spliced version of a second kinase mRNA that results in a second kinase protein having a deletion of at least one amino acid in the second kinase protein as compared to the wild-type second kinase protein), or increased expression (e.g., increased levels) of a wildtype second kinase protein in a mammalian cell due to aberrant cell signaling and/or dysregulated autocrine/paracrine signaling (e.g., as compared to a control non-cancerous cell). As another example, a dysregulation of a second kinase gene, a second kinase protein, or expression or activity, or level of any of the same, can be a mutation in a second kinase gene that encodes a second kinase protein that is constitutively active or has increased activity as compared to a protein encoded by a second kinase gene that does not include the mutation. For example, a dysregulation of a second kinase gene, a second kinase protein, or expression or activity, or level of any of the same, can be the result of a gene or chromosome translocation which results in the expression of a fusion protein that contains a first portion of a second kinase protein that includes a functional kinase domain, and a second portion of a partner protein (i.e., that is not second kinase). In some examples, dysregulation of a second kinase gene, a second kinase protein, or expression or activity or level of any of the same can be a result of a gene translocation of one second kinase gene with another non-second kinase gene. When both a first and a second kinase are present in a method provided herein, the first and second kinase are different. In some embodiments, a second kinase is selected from the group consisting ALK, AKT, aurora, AXL, BRAF, CDK, EGFR, ERK, FGFR1, FGFR2, FGFR3, FGFR4, FLT3, HER2 (also called erbB-2), HER3 (also called erbB-3), HER4 (also called erbB-4), IGFR, JAK1, JAK2, JAK3, Kit, MEK, MET, mTOR, PDGFRα, PDGFRβ, PI3K, RAF, RAS, RET, ROS1, trkA, trkB, trkC, VEGFR-1, VEGFR-2, VEGFR-3.

The phrase "dysregulation of an ALK gene, an ALK protein, or the expression or activity or level of any of the same" refers to a genetic mutation (e.g., a chromosomal translocation that results in the expression of a fusion protein including an ALK kinase domain and a fusion partner, a mutation in an ALK gene that results in the expression an ALK protein that includes a deletion of at least one amino acid as compared to a wildtype ALK protein, a mutation in an ALK gene that results in the expression of an ALK protein with one or more point mutations as compared to a wildtype ALK protein, a mutation in an ALK gene that results in the expression of an ALK protein with at least one inserted amino acid as compared to a wildtype ALK protein, a gene duplication that results in an increased level of ALK protein in a cell, or a mutation in a regulatory sequence (e.g., a promoter and/or enhancer) that results in an increased level of ALK protein in a cell), an alternative spliced version of an ALK mRNA that results in an ALK protein having a deletion of at least one amino acid in the ALK protein as compared to the wild-type ALK protein), or increased expression (e.g., increased levels) of a wildtype ALK protein in a mammalian cell due to aberrant cell signaling and/or dysregulated autocrine/paracrine signaling (e.g., as compared to a control non-cancerous cell). As another example, a dysregulation of an ALK gene, an ALK protein, or expression or activity, or level of any of the same, can be a mutation in an ALK gene that encodes an ALK protein that is constitutively active or has increased activity as compared to a protein encoded by an ALK gene that does not include the mutation. For example, a dysregulation of an ALK gene, an ALK protein, or expression or activity, or level of any of the same, can be the result of a gene or chromosome translocation which results in the expression of a fusion protein that contains a first portion of an ALK protein that includes a functional kinase domain, and a second portion of a partner protein (i.e., that is not ALK). In some examples, dysregulation of an ALK gene, an ALK protein, or expression or activity or level of any of the same can be a result of a gene translocation of one ALK gene with another non-ALK gene.

Non-limiting examples of an ALK inhibitor include crizotinib (Xalkori), ceritinib (Zykadia), alectinib (Alecensa), dalantercept, ACE-041 (Brigatinib) (AP26113), entrectinib (NMS-E628), PF-06463922 (Pfizer), TSR-011 (Tesaro), CEP-37440 (Teva), CEP-37440 (Teva), X-396 (Xcovery), and ASP-3026 (Astellas). Additional examples of an ALK inhibitor are known in the art.

The phrase "dysregulation of an AKT gene, an AKT protein, or the expression or activity or level of any of the same" refers to a genetic mutation (e.g., a chromosomal translocation that results in the expression of a fusion protein including an AKT kinase domain and a fusion partner, a mutation in an AKT gene that results in the expression an AKT protein that includes a deletion of at least one amino acid as compared to a wildtype AKT protein, a mutation in an AKT gene that results in the expression of an AKT protein with one or more point mutations as compared to a wildtype AKT protein, a mutation in an AKT gene that results in the expression of an AKT protein with at least one inserted amino acid as compared to a wildtype AKT protein, a gene duplication that results in an increased level of AKT protein in a cell, or a mutation in a regulatory sequence (e.g., a promoter and/or enhancer) that results in an increased level of AKT protein in a cell), an alternative spliced version of an AKT mRNA that results in an AKT protein having a deletion of at least one amino acid in the AKT protein as compared to the wild-type AKT protein), or increased expression (e.g., increased levels) of a wildtype AKT protein in a mammalian cell due to aberrant cell signaling and/or dysregulated autocrine/paracrine signaling (e.g., as compared to a control non-cancerous cell). As another example, a dysregulation of an AKT gene, an AKT protein, or expression or activity, or level of any of the same, can be a mutation in an AKT gene that encodes an AKT protein that is constitutively active or has increased activity as compared to a protein encoded by an AKT gene that does not include the mutation. For example, a dysregulation of an AKT gene, an AKT protein, or expression or activity, or level of any of the same, can be the result of a gene or chromosome translocation which results in the expression of a fusion protein that contains a first portion of an AKT protein that includes a functional kinase domain, and a second portion of a partner protein (i.e., that is not AKT). In some examples, dysregulation of an AKT gene, an AKT protein, or expression or activity or level of any of the same can be a result of a gene translocation of one AKT gene with another non-AKT gene.

Non-limiting examples of an AKT inhibitor include 2-[4-(2-aminoprop-2-yl)phenyl]-3-phenylquinoxaline; 3-oxo-tirucallic acid; A-443654; A-674563; afuresertib; API-1; ARQ092; AT13148; AT7867; AZD5363; BAY 1125976; boc-Phe-vinyl ketone; CCT128930; DC120; DM-PIT-1; edelfosine; erucylphophocholine; erufosine; GSK2141795; GSK690693; H-89; ipatasertib (GDC-0068, RG7440); lactoquinomycin; miltefosine (IMPADIVO®); MK-2206; N-(4-(5-(3-acetamidophenyl)-2-(2-aminopyridin-3-yl)-3H-imidazo[4,5-b]pyridin-3-yl)benzyl)-3-fluorobenzamide; NL-71-101; ONC201; OSU-A9; perifosine (D-21266); PH-316; PHT-427; PIT-1; SR13668; TCN; TCN-P; triciribine (Triciribine Phosphate Monohydrate); uprosertib; and wortmannin. Additional examples of an AKT inhibitor are known in the art.

The phrase "dysregulation of an aurora gene, an aurora protein, or the expression or activity or level of any of the same" refers to a genetic mutation (e.g., a chromosomal translocation that results in the expression of a fusion protein including an aurora kinase domain and a fusion partner, a mutation in an aurora gene that results in the expression an aurora protein that includes a deletion of at least one amino acid as compared to a wildtype aurora protein, a mutation in an aurora gene that results in the expression of an aurora protein with one or more point mutations as compared to a wildtype aurora protein, a mutation in an aurora gene that results in the expression of an aurora protein with at least one inserted amino acid as compared to a wildtype aurora protein, a gene duplication that results in an increased level of aurora protein in a cell, or a mutation in a regulatory sequence (e.g., a promoter and/or enhancer) that results in an increased level of aurora protein in a cell), an alternative spliced version of an aurora mRNA that results in an aurora protein having a deletion of at least one amino acid in the aurora protein as compared to the wild-type aurora protein), or increased expression (e.g., increased levels) of a wildtype aurora protein in a mammalian cell due to aberrant cell signaling and/or dysregulated autocrine/paracrine signaling (e.g., as compared to a control non-cancerous cell). As another example, a dysregulation of an aurora gene, an aurora protein, or expression or activity, or level of any of the same, can be a mutation in an aurora gene that encodes an aurora protein that is constitutively active or has increased activity as compared to a protein encoded by an aurora gene that does not include the mutation. For example, a dysregulation of an aurora gene, an aurora protein, or expression or activity, or level of any of the same, can be the result of a gene or chromosome translocation which results in the expression of a fusion protein that contains a first portion of an aurora protein that includes a functional kinase domain, and a second portion of a partner protein (i.e., that is not aurora). In some examples, dysregulation of an aurora gene, an aurora protein, or expression or activity or level of any of the same can be a result of a gene translocation of one aurora gene with another non-aurora gene.

Non-limiting examples of an aurora inhibitor include 4-[[9-Chloro-7-(2,6-difluorophenyl)-5H-pyrimido[5,4-d][2]benzazepin-2-yl]amino]-benzoic acid, CAS 869363-13-3); alisertib (MLN8237); AMG900; AT9283 (N-cyclopropyl-N'-[3-[6-(4-morpholinylmethyl)-1H-benzimidazol-2-yl]-1H-pyrazol-4-yl]-urea); barasertib (AZD1152); cenisertib (R-763); CYC116 (4-(2-Amino-4-methyl-5-thiazolyl)-N-[4-(4-morpholinyl)phenyl]-2-pyrimidinamine, CAS 693228-63-6); danusertib (PHA-739358); JNJ-770621; MLN8054 (N-{2-[6-(4-Cyclobutylamino-5-trifluoromethyl-pyrimidine-2-ylamino)-(1S,4R)-1,2,3,4-tetrahydro-1,4-epiazano-naphthalen-9-yl]-2-oxo-ethyl}-acetamide) (PF-03814735); PHA-680632; tozasertib (VX680 or MK-0457, CAS 639089-54-6); and ZM447439 (N-[4-[[6-Methoxy-7-[3-(4-morpholinyl)propoxy]-4-quinazolinyl]amino]phenyl]benzamide, CAS 331771-20-1). Additional examples of an aurora inhibitor are known in the art.

The phrase "dysregulation of an AXL gene, an AXL protein, or the expression or activity or level of any of the same" refers to a genetic mutation (e.g., a chromosomal translocation that results in the expression of a fusion protein including an AXL kinase domain and a fusion partner, a mutation in an AXL gene that results in the expression an AXL protein that includes a deletion of at least one amino acid as compared to a wildtype AXL protein, a mutation in an AXL gene that results in the expression of an AXL protein with one or more point mutations as compared to a wildtype AXL protein, a mutation in an AXL gene that results in the expression of an AXL protein with at least one inserted amino acid as compared to a wildtype AXL protein, a gene duplication that results in an increased level of AXL protein in a cell, or a mutation in a regulatory sequence (e.g., a promoter and/or enhancer) that results in an increased level of AXL protein in a cell), an alternative spliced version of an AXL mRNA that results in an AXL protein having a deletion of at least one amino acid in the AXL protein as compared to the wild-type AXL protein), or increased expression (e.g., increased levels) of a wildtype AXL protein in a mammalian cell due to aberrant cell signaling and/or dysregulated autocrine/paracrine signaling (e.g., as compared to a control non-cancerous cell). As another example, a dysregulation of an AXL gene, an AXL protein, or expression or activity, or level of any of the same, can be a mutation in an AXL gene that encodes an AXL protein that is constitutively active or has increased activity as compared to a protein encoded by an AXL gene that does not include the mutation. For example, a dysregulation of an AXL gene, an AXL protein, or expression or activity, or level of any of the same, can be the result of a gene or chromosome translocation which results in the expression of a fusion protein that contains a first portion of an AXL protein that includes a functional kinase domain, and a second portion of a partner protein (i.e., that is not AXL). In some examples, dysregulation of an AXL gene, an AXL protein, or expression or activity or level of any of the same can be a result of a gene translocation of one AXL gene with another non-AXL gene.

Non-limiting examples of an AXL inhibitor include bemcetinib (R428, BGB324); amuvatinib (MP470); cabozantinib; DCC-2036; DS-1205; gilteritinib (ASP2215); NPS-1034; RXDX-106; and TP-0903. Additional examples of an AXL inhibitor are known in the art.

The phrase "dysregulation of a BRAF gene, a BRAF protein, or the expression or activity or level of any of the same" refers to a genetic mutation (e.g., a chromosomal translocation that results in the expression of a fusion protein including a BRAF kinase domain and a fusion partner, a mutation in a BRAF gene that results in the expression of a BRAF protein that includes a deletion of at least one amino acid as compared to a wildtype BRAF protein, a mutation in a BRAF gene that results in the expression of a BRAF protein with one or more point mutations as compared to a wildtype BRAF protein, a mutation in a BRAF gene that results in the expression of a BRAF protein with at least one inserted amino acid as compared to a wildtype BRAF protein, a gene duplication that results in an increased level of BRAF protein in a cell, or a mutation in a regulatory sequence (e.g., a promoter and/or enhancer) that results in an increased level of BRAF protein in a cell), an alternative spliced version of a BRAF mRNA that results in a BRAF protein having a deletion of at least one amino acid in the BRAF protein as compared to the wild-type BRAF protein), or increased expression (e.g., increased levels) of a wildtype BRAF protein in a mammalian cell due to aberrant cell signaling and/or dysregulated autocrine/paracrine signaling (e.g., as compared to a control non-cancerous cell). As another example, a dysregulation of a BRAF gene, a BRAF protein, or expression or activity, or level of any of the same, can be a mutation in a BRAF gene that encodes a BRAF protein that is constitutively active or has increased activity as compared to a protein encoded by a BRAF gene that does not include the mutation. For example, a dysregulation of a BRAF gene, a BRAF protein, or expression or activity, or level of any of the same, can be the result of a gene or chromosome translocation which results in the expression of a fusion protein that contains a first portion of a BRAF protein that includes a functional kinase domain, and a second portion of a partner protein (i.e., that is not BRAF). In some examples, dysregulation of a BRAF gene, a BRAF protein, or expression or activity or level of any of the same can be a result of a gene translocation of one BRAF gene with another non-BRAF gene.

Non-limiting examples of a BRAF inhibitor include ((S)-2-{4-[3-(5-chloro-2-fluoro-3-methanesulfonylamino-phenyl)-1-isopropyl-1H-pyrazol-4-yl]-pyrimidin-2-ylamino}-1-methyl-ethyl)-carbamic acid methyl ester; BMS-908662 (Bristol-Meyers Squibb); dabrafenib; GDC-0879; GSK2118436 (GlaxoSmithKline); LGX818 (Novartis); PLX3603 (Hofmann-LaRoche); PLX-4720; RAF265 (Novartis); RO5185426 (Hofmann-LaRoche); sorafenib tosylate; and vemurafenib (also called RG7204 or PLX4032). Additional examples of a BRAF inhibitor are known in the art.

The phrase "dysregulation of a CDK gene, a CDK protein, or the expression or activity or level of any of the same" refers to a genetic mutation (e.g., a chromosomal translocation that results in the expression of a fusion protein including a CDK kinase domain and a fusion partner, a mutation in a CDK gene that results in the expression of a CDK protein that includes a deletion of at least one amino acid as compared to a wildtype CDK protein, a mutation in a CDK gene that results in the expression of a CDK protein with one or more point mutations as compared to a wildtype CDK protein, a mutation in a CDK gene that results in the expression of a CDK protein with at least one inserted amino acid as compared to a wildtype CDK protein, a gene duplication that results in an increased level of CDK protein in a cell, or a mutation in a regulatory sequence (e.g., a promoter and/or enhancer) that results in an increased level of CDK protein in a cell), an alternative spliced version of a CDK mRNA that results in a CDK protein having a deletion of at least one amino acid in the CDK protein as compared to the wild-type CDK protein), or increased expression (e.g., increased levels) of a wildtype CDK protein in a mammalian cell due to aberrant cell signaling and/or dysregulated autocrine/paracrine signaling (e.g., as compared to a control non-cancerous cell). As another example, a dysregulation of a CDK gene, a CDK protein, or expression or activity, or level of any of the same, can be a mutation in a CDK gene that encodes a CDK protein that is constitutively active or has increased activity as compared to a protein encoded by a CDK gene that does not include the mutation. For example, a dysregulation of a CDK gene, a CDK protein, or expression or activity, or level of any of the same, can be the result of a gene or chromosome translocation which results in the expression of a fusion protein that contains a first portion of a CDK protein that includes a functional kinase domain, and a second portion of a partner protein (i.e., that is not CDK). In some examples, dysregulation of a CDK gene, a CDK protein, or expression or activity or level of any of the same can be a result of a gene translocation of one CDK gene with another non-CDK gene.

Non-limiting examples of a CDK inhibitor include abemaciclib (LY2835219); AG-024322 (5-[3-(4,6-Difluoro-1H-benzimidazol-2-yl)-1H-indazol-5-yl]-N-ethyl-4-methyl-3-pyridinemethanamine, CAS 837364-57-5); Aloisine A; alvocidib (2-(2-chlorophenyl)-5,7-dihydroxy-8-[(3S,4R)-3-hydroxy-1-methyl-4-piperidinyl]-4-chromenone, flavopiridol, HMR-1275); AT7519 (4-(2,6-Dichlorobenzoylamino)-1H-pyrazole-3-carboxylic acid N-(piperidin-4-yl)amide, CAS 844442-38-2); AZD5438 (4-[2-Methyl-1-(1-methylethyl)-1H-imidazol-5-yl]-N-[4-(methylsulfonyl)phenyl]-2-pyrimidinamine, CAS 602306-29-6); BAY 10000394 U2R, 3R)-3-[[2-[[3-[[S(R)]—S-cyclopropylsulfonimidoyl]-phenyl]amino]-5-(trifluoromethyl)-4-pyrimidinyl]oxy]-2-butanol); BMS 387032 (N-[5-[[(5-tert-Butyloxazol-2-yl) methyl]thio]thiazol-2-yl]piperidine-4-carboxamide, CAS 345627-80-7); Dinaciclib (SCH-727965); G1T38; Indisulam (E7070); JNJ-770621; P276-000 (2-(2-Chlorophenyl)-5,7-dihydroxy-8-[(2R,3S)-2-(hydroxymethyl)-1-methyl-3-pyrrolidinyl]-4H-1-benzopyran-4-one, hydrochloride, CAS 920113-03-7); palbociclib (PD0332991, 6-acetyl-8-cyclopentyl-5-methyl-2-{[5-(1-piperazinyl)-2-pyridinyl]amino}pyrido[2,3-d]pyrimidin-7(8H)-one); ribociclib (LEE011, 7-cyclopentyl-N,N-dimethyl-2-((5-(piperazin-1-yl)pyridin-2-yl)amino)-7H-pyrrolo[2,3-d]pyrimidine-6-carboxamide); Seliciclib (roscovitine or CYC202); trilaciclib (G1T28); and voruciclib. Additional examples of a CDK inhibitor are known in the art.

The phrase "dysregulation of an EGFR gene, an EGFR protein, or the expression or activity or level of any of the same" refers to a genetic mutation (e.g., a chromosomal translocation that results in the expression of a fusion protein including an EGFR kinase domain and a fusion partner, a mutation in an EGFR gene that results in the expression of an EGFR protein that includes a deletion of at least one amino acid as compared to a wildtype EGFR protein, a mutation in an EGFR gene that results in the expression of an EGFR protein with one or more point mutations as compared to a wildtype EGFR protein, a mutation in an EGFR gene that results in the expression of an EGFR protein with at least one inserted amino acid as compared to a wildtype EGFR protein, a gene duplication that results in an increased level of EGFR protein in a cell, or a mutation in a regulatory sequence (e.g., a promoter and/or enhancer) that results in an increased level of EGFR protein in a cell), an alternative spliced version of a EGFR mRNA that results in an EGFR protein having a deletion of at least one amino acid in the EGFR protein as compared to the wild-type EGFR protein), or increased expression (e.g., increased levels) of a wildtype EGFR protein in a mammalian cell due to aberrant cell signaling and/or dysregulated autocrine/paracrine signaling (e.g., as compared to a control non-cancerous cell). As another example, a dysregulation of an EGFR gene, an EGFR protein, or expression or activity, or level of any of the same, can be a mutation in an EGFR gene that encodes an EGFR protein that is constitutively active or has increased activity as compared to a protein encoded by an EGFR gene that does not include the mutation. For example, a dysregulation of an EGFR gene, an EGFR protein, or expression or activity, or level of any of the same, can be the result of a gene or chromosome translocation which results in the expression of a fusion protein that contains a first portion of a EGFR protein that includes a functional kinase domain, and a second portion of a partner protein (i.e., that is not EGFR). In some examples, dysregulation of an EGFR gene, an EGFR protein, or expression or activity or level of any of the same can be a result of a gene translocation of one EGFR gene with another non-EGFR gene.

Non-limiting examples of an EGFR inhibitor include AC0010; AEE788; afatinib; AP26113; ASP8273; avitinib; AZD3759; BIBX-1382 (N8-(3-chloro-4-fluoro-phenyl)-N2-(1-methyl-piperidin-4-yl)-pyrimido[5,4-d]pyrimidine-2,8-diamine); BMS-690514; brigatinib; brivanib; canertinib; Cap-701; CGP 59326A; CHMFL-EGFR-202; CL-387785; CUDC-101; dacomitinib; EA1045; EGF816; erlotinib; gefitinib (ZD1839); GNS-1481; GNS-1486; Gö6976; GW-2016 (GW-572016); HS-10296; icotinib; KU004; lapatinib; nazartinib; neratinib; olmutinib (HM61713, BI 1482694); osimertinib (AZD9291); pelitinib (EKB-569; (E)-N-[4-(3-chloro-4-fluoroanilino)-3-cyano-7-ethoxyquinolin-6-yl]-4-(dimethylamino)but-2-enamide); PD156393; PD 183805 (CI 1033, N-[4-(3-chloro-4-fluoroanilino)-7-(3-morpholin-4-ylpropoxy)quinazolin-6-yl]prop-2-enamide); PF-06747775; PKC412; PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); poziotinib (HM781-36); pyrotinib (HTI-1001); rocilentinib (CO-1686); sapitinib; tyrphostin AG (AG1478); vandetanib; varlitinib; XL647; ZM 105180 ((6-amino-4-(3-methylphenyl-amino)-quinazoline); 7C3; ABX-EGF; cetuximab; depatuxizumab mafodotin (ABT-414); EMD55900; GA201 (RG7160); IMC-11F8; MAb 225 (ATCC CRL 8508); MAb 455 (ATCC CRL HB8507); MAb 528 (ATCC CRL 8509); MAb 579 (ATCC CRL HB 8506); mAb806; mAb806 (humanized); matuzumab (EMD7200); MDX-447; nimotuzumab; panitumumab; Pertuzumab; reshaped human 225 (H225); and zalutumumab. Additional examples of an EGFR inhibitor are known in the art.

The phrase "dysregulation of an ERK gene, an ERK protein, or the expression or activity or level of any of the same" refers to a genetic mutation (e.g., a chromosomal translocation that results in the expression of a fusion protein including an ERK kinase domain and a fusion partner, a mutation in an ERK gene that results in the expression of an ERK protein that includes a deletion of at least one amino acid as compared to a wildtype ERK protein, a mutation in an ERK gene that results in the expression of an ERK protein with one or more point mutations as compared to a wildtype ERK protein, a mutation in an ERK gene that results in the expression of an ERK protein with at least one inserted amino acid as compared to a wildtype ERK protein, a gene duplication that results in an increased level of ERK protein in a cell, or a mutation in a regulatory sequence (e.g., a promoter and/or enhancer) that results in an increased level of ERK protein in a cell), an alternative spliced version of a ERK mRNA that results in an ERK protein having a deletion of at least one amino acid in the ERK protein as compared to the wild-type ERK protein), or increased expression (e.g., increased levels) of a wildtype ERK protein in a mammalian cell due to aberrant cell signaling and/or dysregulated autocrine/paracrine signaling (e.g., as compared to a control non-cancerous cell). As another example, a dysregulation of an ERK gene, an ERK protein, or expression or activity, or level of any of the same, can be a mutation in an ERK gene that encodes an ERK protein that is constitutively active or has increased activity as compared to a protein encoded by an ERK gene that does not include the mutation. For example, a dysregulation of an ERK gene, an ERK protein, or expression or activity, or level of any of the same, can be the result of a gene or chromosome translocation which results in the expression of a fusion protein that contains a first portion of a ERK protein that includes a functional kinase domain, and a second portion of a partner protein (i.e., that is not ERK). In some examples, dysregulation of an ERK gene, an ERK protein, or expression or activity or level of any of the same can be a result of a gene translocation of one ERK gene with another non-ERK gene.

Non-limiting examples of an ERK inhibitor include 25-OH-D3-3-BE (B3CD, bromoacetoxycalcidiol); 5-7-Oxozeaenol; 5-iodotubercidin; AEZ-131 (AEZS-131); AEZS-136; ARRY-142886; ASN007; AZ-13767370; BAY 43-9006; BL-EI-001; CC-90003; FR148083; FR-180204; FRI-20 (ON-01060); GDC-0994 (RG-7482); KO-947; LTT-462; LY294002; LY-3214996; MK-8353 (SCH900353); ONC201; PD0325901; PD184352; PD98059; SB239063; SCH772984; SP600125; U0126; ulixertinib (BVD-523); VTX-11e; and wortmannin. Additional examples of an ERK inhibitor are known in the art.

The phrase "dysregulation of a FLT3 gene, a FLT3 protein, or the expression or activity or level of any of the same" refers to a genetic mutation (e.g., a chromosomal translocation that results in the expression of a fusion protein including a FLT3 kinase domain and a fusion partner, a mutation in a FLT3 gene that results in the expression of a FLT3 protein that includes a deletion of at least one amino acid as compared to a wildtype FLT3 protein, a mutation in a FLT3 gene that results in the expression of a FLT3 protein with one or more point mutations as compared to a wildtype FLT3 protein, a mutation in a FLT3 gene that results in the expression of a FLT3 protein with at least one inserted amino acid as compared to a wildtype FLT3 protein, a gene duplication that results in an increased level of FLT3 protein in a cell, or a mutation in a regulatory sequence (e.g., a promoter and/or enhancer) that results in an increased level of FLT3 protein in a cell), an alternative spliced version of a FLT3 mRNA that results in a FLT3 protein having a deletion of at least one amino acid in the FLT3 protein as compared to the wild-type FLT3 protein), or increased expression (e.g., increased levels) of a wildtype FLT3 protein in a mammalian cell due to aberrant cell signaling and/or dysregulated autocrine/paracrine signaling (e.g., as compared to a control non-cancerous cell). As another example, a dysregulation of a FLT3 gene, a FLT3 protein, or expression or activity, or level of any of the same, can be a mutation in a FLT3 gene that encodes a FLT3 protein that is constitutively active or has increased activity as compared to a protein encoded by a FLT3 gene that does not include the mutation. For example, a dysregulation of a FLT3 gene, a FLT3 protein, or expression or activity, or level of any of the same, can be the result of a gene or chromosome translocation which results in the expression of a fusion protein that contains a first portion of a FLT3 protein that includes a functional kinase domain, and a second portion of a partner protein (i.e., that is not FLT3). In some examples, dysregulation of a FLT3 gene, a FLT3 protein, or expression or activity or level of any of the same can be a result of a gene translocation of one FLT3 gene with another non-FLT3 gene.

Non-limiting examples of a FLT3 inhibitor include AC220 (N-(5-tert-Butyl-isoxazol-3-yl)-N'-{4-[7-(2-morpholin-4-yl-ethoxy)imidazo[2,1-b][1,3]benzothiazol-2-yl]phenyl}urea dihydrochloride); CEP-701; crenolanib; gilteritinib (ASP2215); KW-2449; lestaurtinib; midostaurin (PKC 412); quizartinib; SB1518 (11-(2-Pyrrolidin-1-yl-ethoxy)-14,19-dioxa-5,7,26-triaza-tetracyclo[19.3.1.1(2,6).1(8,12)]heptacosa-1(25),2(26),3,5,8,10,12(27),16,21,23-decaene); SB1578; semaxinib (SU5416); sunitinib (SU11248); and tandutinib (MLN518/CT53518). Additional examples of a FLT3 inhibitor are known in the art.

The phrase "dysregulation of a HER2 gene, a HER2 protein, or the expression or activity or level of any of the same" refers to a genetic mutation (e.g., a chromosomal translocation that results in the expression of a fusion protein including a HER2 kinase domain and a fusion partner, a mutation in a HER2 gene that results in the expression of a HER2 protein that includes a deletion of at least one amino acid as compared to a wildtype HER2 protein, a mutation in a HER2 gene that results in the expression of a HER2 protein with one or more point mutations as compared to a wildtype HER2 protein, a mutation in a HER2 gene that results in the expression of a HER2 protein with at least one inserted amino acid as compared to a wildtype HER2 protein, a gene duplication that results in an increased level of HER2 protein in a cell, or a mutation in a regulatory sequence (e.g., a promoter and/or enhancer) that results in an increased level of HER2 protein in a cell), an alternative spliced version of a HER2 mRNA that results in a HER2 protein having a deletion of at least one amino acid in the HER2 protein as compared to the wild-type HER2 protein), or increased expression (e.g., increased levels) of a wildtype HER2 protein in a mammalian cell due to aberrant cell signaling and/or dysregulated autocrine/paracrine signaling (e.g., as compared to a control non-cancerous cell). As another example, a dysregulation of a HER2 gene, a HER2 protein, or expression or activity, or level of any of the same, can be a mutation in a HER2 gene that encodes a HER2 protein that is constitutively active or has increased activity as compared to a protein encoded by a HER2 gene that does not include the mutation. For example, a dysregulation of a HER2 gene, a HER2 protein, or expression or activity, or level of any of the same, can be the result of a gene or chromosome translocation which results in the expression of a fusion protein that contains a first portion of a HER2 protein that includes a functional kinase domain, and a second portion of a partner protein (i.e., that is not HER2). In some examples, dysregulation of a HER2 gene, a HER2 protein, or expression or activity or level of any of the same can be a result of a gene translocation of one HER2 gene with another non-HER2 gene.

Non-limiting examples of a HER2 inhibitor include AEE788; afatinib (BIBW 2992); AP32788 (TAK-788); ARRY-334543 (ARRY-543, ASLAN001); AST1306; AZD8961; BMS-599626 (AC480); BMS-690514; canertinib (PD 183805, CI 1033, N-[4-(3-chloro-4-fluoroanilino)-7-(3-morpholin-4-ylpropoxy)quinazolin-6-yl]prop-2-enamide); CP-654577; CP724714; CUDC101; D-69491; D-70166; dacomitinib (PF-00299804); DS8201-a; emodin; erlontinib; gefitinib; GW-2016 (GW-572016); HKI-357; KU004; lapatinib; lapatinib ditosylate; MM-111; mubritinib (TAK-165); neratinib (HKI-257); pelitinib (EKB-569, (E)-N-[4-(3-chloro-4-fluoroanilino)-3-cyano-7-ethoxyquinolin-6-yl]-4-(dimethylamino)but-2-enamide); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); poziotinib (HM781-36); pyrotinib (HTI-1001); sapitinib (AZD8930); TAK285; TAS0728; tesevatinib (KD019, XL647, PRIM-001); tucatinib (ONT-380, ARRY-380); varlitinib (ASLAN001, ARRY-543); 7C3; anti-HER2 CAR-T therapy; cetuximab; DXL702; E75; HER2Bi-Armed Activated T Cells; HER2-BsAb; HER2-Peptid-Vakzine; hersintuzumab; herstatin; margetuximab; MED14276; M1130004; NeuVax; osidem; paitumumab; pertuzumab; PX-104.1; SYD985; trastuzumab; trastuzumab emtansine (KADCYLA®, T-DM1); trastuzumab-dkst (OGIVRI®); zemab; and ZW25. Additional examples of a HER2 inhibitor are known in the art.

The phrase "dysregulation of a HER3 gene, a HER3 protein, or the expression or activity or level of any of the same" refers to a genetic mutation (e.g., a chromosomal translocation that results in the expression of a fusion protein including a HER3 kinase domain and a fusion partner, a mutation in a HER3 gene that results in the expression of a HER3 protein that includes a deletion of at least one amino acid as compared to a wildtype HER3 protein, a mutation in a HER3 gene that results in the expression of a HER3 protein with one or more point mutations as compared to a wildtype HER3 protein, a mutation in a HER3 gene that results in the expression of a HER3 protein with at least one inserted amino acid as compared to a wildtype HER3 protein, a gene duplication that results in an increased level of HER3 protein in a cell, or a mutation in a regulatory sequence (e.g., a promoter and/or enhancer) that results in an increased level of HER3 protein in a cell), an alternative spliced version of a HER3 mRNA that results in a HER3 protein having a deletion of at least one amino acid in the HER3 protein as compared to the wild-type HER3 protein), or increased expression (e.g., increased levels) of a wildtype HER3 protein in a mammalian cell due to aberrant cell signaling and/or dysregulated autocrine/paracrine signaling (e.g., as compared to a control non-cancerous cell). As another example, a dysregulation of a HER3 gene, a HER3 protein, or expression or activity, or level of any of the same, can be a mutation in a HER3 gene that encodes a HER3 protein that is constitutively active or has increased activity as compared to a protein encoded by a HER3 gene that does not include the mutation. For example, a dysregulation of a HER3 gene, a HER3 protein, or expression or activity, or level of any of the same, can be the result of a gene or chromosome translocation which results in the expression of a fusion protein that contains a first portion of a HER3 protein that includes a functional kinase domain, and a second portion of a partner protein (i.e., that is not HER3). In some examples, dysregulation of a HER3 gene, a HER3 protein, or expression or activity or level of any of the same can be a result of a gene translocation of one HER3 gene with another non-HER3 gene.

Non-limiting examples of a HER3 inhibitor include AST1306; AZD8961; gefitinib; neratinib; poziotinib (HM781-36); sapitinib; varlitinib (ARRY-334543, ARRY-543, ASLAN001); AV-203; duligotuzumab; istiratumab (MM-141); LIM716; lumretuzumab; patritumab (U3-1287); pertuzumab; REGN1400; seribantumab (MM-121); TK-A3; and TK-A4. Additional examples of a HER3 inhibitor are known in the art.

The phrase "dysregulation of a HER4 gene, a HER4 protein, or the expression or activity or level of any of the same" refers to a genetic mutation (e.g., a chromosomal translocation that results in the expression of a fusion protein including a HER4 kinase domain and a fusion partner, a mutation in a HER4 gene that results in the expression of a HER4 protein that includes a deletion of at least one amino acid as compared to a wildtype HER4 protein, a mutation in a HER4 gene that results in the expression of a HER4 protein with one or more point mutations as compared to a wildtype HER4 protein, a mutation in a HER4 gene that results in the expression of a HER4 protein with at least one inserted amino acid as compared to a wildtype HER4 protein, a gene duplication that results in an increased level of HER4 protein in a cell, or a mutation in a regulatory sequence (e.g., a promoter and/or enhancer) that results in an increased level of HER4 protein in a cell), an alternative spliced version of a HER4 mRNA that results in a HER4 protein having a deletion of at least one amino acid in the HER4 protein as compared to the wild-type HER4 protein), or increased expression (e.g., increased levels) of a wildtype HER4 protein in a mammalian cell due to aberrant cell signaling and/or dysregulated autocrine/paracrine signaling (e.g., as compared to a control non-cancerous cell). As another example, a dysregulation of a HER4 gene, a HER4 protein, or expression or activity, or level of any of the same, can be a mutation in a HER4 gene that encodes a HER4 protein that is constitutively active or has increased activity as compared to a protein encoded by a HER4 gene that does not include the mutation. For example, a dysregulation of a HER4 gene, a HER4 protein, or expression or activity, or level of any of the same, can be the result of a gene or chromosome translocation which results in the expression of a fusion protein that contains a first portion of a HER4 protein that includes a functional kinase domain, and a second portion of a partner protein (i.e., that is not HER4). In some examples, dysregulation of a HER4 gene, a HER4 protein, or expression or activity or level of any of the same can be a result of a gene translocation of one HER4 gene with another non-HER4 gene.

Non-limiting examples of a HER4 inhibitor include AST1306; BMS-599626 (AC480); BMS-690514; canertinib (PD 183805, CI 1033, N-[4-(3-chloro-4-fluoroanilino)-7-(3-morpholin-4-ylpropoxy)quinazolin-6-yl]prop-2-enamide); and pelitinib (EKB-569, (E)-N-[4-(3-chloro-4-fluoroanilino)-3-cyano-7-ethoxyquinolin-6-yl]-4-(dimethylamino)but-2-enamide). Additional examples of a HER4 inhibitor are known in the art.

The phrase "dysregulation of an IGFR gene, an IGFR protein, or the expression or activity or level of any of the same" refers to a genetic mutation (e.g., a chromosomal translocation that results in the expression of a fusion protein including an IGFR kinase domain and a fusion partner, a mutation in an IGFR gene that results in the expression of an IGFR protein that includes a deletion of at least one amino acid as compared to a wildtype IGFR protein, a mutation in an IGFR gene that results in the expression of an IGFR protein with one or more point mutations as compared to a wildtype IGFR protein, a mutation in an IGFR gene that results in the expression of an IGFR protein with at least one inserted amino acid as compared to a wildtype IGFR protein, a gene duplication that results in an increased level of IGFR protein in a cell, or a mutation in a regulatory sequence (e.g., a promoter and/or enhancer) that results in an increased level of IGFR protein in a cell), an alternative spliced version of an IGFR mRNA that results in an IGFR protein having a deletion of at least one amino acid in the IGFR protein as compared to the wild-type IGFR protein), or increased expression (e.g., increased levels) of a wildtype IGFR protein in a mammalian cell due to aberrant cell signaling and/or dysregulated autocrine/paracrine signaling (e.g., as compared to a control non-cancerous cell). As another example, a dysregulation of an IGFR gene, an IGFR protein, or expression or activity, or level of any of the same, can be a mutation in an IGFR gene that encodes an IGFR protein that is constitutively active or has increased activity as compared to a protein encoded by an IGFR gene that does not include the mutation. For example, a dysregulation of an IGFR gene, an IGFR protein, or expression or activity, or level of any of the same, can be the result of a gene or chromosome translocation which results in the expression of a fusion protein that contains a first portion of a IGFR protein that includes a functional kinase domain, and a second portion of a partner protein (i.e., that is not IGFR). In some examples, dysregulation of an IGFR gene, an IGFR protein, or expression or activity or level of any of the same can be a result of a gene translocation of one IGFR gene with another non-IGFR gene.

A non-limiting example of an IGFR inhibitor is lisitinib (OSI-906). Additional examples of an IGFR inhibitor are known in the art.

The phrase "dysregulation of a JAK1 gene, a JAK1 protein, or the expression or activity or level of any of the same" refers to a genetic mutation (e.g., a chromosomal translocation that results in the expression of a fusion protein including a JAK1 kinase domain and a fusion partner, a mutation in a JAK1 gene that results in the expression of a JAK1 protein that includes a deletion of at least one amino acid as compared to a wildtype JAK1 protein, a mutation in a JAK1 gene that results in the expression of a JAK1 protein with one or more point mutations as compared to a wildtype JAK1 protein, a mutation in a JAK1 gene that results in the expression of a JAK1 protein with at least one inserted amino acid as compared to a wildtype JAK1 protein, a gene duplication that results in an increased level of JAK1 protein in a cell, or a mutation in a regulatory sequence (e.g., a promoter and/or enhancer) that results in an increased level of JAK1 protein in a cell), an alternative spliced version of a JAK1 mRNA that results in a JAK1 protein having a deletion of at least one amino acid in the JAK1 protein as compared to the wild-type JAK1 protein), or increased expression (e.g., increased levels) of a wildtype JAK1 protein in a mammalian cell due to aberrant cell signaling and/or dysregulated autocrine/paracrine signaling (e.g., as compared to a control non-cancerous cell). As another example, a dysregulation of a JAK1 gene, a JAK1 protein, or expression or activity, or level of any of the same, can be a mutation in a JAK1 gene that encodes a JAK1 protein that is constitutively active or has increased activity as compared to a protein encoded by a JAK1 gene that does not include the mutation. For example, a dysregulation of a JAK1 gene, a JAK1 protein, or expression or activity, or level of any of the same, can be the result of a gene or chromosome translocation which results in the expression of a fusion protein that contains a first portion of a JAK1 protein that includes a functional kinase domain, and a second portion of a partner protein (i.e., that is not JAK1). In some examples, dysregulation of a JAK1 gene, a JAK1 protein, or expression or activity or level of any of the same can be a result of a gene translocation of one JAK1 gene with another non-JAK1 gene.

Non-limiting examples of a JAK1 inhibitor include baricitinib (OLUMIANT®, LY-3009104, INCB-28050); filgotinib (G-146034, GLPG-0634); itacitinib (INCB039110); momelotinib (GS-0387, CYT-387); oclacitinib; peficitinib (ASP015K, JNJ-54781532); PF-04965842 (N-{cis-3-[Methyl(7H-pyrrolo[2,3-d]pyrimidin-4-yl)amino]cyclobutyl}propane-1-sulfonamide); ruxolitinib (INCB018424); solcitinib (GSK2586184); and upadacitinib (ABT-494). Additional examples of a JAK1 inhibitor are known in the art.

Additional JAK family targeted therapeutics include those described in U.S. Pat. Nos. 8,604,043, 7,834,022, 8,486,902, 8,530,485, 7,598,257, 8,541,425, 8,410,265, 9,987,276, and 9,949,971, and U.S. Patent Application Publication Nos. 2018/0051036 A1, 2010/0298355 A1, 2008/0312258 A1, 2011/0082159 A1, 2011/0086810 A1, 2013/0345157 A1, 2014/0018374 A1, 2014/0005210 A1, 2011/0223210 A1, 2011/0224157 A1, 2007/0135461 A1, 2010/0022522 A1, 2013/0253193 A1, 2013/0253191 A1, 2013/0253190 A1, 2010/0190981 A1, 2013/0338134 A1, 2008/0312259 A1, 2014/0094477 A1, and 2014/0094476 A1, the disclosures of which are incorporated by reference herein.

The phrase "dysregulation of a JAK2 gene, a JAK2 protein, or the expression or activity or level of any of the same" refers to a genetic mutation (e.g., a chromosomal translocation that results in the expression of a fusion protein including a JAK2 kinase domain and a fusion partner, a mutation in a JAK2 gene that results in the expression of a JAK2 protein that includes a deletion of at least one amino acid as compared to a wildtype JAK2 protein, a mutation in a JAK2 gene that results in the expression of a JAK2 protein with one or more point mutations as compared to a wildtype JAK2 protein, a mutation in a JAK2 gene that results in the expression of a JAK2 protein with at least one inserted amino acid as compared to a wildtype JAK2 protein, a gene duplication that results in an increased level of JAK2 protein in a cell, or a mutation in a regulatory sequence (e.g., a promoter and/or enhancer) that results in an increased level of JAK2 protein in a cell), an alternative spliced version of a JAK2 mRNA that results in a JAK2 protein having a deletion of at least one amino acid in the JAK2 protein as compared to the wild-type JAK2 protein), or increased expression (e.g., increased levels) of a wildtype JAK2 protein in a mammalian cell due to aberrant cell signaling and/or dysregulated autocrine/paracrine signaling (e.g., as compared to a control non-cancerous cell). As another example, a dysregulation of a JAK2 gene, a JAK2 protein, or expression or activity, or level of any of the same, can be a mutation in a JAK2 gene that encodes a JAK2 protein that is constitutively active or has increased activity as compared to a protein encoded by a JAK2 gene that does not include the mutation. For example, a dysregulation of a JAK2 gene, a JAK2 protein, or expression or activity, or level of any of the same, can be the result of a gene or chromosome translocation which results in the expression of a fusion protein that contains a first portion of a JAK2 protein that includes a functional kinase domain, and a second portion of a partner protein (i.e., that is not JAK2). In some examples, dysregulation of a JAK2 gene, a JAK2 protein, or expression or activity or level of any of the same can be a result of a gene translocation of one JAK2 gene with another non-JAK2 gene.

Non-limiting examples of a JAK2 inhibitor include pacritinib (SB1578); atiprimod; baricitinib (OLUMIANT®, LY-3009104, INCB-28050); fedratinib (SAR302503); gandotinib (LY-2784544); lestaurtinib (CEP-701); momelotinib (GS-0387, CYT-387); oclacitinib; peficitinib (ASP015K, JNJ-54781532); ruxolitinib (INCB018424); and SB1518 (11-(2-pyrrolidin-1-yl-ethoxy)-14,19-dioxa-5,7,26-triaza-tetracyclo[19.3.1.1(2,6).1(8,12)]heptacosa-1(25),2(26),3,5,8,10,12(27),16,21,23-decaene). Additional examples of a JAK2 inhibitor are known in the art.

The phrase "dysregulation of a JAK3 gene, a JAK3 protein, or the expression or activity or level of any of the same" refers to a genetic mutation (e.g., a chromosomal translocation that results in the expression of a fusion protein including a JAK3 kinase domain and a fusion partner, a mutation in a JAK3 gene that results in the expression of a JAK3 protein that includes a deletion of at least one amino acid as compared to a wildtype JAK3 protein, a mutation in a JAK3 gene that results in the expression of a JAK3 protein with one or more point mutations as compared to a wildtype JAK3 protein, a mutation in a JAK3 gene that results in the expression of a JAK3 protein with at least one inserted amino acid as compared to a wildtype JAK3 protein, a gene duplication that results in an increased level of JAK3 protein in a cell, or a mutation in a regulatory sequence (e.g., a promoter and/or enhancer) that results in an increased level of JAK3 protein in a cell), an alternative spliced version of a JAK3 mRNA that results in a JAK3 protein having a deletion of at least one amino acid in the JAK3 protein as compared to the wild-type JAK3 protein), or increased expression (e.g., increased levels) of a wildtype JAK3 protein in a mammalian cell due to aberrant cell signaling and/or dysregulated autocrine/paracrine signaling (e.g., as compared to a control non-cancerous cell). As another example, a dysregulation of a JAK3 gene, a JAK3 protein, or expression or activity, or level of any of the same, can be a mutation in a JAK3 gene that encodes a JAK3 protein that is constitutively active or has increased activity as compared to a protein encoded by a JAK3 gene that does not include the mutation. For example, a dysregulation of a JAK3 gene, a JAK3 protein, or expression or activity, or level of any of the same, can be the result of a gene or chromosome translocation which results in the expression of a fusion protein that contains a first portion of a JAK3 protein that includes a functional kinase domain, and a second portion of a partner protein (i.e., that is not JAK3). In some examples, dysregulation of a JAK3 gene, a JAK3 protein, or expression or activity or level of any of the same can be a result of a gene translocation of one JAK3 gene with another non-JAK3 gene.

Non-limiting examples of a JAK3 inhibitor include atiprimod; JANEX-3 (4-(3'-hydroxyphenyl)-amino-6,7-dimethoxyquinazoline); pefcitinib (ASP015K, JNJ-54781532); and tofacitinib. Additional examples of a JAK3 inhibitor are known in the art.

The phrase "dysregulation of a Kit gene, a Kit protein, or the expression or activity or level of any of the same" refers to a genetic mutation (e.g., a chromosomal translocation that results in the expression of a fusion protein including a Kit kinase domain and a fusion partner, a mutation in a Kit gene that results in the expression of a Kit protein that includes a deletion of at least one amino acid as compared to a wildtype Kit protein, a mutation in a Kit gene that results in the expression of a Kit protein with one or more point mutations as compared to a wildtype Kit protein, a mutation in a Kit gene that results in the expression of a Kit protein with at least one inserted amino acid as compared to a wildtype Kit protein, a gene duplication that results in an increased level of Kit protein in a cell, or a mutation in a regulatory sequence (e.g., a promoter and/or enhancer) that results in an increased level of Kit protein in a cell), an alternative spliced version of a Kit mRNA that results in a Kit protein having a deletion of at least one amino acid in the Kit protein as compared to the wild-type Kit protein), or increased expression (e.g., increased levels) of a wildtype Kit protein in a mammalian cell due to aberrant cell signaling and/or dysregulated autocrine/paracrine signaling (e.g., as compared to a control non-cancerous cell). As another example, a dysregulation of a Kit gene, a Kit protein, or expression or activity, or level of any of the same, can be a mutation in a Kit gene that encodes a Kit protein that is constitutively active or has increased activity as compared to a protein encoded by a Kit gene that does not include the mutation. For example, a dysregulation of a Kit gene, a Kit protein, or expression or activity, or level of any of the same, can be the result of a gene or chromosome translocation which results in the expression of a fusion protein that contains a first portion of a Kit protein that includes a functional kinase domain, and a second portion of a partner protein (i.e., that is not Kit). In some examples, dysregulation of a Kit gene, a Kit protein, or expression or activity or level of any of the same can be a result of a gene translocation of one Kit gene with another non-Kit gene.

Non-limiting examples of a Kit inhibitor include AMG 706; amuvatinib (MP-470); APcK110; axitinib (AG-013736); AZD2932; dasatinib (BMS-354825); dovitinib (TKI-258, CHIR-258); EXEL-0862; imatinib; KI-328; masitinib (AB1010); midostaurin; MLN518; motesanib; N3-(6-aminopyridin-3-yl)-N1-(2-cyclopentylethyl)-4-methylisophthalamide; nilotinib; OSI-930; pazopanib (GW786034); pexidartinib (PLX3397); PKC412; PLX647; PP1; quizartinib (AC220); regorafenib (BAY 73-4506); semaxinib (SU 5416); sitravatinib (MGCD516); sorafenib; ST1571; SU11248; SU9529; sunitinib; telatinib; tivozanib (AV-951); tyrphostin AG 1296; VX-322; and WBZ_4. Additional examples of a Kit inhibitor are known in the art.

The phrase "dysregulation of a MEK gene, a MEK protein, or the expression or activity or level of any of the same" refers to a genetic mutation (e.g., a chromosomal translocation that results in the expression of a fusion protein including a MEK kinase domain and a fusion partner, a mutation in a MEK gene that results in the expression of a MEK protein that includes a deletion of at least one amino acid as compared to a wildtype MEK protein, a mutation in a MEK gene that results in the expression of a MEK protein with one or more point mutations as compared to a wildtype MEK protein, a mutation in a MEK gene that results in the expression of a MEK protein with at least one inserted amino acid as compared to a wildtype MEK protein, a gene duplication that results in an increased level of MEK protein in a cell, or a mutation in a regulatory sequence (e.g., a promoter and/or enhancer) that results in an increased level of MEK protein in a cell), an alternative spliced version of a MEK mRNA that results in a MEK protein having a deletion of at least one amino acid in the MEK protein as compared to the wild-type MEK protein), or increased expression (e.g., increased levels) of a wildtype MEK protein in a mammalian cell due to aberrant cell signaling and/or dysregulated autocrine/paracrine signaling (e.g., as compared to a control non-cancerous cell). As another example, a dysregulation of a MEK gene, a MEK protein, or expression or activity, or level of any of the same, can be a mutation in a MEK gene that encodes a MEK protein that is constitutively active or has increased activity as compared to a protein encoded by a MEK gene that does not include the mutation. For example, a dysregulation of a MEK gene, a MEK protein, or expression or activity, or level of any of the same, can be the result of a gene or chromosome translocation which results in the expression of a fusion protein that contains a first portion of a MEK protein that includes a functional kinase domain, and a second portion of a partner protein (i.e., that is not MEK). In some examples, dysregulation of a MEK gene, a MEK protein, or expression or activity or level of any of the same can be a result of a gene translocation of one MEK gene with another non-MEK gene.

Non-limiting examples of a MEK inhibitor include AS703026 (MSC1935369); AZD8330 (ARRY-424704); AZD6244 (ARRY-142866); BI-847325; binimetinib (MEKTOVI®, MEK162); B1X02188; B1X02189; CH4987655; CH5126766; CI-1040; cobimetinib (COTELLIC®, GDC-0973, XL-518); CS3006; EBI-1051; G-573; G8935; GDC-0623; hypothemycin; Myricetin; nobiletin; PD0325901; PD184161; PD184352 (CI-1040); PD318088; PD98059; PD325901; PD334581; pimasertib (AS-703026); refametinib (RDEA119, BAY 869766); RO5126766; selumetinib (AZD6244); SHR7390; SL-327; TAK-733; trametinib (MEKINIST®, GSK1120212); U0126; and WX-554. Additional examples of a MEK inhibitor are known in the art.

The phrase "dysregulation of a MET gene, a MET protein, or the expression or activity or level of any of the same" refers to a genetic mutation (e.g., a chromosomal translocation that results in the expression of a fusion protein including a MET kinase domain and a fusion partner, a mutation in a MET gene that results in the expression a MET protein that includes a deletion of at least one amino acid as compared to a wildtype MET protein, a mutation in a MET gene that results in the expression of a MET protein with one or more point mutations as compared to a wildtype MET protein, a mutation in a MET gene that results in the expression of a MET protein with at least one inserted amino acid as compared to a wildtype MET protein, a gene duplication that results in an increased level of MET protein in a cell, or a mutation in a regulatory sequence (e.g., a promoter and/or enhancer) that results in an increased level of MET protein in a cell), an alternative spliced version of a MET mRNA that results in a MET protein having a deletion of at least one amino acid in the MET protein as compared to the wild-type MET protein), or increased expression (e.g., increased levels) of a wildtype MET protein in a mammalian cell due to aberrant cell signaling and/or dysregulated autocrine/paracrine signaling (e.g., as compared to a control non-cancerous cell). As another example, a dysregulation of a MET gene, a MET protein, or expression or activity, or level of any of the same, can be a mutation in a MET gene that encodes a MET protein that is constitutively active or has increased activity as compared to a protein encoded by a MET gene that does not include the mutation. For example, a dysregulation of a MET gene, a MET protein, or expression or activity, or level of any of the same, can be the result of a gene or chromosome translocation which results in the expression of a fusion protein that contains a first portion of a MET protein that includes a functional kinase domain, and a second portion of a partner protein (i.e., that is not MET). In some examples, dysregulation of a MET gene, a MET protein, or expression or activity or level of any of the same can be a result of a gene translocation of one MET gene with another non-MET gene.

Non-limiting examples of a MET inhibitor include (−)-Oleocanthal; ABBV-399; AL2846; AMG-208; AMG-337; AMG-458; amuvatinib (MP740, N-(1,3-benzodioxol-5-ylmethyl)-4-([1]benzofuro[3,2-d]pyrimidin-4-yl)piperazine-1-carbothioamide); APG-8361; ASLAN002; ASP-08001; ASP-08126; BAY-853474; BMS-754807; BMS-777607; BMS-794833; BMS-817378 (prodrug of BMS-794833); BPI-9016M; cabozantinib (XL184, BMS-907351); capmatinib (INCB28060, 2-fluoro-N-methyl-4-{7-[(quinolin-6-yl)methyl]imidazo[1,2-b][1,2,4]triazin-2-yl}benzamide); crizotinib (PF-02341066); DCC-2036; DE605; DP-3590; EMD-1204831; EMD-1214063; foretinib (GSK1363089, XL880); glesatinib (MGCD265); glumetinib (SCC244); GM-604; golvatinib (E7050); HM-5016504; HS-10241; INCB028060; JNJ-38877605 (6-(difluoro[6-(1-methyl-1H-pyrazol-4-yl)[1,2,4]triazolo[4,3-b]pyridazin-3-yl]methyl) quinoline); KRC-408; merestinib (LY2801653); MK-2461; MK8033; NK4; NPS-1034; NVP-BVU972; PF-04217903; PHA-665752; PLB1001; 549076; SAR-125844; savolitinib (volitinib, AZD6094, HMPL-504); sitravatinib (MGCD-516); SGX-523; SU11274; TAS-115; tivatinib (ARQ197, (3R,4R)-3-(5,6-Dihydro-4H-pyrrolo[3,2,1-ij]quinolin-1-yl)-4-(1H-indol-3-yl)-2,5-pyrrolidinedione); tepotinib (EMD 1214063, MSC2156119J); TQ-B3139; XL174; 6-[di-fluoro(6-pyridin-4-yl[1,2,4]triazolo[4,3-b]pyridazin-3-yl)methyl]quinoline; (E)-2-(1-(3-((7-fluoroquinolin-6-yl)methyl)imidazo[1,2-b]pyridazin-6-yl)ethylidene)hydrazinecarboxamide; ABT-700; ABBV-399; ARGX-111; CE-355621; DN30; emibetuzumab; ficlatuzumab (AV-299); HTI-1066; JNJ-61186372; LY2875358 (LA-480); LY3164530; onartuzumab (MetMAb); rilotumumab (AMG 102); SAIT301; Sym015; Tak-701; and YYB101. Additional examples of a MET inhibitor are known in the art.

The phrase "dysregulation of a mTOR gene, a mTOR protein, or the expression or activity or level of any of the same" refers to a genetic mutation (e.g., a chromosomal translocation that results in the expression of a fusion protein including a mTOR kinase domain and a fusion partner, a mutation in a mTOR gene that results in the expression a mTOR protein that includes a deletion of at least one amino acid as compared to a wildtype mTOR protein, a mutation in a mTOR gene that results in the expression of a mTOR protein with one or more point mutations as compared to a wildtype mTOR protein, a mutation in a mTOR gene that results in the expression of a mTOR protein with at least one inserted amino acid as compared to a wildtype mTOR protein, a gene duplication that results in an increased level of mTOR protein in a cell, or a mutation in a regulatory sequence (e.g., a promoter and/or enhancer) that results in an increased level of mTOR protein in a cell), an alternative spliced version of a mTOR mRNA that results in a mTOR protein having a deletion of at least one amino acid in the mTOR protein as compared to the wild-type mTOR protein), or increased expression (e.g., increased levels) of a wildtype mTOR protein in a mammalian cell due to aberrant cell signaling and/or dysregulated autocrine/paracrine signaling (e.g., as compared to a control non-cancerous cell). As another example, a dysregulation of a mTOR gene, a mTOR protein, or expression or activity, or level of any of the same, can be a mutation in a mTOR gene that encodes a mTOR protein that is constitutively active or has increased activity as compared to a protein encoded by a mTOR gene that does not include the mutation. For example, a dysregulation of a mTOR gene, a mTOR protein, or expression or activity, or level of any of the same, can be the result of a gene or chromosome translocation which results in the expression of a fusion protein that contains a first portion of a mTOR protein that includes a functional kinase domain, and a second portion of a partner protein (i.e., that is not mTOR). In some examples, dysregulation of a mTOR gene, a mTOR protein, or expression or activity or level of any of the same can be a result of a gene translocation of one mTOR gene with another non-mTOR gene.

Non-limiting examples of a mTOR inhibitor include anthracimycin; apitolisib (GDC-0980, RG7422); AZD-8055; BGT226 (NVP-BGT226); CC-115; CC-223; CZ415; dactolisib (BEZ235, NVP-BEZ235); DS7423; everolimus (RAD001); GDC-0084 (RG7666); GDC-0349; gedatolisib (PF-05212384, PKI-5587); GSK1059615; INK128; KU-0063794; LY3023414; MLN0128; omipalisib (GSK2126458, GSK458); OSI-027; OSU-53; Palomid 529 (P529); PF-04691502; PI-103; PKI-587; PP242; PQR309; ridaforolimus (AP-23573); sapanisertib (INK 128, MLN0128); SAR245409 (XL765); SF-1126; SF2523; sirolimus (rapamycin); SN32976; TAK228; temsirolimus (CCI-779, NSC 683864); Torin 1; Torin 2; torkinib (PP242); umirolimus; vistusertib (AZD2014); voxtalisib (XL765, SAR245409); VS-5584 (5B2343); WAY-600; WYE-125132 (WYE-132); WYE-354; WYE-687; XL388; and zotarolimus (ABT-578). Additional examples of a mTOR inhibitor are known in the art.

The phrase "dysregulation of a PDGFRα gene, a PDGFRα protein, or the expression or activity or level of any of the same" refers to a genetic mutation (e.g., a chromosomal translocation that results in the expression of a fusion protein including a PDGFRα kinase domain and a fusion partner, a mutation in a PDGFRα gene that results in the expression a PDGFRα protein that includes a deletion of at least one amino acid as compared to a wildtype PDGFRα protein, a mutation in a PDGFRα gene that results in the expression of a PDGFRα protein with one or more point mutations as compared to a wildtype PDGFRα protein, a mutation in a PDGFRα gene that results in the expression of a PDGFRα protein with at least one inserted amino acid as compared to a wildtype PDGFRα protein, a gene duplication that results in an increased level of PDGFRα protein in a cell, or a mutation in a regulatory sequence (e.g., a promoter and/or enhancer) that results in an increased level of PDGFRα protein in a cell), an alternative spliced version of a PDGFRα mRNA that results in a PDGFRα protein having a deletion of at least one amino acid in the PDGFRα protein as compared to the wild-type PDGFRα protein), or increased expression (e.g., increased levels) of a wildtype PDGFRα protein in a mammalian cell due to aberrant cell signaling and/or dysregulated autocrine/paracrine signaling (e.g., as compared to a control non-cancerous cell). As another example, a dysregulation of a PDGFRα gene, a PDGFRα protein, or expression or activity, or level of any of the same, can be a mutation in a PDGFRα gene that encodes a PDGFRα protein that is constitutively active or has increased activity as compared to a protein encoded by a PDGFRα gene that does not include the mutation. For example, a dysregulation of a PDGFRα gene, a PDGFRα protein, or expression or activity, or level of any of the same, can be the result of a gene or chromosome translocation which results in the expression of a fusion protein that contains a first portion of a PDGFRα protein that includes a functional kinase domain, and a second portion of a partner protein (i.e., that is not PDGFRα). In some examples, dysregulation of a PDGFRα gene, a PDGFRα protein, or expression or activity or level of any of the same can be a result of a gene translocation of one PDGFRα gene with another non-PDGFRα gene.

Non-limiting examples of a PDGFRα inhibitor include amuvatinib (MP470); axitinib (Inlyta®); imatinib (Gleevec®); masitinib; motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide); nintedanib (BIBF1120, CAS 928326-83-4); pazopanib; quizartinib (AC220, CAS 950769-58-1); sorafenib (Nexavar®); and sunitinib. Additional examples of a PDGFRα inhibitor are known in the art.

The phrase "dysregulation of a PDGFRβ gene, a PDGFRβ protein, or the expression or activity or level of any of the same" refers to a genetic mutation (e.g., a chromosomal translocation that results in the expression of a fusion protein including a PDGFRβ kinase domain and a fusion partner, a mutation in a PDGFRβ gene that results in the expression a PDGFRβ protein that includes a deletion of at least one amino acid as compared to a wildtype PDGFRβ protein, a mutation in a PDGFRβ gene that results in the expression of a PDGFRβ protein with one or more point mutations as compared to a wildtype PDGFRβ protein, a mutation in a PDGFRβ gene that results in the expression of a PDGFRβ protein with at least one inserted amino acid as compared to a wildtype PDGFRβ protein, a gene duplication that results in an increased level of PDGFRβ protein in a cell, or a mutation in a regulatory sequence (e.g., a promoter and/or enhancer) that results in an increased level of PDGFRβ protein in a cell), an alternative spliced version of a PDGFRβ mRNA that results in a PDGFRβ protein having a deletion of at least one amino acid in the PDGFRβ protein as compared to the wild-type PDGFRβ protein), or increased expression (e.g., increased levels) of a wildtype PDGFRβ protein in a mammalian cell due to aberrant cell signaling and/or dysregulated autocrine/paracrine signaling (e.g., as compared to a control non-cancerous cell). As another example, a dysregulation of a PDGFRβ gene, a PDGFRβ protein, or expression or activity, or level of any of the same, can be a mutation in a PDGFRβ gene that encodes a PDGFRβ protein that is constitutively active or has increased activity as compared to a protein encoded by a PDGFRβ gene that does not include the mutation. For example, a dysregulation of a PDGFRβ gene, a PDGFRβ protein, or expression or activity, or level of any of the same, can be the result of a gene or chromosome translocation which results in the expression of a fusion protein that contains a first portion of a PDGFRβ protein that includes a functional kinase domain, and a second portion of a partner protein (i.e., that is not PDGFRβ). In some examples, dysregulation of a PDGFRβ gene, a PDGFRβ protein, or expression or activity or level of any of the same can be a result of a gene translocation of one PDGFRβ gene with another non-PDGFRβ gene.

Non-limiting examples of a PDGFRβ inhibitor include amuvatinib (MP470); axitinib (Inlyta®); imatinib (Gleevec®); masitinib; motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide); nintedanib (BIBF1120, CAS 928326-83-4); pazopanib; quizartinib (AC220, CAS 950769-58-1); sorafenib (Nexavar®); sunitinib; telatinib (BAY57-9352, CAS 332012-40-5); and vatalanib (PTK787, CAS 212141-51-0). Additional examples of a PDGFRβ inhibitor are known in the art.

The phrase "dysregulation of a PI3K gene, a PI3K protein, or the expression or activity or level of any of the same" refers to a genetic mutation (e.g., a chromosomal translocation that results in the expression of a fusion protein including a PI3K kinase domain and a fusion partner, a mutation in a PI3K gene that results in the expression a PI3K protein that includes a deletion of at least one amino acid as compared to a wildtype PI3K protein, a mutation in a PI3K gene that results in the expression of a PI3K protein with one or more point mutations as compared to a wildtype PI3K protein, a mutation in a PI3K gene that results in the expression of a PI3K protein with at least one inserted amino acid as compared to a wildtype PI3K protein, a gene duplication that results in an increased level of PI3K protein in a cell, or a mutation in a regulatory sequence (e.g., a promoter and/or enhancer) that results in an increased level of PI3K protein in a cell), an alternative spliced version of a PI3K mRNA that results in a PI3K protein having a deletion of at least one amino acid in the PI3K protein as compared to the wild-type PI3K protein), or increased expression (e.g., increased levels) of a wildtype PI3K protein in a mammalian cell due to aberrant cell signaling and/or dysregulated autocrine/paracrine signaling (e.g., as compared to a control non-cancerous cell). As another example, a dysregulation of a PI3K gene, a PI3K protein, or expression or activity, or level of any of the same, can be a mutation in a PI3K gene that encodes a PI3K protein that is constitutively active or has increased activity as compared to a protein encoded by a PI3K gene that does not include the mutation. For example, a dysregulation of a PI3K gene, a PI3K protein, or expression or activity, or level of any of the same, can be the result of a gene or chromosome translocation which results in the expression of a fusion protein that contains a first portion of a PI3K protein that includes a functional kinase domain, and a second portion of a partner protein (i.e., that is not PI3K). In some examples, dysregulation of a PI3K gene, a PI3K protein, or expression or activity or level of any of the same can be a result of a gene translocation of one PI3K gene with another non-PI3K gene.

Non-limiting examples of a PI3K inhibitor include 3-methyladenine; A66; alpelisib (BYL719); AMG319; AMG511; apitolisib (GDC-0980, RG7422); AS-252424; AS-604850; AS-605240; ASN003; AZD6482 (KIN-193); AZD8186; AZD8835; BGT226 (NVP-BGT226); buparlisib (BKM120); CAY10505; CH5132799; copanlisib (BAY 80-6946); CUDC-907; CZC24832; dactolisib (BEZ235, NVP-BEZ235); DS7423; duvelisib (IPI-145, INK1197); GDC-0032; GDC-0077; GDC-0084 (RG7666); GDC-0326; gedatolisib (PF-05212384, PKI-5587); GM-604; GNE-317; GS-9820; GSK1059615; GSK2292767; GSK2636771; HS-173; IC-87114; idelalisib (CAL-101, GS-1101); IPI-145; IPI-3063; IPI-549; LY294002; LY3023414; nemiralisib (GSK2269557); omipalisib (GSK2126458, GSK458); PF-04691502; PF-4989216; PI-103; PI-3065; pictilisib (GDC-0941); PIK-293; PIK-294; PIK-75; PIK-90; PIK-93; PIK-Ill; pilaralisib (XL147, SAR245408); PKI-402; PKI-587; PP-110; PQR309; PW-12; PX-866; quercetin; rigosertib; 514161; SAR245409 (XL765); SAR260301; SAR405; serabelisib (INK-1117, MLN-1117, TAK-1117); SF-1126; SF-2523; SN32976; sonolisib (PX-866); taselisib (GDC-0032); TB101110; TG100-115; TG100-713; TGR-1202; TGX-221; umbralisib (TGR-1202); voxtalisib (XL765, SAR245409); VPS34-IN1; VS-5584 (SB2343); WJD008; WX-037; wortmannin; and ZSTK474. Additional examples of a PI3K inhibitor are known in the art.

The phrase "dysregulation of a RAF gene, a RAF protein, or the expression or activity or level of any of the same" refers to a genetic mutation (e.g., a chromosomal translocation that results in the expression of a fusion protein including a RAF kinase domain and a fusion partner, a mutation in a RAF gene that results in the expression a RAF protein that includes a deletion of at least one amino acid as compared to a wildtype RAF protein, a mutation in a RAF gene that results in the expression of a RAF protein with one or more point mutations as compared to a wildtype RAF protein, a mutation in a RAF gene that results in the expression of a RAF protein with at least one inserted amino acid as compared to a wildtype RAF protein, a gene duplication that results in an increased level of RAF protein in a cell, or a mutation in a regulatory sequence (e.g., a promoter and/or enhancer) that results in an increased level of RAF protein in a cell), an alternative spliced version of a RAF mRNA that results in a RAF protein having a deletion of at least one amino acid in the RAF protein as compared to the wild-type RAF protein), or increased expression (e.g., increased levels) of a wildtype RAF protein in a mammalian cell due to aberrant cell signaling and/or dysregulated autocrine/paracrine signaling (e.g., as compared to a control non-cancerous cell). As another example, a dysregulation of a RAF gene, a RAF protein, or expression or activity, or level of any of the same, can be a mutation in a RAF gene that encodes a RAF protein that is constitutively active or has increased activity as compared to a protein encoded by a RAF gene that does not include the mutation. For example, a dysregulation of a RAF gene, a RAF protein, or expression or activity, or level of any of the same, can be the result of a gene or chromosome translocation which results in the expression of a fusion protein that contains a first portion of a RAF protein that includes a functional kinase domain, and a second portion of a partner protein (i.e., that is not RAF). In some examples, dysregulation of a RAF gene, a RAF protein, or expression or activity or level of any of the same can be a result of a gene translocation of one RAF gene with another non-RAF gene.

Non-limiting examples of a RAF inhibitor include ((S)-2-{4-[3-(5-chloro-2-fluoro-3-methanesulfonylamino-phenyl)-1-isopropyl-1H-pyrazol-4-yl]-pyrimidin-2-ylamino}-1-methyl-ethyl)-carbamic acid methyl ester; ASN003; BMS-908662 (Bristol-Meyers Squibb, XL281); dabrafenib; GDC-0879; GSK2118436 (GlaxoSmithKline); LGX818 (Novartis); PLX3603 (Hofmann-LaRoche); PLX-4720; RAF265 (Novartis); RO4987655; RO5126766 (CH5127566); RO5185426 (Hofmann-LaRoche); sorafenib (Nexavar®); and vemurafenib (RG7204, PLX4032). Additional examples of a RAF inhibitor are known in the art.

The phrase "dysregulation of a RAS gene, a RAS protein, or the expression or activity or level of any of the same" refers to a genetic mutation (e.g., a chromosomal translocation that results in the expression of a fusion protein including a RAS kinase domain and a fusion partner, a mutation in a RAS gene that results in the expression a RAS protein that includes a deletion of at least one amino acid as compared to a wildtype RAS protein, a mutation in a RAS gene that results in the expression of a RAS protein with one or more point mutations as compared to a wildtype RAS protein, a mutation in a RAS gene that results in the expression of a RAS protein with at least one inserted amino acid as compared to a wildtype RAS protein, a gene duplication that results in an increased level of RAS protein in a cell, or a mutation in a regulatory sequence (e.g., a promoter and/or enhancer) that results in an increased level of RAS protein in a cell), an alternative spliced version of a RAS mRNA that results in a RAS protein having a deletion of at least one amino acid in the RAS protein as compared to the wild-type RAS protein), or increased expression (e.g., increased levels) of a wildtype RAS protein in a mammalian cell due to aberrant cell signaling and/or dysregulated autocrine/paracrine signaling (e.g., as compared to a control non-cancerous cell). As another example, a dysregulation of a RAS gene, a RAS protein, or expression or activity, or level of any of the same, can be a mutation in a RAS gene that encodes a RAS protein that is constitutively active or has increased activity as compared to a protein encoded by a RAS gene that does not include the mutation. For example, a dysregulation of a RAS gene, a RAS protein, or expression or activity, or level of any of the same, can be the result of a gene or chromosome translocation which results in the expression of a fusion protein that contains a first portion of a RAS protein that includes a functional kinase domain, and a second portion of a partner protein (i.e., that is not RAS). In some examples, dysregulation of a RAS gene, a RAS protein, or expression or activity or level of any of the same can be a result of a gene translocation of one RAS gene with another non-RAS gene.

Non-limiting examples of a RAS inhibitor include 0375-0604; a covalent quinazoline-based switch II pocket (SIIP) compound; ARS-1620; AZD4785; Kobe0065; Kobe2602; and LP1. Additional examples of a RAS inhibitor are known in the art.

The phrase "dysregulation of a RET gene, a RET protein, or the expression or activity or level of any of the same" refers to a genetic mutation (e.g., a chromosomal translocation that results in the expression of a fusion protein including a RET kinase domain and a fusion partner, a mutation in a RET gene that results in the expression a RET protein that includes a deletion of at least one amino acid as compared to a wildtype RET protein, a mutation in a RET gene that results in the expression of a RET protein with one or more point mutations as compared to a wildtype RET protein, a mutation in a RET gene that results in the expression of a RET protein with at least one inserted amino acid as compared to a wildtype RET protein, a gene duplication that results in an increased level of RET protein in a cell, or a mutation in a regulatory sequence (e.g., a promoter and/or enhancer) that results in an increased level of RET protein in a cell), an alternative spliced version of a RET mRNA that results in a RET protein having a deletion of at least one amino acid in the RET protein as compared to the wild-type RET protein), or increased expression (e.g., increased levels) of a wildtype RET protein in a mammalian cell due to aberrant cell signaling and/or dysregulated autocrine/paracrine signaling (e.g., as compared to a control non-cancerous cell). As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of a RET protein that includes a functional kinase domain, and a second portion of a partner protein (i.e., that is not RAF). In some examples, dysregulation of a RET gene, a RET protein, or expression or activity or level of any of the same can be a result of a gene translocation of one RET gene with another non-RET gene.

Non-limiting examples of a RET inhibitor include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl)piperazine-1-carbothioamide); apatinib (YN968D1) (N-[4-(1-cyanocyclopentyl) phenyl-2-(4-picolyl)amino-3-Nicotinamide methanesulphonate); cabozantinib (Cometriq XL-184) (N-(4-(((6,7-Dimethoxyquinolin-4-yl)oxy)phenyl)-N'-(4-fluorophenyl)cyclopropane-1,1-dicarboxamide); dovitinib (TK1258; GFKI-258; CHIR-258) ((3Z)-4-amino-5-fluoro-3-[5-(4-methylpiperazin-1-yl)-1,3-dihydrobenz-imidazol-2-ylidene]quinolin-2-one); famitinib (5-[2-(diethylamino)ethyl]-2-[(Z)-(5-fluoro-2-oxo-1H-indol-3-ylidene)methyl]-3-methyl-6,7-dihydro-1H-pyrrolo[3,2-c]pyridin-4-one); fedratinib (SAR302503, TG101348) (N-(2-Methyl-2-propanyl)-3-{[5-methyl-2-({4-[2-(1-pyrrolidinyl)ethoxy]phenyl}amino)-4-pyrimidinyl]amino}benzenesulfonamide); foretinib (XL880, EXEL-2880, GSK1363089, GSK089) (N1'-[3-fluoro-4-[[6-methoxy-7-(3-morpholinopropoxy)-4-quinolyl]oxy]phenyl]-N1-(4-fluorophenyl)cyclopropane-1,1-dicarboxamide); fostamantinib (R788) (2H-Pyrido[3,2-b]-1,4-oxazin-3(4H)-one, 6-[[5-fluoro-2-[(3,4,5-trimethoxyphenyl)amino]-4-pyrimidinyl]amino]-2,2-dimethyl-4-[(phosphonooxy)methyl]-, sodium salt (1:2)); ilorasertib (ABT-348) (1-(4-(4-amino-7-(1-(2-hydroxy-ethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methyl-amino)-anilino)-1-phenyl-methylene]-6-methoxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl)phenyl]benzamide); PP242 (a TORKinib) (2-[4-Amino-1-(1-methylethyl)-1H-pyrazolo[3,4-d]pyrimidin-3-yl]-1H-indol-5-ol); quizartinib (1-(5-(tert-Butyl)isoxazol-3-yl)-3-(4-(7-(2-morpholinoethoxy)benzo[d]imidazo[2,1-b]thiazol-2-yl)phenyl)urea); regorafenib (BAY 73-4506, stivarga) (4-[4-({[4-Chloro-3-(trifluoromethyl)phenyl]carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCD516, MG516) (N-(3-Fluoro-4-{[2-(5-{[(2-methoxyethyl)amino]methyl}-2-pyridinyl)thieno[3,2-b]pyridin-7-yl]oxy}phenyl)-N?-(4-fluorophenyl)-1,1-cyclopropanedicarboxamide); sorafenib (BAY 43-9006) (4-[4-[[[[4-chloro-3-(trifluoromethyl)phenyl]amino]carbonyl]amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl)methyl)-3-(trifluoromethyl)phenyl)carbamoyl)-2-methylphenyl)-5-(thiophen-2-yl)nicotinamide); BPR1K871 (1-(3-chlorophenyl)-3-(5-(2-((7-(3-(dimethylamino)propoxy)quinazolin-4-yl)amino)ethyl)thiazol-2-yl)urea); CLM3 (1-phenethyl-N-(1-phenylethyl)-1H-pyrazolo[3,4-d]pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl)phenyl]-N'[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methylsulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl)phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl)phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinib (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-dione); XL-999 ((Z)-5-((1-ethylpiperidin-4-yl)amino)-3-((3-fluorophenyl)(5-methyl-1H-imidazol-2-yl)methylene)indolin-2-one); BPR1J373 (a 5-phenylthiazol-2-ylamine-pyriminide derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD15-44 (N-(4-((4-ethylpiperazin-1-yl)methyl)-3-(trifluoromethyl)phenyl)-4-methyl-3-(pyridin-3-ylethynyl)benzamide (generated from structure)); Y078-DM1 (an antibody drug conjugate composed of a RET antibody (Y078) linked to a derivative of the cytotoxic agent maytansine); Y078-DM4 (an antibody drug conjugate composed of a RET antibody (Y078) linked to a derivative of the cytotoxic agent maytansine); ITRI-305 (D0N5TB, DIB003599); BLU-667 (((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide); BLU6864; DS-5010; GSK3179106; GSK3352589; NMS-E668; and TPX0046. Additional examples of a RET inhibitor are known in the art.

The phrase "dysregulation of a ROS1 gene, a ROS1 protein, or the expression or activity or level of any of the same" refers to a genetic mutation (e.g., a chromosomal translocation that results in the expression of a fusion protein including a ROS1 kinase domain and a fusion partner, a mutation in a ROS1 gene that results in the expression a ROS1 protein that includes a deletion of at least one amino acid as compared to a wildtype ROS1 protein, a mutation in a ROS1 gene that results in the expression of a ROS1 protein with one or more point mutations as compared to a wildtype ROS1 protein, a mutation in a ROS1 gene that results in the expression of a ROS1 protein with at least one inserted amino acid as compared to a wildtype ROS1 protein, a gene duplication that results in an increased level of ROS1 protein in a cell, or a mutation in a regulatory sequence (e.g., a promoter and/or enhancer) that results in an increased level of ROS1 protein in a cell), an alternative spliced version of a ROS1 mRNA that results in a ROS1 protein having a deletion of at least one amino acid in the ROS1 protein as compared to the wild-type ROS1 protein), or increased expression (e.g., increased levels) of a wildtype ROS1 protein in a mammalian cell due to aberrant cell signaling and/or dysregulated autocrine/paracrine signaling (e.g., as compared to a control non-cancerous cell). As another example, a dysregulation of a ROS1 gene, a ROS1 protein, or expression or activity, or level of any of the same, can be a mutation in a ROS1 gene that encodes a ROS1 protein that is constitutively active or has increased activity as compared to a protein encoded by a ROS1 gene that does not include the mutation. For example, a dysregulation of a ROS1 gene, a ROS1 protein, or expression or activity, or level of any of the same, can be the result of a gene or chromosome translocation which results in the expression of a fusion protein that contains a first portion of a ROS1 protein that includes a functional kinase domain, and a second portion of a partner protein (i.e., that is not ROS1). In some examples, dysregulation of a ROS1 gene, a ROS1 protein, or expression or activity or level of any of the same can be a result of a gene translocation of one ROS1 gene with another non-ROS1 gene.

Non-limiting examples of a ROS1 inhibitor include cabozantinib; certinib; crizotinib; DS-605; entrectinib (RXDX-101); lorlatinib (PF-06463922); an TPX-0005. Additional examples of a ROS1 inhibitor are known in the art.

The phrase "dysregulation of a trkA gene, a trkA protein, or the expression or activity or level of any of the same" refers to a genetic mutation (e.g., a chromosomal translocation that results in the expression of a fusion protein including a trkA kinase domain and a fusion partner, a mutation in a trkA gene that results in the expression a trkA protein that includes a deletion of at least one amino acid as compared to a wildtype trkA protein, a mutation in a trkA gene that results in the expression of a trkA protein with one or more point mutations as compared to a wildtype trkA protein, a mutation in a trkA gene that results in the expression of a trkA protein with at least one inserted amino acid as compared to a wildtype trkA protein, a gene duplication that results in an increased level of trkA protein in a cell, or a mutation in a regulatory sequence (e.g., a promoter and/or enhancer) that results in an increased level of trkA protein in a cell), an alternative spliced version of a trkA mRNA that results in a trkA protein having a deletion of at least one amino acid in the trkA protein as compared to the wild-type trkA protein), or increased expression (e.g., increased levels) of a wildtype trkA protein in a mammalian cell due to aberrant cell signaling and/or dysregulated autocrine/paracrine signaling (e.g., as compared to a control non-cancerous cell). As another example, a dysregulation of a trkA gene, a trkA protein, or expression or activity, or level of any of the same, can be a mutation in a trkA gene that encodes a trkA protein that is constitutively active or has increased activity as compared to a protein encoded by a trkA gene that does not include the mutation. For example, a dysregulation of a trkA gene, a trkA protein, or expression or activity, or level of any of the same, can be the result of a gene or chromosome translocation which results in the expression of a fusion protein that contains a first portion of a trkA protein that includes a functional kinase domain, and a second portion of a partner protein (i.e., that is not trkA). In some examples, dysregulation of a trkA gene, a trkA protein, or expression or activity or level of any of the same can be a result of a gene translocation of one trkA gene with another non-trkA gene.

The phrase "dysregulation of a trkB gene, a trkB protein, or the expression or activity or level of any of the same" refers to a genetic mutation (e.g., a chromosomal translocation that results in the expression of a fusion protein including a trkB kinase domain and a fusion partner, a mutation in a trkB gene that results in the expression a trkB protein that includes a deletion of at least one amino acid as compared to a wildtype trkB protein, a mutation in a trkB gene that results in the expression of a trkB protein with one or more point mutations as compared to a wildtype trkB protein, a mutation in a trkB gene that results in the expression of a trkB protein with at least one inserted amino acid as compared to a wildtype trkB protein, a gene duplication that results in an increased level of trkB protein in a cell, or a mutation in a regulatory sequence (e.g., a promoter and/or enhancer) that results in an increased level of trkB protein in a cell), an alternative spliced version of a trkB mRNA that results in a trkB protein having a deletion of at least one amino acid in the trkB protein as compared to the wild-type trkB protein), or increased expression (e.g., increased levels) of a wildtype trkB protein in a mammalian cell due to aberrant cell signaling and/or dysregulated autocrine/paracrine signaling (e.g., as compared to a control non-cancerous cell). As another example, a dysregulation of a trkB gene, a trkB protein, or expression or activity, or level of any of the same, can be a mutation in a trkB gene that encodes a trkB protein that is constitutively active or has increased activity as compared to a protein encoded by a trkB gene that does not include the mutation. For example, a dysregulation of a trkB gene, a trkB protein, or expression or activity, or level of any of the same, can be the result of a gene or chromosome translocation which results in the expression of a fusion protein that contains a first portion of a trkB protein that includes a functional kinase domain, and a second portion of a partner protein (i.e., that is not trkB). In some examples, dysregulation of a trkB gene, a trkB protein, or expression or activity or level of any of the same can be a result of a gene translocation of one trkB gene with another non-trkB gene.

The phrase "dysregulation of a trkC gene, a trkC protein, or the expression or activity or level of any of the same" refers to a genetic mutation (e.g., a chromosomal translocation that results in the expression of a fusion protein including a trkC kinase domain and a fusion partner, a mutation in a trkC gene that results in the expression a trkC protein that includes a deletion of at least one amino acid as compared to a wildtype trkC protein, a mutation in a trkC gene that results in the expression of a trkC protein with one or more point mutations as compared to a wildtype trkC protein, a mutation in a trkC gene that results in the expression of a trkC protein with at least one inserted amino acid as compared to a wildtype trkC protein, a gene duplication that results in an increased level of trkC protein in a cell, or a mutation in a regulatory sequence (e.g., a promoter and/or enhancer) that results in an increased level of trkC protein in a cell), an alternative spliced version of a trkC mRNA that results in a trkC protein having a deletion of at least one amino acid in the trkC protein as compared to the wild-type trkC protein), or increased expression (e.g., increased levels) of a wildtype trkC protein in a mammalian cell due to aberrant cell signaling and/or dysregulated autocrine/paracrine signaling (e.g., as compared to a control non-cancerous cell). As another example, a dysregulation of a trkC gene, a trkC protein, or expression or activity, or level of any of the same, can be a mutation in a trkC gene that encodes a trkC protein that is constitutively active or has increased activity as compared to a protein encoded by a trkC gene that does not include the mutation. For example, a dysregulation of a trkC gene, a trkC protein, or expression or activity, or level of any of the same, can be the result of a gene or chromosome translocation which results in the expression of a fusion protein that contains a first portion of a trkC protein that includes a functional kinase domain, and a second portion of a partner protein (i.e., that is not trkC). In some examples, dysregulation of a trkC gene, a trkC protein, or expression or activity or level of any of the same can be a result of a gene translocation of one trkC gene with another non-trkC gene.

Non-limiting examples of Trk (e.g., trkA, trkB, or trkC) inhibitors include 1-((3S,4R)-4-(3-fluorophenyl)-I-(2-methoxyethyl)pyrrolidin-3-yl)-3-(4-methyl-3-(2-methylpyrimidin-5-yl)-1-phenyl-IH-pyrazol-5-yl)urea; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)); afatinib; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); AR-256; AR-618; AR-772; AR-786; AZ-23 ((S)-5-Chloro-N2-(1-(5-fluoropyridin-2-yl)ethyl)-N4-(5-isopropoxy-1H-pyrazol-3-yl)pyrimidine-2,4-diamine); AZ623; AZ64; AZD6918; cabozantinib (N-(4-((6,7-Dimethoxyquinolin-4-yl)oxy)phenyl)-N'-(4-fluorophenyl)cyclopropane-1,1-dicarboxamide); crizotinib; dabrafenib; danusertib (PHA-739358); dovitinib (4-amino-5-fluoro-3-[6-(4-methylpiperazin-l-yl)-1H-benzimidazol-2-yl]quinolin-2(1H)-one mono 2-hydroxypropanoate hydrate); DS-6051; entrectinib; erlotinib; gefitinib; GNF-5837; GNF-8625 ((R)-1-(6-(6-(2-(3-fluorophenyl)pyrrolidin-1-yl)imidazo[1,2-b]pyridazin-3-yl)-[2,4'-bipyridin]-2'-yl)piperidin-4-ol); Gö 6976 (5,6,7,13-tetrahydro-13-methyl-5-oxo-12H-indolo[2,3-a]pyrrolo[3,4-c]carbazole-12-propanenitrile); GTx-186; GW441756 ((3Z)-3-[(1-methylindol-3-yl)methylidene]-1H-pyrrolo[3,2-b]pyridin-2-one); imatinib; K252a ((9S-(9a,10 (3,12a))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-l-one); lapatinib; lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one); LOXO-101; MGCD516; milciclib (PHA-848125AC); nilotinib; ONO-5390556; pazopanib; PLX7486; regorafenib (4-[4-({[4-Chloro-3-(trifluoromethyl)phenyl]carbamoyl}amino)-3-fluorophenoxy]-N-methylpyridine-2-carboxamide hydrate); RXDX101; sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); sunitinib; TPX-0005; trastuzumab; TSR-011; and VM-902A. Other examples of Trk inhibitors are known in the art.

The phrase "dysregulation of a VEGFR-1 gene, a VEGFR-1 protein, or the expression or activity or level of any of the same" refers to a genetic mutation (e.g., a chromosomal translocation that results in the expression of a fusion protein including a VEGFR-1 kinase domain and a fusion partner, a mutation in a VEGFR-1 gene that results in the expression a VEGFR-1 protein that includes a deletion of at least one amino acid as compared to a wildtype VEGFR-1 protein, a mutation in a VEGFR-1 gene that results in the expression of a VEGFR-1 protein with one or more point mutations as compared to a wildtype VEGFR-1 protein, a mutation in a VEGFR-1 gene that results in the expression of a VEGFR-1 protein with at least one inserted amino acid as compared to a wildtype VEGFR-1 protein, a gene duplication that results in an increased level of VEGFR-1 protein in a cell, or a mutation in a regulatory sequence (e.g., a promoter and/or enhancer) that results in an increased level of VEGFR-1 protein in a cell), an alternative spliced version of a VEGFR-1 mRNA that results in a VEGFR-1 protein having a deletion of at least one amino acid in the VEGFR-1 protein as compared to the wild-type VEGFR-1 protein), or increased expression (e.g., increased levels) of a wildtype VEGFR-1 protein in a mammalian cell due to aberrant cell signaling and/or dysregulated autocrine/paracrine signaling (e.g., as compared to a control non-cancerous cell). As another example, a dysregulation of a VEGFR-1 gene, a VEGFR-1 protein, or expression or activity, or level of any of the same, can be a mutation in a VEGFR-1 gene that encodes a VEGFR-1 protein that is constitutively active or has increased activity as compared to a protein encoded by a VEGFR-1 gene that does not include the mutation. For example, a dysregulation of a VEGFR-1 gene, a VEGFR-1 protein, or expression or activity, or level of any of the same, can be the result of a gene or chromosome translocation which results in the expression of a fusion protein that contains a first portion of a VEGFR-1 protein that includes a functional kinase domain, and a second portion of a partner protein (i.e., that is not VEGFR-1). In some examples, dysregulation of a VEGFR-1 gene, a VEGFR-1 protein, or expression or activity or level of any of the same can be a result of a gene translocation of one VEGFR-1 gene with another non-VEGFR-1 gene.

Non-limiting examples of a VEGFR-1 inhibitor include BMS690514 ((3R,4R)-4-Amino-1-((4-((3-methoxyphenyl)amino)pyrrolo[2,1-f][1,2,4]triazin-5-yl)methyl)piperidin-3-ol); axitinib; motesanib (AMG706, CAS 857876-30-3, N-(2,3-dihydro-3,3-dimethyl-1H-indol-6-yl)-2-[(4-pyridinylmethyl)amino]-3-pyridinecarboxamide); nintedanib (BIBF1120, CAS 928326-83-4); pazopanib; and vatalanib (PTK787, CAS 212141-51-0). Additional examples of a VEGFR-1 inhibitor are known in the art.

The phrase "dysregulation of a VEGFR-2 gene, a VEGFR-2 protein, or the expression or activity or level of any of the same" refers to a genetic mutation (e.g., a chromosomal translocation that results in the expression of a fusion protein including a VEGFR-2 kinase domain and a fusion partner, a mutation in a VEGFR-2 gene that results in the expression a VEGFR-2 protein that includes a deletion of at least one amino acid as compared to a wildtype VEGFR-2 protein, a mutation in a VEGFR-2 gene that results in the expression of a VEGFR-2 protein with one or more point mutations as compared to a wildtype VEGFR-2 protein, a mutation in a VEGFR-2 gene that results in the expression of a VEGFR-2 protein with at least one inserted amino acid as compared to a wildtype VEGFR-2 protein, a gene duplication that results in an increased level of VEGFR-2 protein in a cell, or a mutation in a regulatory sequence (e.g., a promoter and/or enhancer) that results in an increased level of VEGFR-2 protein in a cell), an alternative spliced version of a VEGFR-2 mRNA that results in a VEGFR-2 protein having a deletion of at least one amino acid in the VEGFR-2 protein as compared to the wild-type VEGFR-2 protein), or increased expression (e.g., increased levels) of a wildtype VEGFR-2 protein in a mammalian cell due to aberrant cell signaling and/or dysregulated autocrine/paracrine signaling (e.g., as compared to a control non-cancerous cell). As another example, a dysregulation of a VEGFR-2 gene, a VEGFR-2 protein, or expression or activity, or level of any of the same, can be a mutation in a VEGFR-2 gene that encodes a VEGFR-2 protein that is constitutively active or has increased activity as compared to a protein encoded by a VEGFR-2 gene that does not include the mutation. For example, a dysregulation of a VEGFR-2 gene, a VEGFR-2 protein, or expression or activity, or level of any of the same, can be the result of a gene or chromosome translocation which results in the expression of a fusion protein that contains a first portion of a VEGFR-2 protein that includes a functional kinase domain, and a second portion of a partner protein (i.e., that is not VEGFR-2). In some examples, dysregulation of a VEGFR-2 gene, a VEGFR-2 protein, or expression or activity or level of any of the same can be a result of a gene translocation of one VEGFR-2 gene with another non-VEGFR-2 gene.

Non-limiting examples of a VEGFR-2 inhibitor include BMS690514 ((3R,4R)-4-Amino-1-((4-((3-methoxyphenyl)amino)pyrrolo[2,1-f][1,2,4]triazin-5-yl)methyl)piperidin-3-ol); hypothemycin; glesatinib (MGCD265); sitravatinib (MGCD-516); axitinib; telatinib (BAY57-9352, CAS 332012-40-5); motesanib (AMG706, CAS 857876-30-3, N-(2,3-dihydro-3,3-dimethyl-1H-indol-6-yl)-2-[(4-pyridinylmethyl)amino]-3-pyridinecarboxamide); nintedanib (BIBF1120, CAS 928326-83-4); pazopanib; sorafenib (Nexavar®); and vatalanib (PTK787, CAS 212141-51-0). Additional examples of a VEGFR-2 inhibitor are known in the art.

The phrase "dysregulation of a VEGFR-3 gene, a VEGFR-3 protein, or the expression or activity or level of any of the same" refers to a genetic mutation (e.g., a chromosomal translocation that results in the expression of a fusion protein including a VEGFR-3 kinase domain and a fusion partner, a mutation in a VEGFR-3 gene that results in the expression a VEGFR-3 protein that includes a deletion of at least one amino acid as compared to a wildtype VEGFR-3 protein, a mutation in a VEGFR-3 gene that results in the expression of a VEGFR-3 protein with one or more point mutations as compared to a wildtype VEGFR-3 protein, a mutation in a VEGFR-3 gene that results in the expression of a VEGFR-3 protein with at least one inserted amino acid as compared to a wildtype VEGFR-3 protein, a gene duplication that results in an increased level of VEGFR-3 protein in a cell, or a mutation in a regulatory sequence (e.g., a promoter and/or enhancer) that results in an increased level of VEGFR-3 protein in a cell), an alternative spliced version of a VEGFR-3 mRNA that results in a VEGFR-3 protein having a deletion of at least one amino acid in the VEGFR-3 protein as compared to the wild-type VEGFR-3 protein), or increased expression (e.g., increased levels) of a wildtype VEGFR-3 protein in a mammalian cell due to aberrant cell signaling and/or dysregulated autocrine/paracrine signaling (e.g., as compared to a control non-cancerous cell). As another example, a dysregulation of a VEGFR-3 gene, a VEGFR-3 protein, or expression or activity, or level of any of the same, can be a mutation in a VEGFR-3 gene that encodes a VEGFR-3 protein that is constitutively active or has increased activity as compared to a protein encoded by a VEGFR-3 gene that does not include the mutation. For example, a dysregulation of a VEGFR-3 gene, a VEGFR-3 protein, or expression or activity, or level of any of the same, can be the result of a gene or chromosome translocation which results in the expression of a fusion protein that contains a first portion of a VEGFR-3 protein that includes a functional kinase domain, and a second portion of a partner protein (i.e., that is not VEGFR-3). In some examples, dysregulation of a VEGFR-3 gene, a VEGFR-3 protein, or expression or activity or level of any of the same can be a result of a gene translocation of one VEGFR-3 gene with another non-VEGFR-3 gene.

Non-limiting examples of a VEGFR-3 inhibitor include BMS690514 ((3R,4R)-4-Amino-1-((4-((3-methoxyphenyl)amino)pyrrolo[2,1-f][1,2,4]triazin-5-yl)methyl)piperidin-3-ol); sitravatinib (MGCD-516); axitinib; telatinib (BAY57-9352, CAS 332012-40-5); motesanib (AMG706, CAS 857876-30-3, N-(2,3-dihydro-3,3-dimethyl-1H-indol-6-yl)-2-[(4-pyridinylmethyl)amino]-3-pyridinecarboxamide); nintedanib (BIBF1120, CAS 928326-83-4); pazopanib; and vatalanib (PTK787, CAS 212141-51-0). Additional examples of a VEGFR-3 inhibitor are known in the art.

Non-limiting examples of VEGFR (e.g., VEGFR-1, VEGFR-2, or VEGFR-3) include apatinib (YN968D1, CAS 811803-05-1); Aflibercept (Eylea®); axitinib; Bevacizumab; BHG712 (4-Methyl-3-[[1-methyl-6-(3-pyridinyl)-1H-pyrazolo[3,4-d]pyrimidin-4-yl]amino]-N-[3-(trifluoromethyl)phenyl]-benzamide, CAS 940310-85-0); BMS38703 (N-[5-[[[5-(1,1-Dimethylethyl)-2-oxazolyl]methyl]thio]-2-thiazolyl]-4-piperidinecarboxamide, CAS 345627-80-7); BMS690514 ((3R,4R)-4-Amino-1-((4-((3-methoxyphenyl)amino)pyrrolo[2,1-f][1,2,4]triazin-5-yl)methyl)piperidin-3-ol); brivanib (BMS-540215, CAS 649735-46-6); cabozantinib (XL184, CAS 849217-68-1); cediranib (AZD2171, CAS 288383-20-1); foretinib (GSK1363089); fovitinib dilactic acid (TK1258, CAS 852433-84-2); glesatinib (MGCD265); hypothemycin; imatinib (Gleevec®); lenvatinib; lestaurtinib (CAS 111358-88-4); linfanib (ABT869, CAS 796967-16-3); Linifanib (ABT-869); motesanib (AMG706, CAS 857876-30-3, N-(2,3-dihydro-3,3-dimethyl-1H-indol-6-yl)-2-[(4-pyridinylmethyl)amino]-3-pyridinecarboxamide); nintedanib (BIBF1120, CAS 928326-83-4); pazopanib; ponatinib (AP24534, CAS 943319-70-8); regorafenib (BAY73-4506, CAS 755037-03-7); Semaxinib (SU5416); sitravatinib (MGCD-516); sorafenib (Nexavar®); sunitinib; telatinib (BAY57-9352, CAS 332012-40-5); tesevatinib (N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine, XL647, CAS 781613-23-8); tivozanib (AV951, CAS 475108-18-0); vandetanib; and vatalanib (PTK787, CAS 212141-51-0). Other examples of a VEGFR inhibitor are known in the art.

The phrase "dysregulation of a aromatase gene, an aromatase protein, or the expression or activity or level of any of the same" refers to a genetic mutation (e.g., a mutation in an aromatase gene that results in the expression an aromatase protein that includes a deletion of at least one amino acid as compared to a wildtype aromatase protein, a mutation in an aromatase gene that results in the expression of an aromatase protein with one or more point mutations as compared to a wildtype aromatase protein, a mutation in an aromatase gene that results in the expression of an aromatase protein with at least one inserted amino acid as compared to a wildtype aromatase protein, a gene duplication that results in an increased level of aromatase protein in a cell, or a mutation in a regulatory sequence (e.g., a promoter and/or enhancer) that results in an increased level of aromatase protein in a cell), an alternative spliced version of an aromatase mRNA that results in an aromatase protein having a deletion of at least one amino acid in the aromatase protein as compared to the wild-type aromatase protein), or increased expression (e.g., increased levels) of a wildtype aromatase in a mammalian cell due to aberrant cell signaling and/or dysregulated autocrine/paracrine signaling (e.g., as compared to a control non-cancerous cell). As another example, a dysregulation of an aromatase gene, an aromatase protein, or expression or activity, or level of any of the same, can be a mutation in an aromatase gene that encodes an aromatase protein that is constitutively active or has increased activity as compared to a protein encoded by an aromatase gene that does not include the mutation.

Non-limiting examples of an aromatase inhibitor include aminoglutethimide, Arimidex (anastrozole), Aromasin (exemestane), Femara (letrozole), Teslac (testolactone), formestane, and vorozole. Additional examples of an aromatase inhibitor are known in the art.

The phrase "dysregulation of a EHMT2 gene, an EHMT2 protein, or the expression or activity or level of any of the same" refers to a genetic mutation (e.g., a mutation in an EHMT2 gene that results in the expression an EHMT2 protein that includes a deletion of at least one amino acid as compared to a wildtype EHMT2 protein, a mutation in an EHMT2 gene that results in the expression of an EHMT2 protein with one or more point mutations as compared to a wildtype EHMT2 protein, a mutation in an EHMT2 gene that results in the expression of an EHMT2 protein with at least one inserted amino acid as compared to a wildtype EHMT2 protein, a gene duplication that results in an increased level of EHMT2 protein in a cell, or a mutation in a regulatory sequence (e.g., a promoter and/or enhancer) that results in an increased level of EHMT2 protein in a cell), an alternative spliced version of an EHMT2 mRNA that results in an EHMT2 protein having a deletion of at least one amino acid in the EHMT2 protein as compared to the wild-type EHMT2 protein), or increased expression (e.g., increased levels) of a wildtype EHMT2 in a mammalian cell due to aberrant cell signaling and/or dysregulated autocrine/paracrine signaling (e.g., as compared to a control non-cancerous cell). As another example, a dysregulation of an EHMT2 gene, an EHMT2 protein, or expression or activity, or level of any of the same, can be a mutation in an EHMT2 gene that encodes an EHMT2 protein that is constitutively active or has increased activity as compared to a protein encoded by an EHMT2 gene that does not include the mutation.

Non-limiting examples of an EHMT2 inhibitor include 2-(4,4-difluoropiperidin-1-yl)-N-(1-isopropylpiperidin-4-yl)-6-methoxy-7-(3-(pyrrolidin-1-yl)propoxy)quinazolin-4-amine; 2-(4-isopropyl-1,4-diazepan-1-yl)-N-(1-isopropylpiperidin-4-yl)-6-methoxy-7-(3-(piperidin-1-yl)propoxy) quinazolin-4-amine; A-366; BIX-01294 (BIX); BIX-01338; BRD4770; DCG066; EZM8266; N-(1-isopropylpiperidin-4-yl)-6-methoxy-2-(4-methyl-1,4-diazepan-1-yl)-7-(3-(piperidin-1-yl)propoxy)quinazolin-4-amine; UNC0224; UNC0321; UNC0631; UNC0638 (2-cyclohexyl-6-methoxy-N-[1-(1-methylethyl)-4-piperidinyl]-7-[3-(1-pyrrolidinyl)propoxy]-4-quinazolinamine); UNC0642 (2-(4,4-Difluoro-1-piperidinyl)-6-methoxy-N-[1-(1-methylethyl)-4-piperidinyl]-7-[3-(1-pyrrolidinyl)propoxy]-4-quinazolinamine); and UNC0646. Additional examples of an EHMT2 inhibitor are known in the art.

The phrase "dysregulation of a RAC1 gene, an RAC1 protein, or the expression or activity or level of any of the same" refers to a genetic mutation (e.g., a mutation in an RAC1 gene that results in the expression an RAC1 protein that includes a deletion of at least one amino acid as compared to a wildtype RAC1 protein, a mutation in an RAC1 gene that results in the expression of an RAC1 protein with one or more point mutations as compared to a wildtype RAC1 protein, a mutation in an RAC1 gene that results in the expression of an RAC1 protein with at least one inserted amino acid as compared to a wildtype RAC1 protein, a gene duplication that results in an increased level of RAC1 protein in a cell, or a mutation in a regulatory sequence (e.g., a promoter and/or enhancer) that results in an increased level of RAC1 protein in a cell), an alternative spliced version of an RAC1 mRNA that results in an RAC1 protein having a deletion of at least one amino acid in the RAC1 protein as compared to the wild-type RAC1 protein), or increased expression (e.g., increased levels) of a wildtype RAC1 in a mammalian cell due to aberrant cell signaling and/or dysregulated autocrine/paracrine signaling (e.g., as compared to a control non-cancerous cell). As another example, a dysregulation of an RAC1 gene, an RAC1 protein, or expression or activity, or level of any of the same, can be a mutation in an RAC1 gene that encodes an RAC1 protein that is constitutively active or has increased activity as compared to a protein encoded by an RAC1 gene that does not include the mutation.

Non-limiting examples of an RAC1 inhibitor include azathioprine; EHop-016; EHT 1864; and NSC23766. Additional examples of an RAC1 inhibitor are known in the art.

The phrase "dysregulation of a SOS1 gene, an SOS1 protein, or the expression or activity or level of any of the same" refers to a genetic mutation (e.g., a mutation in an SOS1 gene that results in the expression an SOS1 protein that includes a deletion of at least one amino acid as compared to a wildtype SOS1 protein, a mutation in an SOS1 gene that results in the expression of an SOS1 protein with one or more point mutations as compared to a wildtype SOS1 protein, a mutation in an SOS1 gene that results in the expression of an SOS1 protein with at least one inserted amino acid as compared to a wildtype SOS1 protein, a gene duplication that results in an increased level of SOS1 protein in a cell, or a mutation in a regulatory sequence (e.g., a promoter and/or enhancer) that results in an increased level of SOS1 protein in a cell), an alternative spliced version of an SOS1 mRNA that results in an SOS1 protein having a deletion of at least one amino acid in the SOS1 protein as compared to the wild-type SOS1 protein), or increased expression (e.g., increased levels) of a wildtype SOS1 in a mammalian cell due to aberrant cell signaling and/or dysregulated autocrine/paracrine signaling (e.g., as compared to a control non-cancerous cell). As another example, a dysregulation of an SOS1 gene, an SOS1 protein, or expression or activity, or level of any of the same, can be a mutation in an SOS1 gene that encodes an SOS1 protein that is constitutively active or has increased activity as compared to a protein encoded by an SOS1 gene that does not include the mutation.

Non-limiting examples of an SOS1 inhibitor are described in PCT Publication No. 2018/115380, incorporated herein by reference. Additional examples of an SOS1 inhibitor are known in the art.

Non-limiting examples of multi-kinase inhibitors (MKIs) include dasatinib and sunitinib.

In some embodiments, the treatment period is at least 7 days (e.g., at least or about 8 days, at least or about 9 days, at least or about 10 days, at least or about 11 days, at least or about 12 days, at least or about 13 days, at least or about 14 days, at least or about 15 days, at least or about 16 days, at least or about 17 days, at least or about 18 days, at least or about 19 days, at least or about 20 days, at least or about 21 days, at least or about 22 days, at least or about 23 days, at least or about 24 days, at least or about 25 days, at least or about 26 days, at least or about 27 days, at least or about 28 days, at least or about 29 days, or at least or about 30 days), the FGFR inhibitor is JNJ-42756493, and a daily dose of about 6 mg to about 12 mg (e.g., about 6 mg to about 11 mg, about 10 mg, about 9 mg, about 8 mg, or about 7 mg; about 7 mg to about 12 mg, about 11 mg, about 10 mg, about 9 mg, or about 8 mg; about 8 mg to about 12 mg, about 11 mg, about 10 mg, or about 9 mg; about 9 mg to about 12 mg, about 11 mg, or about 10 mg; about 10 mg to about 12 mg or about 11 mg; or about 11 mg to about 12 mg) of the first FGFR inhibitor is administered to the patient over the treatment period.

In some embodiments, the treatment period is at least 21 days (e.g., at least or about 22 days, at least or about 23 days, at least or about 24 days, at least or about 25 days, at least or about 26 days, at least or about 27 days, at least or about 28 days, at least or about 29 days, at least or about 30 days, at least or about 31 days, at least or about 32 days, at least or about 33 days, at least or about 34 days, at least or about 35 days, at least or about 36 days, at least or about 37 days, at least or about 38 days, at least or about 39 days, or at least or about 40 days) the first FGFR is BGJ398, and a daily dose of about 50 mg to about 125 mg (e.g., about 50 mg to about 120 mg, about 115 mg, about 110 mg, about 105 mg, about 100 mg, about 95 mg, about 90 mg, about 85 mg, about 80 mg, about 75 mg, about 70 mg, about 65 mg, about 60 mg, or about 55 mg; about 55 mg to about 120 mg, about 115 mg, about 110 mg, about 105 mg, about 100 mg, about 95 mg, about 90 mg, about 85 mg, about 80 mg, about 75 mg, about 70 mg, about 65 mg, or about 60 mg; about 60 mg to about 120 mg, about 115 mg, about 110 mg, about 105 mg, about 100 mg, about 95 mg, about 90 mg, about 85 mg, about 80 mg, about 75 mg, about 70 mg, or about 65 mg; about 65 mg to about 120 mg, about 115 mg, about 110 mg, about 105 mg, about 100 mg, about 95 mg, about 90 mg, about 85 mg, about 80 mg, about 75 mg, or about 70 mg; about 70 mg to about 120 mg, about 115 mg, about 110 mg, about 105 mg, about 100 mg, about 95 mg, about 90 mg, about 85 mg, about 80 mg, or about 75 mg; about 75 mg to about 120 mg, about 115 mg, about 110 mg, about 105 mg, about 100 mg, about 95 mg, about 90 mg, about 85 mg, or about 80 mg; about 80 mg to about 120 mg, about 115 mg, about 110 mg, about 105 mg, about 100 mg, about 95 mg, about 90 mg, or about 85 mg; about 85 mg to about 120 mg, about 115 mg, about 110 mg, about 105 mg, about 100 mg, about 95 mg, or about 90 mg; about 90 mg to about 120 mg, about 115 mg, about 110 mg, about 105 mg, about 100 mg, or about 95 mg; about 95 mg to about 120 mg, about 115 mg, about 110 mg, about 105 mg, or about 100 mg; about 100 mg to about 120 mg, about 115 mg, about 110 mg, or about 105 mg; about 105 mg to about 120 mg, about 115 mg, or about 110 mg; about 110 mg to about 120 mg or about 115 mg; or about 115 mg to about 120 mg) of the first FGFR inhibitor is administered to the patient over the treatment period.

Also provided are methods of treating a FGFR-associated cancer in a patient, which include: (a) administering to a patient identified or diagnosed as having an FGFR-associated cancer one or more doses of a first FGFR inhibitor over a treatment period; (b) determining the level of phosphate in a biological sample comprising blood, serum, or plasma obtained from the patient after the treatment period; (c) selecting a patient having an elevated level of phosphate in the biological sample as compared to a reference level of phosphate; and (d) ceasing administration of the first FGFR inhibitor and initiating administration of a therapeutically effective amount of a compound as described herein or a pharmaceutically acceptable salt or solvate thereof, or a pharmaceutical composition containing the same, to the selected patient. In certain embodiments, the treatment period is at least 7 days. In other embodiments, the treatment period is at least 21 days. In certain embodiments, the first FGFR inhibitor is JNJ-42756493 or BGJ398. By way of example, the first FGFR inhibitor can be JNJ-42756493 and a daily dose of 6 mg to 12 mg of the first FGFR inhibitor is administered to the patient over the treatment period (e.g., 7 days). As another example, the first FGFR inhibitor can be BGJ398 and a daily dose of 50 mg to 125 mg of the first FGFR inhibitor is administered to the patient over the treatment period (e.g., 21 days). In certain embodiments, the patient is administered a therapeutically effective amount of a phosphate binder over the treatment period. In certain embodiments, step (d) further comprises ceasing administration of the phosphate binder to the selected patient. In certain embodiments, step (d) further includes administering a decreased dose of the phosphate binder to the selected patient relative to the dose of the phosphate binder administered to the patient over the treatment period. JNJ-42756493 (erdafitinib) is also known as JNJ-493 and has the following systematic name, N1-(3,5-dimethoxyphenyl)-N2-isopropyl-N1-(3-(1-methyl-1H-pyrazol-4-yl)quinoxalin-6-yl)ethane-1,2-diamine, and the following structure:

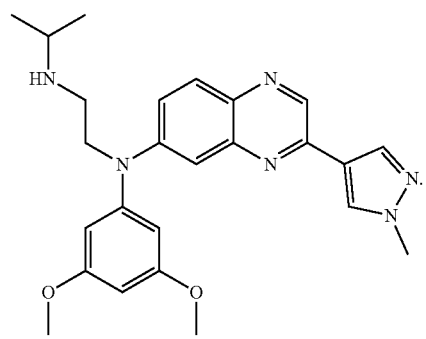 [SMILES: COc1cc(OC)cc(N(CCNC(C)C)c2ccc3ncc(-c4cnn(C)c4)nc3c2)c1]

BGJ398 (infigratinib) has the following systematic name, 3-(2,6-dichloro-3,5-dimethoxyphenyl)-1-(6-((4-(4-ethylpiperazin-1-yl)phenyl)amino)pyrimidin-4-yl)-1-methylurea, and the following chemical structure:

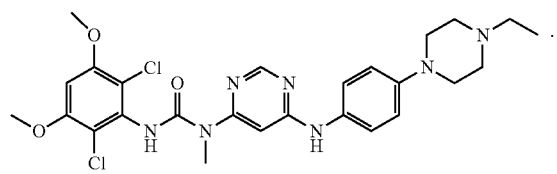 [SMILES: CCN1CCN(c2ccc(Nc3cc(N(C)C(=O)Nc4c(Cl)c(OC)cc(OC)c4Cl)ncn3)cc2)CC1]

Also provided are methods of increasing the time of remission of a FGFR-associated cancer in a patient that include (a) selecting, identifying, or diagnosing a patient as having a FGFR-associated cancer (e.g., any of the FGFR-associated cancers described herein), and (b) administering a therapeutically effective amount of a compound of Formula I (e.g., any of the exemplary compounds described herein), or a pharmaceutically acceptable salt or solvate thereof. Also provided are methods of increasing the time of remission of a FGFR-associated cancer in a patient that include administering a therapeutically effective amount of a compound of Formula I (e.g., any of the exemplary compounds described herein), or a pharmaceutically acceptable salt or solvate thereof to a patient having a FGFR-associated cancer (e.g., any of the exemplary FGFR-associated cancers described herein).

In some examples of any of the methods of increasing the time of remission of a FGFR-associated cancer in a patient, the increase in the time of remission is compared to a control patient (e.g., a patient or a population of patients having the same or a similar type of FGFR-associated cancer). In some examples, the patient is not yet in remission. In other examples, the patient is already in remission. In some examples, the increase in remission is a statistically significant increase. In some examples, the increase in the time of remission is about 1 day to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, about 1 month, or about 2 weeks; about 2 weeks to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, or about 1 month; about 1 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, or about 2 months; about 2 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, or about 4 months; about 4 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, or about 6 months; about 6 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, or about 8 months; about 8 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, or about 10 months; about 10 month to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, or about 1 year; about 1 year to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, or about 1.5 years; about 1.5 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, to about 2 years; about 2 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, or about 2.5 years; about 2.5 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, or about 3 years; about 3 years to about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, or about 3.5 years; about 3.5 years to about 10 years, about 9.5 years, about 9 years, about 8.5 years, about 8 years, about 7.5 years, about 7 years, about 6.5 years, about 6 years, about 5.5 years, about 5 years, about 4.5 years, or about 4 years; about 4 years to about 10 years, about 9.5 years, about 9 years, about 8.5 years, about 8 years, about 7.5 years, about 7 years, about 6.5 years, about 6 years, about 5.5 years, about 5 years, or about 4.5 years; about 4.5 years to about 10 years, about 9.5 years, about 9 years, about 8.5 years, about 8 years, about 7.5 years, about 7 years, about 6.5 years, about 6 years, about 5.5 years, or about 5 years; about 5 years to about 10 years, about 9.5 years, about 9 years, about 8.5 years, about 8 years, about 7.5 years, about 7 years, about 6.5 years, about 6 years, or about 5.5 years; about 5.5 years to about 10 years, about 9.5 years, about 9 years, about 8.5 years, about 8 years, about 7.5 years, about 7 years, about 6.5 years, or about 6 years; about 6 years to about 10 years, about 9.5 years, about 9 years, about 8.5 years, about 8 years, about 7.5 years, about 7 years, or about 6.5 years; about 6.5 years to about 10 years, about 9.5 years, about 9 years, about 8.5 years, about 8 years, about 7.5 years, or about 7 years; about 7 years to about 10 years, about 9.5 years, about 9 years, about 8.5 years, about 8 years, or about 7.5 years; about 7.5 years to about 10 years, about 9.5 years, about 9 years, about 8.5 years, or about 8 years; about 8 years to about 10 years, about 9.5 years, about 9 years, or about 8.5 years; about 8.5 years to about 10 years, about 9.5 years, or about 9 years; about 9 years to about 10 years or about 9.5 years; or about 9.5 years to about 10 years (e.g., compared to a control patient, e.g., a patient or a population of patients having the same or a similar type of FGFR-associated cancer).

Also provided is a compound of Formula I or pharmaceutically acceptable salt or solvate thereof for use in increasing the time of remission of a FGFR-associated cancer in a patient. Also provided is the use of a compound of Formula I or a pharmaceutically acceptable salt or solvate thereof in the manufacture of a medicament for increasing the time of remission of a FGFR-associated cancer in a patient.

Methods for determining whether or not a patient is in remission are known by those skilled in the art. For example, a PET scan, MRI, CT scan, ultrasound, and X-ray of the patient's body may be obtained, and such data can be used to determine whether or not a patient is in remission. In some examples, diagnostic tests can be performed on samples from a patient (e.g., a blood sample or a biopsy) to determine whether or not the patient is still in remission.

Also provided are methods of increasing the time of survival of a patient having a FGFR-associated cancer that include: selecting, diagnosing, or identifying a patient as having a FGFR-associated cancer; and administering to a subject selected, diagnosed, or identified as having a FGFR-associated cancer a therapeutically effective amount of a compound of Formula I or a pharmaceutically acceptable salt or solvate thereof. Also provided are methods of increasing the time of survival of a patient having a FGFR-associated cancer that include administering to a subject having a FGFR-associated cancer a therapeutically effective amount of a compound of Formula I or a pharmaceutically acceptable salt or solvate thereof. In some embodiments of any of the methods of increasing the time of survival of a subject having a FGFR-associated cancer, the increase in the time of survival is compared to a control patient (e.g., a patient or a population of patients having the same or a similar type of FGFR-associated cancer). In some examples, the patient can have an early stage of a FGFR-associated cancer (e.g., Stage 1 or 2). In some embodiments, the patient can have a late stage of a FGFR-associated cancer (e.g., Stage 3 or 4). In some examples, the increase in the time of survival is a statistically significant increase. In some examples, the increase in the time of survival is about 1 day to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, about 1 month, or about 2 weeks; about 2 weeks to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, about 2 months, or about 1 month; about 1 month to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, about 4 months, or about 2 months; about 2 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, about 8 months, about 6 months, or about 4 months; about 4 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, or about 6 months; about 6 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, about 10 months, or about 8 months; about 8 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, about 1 year, or about 10 months; about 10 months to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, about 1.5 years, or about 1 year; about 1 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, about 2 years, or about 1.5 years; about 1.5 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, about 2.5 years, or about 2 years; about 2 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, about 3 years, or about 2.5 years; about 2.5 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, about 3.5 years, or about 3 years; about 3 year to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, about 4 years, or about 3.5 years; about 3.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, about 4.5 years, or about 4 years; about 4 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, about 5 years, or about 4.5 years; about 4.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, about 5.5 years, or about 5 years; about 5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, about 6 years, or about 5.5 years; about 5.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, about 6.5 years, or about 6 years; about 6 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, about 7 years, or about 6.5 years; about 6.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, about 7.5 years, or about 7 years; about 7 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, about 8 years, or about 7.5 years; about 7.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, about 8.5 years, or about 8 years; about 8 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, about 9 years, or about 8.5 years; about 8.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, about 9.5 years, or about 9 years; about 9 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, about 10 years, or about 9.5 years; about 9.5 years to about 40 years, about 38 years, about 36 years, about 34 years, about 32 years, about 30 years, about 28 years, about 26 years, about 24 years, about 22 years, about 20 years, about 18 years, about 16 years, about 14 years, about 12 years, or about 10 years; about 10 years to about 40 years, about 38 years, about 36 years, about 34 years, about 32 years, about 30 years, about 28 years, about 26 years, about 24 years, about 22 years, about 20 years, about 18 years, about 16 years, about 14 years, or about 12 years; about 12 years to about 40 years, about 38 years, about 36 years, about 34 years, about 32 years, about 30 years, about 28 years, about 26 years, about 24 years, about 22 years, about 20 years, about 18 years, about 16 years, or about 14 years; about 14 years to about 40 years, about 38 years, about 36 years, about 34 years, about 32 years, about 30 years, about 28 years, about 26 years, about 24 years, about 22 years, about 20 years, about 18 years, or about 16 years; about 16 years to about 40 years, about 38 years, about 36 years, about 34 years, about 32 years, about 30 years, about 28 years, about 26 years, about 24 years, about 22 years, about 20 years, or about 18 years; about 18 years to about 40 years, about 38 years, about 36 years, about 34 years, about 32 years, about 30 years, about 28 years, about 26 years, about 24 years, about 22 years, or about 20 years; about 20 years to about 40 years, about 38 years, about 36 years, about 34 years, about 32 years, about 30 years, about 28 years, about 26 years, about 24 years, or about 22 years; about 22 years to about 40 years, about 38 years, about 36 years, about 34 years, about 32 years, about 30 years, about 28 years, about 26 years, or about 24 years; about 24 years to about 40 years, about 38 years, about 36 years, about 34 years, about 32 years, about 30 years, about 28 years, or about 26 years; about 26 years to about 40 years, about 38 years, about 36 years, about 34 years, about 32 years, about 30 years, or about 28 years; about 28 years to about 40 years, about 38 years, about 36 years, about 34 years, about 32 years, or about 30 years; about 30 years to about 40 years, about 38 years, about 36 years, about 34 years, or about 32 years; about 32 years to about 40 years, about 38 years, about 36 years, or about 34 years; about 34 years to about 40 years, about 38 years, or about 36 years; about 36 years to about 40 years or about 38 years; or about 38 years to about 40 years (e.g., compared to a control patient, e.g., a patient or a population of patients having the same or a similar type of FGFR-associated cancer).

Also provided is the use of a compound of Formula I or a pharmaceutically acceptable salt or solvate thereof for increasing the time of survival of a patient having a FGFR-associated cancer. Also provided is the use of a compound of Formula I or a pharmaceutically acceptable salt or solvate thereof for the manufacture of a medicament for increasing the time of survival of a patient having a FGFR-associated cancer.

Also provided are methods of increasing sensitivity of a resistant cancer cell to an anti-cancer drug that include: selecting, identifying, or diagnosing a patient as having a resistant cancer cell (e.g., a resistant FGFR-associated cancer cell, e.g., a cancer cell identified as having one or more of the point mutations listed in Table BE), and administering to the selected, identified, or diagnosed subject a therapeutically effective amount of a compound of Formula I or a pharmaceutically acceptable salt or solvate thereof. Also provided are methods of increasing sensitivity of a resistant cancer cell to an anti-cancer drug that include administering to a patient having a resistant cancer cell to an anti-cancer drug a therapeutically effective amount of a compound of Formula I or a pharmaceutically acceptable salt or solvate thereof. Some embodiments of any of these methods further include administering the anti-cancer drug to the patient. In such examples, the anti-cancer drug can be co-administered with the compound of Formula I or a pharmaceutically acceptable salt or solvate thereof. In some examples, the anti-cancer drug can be administered at substantially the same time as the compound of Formula I or a pharmaceutically acceptable salt or solvate thereof. In some examples, a first dose of the compound of Formula I is administered prior to the first dose of the anti-cancer compound. In some examples, a first dose of the anti-cancer compound is administered prior to the first dose of the compound of Formula I or a pharmaceutically acceptable salt or solvate thereof. In some examples, the increase in the sensitivity of the resistant cancer cell to the anti-cancer drug can result in a decrease in the rate of growth and/or proliferation of the resistant cancer cell when contacted with the anti-cancer drug and at least one of the compounds described herein, of between about 1% to about 100%, 95%, 90%, 85%, 80%, 75%, 70%, 65%, 60%, 55%, 50%, 45%, 40%, 35%, 30%, 25%, 20%, 15%, 10%, or 5%; about 2% to about 100%, 95%, 90%, 85%, 80%, 75%, 70%, 65%, 60%, 55%, 50%, 45%, 40%, 35%, 30%, 25%, 20%, 15%, 10%, or 5%; about 3% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, 15%, or 10%; about 5% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, 15%, 10%, or 10%; about 10% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, or 15%; about 15% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, or 20%; about 20% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, or 25%; about 25% to about 100%, 95%, 90%, 85%, 80%, 75%, 70%, 65%, 60%, 55%, 50%, 45%, 40%, 35%, 30%, 25%, or 20%; about 20% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, or 30%; about 30% to about 100%, 95%, 90%, 85%, 80%, 75%, 70%, 65%, 60%, 55%, 50%, 45%, 40%, or 35%; about 35% to 100%, 95%, 90%, 85%, 80%, 75%, 70%, 65%, 60%, 55%, 50%, 45%, or 40%; about 40% to about 100%, 95%, 90%, 85%, 80%, 75%, 70%, 65%, 60%, 55%, 50%, or 45%; about 45% to about 100%, 95%, 90%, 85%, 80%, 75%, 70%, 65%, 60%, 55%, or 50%; about 50% to about 100%, 95%, 90%, 85%, 80%, 75%, 70%, 65%, 60%, or 55%; about 55% to about 100%, 95%, 90%, 85%, 80%, 75%, 70%, 65%, or 60%; about 60% to about 100%, 95%, 90%, 85%, 80%, 75%, 70%, or 65%; about 65% to about 100%, 95%, 90%, 85%, 80%, 75%, or 70%; about 70% to about 100%, 95%, 90%, 85%, 80%, or 75%; about 75% to about 100%, 95%, 90%, 85%, or 80%; about 80% to about 100%, 95%, 90%, or 85%; about 85% to about 100%, 95%, or 90%; about 90% to about 100% or 95%; or about 95% to about 100%, as compared to the rate of growth and/or proliferation of a resistant cancer cell when contacted with the anti-cancer drug alone.

Also provided herein are methods for reversing or preventing acquired resistance to an anticancer drug, comprising administering a therapeutically effective amount of a compound of Formula I or a pharmaceutically acceptable salt or solvate thereof, to a patient at risk for developing or having acquired resistance to an anticancer drug. In some embodiments, the patient is administered a dose of the anticancer drug (e.g., at substantially the same time as a dose of a compound of Formula I or a pharmaceutically acceptable salt or solvate thereof is administered to the patient).

Also provided herein are methods of delaying and/or preventing development of cancer resistant to an anticancer drug in an individual, comprising concomitantly administering to the individual (a) an effective amount of a compound of Formula I and (b) an effective amount of the anticancer drug.

Also provided herein are methods of treating a subject with cancer who has increased likelihood of developing resistance to an anticancer drug, comprising concomitantly administering to the individual (a) an effective amount of a compound of Formula I and (b) an effective amount of the anticancer drug.

In some embodiments, treatment with a first FGFR1 inhibitor (e.g., a FGFR inhibitor not of Formula I) can cause an elevated serum phosphate level (e.g., hyperphosphatemia) in a subject. Without being bound by theory, it is believed that inhibition of FGFR1 causes an elevated serum phosphate level (e.g., hyperphosphatemia) by blocking FGF23 signaling (see, e.g., Ornitz and Itoh, *Wiley Interdiscip Rev Dev Biol*, 4(3):215-266, 2015; Erben and Andrukhova, *Bone*, 100:62-62, 2017). An elevated phosphate level can be determined in comparison to an earlier time point, e.g., before administration of the first dose of the first FGFR1 inhibitor. An elevated phosphate level can be determined following administration of one or more doses of the first FGFR1 inhibitor, e.g., about 1 day to about 12 days (e.g., about 1 day to about 2 days, about 1 day to about 3 days about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) following administration of one or more doses of the first FGFR inhibitor. In some embodiments, a first FGFR1 inhibitor is a FGFR inhibitor having FGFR1 activity at least one of: FGFR2 activity, FGFR3 activity, or FGFR4 activity. For example, a first FGFR inhibitor can have a FGFR1 activity of less than about 500 nM in an in vitro FGFR1 kinase assay. An elevated phosphate level can also be determined in comparison to a reference value, e.g., an elevated phosphate level can be at least or about 5.5 mg/dL, at least or about 6.0 mg/dL, at least or about 6.5 mg/dL, at least or about 7.0 mg/dL, at least or about 7.5 mg/dL, at least or about 8.0 mg/dL, at least or about 8.5 mg/dL, at least or about 9.0 mg/dL, at least or about 9.5 mg/dL, at least or about 10 mg/dL, at least or about 10.5 mg/dL, at least or about 11 mg/dL, at least or about 11.5 mg/dL, at least or about 12 mg/dL, at least or about 12.5 mg/dL, at least or about 13 mg/dL, at least or about 13.5 mg/dL, at least or about 14 mg/dL, or at least or about 15 mg/dL.

In some embodiments, the presence of an elevated serum phosphate level (e.g., hyperphosphatemia) in a subject (e.g., a subject) can be determined by measuring a level(s) of phosphate in a biological sample including blood, serum, or plasma (e.g., peripheral blood) obtained from the subject after a particular treatment period (e.g., any of the treatment periods described herein). Determining the phosphate level in peripheral blood can be achieved using conventional methods known in the art (see, e.g., serum phosphate test offered, e.g., by the Mayo Clinic Laboratories, which utilizes the Roche Phosphorus reagent (Roche Diagnostics, Inc.; the test is based on the reaction of phosphate with ammonium molybdate to form ammonium phosphomolybdate (without reduction)).

In certain embodiments, the serum phosphate level exhibited by a subject (e.g., a subject treated with a first FGFR1 inhibitor) can be at least or about 5 mg/dL, at least or about 5.5 mg/dL, at least or about 6.0 mg/dL, at least or about 6.5 mg/dL, at least or about 7.0 mg/dL, at least or about 7.5 mg/dL, at least or about 8.0 mg/dL, at least or about 8.5 mg/dL, at least or about 9.0 mg/dL, at least or about 9.5 mg/dL, at least or about 10 mg/dL, at least or about 10.5 mg/dL, at least or about 11 mg/dL, at least or about 11.5 mg/dL, at least or about 12 mg/dL, at least or about 12.5 mg/dL, at least or about 13 mg/dL, at least or about 13.5 mg/dL, at least or about 14 mg/dL, or at least or about 15 mg/dL. In some embodiments, the reference level of phosphate can be the level in a healthy subject or the average level in a population of healthy subjects (e.g., subjects not having an elevated serum phosphate level (e.g., hyperphosphatemia) or a subjects not at risk for developing an elevated phosphate level (e.g., hyperphosphatemia), such as those having a serum phosphate level of from about 2.0 mg/dL to about 5.0 mg/dL; e.g., from about 2.5 mg/dL to about 4.5 mg/dL).

In some embodiments, a subject (e.g., a subject treated with a first FGFR1 inhibitor) with an elevated phosphate level using methods provided herein can also exhibit one or both of: (i) a calcium-phosphate product (serum calcium in mg/dL×serum phosphate in mg/dL) of at least or about 50 mg$^2$/dL$^2$ (e.g., at least or about 52 mg$^2$/dL$^2$, at least or about 54 mg$^2$/dL$^2$, at least or about 56 mg$^2$/dL$^2$, at least or about 58 mg$^2$/dL$^2$, at least or about 60 mg$^2$/dL$^2$, at least or about 62 mg$^2$/dL$^2$, at least or about 64 mg$^2$/dL$^2$, at least or about 66 mg$^2$/dL$^2$, at least or about 68 mg$^2$/dL$^2$, at least or about 70 mg$^2$/dL$^2$, at least or about 72 mg$^2$/dL$^2$, at least or about 74 mg$^2$/dL$^2$, at least or about 76 mg$^2$/dL$^2$, at least or about 78 mg$^2$/dL$^2$, at least or about 80 mg$^2$/dL$^2$, at least or about 82 mg$^2$/dL$^2$, at least or about 84 mg$^2$/dL$^2$, at least or about 86 mg$^2$/dL$^2$, at least or about 88 mg$^2$/dL$^2$, at least about 90 mg$^2$/dL$^2$, at least or about 92 mg$^2$/dL$^2$, at least or about 94 mg$^2$/dL$^2$, at least or about 96 mg$^2$/dL$^2$, at least about 98 mg$^2$/dL$^2$, or at least about 100 mg$^2$/dL$^2$) in a biological sample and (ii) a serum creatinine level of grade 1 or greater (e.g., grade 2, grade 3) in a biological sample. Exemplary assays for determining the calcium level of a biological sample including blood, serum, or plasma are commercially available from BioVision Inc. (Milpitas, CA) and Sigma-Aldrich (St. Louis, MO). Exemplary assays for determining the creatinine level in a biological sample including blood, serum, or plasma are commercially available from BioVision Inc. (Milpitas, CA) and Diazyme (Poway, CA). In some embodiments, the subject can exhibit a serum phosphate level of greater than about 7.0 mg/dL (e.g., a serum phosphate level of greater than 7 mg/dL lasting for more than 7 days despite phosphate-lowering therapies). In some embodiments, the subject exhibits a serum phosphate level of greater than about 9.0 mg/dL (e.g., a serum phosphate level of greater than about 9.0 mg/dL for any duration despite phosphate-lowering therapies). In still other embodiments, the subject exhibits a serum phosphate level of greater than about 10.0 mg/dL (e.g., a serum phosphate level of greater than about 10.0 mg/dL for any duration).

In some embodiments of these methods, a subject can be administered a phosphate binder (e.g., any of the exemplary phosphate binders described herein or known in the art). In some embodiments of these methods, the phosphate binder is sevelamer hydrochloride. In some embodiments of these methods, administration of the phosphate binder (e.g., sevelamer hydrochloride) can be a total daily administration of about 0.1 g to about 2.0 g (e.g., about 0.1 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, about 0.5 g, about 0.4 g, about 0.3 g, or about 0.2 g; about 0.2 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, about 0.5 g, about 0.4 g, or about 0.3 g; about 0.3 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, about 0.5 g, or about 0.4 g; about 0.4 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, about 0.6 g, or about 0.5 g; about 0.5 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, about 0.7 g, or about 0.6 g; about 0.6 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, about 0.8 g, or about 0.7 g; about 0.7 g to about 1.9 g, about 1.8 g., about 1.7 g, about 1.6 g, about 1.5 g, about 1.4 g, about 1.3 g, about 1.2 g, about 1.1 g, about 1.0 g, about 0.9 g, or about 0.8 g; about 0.8 g to about 1.9 g, about 1.8 g., about 1.7 g, about 1.6 g, about 1.5 g, about 1.4 g, 1.3 g, about 1.2 g, about 1.1 g, about 1.0 g, or about 0.9 g; about 0.9 g to about 1.9 g, about 1.8 g., about 1.7 g, 1.6 g, about 1.5 g, about 1.4 g, about 1.3 g, about 1.2 g, about 1.1 g, or about 1.0 g; about 1.0 g to about 1.9 g, about 1.8 g., about 1.7 g, about 1.6 g, about 1.5 g, about 1.4 g, about 1.3 g, about 1.2 g, or about 1.1 g; about 1.1 g to about 1.9 g, about 1.8 g., about 1.7 g, about 1.6 g, about 1.5 g, about 1.4 g, about 1.3 g, or about 1.2 g; about 1.2 g to about 1.9 g, about 1.8 g., about 1.7 g, about 1.6 g, about 1.5 g, about 1.4 g, or about 1.3 g; about 1.3 g to about 1.9 g, about 1.8 g., about 1.7 g, about 1.6 g, about 1.5 g, or about 1.4 g; about 1.4 g to about 1.9 g, about 1.8 g., about 1.7 g, about 1.6 g, or about 1.5 g; about 1.5 g to about 1.9 g, about 1.8 g., about 1.7 g, or about 1.6 g; about 1.6 g to about 1.9 g, about 1.8 g., or about 1.7 g; about 1.7 g to about 2.0 g, about 1.9 g, or about 1.8 g; about 1.8 g to about 2.0 g or about 1.9 g; or about 1.9 g to about 2.0 g) of the phosphate binder.

In some embodiments, the subject is determined to have about the same or a decreased level of phosphate in one or more (e.g., two, three, four, five, or six) sample(s) including blood, serum, or plasma obtained from the subject at 1 day, 2 days, 3 days, 4 days, 5 days, 6 days, 7 days (1 week), 8 days, 9 days, 10 days, 11 days, 12 days, 13 days, 14 days (2 weeks), 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days, or 100 days following the start of the administration of a therapeutic (e.g., a first FGFR1 inhibitor with or without a phosphate binder, a compound of Formula I or a pharmaceutically acceptable salt or solvate thereof) as compared to a reference level of phosphate (e.g., any of the reference levels of phosphate described herein).

In some embodiments, a subject is administered a therapeutically effective amount of a phosphate binder. Non-limiting examples of phosphate binders include aluminum salts (e.g., Alucaps and Basaljel), calcium carbonate (e.g., Calcichew and Titralac), calcium acetate (e.g., Lenal Ace and PhosLo), sevelamer hydrochloride (e.g., Renegel or Renvela), and lanthanum carbonate (e.g., Fosrenol). A phosphate binder can be administered at a total daily dose of about 2.0 g to about 5.0 g (e.g., about 2.0 g to about 4.8 g, about 4.6 g, about 4.4 g, about 4.2 g, about 4.0 g, about 3.8 g, about 3.6 g, about 3.4 g, about 3.2 g, about 3.0 g, about 2.8 g, about 2.6 g, about 2.4 g, or about 2.2 g; about 2.2 g to about 5.0 g, about 4.8 g, about 4.6 g, about 4.4 g, about 4.2 g, about 4.0 g, about 3.8 g, about 3.6 g, about 3.4 g, about 3.2, about 3.0 g, about 2.8 g, about 2.6 g, or about 2.4 g; about 2.4 to about 5.0 g, about 4.8 g, about 4.6 g, about 4.4 g, about 4.2 g, about 4.0 g, about 3.8 g, about 3.6 g, about 3.4 g, about 3.2, about 3.0 g, or about 2.8 g; about 2.8 g to about 5.0 g, about 4.8 g, about 4.6 g, about 4.4 g, about 4.2 g, about 4.0 g, about 3.8 g, about 3.6 g, about 3.4 g, about 3.2, or about 3.0 g; about 3.0 g to about 5.0 g, about 4.8 g, about 4.6 g, about 4.4 g, about 4.2 g, about 4.0 g, about 3.8 g, about 3.6 g, about 3.4 g, or about 3.2 g; about 3.2 g to about 5.0 g, about 4.8 g, about 4.6 g, about 4.4 g, about 4.2 g, about 4.0 g, about 3.8 g, about 3.6 g, or about 3.4 g; about 3.4 g to about 5.0 g, about 4.8 g, about 4.6 g, about 4.4 g, about 4.2 g, about 4.0 g, about 3.8 g, or about 3.6 g; about 3.6 g to about 5.0 g, about 4.8 g, about 4.6 g, about 4.4 g, about 4.2 g, about 4.0 g, or about 3.8 g; about 3.8 g to about 5.0 g, about 4.8 g, about 4.6 g, about 4.4 g, about 4.2 g, or about 4.0 g; about 4.0 g to about 5.0 g, about 4.8 g, about 4.6 g, about 4.4 g, or about 4.2 g; about 4.2 g to about 5.0 g, about 4.8 g, about 4.6 g, or about 4.4 g; about 4.4 g to about 5.0 g, about 4.8 g, or about 4.6 g; about 4.6 g to about 5.0 g or about 4.8 g; or about 4.8 g to about 5.0 g). In some embodiments of any of the methods described herein, the method further comprises administering a phosphate binder to the subject. In some embodiments of these methods, the method further includes ceasing administration of the phosphate binder to a subject or instructing a subject to cease administration of the phosphate binder. In some embodiments of these methods, the method further includes administering a decreased dose of the phosphate binder to a subject relative to a dose of the phosphate binder previously administered to the subject.

In some embodiments of any of the methods described herein, a subject is not administered a phosphate binder.

Methods useful when a subject has elevated blood phosphate levels are described below. For example, provided herein are methods of treating a subject having a cancer that include: identifying a subject demonstrating an elevated phosphate level and a FGFR-associated cancer (e.g., any of the FGFR-associated cancers described herein or known in the art); and administering to the identified subject a compound of Formula I or a pharmaceutically acceptable salt or solvate thereof. In some embodiments, the identifying step comprises identifying a subject exhibiting an elevated phosphate level and at least one of: (i) a calcium-phosphate product of at least about 50 mg$^2$/dL$^2$ and (ii) a serum creatinine level of grade 1 or greater. Also provided are methods of treating a subject identified as having an elevated phosphate level and a FGFR-associated cancer (e.g., any of the FGFR-associated cancers described herein or known in the art) that include administering to the subject a compound of Formula I or a pharmaceutically acceptable salt or solvate thereof. In some embodiments, the identified subject also exhibits at least one of: (i) a calcium-phosphate product of at least about 50 mg$^2$/dL$^2$ and (i) a serum creatinine level of grade 1 or greater. In some embodiments, demonstration of an elevated phosphate level occurs about 1 day to about 12 days (e.g., about 1 day to about 2 days, about 1 day to about 3 days about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) following administration of one or more doses of a first FGFR inhibitor. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 $mg^2/dL^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay.

For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 $mg^2/dL^2$ and (ii) a serum creatinine level of grade 1 or greater; and (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 $mg^2/dL^2$ and (ii) a serum creatinine level of grade 1 or greater; or (e) administering additional doses of the first FGFR1 inhibitor of step (b) to the subject if the sample from the subject does not demonstrate an elevated phosphate level and at least one of: (i) a calcium-phosphate product of at least about 50 $mg^2/dL^2$ and (2) a serum creatinine level of grade 1 or greater. In some embodiments, when the method comprises administering a compound of Formula I, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 $mg^2/dL^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and at least one of: (i) a calcium-phosphate product of at least about 50 mg$^2$/dL$^2$ and (2) a serum creatinine level of grade 1 or greater. In some embodiments, when the method comprises administering a compound of Formula I selected from Examples 1-135, 137-146, and 148-196, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I selected from Examples 1-135, 137-146, and 148-196. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 me/dL$^2$ and (ii) a serum creatinine level of grade 1 or greater; and (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 me/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I selected from Examples 1-135, 137-146, and 148-196, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I selected from Examples 1-135, 137-146, and 148-196. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and (d) administering a compound of Formula I or a pharmaceutically acceptable salt or solvate thereof selected from the group consisting of a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and (d) administering a compound of Formula I or a pharmaceutically acceptable salt or solvate thereof selected from the group consisting of a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, a compound of Formula I is at least about 3-fold more selective for FGFR3 over FGFR1. In some embodiments, a compound of Formula I is at least about 3-fold more selective for FGFR2 over FGFR1. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12) days after step (b). In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and (d) administering a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and (d) administering a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I selected from Examples 1-135, 137-146, and 148-196, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I selected from Examples 1-135, 137-146, and 148-196. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and at least one of: (i) a calcium-phosphate product of at least about 50 mg$^2$/dL$^2$ and (2) a serum creatinine level of grade 1 or greater. In some embodiments, when the method comprises administering a compound of Formula I, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and at least one of: (i) a calcium-phosphate product of at least about 50 mg$^2$/dL$^2$ and (2) a serum creatinine level of grade 1 or greater. In some embodiments, when the method comprises administering a compound of Formula I selected from Examples 1-135, 137-146, and 148-196, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I selected from Examples 1-135, 137-146, and 148-196. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12) days after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg/dL and (ii) a serum creatinine level of grade 1 or greater; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I selected from Examples 1-135, 137-146, and 148-196, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120.

In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I selected from Examples 1-135, 137-146, and 148-196. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I or a pharmaceutically acceptable salt or solvate thereof selected from the group consisting of a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I or a pharmaceutically acceptable salt or solvate thereof selected from the group consisting of a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, when the method comprises administering a compound of Formula I selected from Examples 1-135, 137-146, and 148-196, the method further comprises (f) determining that a sample from the subject does not demonstrate an elevated phosphate level. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I selected from Examples 1-135, 137-146, and 148-196. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

For example, provided herein are methods of treating a subject having a cancer that include: identifying a subject having a FGFR-associated cancer (e.g., any of the FGFR-associated cancers described herein or known in the art) and previously demonstrating an elevated phosphate level; and administering to the identified subject a compound of Formula I or a pharmaceutically acceptable salt or solvate thereof. In some embodiments, following administration of a compound of Formula I, the methods further comprise determining that a sample from the subject does not demonstrate an elevated phosphate level. In some embodiments, demonstration of an elevated phosphate level occurs about 1 day to about 12 days (e.g., about 1 day to about 2 days, 1 day to about 3 days about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) following administration of one or more doses of a first FGFR inhibitor. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg/dL and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

For example, provided herein are methods for treating a FGFR-associated cancer in a subject previously administered one or more doses of a first FGFR1 inhibitor and previously demonstrating an elevated phosphate level, the method comprising administering a compound of Formula I, or a pharmaceutically acceptable salt or solvate thereof as a monotherapy or in conjunction with an additional therapy or therapeutic agent to the subject. In some embodiments, following administration of a compound of Formula I, the methods further comprise determine that a sample from the subject does not demonstrate an elevated phosphate level. In some embodiments, the first FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, demonstration of an elevated phosphate level occurs about 1 day to about 12 days (e.g., about 1 day to about 2 days, about 1 day to about 3 days about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) following administration of one or more doses of a first FGFR inhibitor. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 $mg^2/dL^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

For example, provided herein are methods for treating a FGFR-associated cancer in a subject previously administered one or more doses of a first FGFR1 inhibitor and previously demonstrating an elevated phosphate level, the method comprising administering a compound of Formula I selected from Examples 1-135, 137-146, and 148-196, or a pharmaceutically acceptable salt or solvate thereof as a monotherapy or in conjunction with an additional therapy or therapeutic agent to the subject. In some embodiments, following administration of a compound of compound of Formula I selected from Examples 1-135, 137-146, and 148-196, the methods further determining that a sample from the subject does not demonstrate an elevated phosphate level. In some embodiments, the first FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, demonstration of an elevated phosphate level occurs about 1 day to about 12 days (e.g., about 1 day to about 2 days, about 1 day to about 3 days about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) following administration of one or more doses of a first FGFR inhibitor. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I selected from Examples 1-135, 137-146, and 148-196. In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, an additional therapy or therapeutic agent is not an FGFR1 inhibitor.

For example, provided herein are methods of treating a subject having a cancer that include: identifying a subject demonstrating an elevated phosphate level and a FGFR-associated cancer (e.g., any of the FGFR-associated cancers described herein or known in the art); and administering to the identified subject a compound of Formula I or a pharmaceutically acceptable salt or solvate thereof, where, following administration of one or more doses of the compound of Formula I, the subject does not demonstrate an elevated phosphate level. In some embodiments, the compound of Formula I is administered as a monotherapy or in conjunction with an additional therapy or therapeutic agent. In some embodiments, the additional therapy or therapeutic agent is not a FGFR1 inhibitor. In some embodiments, the identifying step comprises identifying a subject exhibiting an elevated phosphate level and at least one of: (i) a calcium-phosphate product of at least about 50 mg$^2$/dL$^2$ and (ii) a serum creatinine level of grade 1 or greater. Also provided are methods of treating a subject identified as having an elevated phosphate level and a FGFR-associated cancer (e.g., any of the FGFR-associated cancers described herein or known in the art) that include administering to the subject a compound of Formula I or a pharmaceutically acceptable salt or solvate thereof, where, following administration of one or more doses of the compound of Formula I, the subject does not demonstrate an elevated phosphate level. In some embodiments, the compound of Formula I is administered as a monotherapy or in conjunction with an additional therapy or therapeutic agent. In some embodiments, the additional therapy or therapeutic agent is not a FGFR1 inhibitor. In some embodiments, the identified subject also exhibits at least one of: (i) a calcium-phosphate product of at least about 50 mg$^2$/dL$^2$ and (i) a serum creatinine level of grade 1 or greater. In some embodiments, demonstration of an elevated phosphate level occurs about 1 day to about 12 days (e.g., about 1 day to about 2 days, about 1 day to about 3 days about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 1 day to about 12 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) following administration of one or more doses of a first FGFR1 inhibitor. In some embodiments, demonstration of a phosphate level that is not an elevated phosphate level occurs about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administration of one or more doses of the compound of Formula I. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, a phosphate level that is not an elevated phosphate level (e.g., in a blood sample) is a phosphate level of at between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, the first FGFR1 inhibitor has a FGFR1 activity of less than about 500 nM in an in vitro FGFR1 kinase assay.

For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 $mg^2/dL^2$ and (ii) a serum creatinine level of grade 1 or greater; or (e) administering additional doses of the first FGFR1 inhibitor of step (b) to the subject if the sample from the subject does not demonstrate an elevated phosphate level and at least one of: (i) a calcium-phosphate product of at least about 50 $mg^2/dL^2$ and (2) a serum creatinine level of grade 1 or greater. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 $mg^2/dL^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay.

For example, provided herein are methods for treating a FGFR-associated cancer in a subject in need of such treatment, the method comprising (a) detecting a dysregulation of a FGFR gene, a FGFR kinase, or the expression or activity or level of any of the same in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 $mg^2/dL^2$ and (ii) a serum creatinine level of grade 1 or greater; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 $mg^2/dL^2$ and (ii) a serum creatinine level of grade 1 or greater; or (e) administering additional doses of the first FGFR1 inhibitor of step (b) to the subject if the sample from the subject does not demonstrate an elevated phosphate level and at least one of: (i) a calcium-phosphate product of at least about 50 $mg^2/dL^2$ and (2) a serum creatinine level of grade 1 or greater. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 me/dL$^2$ and (ii) a serum creatinine level of grade 1 or greater; and after a period of time, (d) administering a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay.

In some embodiments, provided herein are methods for treating a FGFR-associated cancer in a subject in need of such treatment, the method comprising (a) detecting one or more fusion proteins of Table BA and/or one or more FGFR kinase protein point mutations/insertions/deletions of Table BC in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I or a pharmaceutically acceptable salt or solvate thereof selected from the group consisting of a compound of Formula I, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 mg$^2$/dL$^2$ and (ii) a serum creatinine level of grade 1 or greater; and after a period of time, (d) administering a compound of Formula I or a pharmaceutically acceptable salt or solvate thereof selected from the group consisting of a compound of Formula I, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, the FGFR1 inhibitor of step (b) is selected from the group consisting of ARQ-087, ASP5878, AZD4547, BGJ398, brivanib, Debio 1347, dovitinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay.

In some embodiments, provided herein are methods for treating a FGFR-associated cancer in a subject in need of such treatment, the method comprising (a) detecting the fusion protein FGFR3-TACC3 in a sample from the subject; and (b) administering to the subject a therapeutically effective amount of a first FGFR1 inhibitor. In some embodiments, the methods further comprise (after (b)) (c) determining whether a sample from a subject demonstrates an elevated phosphate level; and after a period of time, (d) administering a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level; or (e) administering additional doses of the first FGFR1 inhibitor of step (b) to the subject if the sample from the subject does not demonstrate an elevated phosphate level. In some embodiments, the methods further comprise (after (b)) (c) determining whether a sample from a subject demonstrates an elevated phosphate level and least one of: (i) a calcium-phosphate product of at least about 50 me/dL$^2$ and (ii) a serum creatinine level of grade 1 or greater; and after a period of time, (d) administering a compound of Formula I or a pharmaceutically acceptable salt or solvate thereof selected from the group consisting of a compound of Formula I selected from Examples 1-135, 137-146, and 148-196, or a pharmaceutically acceptable salt or solvate thereof as a monotherapy or in conjunction with an additional therapy or therapeutic agent to the subject if the sample from the subject demonstrates an elevated phosphate level and least one of: (i) a calcium-phosphate product of at least about 50 mg$^2$/dL$^2$ and (ii) a serum creatinine level of grade 1 or greater; or (e) administering additional doses of the first FGFR1 inhibitor of step (b) to the subject if the sample from the subject does not demonstrate an elevated phosphate level and least one of: (i) a calcium-phosphate product of at least about 50 mg$^2$/dL$^2$ and (ii) a serum creatinine level of grade 1 or greater. In some embodiments, the FGFR1 inhibitor of step (b) is selected from the group consisting of ARQ-087, ASP5878, AZD4547, BGJ398, brivanib, Debio 1347, dovi-tinib, E7090, erdafitinib, HMPL-453, INCB054828, lenvatinib, lucitanib, MAX-40279, nintedanib, orantinib, pemigatinib, ponatinib, PRN1371, rogaratinib, sulfatinib, and TAS-120. In some embodiments, the sample of step (c) is a blood sample. In some embodiments of any of these methods, step (b) further includes administering to the subject a phosphate binder. In some embodiments, step (c) occurs about 1 to about 12 days (e.g., about 1 day to about 2 days, about 1 day to about 3 days, about 1 day to about 4 days, about 1 day to about 5 days, about 1 day to about 6 days, about 1 day to about 7 days, about 1 day to about 8 days, about 1 day to about 9 days, about 1 day to about 10 days, about 1 day to about 11 days, about 2 days to about 12 days, about 3 days to about 12 days, about 4 days to about 12 days, about 5 days to about 12 days, about 6 days to about 12 days, about 7 days to about 12 days, about 8 days to about 12 days, about 9 days to about 12 days, about 10 days to about 12 days, about 11 days to about 12 days, about 1 day, about 2 days, about 3 days, about 4 days, about 5 days, about 6 days, about 7 days, about 8 days, about 9 days, about 10 days, about 11 days, or about 12 days) after step (b). In some embodiments, the period of time between step (c) and step (d) is about 1 day, about 1.5 days, about 2 days, about 3 days, about 4 days, about 5 days, about 6 days, about 7 days, about 8 days, about 9 days, about 10 days, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 1.5 years, about 2 years, about 3 years, about 4 years, about 5 years, about 6 years, about 7 years, about 8 years, about 9 years, about 10 years, about 12 years, about 14 years, about 16 years, about 18 years, about 20 years, about 22 years, about 24 years, about 26 years, about 28 years, about 30 years, about 35 years, about 40 years, or about 50 years. In some embodiments, an elevated phosphate level is a phosphate level (e.g., in a blood sample) of at least about 5 mg/dL (e.g., at least about 5.5 mg/dL, 6.0 mg/dL, 6.5 mg/dL, 7.0 mg/dL, 7.5 mg/dL, 8.0 mg/dL, 8.5 mg/dL, 9.0 mg/dL, 9.5 mg/dL, or 10.0 mg/dL). In some embodiments, demonstration of an elevated phosphate level comprises demonstrating an elevated phosphate level and at least one of: (i) a calcium-phosphate product of at least about 50 mg$^2$/dL$^2$ and (ii) a serum creatinine level of grade 1 or greater. In some embodiments, an elevated phosphate level is demonstrated in comparison to an earlier sample from the same subject (e.g., before administration of one or more doses of a first FGFR1 inhibitor). In some embodiments, the first FGFR1 inhibitor has a FGFR1 activity of less than about 500 nM in an in vitro FGFR1 kinase assay.

Also provided herein are methods of treating a FGFR-associated cancer in a subject, the method comprising administering to the subject a compound of Formula I or a pharmaceutically acceptable salt or solvate thereof, where, following administration of the compound of Formula I or a pharmaceutically acceptable salt or solvate thereof, a sample from the subject has a phosphate level that is lower than the phosphate level of a sample from a second subject having an FGFR-associated cancer following administration of a compound that is not a compound of Formula I or a pharmaceutically acceptable salt or solvate thereof. In some embodiments, the compound that is not a compound of compound that is not a compound of Formula I or a pharmaceutically acceptable salt or solvate thereof is a FGFR1 inhibitor. In some embodiments, the compound that is not a compound of Formula I or a pharmaceutically acceptable salt or solvate thereof is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the compound that is not a compound of Formula I or a pharmaceutically acceptable salt or solvate thereof has an FGFR1 activity of less than 50 nM in an in vitro FGFR1 kinase assay. In some embodiments, the sample from the subject and the sample from the second subject are blood samples. In some embodiments, the sample from the subject is taken about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administering to the subject one or more doses of the compound of Formula I. In some embodiments, the sample from the second subject is taken about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administering to the subject one or more doses of the compound that is not a compound of Formula I. In some embodiments, the sample from the subject and the sample from the second subject are taken at approximately equal times after administering one or more doses of a compound of Formula I or a compound that is not a compound of Formula I, respectively. In some embodiments, the sample from the subject demonstrates a phosphate level of between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, the sample from the subject demonstrates a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, the method further comprises reducing the dose of a FGFR1 inhibitor administered to the subject, ceasing to administer a FGFR1 to the subject, or not administering a FGFR1 inhibitor to the subject.

Also provided are methods of treating a FGFR-associated cancer in a subject, the method comprising administering to the subject a compound of Formula I or a pharmaceutically acceptable salt or solvate thereof, wherein following administration of the compound of Formula I, a sample from the subject does not demonstrate an elevated phosphate level. In some embodiments, the sample from the subject is a blood sample. In some embodiments, the sample from the subject is taken about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administering to the subject one or more doses of the compound of Formula I. In some embodiments, a phosphate level that is not an elevated phosphate level (e.g., in a blood sample) is a phosphate level of between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, a phosphate level that is not an elevated phosphate level (e.g., in a blood sample) is a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, the method further comprises reducing the dose of a FGFR1 inhibitor administered to the subject, ceasing to administer a FGFR1 to the subject, or not administering a FGFR1 inhibitor to the subject. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, the FGFR1 inhibitor has an FGFR1 activity of less than 50 nM in an in vitro FGFR1 kinase assay.

Also provided are methods of reducing the risk of an elevated serum phosphate level (e.g., hyperphosphatemia) in a subject with a FGFR-associated cancer, the method comprising administering to the subject a compound of Formula I or a pharmaceutically acceptable salt or solvate thereof. In some embodiments, the method further comprises reducing the dose of a FGFR1 inhibitor administered to the subject, ceasing to administer a FGFR1 to the subject, or not administering a FGFR1 inhibitor to the subject. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120.

Also provided are methods of reversing elevated serum phosphate level (e.g., hyperphosphatemia) in a subject with a FGFR-associated cancer being treated with a FGFR1 inhibitor, the method comprising (a) reducing the dose or ceasing administration of the FGFR1 inhibitor; and (b) administering to the subject a compound of Formula I or a pharmaceutically acceptable salt or solvate thereof. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-1200. In some embodiments, the FGFR1 inhibitor has an FGFR1 activity of less than 50 nM in an in vitro FGFR1 kinase assay. Also provided herein are methods of treating a FGFR-associated cancer in a subject, the method comprising administering to the subject a compound of Formula I or a pharmaceutically acceptable salt or solvate thereof, where, following administration of the compound of Formula I or a pharmaceutically acceptable salt or solvate thereof, a sample from the subject has a phosphate level that is lower than the phosphate level of a sample from a second subject having an FGFR-associated cancer following administration of a compound that is not a compound of Formula I or a pharmaceutically acceptable salt or solvate thereof. In some embodiments, the compound that is not a compound of compound that is not a compound of Formula I or a pharmaceutically acceptable salt or solvate thereof is a FGFR1 inhibitor. In some embodiments, the compound that is not a compound of Formula I or a pharmaceutically acceptable salt or solvate thereof is selected from the group consisting of ARQ-087, ASP5878, AZD4547, B-701, BAY1179470, BAY1187982, BGJ398, brivanib, Debio 1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, and TAS-120. In some embodiments, the compound that is not a compound of Formula I or a pharmaceutically acceptable salt or solvate thereof has an FGFR1 activity of less than 50 nM in an in vitro FGFR1 kinase assay. In some embodiments, the sample from the subject and the sample from the second subject are blood samples. In some embodiments, the sample from the subject is taken about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administering to the subject one or more doses of the compound of Formula I. In some embodiments, the sample from the second subject is taken about 6 hours, about 12 hours, about 18 hours, about 1 day, about 1.5 days, about 2 days, about 3 days, about 4 days, about 5 days, about 6 days, about 7 days, about 8 days, about 9 days, about 10 days, about 2 weeks, about 3 weeks, or about 4 weeks after administering to the subject one or more doses of the compound that is not a compound of Formula I. In some embodiments, the sample from the subject and the sample from the second subject are taken at approximately equal times after administering one or more doses of a compound of Formula I or a compound that is not a compound of Formula I, respectively. In some embodiments, the sample from the subject demonstrates a phosphate level of between about 2.5 and about 4.5 mg/dL (e.g., between about 2.5 and about 3.0 mg/dL, about 2.5 and about 3.5 mg/dL, about 2.5 and about 4.0 mg/dL, about 3.0 to about 4.5 mg/dL, about 3.5 to about 4.5 mg/dL, or about 4.0 to about 4.5 mg/dL). In some embodiments, the sample from the subject demonstrates a phosphate level of at less than about 5 mg/dL (e.g., less than about 4.5 mg/dL, 4.0 mg/dL, 3.5 mg/dL, or 3.0 mg/dL, or 2.5 mg d/L). In some embodiments, the method further comprises reducing the dose of a FGFR1 inhibitor administered to the subject, ceasing to administer a FGFR1 to the subject, or not administering a FGFR1 inhibitor to the subject.

Also provided herein are methods of treating a FGFR-associated cancer (e.g., any of the FGFR-associated cancers described herein or known in the art) in a subject that includes administering a therapeutically effective dose of a compound of Formula I or a pharmaceutically acceptable salt or solvate thereof, or a pharmaceutical composition including a compound of Formula I or a pharmaceutically acceptable salt or solvate thereof, to a subject identified or diagnosed as having a FGFR-associated cancer over a treatment period of at least 8 days, where the subject is determined to have about the same or a decreased level of phosphate in one or more sample(s) including blood, serum, or plasma obtained from the subject over the treatment period as compared to a reference level of phosphate (e.g., any of the reference levels of phosphate described herein). In some embodiments of any of these methods, the subject is identified or diagnosed as having a FGFR-associated cancer using any of the methods described herein or known in the art. Some embodiments of any of these methods can further include identifying or diagnosing a subject as having a FGFR-associated cancer using any of the methods described herein or known in the art. In some embodiments, the treatment period of at least 8 days can be any of the exemplary treatment periods (or ranges of treatment periods) described herein. In some embodiments, the subject is administered a daily dose of a compound of Formula I or a pharmaceutically acceptable salt or solvate thereof, or a pharmaceutical composition including a compound of Formula I or a pharmaceutically acceptable salt or solvate thereof (e.g., any of the pharmaceutical compositions described herein) over the treatment period.

Also provided are methods of treating a FGFR-associated cancer (e.g., any of the FGFR-associated cancers described herein or known in the art) that include administering a therapeutically effective dose of a compound of Formula I or a pharmaceutically acceptable salt or solvate thereof to a subject identified or diagnosed as having a FGFR-associated cancer, wherein the subject is not administered a phosphate binder (e.g., any of the phosphate binders described herein or known in the art). In some embodiments of any of these methods, the subject is identified or diagnosed as having a FGFR-associated cancer using any of the methods described herein or known in the art. Some embodiments of any of these methods can further include identifying or diagnosing a subject as having a FGFR-associated cancer using any of the methods described herein or known in the art. In some embodiments, the subject is administered a daily dose of a compound of Formula I or a pharmaceutically acceptable salt or solvate thereof.

Also provided herein are methods of treating a FGFR-associated cancer (e.g., any FGFR-associated cancer described herein or known in the art) in a subject that include administering a therapeutically effective dose of a compound of Formula I or pharmaceutically acceptable salt or solvate thereof to a subject identified or diagnosed as having a FGFR-associated cancer, wherein the subject is further administered a phosphate binder (e.g., any of the phosphate binders described herein, e.g., sevelamer hydrochloride). Some embodiments of any of these methods can further include identifying or diagnosing a subject as having a FGFR-associated cancer using any of the methods described herein or known in the art. In some embodiments, the subject is administered a daily dose of a compound of Formula I or a pharmaceutically acceptable salt or solvate thereof.

Also provided herein are methods of treating a FGFR-associated disease (e.g., a FGFR-associated cancer, e.g., any of the FGFR-associated cancers described herein or known in the art) in a subject that include: (a) administering to a subject identified or diagnosed as having a FGFR-associated disease (e.g., a FGFR-associated cancer) one or more doses of a first FGFR inhibitor over a treatment period; (b) determining a level of phosphate in a sample including blood, serum, or plasma obtained from the subject after the treatment period; (c) selecting a subject having an elevated level of phosphate in the biological sample as compared to a reference level of phosphate; and (d) ceasing administration of the first FGFR inhibitor (or instructing the selected subject to cease administration) and initiating administration of a therapeutically effective amount of a compound of Formula I or pharmaceutically acceptable salt or solvate thereof, or a pharmaceutical agent or composition comprising a compound of Formula I or pharmaceutically acceptable salt or solvate thereof (e.g., any of the pharmaceutical agents or compositions described herein), to the selected subject. Some embodiments of these methods can further include identifying or diagnosing a subject as having a FGFR-associated disease (e.g., a FGFR-associated cancer) using any of the methods described herein.

Administration of a first FGFR inhibitor to a subject can cause adverse effects. In some embodiments, the adverse effects can include one or more of: anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis. Accordingly, provided herein are methods useful when a first FGFR inhibitor causes adverse affects.

Provided are methods of treating a subject having a FGFR-associated cancer (e.g., any of the FGFR-associated cancers described herein or known in the art) that include: administering a therapeutically effective dose of a compound of Formula I or a pharmaceutically acceptable salt or solvate thereof to a subject identified or diagnosed as having a FGFR-associated cancer, where the subject does not experience or is less likely to experience one or more (e.g., two, three, four, five, six, seven, eight, nine, ten, eleven, twelve, thirteen, fourteen, or fifteen) of anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis over the treatment period or after the treatment period (e.g., as compared to a subject or a population of subjects having the same FGFR-associated cancer and administered a therapeutically effective dose of a FGFR inhibitor that is not a compound of Formula I or a pharmaceutically acceptable salt or solvate thereof). Some embodiments of any of these methods can further include identifying or diagnosing a subject as having a FGFR-associated cancer using any of the methods described herein or known in the art. In some embodiments, the subject is administered a daily dose of a compound of Formula I or a pharmaceutically acceptable salt or solvate thereof.

In some embodiments of the methods described herein, the subject is administered a compound of Formula I and not administered a phosphate binder (e.g., any of the phosphate binders described herein or known in the art). In such methods, the subject can be, e.g., less likely to experience one or more (e.g., two, three, four, five, six, seven, eight, nine, ten, eleven, twelve, thirteen, fourteen, or fifteen) of anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis over the treatment period or after the treatment period (e.g., as compared to a subject or a population of subjects having the same FGFR-associated cancer and administered a therapeutically effective dose of a FGFR inhibitor that is not a compound of Formula I or a pharmaceutically acceptable salt or solvate thereof, and is not administered a phosphate binder).

In some embodiments of the methods described herein, the subject is administered a phosphate binder (e.g., any of the phosphate binders described herein, e.g., sevelamer hydrochloride). In such methods, the subject can be, e.g., less likely to experience one or more (e.g., two, three, four, five, six, seven, eight, nine, ten, eleven, twelve, thirteen, fourteen, or fifteen) of anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis over the treatment period or after the treatment period (e.g., as compared to a subject or a population of subjects having the same FGFR-associated cancer and administered a therapeutically effective dose of a FGFR inhibitor that is not a compound of Formula I or a pharmaceutically acceptable salt or solvate thereof, and is administered the same phosphate binder).

In some embodiments, a subject is less likely to experience one or more (e.g., two, three, four, five, six, seven, eight, nine, ten, eleven, twelve, thirteen, fourteen, or fifteen) of anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis (e.g., as compared to a subject or a population of subjects having the same FGFR-associated cancer and administered a therapeutically effective dose of a FGFR inhibitor that is not a compound of Formula I or a pharmaceutically acceptable salt or solvate thereof, or a pharmaceutical composition including a compound of Formula I or a pharmaceutically acceptable salt or solvate thereof, and is administered the same phosphate binder).

The level of soft tissue calcification can be detected/determined in a subject by a medical professional using, e.g., ultrasound, radiography, computed tomography, and magnetic resonance imaging. The level of stomatitis, dry mouth, nail changes, fatigue, asthenia, anorexia, malaise, and muscle aches in a subject can be determined by a medical professional through the physical examination of the subject and/or interviewing the subject (e.g., using a survey).

Also provided are methods of changing the adverse effects of treatment of a subject with a FGFR-associated cancer, the method comprising administering to the subject a compound of Formula I or a pharmaceutically acceptable salt or solvate thereof; and reducing a dose of a FGFR1 inhibitor administered to the subject, not administering a FGFR1 inhibitor to the subject, or ceasing to administer a FGFR1 inhibitor to the subject. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, the adverse effects can include one or more of: anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis. In some embodiments, the FGFR1 inhibitor has an FGFR1 activity of less than 50 nM in an in vitro FGFR1 kinase assay.

Also provided are methods of decreasing the number of the adverse effects of treatment of a subject with a FGFR-associated cancer, the method comprising administering to the subject a compound of Formula I or a pharmaceutically acceptable salt or solvate thereof; and reducing a dose of a FGFR1 inhibitor administered to the subject, not administering a FGFR1 inhibitor to the subject, or ceasing to administer a FGFR1 inhibitor to the subject. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, the adverse effects can include one or more of: anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis. In some embodiments, the FGFR1 inhibitor has an FGFR1 activity of less than 50 nM in an in vitro FGFR1 kinase assay.

Also provided are methods of decreasing the severity of the adverse effects of treatment of a subject with a FGFR-associated cancer, the method comprising administering to the subject a compound of Formula I or a pharmaceutically acceptable salt or solvate thereof; and reducing a dose of a FGFR1 inhibitor administered to the subject, not administering a FGFR1 inhibitor to the subject, or ceasing to administer a FGFR1 inhibitor to the subject. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, the adverse effects can include one or more of: anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis. In some embodiments, the FGFR1 inhibitor has an FGFR1 activity of less than 50 nM in an in vitro FGFR1 kinase assay.

Also provided are methods of preventing one or more adverse effects of treatment of a subject with a FGFR-associated cancer, the method comprising administering to the subject a compound of Formula I or a pharmaceutically acceptable salt or solvate thereof; and reducing a dose of a FGFR1 inhibitor administered to the subject, not administering a FGFR1 inhibitor to the subject, or ceasing to administer a FGFR1 inhibitor to the subject. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, the adverse effects can include one or more of: anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis. In some embodiments, the FGFR1 inhibitor has an FGFR1 activity of less than 50 nM in an in vitro FGFR1 kinase assay.

Also provided are methods of treating the adverse effects of treatment of a subject with a FGFR-associated cancer, the method comprising administering to the subject a compound of Formula I or a pharmaceutically acceptable salt or solvate thereof; and reducing a dose of a FGFR1 inhibitor administered to the subject, not administering a FGFR1 inhibitor to the subject, or ceasing to administer a FGFR1 inhibitor to the subject. In some embodiments, the FGFR1 inhibitor is selected from the group consisting of brivanib, dovitinib, erdafitinib, nintedanib, orantinib, pemigatinib, ponatinib, rogaratinib, sulfatinib, ARQ-087, ASP5878, AZD4547, BGJ398, Debio 1347, E7090, HMPL-453, INCB054828, MAX-40279, PRN1371, and TAS-120. In some embodiments, the adverse effects can include one or more of: anorexia, asthenia, constipation, decreased appetite, diarrhea, dry mouth, elevated phosphate level (e.g., hyperphosphatemia), fatigue, liver enzyme abnormalities, malaise, muscle aches, nail changes, nausea, soft tissue calcification, and stomatitis. In some embodiments, the FGFR1 inhibitor has an FGFR1 activity of less than 50 nM in an in vitro FGFR1 kinase assay.

Also provided is a method for inhibiting FGFR kinase activity in a cell, comprising contacting the cell with a compound of Formula I. In some embodiments, the contacting is in vitro. In some embodiments, the contacting is in vivo. In some embodiments, the contacting is in vivo, wherein the method comprises administering an effective amount of a compound of Formula I or a pharmaceutically acceptable salt or solvate thereof to a subject having a cell having FGFR kinase activity. In some embodiments, the cell is a cancer cell. In some embodiments, the cancer cell is any cancer as described herein. In some embodiments, the cancer cell is a FGFR-associated cancer cell. In some embodiments, the cell is a bladder cancer cell.

Also provided is a compound of Formula I or a pharmaceutically acceptable salt or solvate thereof for use in the inhibition of FGFR1, FGFR2, FGFR2, and/or FGFR4.

Also provided is the use of a compound of Formula I or a pharmaceutically acceptable salt or solvate thereof in the manufacture of a medicament for the inhibition of activity of FGFR1, FGFR2, FGFR3, or FGFR4.

Also provided is a method for inhibiting FGFR kinase activity in a mammalian cell, comprising contacting the cell with a compound of Formula I. In some embodiments, the contacting is in vitro. In some embodiments, the contacting is in vivo. In some embodiments, the contacting is in vivo, wherein the method comprises administering an effective amount of a compound of Formula I or a pharmaceutically acceptable salt or solvate thereof to a mammal having a cell having FGFR kinase activity. In some embodiments, the mammalian cell is a mammalian cancer cell. In some embodiments, the mammalian cancer cell is any cancer as described herein. In some embodiments, the mammalian cancer cell is a FGFR-associated cancer cell. In some embodiments, the mammalian cell is a bladder cancer cell.

As used herein, the term "contacting" refers to the bringing together of indicated moieties in an in vitro system or an in vivo system. For example, "contacting" a FGFR kinase with a compound provided herein includes the administration of a compound provided herein to an individual or subject, such as a human, having a FGFR kinase, as well as, for example, introducing a compound provided herein into a sample containing a cellular or purified preparation containing the FGFR kinase.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein.

The phrase "effective amount" means an amount of compound that, when administered to a subject in need of such treatment, is sufficient to (i) treat a FGFR kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound (e.g., a compound of Formula I) that will correspond to such an amount will vary depending upon factors such as the particular compound, disease condition and its severity, the identity (e.g., weight) of the subject in need of treatment, but can nevertheless be routinely determined by one skilled in the art.

FGFR-associated diseases and disorders can include diseases and disorders that are not cancer. Accordingly, provided herein are methods treating a subject, the method comprising administering a therapeutically effective amount of a compound of Formula I or a pharmaceutically acceptable salt or solvate thereof, to a subject having a clinical record that indicates that the subject has a dysregulation of a FGFR gene, a FGFR kinase, or expression or activity or level of any of the same.

FGF/FGFR signaling plays a key role in development, including in organogensesis, skeletal development, and neuronal development. See, for example, Kelleher et al, *Carcinogenesis* 34(2):2198-2205, 2013; Su et al., *Bone Res.*

2:14003, 2014; McDonnel et al., *Hum Mol Genet,* 24(R1): R60-6, 2015; and Ornitz and Itoh, *Wiley Interdiscip Rev Dev Bio* 4(3):215-266, 2015.

Non-limiting examples of FGFR-associated diseases and disorders include Acanthosis *nigricans,* Achondroplasia, Apert syndrome, Beare-Stevenson syndrome (BSS), Camptodactyly, tall stature, and hearing loss syndrome (CATSHL) syndrome, cleft lip and palate, congenital heart disease (e.g., associated with ambiguous genitalia), craniosynostosis, Crouzon syndrome, ectrodactyly, encephalocraniocutaneous lipomatosis, Hartsfield syndrome, hypochondroplasia, hypogonadoropic hypogonadism (e.g., hypogonadotropic hypogonadism 2 with or without anosmia, Kallman syndrome), ichthyosis vulgaris and/or atopic dermatitis, Jackson-Weiss syndrome, lethal pulmonary acinar dysplasia, microphthalmia, Muenke coronal craniosynostosis, osteoglophonic dysplasia, Pfeiffer syndrome, seborrheic keratosis, syndactyly, thanatophoric dysplasia (e.g., type I or type II), trigonocephaly 1 (also called metopic craniosynostosis), and tumor-induced osteomalacia. Non-limiting examples of FGFR1-associated diseases and disorders include congenital heart disease (e.g., associated with ambiguous genitalia), craniosynostosis, encephalocraniocutaneous lipomatosis, Hartsfield syndrome, hypogonadoropic hypogonadism (e.g., hypogonadotropic hypogonadism 2 with or without anosmia, Kallman syndrome), ichthyosis vulgaris and/or atopic dermatitis, Jackson-Weiss syndrome, osteoglophonic dysplasia, Pfeiffer syndrome, trigonocephaly 1 (also called metopic craniosynostosis), and tumor-induced osteomalacia. Non-limiting examples of FGFR2-associated diseases and disorders include Apert syndrome, Beare-Stevenson syndrome (BSS), Crouzon syndrome, ectrodactyly, Jackson-Weiss syndrome, lethal pulmonary acinar dysplasia, Pfeiffer syndrome, and syndactyly. Non-limiting examples of FGFR3-associated diseases and disorders include acanthosis *nigricans,* achondroplasia, Camptodactyly, tall stature, and hearing loss syndrome (CATSHL) syndrome, cleft lip and palate, craniosynostosis, hypochondroplasia, microphthalmia, Muenke coronal craniosynostosis, seborrheic keratosis, and thanatophoric dysplasia (e.g., type I or type II). Other non-limiting examples of FGFR-associated diseases and disorders can be found, for example, in Table BD.

Accordingly, provided herein are methods for treating a subject diagnosed with (or identified as having) any of the FGFR-associated diseases or disorders in Table BD (e.g., achondroplasia, hypochondroplasia, or thanatophoric dysplasia) that include administering to the subject a therapeutically effective amount of a compound of Formula I or a pharmaceutically acceptable salt or solvate thereof. Also provided herein are methods for treating a subject identified or diagnosed as having any of the FGFR-associated diseases or disorders in Table BD (e.g., achondroplasia, hypochondroplasia, or thanatophoric dysplasia) that include administering to the subject a therapeutically effective amount of a compound of Formula I or pharmaceutically acceptable salt or solvate thereof. For example, the FGFR-associated disease or disorder can be any of the FGFR-associated diseases or disorders in Table BD (e.g., achondroplasia, hypochondroplasia, or thanatophoric dysplasia) that includes one or more FGFR inhibitor resistance mutations.

Also provided are methods for treating a FGFR-associated disease or disorder (e.g., a FGFR-associated disease or disorder that is not a cancer) in a subject in need thereof, the method comprising: (a) detecting any of the FGFR-associated diseases or disorders in Table BD (e.g., achondroplasia, hypochondroplasia, or thanatophoric dysplasia) in the subject; and (b) administering to the subject a therapeutically effective amount of a compound of Formula I or pharmaceutically acceptable salt or solvate thereof. Some embodiments of these methods further include administering to the subject an additional therapy or therapeutic agent (e.g., a second FGFR inhibitor, a second compound of Formula I or a pharmaceutically acceptable salt or solvate thereof, an immunotherapy, a guanylyl cyclase B activator, a growth hormone, or a natriuretic peptide precursor C (CNP) agonist). In some embodiments, the subject was previously treated with a first FGFR inhibitor or previously treated with another therapy or therapeutic agent. In some embodiments, the subject is determined to have any of the FGFR-associated diseases or disorders in Table BD (e.g., achondroplasia, hypochondroplasia, or thanatophoric dysplasia) through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. For example, the FGFR-associated disease or disorder can be any of the FGFR-associated diseases or disorders in Table BD (e.g., achondroplasia, hypochondroplasia, or thanatophoric dysplasia) that includes one or more FGFR mutations.

Also provided are methods of treating a subject that include performing an assay on a sample obtained from a subject to determine whether the subject has a dysregulation of a FGFR gene, a FGFR kinase, or expression or activity or level of any of the same, and administering (e.g., specifically or selectively administering) a therapeutically effective amount of a compound of Formula I or a pharmaceutically acceptable salt or solvate thereof to the subject determined to have a dysregulation of a FGFR gene, a FGFR kinase, or expression or activity or level of any of the same. Some embodiments of these methods further include administering to the subject an additional therapy or therapeutic agent (e.g., a second FGFR inhibitor, a second compound of Formula I or a pharmaceutically acceptable salt or solvate thereof, an immunotherapy, a guanylyl cyclase B activator, a growth hormone, or a natriuretic peptide precursor C (CNP) agonist). In some embodiments of these methods, the subject was previously treated with a first FGFR inhibitor or previously treated with another therapy or therapeutic agent. In some embodiments, the subject is a subject suspected of having a FGFR-associated disease or disorder, a subject presenting with one or more symptoms of a FGFR-associated disease or disorder. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a FGFR gene, a FGFR kinase, or expression or activity or level of any of the same includes one or more FGFR mutations (e.g., any of the mutations in Table BD).

In some embodiments, provided herein are methods for treating a FGFR-associated disease or disorder (e.g., a FGFR-associated disease or disorder that is not a cancer) in a subject in need of such treatment, the method comprising a) detecting a dysregulation of a FGFR gene, a FGFR kinase, or the expression or activity or level of any of the same in a sample from the subject; and b) administering a therapeutically effective amount of a compound of Formula I or a pharmaceutically acceptable salt or solvate thereof. In some embodiments, the dysregulation of a FGFR gene, a FGFR kinase, or the expression or activity or level of any of the same includes one or more FGFR kinase protein point mutations/insertions/deletions. Non-limiting examples of FGFR kinase protein point mutations/insertions/deletions are described in Table BD. In some embodiments, the FGFR kinase protein point mutations/insertions/deletions are selected from the group consisting of point mutations/insertions/deletions corresponding to V561M in SEQ ID NO. 1, V564I or V564F in SEQ ID NO. 3, or V555M in SEQ ID NO. 5.

Also provided is a compound of Formula I or pharmaceutically acceptable salt or solvate thereof for use in treating any of the FGFR-associated diseases or disorders in Table BD (e.g., achondroplasia, hypochondroplasia, or thanatophoric dysplasia) in a subject identified or diagnosed as having any of the FGFR-associated diseases or disorders in Table BD (e.g., achondroplasia, hypochondroplasia, or thanatophoric dysplasia) through a step of performing an assay (e.g., an in vitro assay) on a sample obtained from the subject to determine whether the subject has a dysregulation of a FGFR gene, a FGFR kinase, or expression or activity or level of any of the same, where the presence of a dysregulation of a FGFR gene, a FGFR kinase, or expression or activity or level of any of the same, identifies that the subject has a FGFR-associated disease or disorder. Also provided is the use of a compound of Formula I or a pharmaceutically acceptable salt or solvate thereof for the manufacture of a medicament for treating any of the FGFR-associated diseases or disorders in Table BD (e.g., achondroplasia, hypochondroplasia, or thanatophoric dysplasia) in a subject identified or diagnosed as having any of the FGFR-associated diseases or disorders in Table BD (e.g., achondroplasia, hypochondroplasia, or thanatophoric dysplasia) through a step of performing an assay on a sample obtained from the subject to determine whether the subject has a dysregulation of a FGFR gene, a FGFR kinase, or expression or activity or level of any of the same where the presence of dysregulation of a FGFR gene, a FGFR kinase, or expression or activity or level of any of the same, identifies that the subject has a FGFR-associated disease or disorder. Some embodiments of any of the methods or uses described herein further include recording in the subject's clinical record (e.g., a computer readable medium) that the subject is determined to have a dysregulation of a FGFR gene, a FGFR kinase, or expression or activity or level of any of the same, through the performance of the assay, should be administered a compound of Formula I or pharmaceutically acceptable salt or solvate thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy.

Also provided is a compound of Formula I or a pharmaceutically acceptable salt or solvate thereof, for use in the treatment of any of the FGFR-associated diseases or disorders in Table BD (e.g., achondroplasia, hypochondroplasia, or thanatophoric dysplasia) in a subject in need thereof or a subject identified or diagnosed as having a FGFR-associated disease or disorder (e.g., a FGFR-associated disease or disorder that is not a cancer). Also provided is the use of a compound of Formula I or a pharmaceutically acceptable salt or solvate thereof for the manufacture of a medicament for treating any of the FGFR-associated diseases or disorders in Table BD (e.g., achondroplasia, hypochondroplasia, or thanatophoric dysplasia) in a subject identified or diagnosed as having a FGFR-associated disease or disorder. In some embodiments, the FGFR-associated disease or disorder is, for example, any of the FGFR-associated diseases or disorders in Table BD (e.g., achondroplasia, hypochondroplasia, or thanatophoric dysplasia) having one or more FGFR mutation (e.g., any of the mutations in Table BD). In some embodiments, a subject is identified or diagnosed as having any of the FGFR-associated diseases or disorders in Table BD (e.g., achondroplasia, hypochondroplasia, or thanatophoric dysplasia) through the use of a regulatory agency-approved, e.g., FDA-approved, kit for identifying dysregulation of a FGFR gene, a FGFR kinase, or expression or activity or level of any of the same, in a subject or a biopsy sample from the sample. As provided herein, any of the FGFR-associated diseases or disorders in Table BD (e.g., achondroplasia, hypochondroplasia, or thanatophoric dysplasia) includes those described herein and known in the art.

FGF/FGFR signaling is also involved in angiogenesis. See, for example, Carmeliet and Jain, Nature 473(7347): 298-307, 2011; Presta et al., *Cytokine Growth Factor Rev.*, 16(2):159-178, 2005; and Cross and Claesson-Welsh, *Trends Parmacol Sci.*, 22(4): 201-207, 2001. Aberrant angiogenesis can be present in cancer, or in other diseases or conditions, such as ocular diseases or conditions (e.g., macular degeneration (e.g., exudative macular degeneration), diabetic retinopathy (e.g., proliferative diabetic retinopathy)) or inflammatory diseases or conditions (e.g., rheumatoid arthritis). In some embodiments, an angiogenesis-related disorder is selected from the group consisting of macular degeneration, diabetic retinopathy, ischemic retinopathy, retinopathy of prematurity, neovascular glaucoma, iritis rubeosis, corneal neovascularization, cyclitis, sickle cell retinopathy, pterygium, and rheumatoid arthritis.

Accordingly, provided herein are methods for treating a subject diagnosed with (or identified as having) an angiogenesis-related disorder that include administering to the subject a therapeutically effective amount of a compound of Formula I or a pharmaceutically acceptable salt or solvate thereof. Also provided herein are methods for treating a subject identified or diagnosed as having an angiogenesis-related disorder that include administering to the subject a therapeutically effective amount of a compound of Formula I or pharmaceutically acceptable salt or solvate thereof. In some embodiments, the subject that has been identified or diagnosed as having an angiogenesis-related disorder through the use of a regulatory agency-approved, e.g., FDA-approved test or assay, in a subject or a biopsy sample from the subject or by performing any of the non-limiting examples of assays described herein. In some embodiments, the test or assay is provided as a kit. For example, the angiogenesis-related disorder can be a FGFR-associated disease or disorder that includes one or more FGFR inhibitor resistance mutations.

Also provided are methods for treating an angiogenesis-related disorder in a subject in need thereof, the method comprising: (a) detecting an angiogenesis-related disorder in the subject; and (b) administering to the subject a therapeutically effective amount of a compound of Formula I or pharmaceutically acceptable salt or solvate thereof. Some embodiments of these methods further include administering to the subject an additional therapy or therapeutic agent (e.g., a second FGFR inhibitor, a second compound of Formula I or a pharmaceutically acceptable salt or solvate thereof, or an immunotherapy). Some embodiments of these methods further include administering to the subject an additional therapy or therapeutic agent. In some embodiments, the subject was previously treated with a first FGFR inhibitor or previously treated with another therapy or therapeutic therapy. In some embodiments, the subject is determined to have an angiogenesis-related disorder through the use of a regulatory agency-approved, e.g., FDA-approved test or assay, in a subject or a biopsy sample from the subject or by performing any of the non-limiting examples of assays described herein. In some embodiments, the test or assay is provided as a kit. For example, the angiogenesis-related disorder can be a FGFR-associated disease or disorder that includes one or more FGFR mutations.

Also provided are methods of treating a subject that include performing an assay on a sample obtained from a subject to determine whether the subject has an angiogenesis-related disorder, and administering (e.g., specifically or selectively administering) a therapeutically effective amount of a compound of Formula I or a pharmaceutically acceptable salt or solvate thereof to the subject determined to have an angiogenesis-related disorder. Some embodiments of these methods further include administering to the subject an additional therapy or therapeutic agent (e.g., a second FGFR inhibitor, a second compound of Formula I or a pharmaceutically acceptable salt or solvate thereof, or immunotherapy). In some embodiments of these methods, the subject was previously treated with a first FGFR inhibitor or previously treated with another therapy or therapeutic agent. In some embodiments, the subject is a subject suspected of having an angiogenesis-related disorder, or a subject presenting with one or more symptoms of an angiogenesis-related disorder. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, angiogenesis-related disorder includes one or more FGFR mutations (e.g., any of the mutations in Table BC or Table BD).

In some embodiments, provided herein are methods for treating an angiogenesis-related disorder in a subject in need of such treatment, the method comprising a) detecting an angiogenesis-related disorder in a sample from the subject; and b) administering a therapeutically effective amount of a compound of Formula I or a pharmaceutically acceptable salt or solvate thereof. In some embodiments, the angiogenesis-related disorder is a dysregulation of a FGFR gene, a FGFR kinase, or the expression or activity or level of any of the same and includes one or more FGFR kinase protein point mutations/insertions/deletions. Non-limiting examples of FGFR kinase protein point mutations/insertions/deletions are described in Table BC and Table BD. In some embodiments, the FGFR kinase protein point mutations/insertions/deletions are selected from the group consisting of point mutations/insertions/deletions corresponding to V561M in SEQ ID NO. 1, V564I or V564F in SEQ ID NO. 3, or V555M in SEQ ID NO. 5.

In some embodiments of any of the methods disclosed herein, treating with a compound of Formula I can result in a decrease in the diameter of a blood vessel and/or a decrease in the number of blood vessels in a tissue in need of a reduction in the number of blood vessels (e.g., as compared to the diameter of the blood vessel and/or the number of blood vessels in the tissue in the patient prior to treatment). In some examples the methods can result in, e.g., a decrease in the diameter of a blood vessel of about 1% to about 80%, 75%, 70%, 65%, 60%, 55%, 50%, 45%, 40%, 35%, 30%, 25%, 20%, 15%, 10%, or 5%; about 2% to about 80%, 75%, 70%, 65%, 60%, 55%, 50%, 45%, 40%, 35%, 30%, 25%, 20%, 15%, 10%, or 5%; about 3% to about 80%, 75%, 70%, 65%, 60%, 55%, 50%, 45%, 40%, 35%, 30%, 25%, 20%, 15%, 10%, or 5%; about 5% to about 80%, 75%, 70%, 65%, 60%, 55%, 50%, 45%, 40%, 35%, 30%, 25%, 20%, 15%, or 10%; about 10% to about 80%, 75%, 70%, 65%, 60%, 55%, 50%, 45%, 40%, 35%, 30%, 25%, 20%, or 15%; about 15% to about 80%, 75%, 70%, 65%, 60%, 55%, 50%, 45%, 40%, 35%, 30%, 25%, or 20%; about 20% to about 80%, 75%, 70%, 65%, 60%, 55%, 50%, 45%, 40%, 35%, 30%, or 25%; about 25% to about 80%, 75%, 70%, 65%, 60%, 55%, 50%, 45%, 40%, 35%, or 30%; about 30% to about 80%, 75%, 70%, 65%, 60%, 55%, 50%, 45%, 40%, or 35%; about 35% to about 80%, 75%, 70%, 65%, 60%, 55%, 50%, 45%, or 40%; about 40% to about 80%, 75%, 70%, 65%, 60%, 55%, 50%, or 45%; about 45% to about 80%, 75%, 70%, 65%, 60%, 55%, or 50%; about 50% to about 80%, 75%, 70%, 65%, 60%, or 55%; about 55% to about 80%, 75%, 70%, 65%, or 60%; about 60% to about 80%, 75%, 70%, or 65%; about 65% to about 80%, 75%, or 70%; about 70% to about 80% or 75%; or about 75% to about 80% (e.g., as compared to the diameter of the blood vessel in the patient prior to treatment). In some examples the methods can result in, e.g., a decrease in the number of blood vessels in a tissue in need of a reduction in the number of blood vessels of about 5% to about 80%, 75%, 70%, 65%, 60%, 55%, 50%, 45%, 40%, 35%, 30%, 25%, 20%, 15%, or 10%; about 10% to about 80%, 75%, 70%, 65%, 60%, 55%, 50%, 45%, 40%, 35%, 30%, 25%, 20%, or 15%; about 15% to about 80%, 75%, 70%, 65%, 60%, 55%, 50%, 45%, 40%, 35%, 30%, 25%, or 20%; about 20% or about 80%, 75%, 70%, 65%, 60%, 55%, 50%, 45%, 40%, 35%, 30%, or 25%; about 25% to about 80%, 75%, 70%, 65%, 60%, 55%, 50%, 45%, 40%, 35%, or 30%; about 30% to about 80%, 75%, 70%, 65%, 60%, 55%, 50%, 45%, 40%, or 35%; about 35% to about 80%, 75%, 70%, 65%, 60%, 55%, 50%, 45%, or 40%; about 40% to about 80%, 75%, 70%, 65%, 60%, 55%, 50%, or 45%; about 45% to about 80%, 75%, 70%, 65%, 60%, 55%, or 50%; about 50% to about 80%, 75%, 70%, 65%, 60%, or 55%; about 55% to about 80%, 75%, 70%, 65%, or 60%; about 60% to about 80%, 75%, 70%, or 65%; about 65% to about 80%, 75%, or 70%; about 70% to about 80% or 75%; or about 75% to about 80% (e.g., as compared to the diameter of the blood vessel and/or the number of blood vessels in the tissue in the patient prior to treatment). These methods can also result in a decrease in the rate of formation of new blood vessels in a tissue in need thereof in a patient having an angiogenesis-related disorder (e.g., as compared to the rate of formation of new blood vessels in the tissue in the patient prior to treatment, or the rate of formation of new blood vessels in a patient or a population of patients having the same or similar angiogenesis-related disorder). The decrease in the rate of formation of a new blood vessels in a tissue in need thereof in a patient having an angiogenesis-related disorder can be about 1% to about 100%, 95%, 90%, 85%, 80%, 75%, 70%, 65%, 60%, 55%, 50%, 45%, 40%, 35%, 30%, 25%, 20%, 15%, 10%, or 5%; about 5% to about 100%, 95%, 90%, 85%, 80%, 75%, 70%, 65%, 60%, 55%, 50%, 45%, 40%, 35%, 30%, 25%, 20%, 15%, or 10%; about 10% to about 100%, 95%, 90%, 85%, 80%, 75%, 70%, 65%, 60%, 55%, 50%, 45%, 40%, 35%, 30%, 25%, 20%, or 15%; about 15% to 100%, 95%, 90%, 85%, 80%, 75%, 70%, 65%, 60%, 55%, 50%, 45%, 40%, 35%, 30%, 25%, or 20%; about 20% to 100%, 95%, 90%, 85%, 80%, 75%, 70%, 65%, 60%, 55%, 50%, 45%, 40%, 35%, 30%, or 25%; about 25% to 100%, 95%, 90%, 85%, 80%, 75%, 70%, 65%, 60%, 55%, 50%, 45%, 40%, 35%, or 30%; about 30% to 100%, 95%, 90%, 85%, 80%, 75%, 70%, 65%, 60%, 55%, 50%, 45%, 40%, or 35%; about 35% to 100%, 95%, 90%, 85%, 80%, 75%, 70%, 65%, 60%, 55%, 50%, 45%, or 40%; about 40% to 100%, 95%, 90%, 85%, 80%, 75%, 70%, 65%, 60%, 55%, 50%, or 45%; about 45% to 100%, 95%, 90%, 85%, 80%, 75%, 70%, 65%, 60%, 55%, or 50%; about 50% to 100%, 95%, 90%, 85%, 80%, 75%, 70%, 65%, 60%, or 55%; about 55% to 100%, 95%, 90%, 85%, 80%, 75%, 70%, 65%, or 60%; about 60% to 100%, 95%, 90%, 85%, 80%, 75%, 70%, or 65%; about 65% to 100%, 95%, 90%, 85%, 80%, 75%, or 70%; about 70% to 100%, 95%, 90%, 85%, 80%, or 75%; about 75% to 100%, 95%, 90%, 85%, or 80%; about 80% to 100%, 95%, 90%, or 85%; about 85% to 100%, 95%, or 90%; about 90% to about 100% or 95%; or about 95% to about 100% (e.g., as compared to the rate of formation of new blood vessels in the tissue in the patient prior to treatment, or the rate of formation of new blood vessels in a patient or a population of patients having the same or similar angiogenesis-related disorder).

Also provided is the use of a compound of Formula I or a pharmaceutically acceptable salt or solvent thereof for treating an angiogenesis-related disorder in a patient. Also provided is the use of a compound of Formula I or a pharmaceutically acceptable salt or solvate thereof in the manufacture of a medicament for treating an angiogenesis-related disorder in a patient.

Also provided is a compound of Formula I or a pharmaceutically acceptable salt or solvate thereof for use in treating an angiogenesis-related disorder in a subject identified or diagnosed as having an angiogenesis-related disorder through a step of performing an assay (e.g., an in vitro assay) on a sample obtained from the subject. Some embodiments of any of the methods or uses described herein further include recording in the subject's clinical record (e.g., a computer readable medium) that the subject is determined to have an angiogenesis-related disorder and should be administered a compound of Formula I or pharmaceutically acceptable salt or solvate thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the angiogenesis-related disorder is a dysregulation of a FGFR gene, a FGFR kinase, or expression or activity or level of any of the same includes one or more FGFR mutation (e.g., any of the mutations in Table BC or Table BD).

Also provided is a compound of Formula I or a pharmaceutically acceptable salt or solvate thereof, for use in the treatment of an angiogenesis-related disorder in a subject in need thereof or a subject identified or diagnosed as having an angiogenesis-related disorder. Also provided is the use of a compound of Formula I or a pharmaceutically acceptable salt or solvate thereof for the manufacture of a medicament for treating an angiogenesis-related disorder in a subject identified or diagnosed as having an angiogenesis-related disorder. In some embodiments, the angiogenesis-related disorder is, for example, an angiogenesis-related disorder having one or more FGFR mutations (e.g., any of the mutations in Table BC or Table BD). In some embodiments, a subject is identified or diagnosed as having an angiogenesis-related disorder through the use of a regulatory agency-approved, e.g., FDA-approved, kit for identifying dysregulation of a FGFR gene, a FGFR kinase, or expression or activity or level of any of the same, in a subject or a biopsy sample from the sample. As provided herein, an angiogenesis-related disorder includes those described herein and known in the art.

Also provided herein are methods for treating a disease involving angiogenesis and/or neovascularization, comprising administering to a subject in need thereof, a therapeutically effective amount of a compound of Formula I.

Also provided herein are methods for inhibiting angiogenesis in a tumor, which comprises contacting the tumor with a compound of Formula I.

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions that contain, as the active ingredient, a compound of Formula I or a pharmaceutically acceptable salt or solvate thereof, in combination with one or more pharmaceutically accepTable BCarriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is formulated as a tablet or capsule.

The compositions comprising a compound of Formula I or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suiTable BAs unitary dosages for human subjects and other subjects, each unit containing a predetermined quantity of active material (i.e., a compound of Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

Provided herein are pharmaceutical kits useful, for example, in the treatment of FGFR-associated diseases or disorders, such as cancer or any of the FGFR-associated diseases in Table BD (e.g., achondroplasia, hypochondroplasia, or thanatophoric dysplasia), which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically accepTable BCarriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy subjects and/or those suffering from a given disorder, may be completed according to methods well known in the clinical and medical arts.

EXAMPLES

The following examples illustrate the invention. Synthetic Examples

Intermediate P1

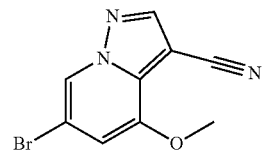

6-bromo-4-methoxypyrazolo[1,5-a]pyridine-3-carbonitrile

Step 1: Preparation of (E)-6-bromo-4-methoxypyrazolo[1,5-a]pyridine-3-carbaldehyde oxime. To a suspension of 6-bromo-4-methoxypyrazolo[1,5-a]pyridine-3-carbaldehyde (0.76 g, 3.0 mmol) and hydroxylamine hydrochloride (0.31 g, 4.5 mmol) in EtOH (40 mL) was added water (20 mL), and the reaction was stirred at 50° C. for 4 h. After cooling to ambient temperature, the reaction mixture was concentrated in vacuo. The residue was suspended in water, then treated with saturated $NaHCO_{3(aq)}$ and vacuum filtered. The solids were rinsed sequentially with $H_2O$ (25 mL) and MTBE (50 mL) to yield the title compound (0.68 g, 84% yield). MS (apci) m/z=271.9 (M+H).

Step 2: Preparation of 6-bromo-4-methoxypyrazolo[1,5-a]pyridine-3-carbonitrile. A solution of (E)-6-bromo-4-methoxypyrazolo[1,5-a]pyridine-3-carbaldehyde oxime (17.15 g, 63.50 mmol) in acetic anhydride (707 mL, 7.49 mol) was heated at 120° C. overnight. Following subsequent distillation to remove the acetic anhydride, the remaining residue was dried in vacuo to yield the title compound (15.92 g, 99.4% yield). $^1H$ NMR ($CDCl_3$) δ 8.32 (m, 1H), 8.12 (s, 1H), 6.74 (m, 1H), 4.03 (s, 3H).

Intermediate P2

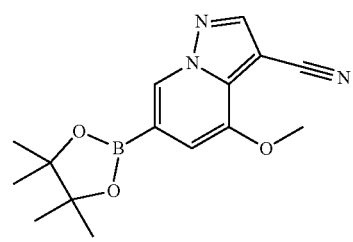 [SMILES: COc1cc(B2OC(C)(C)C(C)(C)O2)cn2ncc(C#N)c12]

4-methoxy-6-(4,4,5,5-tetramethyl-1,3,2-dioxaborolan-2-yl)pyrazolo[1,5-a]pyridine-3-carbonitrile A solution of 6-bromo-4-methoxypyrazolo[1,5-a]pyridine-3-carbonitrile (Intermediate P1; 10.0 g, 39.7 mmol) in dioxane (265 mL) was treated with bis(pinacolato)diboron (10.6 g, 41.7 mmol), PdCl$_2$(dppf).CH$_2$Cl$_2$ (1.62 g, 1.98 mmol) and KOAc$_{(s)}$ (11.7 g, 119 mmol). The resulting mixture was sparged with Ar$_{(g)}$, before sealing the reaction vessel. The mixture then was stirred overnight at 80° C. After cooling to ambient temperature, additional bis(pinacolato)diboron (1.01 g, 3.98 mmol) and PdCl$_2$(dppf).CH$_2$Cl$_2$ (1.62 g, 1.98 mmol) were introduced, and the mixture was sparged with Ar$_{(g)}$. The vessel then was sealed, and the mixture was stirred for an additional 24 h at 80° C. After cooling to ambient temperature, the reaction mixture was diluted with EtOAc then washed successively with water (2×) and brine (1×). The organic extracts were dried over anhydrous Na$_2$SO$_{4(s)}$, filtered, and concentrated in vacuo. The crude residue was purified twice by silica chromatography (using 5-95% DCM-Acetone then 5-95% Hexanes-EtOAc as the gradient eluents) to cleanly provide the title compound (9.87 g, 83% yield). $^1$H NMR (400 MHz, d$^6$-DMSO) δ 8.59 (s, 1H), 8.46 (s, 1H), 6.89 (s, 1H), 3.99 (s, 1H), 1.30 (s, 12H).

Intermediate P3

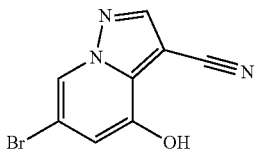 [SMILES: N#Cc1cnn2cc(Br)cc(O)c12]

6-bromo-4-hydroxypyrazolo[1,5-a]pyridine-3-carbonitrile

Under an inert atmosphere (N$_{2(g)}$), a solution of 6-bromo-4-methoxypyrazolo[1,5-a]pyridine-3-carbonitrile (Intermediate P1; 200 g, 873 mmol) in DMA (2494 mL) was stirred at 40° C., and treated dropwise (3 drops/second) with 2 M NaOH$_{(aq)}$ (105 mL, 1746 mmol) followed by water (5 mL; to rinse the addition funnel). Dodecyl mercaptan (418 mL, 1746 mmol) was added dropwise (3 drops/second). The resulting reaction mixture was stirred for 2 h at 40° C. After cooling to ambient temperature, the reaction mixture was poured into cold (~10° C.) water (8 L), and the pH was adjusted to ~5 with the addition of a 10% aqueous solution of citric acid. The quenched reaction mixture was stirred for 4 h at ambient temperature then left resting for 12 h at ambient temperature to allow more precipitate to form. The mixture was then stirred 1 h at ambient temperature before it was vacuum filtered, rinsing with water (1.5 L). The filter cake was dried for 2 h, then triturated with heptane (2 L), filtered and dried in vacuo to afford the title compound (181 g, 87% yield). $^1$H NMR (400 MHz, d$^6$-DMSO) δ 11.81 (br s, 1H), 8.82 (d, 1H), 8.55 (s, 1H), 6.87 (d, 1H).

Intermediate P4

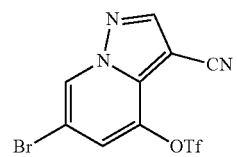 [SMILES: N#Cc1cnn2cc(Br)cc(OS(=O)(=O)C(F)(F)F)c12]

6-bromo-3-cyanopyrazolo[1,5-a]pyridin-4-yl trifluoromethanesulfonate

A cold (0° C.) solution of 6-bromo-4-hydroxypyrazolo[1,5-a]pyridine-3-carbonitrile (Intermediate P3; 13.3 g, 55.9 mmol) in DMA (279 mL) was treated with PhN(Tf)$_2$ (22.0 g, 61.5 mmol), and then slowly with DIEA (19.9 mL, 112 mmol). The resulting mixture was stirred for 30 min at 0° C., then for 2 h at ambient temperature. Subsequently, the reaction was poured onto ice (~500 g) in water (500 mL). After stirring for 0.5 h, the resulting suspension was filtered slowly. The solids obtained were washed with water (~100 mL), then dried in vacuo overnight. The crude material was purified by silica chromatography (using 10-50% EtOAc-Hexanes as gradient eluent) to provide the title compound (13.4 g, 65% yield). MS (apci) m/z=367.9, 369.9 (M−H).

Intermediate P6

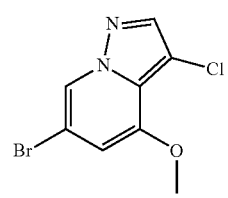

6-bromo-3-chloro-4-methoxypyrazolo[1,5-a]pyridine

A solution of 6-bromo-4-methoxy-pyrazolo[1,5-a]pyridine (10 g, 44.0 mmol) in DCM (176 mL, 44.0 mmol) was treated sequentially with PPTS (1.11 g, 4.40 mmol) and NCS (6.17 g, 46.2 mmol). After stirring overnight at ambient temperature, the reaction mixture was washed with 2.0 M NaOH$_{(aq)}$ (2×). The combined organic extracts were dried over anhydrous Na$_2$SO$_{4(s)}$, filtered, and concentrated in vacuo to cleanly afford the title compound (11.4 g, 99% yield). MS (apci) m/z=262.9 (M+H).

Intermediate P7

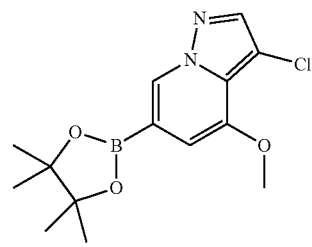 [SMILES: COc1cc(B2OC(C)(C)C(C)(C)O2)cn2ncc(Cl)c12]

3-chloro-4-methoxy-6-(4,4,5,5-tetramethyl-1,3,2-dioxaborolan-2-yl)pyrazolo[1,5-a]pyridine A solution of 6-bromo-3-chloro-4-methoxypyrazolo[1,5-a]pyridine (Intermediate P6; 598.5 mg, 2.289 mmol) in dioxanes (11.5 mL) was treated sequentially bis(pinacolato)diboron (639.310 mg, 2.51756 mmol), PdCl$_2$(dppf).CH$_2$Cl$_2$ (186.9 mg, 0.2289 mmol), and KOAc$_{(s)}$ (673.9 mg, 6.867 mmol). The resulting mixture was sparged with Ar$_{(g)}$, before sealing the reaction vessel. The mixture then was stirred for 16 h at 80° C. After cooling to ambient temperature, the reaction mixture was diluted with EtOAc then washed successively with water (2×) and brine (1×). The organic extracts were dried over anhydrous Na$_2$SO$_{4(s)}$, filtered, and concentrated in vacuo. The crude residue was purified by silica chromatography (using 5-95% Hexanes-Acetone as gradient eluent) to cleanly afford the title compound (682.7 mg, 97% yield). MS (apci) m/z=309.1 (M+H).

Intermediate P8

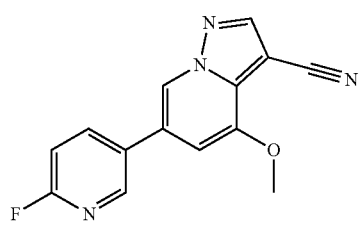 [SMILES: COc1cc(-c2ccc(F)nc2)cn2ncc(C#N)c12]

6-(6-fluoropyridin-3-yl)-4-methoxypyrazolo[1,5-a]pyridine-3-carbonitrile

A solution of 6-bromo-4-methoxypyrazolo[1,5-a]pyridine-3-carbonitrile (Intermediate P1; 5.00 g, 19.8 mmol) in 4:1 dioxane:water (198.36 mL) was treated sequentially with 2-fluoro-5-(4,4,5,5-tetramethyl-[1,3,2]-dioxaborolan-2-yl)-pyridine (4.646 g, 20.83 mmol), K$_2$CO$_{3(s)}$ (8.224 g, 59.51 mmol) and Pd(PPh$_3$)$_4$ (1.146 g, 0.9918 mmol). The resulting mixture was sparged with Ar$_{(g)}$, before sealing the reaction vessel. The mixture then was stirred overnight at 80° C. After cooling to ambient temperature, the reaction mixture was diluted with water, and extracted with 4:1 DCM:iPrOH (3×). The combined organic extracts were washed sequentially with water (2×) and brine (2×), then dried over anhydrous Na$_2$SO$_{4(s)}$, filtered, and concentrated in vacuo. The crude residue were triturated with MTBE (stirred 30 min). The solids were filtered and dried in vacuo to cleanly provide the title compound (4.039 g, 76% yield). MS (apci) m/z=269.1 (M+H).

Intermediate P9 and Intermediate P10

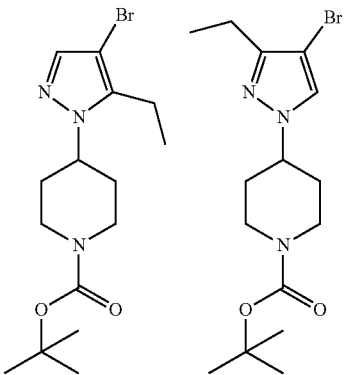 [SMILES: CCc1c(Br)cnn1C1CCN(C(=O)OC(C)(C)C)CC1 ; CCc1nn(C2CCN(C(=O)OC(C)(C)C)CC2)cc1Br]

tert-butyl 4-(4-bromo-3-ethyl-1H-pyrazol-1-yl)piperidine-1-carboxylate (Intermediate P9) and tert-butyl 4-(4-bromo-5-ethyl-1H-pyrazol-1-yl)piperidine-1-carboxylate (Intermediate P10)

A mixture of 4-bromo-3-ethyl-1H-pyrazole (1 g, 5.713 mmol) and DMA (28.57 mL) was treated sequentially with NaH (60 wt. % mineral oil dispersion; 457.0 mg, 11.43 mmol) and 4-methanesulfonyloxy-piperidine-1-carboxylic acid tert-butyl ester (2.394 g, 8.570 mmol), then stirred overnight at 70° C. After cooling to ambient temperature, the reaction mixture was diluted with water and extracted with EtOAc (3×). The combined organic extracts were washed successively with water (2×) and brine (1×), then dried over anhydrous Na$_2$SO$_{4(s)}$, filtered and concentrated in vacuo. The resulting oil was purified by silica chromatography (using isocratic 10% EtOAc in DCM as the eluent) to separately afford the title compounds.

Intermediate P9 tert-butyl 4-(4-bromo-3-ethyl-1H-pyrazol-1-yl)piperidine-1-carboxylate was afforded as the more polar product (1.074 g, 52% yield). MS (apci) m/z=358.1 (M+H).

Intermediate P10 tert-butyl 4-(4-bromo-5-ethyl-1H-pyrazol-1-yl)piperidine-1-carboxylate was afforded as the less polar product (366 mg, 18% yield). $^1$H NMR (400 MHz, d$^6$-DMSO) δ 7.46 (s, 1H), 4.38 (m, 1H), 4.01 (m, 2H), 2.88 (m, 2H), 2.66 (m, 2H), 1.75 (m, 4H), 1.36 (s, 9H).

Intermediate P11

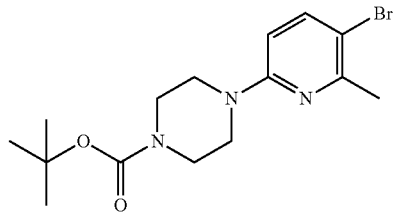 [SMILES: Cc1nc(N2CCN(C(=O)OC(C)(C)C)CC2)ccc1Br]

tert-butyl 4-(5-bromo-6-methylpyridin-2-yl)piperazine-1-carboxylate

A solution of 5-bromo-2-chloro-6-methylpyridine (812.0 mg, 3.933 mmol) in DMSO (4.0 mL) was treated with tert-butyl 1-piperazinecarboxylate (1465 mg, 7.866 mmol) and DIEA (1370 µL, 7.866 mmol). The resulting mixture was stirred for 16 h at 90° C. in a sealed tube. After cooling to ambient temperature, the reaction mixture was diluted with water and extracted with EtOAc (2×). The combined organic extracts were washed successively with water (3×) and brine (1×), then dried over anhydrous Na$_2$SO$_{4(s)}$, filtered, and concentrated in vacuo. The crude residue was purified by silica chromatography (using 5-70% Hexanes-EtOAc as the gradient eluent) to afford the title compound (80.1 mg, 6% yield). MS (apci) m/z=358.1 (M+H).

Intermediate P12 and Intermediate P13

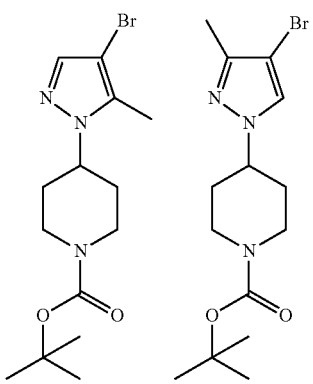 [SMILES: Cc1c(Br)cnn1C1CCN(C(=O)OC(C)(C)C)CC1 ; Cc1nn(C2CCN(C(=O)OC(C)(C)C)CC2)cc1Br]

tert-butyl 4-(4-bromo-3-methyl-1H-pyrazol-1-yl)piperidine-1-carboxylate (Intermediate P12) and tert-butyl 4-(4-bromo-5-methyl-1H-pyrazol-1-yl)piperidine-1-carboxylate (Intermediate P13)

A solution of 4-bromo-3-methylpyrazole (1.5 g, 9.32 mmol) in DMA (46.6 mL) was treated sequentially with NaH (60 wt. % mineral oil dispersion; 0.745 g, 18.6 mmol) and 4-methanesulfonyloxy-piperidine-1-carboxylic acid tert-butyl ester (3.90 g, 14.0 mmol). The reaction was stirred overnight at 70° C. After cooling to ambient temperature, the reaction mixture was diluted with water, and extracted with EtOAc (3×). The combined organic extracts were washed with water (2×) and brine (1×), dried over anhydrous Na$_2$SO$_{4(s)}$, filtered and concentrated in vacuo. The resulting oil was purified by silica chromatography (using 0-100% DCM-EtOAc as the gradient eluents) to separately afford the title compounds:

Intermediate P12 4-(4-bromo-3-methyl-1H-pyrazol-1-yl)piperidine-1-carboxylate was obtained as the more polar product (1.7 g, 53% yield). $^1$H NMR (400 MHz, d$^6$-DMSO) δ 7.89 (s, 1H), 4.21 (m, 1H), 3.96 (m, 2H), 2.82 (m, 2H), 2.07 (s, 3H), 1.90 (m, 2H), 1.68 (m, 2H), 1.37 (s, 9H).

Intermediate P13 tert-butyl 4-(4-bromo-5-methyl-1H-pyrazol-1-yl)piperidine-1-carboxylate was obtained as the less polar product (860 mg, 27% yield). $^1$H NMR (400 MHz, d$^6$-DMSO) δ 7.45 (s, 1H), 4.35 (m, 1H), 4.01 (m, 2H), 2.86 (m, 2H), 2.23 (s, 3H), 1.75 (m, 4H), 1.38 (s, 9H).

Intermediate P14 and Intermediate P15

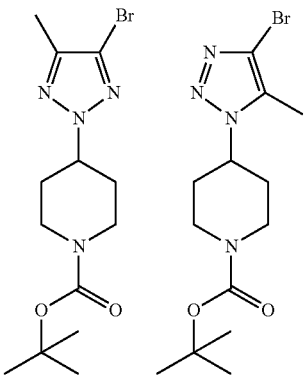 [SMILES: Cc1nn(C2CCN(C(=O)OC(C)(C)C)CC2)nc1Br ; Cc1c(Br)nnn1C1CCN(C(=O)OC(C)(C)C)CC1]

tert-butyl 4-(4-bromo-5-methyl-2H-1,2,3-triazol-2-yl)piperidine-1-carboxylate (Intermediate P14) and tert-butyl 4-(4-bromo-5-methyl-1H-1,2,3-triazol-1-yl)piperidine-1-carboxylate (Intermediate P15)

A solution of 5-bromo-4-methyl-1H-1,2,3-triazole (961.7 mg, 5.937 mmol) in DMF (24 mL) was treated with 4-methanesulfonyloxy-piperidine-1-carboxylic acid tert-butyl ester (2488 mg, 8.905 mmol) and NaH (60 wt. % mineral oil dispersion; 474.9 mg, 11.87 mmol). The reaction mixture was stirred overnight at 70° C. overnight, after which it was cooled to ambient temperature, diluted with water, and extracted with EtOAc (2×). The combined organic extracts were washed successively with water (3×) and brine (1×), dried over anhydrous Na$_2$SO$_{4(s)}$, filtered, and concentrated in vacuo. The crude residue was purified by silica chromatography (using 5-60% Hexanes-Acetone as gradient eluent) to separately afford the title compounds:

Intermediate P14 tert-butyl 4-(4-bromo-5-methyl-2H-1,2,3-triazol-2-yl)piperidine-1-carboxylate was obtained as the first peak to come off (1.65 g, 81% yield). MS (apci) m/z=347 (M+H).

Intermediate P15 tert-butyl 4-(4-bromo-5-methyl-1H-1,2,3-triazol-1-yl)piperidine-1-carboxylate was obtained as third first peak to come off (280.3 mg, 14% yield). MS (apci) m/z=345 (M+H).

Intermediate P16

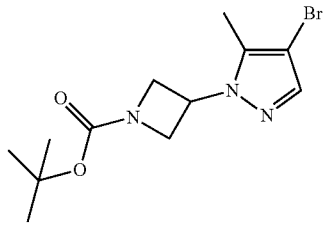 [SMILES: Cc1c(Br)cnn1C1CN(C(=O)OC(C)(C)C)C1]

tert-butyl 3-(4-bromo-5-methyl-1H-pyrazol-1-yl)azetidine-1-carboxylate

A solution of 4-bromo-3-methylpyrazole (2.73 g, 16.96 mmol) in DMF (68 mL) was treated with tert-butyl 3-[(methylsulfonyl)oxy]-1-azetanecarboxylate (4.474 g, 17.80 mmol) followed by NaH (60 wt. % mineral oil dispersion; 1.017 g, 25.43 mmol). The reaction mixture was stirred for 4 h at 70° C., after which it was cooled to ambient temperature, diluted with water, and extracted with EtOAc (2×). The combined organic extracts were washed successively with water (3×) and brine (1×), then dried over anhydrous $Na_2SO_{4(s)}$, filtered, and concentrated in vacuo. The crude residue was purified by silica chromatography (using 5-95% Hexanes-MTBE as gradient eluent) to afford the title compound as a ~1:1 mixture with its isomer. This mixture was further purified by silica chromatography (using isochratic 19:1 DCM-MTBE as the eluent) to cleanly afford the title compound (954.0 mg, 18% yield). $^1$H NMR (400 MHz, $d^6$-DMSO) δ 7.60 (s, 1H), 5.17 (m, 1H), 4.21 (m, 2H), 4.08 (m, 2H), 2.17 (s, 3H), 1.36 (s, 9H).

Intermediate P17

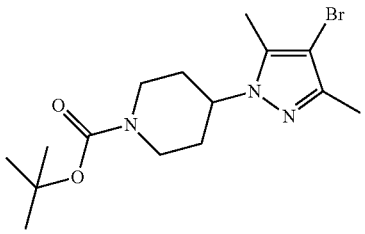 [SMILES: Cc1nn(C2CCN(C(=O)OC(C)(C)C)CC2)c(C)c1Br]

tert-butyl 4-(4-bromo-3,5-dimethyl-1H-pyrazol-1-yl)piperidine-1-carboxylate

A solution of 4-bromo-3,5-dimethylpyrazole (3.00 g, 17.1 mmol) in DMF (100 mL) was treated sequentially with 4-methanesulfonyloxy-piperidine-1-carboxylic acid tert-butyl ester (5.75 g, 20.6 mmol) and NaH (60 wt. % mineral oil dispersion; 1.03 g, 25.7 mmol). The reaction mixture was stirred for 16 h at 70° C. overnight, before sequentially introducing additional NaH (60 wt. % mineral oil dispersion; 1.03 g, 25.7 mmol) and methanesulfonyloxy-piperidine-1-carboxylic acid tert-butyl ester (2.39 g, 8.55 mmol). The resulting mixture was stirred for an additional 24 h at 70° C. After cooling to ambient temperature, the reaction mixture was treated with water and extracted with EtOAc (2×). The combined organic extracts were washed successively with water (3×) and brine (1×), then dried over anhydrous $Na_2SO_{4(s)}$, filtered, and concentrated in vacuo. The resulting residue was purified by silica chromatography (using 10-50% EtOAc-Hexanes as gradient eluent) to provide the title compound (5.72 g, 93% yield). MS (apci) m/z=358.1 (M+H).

Intermediate P18

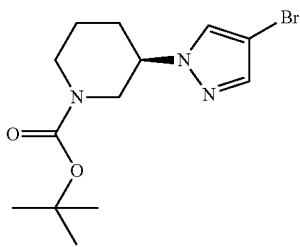 [SMILES: CC(C)(C)OC(=O)N1CCC[C@@H](n2cc(Br)cn2)C1]

tert-butyl (R)-3-(4-bromo-1H-pyrazol-1-yl)piperidine-1-carboxylate

A solution of (S)-1-Boc-3-hydroxypiperidine (4.0 g, 20 mmol) in THF (200 mL) was treated with 4-bromopyrazole (3.067 g, 20.87 mmol), and $PPh_3$ (7.819 g, 29.81 mmol), then cooled to 0° C. The resulting mixture then was treated with DIAD (5.870 mL, 29.81 mmol), and stirred for 16 h at ambient temperature. Subsequently, the reaction mixture was concentrated in vacuo and the resulting residue was purified by silica chromatography (using 5-70% Hexanes-EOAc as gradient eluent) to provide the title compound (2.42 g, 37% yield). $^1$H NMR (400 MHz, $d^6$-DMSO) δ 8.02 (s, 1H), 7.54 (s, 1H), 4.14 (m, 1H), 3.72 (m, 1H), 2.86 (m, 1H), 2.02 (m, 1H), 1.94 (m, 1H), 1.69 (m, 1H), 1.45 (m, 1H), 1.36 (s, 9H), 1.18 (m, 2H).

Intermediate P19

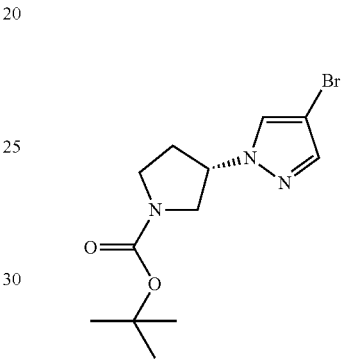

tert-butyl (S)-3-(4-bromo-1H-pyrazol-1-yl)pyrrolidine-1-carboxylate

A solution of N-tert-butoxycarbonyl-(R)-(−)-3-pyrrolidinol (5.1 g, 27 mmol) in THF (275 mL) was treated sequentially with 4-bromopyrazole (4.4 g, 30 mmol) and $PPh_3$ (11 g, 41 mmol), then cooled to 0° C. The resulting mixture was treated with DIAD (8.0 mL, 41 mmol), then stirred for 16 h at ambient temperature. The reaction mixture then was concentrated in vacuo. The resulting residue was purified twice by silica chromatography (using 5-95% DCM-EtOAc then 5-95% Hexanes-acetone as gradient eluent) to afford the title compound (8.61 g, quantitative yield assumed). MS (apci) m/z=318.2 (M+H).

Intermediate P20

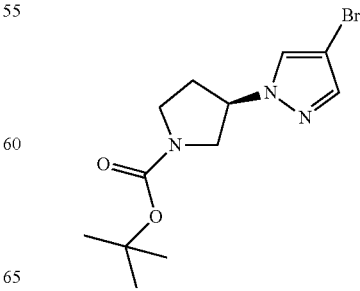

339 tert-butyl (R)-3-(4-bromo-1H-pyrazol-1-yl)pyrrolidine-1-carboxylate

A solution of N-tert-butoxycarbonyl-(S)-(−)-3-pyrrolidinol (5.6 g, 30 mmol) in THF (300 mL) was treated sequentially with 4-bromopyrazole (4.8 g, 33 mmol) and PPh$_3$ (12 g, 45 mmol), then cooled to 0° C. The resulting mixture was treated with DIAD (8.8 mL, 45 mmol), then stirred for 16 h at ambient temperature. The reaction mixture then was concentrated in vacuo. The resulting residue was purified twice by silica chromatography (using 5-95% DCM-EtOAc then 5-95% Hexanes-acetone as gradient eluent) to afford the title compound (9.45 g, quantitative yield assumed). MS (apci) m/z=318.1 (M+H).

Intermediate P21

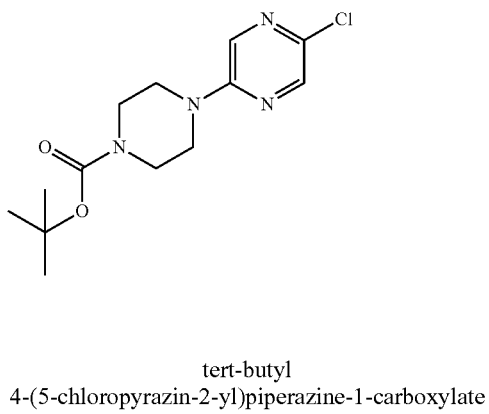

tert-butyl 4-(5-chloropyrazin-2-yl)piperazine-1-carboxylate

A solution of 2,5-dichloropyrazine (1.03 g, 6.914 mmol) in DMSO (10 mL) was treated sequentially with K$_2$CO$_{3(s)}$ (2.867 g, 20.74 mmol) and tert-butyl piperazine-1-carboxylate (1.288 g, 6.914 mmol). The resulting mixture was stirred overnight at 75° C. After cooling to room temperature, the resulting suspension was diluted with EtOAc (10 mL) and extracted with water (20 mL). The organic extracts were concentrated to afford the title compound (1.928 g, 93% yield). MS (apci) m/z=199.1 (M-Boc). $^1$H NMR (CDCl$_3$) δ ᴤ 8.07 (m, 1H), 7.86 (m, 1H), 3.56 (s, 8H), 1.48 (s, 9H).

Intermediate P22

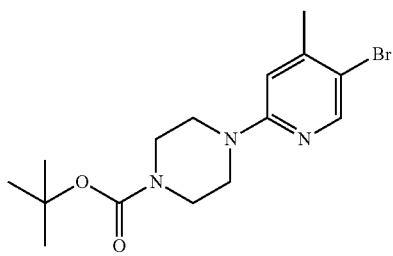 [SMILES: Cc1cc(N2CCN(C(=O)OC(C)(C)C)CC2)ncc1Br]

340 tert-butyl 4-(5-bromo-4-methylpyridin-2-yl)piperazine-1-carboxylate

A solution of 5-bromo-2-fluoro-4-methylpyridine (910.3 mg, 4.791 mmol) in DMSO (4.8 mL, 1.0 M) was treated with tert-butyl 1-piperazinecarboxylate (1785 mg, 9.581 mmol) and DIEA (1669 μL, 9.581 mmol). The resulting mixture was stirred for 16 h at 90° C. in a sealed tube. Subsequently, the mixture was cooled to ambient temperature, diluted with water, and extracted with EtOAc (2×). The combined organic extracts were washed successively with water (3×) and brine (1×), dried over anhydrous Na$_2$SO$_{4(s)}$, filtered, and concentrated in vacuo. The resulting residue was purified by silica chromatography (using 5-70% Hexanes-EtOAc as gradient eluent) to cleanly afford the title compound (1.09 g, 64%). MS (apci) m/z=358 (M+H).

Intermediate P23

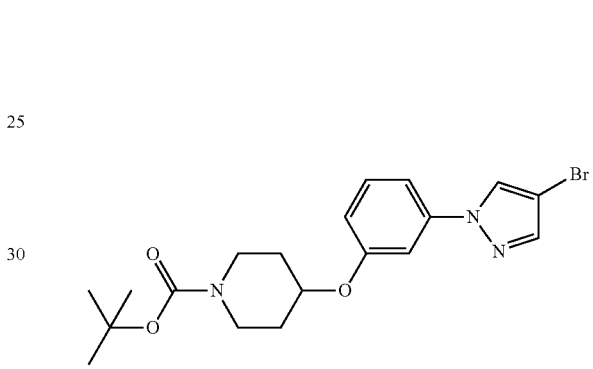

tert-butyl 4-(3-(4-bromo-1H-pyrazol-1-yl)phenoxy)piperidine-1-carboxylate

Step 1: Preparation of 3-(4-bromo-1H-pyrazol-1-yl)phenol. A solution of 4-bromopyrazole (2.09 g, 14.2 mmol) in DCM (140 mL, 0.1 M) was treated with 3-hydroxyphenylboronic acid (2.16 g, 15.6 mmol), Cu(OAc)$_2$ (5.17 g, 28.4 mmol), and pyridine (2.30 mL, 28.4 mmol). The resulting mixture was stirred for 60 h at room temperature open to atmosphere, after which it was filtered through GF/F paper, rinsing with DCM. The filtrate was collected and concentrated in vacuo. The resulting residue was purified by silica chromatography (using 5-70% DCM-EtOAc as gradient eluent) to cleanly provide the title compound (2.46 g, 72% yield). MS (apci) m/z=239 (M+H).

Step 2: Preparation of tert-butyl 4-(3-(4-bromo-1H-pyrazol-1-yl)phenoxy)piperidine-1-carboxylate. A solution of 3-(4-bromo-1H-pyrazol-1-yl)phenol (2.46 g, 10.29 mmol) in THF (52 mL) was treated with tert-butyl 4-hydroxypiperidine-1-carboxylate (2.485 g, 12.35 mmol) and PPh$_3$ (4.048 g, 15.43 mmol), then cooled to 0° C. The resulting mixture was treated DIAD (3.039 mL, 15.43 mmol) then stirred for 16 h at ambient temperature. The reaction mixture then was concentrated in vacuo, and the resulting residue was purified by silica chromatography (using 5-70% Hexanes-EtOAc as gradient eluent) to provide the title compound (2.02 g, 46% yield). MS (apci) m/z=322 (M-Boc).

Intermediate P24

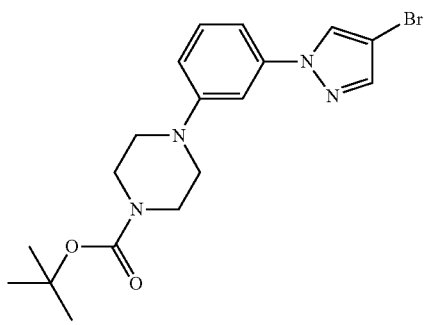 [SMILES: CC(C)(C)OC(=O)N1CCN(c2cccc(-n3cc(Br)cn3)c2)CC1]

tert-butyl 4-(3-(4-bromo-1H-pyrazol-1-yl)phenyl)
piperazine-1-carboxylate

A solution of 4-bromopyrazole (69.4 mL, 6.94 mmol) in DCM (70 mL, 0.1 M) was treated with (3-[4-(tert-butoxycarbonyl)piperazin-1-yl]phenyl)boronic acid (2.55 g, 8.33 mmol), Cu(OAc)$_2$ (2.52 g, 13.9 mmol), and pyridine (1.12 mL, 13.9 mmol). The reaction mixture was stirred for 16 h at ambient temperature overnight open to atmosphere, after which it was filtered through GF/F paper, rinsing with DCM. The filtrate was collected and concentrated in vacuo. The resulting residue was purified by silica chromatography (using 5-95% Hexanes-EtOAc as gradient eluent) to provide the title compound (2.38 g, 84% yield). MS (apci) m/z=407 (M+H).

Intermediate P25

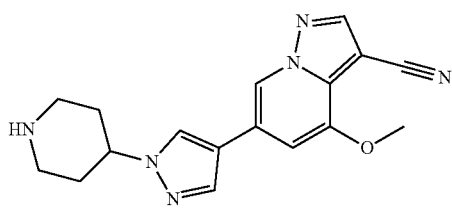 [SMILES: COc1cc(-c2cnn(C3CCNCC3)c2)cn2ncc(C#N)c12]

4-methoxy-6-(1-(piperidin-4-yl)-1H-pyrazol-4-yl)
pyrazolo[1,5-a]pyridine-3-carbonitrile Step 1: Preparation of tert-butyl 4-(4-(3-cyano-4-methoxypyrazolo[1,5-a]pyridin-6-yl)-1H-pyrazol-1-yl)piperidine-1-carboxylate. A solution of 6-bromo-4-methoxypyrazolo[1,5-a]pyridine-3-carbonitrile (Intermediate P1; 5.00 g, 19.8 mmol) in 4:1 dioxane:water (200 mL) was treated sequentially with tert-butyl 4-[4-(4,4,5,5-tetramethyl-1,3,2-dioxaborolan-2-yl)-1H-pyrazol-1-yl]piperidine-1-carboxylate (7.86 g, 20.8 mmol), Pd(PPh$_3$)$_4$ (1.15 g, 0.992 mmol) and K$_2$CO$_{3(s)}$ (8.22 g, 59.5 mmol). The resulting mixture was sparged with Ar$_{(g)}$, before sealing the reaction vessel. The mixture then was stirred for 16 h at 90° C. After cooling to ambient temperature, the reaction mixture was diluted with EtOAc, then sequentially washed with water (2×), and brine (1×). The organic extracts then were dried over anhydrous Na$_2$SO$_{4(s)}$, filtered, and concentrated in vacuo. The crude residue was purified by silica chromatography (using 5-95% DCM-Acetone as the gradient eluent) to cleanly provide the title compound, which was carried directly into Step 2 (~8.5 g, quantitative yield assumed). MS (apci) m/z=423.1 (M+H).

Step 2: Preparation of 4-methoxy-6-(1-(piperidin-4-yl)-1H-pyrazol-4-yl)pyrazolo[1,5-a]pyridine-3-carbonitrile.

The tert-butyl 4-(4-(3-cyano-4-methoxypyrazolo[1,5-a]pyridin-6-yl)-1H-pyrazol-1-yl)piperidine-1-carboxylate (residue from Step 1; ~8.5 g, 20.23 mmol) was dissolved in 1:1 DCM:TFA (50 mL), and stirred for 1 h at ambient temperature. Subsequently, the reaction mixture was concentrated in vacuo. The resulting residue was suspended in 4:1 DCM:iPrOH, and washed with saturated NaHCO$_{3(aq)}$. The organic extracts then were dried over anhydrous Na$_2$SO$_{4(s)}$, filtered, and concentrated in vacuo. The crude residue was triturated with 4:1 DCM:iPrOH. The suspension then was filtered, and the solids were rinsed with DCM. The solids from the filtration were dried in vacuo, while the filtrate was concentrated and purified by silica chromatography (using 1-30% DCM-MeOH with 2% NH$_4$OH as gradient eluent). Pure fractions from the chromatography were concentrated in vacuo and combined with the solids from the filtration to cleanly afford maximum yield of the title compound (5.95 g, 93% yield). MS (apci) m/z=323.2 (M+H).

The compounds in Table CA[1] were prepared using a similar 2 Step method to that described in the synthesis of 4-methoxy-6-(1-(piperidin-4-yl)-1H-pyrazol-4-yl)pyrazolo[1,5-a]pyridine-3-carbonitrile (Intermediate P25), employing the following modifications: in Step 1, reactions were conducted at 80-90° C., using 1.5-3 equivalents of base (K$_2$CO$_{3(s)}$ or Na$_2$CO$_{3(s)}$), 0.05-0.1 equivalents of Pd(PPh$_3$)$_4$, solvent (4:1 dioxanes:water) concentration of 0.1-0.28 M, 1.0 equivalent of 6-bromo-4-methoxypyrazolo[1,5-a]pyridine-3-carbonitrile (Intermediate P1) and replacing tert-butyl 4-[4-(4,4,5,5-tetramethyl-1,3,2-dioxaborolan-2-yl)-1H-pyrazol-1-yl]piperidine-1-carboxylate respectively with 1.0-1.1 equivalents of the appropriate boronic ester (or acid) from Table CA[1]i; and in Step 2, using DCM:TFA ratios of 1:1-2:1 and replacing the tert-butyl 4-(4-(3-cyano-4-methoxypyrazolo[1,5-a]pyridin-6-yl)-1H-pyrazol-1-yl)piperidine-1-carboxylate (Step 1) with the appropriate Boc-protected coupling product from Step 1 in each. All reactions were monitored for completion by LCMS, as such reaction durations were adjusted accordingly. When necessary, title compounds (Step 1 and/or Step 2) were isolated via silica gel chromatographic purification using an appropriate gradient eluent or reverse phase chromatographic purification using an appropriate gradient eluent followed by a basic aqueous wash.

TABLE CA[1]

| Intermediate # | Structure | Chemical Name | MS apci (m/z) |
|---|---|---|---|
| P26 | 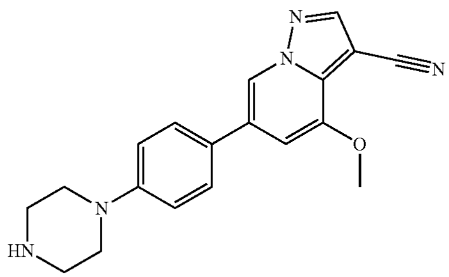 [SMILES: COc1cc(-c2ccc(N3CCNCC3)cc2)cn2ncc(C#N)c12] | 4-methoxy-6-(4-(piperazin-1-yl)phenyl)pyrazolo[1,5-a]pyridine-3-carbonitrile | 334.1 (M + H) |
| P27 | 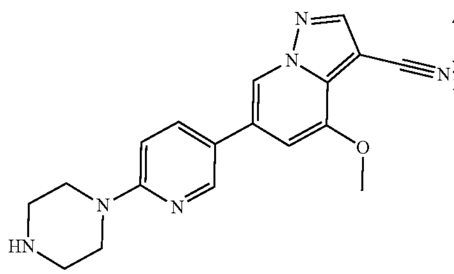 | 4-methoxy-6-(6-(piperazin-1-yl)pyridin-3-yl)pyrazolo[1,5-a]pyridine-3-carbonitrile | 335.1 (M + H) |
| P28 | 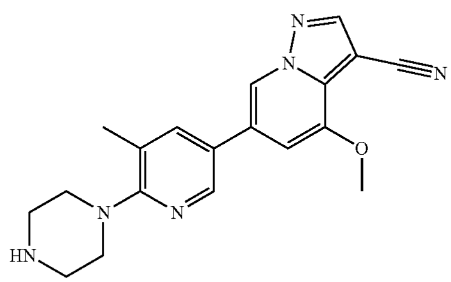 [SMILES: COc1cc(-c2cnc(N3CCNCC3)c(C)c2)cn2ncc(C#N)c12] | 4-methoxy-6-(5-methyl-6-(piperazin-1-yl)pyridin-3-yl)pyrazolo[1,5-a]pyridine-3-carbonitrile | 349.1 (M + H) |
| P29 | 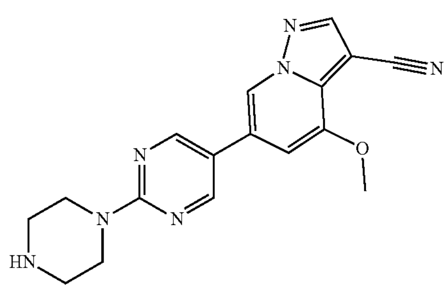 [SMILES: COc1cc(-c2cnc(N3CCNCC3)nc2)cn2ncc(C#N)c12] | 4-methoxy-6-(2-(piperazin-1-yl)pyrimidin-5-yl)pyrazolo[1,5-a]pyridine-3-carbonitrile | 336.2 (M + H) |
| P30 | 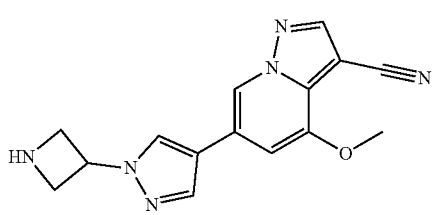 [SMILES: COc1cc(-c2cnn(C3CNC3)c2)cn2ncc(C#N)c12] | 6-(1-(azetidin-3-yl)-1H-pyrazol-4-yl)-4-methoxypyrazolo[1,5-a]pyridine-3-carbonitrile | 295.1 (M + H) |
| P31 | 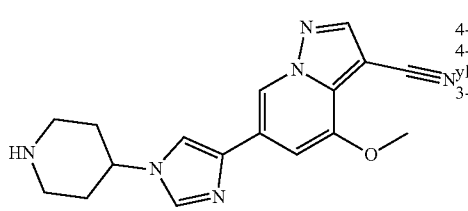 | 4-methoxy-6-(1-(piperidin-4-yl)-1H-imidazol-4-yl)pyrazolo[1,5-a]pyridine-3-carbonitrile | 323.1 (M + H) |

Intermediate P32

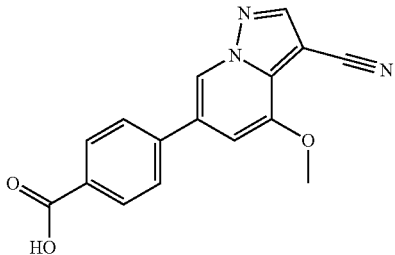 [SMILES: COc1cc(-c2ccc(C(=O)O)cc2)cn2ncc(C#N)c12]

methyl 4-(3-cyano-4-methoxypyrazolo[1,5-a]pyridin-6-yl)benzoate

Step 1: Preparation of methyl 4-(3-cyano-4-methoxypyrazolo[1,5-a]pyridin-6-yl)benzoate. A mixture of 6-bromo-4-methoxypyrazolo[1,5-a]pyridine-3-carbonitrile (1.055 g, 4.185 mmol), (4-(methoxycarbonyl)phenyl)boronic acid (0.8285 g, 4.604 mmol), Pd(PPh$_3$)$_4$ (0.2418 g, 0.2093 mmol) and Na$_2$CO$_{3(s)}$ (0.6654 g, 6.278 mmol) was suspended in 4:1 dioxanes/water (16 mL). The reaction mixture was purged with Ar$_{(g)}$, and placed under a balloon of Ar$_{(g)}$. The mixture was stirred for 12 h at 90° C., and then for 5 d at ambient temperature. The reaction mixture was diluted with EtOAc and water and stirred for 30 min at ambient temperature. The resulting suspension was filtered, and the solids collected were dried in vacuo to afford the title compound (1.018 g, 79%). $^1$H NMR (400 MHz, d$^6$-DMSO) δ 8.99 (s, 1H), 8.61 (s, 1H), 8.02 (m, 4H), 7.37 (s, 1H), 4.10 (s, 3H), 3.86 (s, 3H).

Step 2: Preparation of 4-(3-cyano-4-methoxypyrazolo[1,5-a]pyridin-6-yl)benzoic acid. A suspension of methyl 4-(3-cyano-4-methoxypyrazolo[1,5-a]pyridin-6-yl)benzoate (Step 1; 1.018 g, 3.313 mmol) in MeOH (30 mL) was treated with 2 N NaOH$_{(aq)}$ (3.313 mL, 6.625 mmol) then stirred overnight at reflux. After cooling to ambient temperature, the resulting mixture was concentrated in vacuo. The residue was suspended in water, and acidified to pH~5 with the addition of acetic acid. The resulting suspension was filtered, and the solids collected were washed with water and dried in vacuo to afford the title compound (970 mg, 100% yield). MS (apci) m/z=292.1 (M−H).

Intermediate P33

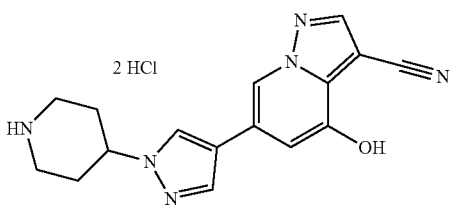 [SMILES: N#Cc1cnn2cc(-c3cnn(C4CCNCC4)c3)cc(O)c12]

4-hydroxy-6-(1-(piperidin-4-yl)-1H-pyrazol-4-yl)pyrazolo[1,5-a]pyridine-3-carbonitrile dihydrochloride Step 1: Preparation of tert-butyl 4-(4-(3-cyano-4-hydroxypyrazolo[1,5-a]pyridin-6-yl)-1H-pyrazol-1-yl)piperidine-1-carboxylate. A solution of 6-bromo-4-hydroxypyrazolo[1,5-a]pyridine-3-carbonitrile (Intermediate P3; 5.52 g, 23.2 mmol) in 4:1 dioxane:water (250 mL) was treated with tert-butyl 4-[4-(4,4,5,5-tetramethyl-1,3,2-dioxaborolan-2-yl)-1H-pyrazol-1-yl]piperidine-1-carboxylate (9.19 g, 24.3 mmol), Pd(PPh$_3$)$_4$ (1.34 g, 1.16 mmol), and K$_2$CO$_{3(s)}$ (9.61 g, 69.6 mmol). The reaction mixture then was sparged with Ar$_{(g)}$, before sealing the reaction vessel. The reaction mixture then was stirred for 16 h at 80° C. overnight. After cooling to room temperature, the resulting mixture was diluted with water, acidified to pH~5 using 10% aqueous citric acid solution, then extracted with 4:1 DCM:iPrOH (2×). The combined organic extracts were dried over anhydrous Na$_2$SO$_{4(s)}$, filtered, and concentrated in vacuo. The resulting residue was purified by silica chromatography (using 5-95% DCM-EtOAc as gradient eluent) to provide the title compound (23.2 mmol, quantitative yield assumed).

Step 2: Preparation of 4-hydroxy-6-(1-(piperidin-4-yl)-1H-pyrazol-4-yl)pyrazolo[1,5-a]pyridine-3-carbonitrile dihydrochloride. The tert-butyl 4-(4-(3-cyano-4-hydroxypyrazolo[1,5-a]pyridin-6-yl)-1H-pyrazol-1-yl)piperidine-1-carboxylate (23.2 mmol) was dissolved in 1:1 DCM:TFA (50 mL) and stirred at room temperature for 30 min. The resulting mixture then was concentrated in vacuo, and the residue was diluted with MeOH (200 mL). The methanolic solution then was treated slowly with 5-6 N HCl solution in iPrOH (92.8 mL, 464 mmol) and stirred for 30 min at ambient temperature. The resulting suspension then was filtered, rinsing the solids collected with 1:1 MTBE:MeOH (200 mL). The solids collected were dried in vacuo to afford the title compound (5.27 g, 60% yield). MS (apci) m/z=309.1 (M+H).

Intermediate P34

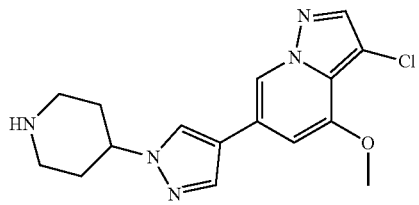 [SMILES: COc1cc(-c2cnn(C3CCNCC3)c2)cn2ncc(Cl)c12]

3-chloro-4-methoxy-6-(1-(piperidin-4-yl)-1H-pyrazol-4-yl)pyrazolo[1,5-a]pyridine Step 1: Preparation of tert-butyl 4-(4-(3-chloro-4-methoxypyrazolo[1,5-a]pyridin-6-yl)-1H-pyrazol-1-yl)piperidine-1-carboxylate. A solution of 6-bromo-3-chloro-4-methoxypyrazolo[1,5-a]pyridine (Intermediate P6; 2 g, 7.65 mmol) in 4:1 dioxane:water (76.5 mL) was treated sequentially with tert-butyl 4-[4-(4,4,5,5-tetramethyl-1,3,2-dioxaborolan-2-yl)-1H-pyrazol-1-yl]piperidine-1-carboxylate (3.03 g, 8.03 mmol), K$_2$CO$_{3(s)}$ (3.17 g, 22.9 mmol), and then Pd(PPh$_3$)$_4$ (0.442 g, 0.382 mmol). The resulting mixture was sparged with N$_{2(g)}$ for 5 minutes, before sealing the reaction vessel. The reaction mixture then was stirred overnight at 80° C. After cooling to room temperature, the reaction mixture was diluted with water and extracted with 4:1 DCM:iPrOH (3×). The combined organic extracts were washed successively with water (2×) and brine (2×), then dried over anhydrous Na$_2$SO$_{4(s)}$, filtered, and concentrated in vacuo. The residue was purified by silica chromatography (using 0-100% DCM:EtOAc as the gradient eluent) to cleanly provide the title compound (3.3 g, 100% yield). MS (apci) m/z=432.1 (M+H).

Step 2: Preparation of 3-chloro-4-methoxy-6-(1-(piperidin-4-yl)-1H-pyrazol-4-yl)pyrazolo[1,5-a]pyridine. Tert-butyl 4-(4-(3-chloro-4-methoxypyrazolo[1,5-a]pyridin-6-yl)-1H-pyrazol-1-yl)piperidine-1-carboxylate (3.3 g, 7.6 mmol) was added to a 1:1 mix of DCM:TFA (15.2 mL). The reaction was stirred at ambient temperature for 3 h. The resulting mixture was concentrated in vacuo. The resulting residue was dissolved in 4:1 DCM:iPrOH, washed with saturated NaHCO$_{3(aq)}$, then dried over anhydrous Na$_2$SO$_{4(s)}$, filtered, and concentrated in vacuo to yield the title compound (2.4 g, 95% yield). MS (apci) m/z=332.1 (M+H).

Intermediate P35

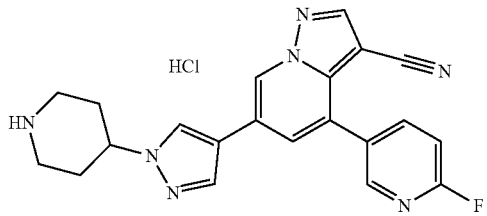 [SMILES: N#Cc1cnn2cc(-c3cnn(C4CCNCC4)c3)cc(-c3ccc(F)nc3)c12 ; Cl]

4-(6-fluoropyridin-3-yl)-6-(1-(piperidin-4-yl)-1H-pyrazol-4-yl)pyrazolo[1,5-a]pyridine-3-carbonitrile hydrochloride Step 1: Preparation of tert-butyl 4-(4-(3-cyano-4-(6-fluoropyridin-3-yl)pyrazolo[1,5-a]pyridin-6-yl)-1H-pyrazol-1-yl)piperidine-1-carboxylate. A mixture of 6-bromo-4-(6-fluoropyridin-3-yl)pyrazolo[1,5-a]pyridine-3-carbonitrile (Intermediate P5; 1.00 g, 3.15 mmol), tert-butyl 4-(4-(4,4,5,5-tetramethyl-1,3,2-dioxaborolan-2-yl)-1H-pyrazol-1-yl)piperidine-1-carboxylate (1.19 g, 3.15 mmol), Pd(PPh$_3$)$_4$ (0.0911 g, 0.0788 mmol), 2M K$_2$CO$_{3(s)}$ (5.52 mL, 11.0 mmol) in dioxanes (15.8 mL, 3.15 mmol). The resulting mixture was sparged with N$_{2(g)}$ for 5 minutes, before sealing the reaction vessel. The reaction mixture was stirred overnight at 80° C. After cooling to ambient temperature, the mixture then was diluted with water and extracted with EtOAc (3×). The combined organic extracts were dried over anhydrous Na$_2$SO$_{4(s)}$, filtered and concentrated in vacuo. The residue was purified by silica chromatography (using 0-100% EtOAc-Hexanes as gradient eluent) to cleanly afford the title compound (1.5 g, 98% yield).

Step 2: Preparation of 4-(6-fluoropyridin-3-yl)-6-(1-(piperidin-4-yl)-1H-pyrazol-4-yl)pyrazolo[1,5-a]pyridine-3-carbonitrile hydrochloride. A solution of tert-butyl 4-(4-(3-cyano-4-(6-fluoropyridin-3-yl)pyrazolo[1,5-a]pyridin-6-yl)-1H-pyrazol-1-yl)piperidine-1-carboxylate (1.5 g, 3.1 mmol) in 1:1 DCM/TFA (16 mL) was stirred at room temperature for 1 d. Subsequently, the reaction mixture was concentrated in vacuo. The resulting residue was sequentially treated with 5-6 N HCl in iPrOH (2 mL), sonicated for 1 min, then concentrated in vacuo (3×). The resulting solid was dried in vacuo overnight to afford the title compound (1.3 g, quantitative yield). MS (apci) m/z=388.1 (M+).

Intermediate P36

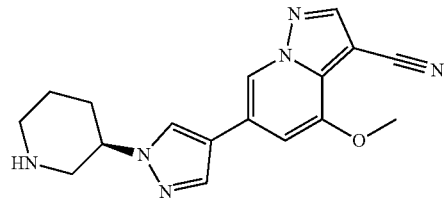 [SMILES: COc1cc(-c2cnn([C@@H]3CCCNC3)c2)cn2ncc(C#N)c12]

(R)-4-methoxy-6-(1-(piperidin-3-yl)-1H-pyrazol-4-yl)pyrazolo[1,5-a]pyridine-3-carbonitrile Step 1: Preparation of tert-butyl (R)-3-(4-(3-cyano-4-methoxypyrazolo[1,5-a]pyridin-6-yl)-1H-pyrazol-1-yl)piperidine-1-carboxylate. A solution of tert-butyl (R)-3-(4-bromo-1H-pyrazol-1-yl)piperidine-1-carboxylate (Intermediate P18; 2.42 g, 7.33 mmol) in 4:1 dioxane:water (72 mL) was treated sequentially with 4-methoxy-6-(4,4,5,5-tetramethyl-1,3,2-dioxaborolan-2-yl)pyrazolo[1,5-a]pyridine-3-carbonitrile (Intermediate P2; 2.41 g, 8.06 mmol), Pd(PPh$_3$)$_4$ (847 mg, 0.733 mmol) and K$_2$CO$_{3(s)}$ (3.04 g, 22.0 mmol). The resulting mixture was sparged with Ar$_{(g)}$, before sealing the reaction vessel. The resulting mixture was stirred for 16 h at 80° C. After cooling to ambient temperature, the reaction mixture was diluted with 4:1 DCM:iPrOH, and washed with water (2×). The organic extracts then were dried over anhydrous Na$_2$SO$_{4(s)}$, filtered, and concentrated in vacuo. The crude residue was purified by silica chromatography (using 5-75% DCM-Acetone as the gradient eluent) to cleanly afford the title compound, which was carried directly into Step 2 (quantitative yield assumed). MS (apci) m/z=423.2 (M+H).

Step 2: Preparation of (R)-4-methoxy-6-(1-(piperidin-3-yl)-1H-pyrazol-4-yl)pyrazolo[1,5-a]pyridine-3-carbonitrile. The tert-butyl (R)-3-(4-(3-cyano-4-methoxypyrazolo[1,5-a]pyridin-6-yl)-1H-pyrazol-1-yl)piperidine-1-carboxylate (residue from Step 1, ~7.33 mmol) was dissolved in 1:1 DCM:TFA (50 mL), and stirred for 30 min at ambient temperature. Subsequently, the reaction mixture was concentrated in vacuo. The resulting residue was suspended in 4:1 DCM:iPrOH and washed with saturated NaHCO$_{3(aq)}$ (2×). The organic extracts then were dried over anhydrous Na$_2$SO$_{4(s)}$, filtered, and concentrated in vacuo to cleanly afford the title compound (1.20 g, 51% yield). MS (apci) m/z=323.1 (M+H).

The compounds in Table CA$^2$ were prepared using a similar 2 step method to that described in the synthesis of (R)-4-methoxy-6-(1-(piperidin-3-yl)-1H-pyrazol-4-yl)pyrazolo[1,5-a]pyridine-3-carbonitrile (Intermediate P36), employing the following modifications: in Step 1, reactions were conducted at 80-90° C., using 1.5-3 equivalents of base (K$_2$CO$_{3(s)}$), 0.05-0.1 equivalents of Pd(PPh$_3$)$_4$, solvent (4:1 dioxanes:water) concentration of 0.1-0.2 M and replacing both the tert-butyl (R)-3-(4-bromo-1H-pyrazol-1-yl)piperidine-1-carboxylate (Intermediate P18) and 4-methoxy-6-(4,4,5,5-tetramethyl-1,3,2-dioxaborolan-2-yl)pyrazolo[1,5-a]pyridine-3-carbonitrile (Intermediate P2) respectively with 1.0-2.1 equivalents of the appropriate aryl bromide from Table CA$^2$i and 1.0-1.1 equivalents of the appropriate boronic ester or acid (where noted * addition of boronic ester and aryl bromide were inverted); and in Step 2, using DCM:

TFA ratios of 1:1-2:1 by volume (1-100 equivalents TFA), and replacing the tert-butyl (R)-3-(4-(3-cyano-4-methoxy-pyrazolo[1,5-a]pyridin-6-yl)-1H-pyrazol-1-yl)piperidine-1-carboxylate (Step 1) with the appropriate Boc-protected coupling product from Step 1 in each. All reactions were monitored for completion by LCMS, as such reaction durations were adjusted accordingly. When necessary, title compounds (Step 1 and/or Step 2) were isolated via silica gel chromatographic purification using an appropriate gradient eluent or reverse phase chromatographic purification using an appropriate gradient eluent followed by a basic aqueous wash.

TABLE CA2

| Intermediate # | Structure | Chemical Name | MS apci (m/z) |
|---|---|---|---|
| P37* | 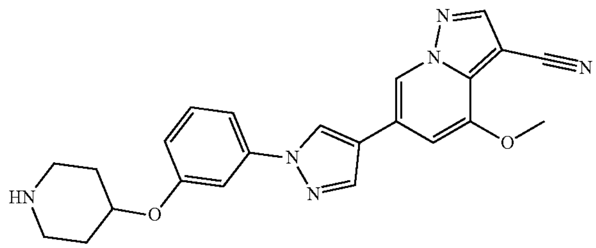 [SMILES: COc1cc(-c2cnn(-c3cccc(OC4CCNCC4)c3)c2)cn2ncc(C#N)c12] | 4-methoxy-6-(1-(3-(piperidin-4-yloxy)phenyl)-1H-pyrazol-4-yl)pyrazolo[1,5-a]pyridine-3-carbonitrile | 415.1 (M + H) |
| P38* | 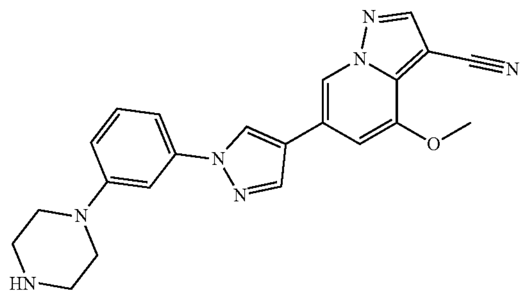 [SMILES: COc1cc(-c2cnn(-c3cccc(N4CCNCC4)c3)c2)cn2ncc(C#N)c12] | 4-methoxy-6-(1-(3-(piperazin-1-yl)phenyl)-1H-pyrazol-4-yl)pyrazolo[1,5-a]pyridine-3-carbonitrile | 400.1 (M + H) |
| P39 | 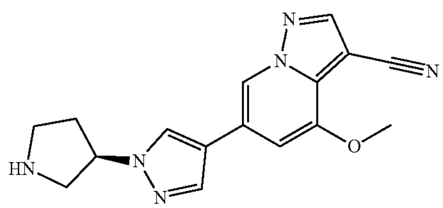 [SMILES: COc1cc(-c2cnn([C@@H]3CCNC3)c2)cn2ncc(C#N)c12] | (R)-4-methoxy-6-(1-(pyrrolidin-3-yl)-1H-pyrazol-4-yl)pyrazolo[1,5-a]pyridine-3-carbonitrile | 309.2 (M + H) |
| P40* | 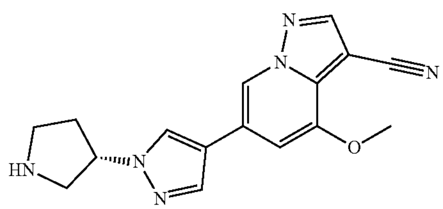 [SMILES: COc1cc(-c2cnn([C@H]3CCNC3)c2)cn2ncc(C#N)c12] | (S)-4-methoxy-6-(1-(pyrrolidin-3-yl)-1H-pyrazol-4-yl)pyrazolo[1,5-a]pyridine-3-carbonitrile | 309.2 (M + H) |
| P41 | 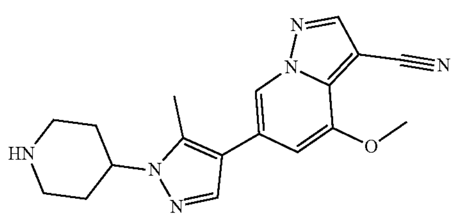 [SMILES: COc1cc(-c2cnn(C3CCNCC3)c2C)cn2ncc(C#N)c12] | 4-methoxy-6-(5-methyl-1-(piperidin-4-yl)-1H-pyrazol-4-yl)pyrazolo[1,5-a]pyridine-3-carbonitrile | 337.2 (M + H) |
| P42 | 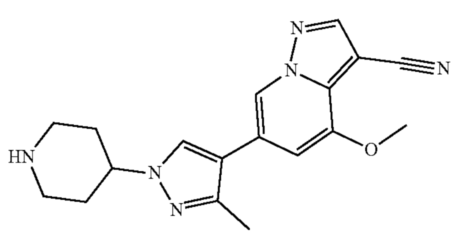 [SMILES: COc1cc(-c2cn(C3CCNCC3)nc2C)cn2ncc(C#N)c12] | 4-methoxy-6-(3-methyl-1-(piperidin-4-yl)-1H-pyrazol-4-yl)pyrazolo[1,5-a]pyridine-3-carbonitrile | 337.2 (M + H) |

TABLE CA2-continued

| Intermediate # | Structure | Chemical Name | MS apci (m/z) |
|---|---|---|---|
| P43 | 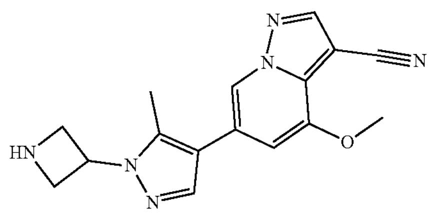 [SMILES: COc1cc(-c2cnn(C3CNC3)c2C)cn2ncc(C#N)c12] | 6-(1-(azetidin-3-yl)-5-methyl-1H-pyrazol-4-yl)-4-methoxypyrazolo[1,5-a]pyridine-3-carbonitrile | 309.1 (M + H) |
| P44 | 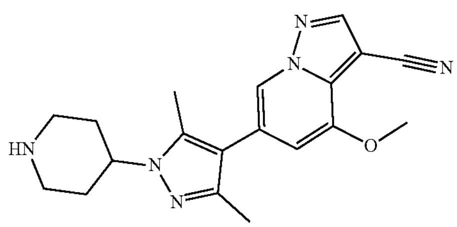 [SMILES: COc1cc(-c2c(C)nn(C3CCNCC3)c2C)cn2ncc(C#N)c12] | 6-(3,5-dimethyl-1-(piperidin-4-yl)-1H-pyrazol-4-yl)-4-methoxypyrazolo[1,5-a]pyridine-3-carbonitrile | 351.1 (M + H) |
| P45 | 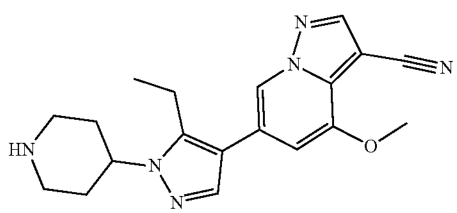 [SMILES: CCc1c(-c2cc(OC)c3c(C#N)cnn3c2)cnn1C1CCNCC1] | 6-(5-ethyl-1-(piperidin-4-yl)-1H-pyrazol-4-yl)-4-methoxypyrazolo[1,5-a]pyridine-3-carbonitrile | 351.2 (M + H) |
| P46 | 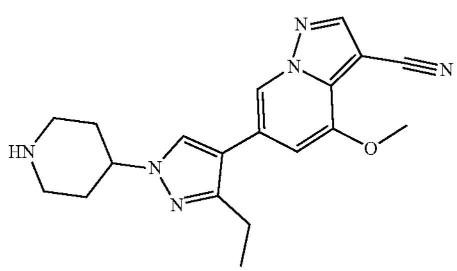 [SMILES: CCc1nn(C2CCNCC2)cc1-c1cc(OC)c2c(C#N)cnn2c1] | 6-(3-ethyl-1-(piperidin-4-yl)-1H-pyrazol-4-yl)-4-methoxypyrazolo[1,5-a]pyridine-3-carbonitrile | 351.2 (M + H) |
| P47* | 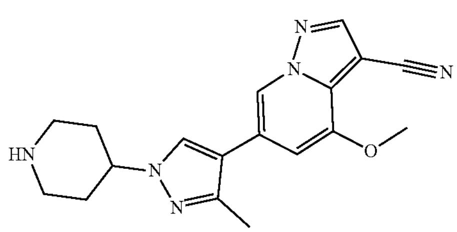 [SMILES: COc1cc(-c2cn(C3CCNCC3)nc2C)cn2ncc(C#N)c12] | 4-methoxy-6-(5-methyl-2-(piperidin-4-yl)-2H-1,2,3-triazol-4-yl)pyrazolo[1,5-a]pyridine-3-carbonitrile | 338.1 (M + H) |
| P48* | 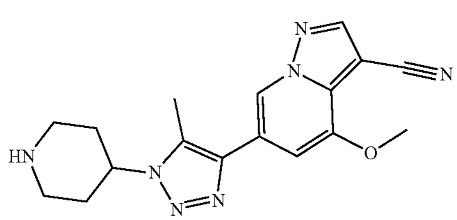 [SMILES: COc1cc(-c2nnn(C3CCNCC3)c2C)cn2ncc(C#N)c12] | 4-methoxy-6-(5-methyl-1-(piperidin-4-yl)-1H-1,2,3-triazol-4-yl)pyrazolo[1,5-a]pyridine-3-carbonitrile | 338.2 (M + H) |

TABLE CA2-continued

| Intermediate # | Structure | Chemical Name | MS apci (m/z) |
|---|---|---|---|
| P49 | 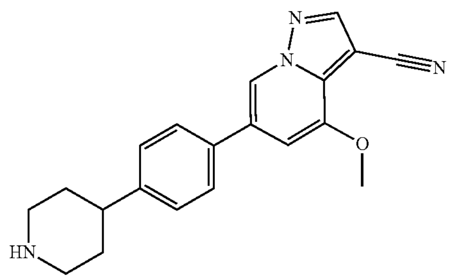 [SMILES: COc1cc(-c2ccc(C3CCNCC3)cc2)cn2ncc(C#N)c12] | 4-methoxy-6-(4-(piperidin-4-yl)phenyl)pyrazolo[1,5-a]pyridine-3-carbonitrile | 333.1 (M + H) |
| P50* | 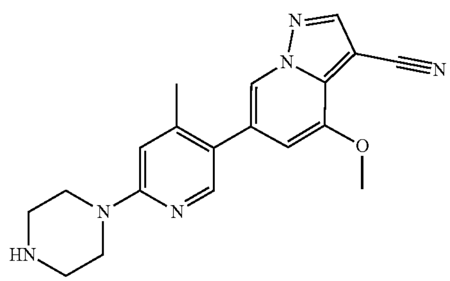 [SMILES: COc1cc(-c2cnc(N3CCNCC3)cc2C)cn2ncc(C#N)c12] | 4-methoxy-6-(4-methyl-6-(piperazin-1-yl)pyridin-3-yl)pyrazolo[1,5-a]pyridine-3-carbonitrile | 349.1 (M + H) |
| P51* | 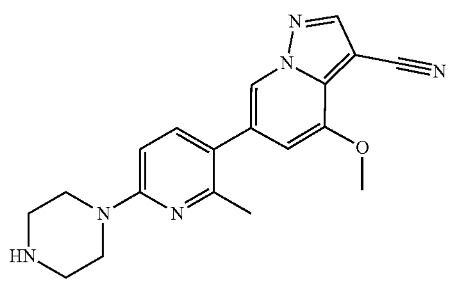 [SMILES: COc1cc(-c2ccc(N3CCNCC3)nc2C)cn2ncc(C#N)c12] | 4-methoxy-6-(2-methyl-6-(piperazin-1-yl)pyridin-3-yl)pyrazolo[1,5-a]pyridine-3-carbonitrile | 349.2 (M + H) |
| P52* | 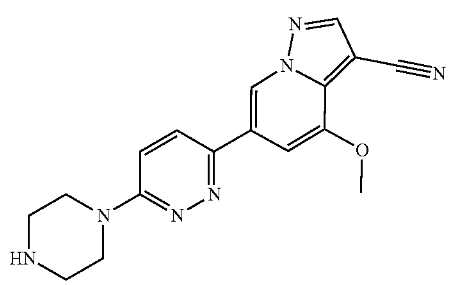 [SMILES: COc1cc(-c2ccc(N3CCNCC3)nn2)cn2ncc(C#N)c12] | 4-methoxy-6-(6-(piperazin-1-yl)pyridazin-3-yl)pyrazolo[1,5-a]pyridine-3-carbonitrile | 336.1 (M + H) |
| P53* | 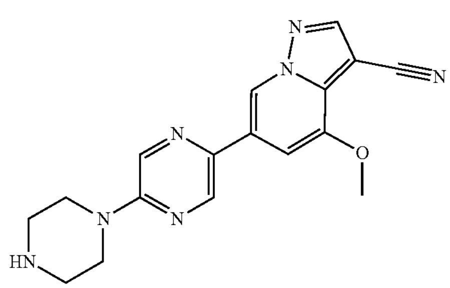 [SMILES: COc1cc(-c2cnc(N3CCNCC3)cn2)cn2ncc(C#N)c12] | 4-methoxy-6-(5-(piperazin-1-yl)pyrazin-2-yl)pyrazolo[1,5-a]pyridine-3-carbonitrile | 336.1 (M + H) |

Intermediate P54

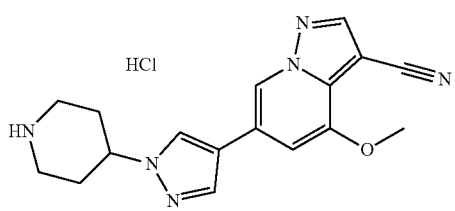 [SMILES: COc1cc(-c2cnn(C3CCNCC3)c2)cn2ncc(C#N)c12 ; Cl]

4-methoxy-6-(1-(piperidin-4-yl)-1H-pyrazol-4-yl)
pyrazolo[1,5-a]pyridine-3-carbonitrile hydrochloride A solution of tert-butyl 4-(4-(3-cyano-4-methoxypyrazolo[1,5-a]pyridin-6-yl)-1H-pyrazol-1-yl)piperidine-1-carboxylate (Step 1, Intermediate P25; 40 mg, 0.095 mmol) in DCM (379 μL) was treated with TFA (365 μL, 4.7 mmol), and stirred for 1 d at ambient temperature. Subsequently, the reaction mixture was concentrated in vacuo. The resulting residue was sequentially suspended in 6 N HCl in iPrOH (2 mL), sonicated for 1 min and concentrated in vacuo (3×). The resulting solid was dried overnight under high vacuum to cleanly afford the title compound (34 mg, quantitative yield). MS (apci) m/z=322.2 (M+).

Intermediate P55

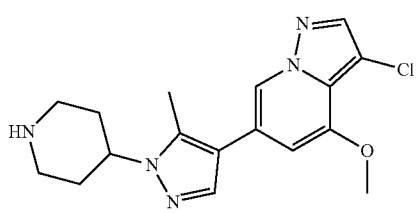 [SMILES: COc1cc(-c2cnn(C3CCNCC3)c2C)cn2ncc(Cl)c12]

3-chloro-4-methoxy-6-(5-methyl-1-(piperidin-4-yl)-1H-pyrazol-4-yl)pyrazolo[1,5-a]pyridine Step 1: Preparation of tert-butyl 4-(4-(3-chloro-4-methoxypyrazolo[1,5-a]pyridin-6-yl)-5-methyl-1H-pyrazol-1-yl)piperidine-1-carboxylate A solution of tert-butyl 4-(4-bromo-5-methyl-1H-pyrazol-1-yl)piperidine-1-carboxylate (Intermediate P13) (761.6 mg, 2.212 mmol) in 4:1 dioxane:water (10 mL) was treated with 3-chloro-4-methoxy-6-(4,4,5,5-tetramethyl-1,3,2-dioxaborolan-2-yl)pyrazolo[1,5-a]pyridine (Intermediate P7) (682.7 mg, 2.212 mmol), $K_2CO_{3(s)}$ (611.5 mg, 4.425 mmol), and $Pd(PPh_3)_4$ (127.8 mg, 0.1106 mmol). The reaction mixture was sparged with $Ar_{(g)}$ for 10 min. The resulting mixture then was stirred overnight at 80° C. under an atmosphere of $Ar_{(g)}$. After cooling to ambient temperature, the reaction mixture was concentrated in vacuo. The resultant residue was diluted with water and extracted with EtOAc (3×). The combined organic extracts were washed with water (2×) and brine (2×), dried over anhydrous $Na_2SO_{4(s)}$, filtered, and concentrated in vacuo. The crude residue was purified by silica chromatography (using 10-80% EtOAc in Hexanes as gradient eluent) to cleanly afford the title compound (566 mg, 57% yield). MS (apci) m/z=446.1 (M+H).

Step 2: Preparation of 3-chloro-4-methoxy-6-(5-methyl-1-(piperidin-4-yl)-1H-pyrazol-4-yl)pyrazolo[1,5-a]pyridine A solution of tert-butyl 4-(4-(3-chloro-4-methoxypyrazolo[1,5-a]pyridin-6-yl)-5-methyl-1H-pyrazol-1-yl)piperidine-1-carboxylate (566 mg, 1.27 mmol) in DCM (4 mL) was treated with TFA (2 mL). The reaction mixture was stirred at ambient temperature for 15 min. The mixture then was concentrated in vacuo, and the residue was partitioned between saturated $NaHCO_{3(aq)}$ and 4:1 DCM:iPrOH. The combined organic extracts were dried over anhydrous $Na_2SO_{4(s)}$, filtered, and concentrated in vacuo to afford the title compound (390 mg, 89% yield). MS (apci) m/z=346.1 (M+H).

Intermediate P56

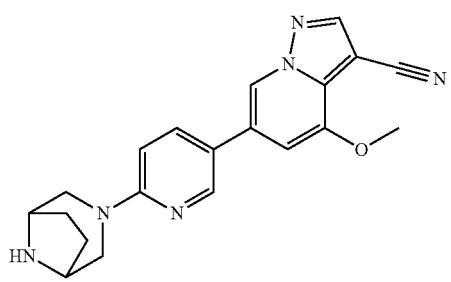 [SMILES: COc1cc(-c2ccc(N3CC4CCC(C3)N4)nc2)cn2ncc(C#N)c12]

6-(6-(3,8-diazabicyclo[3.2.1]octan-3-yl)pyridin-3-yl)-4-methoxypyrazolo[1,5-a]pyridine-3-carbonitrile Step 1: Preparation of tert-butyl 3-(5-(3-cyano-4-methoxypyrazolo[1,5-a]pyridin-6-yl)pyridin-2-yl)-3,8-diazabicyclo[3.2.1]octane-8-carboxylate. A solution of 6-(6-fluoropyridin-3-yl)-4-methoxypyrazolo[1,5-a]pyridine-3-carbonitrile (Intermediate P8; 151.9 mg, 0.5663 mmol) in DMSO (2.8 mL) was treated sequentially with 8-Boc-3,8-diazabicyclo[3.2.1]octane (240.4 mg, 1.133 mmol) and DIEA (493.2 μL, 2.831 mmol), then stirred for 16 h at 130° C. After cooling to ambient temperature, the reaction mixture was diluted with water, and extracted with EtOAc (3×). The combined organic extracts then were washed sequentially with water (3×) and brine (1×), then dried over anhydrous $Na_2SO_{4(s)}$, filtered and concentrated in vacuo. The crude residue was purified by silica chromatography (using 5-75% DCM-Acetone as the gradient eluent) to afford the title compound (quantitative yield assumed). MS (apci) m/z=547.2 (M+H).

Step 2: Preparation of 6-(6-(3,8-diazabicyclo[3.2.1]octan-3-yl)pyridin-3-yl)-4-methoxypyrazolo[1,5-a]pyridine-3-carbonitrile. A solution of tert-butyl 3-(5-(3-cyano-4-methoxypyrazolo[1,5-a]pyridin-6-yl)pyridin-2-yl)-3,8-diazabicyclo[3.2.1]octane-8-carboxylate (Step 1, assume 0.5663 mmol) in 1:1 DCM:TFA (2 mL) was stirred for 15 min at ambient temperature. Subsequently, the reaction mixture was concentrated in vacuo. The crude residue was diluted with 4:1 DCM:iPrOH and washed with saturated $NaHCO_{3(aq)}$ (1×). The organic extracts then were dried over anhydrous Na$_2$SO$_{4(s)}$, filtered, and concentrated in vacuo to cleanly afford the title compound (107.6 mg, 53% yield). MS (apci) m/z=361.2 (M+H).

The compounds in Table CB were prepared using a similar 2 step method to that described in the synthesis of 6-(6-(3,8-diazabicyclo[3.2.1]octan-3-yl)pyridin-3-yl)-4-methoxypyrazolo[1,5-a]pyridine-3-carbonitrile (Intermediate P56), employing the following modifications: in Step 1, replacing 8-Boc-3,8-diazabicyclo[3.2.1]octane with 1-2.5 equivalents of the appropriate mono-Boc-protected diamine from Table CBi; and in Step 2, using DCM: TFA ratios of 1:1-2:1 and replacing the tert-butyl 3-(5-(3-cyano-4-methoxypyrazolo[1,5-a]pyridin-6-yl)pyridin-2-yl)-3,8-diazabicyclo[3.2.1]octane-8-carboxylate (Step 1) with the appropriate Boc-protected coupling product from Step 1 in each. All reactions were monitored for completion by LCMS, as such reaction durations were adjusted accordingly. When necessary, the title compounds (Step 1 and/or Step 2) were isolated via silica gel chromatographic purification using an appropriate gradient eluent or reverse phase chromatographic purification using an appropriate gradient eluent followed by a basic aqueous wash.

TABLE CB

| Intermediate # | Structure | Chemical Name | MS apci (m/z) |
| --- | --- | --- | --- |
| P57 | 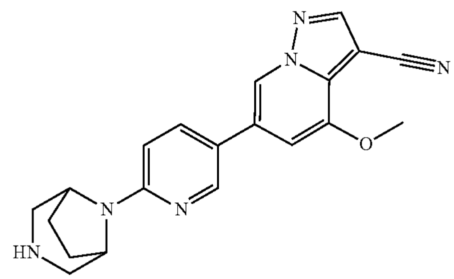 [SMILES: COc1cc(-c2ccc(N3C4CCC3CNC4)nc2)cn2ncc(C#N)c12] | 6-(6-(3,8-diazabicyclo[3.2.1]octan-8-yl)pyridin-3-yl)-4-methoxypyrazolo[1,5-a]pyridine-3-carbonitrile | 361.1 (M + H) |
| P58 | 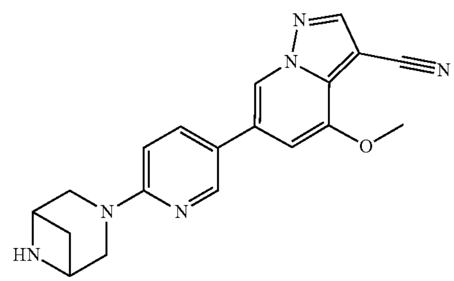 [SMILES: COc1cc(-c2ccc(N3CC4CC(C3)N4)nc2)cn2ncc(C#N)c12] | 6-(6-(3,6-diazabicyclo[3.1.1]heptan-3-yl)pyridin-3-yl)-4-methoxypyrazolo[1,5-a]pyridine-3-carbonitrile | 347.1 (M + H) |
| P59 | 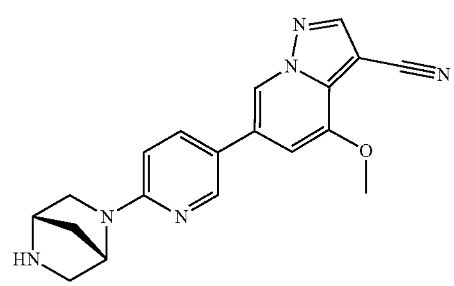 [SMILES: COc1cc(-c2ccc(N3C[C@@H]4C[C@H]3CN4)nc2)cn2ncc(C#N)c12] | 6-(6-((1S,4S)-2,5-diazabicyclo[2.2.1]heptan-2-yl)pyridin-3-yl)-4-methoxypyrazolo[1,5-a]pyridine-3-carbonitrile | 347.1 (M + H) |
| P60* | 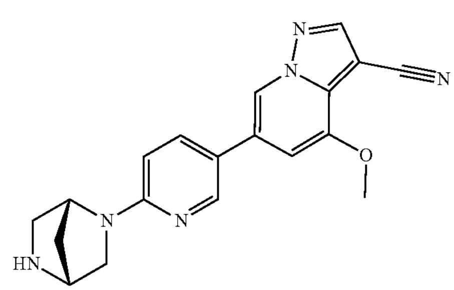 [SMILES: COc1cc(-c2ccc(N3C[C@H]4C[C@@H]3CN4)nc2)cn2ncc(C#N)c12] | 6-(6-((1R,4R)-2,5-diazabicyclo[2.2.1]heptan-2-yl)pyridin-3-yl)-4-methoxypyrazolo[1,5-a]pyridine-3-carbonitrile | 347.1 (M + H) |

TABLE CB-continued

| Intermediate # | Structure | Chemical Name | MS apci (m/z) |
|---|---|---|---|
| P61 | 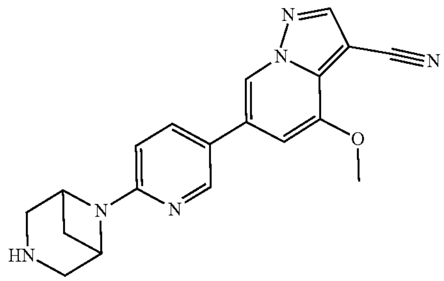 [SMILES: COc1cc(-c2ccc(N3C4CNCC3C4)nc2)cn2ncc(C#N)c12] | 6-(6-(3,6-diazabicyclo[3.1.1]heptan-6-yl)pyridin-3-yl)-4-methoxypyrazolo[1,5-a]pyridine-3-carbonitrile | 347.1 (M + H) |
| P62 | 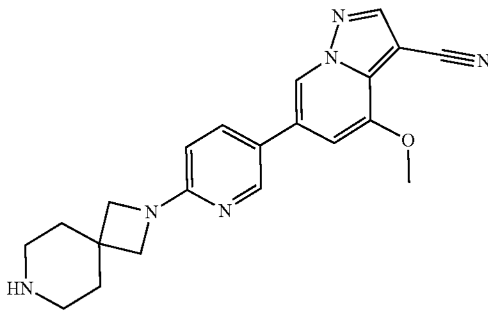 [SMILES: COc1cc(-c2ccc(N3CC4(CCNCC4)C3)nc2)cn2ncc(C#N)c12] | 6-(6-(2,7-diazaspiro[3.5]nonan-2-yl)pyridin-3-yl)-4-methoxypyrazolo[1,5-a]pyridine-3-carbonitrile | 375.2 (M + H) |
| P63 | 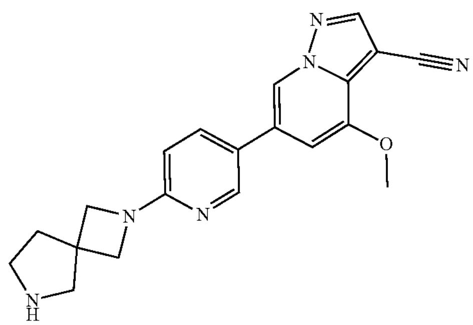 [SMILES: COc1cc(-c2ccc(N3CC4(CCNC4)C3)nc2)cn2ncc(C#N)c12] | 6-(6-(2,6-diazaspiro[3.4]octan-2-yl)pyridin-3-yl)-4-methoxypyrazolo[1,5-a]pyridine-3-carbonitrile | 361.2 (M + H) |
| P64 | 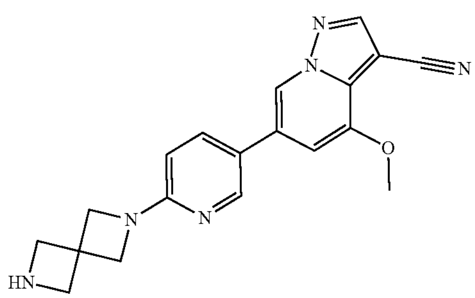 [SMILES: COc1cc(-c2ccc(N3CC4(CNC4)C3)nc2)cn2ncc(C#N)c12] | 6-(6-(2,6-diazaspiro[3.3]heptan-2-yl)pyridin-3-yl)-4-methoxypyrazolo[1,5-a]pyridine-3-carbonitrile | 347.1 (M + H) |

Intermediate P65

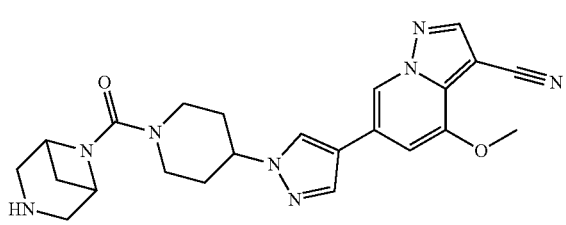 [SMILES: COc1cc(-c2cnn(C3CCN(C(=O)N4C5CNCC4C5)CC3)c2)cn2ncc(C#N)c12]

6-(1-(1-(3,6-diazabicyclo[3.1.1]heptane-6-carbonyl)piperidin-4-yl)-1H-pyrazol-4-yl)-4-methoxypyrazolo[1,5-a]pyridine-3-carbonitrile Step 1: Preparation of tert-butyl 6-(4-(4-(3-cyano-4-methoxypyrazolo[1,5-a]pyridin-6-yl)-1H-pyrazol-1-yl)piperidine-1-carbonyl)-3,6-diazabicyclo[3.1.1]heptane-3-carboxylate. A solution of 4-methoxy-6-(1-(piperidin-4-yl)-1H-pyrazol-4-yl)pyrazolo[1,5-a]pyridine-3-carbonitrile (Intermediate P25; 72.3 mg, 0.224 mmol) in DMA (2.2 mL) was treated sequentially with DIEA (195.3 µL, 1.121 mmol) and 4-nitrophenyl chloroformate (54.25 mg, 0.2691 mmol). After stirring the resulting mixture for 1 h at ambient temperature, 3,6-diazabicyclo[3.1.1]heptane-3-carboxylic acid tert-butyl ester (133.4 mg, 0.6728 mmol) was introduced. The reaction mixture was stirred for 16 h at 80° C. After cooling to ambient temperature, the reaction mixture was diluted with EtOAc and sequentially washed with water (3×) and brine (1×). The organic extracts were dried over anhydrous $Na_2SO_{4(s)}$, filtered and concentrated in vacuo. The crude residue was purified by silica chromatography (using 5-95% DCM-Acetone as the gradient eluent) to afford the title compound (quantitative yield). MS (apci) m/z=547.2 (M+H).

Step 2: Preparation of 6-(1-(1-(3,6-diazabicyclo[3.1.1] heptane-6-carbonyl)piperidin-4-yl)-1H-pyrazol-4-yl)-4-methoxypyrazolo[1,5-a]pyridine-3-carbonitrile. A solution of tert-butyl 6-(4-(4-(3-cyano-4-methoxypyrazolo[1,5-a]pyridin-6-yl)-1H-pyrazol-1-yl)piperidine-1-carbonyl)-3,6-diazabicyclo[3.1.1]heptane-3-carboxylate (Step 1; approx. 122.6 mg, 0.224 mmol) in 1:1 DCM:TFA (2 mL), and stirred for 30 min at ambient temperature. Subsequently, the reaction mixture was concentrated in vacuo. The crude residue was diluted with 4:1 DCM:iPrOH and saturated $NaHCO_{3(aq)}$ (1×). The organic extracts then were dried over anhydrous $Na_2SO_{4(s)}$, filtered, and concentrated in vacuo to cleanly afford the title compound (100.0 mg, 100% yield). MS (apci) m/z=447.2 (M+H).

The compounds in Table CC were prepared using a similar 2 step method to that described in the synthesis of 6-(1-(1-(3,6-diazabicyclo[3.1.1]heptane-6-carbonyl)piperidin-4-yl)-1H-pyrazol-4-yl)-4-methoxypyrazolo[1,5-a]pyridine-3-carbonitrile (Intermediate P65), employing the following modifications: in Step 1, using 1.0-1.2 equivalents of 4-nitrophenyl chloroformate, 3-5 equivalents of amine base (DIEA or TEA), solvent (DMA or DCM) concentration of 0.1-0.2 M and replacing 3,6-diazabicyclo[3.1.1]heptane-3-carboxylic acid tert-butyl ester with 1-3 equivalents of the appropriate mono-Boc-protected diamine from Table CCi; and in Step 2, using DCM: TFA ratios between 1:1 and 2:1 (excess TFA) and replacing the tert-butyl 6-(4-(4-(3-cyano-4-methoxypyrazolo[1,5-a]pyridin-6-yl)-1H-pyrazol-1-yl)piperidine-1-carbonyl)-3,6-diazabicyclo[3.1.1]heptane-3-carboxylate (Step 2) with the appropriate Boc-protected coupling product from Step 1 in each. All reactions were monitored for completion by LCMS, as such reaction durations were adjusted accordingly. When necessary, the title compounds (Step 1 and/or Step 2) were isolated via silica gel chromatographic purification using an appropriate gradient eluent or reverse phase chromatographic purification using an appropriate gradient eluent followed by a basic aqueous wash.

TABLE CC

| Intermediate # | Structure | Chemical Name | MS apci (m/z) |
|---|---|---|---|
| P66 | 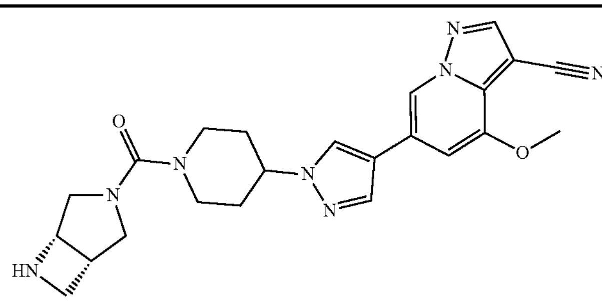 | 6-(1-(1-((1S,5S)-3,6-diazabicyclo[3.2.0]heptane-3-carbonyl)piperidin-4-yl)-1H-pyrazol-4-yl)-4-methoxypyrazolo[1,5-a]pyridine-3-carbonitrile | 447.2 (M + H) |
| P67 | 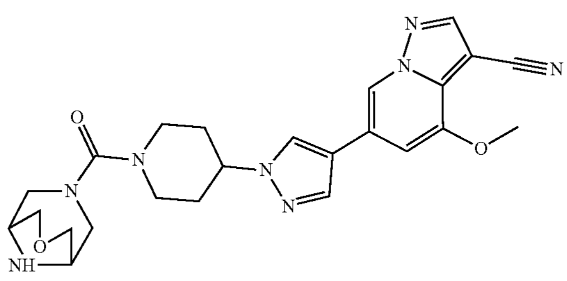 [SMILES: COc1cc(-c2cnn(C3CCN(C(=O)N4CC5COCC(C4)N5)CC3)c2)cn2ncc(C#N)c12] | 6-(1-(1-(3-oxa-7,9-diazabicyclo[3.3.1]nonane-7-carbonyl)piperidin-4-yl)-1H-pyrazol-4-yl)-4-methoxypyrazolo[1,5-a]pyridine-3-carbonitrile | 477.2 (M + H) |
| P68 | 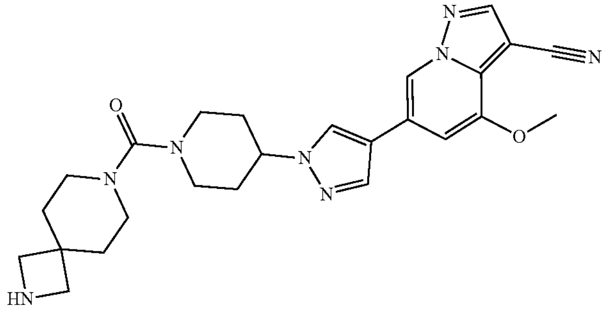 [SMILES: COc1cc(-c2cnn(C3CCN(C(=O)N4CCC5(CC4)CNC5)CC3)c2)cn2ncc(C#N)c12] | 6-(1-(1-(2,7-diazaspiro[3.5]nonane-7-carbonyl)piperidin-4-yl)-1H-pyrazol-4-yl)-4-methoxypyrazolo[1,5-a]pyridine-3-carbonitrile | 475.3 (M + H) |

TABLE CC-continued

| Intermediate # | Structure | Chemical Name | MS apci (m/z) |
|---|---|---|---|
| P69 | 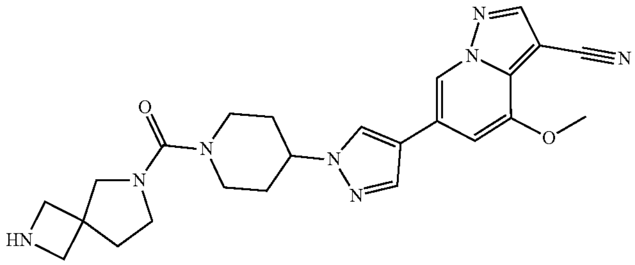 [SMILES: COc1cc(-c2cnn(C3CCN(C(=O)N4CCC5(CNC5)C4)CC3)c2)cn2ncc(C#N)c12] | 6-(1-(1-(2,6-diazaspiro[3.4]octane-6-carbonyl)piperidin-4-yl)-1H-pyrazol-4-yl)-4-methoxypyrazolo[1,5-a]pyridine-3-carbonitrile | 461.2 (M + H) |
| P70 | 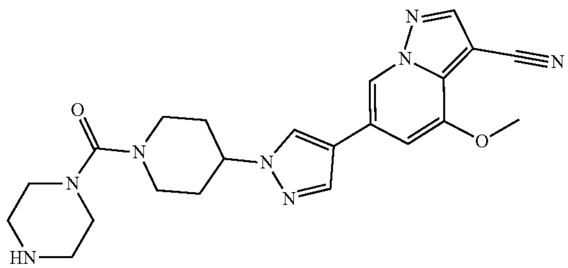 [SMILES: COc1cc(-c2cnn(C3CCN(C(=O)N4CCNCC4)CC3)c2)cn2ncc(C#N)c12] | 4-methoxy-6-(1-(1-(piperazine-1-carbonyl)piperidin-4-yl)-1H-pyrazol-4-yl)pyrazolo[1,5-a]pyridine-3-carbonitrile | 435.2 (M + H) |
| P71 | 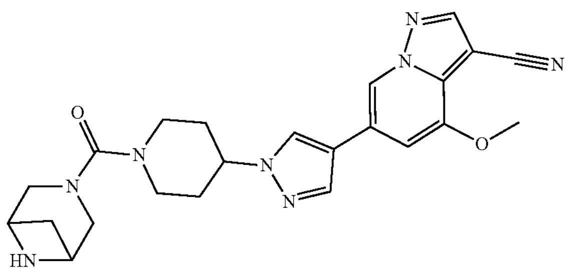 [SMILES: COc1cc(-c2cnn(C3CCN(C(=O)N4CC5CC(C4)N5)CC3)c2)cn2ncc(C#N)c12] | 6-(1-(1-(3,6-diazabicyclo[3.1.1]heptane-3-carbonyl)piperidin-4-yl)-1H-pyrazol-4-yl)-4-methoxypyrazolo[1,5-a]pyridine-3-carbonitrile | 447.1 (M + H) |
| P72 | 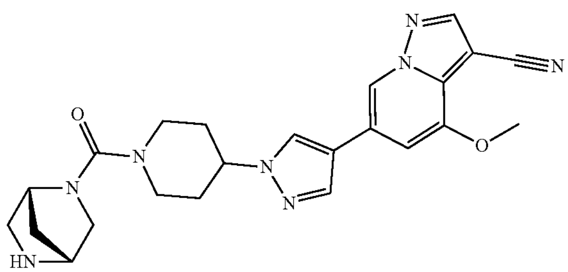 [SMILES: COc1cc(-c2cnn(C3CCN(C(=O)N4C[C@H]5C[C@@H]4CN5)CC3)c2)cn2ncc(C#N)c12] | 6-(1-(1-((1R,4R)-2,5-diazabicyclo[2.2.1]heptane-2-carbonyl)piperidin-4-yl)-1H-pyrazol-4-yl)-4-methoxypyrazolo[1,5-a]pyridine-3-carbonitrile | 447.3 (M + H) |

Intermediate P73

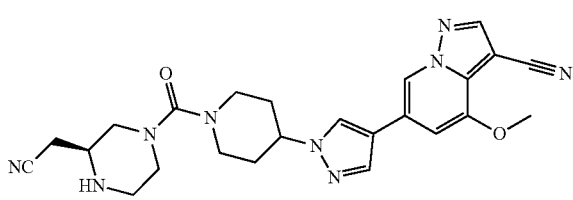 [SMILES: COc1cc(-c2cnn(C3CCN(C(=O)N4CCN[C@@H](CC#N)C4)CC3)c2)cn2ncc(C#N)c12]

(S)-6-(1-(1-(3-(cyanomethyl)piperazine-1-carbonyl)piperidin-4-yl)-1H-pyrazol-4-yl)-4-methoxypyrazolo[1,5-a]pyridine-3-carbonitrile Step 1: Preparation of 1-benzyl 4-(4-nitrophenyl) (S)-2-(cyanomethyl)piperazine-1,4-dicarboxylate. To a solution of benzyl (S)-2-(cyanomethyl)piperazine-1-carboxylate (96.5 mg, 0.372 mmol) and 4-nitrophenyl carbonochloridate (75.0 mg, 0.372 mmol) in DCM (6 mL) was added TEA (d. 0.726) (259 µL, 1.86 mmol) and the reaction mixture was stirred at ambient temperature for 1 h. The reaction mixture was concentrated and used as it is in step 2 (assumed quantitative yield).

Step 2: Preparation of benzyl (S)-4-(4-(4-(3-cyano-4-methoxypyrazolo[1,5-a]pyridin-6-yl)-1H-pyrazol-1-yl)piperidine-1-carbonyl)-2-(cyanomethyl)piperazine-1-carboxylate. A solution of 4-methoxy-6-(1-(piperidin-4-yl)-1H-pyrazol-4-yl)pyrazolo[1,5-a]pyridine-3-carbonitrile (Intermediate P25; 120 mg, 0.372 mmol), 1-benzyl 4-(4-nitrophenyl) (S)-2-(cyanomethyl)piperazine-1,4-dicarboxylate (Step 1; 158 mg, 0.372 mmol) and TEA (156 µL, 1.12 mmol) in DMA (2 mL) was stirred overnight at 80° C. After cooling to ambient temperature, the reaction mixture was partitioned between EtOAc and water. The organic extracts then were dried over anhydrous Na₂SO₄(s), filtered, and concentrated in vacuo. The crude residue was purified by silica chromatography (using 5-10% MeOH in EtOAc as the gradient eluent) to cleanly provide the title compound (113 mg, 50% yield). MS (apci) m/z=608.2 (M+H).

Step 3: Preparation of (S)-6-(1-(1-(3-(cyanomethyl)piperazine-1-carbonyl)piperidin-4-yl)-1H-pyrazol-4-yl)-4-methoxypyrazolo[1,5-a]pyridine-3-carbonitrile. A solution of benzyl (S)-4-(4-(4-(3-cyano-4-methoxypyrazolo[1,5-a]pyridin-6-yl)-1H-pyrazol-1-yl)piperidine-1-carbonyl)-2-(cyanomethyl)piperazine-1-carboxylate (Step 2; 113 mg, 0.186 mmol) in 1:1 EtOAc: MeOH (4 mL) was treated with 10% Pd/C (19.8 mg, 0.0186 mmol). The resulting mixture was sparged with Ar(g) for 10 min, evacuated then back filled with H₂(g) at atmospheric pressure. The reaction mixture was stirred under a balloon of H₂(g) for 3 days at ambient temperature before filtering the mixture through Celite®. The filtrate was concentrated in vacuo, and the residue was purified by C18 reverse phase chromatography (using 5-95% ACN in water with 0.1% TFA as the gradient eluent). Pure fractions were combined, treated with saturated NaHCO₃(aq) and then extracted with 20% iPrOH in DCM. The organic extracts were dried over anhydrous Na₂SO₄(s), filtered and concentrated in vacuo to cleanly afford the title compound (63 mg, 72% yield). MS (apci) m/z=474.2 (M+H).

Intermediate P74

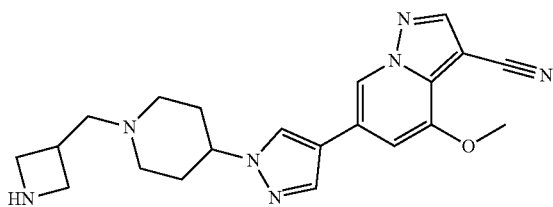 [SMILES: COc1cc(-c2cnn(C3CCN(CC4CNC4)CC3)c2)cn2ncc(C#N)c12]

6-(1-(1-(azetidin-3-ylmethyl)piperidin-4-yl)-1H-pyrazol-4-yl)-4-methoxypyrazolo[1,5-a]pyridine-3-carbonitrile Step 1: Preparation of tert-butyl 3-((4-(4-(3-cyano-4-methoxypyrazolo[1,5-a]pyridin-6-yl)-1H-pyrazol-1-yl)piperidin-1-yl)methyl)azetidine-1-carboxylate. A solution of 4-methoxy-6-(1-(piperidin-4-yl)-1H-pyrazol-4-yl)pyrazolo[1,5-a]pyridine-3-carbonitrile (Intermediate P25; 50 mg, 0.1551 mmol) and 1-Boc-3-azetidinecarboxaldehyde (29.02 µL, 0.1861 mmol) in DCM (1.55 mL) was treated with NaBH(OAc)₃ (164.4 mg, 0.7755 mmol). The resulting mixture then was stirred overnight at ambient temperature. Subsequently, the reaction mixture was diluted with 4:1 DCM:iPrOH and washed sequentially with water and brine. The organic extracts were dried over anhydrous Na₂SO₄(s), filtered, and concentrated in vacuo to afford the title compound (76 mg, 100% yield). MS (apci) m/z=492.2 (M+H).

Step 2: Preparation of 6-(1-(1-(azetidin-3-ylmethyl)piperidin-4-yl)-1H-pyrazol-4-yl)-4-methoxypyrazolo[1,5-a]pyridine-3-carbonitrile. A solution tert-butyl 3-((4-(4-(3-cyano-4-methoxypyrazolo[1,5-a]pyridin-6-yl)-1H-pyrazol-1-yl)piperidin-1-yl)methyl)azetidine-1-carboxylate (Step 1; 76 mg, 0.15 mmol) in 1:1 DCM:TFA (22 µL, 0.15 mmol TFA) was stirred for 30 min at ambient temperature. Subsequently, the reaction mixture was concentrated in vacuo. The crude residue was diluted with 4:1 DCM:iPrOH, and washed sequentially with saturated NaHCO₃(aq), water and brine. The organic extracts then were dried over anhydrous Na₂SO₄(s), filtered, and concentrated in vacuo to cleanly afford the title compound (61 mg, quantitative yield). MS (apci) m/z=392.2 (M+H).

The compounds in Table CD were prepared using a similar 2 step method to that described in the synthesis of 6-(1-(1-(azetidin-3-ylmethyl)piperidin-4-yl)-1H-pyrazol-4-yl)-4-methoxypyrazolo[1,5-a]pyridine-3-carbonitrile (Intermediate P74), employing the following modifications: in Step 1 using, 1.5-10.0 equivalents of NaBH(OAc)₃, with or without 1-3 drops (~17 µL or 1 equivalent) of acetic acid, DCM concentration of 0.1-0.5 M replacing both the 1-Boc-3-azetidinecarboxaldehyde and the 4-methoxy-6-(1-(piperidin-4-yl)-1H-pyrazol-4-yl)pyrazolo[1,5-a]pyridine-3-carbonitrile (Intermediate P25) respectively with 1.0-3.0 equivalents of the appropriate Boc-protected aldehyde from Table CDi and 1.0 equivalent of the appropriate amine core in the synthetic intermediates section (e.g. Table CA¹, CA², etc.); and in Step 2, using DCM:TFA ratios between 1:1-2:1 by volume (1-60 equivalents of TFA) and replacing the tert-butyl 3-((4-(4-(3-cyano-4-methoxypyrazolo[1,5-a]pyridin-6-yl)-1H-pyrazol-1-yl) piperidin-1-yl)methyl)azetidine-1-carboxylate (Step 1, Intermediate P74) with the appropriate Boc-protected coupling product from Step 1 in each. All reactions were monitored for completion by LCMS, as such reaction durations were adjusted accordingly. When necessary title compounds (Step 1 and/or Step 2), were purified via silica gel chromatographic purification using an appropriate gradient eluent or reverse phase chromatographic purification using an appropriate gradient eluent followed by a basic aqueous wash.

TABLE CD

| Intermediate # | Structure | Chemical Name | MS apci (m/z) |
|---|---|---|---|
| P75 | 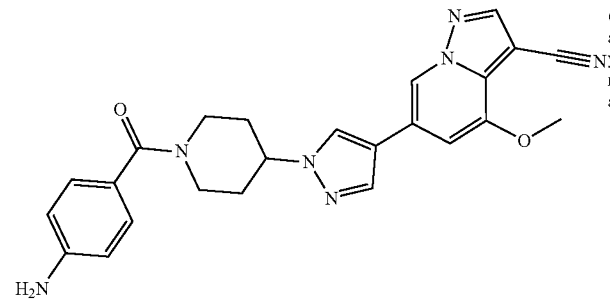 | 6-(1-(1-(4-aminobenzyl)piperidin-4-yl)-1H-pyrazol-4-yl)-4-methoxypyrazolo[1,5-a]pyridine-3-carbonitrile | 428.2 (M + H) |

TABLE CD-continued

| Intermediate # | Structure | Chemical Name | MS apci (m/z) |
|---|---|---|---|
| P76 | 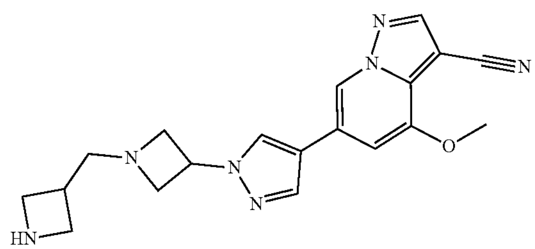 [SMILES: COc1cc(-c2cnn(C3CN(CC4CNC4)C3)c2)cn2ncc(C#N)c12] | 6-(1-(1-(azetidin-3-ylmethyl)azetidin-3-yl)-1H-pyrazol-4-yl)-4-methoxypyrazolo[1,5-a]pyridine-3-carbonitrile | 364.2 (M + H) |
| P77 | 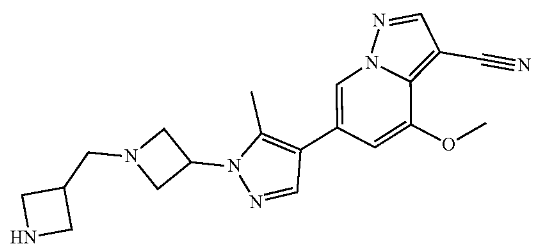 | 6-(1-(1-(azetidin-3-ylmethyl)piperidin-4-yl)-5-methyl-1H-pyrazol-4-yl)-4-methoxypyrazolo[1,5-a]pyridine-3-carbonitrile | 406.2 (M + H) |
| P78 | 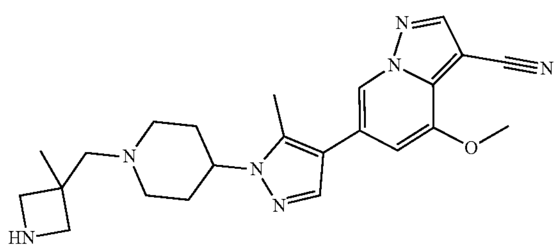 [SMILES: COc1cc(-c2cnn(C3CCN(CC4(C)CNC4)CC3)c2C)cn2ncc(C#N)c12] | 4-methoxy-6-(5-methyl-1-(1-((3-methylazetidin-3-yl)methyl)piperidin-4-yl)-1H-pyrazol-4-yl)pyrazolo[1,5-a]pyridine-3-carbonitrile | 420.2 (M + H) |
| P79 | 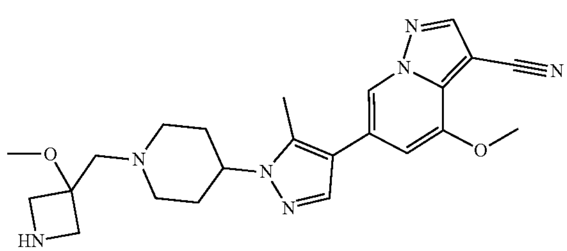 [SMILES: COc1cc(-c2cnn(C3CCN(CC4(OC)CNC4)CC3)c2C)cn2ncc(C#N)c12] | 4-methoxy-6-(1-(1-((3-methoxyazetidin-3-yl)methyl)piperidin-4-yl)-5-methyl-1H-pyrazol-4-yl)pyrazolo[1,5-a]pyridine-3-carbonitrile | 436.2 (M + H) |
| P80 | 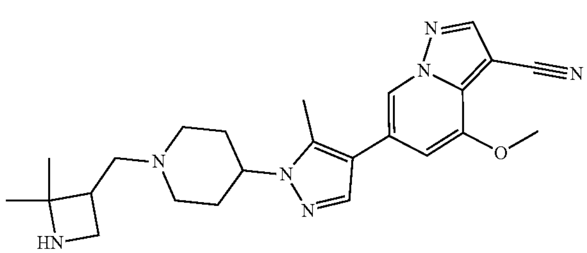 [SMILES: COc1cc(-c2cnn(C3CCN(CC4CNC4(C)C)CC3)c2C)cn2ncc(C#N)c12] | 6-(1-(1-((2,2-dimethylazetidin-3-yl)methyl)piperidin-4-yl)-5-methyl-1H-pyrazol-4-yl)-4-methoxypyrazolo[1,5-a]pyridine-3-carbonitrile | 434.3 (M + H) |
| P81 | 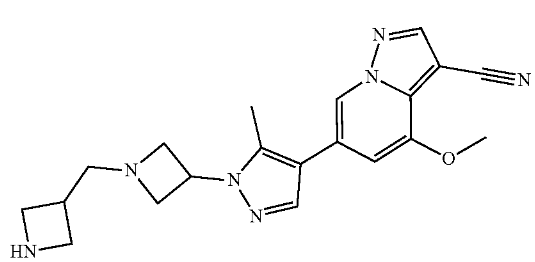 [SMILES: COc1cc(-c2cnn(C3CN(CC4CNC4)C3)c2C)cn2ncc(C#N)c12] | 6-(1-(1-(azetidin-3-ylmethyl)azetidin-3-yl)-5-methyl-1H-pyrazol-4-yl)-4-methoxypyrazolo[1,5-a]pyridine-3-carbonitrile | 378.1 (M + H) |

TABLE CD-continued

| Intermediate # | Structure | Chemical Name | MS apci (m/z) |
|---|---|---|---|
| P82 | 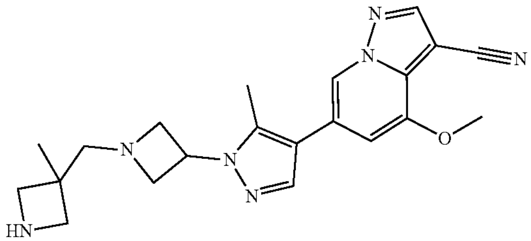 [SMILES: COc1cc(-c2cnn(C3CN(CC4(C)CNC4)C3)c2C)cn2ncc(C#N)c12] | 4-methoxy-6-(5-methyl-1-(1-((3-methylazetidin-3-yl)methyl)azetidin-3-yl)-1H-pyrazol-4-yl)pyrazolo[1,5-a]pyridine-3-carbonitrile | 392.2 (M + H) |
| P83 | 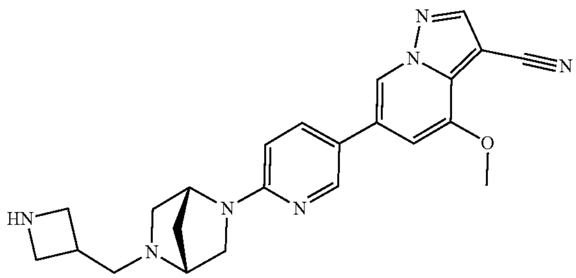 [SMILES: COc1cc(-c2ccc(N3C[C@H]4C[C@@H]3CN4CC3CNC3)nc2)cn2ncc(C#N)c12] | 6-(6-((1R,4R)-5-(azetidin-3-ylmethyl)-2,5-diazabicyclo[2.2.1]heptan-2-yl)pyridin-3-yl)-4-methoxypyrazolo[1,5-a]pyridine-3-carbonitrile | 416.2 (M + H) |
| P84 | 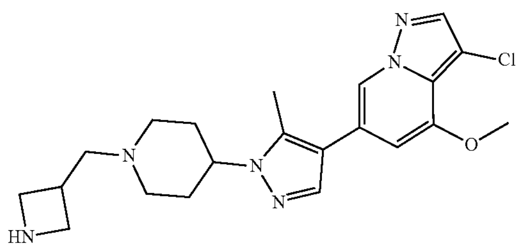 [SMILES: COc1cc(-c2cnn(C3CCN(CC4CNC4)CC3)c2C)cn2ncc(Cl)c12] | 6-(1-(1-(azetidin-3-ylmethyl)piperidin-4-yl)-5-methyl-1H-pyrazol-4-yl)-3-chloro-4-methoxypyrazolo[1,5-a]pyridine | 415.2 (M + H) |
| P85* | 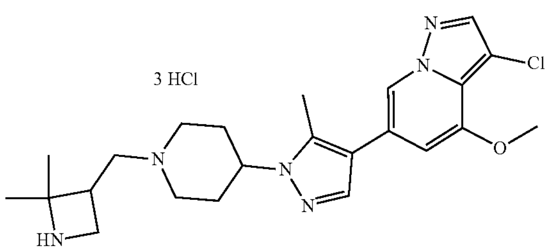 | 3-chloro-6-(1-(1-((2,2-dimethylazetidin-3-yl)methyl)piperidin-4-yl)-5-methyl-1Hpyrazol-4-yl)-4-methoxypyrazolo[1,5-a]pyridine trihydrochloride | 443.2 (M + H) |

*The intermediate obtained upon treatment with DCM and TFA was dissolved in MeOH (0.09 M concentration), treated with HCl (5-6 N soluition in isopropanol, 10 equivalents), stirred at room temperature for 15 minutes, and concentrated.

Intermediate P86

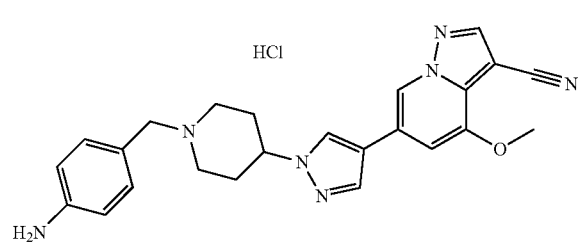 [SMILES: COc1cc(-c2cnn(C3CCN(Cc4ccc(N)cc4)CC3)c2)cn2ncc(C#N)c12 ; Cl]

6-(1-(1-(4-aminobenzyl)piperidin-4-yl)-1H-pyrazol-4-yl)-4-methoxypyrazolo[1,5-a]pyridine-3-carbonitrile hydrochloride A solution of tert-butyl (4-((4-(4-(3-cyano-4-methoxypyrazolo[1,5-a]pyridin-6-yl)-1H-pyrazol-1-yl)piperidin-1-yl)methyl)phenyl)carbamate (Step 1, from preparation of Intermediate P75, Table CD; 33 mg, 0.0625 mmol) and TFA (482 µL, 6.25 mmol) in DCM (1251 µL), and stirred for 10 min at ambient temperature. Subsequently, the reaction mixture was concentrated in vacuo while heating to 50° C. The resulting residue was sequentially suspended in 6 N HCl in iPrOH (1042 µL, 6.25 mmol) and concentrated in vacuo (2×) to cleanly afford the title compound as the hydrochloride salt (25.5 mg, 95% yield). MS (apci) m/z=428.2 (M+H).

Intermediate P87

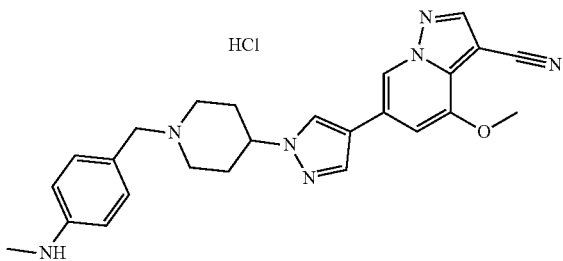 [SMILES: CNc1ccc(CN2CCC(n3cc(-c4cc(OC)c5c(C#N)cnn5c4)cn3)CC2)cc1 ; Cl]

4-methoxy-6-(1-(1-(4-(methylamino)benzyl)piperidin-4-yl)-1H-pyrazol-4-yl)pyrazolo[1,5-a]pyridine-3-carbonitrile hydrochloride Step 1: Preparation of tert-butyl (4-((4-(4-(3-cyano-4-methoxypyrazolo[1,5-a]pyridin-6-yl)-1H-pyrazol-1-yl)piperidin-1-yl)methyl)phenyl)(methyl)carbamate. A solution of tert-butyl (4-((4-(4-(3-cyano-4-methoxypyrazolo[1,5-a]pyridin-6-yl)-1H-pyrazol-1-yl)piperidin-1-yl)methyl)phenyl)carbamate (Step 1, from preparation of Intermediate P75, Table CD; 50 mg, 0.0948 mmol) in DMF (474 µL) was treated with NaH (60 wt. % mineral oil dispersion; 4.74 mg, 0.118 mmol). After stirring for 5 min at ambient temperature, the resulting suspension was treated with MeI (6.52 µL, 0.104 mmol), and stirred for another 5 min at ambient temperature. The resulting mixture was diluted with EtOAc, washed with water (3×) and brine (1×). The organic extracts were dried over $Na_2SO_{4(s)}$, then filtered, and concentrated in vacuo to afford the title compound (48 mg, 94% yield). MS (apci) m/z=542.3 (M+H).

Step 2: Preparation of 4-methoxy-6-(1-(1-(4-(methylamino)benzyl)piperidin-4-yl)-1H-pyrazol-4-yl)pyrazolo[1,5-a]pyridine-3-carbonitrile hydrochloride. A solution of tert-butyl (4-((4-(4-(3-cyano-4-methoxypyrazolo[1,5-a]pyridin-6-yl)-1H-pyrazol-1-yl)piperidin-1-yl)methyl)phenyl)(methyl)carbamate (Step 1; 48 mg, 0.0886 mmol) and TFA (683 µL, 8.86 mmol) in DCM (1772 µL), was stirred for 10 min at ambient temperature. Subsequently, the reaction mixture was concentrated in vacuo while heating to 50° C. The resulting residue was sequentially suspended in 6 N HCl in iPrOH (1477 µL, 8.86 mmol) and concentrated in vacuo (2×) to cleanly afford the title compound as the hydrochloride salt (46 mg, quantitative yield). MS (apci) m/z=442.3 (M+H).

Intermediate P88

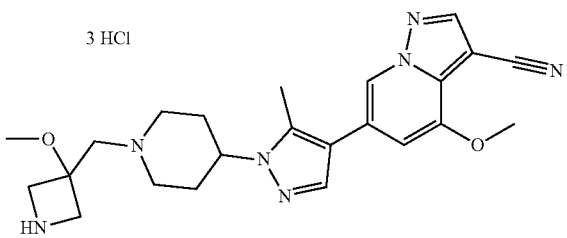 [SMILES: COc1cc(-c2cnn(C3CCN(CC4(OC)CNC4)CC3)c2C)cn2ncc(C#N)c12 ; "3 HCl"]

4-methoxy-6-(1-(1-((3-methoxyazetidin-3-yl)methyl)piperidin-4-yl)-5-methyl-1H-pyrazol-4-yl)pyrazolo[1,5-a]pyridine-3-carbonitrile trihydrochloride Step 1: Preparation of tert-butyl 3-((4-(4-(3-cyano-4-methoxypyrazolo[1,5-a]pyridin-6-yl)-5-methyl-1H-pyrazol-1-yl)piperidin-1-yl)methyl)-3-methoxyazetidine-1-carboxylate. A solution of 4-methoxy-6-(5-methyl-1-(piperidin-4-yl)-1H-pyrazol-4-yl)pyrazolo[1,5-a]pyridine-3-carbonitrile (Intermediate P41, Table CA[2]; 205.0 mg, 0.6094 mmol) in DCM (1.55 mL) was treated sequentially with tert-butyl 3-formyl-3-methoxyazetidine-1-carboxylate (327.93 mg, 1.5235 mmol), $NaBH(OAc)_3$ (322.89 mg, 1.5235 mmol) and a few drops of acetic acid. The resulting mixture then was stirred overnight at ambient temperature. Subsequently, the reaction mixture was concentrated in vacuo and the residue was purified by C18 reverse phase chromatography (using 5-95% ACN in water with 0.1% TFA as the gradient eluent) to cleanly afford the title compound as the TFA salt. The TFA salt then was diluted with 4:1 DCM:iPrOH and washed with saturated $NaHCO_3$ (aq) (2×). The organic extracts then were dried over anhydrous $Na_2SO_{4(s)}$, filtered, and concentrated in vacuo to cleanly afford the title compound (quantitative yield assumed). MS (apci) m/z=536.3 (M+H).

Step 2: Preparation of 4-methoxy-6-(1-(1-((3-methoxyazetidin-3-yl)methyl)piperidin-4-yl)-5-methyl-1H-pyrazol-4-yl)pyrazolo[1,5-a]pyridine-3-carbonitrile trihydrochloride. A solution tert-butyl 3-((4-(4-(3-cyano-4-methoxypyrazolo[1,5-a]pyridin-6-yl)-5-methyl-1H-pyrazol-1-yl)piperidin-1-yl)methyl)-3-methoxyazetidine-1-carboxylate (Step 1, ~0.609 mmol) in 1:1 DCM:TFA (5 mL) was stirred for 15 min at ambient temperature. Subsequently, the reaction mixture was concentrated in vacuo. The crude residue was dissolved in MeOH (5.0 mL) and then treated with 5-6 N HCl in iPrOH (1.219 mL, 6.094 mmol). The resulting mixture was stirred for 15 min at ambient temperature before concentrating in vacuo to cleanly afford the title compound (197.2 mg, 59% yield). MS (apci) m/z=436.2 (M+H).

Intermediate P89

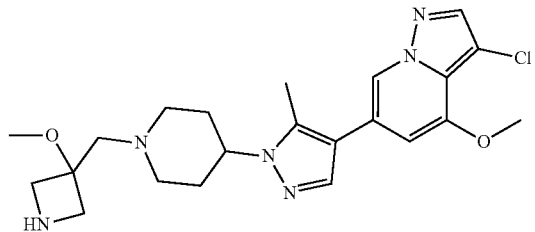

3-chloro-4-methoxy-6-(1-(1-((3-methoxyazetidin-3-yl)methyl)piperidin-4-yl)-5-methyl-1H-pyrazol-4-yl)pyrazolo[1,5-a]pyridine Step 1: Preparation of tert-butyl 3-((4-(4-(3-chloro-4-methoxypyrazolo[1,5-a]pyridin-6-yl)-5-methyl-1H-pyrazol-1-yl)piperidin-1-yl)methyl)-3-methoxyazetidine-1-carboxylate. A solution of 3-chloro-4-methoxy-6-(5-methyl-1-(piperidin-4-yl)-1H-pyrazol-4-yl)pyrazolo[1,5-a]pyridine (Intermediate P55; 40.0 mg, 0.116 mmol) and tert-butyl 3-formyl-3-methoxyazetidine-1-carboxylate (Intermediate R1; 49.8 mg, 0.231 mmol) in DCM (1157 µL) was treated sequentially with a few drops of acetic acid (6.62 µL, 0.116 mmol) and NaBH(OAc)₃ (29.4 mg, 0.139 mmol), then stirred at room temperature for 3 h. Subsequently the reaction mixture was purified directly by silica chromatography (using 0-100% DCM:Acetone as the gradient eluent) to cleanly afford the title compound (50 mg, 79% yield). MS (apci) m/z=545.2 (M+H).

Step 2: Preparation of 3-chloro-4-methoxy-6-(1-(1-((3-methoxyazetidin-3-yl)methyl)piperidin-4-yl)-5-methyl-1H-pyrazol-4-yl)pyrazolo[1,5-a]pyridine. A mixture of tert-butyl 3-((4-(4-(3-chloro-4-methoxypyrazolo[1,5-a]pyridin-6-yl)-5-methyl-1H-pyrazol-1-yl) piperidin-1-yl)methyl)-3-methoxyazetidine-1-carboxylate (50 mg, 0.092 mmol) and TFA (71 µL) in DCM (459 µL) was stirred at room temperature for 1 h. Subsequently, the reaction mixture was concentrated in vacuo. The resulting oil was dissolved in 4:1 DCM:iPrOH, then washed with saturated NaHCO₃(aq). The organic extracts were dried over anhydrous Na₂SO₄(s), filtered, and concentrated to afford the title compound (41 mg, 100% yield). MS (apci) m/z=445.2 (M+H).

Intermediate P90

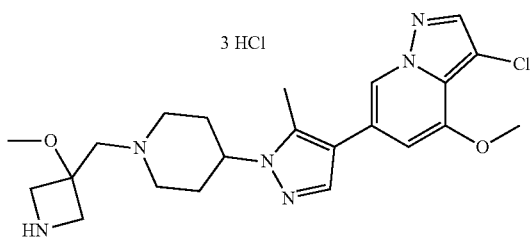

3-chloro-4-methoxy-6-(1-(1-((3-methoxyazetidin-3-yl)methyl)piperidin-4-yl)-5-methyl-1H-pyrazol-4-yl) pyrazolo[1,5-a]pyridine trihydrochloride Step 1: Preparation of tert-butyl 3-((4-(4-(3-chloro-4-methoxypyrazolo[1,5-a]pyridin-6-yl)-5-methyl-1H-pyrazol-1-yl)piperidin-1-yl)methyl)-3-methoxyazetidine-1-carboxylate. A solution of 3-chloro-4-methoxy-6-(5-methyl-1-(piperidin-4-yl)-1H-pyrazol-4-yl)pyrazolo[1,5-a]pyridine (Intermediate P55; 251.8 mg, 0.7281 mmol) in DCM (7.3 mL) was added tert-butyl 3-formyl-3-methoxyazetidine-1-carboxylate (Intermediate R1; 391.8 mg, 1.820 mmol), sodium triacetoxyborohydride (385.8 mg, 1.820 mmol), and a few drops of AcOH. The reaction mixture was stirred for 16 h at ambient temperature, after which it was concentrated. The resulting residue was purified by reverse phase C18 chromatography (using 5-95% water-ACN with 0.1% TFA as gradient eluent). The combined desired fractions were partitioned between 4:1 DCM:iPrOH and sat. NaHCO₃(aq). The organic phase was dried over Na₂SO₄(aq), filtered, and concentrated in vacuo to afford the title compound (0.728 mmol, quantitative yield assumed).

Step 2: Preparation of 3-chloro-4-methoxy-6-(1-(1-((3-methoxyazetidin-3-yl)methyl)piperidin-4-yl)-5-methyl-1H-pyrazol-4-yl)pyrazolo[1,5-a]pyridine trihydrochloride. The tert-butyl 3-((4-(4-(3-chloro-4-methoxypyrazolo[1,5-a]pyridin-6-yl)-5-methyl-1H-pyrazol-1-yl) piperidin-1-yl)methyl)-3-methoxyazetidine-1-carboxylate (Step 1, 0.7281 mmol) was dissolved in 1:1 DCM:TFA (5.0 mL) and stirred at ambient temperature for 30 min, after which the mixture was concentrated in vacuo. The residue was dissolved in MeOH (10.0 mL), and treated with 5-6 N HCl in iPrOH (1.456 mL, ~7.28 mmol). The mixture was stirred at ambient temperature for 15 min, and then was concentrated to afford the title compound (256.5 mg 64% yield). MS (apci) m/z=445.2 (M+H).

Intermediate P91

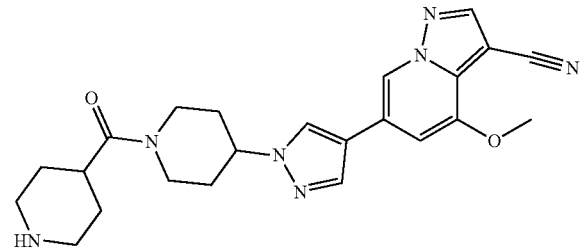 [SMILES: COc1cc(-c2cnn(C3CCN(C(=O)C4CCNCC4)CC3)c2)cn2ncc(C#N)c12]

4-methoxy-6-(1-(1-(piperidine-4-carbonyl)piperidin-4-yl)-1H-pyrazol-4-yl)pyrazolo[1,5-a]pyridine-3-carbonitrile Step 1: Preparation of tert-butyl 4-(4-(4-(3-cyano-4-methoxypyrazolo[1,5-a]pyridin-6-yl)-1H-pyrazol-1-yl)piperidine-1-carbonyl)piperidine-1-carboxylate. A solution of 4-methoxy-6-(1-(piperidin-4-yl)-1H-pyrazol-4-yl)pyrazolo[1,5-a]pyridine-3-carbonitrile (Intermediate P25; 2.03 g, 6.30 mmol) in DCM (2.33 mL) was treated sequentially with Boc-Inp-OH (1.73 g, 7.56 mmol), HATU (2.87 g, 7.56 mmol) and DIEA (4.39 mL, 25.2 mmol). The reaction mixture was stirred overnight at ambient temperature then concentrated in vacuo. The resulting residue was purified by silica chromatography (using 5-95% DCM-Acetone as the gradient eluent) to cleanly afford the title compound (quantitative yield assumed), which was carried directly into Step 2. MS (apci) m/z=534.2 (M+H).

Step 2: Preparation of 4-methoxy-6-(1-(1-(piperidine-4-carbonyl)piperidin-4-yl)-1H-pyrazol-4-yl)pyrazolo[1,5-a]pyridine-3-carbonitrile. A solution of tert-butyl 4-(4-(4-(3-cyano-4-methoxypyrazolo[1,5-a]pyridin-6-yl)-1H-pyrazol-1-yl)piperidine-1-carbonyl)piperidine-1-carboxylate (Step 1; 6.30 mmol) in 1:1 DCM:TFA (20 mL) was stirred for 1 h at ambient temperature. Subsequently, the reaction mixture was concentrated in vacuo. The crude residue was free based by diluting with 4:1 DCM:iPrOH and washed with saturated NaHCO₃(aq) (2×). The organic extracts then were dried over anhydrous Na₂SO₄(s), filtered, and concentrated in vacuo to cleanly afford the title compound (2.50 g, 92% yield). MS (apci) m/z=434.2 (M+H).

The compounds in Table CE were prepared using a similar 2 Step method to that described in the synthesis of 4-methoxy-6-(1-(1-(piperidine-4-carbonyl)piperidin-4-yl)-1H-pyrazol-4-yl)pyrazolo[1,5-a]pyridine-3-carbonitrile (Intermediate P91), employing the following modifications: in Step 1, using 1.1-3.0 equivalents of HATU, 2-5 equivalents of DIEA, solvent (DCM or DMF) concentration of 0.03-0.2 M and replacing both the Boc-Inp-OH and the 4-methoxy-6-(1-(piperidin-4-yl)-1H-pyrazol-4-yl)pyrazolo[1,5-a]pyridine-3-carbonitrile (Intermediate P25) respectively with 1.0-1.2 equivalents of the appropriate Boc-protected amino acid from Table CEi and 1.0 equivalent of the appropriate amine-core from the synthetic intermediates section (e.g. Table CA[1], Table CA[2], Table CB, etc.) and when DMF was used products were precipitated from water, collecting pure product by filtration instead of by chromatography; and in Step 2, using DCM:TFA ratios between 1:1-10:1 by volume (1-500 equivalents of TFA except where noted *) and replacing the tert-butyl 4-(4-(4-(3-cyano-4-methoxypyrazolo[1,5-a]pyridin-6-yl)-1H-pyrazol-1-yl)piperidine-1-carbonyl)piperidine-1-carboxylate (Step 2, Intermediate P91) with the appropriate Boc-protected coupling product from Step 1 in each. All reactions were monitored for completion by LCMS, as such reaction durations were adjusted accordingly. When necessary, title compounds (Step 1 and/or Step 2) were purified via silica gel chromatographic purification using an appropriate gradient eluent or reverse phase chromatographic purification using an appropriate gradient eluent followed by a basic aqueous wash.

TABLE CE

| Intermediate # | Structure | Chemical Name | MS apci (m/z) |
|---|---|---|---|
| P92* | 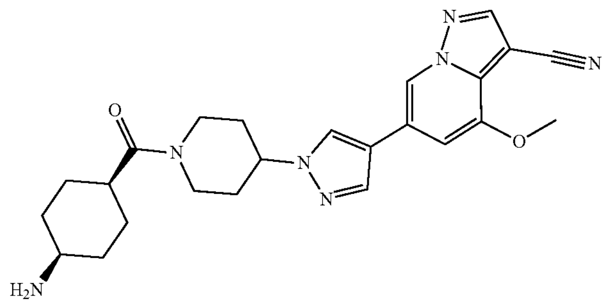 [SMILES: COc1cc(-c2cnn(C3CCN(C(=O)[C@H]4CC[C@@H](N)CC4)CC3)c2)cn2ncc(C#N)c12] | 6-(1-(1-((1s,4s)-4-aminocyclohexane-1-carbonyl)piperidin-4-yl)-1H-pyrazol-4-yl)-4-methoxypyrazolo[1,5-a]pyridine-3-carbonitrile | 448.2 (M + H) |
| P93 | 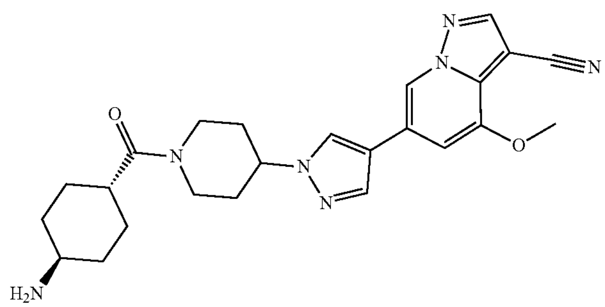 [SMILES: COc1cc(-c2cnn(C3CCN(C(=O)[C@H]4CC[C@H](N)CC4)CC3)c2)cn2ncc(C#N)c12] | 6-(1-(1-((1r,4r)-4-aminocyclohexane-1-carbonyl)piperidin-4-yl)-1H-pyrazol-4-yl)-4-methoxypyrazolo[1,5-a]pyridine-3-carbonitrile | 448.3 (M + H) |
| P94 | 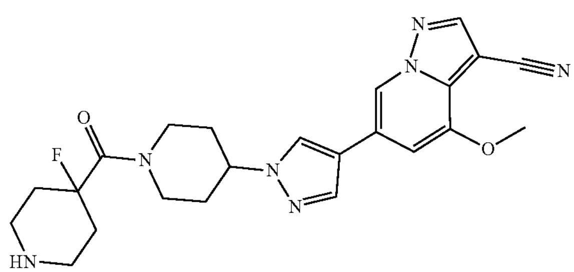 [SMILES: COc1cc(-c2cnn(C3CCN(C(=O)C4(F)CCNCC4)CC3)c2)cn2ncc(C#N)c12] | 6-(1-(1-(4-fluoropiperidine-4-carbonyl)piperidin-4-yl)-1H-pyrazol-4-yl)-4-methoxypyrazolo[1,5-a]pyridine-3-carbonitrile | 452.2 (M + H) |
| P95 | 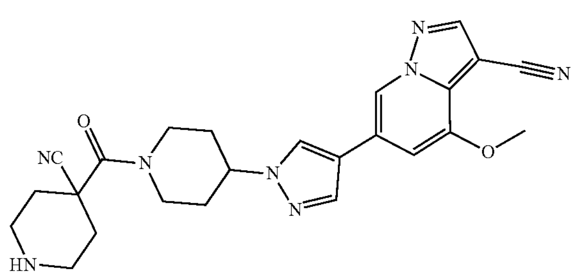 [SMILES: COc1cc(-c2cnn(C3CCN(C(=O)C4(C#N)CCNCC4)CC3)c2)cn2ncc(C#N)c12] | 6-(1-(1-(4-cyanopiperidine-4-carbonyl)piperidin-4-yl)-1H-pyrazol-4-yl)-4-methoxypyrazolo[1,5-a]pyridine-3-carbonitrile | 459.2 (M + H) |

TABLE CE-continued

| Intermediate # | Structure | Chemical Name | MS apci (m/z) |
|---|---|---|---|
| P96 | 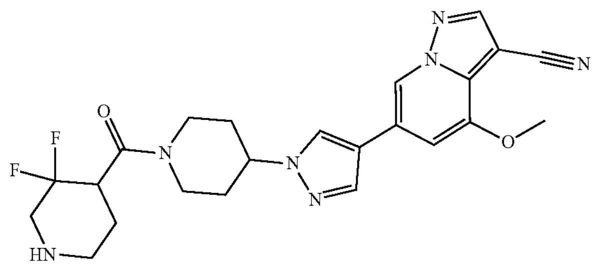 [SMILES: COc1cc(-c2cnn(C3CCN(C(=O)C4CCNCC4(F)F)CC3)c2)cn2ncc(C#N)c12] | 6-(1-(1-(3,3-difluoropiperidine-4-carbonyl)piperidin-4-yl)-1H-pyrazol-4-yl)-4-methoxypyrazolo[1,5-a]pyridine-3-carbonitrile | 470.2 (M + H) |
| P97 | 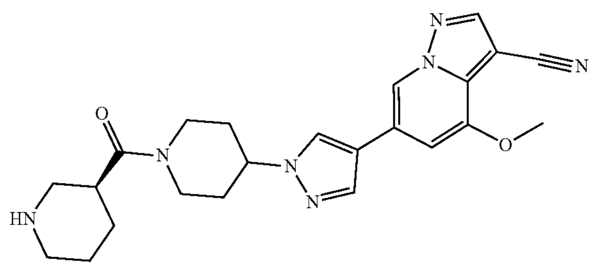 [SMILES: COc1cc(-c2cnn(C3CCN(C(=O)[C@H]4CCCNC4)CC3)c2)cn2ncc(C#N)c12] | (S)-4-methoxy-6-(1-(1-(piperidine-3-carbonyl)piperidin-4-yl)-1H-pyrazol-4-yl)pyrazolo[1,5-a]pyridine-3-carbonitrile | 434.2 (M + H) |
| P98 | 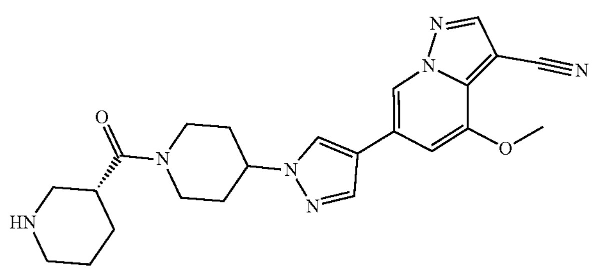 [SMILES: COc1cc(-c2cnn(C3CCN(C(=O)[C@@H]4CCCNC4)CC3)c2)cn2ncc(C#N)c12] | (R)-4-methoxy-6-(1-(1-(piperidine-3-carbonyl)piperidin-4-yl)-1H-pyrazol-4-yl)pyrazolo[1,5-a]pyridine-3-carbonitrile | 434.2 (M + H) |
| P99 | 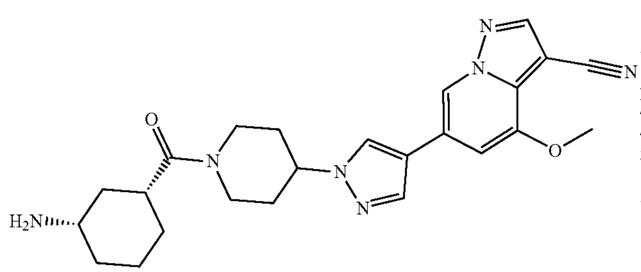 [SMILES: COc1cc(-c2cnn(C3CCN(C(=O)[C@@H]4CCC[C@H](N)C4)CC3)c2)cn2ncc(C#N)c12] | 6-(1-(1-((1R,3S)-3-aminocyclohexane-1-carbonyl)piperidin-4-yl)-1H-pyrazol-4-yl)-4-methoxypyrazolo[1,5-a]pyridine-3-carbonitrile | 448.2 (M + H) |
| P100 | 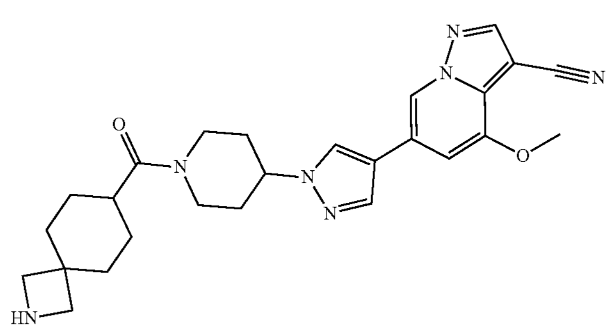 [SMILES: COc1cc(-c2cnn(C3CCN(C(=O)C4CCC5(CC4)CNC5)CC3)c2)cn2ncc(C#N)c12] | 6-(1-(1-(2-azaspiro[3.5]nonane-7-carbonyl)piperidin-4-yl)-1H-pyrazol-4-yl)-4-methoxypyrazolo[1,5-a]pyridine-3-carbonitrile | 474.2 (M + H) |

TABLE CE-continued

| Intermediate # | Structure | Chemical Name | MS apci (m/z) |
|---|---|---|---|
| P101* | 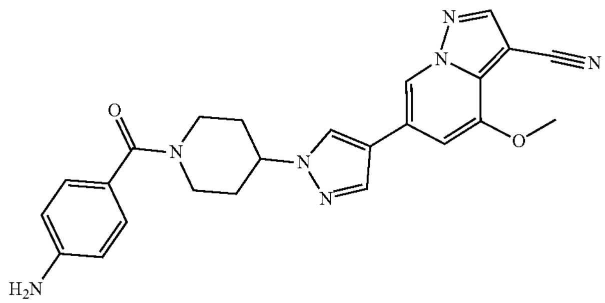 [SMILES: COc1cc(-c2cnn(C3CCN(C(=O)c4ccc(N)cc4)CC3)c2)cn2ncc(C#N)c12] | 6-(1-(1-(4-aminobenzoyl)piperidin-4-yl)-1H-pyrazol-4-yl)-4-methoxypyrazolo[1,5-a]pyridine-3-carbonitrile | 442.2 (M + H) |
| P102 | 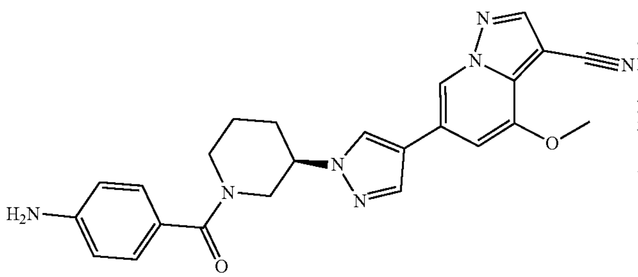 [SMILES: COc1cc(-c2cnn([C@@H]3CCCN(C(=O)c4ccc(N)cc4)C3)c2)cn2ncc(C#N)c12] | (R)-6-(1-(1-(4-aminobenzoyl)piperidin-3-yl)-1H-pyrazol-4-yl)-4-methoxypyrazolo[1,5-a]pyridine-3-carbonitrile | 442.2 (M + H) |
| P103 | 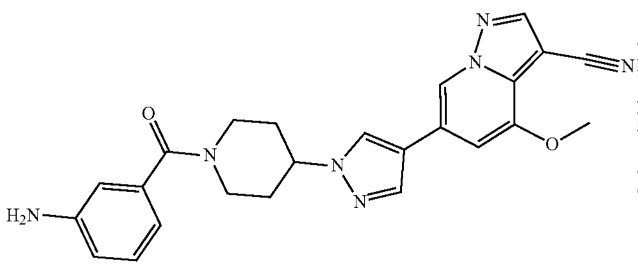 [SMILES: COc1cc(-c2cnn(C3CCN(C(=O)c4cccc(N)c4)CC3)c2)cn2ncc(C#N)c12] | 6-(1-(1-(3-aminobenzoyl)piperidin-4-yl)-1H-pyrazol-4-yl)-4-methoxypyrazolo[1,5-a]pyridine-3-carbonitrile | 442.2 (M + H) |
| P104 | 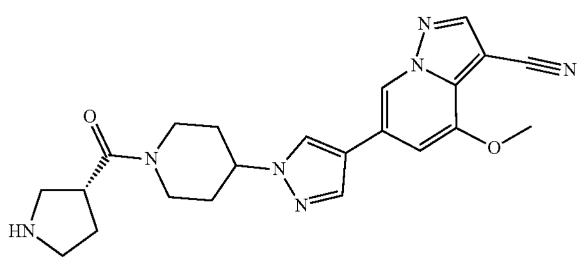 [SMILES: COc1cc(-c2cnn(C3CCN(C(=O)[C@@H]4CCNC4)CC3)c2)cn2ncc(C#N)c12] | (R)-4-methoxy-6-(1-(1-(pyrrolidine-3-carbonyl)piperidin-4-yl)-1H-pyrazol-4-yl)pyrazolo[1,5-a]pyridine-3-carbonitrile | 420.2 (M + H) |
| P105 | 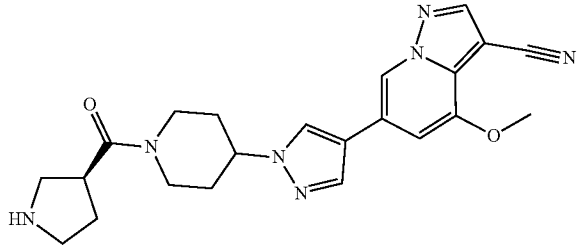 [SMILES: COc1cc(-c2cnn(C3CCN(C(=O)[C@H]4CCNC4)CC3)c2)cn2ncc(C#N)c12] | (S)-4-methoxy-6-(1-(1-(pyrrolidine-3-carbonyl)piperidin-4-yl)-1H-pyrazol-4-yl)pyrazolo[1,5-a]pyridine-3-carbonitrile | 420.2 (M + H) |

TABLE CE-continued

| Intermediate # | Structure | Chemical Name | MS apci (m/z) |
|---|---|---|---|
| P106 | 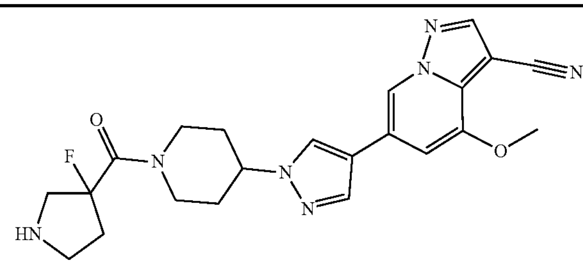 | 6-(1-(1-(3-fluoropyrrolidine-3-carbonyl)piperidin-4-yl)-1H-pyrazol-4-yl)-4-methoxypyrazolo[1,5-a]pyridine-3-carbonitrile | 438.2 (M + H) |
| P107 | 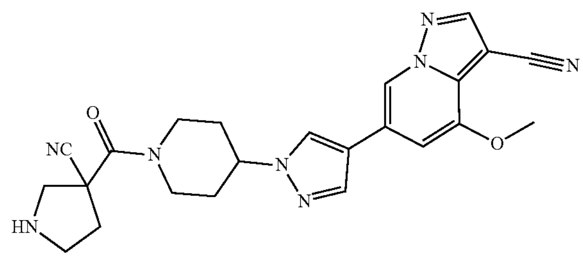 [SMILES: COc1cc(-c2cnn(C3CCN(C(=O)C4(C#N)CCNC4)CC3)c2)cn2ncc(C#N)c12] | 6-(1-(1-(3-cyanopyrrolidine-3-carbonyl)piperidin-4-yl)-1H-pyrazol-4-yl)-4-methoxypyrazolo[1,5-a]pyridine-3-carbonitrile | 445.2 (M + H) |
| P108* | 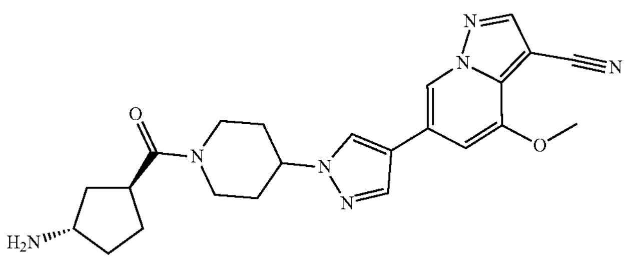 [SMILES: COc1cc(-c2cnn(C3CCN(C(=O)[C@H]4CC[C@H](N)C4)CC3)c2)cn2ncc(C#N)c12] | 6-(1-(1-((1S,3S)-3-aminocyclopentane-1-carbonyl)piperidin-4-yl)-1H-pyrazol-4-yl)-4-methoxypyrazolo[1,5-a]pyridine-3-carbonitrile | 434.2 (M + H) |
| P109 | 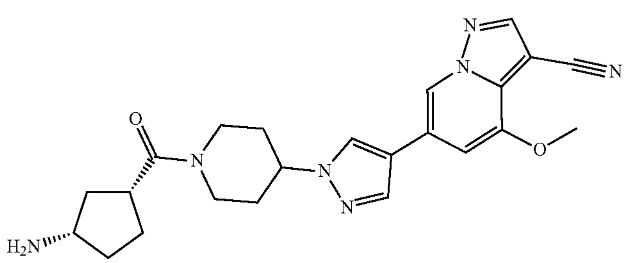 [SMILES: COc1cc(-c2cnn(C3CCN(C(=O)[C@@H]4CC[C@H](N)C4)CC3)c2)cn2ncc(C#N)c12] | 6-(1-(1-((1R,3S)-3-aminocyclopentane-1-carbonyl)piperidin-4-yl)-1H-pyrazol-4-yl)-4-methoxypyrazolo[1,5-a]pyridine-3-carbonitrile | 434.2 (M + H) |
| P110 | 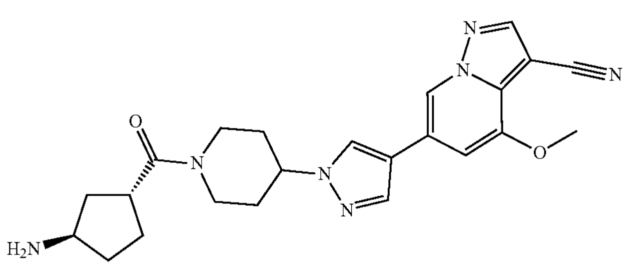 [SMILES: COc1cc(-c2cnn(C3CCN(C(=O)[C@@H]4CC[C@@H](N)C4)CC3)c2)cn2ncc(C#N)c12] | 6-(1-(1-((1R,3R)-3-aminocyclopentane-1-carbonyl)piperidin-4-yl)-1H-pyrazol-4-yl)-4-methoxypyrazolo[1,5-a]pyridine-3-carbonitrile | 434.2 (M + H) |
| P111 | 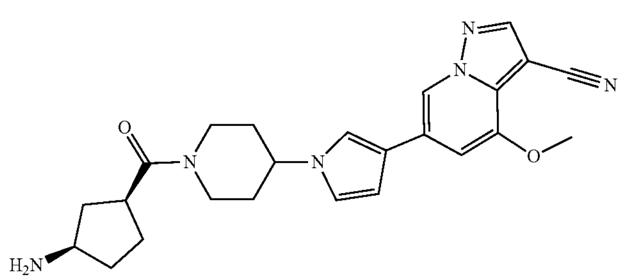 | 6-(1-(1-((1S,3R)-3-aminocyclopentane-1-carbonyl)piperidin-4-yl)-1H-pyrazol-4-yl)-4-methoxypyrazolo[1,5-a]pyridine-3-carbonitrile | 434.2 (M + H) |

TABLE CE-continued

| Intermediate # | Structure | Chemical Name | MS apci (m/z) |
|---|---|---|---|
| P112 | 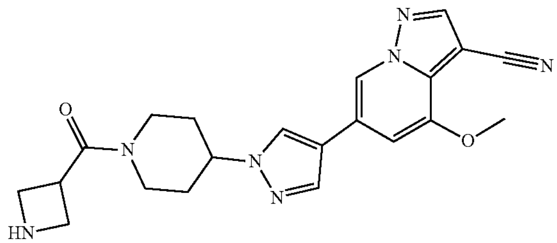 [SMILES: COc1cc(-c2cnn(C3CCN(C(=O)C4CNC4)CC3)c2)cn2ncc(C#N)c12] | 6-(1-(1-(azetidine-3-carbonyl)piperidin-4-yl)-1H-pyrazol-4-yl)-4-methoxypyrazolo[1,5-a]pyridine-3-carbonitrile | 406.2 (M + H) |
| P113 | 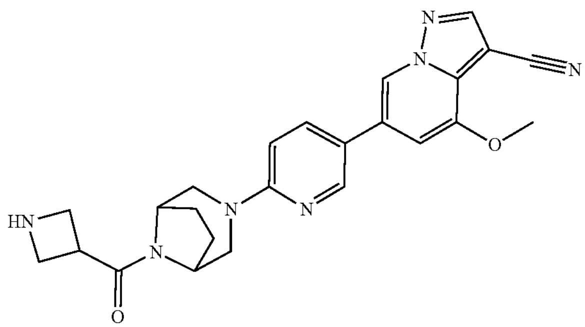 [SMILES: COc1cc(-c2ccc(N3CC4CCC(C3)N4C(=O)C3CNC3)nc2)cn2ncc(C#N)c12] | 6-(6-(8-(azetidine-3-carbonyl)-3,8-diazabicyclo[3.2.1]octan-3-yl)pyridin-3-yl)-4-methoxypyrazolo[1,5-a]pyridine-3-carbonitrile | 444.2 (M + H) |
| P114 | 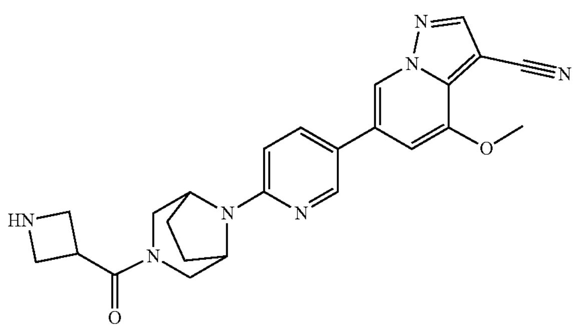 [SMILES: COc1cc(-c2ccc(N3C4CCC3CN(C(=O)C3CNC3)C4)nc2)cn2ncc(C#N)c12] | 6-(6-(3-(azetidine-3-carbonyl)-3,8-diazabicyclo[3.2.1]octan-8-yl)pyridin-3-yl)-4-methoxypyrazolo[1,5-a]pyridine-3-carbonitrile | 444.2 (M + H) |
| P115 | 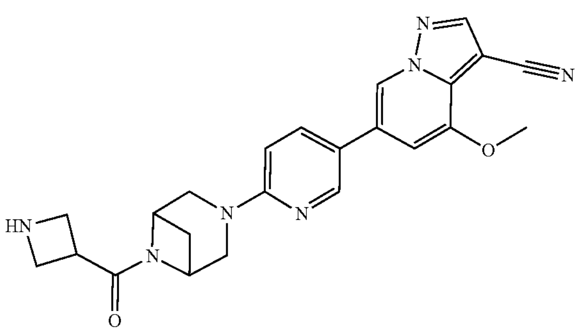 [SMILES: COc1cc(-c2ccc(N3CC4CC(C3)N4C(=O)C3CNC3)nc2)cn2ncc(C#N)c12] | 6-(6-(6-(azetidine-3-carbonyl)-3,6-diazabicyclo[3.1.1]heptan-3-yl)pyridin-3-yl)-4-methoxypyrazolo[1,5-a]pyridine-3-carbonitrile | 430.2 (M + H) |
| P116 | 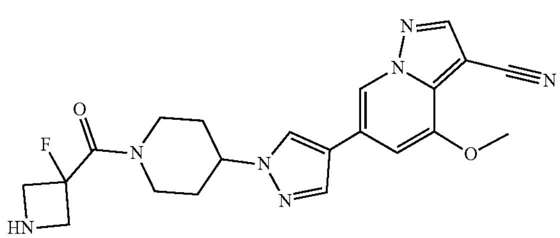 [SMILES: COc1cc(-c2cnn(C3CCN(C(=O)C4(F)CNC4)CC3)c2)cn2ncc(C#N)c12] | 6-(1-(1-(3-fluoroazetidine-3-carbonyl)piperidin-4-yl)-1H-pyrazol-4-yl)-4-methoxypyrazolo[1,5-a]pyridine-3-carbonitrile | 406.2 (M + H) |

TABLE CE-continued

| Intermediate # | Structure | Chemical Name | MS apci (m/z) |
|---|---|---|---|
| P117 | 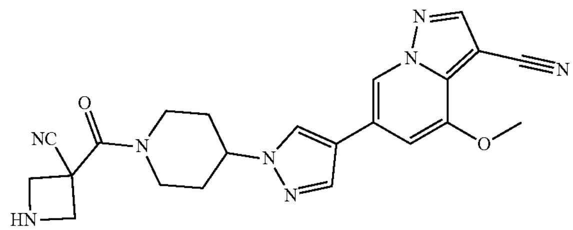 [SMILES: COc1cc(-c2cnn(C3CCN(C(=O)C4(C#N)CNC4)CC3)c2)cn2ncc(C#N)c12] | 6-(1-(1-(3-cyanoazetidine-3-carbonyl)piperidin-4-yl)-1H-pyrazol-4-yl)-4-methoxypyrazolo[1,5-a]pyridine-3-carbonitrile | 431.2 (M + H) |
| P118 | 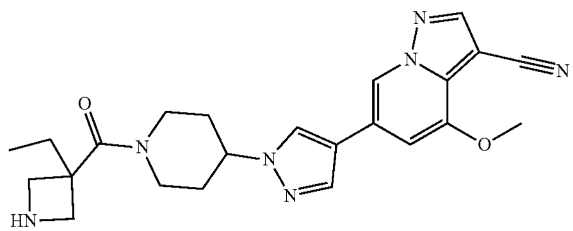 [SMILES: CCC1(C(=O)N2CCC(n3cc(-c4cc(OC)c5c(C#N)cnn5c4)cn3)CC2)CNC1] | 6-(1-(1-(3-ethylazetidine-3-carbonyl)piperidin-4-yl)-1H-pyrazol-4-yl)-4-methoxypyrazolo[1,5-a]pyridine-3-carbonitrile | 434.2 (M + H) |
| P119 | 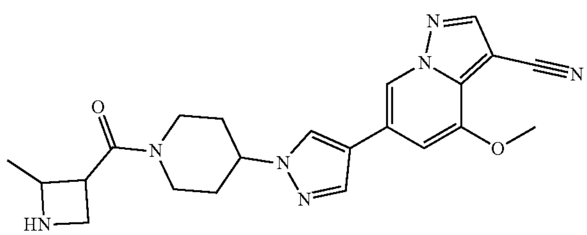 [SMILES: COc1cc(-c2cnn(C3CCN(C(=O)C4CNC4C)CC3)c2)cn2ncc(C#N)c12] | 4-methoxy-6-(1-(1-(2-methylazetidine-3-carbonyl)piperidin-4-yl)-1H-pyrazol-4-yl)pyrazolo[1,5-a]pyridine-3-carbonitrile | 420.2 (M + H) |
| P120 | 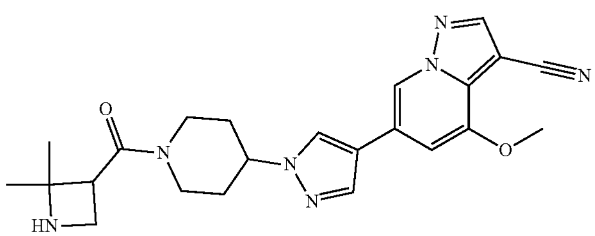 [SMILES: COc1cc(-c2cnn(C3CCN(C(=O)C4CNC4(C)C)CC3)c2)cn2ncc(C#N)c12] | 6-(1-(1-(2,2-dimethylazetidine-3-carbonyl)piperidin-4-yl)-1H-pyrazol-4-yl)-4-methoxypyrazolo[1,5-a]pyridine-3-carbonitrile | 434.2 (M + H) |
| P121 | 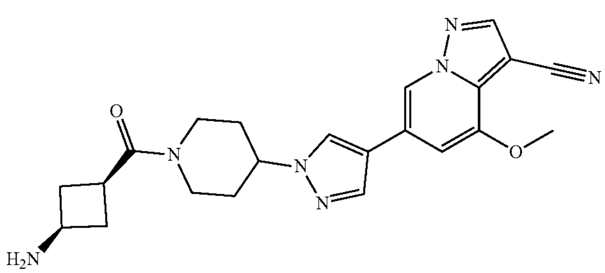 [SMILES: COc1cc(-c2cnn(C3CCN(C(=O)[C@H]4C[C@@H](N)C4)CC3)c2)cn2ncc(C#N)c12] | 6-(1-(1-((1s,3s)-3-aminocyclobutane-1-carbonyl)piperidin-4-yl)-1H-pyrazol-4-yl)-4-methoxypyrazolo[1,5-a]pyridine-3-carbonitrile | 420.2 (M + H) |
| P122* | 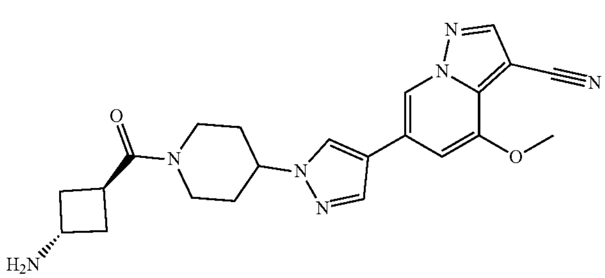 [SMILES: COc1cc(-c2cnn(C3CCN(C(=O)[C@H]4C[C@H](N)C4)CC3)c2)cn2ncc(C#N)c12] | 6-(1-(1-((1r,3r)-3-aminocyclobutane-1-carbonyl)piperidin-4-yl)-1H-pyrazol-4-yl)-4-methoxypyrazolo[1,5-a]pyridine-3-carbonitrile | 420.2 (M + H) |

TABLE CE-continued

| Intermediate # | Structure | Chemical Name | MS apci (m/z) |
|---|---|---|---|
| P123 | 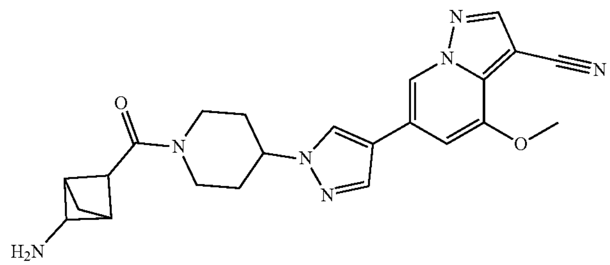 [SMILES: COc1cc(-c2cnn(C3CCN(C(=O)C4C5CC4C5N)CC3)c2)cn2ncc(C#N)c12] | 6-(1-(1-(4-aminobicyclo[1.1.1]pentane-2-carbonyl)piperidin-4-yl)-1H-pyrazol-4-yl)-4-methoxypyrazolo[1,5-a]pyridine-3-carbonitrile | 432.1 (M + H) |
| P124* | 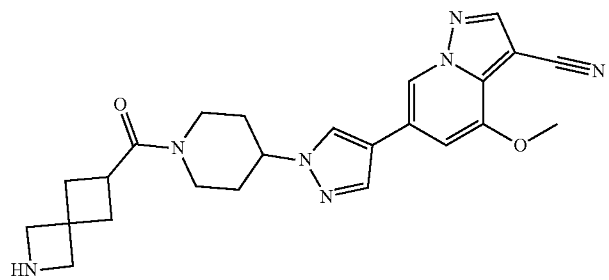 [SMILES: COc1cc(-c2cnn(C3CCN(C(=O)C4CC5(CNC5)C4)CC3)c2)cn2ncc(C#N)c12] | 6-(1-(1-(2-azaspiro[3.3]heptane-6-carbonyl)piperidin-4-yl)-1H-pyrazol-4-yl)-4-methoxypyrazolo[1,5-a]pyridine-3-carbonitrile | 446.2 (M + H) |
| P125* | 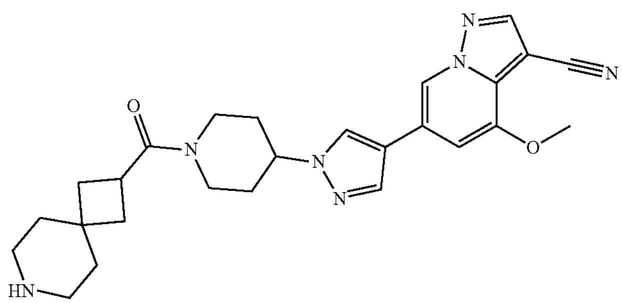 [SMILES: COc1cc(-c2cnn(C3CCN(C(=O)C4CC5(CCNCC5)C4)CC3)c2)cn2ncc(C#N)c12] | 6-(1-(1-(7-azaspiro[3.5]nonane-2-carbonyl)piperidin-4-yl)-1H-pyrazol-4-yl)-4-methoxypyrazolo[1,5-a]pyridine-3-carbonitrile | 474.3 (M + H) |
| P126 | 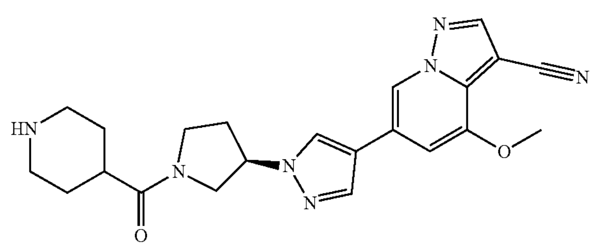 [SMILES: COc1cc(-c2cnn([C@@H]3CCN(C(=O)C4CCNCC4)C3)c2)cn2ncc(C#N)c12] | (R)-4-methoxy-6-(1-(1-(piperidine-4-carbonyl)pyrrolidin-3-yl)-1H-pyrazol-4-yl)pyrazolo[1,5-a]pyridine-3-carbonitrile | 420.2 (M + H) |
| P127 | 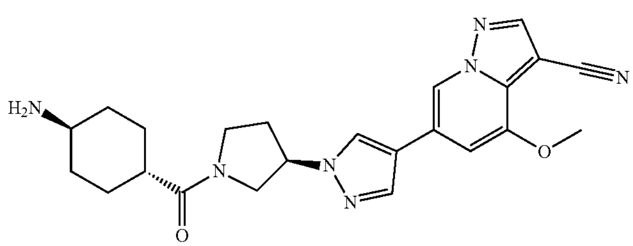 [SMILES: COc1cc(-c2cnn([C@@H]3CCN(C(=O)[C@H]4CC[C@H](N)CC4)C3)c2)cn2ncc(C#N)c12] | 6-(1-((R)-1-((1r,4R)-4-aminocyclohexane-1-carbonyl)pyrrolidin-3-yl)-1H-pyrazol-4-yl)-4-methoxypyrazolo[1,5-a]pyridine-3-carbonitrile | 434.2 (M + H) |
| P128 | 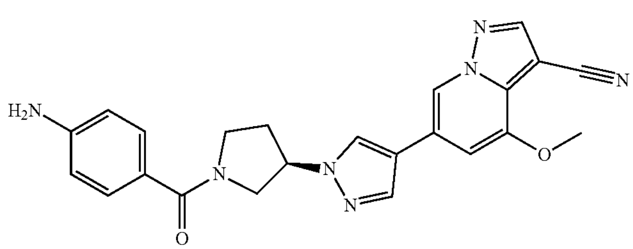 [SMILES: COc1cc(-c2cnn([C@@H]3CCN(C(=O)c4ccc(N)cc4)C3)c2)cn2ncc(C#N)c12] | (R)-6-(1-(1-(4-aminobenzoyl)pyrrolidin-3-yl)-1H-pyrazol-4-yl)-4-methoxypyrazolo[1,5-a]pyridine-3-carbonitrile | 428.2 (M + H) |

TABLE CE-continued

| Intermediate # | Chemical Name | MS apci (m/z) |
|---|---|---|
| P129 | (R)-6-(1-(1-(3-aminobenzoyl)pyrrolidin-3-yl)-1H-pyrazol-yl)-4-methoxypyrazolo[1,5-a]pyridine-3-carbonitrile | 428.2 (M + H) |
| P130 | 4-methoxy-6-(1-((R)-1-((S)-pyrrolidine-3-carbonyl)pyrrolidin-3-yl)-1H-pyrazol-4-yl)pyrazolo[1,5-a]pyridine-3-carbonitrile | 406.2 (M + H) |
| P131 | 4-methoxy-6-(1-((R)-1-((S)-pyrrolidine-3-carbonyl)pyrrolidin-3-yl)-1H-pyrazol-4-yl)pyrazolo[1,5-a]pyridine-3-carbonitrile | 406.2 (M + H) |
| P132 | (R)-6-(1-(1-(azetidine-3-carbonyl)pyrrolidin-3-yl)-1H-pyrazol-4-yl)-4-methoxypyrazolo[1,5-a]pyridine-3-carbonitrile | 392.2 (M + H) |
| P133 | 6-(1-((R)-1-((1r,3R)-3-aminocyclobutane-1-carbonyl)pyrrolidin-3-yl)-1H-pyrazol-4-yl)-4-methoxypyrazolo[1,5-a]pyridine-3-carbonitrile | 406.2 (M + H) |
| P134 | 6-(1-((R)-1-((1s,3S)-3-aminocyclobutane-1-carbonyl)pyrrolidin-3-yl)-1H-pyrazol-4-yl)-4-methoxypyrazolo[1,5-a]pyridine-3-carbonitrile | 406.2 (M + H) |

TABLE CE-continued

| Intermediate # | Chemical Name | MS apci (m/z) |
|---|---|---|
| P135 | (S)-4-methoxy-6-(1-(1-(piperidine-4-carbonyl)pyrrolidin-3-yl)-1H-pyrazol-4-yl)pyrazolo[1,5-a]pyridine-3-carbonitrile | 420.2 (M + H) |
| P136 | 4-methoxy-6-(1-((R)-1-((S)-piperidine-3-carbonyl)pyrrolidin-3-yl)-1H-pyrazol-4-yl)pyrazolo[1,5-a]pyridine-3-carbonitrile | 420.3 (M + H) |
| P137 | 4-methoxy-6-piperidine-3-carbonyl)pyrrolidin-3-yl)-1H-pyrazol-4-yl)pyrazolo[1,5-a]pyridine-3-carbonitrile | 420.2 (M + H) |
| P138 | 6-(1-((S)-1-((1r,4S)-4-aminocyclohexane-1-carbonyl)pyrrolidin-3-yl)-1H-pyrazol-4-yl)-4-methoxypyrazolo[1,5-a]pyridine-3-carbonitrile | 434.2 (M + H) |
| P139 | (S)-6-(1-(1-(4-aminobenzoyl)pyrrolidin-3-yl)-1H-pyrazol-4-yl)-4-methoxypyrazolo[1,5-a]pyridine-3-carbonitrile | 428.2 (M + H) |
| P140 | (S)-6-(1-(1-(3-aminobenzoyl)pyrrolidin-3-yl)-1H-pyrazol-4-yl)-4-methoxypyrazolo[1,5-a]pyridine-3-carbonitrile | 428.2 (M + H) |

TABLE CE-continued

| Intermediate # | Structure | Chemical Name | MS apci (m/z) |
|---|---|---|---|
| P141 | 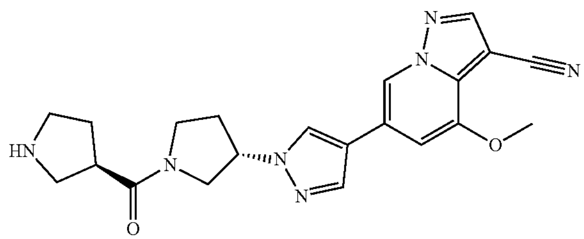 [SMILES: COc1cc(-c2cnn([C@H]3CCN(C(=O)[C@@H]4CCNC4)C3)c2)cn2ncc(C#N)c12] | 4-methoxy-6-(1-((S)-1-((R)-pyrrolidine-3-carbonyl)pyrrolidin-3-yl)-1H-pyrazol-4-yl)pyrazolo[1,5-a]pyridine-3-carbonitrile | 406.2 (M + H) |
| P142 | 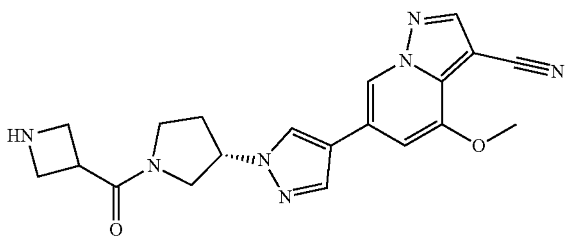 [SMILES: COc1cc(-c2cnn([C@H]3CCN(C(=O)C4CNC4)C3)c2)cn2ncc(C#N)c12] | (S)-6-(1-(1-(azetidine-3-carbonyl)pyrrolidin-3-yl)-1H-pyrazol-4-yl)-4-methoxypyrazolo[1,5-a]pyridine-3-carbonitrile | 392.2 (M + H) |
| P143 | 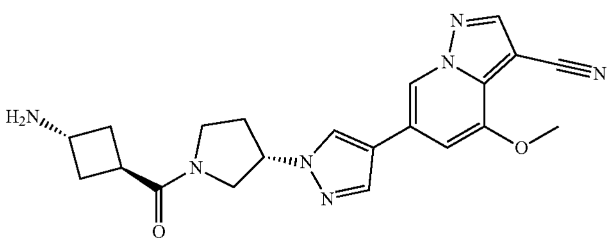 [SMILES: COc1cc(-c2cnn([C@H]3CCN(C(=O)[C@H]4C[C@H](N)C4)C3)c2)cn2ncc(C#N)c12] | 6-(1-((S)-1-((1r,3S)-3-aminocyclobutane-1-carbonyl)pyrrolidin-3-yl)-1H-pyrazol-4-yl)-4-methoxypyrazolo[1,5-a]pyridine-3-carbonitrile | 406.2 (M + H) |
| P144 | 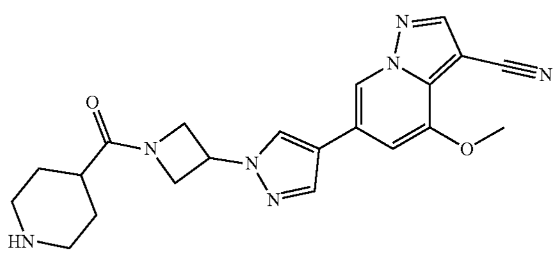 [SMILES: COc1cc(-c2cnn(C3CN(C(=O)C4CCNCC4)C3)c2)cn2ncc(C#N)c12] | 4-methoxy-6-(1-(1-(piperidine-4-carbonyl)azetidin-3-yl)-1H-pyrazol-4-yl)pyrazolo[1,5-a]pyridine-3-carbonitrile | 406.2 (M + H) |
| P145 | 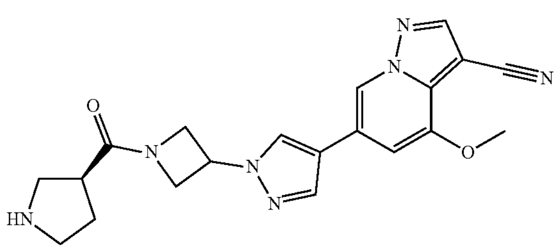 [SMILES: COc1cc(-c2cnn(C3CN(C(=O)[C@H]4CCNC4)C3)c2)cn2ncc(C#N)c12] | (S)-4-methoxy-6-(1-(1-(pyrrolidine-3-carbonyl)azetidin-3-yl)-1H-pyrazol-4-yl)pyrazolo[1,5-a]pyridine-3-carbonitrile | 392.2 (M + H) |
| P146 | 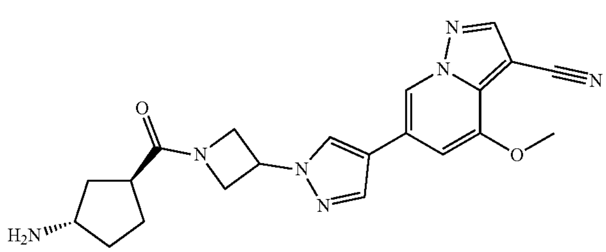 [SMILES: COc1cc(-c2cnn(C3CN(C(=O)[C@H]4CC[C@H](N)C4)C3)c2)cn2ncc(C#N)c12] | 6-(1-(1-((1S,3S)-3-aminocyclopentane-1-carbonyl)azetidin-3-yl)-1H-pyrazol-4-yl)-4-methoxypyrazolo[1,5-a]pyridine-3-carbonitrile | 406.2 (M + H) |

TABLE CE-continued

| Intermediate # | Structure | Chemical Name | MS apci (m/z) |
|---|---|---|---|
| P147 | 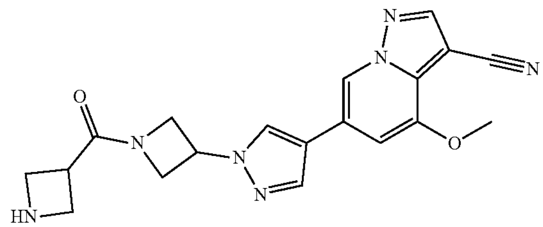 [SMILES: COc1cc(-c2cnn(C3CN(C(=O)C4CNC4)C3)c2)cn2ncc(C#N)c12] | 6-(1-(1-(azetidine-3-carbonyl)azetidin-3-yl)-1H-pyrazol-4-yl)-4-methoxypyrazolo[1,5-a]pyridine-3-carbonitrile | 378.2 (M + H) |
| P148 | 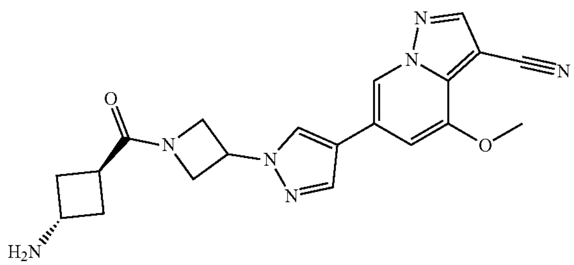 [SMILES: COc1cc(-c2cnn(C3CN(C(=O)[C@H]4C[C@H](N)C4)C3)c2)cn2ncc(C#N)c12] | 6-(1-(1-((1r,3r)-3-aminocyclobutane-1-carbonyl)azetidin-3-yl)-1H-pyrazol-4-yl)-4-methoxypyrazolo[1,5-a]pyridine-3-carbonitrile | 392.2 (M + H) |
| P149 | 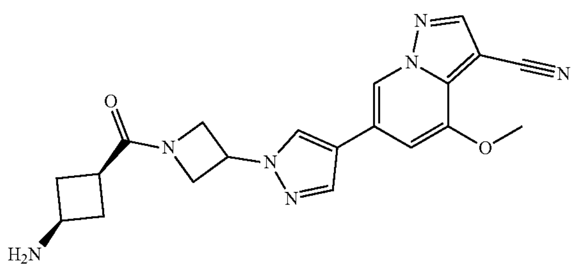 [SMILES: COc1cc(-c2cnn(C3CN(C(=O)[C@H]4C[C@@H](N)C4)C3)c2)cn2ncc(C#N)c12] | 6-(1-(1-((1s,3s)-3-aminocyclobutane-1-carbonyl)azetidin-3-yl)-1H-pyrazol-4-yl)-4-methoxypyrazolo[1,5-a]pyridine-3-carbonitrile | 392.2 (M + H) |
| P150 | 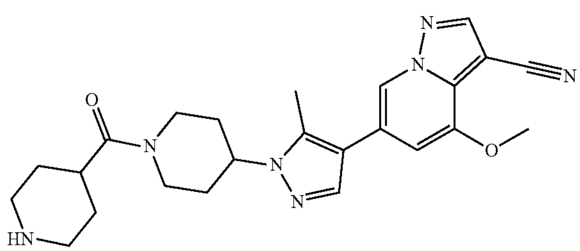 [SMILES: COc1cc(-c2cnn(C3CCN(C(=O)C4CCNCC4)CC3)c2C)cn2ncc(C#N)c12] | 4-methoxy-6-(5-methyl-1-(1-(piperidine-4-carbonyl)piperidin-4-yl)-1H-pyrazol-4-yl)pyrazolo[1,5-a]pyridine-3-carbonitrile | 448.2 (M + H) |
| P151 | 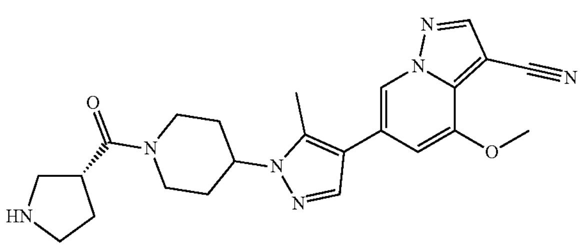 [SMILES: COc1cc(-c2cnn(C3CCN(C(=O)[C@@H]4CCNC4)CC3)c2C)cn2ncc(C#N)c12] | (R)-4-methoxy-6-(5-methyl-1-(1-(pyrrolidine-3-carbonyl)piperidin-4-yl)-1H-pyrazol-4-yl)pyrazolo[1,5-a]pyridine-3-carbonitrile | 434.2 (M + H) |
| P152 | 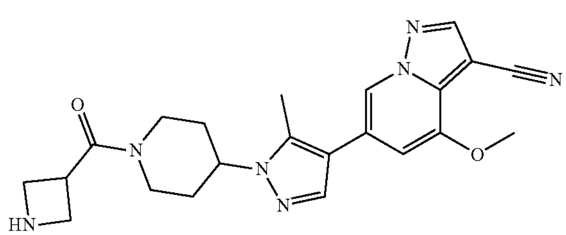 [SMILES: COc1cc(-c2cnn(C3CCN(C(=O)C4CNC4)CC3)c2C)cn2ncc(C#N)c12] | 6-(1-(1-(azetidine-3-carbonyl)piperidin-4-yl)-5-methyl-1H-pyrazol-4-yl)-4-methoxypyrazolo[1,5-a]pyridine-3-carbonitrile | 420.2 (M + H) |

TABLE CE-continued

| Intermediate # | Structure | Chemical Name | MS apci (m/z) |
|---|---|---|---|
| P153 | 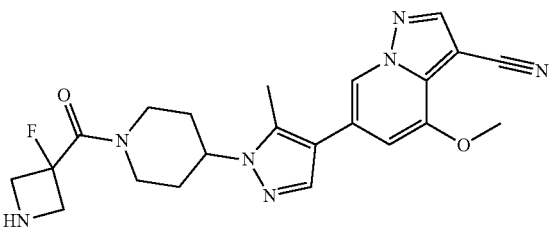 [SMILES: COc1cc(-c2cnn(C3CCN(C(=O)C4(F)CNC4)CC3)c2C)cn2ncc(C#N)c12] | 6-(1-(1-(3-fluoroazetidine-3-carbonyl)piperidin-4-yl)-5-methyl-1H-pyrazol-4-yl)-4-methoxypyrazolo[1,5-a]pyridine-3-carbonitrile | 438.2 (M + H) |
| P154 | 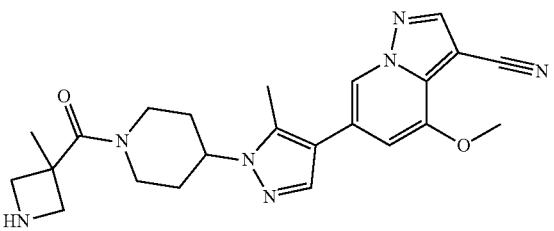 | 4-methoxy-6-(5-methyl-1-(1-(3-methylazetidine-3-carbonyl)piperidin-4-yl)-1H-pyrazol-4-yl)pyrazolo[1,5-a]pyridine-3-carbonitrile | 434.2 (M + H) |
| P155 | 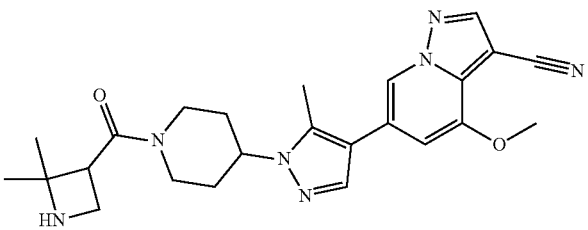 [SMILES: COc1cc(-c2cnn(C3CCN(C(=O)C4CNC4(C)C)CC3)c2C)cn2ncc(C#N)c12] | 6-(1-(1-(2,2-dimethylazetidine-3-carbonyl)piperidin-4-yl)-5-methyl-1H-pyrazol-4-yl)-4-methoxypyrazolo[1,5-a]pyridine-3-carbonitrile | 448.2 (M + H) |
| P156 | 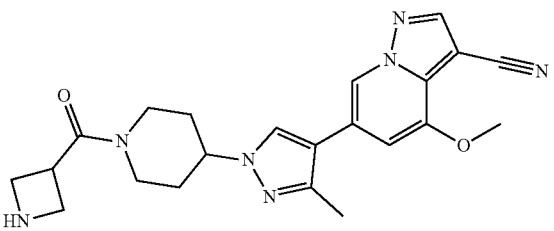 [SMILES: COc1cc(-c2cn(C3CCN(C(=O)C4CNC4)CC3)nc2C)cn2ncc(C#N)c12] | 6-(1-(1-(azetidine-3-carbonyl)piperidin-4-yl)-3-methyl-1H-pyrazol-4-yl)-4-methoxypyrazolo[1,5-a]pyridine-3-carbonitrile | 420.2 (M + H) |
| P157 | 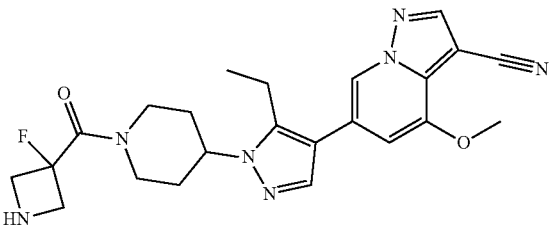 [SMILES: CCc1c(-c2cc(OC)c3c(C#N)cnn3c2)cnn1C1CCN(C(=O)C2(F)CNC2)CC1] | 6-(5-ethyl-1-(1-(3-fluoroazetidine-3-carbonyl)piperidin-4-yl)-1H-pyrazol-4-yl)-4-methoxypyrazolo[1,5-a]pyridine-3-carbonitrile | 452.2 (M + H) |
| P158 | 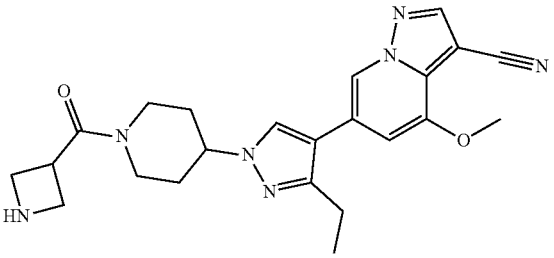 [SMILES: CCc1nn(C2CCN(C(=O)C3CNC3)CC2)cc1-c1cc(OC)c2c(C#N)cnn2c1] | 6-(1-(1-(azetidine-3-carbonyl)piperidin-4-yl)-3-ethyl-1H-pyrazol-4-yl)-4-methoxypyrazolo[1,5-a]pyridine-3-carbonitrile | 434.2 (M + H) |

TABLE CE-continued

| Intermediate # | Chemical Name | MS apci (m/z) |
|---|---|---|
| P159 | 6-(1-(1-(azetidine-3-carbonyl)piperidin-4-yl)-1H-imidazol-4-yl)-methoxypyrazolo[1,5-a]pyridine-3-carbonitrile | 406.1 (M + H) |
| P160 | 6-(1-(1-(3-fluoroazetidine-3-carbonyl)azetidin-3-yl)-5-methyl-1H-pyrazol-4-yl)-4-methoxypyrazolo[1,5-a]pyridine-3-carbonitrile | 410.1 (M + H) |
| P161 | 6-(1-(1-(3-fluoroazetidine-3-carbonyl)piperidin-4-yl)-3,5-dimethyl-1H-pyrazol-4-yl)-4-methoxypyrazolo[1,5-a]pyridine-3-carbonitrile | 452.2 (M + H) |
| P162 | 6-(2-(1-(3-fluoroazetidine-3-carbonyl)piperidin-4-yl)-5-methyl-2H-1,2,3-triazol-4-4-yl)-5-yl)-4-methoxypyrazolo[1,5-a]pyridine-3-carbonitrile | 439.2 (M + H) |
| P163 | 6-(1-(1-(3-fluoroazetidine-3-carbonyl)piperidin-4-yl)-5-methyl-1H-1,2,3-triazol-4-yl)-4-methoxypyrazolo[1,5-a]pyridine-3-carbonitrile | 439.2 (M + H) |
| P164 | 6-(4-(4-(azetidine-3-carbonyl)piperazin-1-yl)phenyl)-4-methoxypyrazolo[1,5-a]pyridine-3-carbonitrile | 417.2 (M + H) |

TABLE CE-continued

| Intermediate # | Structure | Chemical Name | MS apci (m/z) |
|---|---|---|---|
| P165 | 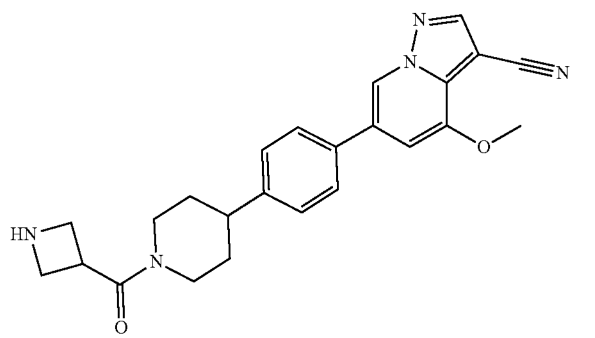 [SMILES: COc1cc(-c2ccc(C3CCN(C(=O)C4CNC4)CC3)cc2)cn2ncc(C#N)c12] | 6-(4-(1-(azetidine-3-carbonyl)piperidin-4-yl)phenyl)-4-methoxypyrazolo[1,5-a]pyridine-3-carbonitrile | 416.2 (M + H) |
| P166 | 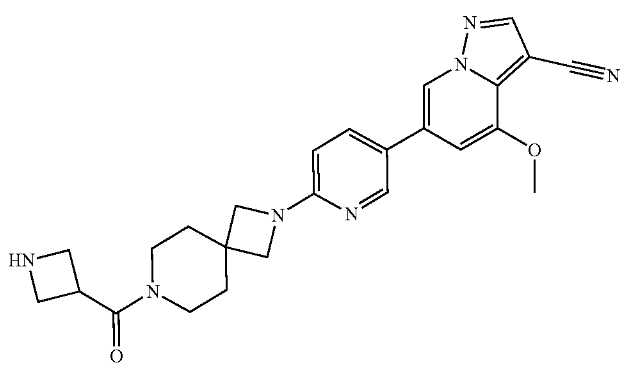 [SMILES: COc1cc(-c2ccc(N3CC4(CCN(C(=O)C5CNC5)CC4)C3)nc2)cn2ncc(C#N)c12] | 6-(6-(7-(azetidine-3-carbonyl)-2,7-diazaspiro[3.5]nonan-2-yl)pyridin-3-yl)-methoxypyrazolo[1,5-a]pyridine-3-carbonitrile | 458.2 (M + H) |
| P167 | 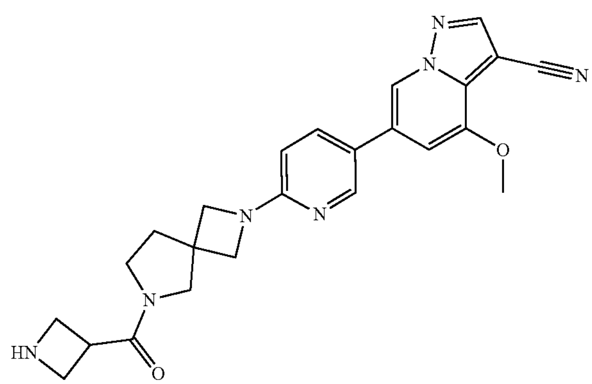 [SMILES: COc1cc(-c2ccc(N3CC4(CCN(C(=O)C5CNC5)C4)C3)nc2)cn2ncc(C#N)c12] | 6-(6-(6-(azetidine-3-carbonyl)-2,6-diazaspiro[3.4]octan-2-yl)pyridin-3-yl)-4-methoxypyrazolo[1,5-a]pyridine-3-carbonitrile | 444.2 (M + H) |
| P168 | 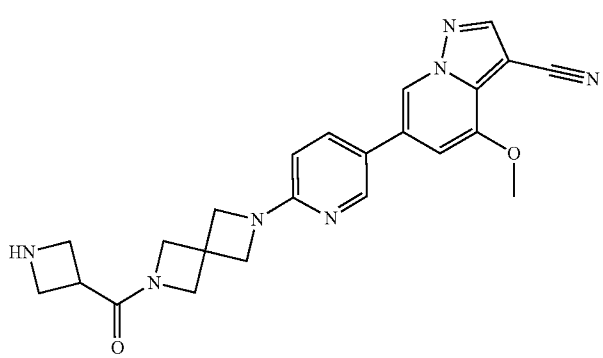 [SMILES: COc1cc(-c2ccc(N3CC4(CN(C(=O)C5CNC5)C4)C3)nc2)cn2ncc(C#N)c12] | 6-(6-(6-(azetidine-3-carbonyl)-2,6-diazaspiro[3.3]heptan-2-yl)pyridin-3-yl)-4-methoxypyrazolo[1,5-a]pyridine-3-carbonitrile | 430.2 (M + H) |

TABLE CE-continued

| Intermediate # | Structure | Chemical Name | MS apci (m/z) |
|---|---|---|---|
| P169 | 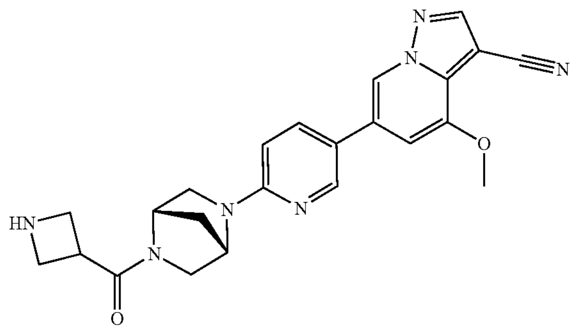 [SMILES: COc1cc(-c2ccc(N3C[C@@H]4C[C@H]3CN4C(=O)C3CNC3)nc2)cn2ncc(C#N)c12] | 6-(6-((1S,4S)-5-(azetidine-3-carbonyl)-2,5-diazabicyclo[2.2.1]heptan-2-yl)pyridin-3-yl)-4-methoxypyrazolo[1,5-a]pyridine-3-carbonitrile | 430.2 (M + H) |
| P170 | 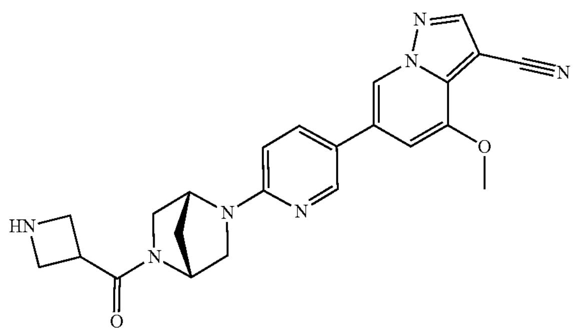 [SMILES: COc1cc(-c2ccc(N3C[C@H]4C[C@@H]3CN4C(=O)C3CNC3)nc2)cn2ncc(C#N)c12] | 6-(6-((1R,4R)-5-(azetidine-3-carbonyl)-2,5-diazabicyclo[2.2.1]heptan-2-yl)pyridin-3-yl)-methoxypyrazolo[1,5-a]pyridine-3-carbonitrile | 430.2 (M + H) |
| P171 | 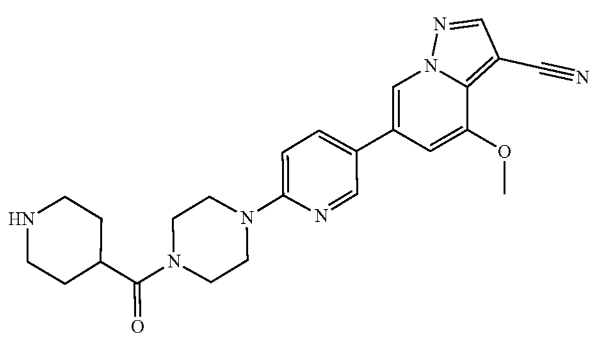 [SMILES: COc1cc(-c2ccc(N3CCN(C(=O)C4CCNCC4)CC3)nc2)cn2ncc(C#N)c12] | 4-methoxy-6-(6-(4-(piperidine-4-carbonyl)piperazin-1-yl)pyridin-3-yl)pyrazolo[1,5-a]pyridine-3-carbonitrile | 446.2 (M + H) |
| P172 | 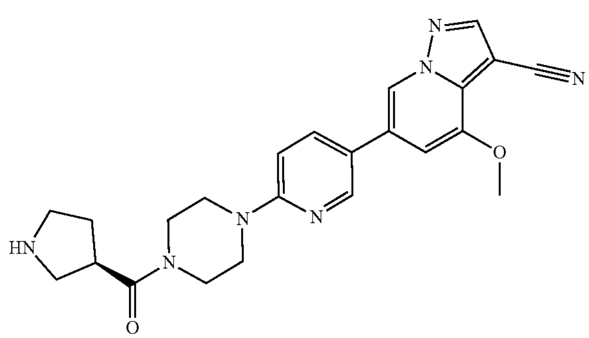 [SMILES: COc1cc(-c2ccc(N3CCN(C(=O)[C@@H]4CCNC4)CC3)nc2)cn2ncc(C#N)c12] | (R)-4-methoxy-6-(6-(4-(pyrrolidine-3-carbonyl)piperazin-1-yl)pyridin-3-yl)pyrazolo[1,5-a]pyridine-3-carbonitrile | 432.2 (M + H) |

TABLE CE-continued

| Intermediate # | Structure | Chemical Name | MS apci (m/z) |
|---|---|---|---|
| P173 | 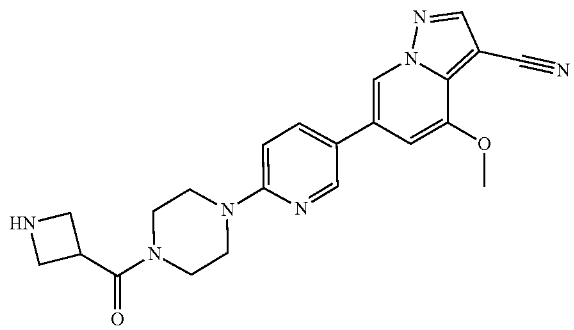 [SMILES: COc1cc(-c2ccc(N3CCN(C(=O)C4CNC4)CC3)nc2)cn2ncc(C#N)c12] | 6-(6-(4-(azetidine-3-carbonyl)piperazin-1-yl)pyridin-3-yl)-methoxypyrazolo[1,5-a]pyridine-3-carbonitrile | 418.2 (M + H) |
| P174 | 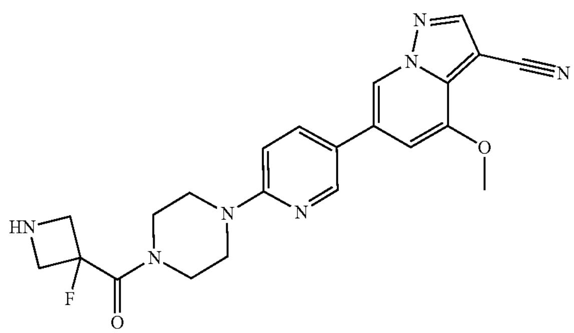 [SMILES: COc1cc(-c2ccc(N3CCN(C(=O)C4(F)CNC4)CC3)nc2)cn2ncc(C#N)c12] | 6-(6-(4-(3-fluoroazetidine-3-carbonyl)piperazin-1-yl)pyridin-3-yl)-4-methoxypyrazolo[1,5-a]pyridine-3-carbonitrile | 436.1 (M + H) |
| P175 | 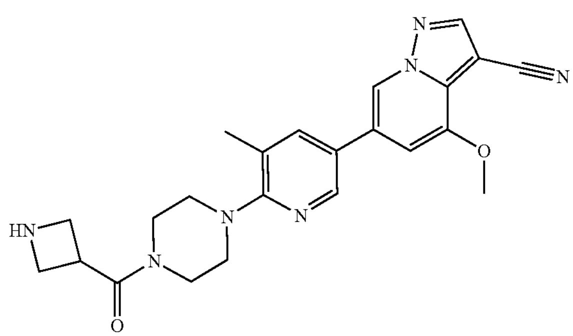 [SMILES: COc1cc(-c2cnc(N3CCN(C(=O)C4CNC4)CC3)c(C)c2)cn2ncc(C#N)c12] | 6-(6-(4-(azetidine-3-carbonyl)piperazin-1-yl)-5-methylpyridin-3-yl)-4-methoxypyrazolo[1,5-a]pyridine-3-carbonitrile | 432.1 (M + H) |
| P176 | 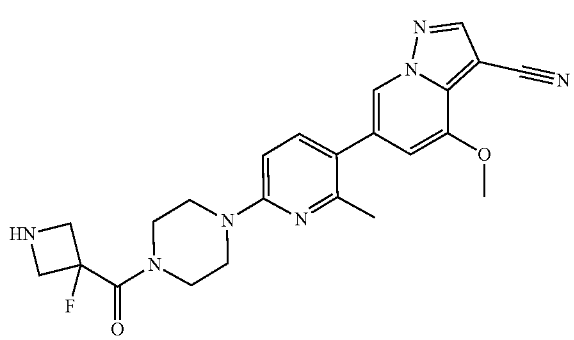 [SMILES: COc1cc(-c2ccc(N3CCN(C(=O)C4(F)CNC4)CC3)nc2C)cn2ncc(C#N)c12] | 6-(6-(4-(3-fluoroazetidine-3-carbonyl)piperazin-1-yl)-2-methylpyridin-3-yl)-4-methoxypyrazolo[1,5-a]pyridine-3-carbonitrile | 450.1 (M + H) |

TABLE CE-continued

| Intermediate # | Structure | Chemical Name | MS apci (m/z) |
|---|---|---|---|
| P177 | 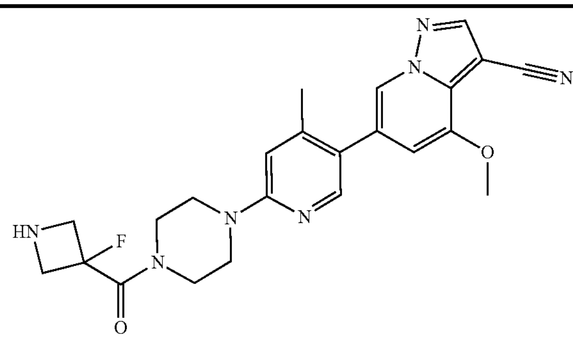 | 6-(6-(4-(3-fluoroazetidine-3-carbonyl)piperazin-1-yl)-4-methylpyridin-3-yl)-4-methoxypyrazolo[1,5-a]pyridine-3-carbonitrile | 450.2 (M + H) |
| P178 | 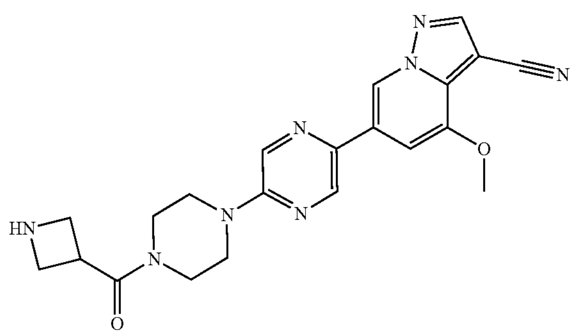 [SMILES: COc1cc(-c2cnc(N3CCN(C(=O)C4CNC4)CC3)cn2)cn2ncc(C#N)c12] | 6-(5-(4-(azetidine-3-carbonyl)piperazin-yl)pyrazin-2-yl)-4-methoxypyrazolo[1,5-a]pyridine-3-carbonitrile | 419.1 (M + H) |
| P179 | 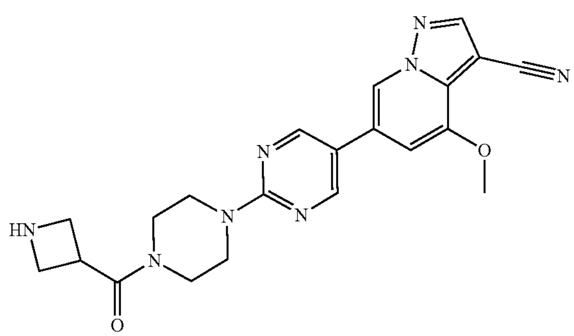 [SMILES: COc1cc(-c2cnc(N3CCN(C(=O)C4CNC4)CC3)nc2)cn2ncc(C#N)c12] | 6-(2-(4-(azetidine-3-carbonyl)piperazin-yl)pyrimidin-5-yl)-4-methoxypyrazolo[1,5-a]pyridine-3-carbonitrile | 419.2 (M + H) |
| P180 | 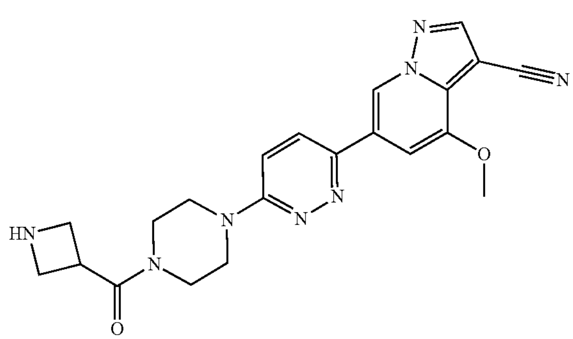 [SMILES: COc1cc(-c2ccc(N3CCN(C(=O)C4CNC4)CC3)nn2)cn2ncc(C#N)c12] | 6-(6-(4-(azetidine-3-carbonyl)piperazin-yl)pyridazin-3-yl)-4-methoxypyrazolo[1,5-a]pyridine-3-carbonitrile | 419.2 (M + H) |
| P181 | 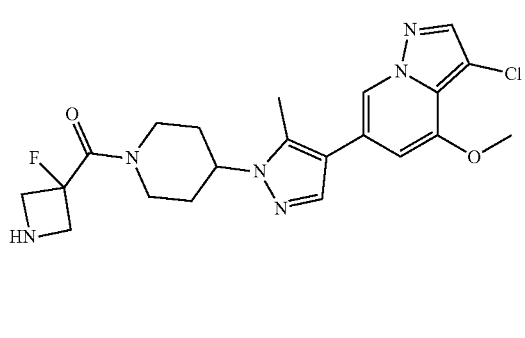 [SMILES: COc1cc(-c2cnn(C3CCN(C(=O)C4(F)CNC4)CC3)c2C)cn2ncc(Cl)c12] | (4-(4-(3-chloro-4-methoxypyrazolo[1,5-a]pyridin-6-yl)-5-methyl-1H-pyrazol-1-yl)piperidin-1-yl)(3-fluoroazetidin-3-yl)methanone | 447.1 (M + H) |

TABLE CE-continued

| Intermediate # | Structure | Chemical Name | MS apci (m/z) |
|---|---|---|---|
| P182 | 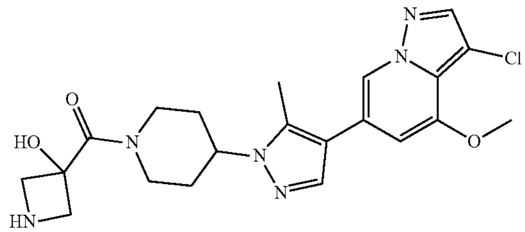 [SMILES: COc1cc(-c2cnn(C3CCN(C(=O)C4(O)CNC4)CC3)c2C)cn2ncc(Cl)c12] | (4-(4-(3-chloro-4-methoxypyrazolo[1,5-a]pyridin-6-yl)-5-methyl-1H-pyrazol-1-yl)piperidin-1-yl)(3-hydroxyazetidin-3-yl)methanone | 445.1 (M + H) |
| P183 | 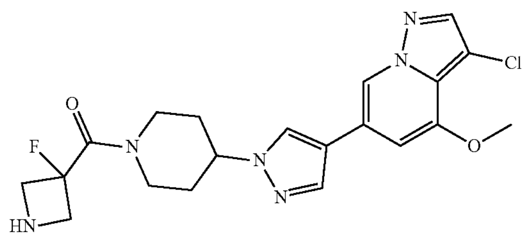 [SMILES: COc1cc(-c2cnn(C3CCN(C(=O)C4(F)CNC4)CC3)c2)cn2ncc(Cl)c12] | (4-(4-(3-chloro-4-methoxypyrazolo[1,5-a]pyridin-6-yl)-1H-pyrazol-1-yl)piperidin-1-yl)(3-fluoroazetidin-3-yl)methanone | 433.1 (M + H) |
| P184 | 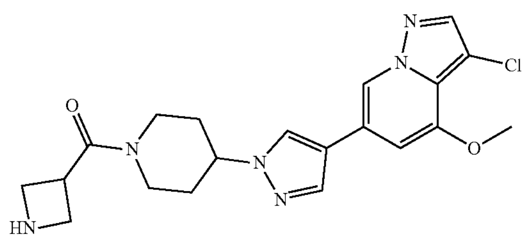 [SMILES: COc1cc(-c2cnn(C3CCN(C(=O)C4CNC4)CC3)c2)cn2ncc(Cl)c12] | azetidin-3-yl(4-(4-(3-chloro-4-methoxypyrazolo[1,5-a]pyridin-6-yl)-1H-pyrazol-1-yl)piperidin-1-yl)methanone | 415.1 (M + H) |
| P185 | 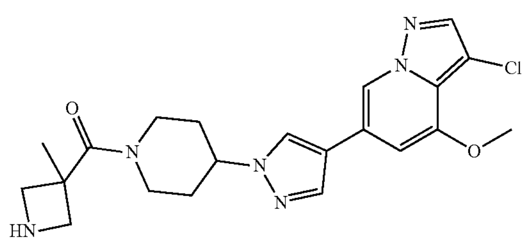 [SMILES: COc1cc(-c2cnn(C3CCN(C(=O)C4(C)CNC4)CC3)c2)cn2ncc(Cl)c12] | (4-(4-(3-chloro-4-methoxypyrazolo[1,5-a]pyridin-6-yl)-1H-pyrazol-1-yl)piperidin-1-yl)(3-methylazetidin-3-yl)methanone | 429.2 (M + H) |

Intermediate P186

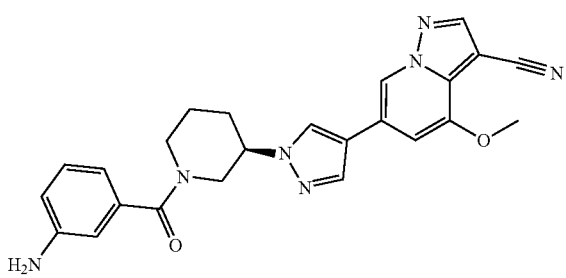 [SMILES: COc1cc(-c2cnn([C@@H]3CCCN(C(=O)c4cccc(N)c4)C3)c2)cn2ncc(C#N)c12]

(R)-6-(1-(1-(3-aminobenzoyl)piperidin-3-yl)-1H-pyrazol-4-yl)-4-methoxypyrazolo[1,5-a]pyridine-3-carbonitrile Step 1: Preparation of (R)-4-methoxy-6-(1-(1-(3-nitrobenzoyl)piperidin-3-yl)-1H-pyrazol-4-yl)pyrazolo[1,5-a]pyridine-3-carbonitrile. A mixture of (R)-4-methoxy-6-(1-(piperidin-3-yl)-1H-pyrazol-4-yl)pyrazolo[1,5-a]pyridine-3-carbonitrile (Intermediate P36; 209.4 mg, 0.6496 mmol), 3-nitrobenzoic acid (130.265 mg, 0.779472 mmol) and HATU (296.4 mg, 0.7795 mmol) in DCM (6.5 mL) was treated with DIEA (226.3 µL, 1.299 mmol), then stirred overnight at ambient temperature. Subsequently, the reaction mixture was concentrated in vacuo, and the resulting residue was purified by silica chromatography (using 5-95% DCM-Acetone as the gradient eluent) to cleanly afford the title compound (quantitative yield assumed).

Step 2: Preparation of (R)-6-(1-(1-(3-aminobenzoyl)piperidin-3-yl)-1H-pyrazol-4-yl)-4-methoxypyrazolo[1,5-a]pyridine-3-carbonitrile. A cold (0° C.) solution of (R)-4-methoxy-6-(1-(1-(3-nitrobenzoyl)piperidin-3-yl)-1H-pyrazol-4-yl)pyrazolo[1,5-a]pyridine-3-carbonitrile (Step 1; ~0.6496 mmol) in 1:1 THF: saturated $NH_4Cl_{(aq)}$ (6.5 mL) was treated with Zn dust (<10 µm, 98+%, 424.7 mg, 6.496 mmol). After being allowed to warm to ambient temperature, the reaction mixture was stirred for an additional 1 h. The mixture then was diluted with EtOAc and washed sequentially with water (2×) and brine (1×). The organic extracts were sequentially dried over $Na_2SO_{4(s)}$, filtered, and concentrated in vacuo. The crude product was purified by silica chromatography (using 5-95% DCM:

Acetone as the gradient eluent) to cleanly afford the title compound (215.9 mg, 75% yield). MS (apci) m/z=442.2 (M+H).

The compounds in Table CE² were prepared using a similar 2 Step method to that described in the synthesis of (R)-6-(1-(1-(3-aminobenzoyl)piperidin-3-yl)-1H-pyrazol-4-yl)-4-methoxypyrazolo[1,5-a]pyridine-3-carbonitrile (Intermediate P186) employing the following modifications: in Step 1, using 1.2-2.5 equivalents of HATU, 2-5 equivalents of DIEA, solvent (DCM) concentration of 0.1-0.2 M and replacing both the 3-nitrobenzoic acid and the (R)-4-methoxy-6-(1-(piperidin-3-yl)-1H-pyrazol-4-yl)pyrazolo[1,5-a]pyridine-3-carbonitrile (Intermediate P36) respectively with 1.2 equivalents of the appropriate nitrobenzoic acid from Table CE²i and 1.0 equivalent of the appropriate amine-core from the synthetic intermediates section (e.g. Table CA¹, Table CA², Table CB, etc.); and in Step 2, using 10 equivalents of Zn dust (<10 μm, 98+%), 1:1 THF:saturated NH₄Cl$_{(aq)}$ ratio except where noted (*) and replacing (R)-4-methoxy-6-(1-(1-(3-nitrobenzoyl)piperidin-3-yl)-1H-pyrazol-4-yl)pyrazolo[1,5-a]pyridine-3-carbonitrile (Step 2, Intermediate P186) with the appropriate coupling product from Step 1 in each. All reactions were monitored for completion by LCMS, as such reaction durations were adjusted accordingly. When necessary, title compounds (Step 1 and/or Step 2) were purified via silica gel chromatographic purification using an appropriate gradient eluent or reverse phase chromatographic purification using an appropriate gradient eluent followed by a basic aqueous wash.

TABLE CE²

| Intermediate # | Structure | Chemical Name | MS apci (m/z) |
|---|---|---|---|
| P187 | 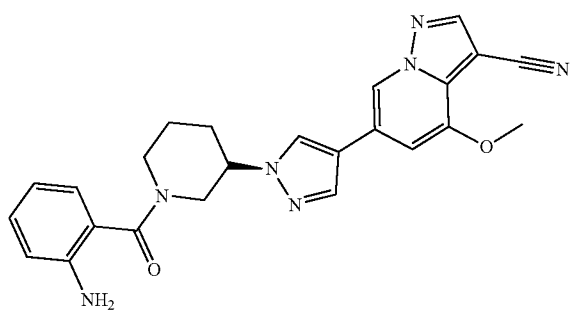 | (R)-6-(1-(1-(2-aminobenzoyl)piperidin-3-yl)-1H-pyrazol-4-yl)-4-methoxypyrazolo[1,5-a]pyridine-3-carbonitrile | 442.2 (M + H) |
| P188 | 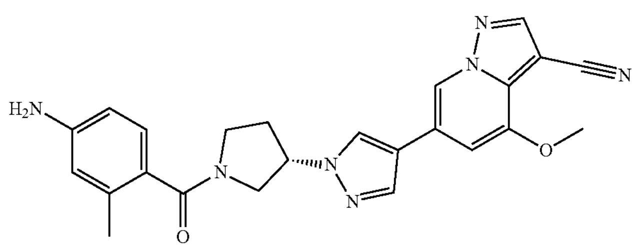 [SMILES: COc1cc(-c2cnn([C@H]3CCN(C(=O)c4ccc(N)cc4C)C3)c2)cn2ncc(C#N)c12] | (S)-6-(1-(1-(4-amino-2-methylbenzoyl)pyrrolidin-3-yl)-1H-pyrazol-4-yl)-4-methoxypyrazolo[1,5-a]pyridine-3-carbonitrile | 442.2 (M + H) |
| P189 | 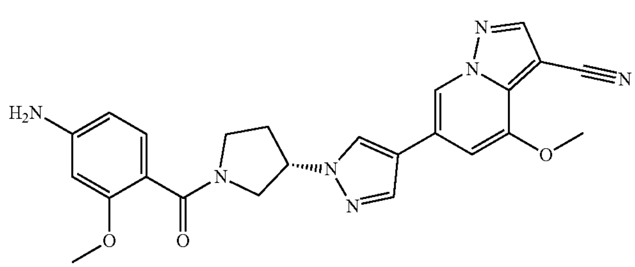 [SMILES: COc1cc(N)ccc1C(=O)N1CC[C@H](n2cc(-c3cc(OC)c4c(C#N)cnn4c3)cn2)C1] | (S)-6-(1-(1-(4-amino-2-methoxybenzoyl)pyrrolidin-3-yl)-1H-pyrazol-4-yl)-4-methoxypyrazolo[1,5-a]pyridine-3-carbonitrile | 458.2 (M + H) |
| P190 | 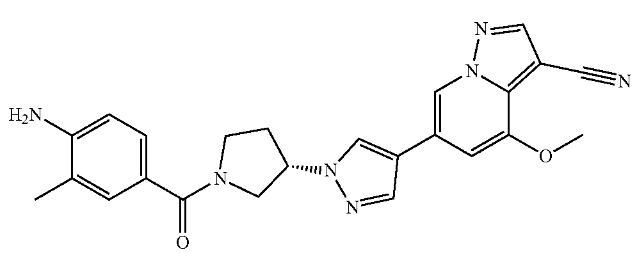 [SMILES: COc1cc(-c2cnn([C@H]3CCN(C(=O)c4ccc(N)c(C)c4)C3)c2)cn2ncc(C#N)c12] | (S)-6-(1-(1-(4-amino-3-methylbenzoyl)pyrrolidin-3-yl)-1H-pyrazol-4-yl)-4-methoxypyrazolo[1,5-a]pyridine-3-carbonitrile | 442.2 (M + H) |

TABLE CE²-continued

| Intermediate # | Structure | Chemical Name | MS apci (m/z) |
|---|---|---|---|
| P191 | 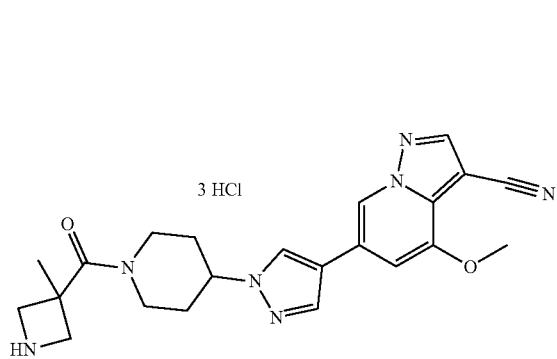 | (S)-6-(1-(1-(4-amino-3-methoxybenzoyl)pyrrolidin-3-yl)-1H-pyrazol-4-yl)-4-methoxypyrazolo[1,5-a]pyridine-3-carbonitrile | 458.1 (M + H) |

Intermediate P193

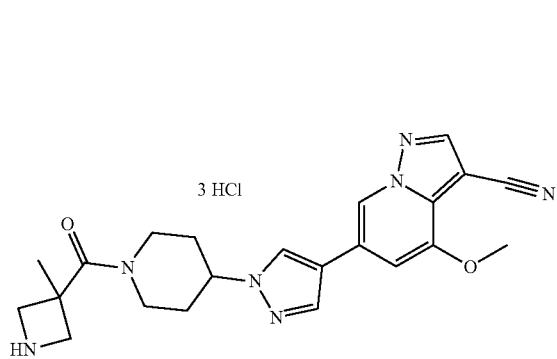 [SMILES: COc1cc(-c2cnn(C3CCN(C(=O)C4(C)CNC4)CC3)c2)cn2ncc(C#N)c12]

4-methoxy-6-(1-(1-(3-methylazetidine-3-carbonyl)piperidin-4-yl)-1H-pyrazol-4-yl)pyrazolo[1,5-a]pyridine-3-carbonitrile trihydrochloride Step 1: Preparation of tert-butyl 3-(4-(4-(3-cyano-4-methoxypyrazolo[1,5-a]pyridin-6-yl)-1H-pyrazol-1-yl)piperidine-1-carbonyl)-3-methylazetidine-1-carboxylate. A mixture of 4-methoxy-6-(1-(piperidin-4-yl)-1H-pyrazol-4-yl)pyrazolo[1,5-a]pyridine-3-carbonitrile (Intermediate P25; 100 mg, 0.310 mmol), 1-Boc-3-methylazetidine-3-carboxylic acid (80.1 mg, 0.372 mmol) and HATU (2.87 g, 7.56 mmol) in DCM (1.55 mL) was treated with DIEA (271 µL, 1.55 mmol), then stirred for 1 h at ambient temperature. The reaction mixture then was purified directly by silica chromatography (using 0-100% DCM-Acetone as the gradient eluent) to cleanly afford the title compound (103 mg, 64% yield). MS (apci) m/z=520.2 (M+H).

Step 2: Preparation of 4-methoxy-6-(1-(1-(3-methylazetidine-3-carbonyl)piperidin-4-yl)-1H-pyrazol-4-yl)pyrazolo[1,5-a]pyridine-3-carbonitrile trihydrochloride. A solution of tert-butyl 3-(4-(4-(3-cyano-4-methoxypyrazolo[1,5-a]pyridin-6-yl)-1H-pyrazol-1-yl)piperidine-1-carbonyl)-3-methylazetidine-1-carboxylate (Step 1, 150 mg, 0.096 mmol) in DCM (962 µL) was treated with 5 N HCl (192 µL), then stirred overnight at ambient temperature Subsequently, the reaction mixture was concentrated in vacuo to cleanly afford the title compound (51 mg, quantitative yield). MS (apci) m/z=420.2 (M+H).

Intermediate P194

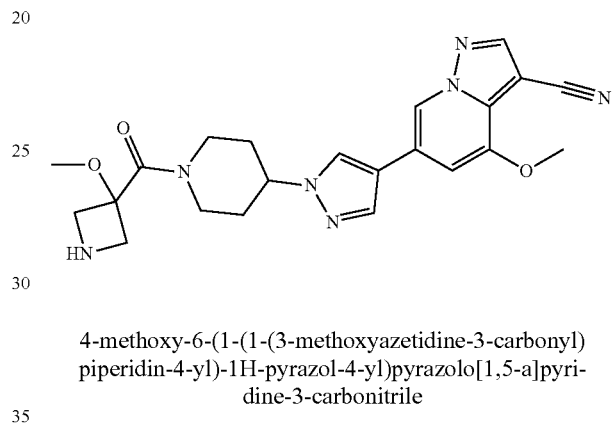

4-methoxy-6-(1-(1-(3-methoxyazetidine-3-carbonyl)piperidin-4-yl)-1H-pyrazol-4-yl)pyrazolo[1,5-a]pyridine-3-carbonitrile Step 1: Preparation of tert-butyl 3-(4-(4-(3-cyano-4-methoxypyrazolo[1,5-a]pyridin-6-yl)-1H-pyrazol-1-yl)piperidine-1-carbonyl)-3-hydroxyazetidine-1-carboxylate. A mixture of 4-methoxy-6-(1-(piperidin-4-yl)-1H-pyrazol-4-yl)pyrazolo[1,5-a]pyridine-3-carbonitrile (Intermediate P25; 150 mg, 0.465 mmol), 1-[(tert-butoxy)carbonyl]-3-hydroxyazetidine-3-carboxylic acid (121 mg, 0.558 mmol) and HATU (442 mg, 1.16 mmol) in DCM (2.33 mL) was treated with DIEA (406 µL, 2.33 mmol), then stirred for 2 h at ambient temperature. Subsequently, additional 1-[(tert-butoxy)carbonyl]-3-hydroxyazetidine-3-carboxylic acid (121 mg, 0.558 mmol), DCM (2.33 mL) and DIEA (406 µL, 2.33 mmol) were introduced. The resulting reaction mixture was stirred and monitored by LCMS for complete consumption of the starting 4-methoxy-6-(1-(piperidin-4-yl)-1H-pyrazol-4-yl)pyrazolo[1,5-a]pyridine-3-carbonitrile (Intermediate P25). The reaction mixture then was purified directly by silica chromatography (using 0-100% DCM-Acetone as the gradient eluent) to cleanly afford the title compound (150 mg, 62% yield). MS (apci) m/z=520.2 (M+H).

Step 2: Preparation of tert-butyl 3-(4-(4-(3-cyano-4-methoxypyrazolo[1,5-a]pyridin-6-yl)-1H-pyrazol-1-yl)piperidine-1-carbonyl)-3-methoxyazetidine-1-carboxylate. A solution of tert-butyl 3-(4-(4-(3-cyano-4-methoxypyrazolo[1,5-a]pyridin-6-yl)-1H-pyrazol-1-yl)piperidine-1-carbonyl)-3-hydroxyazetidine-1-carboxylate (Step 1; 150 mg, 0.288 mmol) in DMF (2876 µL) was treated sequentially with MeI (6.52 µL, 0.104 mmol) and NaH (60 wt. % mineral oil dispersion; 17.3 mg, 0.431 mmol). After stirring overnight at ambient temperature, the resulting suspension was partitioned between water and EtOAc. The organic extracts were washed with brine (1×), then sequentially dried over $Na_2SO_{4(s)}$, filtered, and concentrated in vacuo. The crude product was purified by silica chromatography (using 0-100% DCM: Acetone as the gradient eluent) to cleanly afford the title compound (124 mg, 81% yield). MS (apci) m/z=536.2 (M+H).

Step 3: Preparation of 4-methoxy-6-(1-(1-(3-methoxyazetidine-3-carbonyl)piperidin-4-yl)-1H-pyrazol-4-yl)pyrazolo[1,5-a]pyridine-3-carbonitrile. A solution tert-butyl 3-(4-(4-(3-cyano-4-methoxypyrazolo[1,5-a]pyridin-6-yl)-1H-pyrazol-1-yl)piperidine-1-carbonyl)-3-methoxyazetidine-1-carboxylate (Step 2; 124 mg, 0.232 mmol) and TFA (178 µL, 2.32 mmol) in DCM (2315 µL), was stirred for 1 h at ambient temperature. Subsequently, the reaction mixture was concentrated in vacuo. The crude residue was purified by C18 reverse phase chromatography (using 5-95% ACN in water with 0.1% TFA as the gradient eluent). Pure fractions from the chromatography were combined then extracted with 4:1 DCM:iPrOH and saturated $NaHCO_{3(aq)}$. The organic extracts then were dried over anhydrous $Na_2SO_{4(s)}$, filtered, and concentrated in vacuo to cleanly afford the title compound (91 mg, 90% yield). MS (apci) m/z=436.2 (M+H).

Intermediate P195

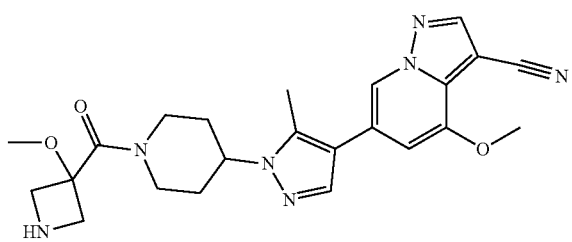 [SMILES: COc1cc(-c2cnn(C3CCN(C(=O)C4(OC)CNC4)CC3)c2C)cn2ncc(C#N)c12]

4-methoxy-6-(1-(1-(3-methoxyazetidine-3-carbonyl) piperidin-4-yl)-5-methyl-1H-pyrazol-4-yl)pyrazolo [1,5-a]pyridine-3-carbonitrile The title compound (142 mg, 73% overall yield) was prepared, worked-up and purified using a similar 3 Step procedure to that described for the synthesis of 4-methoxy-6-(1-(1-(3-methoxyazetidine-3-carbonyl)piperidin-4-yl)-1H-pyrazol-4-yl)pyrazolo[1,5-a]pyridine-3-carbonitrile (Intermediate P194), employing the following modifications: in Step 1 no second addition of reagents was necessary but the reaction was stirred overnight at ambient temperature and the 4-methoxy-6-(1-(piperidin-4-yl)-1H-pyrazol-4-yl)pyrazolo[1,5-a]pyridine-3-carbonitrile (Intermediate P25) was replaced with 4-methoxy-6-(5-methyl-1-(piperidin-4-yl)-1H-pyrazol-4-yl)pyrazolo[1,5-a]pyridine-3-carbonitrile (Intermediate P41); in Step 2 the reaction was only stirred for 1 h at ambient temperature and the product was carried into Step 3 crude (after work up); in Step 3 no purification was necessary. MS (apci) m/z=450.2 (M+H).

Intermediate P196

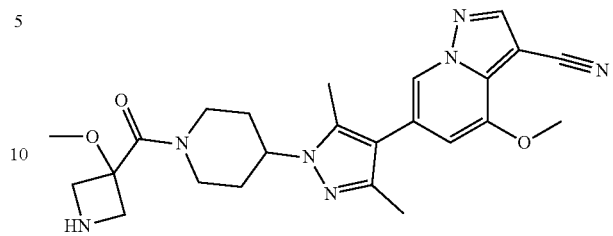

4-methoxy-6-(1-(1-(3-methoxyazetidine-3-carbonyl) piperidin-4-yl)-3,5-dimethyl-1H-pyrazol-4-4pyrazolo[1,5-a]pyridine-3-carbonitrile The title compound (118 mg, 89% overall yield) was prepared, worked-up and purified using a similar 3 Step procedure to that described for the synthesis of 4-methoxy-6-(1-(1-(3-methoxyazetidine-3-carbonyl)piperidin-4-yl)-1H-pyrazol-4-yl)pyrazolo[1,5-a]pyridine-3-carbonitrile (Intermediate P194), employing the following modifications: in Step 1 no second addition of reagents was necessary but 3 equivalents of HATU was used and the reaction was stirred overnight at ambient temperature. Additionally, the 4-methoxy-6-(1-(piperidin-4-yl)-1H-pyrazol-4-yl)pyrazolo[1,5-a]pyridine-3-carbonitrile (Intermediate P25) was replaced with 6-(3,5-dimethyl-1-(piperidin-4-yl)-1H-pyrazol-4-yl)-4-methoxypyrazolo[1,5-a]pyridine-3-carbonitrile (Intermediate P44); in Step 2 the reaction was only stirred for 1 h at ambient temperature and the product was carried into Step 3 crude (after work up); in Step 3 no purification was necessary. MS (apci) m/z=464.2 (M+H).

Intermediate P197

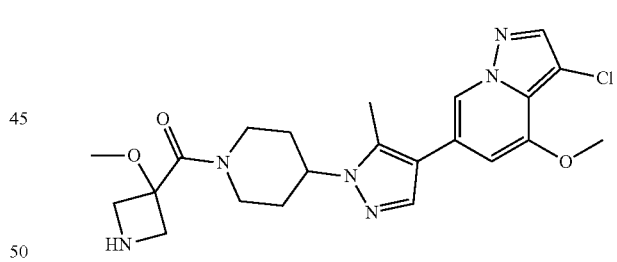

(4-(4-(3-chloro-4-methoxypyrazolo[1,5-a]pyridin-6-yl)-5-methyl-1H-pyrazol-1-yl)piperidin-1-yl)(3-methoxyazetidin-3-yl)methanone Procedure 1
Step 1: Preparation of tert-butyl 3-(4-(4-(3-chloro-4-methoxypyrazolo[1,5-a]pyridin-6-yl)-5-methyl-1H-pyrazol-1-yl)piperidine-1-carbonyl)-3-hydroxyazetidine-1-carboxylate. A mixture of 3-chloro-4-methoxy-6-(5-methyl-1-(piperidin-4-yl)-1H-pyrazol-4-yl)pyrazolo[1,5-a]pyridine (Intermediate P55) (100 mg, 0.289 mmol), 1-[(tert-butoxy)carbonyl]-3-hydroxyazetidine-3-carboxylic acid (75.4 mg, 0.347 mmol), and HATU (330 mg, 0.867 mmol) in DCM (1446 µL) was treated with DIEA (253 µL, 1.45 mmol). The reaction mixture was stirred for 1 h at ambient temperature.

417

The resulting mixture was concentrated in vacuo and the resulting residue purified by silica chromatography (using 0-100% DCM:Acetone as the gradient eluent) to cleanly afford the title compound (118 mg, 75% yield). MS (apci) m/z=545.2.

Step 2: Preparation of tert-butyl 3-(4-(4-(3-chloro-4-methoxypyrazolo[1,5-a]pyridin-6-yl)-5-methyl-1H-pyrazol-1-yl)piperidine-1-carbonyl)-3-methoxyazetidine-1-carboxylate. A solution of tert-butyl 3-(4-(4-(3-chloro-4-methoxypyrazolo[1,5-a]pyridin-6-yl)-5-methyl-1H-pyrazol-1-yl)piperidine-1-carbonyl)-3-hydroxyazetidine-1-carboxylate (step 1; 118 mg, 0.216 mmol) in DMF (2165 μL) was treated sequentially with MeI (16.2 μL, 0.260 mmol) and NaH (60 wt. % mineral oil suspension, 13.0 mg, 0.325 mmol). The reaction mixture was stirred at ambient temperature for 1 h. Subsequently, the reaction mixture was diluted with water and extracted with EtOAc. The organic extracts were washed with brine, dried over anhydrous $Na_2SO_{4(s)}$, filtered, and concentrated in vacuo to afford the title compound (91 mg, 75% yield). MS (apci) m/z=559.2 (M+H).

Step 3: Preparation of (4-(4-(3-chloro-4-methoxypyrazolo[1,5-a]pyridin-6-yl)-5-methyl-1H-pyrazol-1-yl)piperidin-1-yl)(3-methoxyazetidin-3-yl)methanone.

Tert-butyl 3-(4-(4-(3-chloro-4-methoxypyrazolo[1,5-a]pyridin-6-yl)-5-methyl-1H-pyrazol-1-yl)piperidine-1-carbonyl)-3-methoxyazetidine-1-carboxylate (91 mg, 0.16 mmol) added to a 1:1 mix of DCM:TFA. After stirring at room temperature for 1 h, the reaction was concentrated in vacuo. The resulting oil was taken up in 4:1 DCM:iPrOH, washed with saturated $NaHCO_{3(aq)}$, dried over anhydrous $Na_2SO_{4(s)}$, filtered, and concentrated in vacuo to afford the title compound (70 mg, 94% yield). MS (apci) m/z=459.1 (M+H).

Procedure 2

Step 1: Preparation of tert-butyl 3-(4-(4-(3-chloro-4-methoxypyrazolo[1,5-a]pyridin-6-yl)-5-methyl-1H-pyrazol-1-yl)piperidine-1-carbonyl)-3-methoxyazetidine-1-carboxylate. 3-Chloro-4-methoxy-6-(5-methyl-1-(piperidin-4-yl)-1H-pyrazol-4-yl)pyrazolo[1,5-a]pyridine (5.0 g, 12 mmol) (Intermediate P55) was dissolved in DCM (145 mL). To the solution was added 1-(tert-butoxycarbonyl)-3-methoxyazetidine-3-carboxylic acid (3.13 g, 13.5 mmol), HATU (5.14 g, 13.5 mmol), and N,N-diisoporpylethylamine (4.28 mL, 24.6 mmol). The reaction mixture was stirred at room temperature overnight (16 hrs), after which it was concentrated. The resulting residue was purified by silica chromatography (using 5-60% DCM-Acetone as gradient eluent).

Step 2: Preparation of (4-(4-(3-chloro-4-methoxypyrazolo[1,5-a]pyridin-6-yl)-5-methyl-1H-pyrazol-1-yl)piperidin-1-yl)(3-methoxyazetidin-3-yl)methanone. The resulting intermediate from the chromatographic purification was dissolved in 1:1 DCM:TFA (25 mL). The mixture was stirred at room temperature for 30 minutes and subsequently concentrated. The residue thus obtained was purified by reverse phase C18 chromatography (using 5-95% water-ACN with 0.1% TFA as gradient eluent). The combined fractions were concentrated to a reduced volume to remove most of organic solvent. The resulting mixture was partitioned between 4:1 DCM:iPrOH and sat. $NaHCO_{3(aq)}$ (1×). The organic phase was dried over anhydrous $Na_2SO_{4(s)}$, filtered, and concentrated to provide the title compound (4.72 g, 84% yield). MS (apci) m/z=459.2 (M+H).

418

Intermediate P198

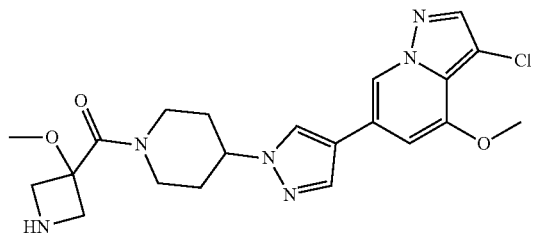

(4-(4-(3-chloro-4-methoxypyrazolo[1,5-a]pyridin-6-yl)-1H-pyrazol-1-yl)piperidin-1-yl)(3-methoxyazetidin-3-yl)methanone Step 1: Preparation of tert-butyl 3-(4-(4-(3-chloro-4-methoxypyrazolo[1,5-a]pyridin-6-yl)-1H-pyrazol-1-yl)piperidine-1-carbonyl)-3-hydroxyazetidine-1-carboxylate. A mixture of 3-Chloro-4-methoxy-6-(1-(piperidin-4-yl)-1H-pyrazol-4-yl)pyrazolo[1,5-a]pyridine (Intermediate P34; 100 mg, 0.301 mmol), 1-[(tert-butoxy)carbonyl]-3-hydroxyazetidine-3-carboxylic acid (78.6 mg, 0.362 mmol) and HATU (286 mg, 0.753 mmol) in DCM (1507 μL) was treated with DIEA (263 μL, 1.51 mmol). The reaction mixture was stirred for 1 h at ambient temperature. The resulting mixture was purified directly by silica chromatography (using 0-100% DCM:Acetone as the gradient eluent) to afford the title compound (160 mg, 100% yield). MS (apci) m/z=531.2 (M+H).

Step 2: Preparation of tert-butyl 3-(4-(4-(3-chloro-4-methoxypyrazolo[1,5-a]pyridin-6-yl)-1H-pyrazol-1-yl)piperidine-1-carbonyl)-3-methoxyazetidine-1-carboxylate. A solution of tert-butyl 3-(4-(4-(3-chloro-4-methoxypyrazolo[1,5-a]pyridin-6-yl)-1H-pyrazol-1-yl)piperidine-1-carbonyl)-3-hydroxyazetidine-1-carboxylate (Step 1; 160 mg, 0.301 mmol) in DMF (3013 μL) was treated sequentially with MeI (22.5 μL, 0.362 mmol) and NaH (60 wt. % dispersion in mineral oil, 18.1 mg, 0.452 mmol). The resulting mixture was stirred for 1 h at ambient temperature. The mixture then was diluted with water and extracted with EtOAc. The combined organic extracts were washed with brine, dried over anhydrous $Na_2SO_{4(s)}$, filtered, and concentrated in vacuo to afford the title compound (164 mg, 100% yield). MS (apci) m/z=545.2 (M+H).

Step 3: Preparation of (4-(4-(3-chloro-4-methoxypyrazolo[1,5-a]pyridin-6-yl)-1H-pyrazol-1-yl)piperidin-1-yl)(3-methoxyazetidin-3-yl)methanone A mixture of tert-butyl 3-(4-(4-(3-chloro-4-methoxypyrazolo[1,5-a]pyridin-6-yl)-1H-pyrazol-1-yl)piperidine-1-carbonyl)-3-methoxyazetidine-1-carboxylate (164 mg, 0.301 mmol) in a 1:1 mix of DCM:TFA was stirred for 3 h at room temperature. The resulting mixture then was concentrated in vacuo. The residue was dissolved in 4:1 DCM:iPrOH, washed with saturated $NaHCO_{3(aq)}$, dried over anhydrous $Na_2SO_{4(s)}$, filtered, and concentrated in vacuo to afford the title compound (134 mg, 100% yield). MS (apci) m/z=445.1 (M+H).

Intermediate P199

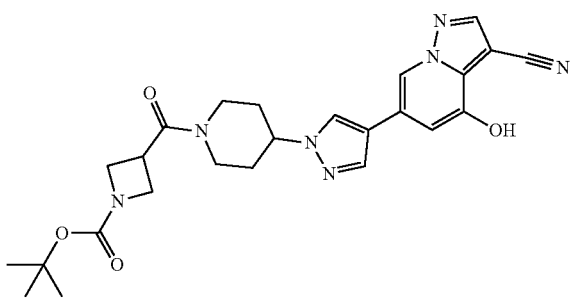 [SMILES: CC(C)(C)OC(=O)N1CC(C(=O)N2CCC(n3cc(-c4cc(O)c5c(C#N)cnn5c4)cn3)CC2)C1]

tert-butyl 3-(4-(4-(3-cyano-4-hydroxypyrazolo[1,5-a]pyridin-6-yl)-1H-pyrazol-1-yl)piperidine-1-carbonyl)azetidine-1-carboxylate A solution of 4-hydroxy-6-(1-(piperidin-4-yl)-1H-pyrazol-4-yl)pyrazolo[1,5-a]pyridine-3-carbonitrile dihydrochloride (Intermediate P33; 3.00 g, 7.87 mmol) in DCM (79 mL) was treated with 1-(tert-butoxycarbonyl)azetidine-3-carboxylic acid (1.74 g, 8.66 mmol), HATU (3.29 g, 8.66 mmol), and DIEA (6.85 mL, 39.3 mmol). The reaction mixture was stirred for 16 h at ambient temperature. The resulting mixture was concentrated in vacuo, and the residue was purified by silica chromatography (using 5-95% DCM-Acetone as gradient eluent) to provide the title compound (3.10 g, 80% yield). MS (apci) m/z=492.2 (M+H).

Intermediate P200

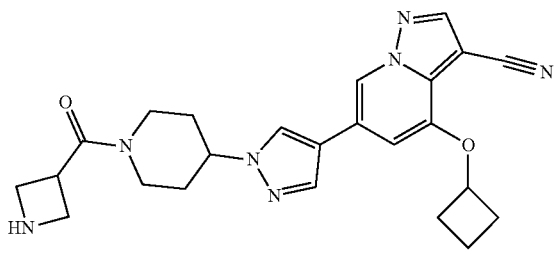 [SMILES: N#Cc1cnn2cc(-c3cnn(C4CCN(C(=O)C5CNC5)CC4)c3)cc(OC3CCC3)c12]

6-(1-(1-(azetidine-3-carbonyl)piperidin-4-yl)-1H-pyrazol-4-yl)-4-cyclobutoxypyrazolo[1,5-a]pyridine-3-carbonitrile Step 1: Preparation of tert-butyl 3-(4-(4-(3-cyano-4-cyclobutoxypyrazolo[1,5-a]pyridin-6-yl)-1H-pyrazol-1-yl)piperidine-1-carbonyl)azetidine-1-carboxylate. A mixture of tert-butyl 3-(4-(4-(3-cyano-4-hydroxypyrazolo[1,5-a]pyridin-6-yl)-1H-pyrazol-1-yl) piperidine-1-carbonyl)azetidine-1-carboxylate (Intermediate P199; 100 mg, 0.2034 mmol) and $K_2CO_{3(s)}$ (140.6 mg, 1.017 mmol) in DMF (2034 μL) was treated with cyclobutyl bromide (38.31 μL, 0.4069 mmol). The reaction mixture was stirred for 1 h at 50° C., after which it was cooled to ambient temperature and stirred overnight. The resulting mixture was diluted with water, and extracted with EtOAc (2×). The combined organic extracts were washed with brine (2×), dried over anhydrous $Na_2SO_{4(s)}$, filtered, and concentrated in vacuo to yield the title compound which was used in the next Step without purifications (111 mg, quantitative yield assumed). MS (apci) m/z=546.2 (M+H).

Step 2: Preparation of 6-(1-(1-(azetidine-3-carbonyl)piperidin-4-yl)-1H-pyrazol-4-yl)-4-cyclobutoxypyrazolo[1,5-a]pyridine-3-carbonitrile A solution of tert-butyl 3-(4-(4-(3-cyano-4-cyclobutoxypyrazolo[1,5-a]pyridin-6-yl)-1H-pyrazol-1-yl)piperidine-1-carbonyl)azetidine-1-carboxylate (step 1; 111 mg, 0.203 mmol) in 1:1 mix of DCM:TFA (0.8 mL) was stirred for 30 min at ambient temperature. The resulting mixture then was partitioned between 4:1 DCM:iPrOH and saturated $NaHCO_{3(aq)}$. The aqueous layer was extracted with 4:1 DCM:iPrOH. The combined organic extracts were washed successively with brine, dried over anhydrous $Na_2SO_{4(s)}$, filtered, and concentrated in vacuo to afford the title compound (27 mg, 30% yield). MS (apci) m/z=446.2 (M+H).

Intermediate P201

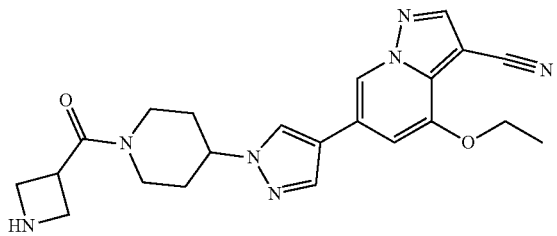 [SMILES: CCOc1cc(-c2cnn(C3CCN(C(=O)C4CNC4)CC3)c2)cn2ncc(C#N)c12]

6-(1-(1-(azetidine-3-carbonyl)piperidin-4-yl)-1H-pyrazol-4-yl)-4-ethoxypyrazolo[1,5-a]pyridine-3-carbonitrile Step 1: Preparation of tert-butyl 3-(4-(4-(3-cyano-4-ethoxypyrazolo[1,5-a]pyridin-6-yl)-1H-pyrazol-1-yl)piperidine-1-carbonyl)azetidine-1-carboxylate. A mixture of tert-butyl 3-(4-(4-(3-cyano-4-hydroxypyrazolo[1,5-a]pyridin-6-yl)-1H-pyrazol-1-yl) piperidine-1-carbonyl)azetidine-1-carboxylate (Intermediate P199; 100 mg, 0.203 mmol) and $K_2CO_{3(s)}$ (141 mg, 1.02 mmol) in DMF (2034 μL) was treated with EtI (32.7 μL, 0.407 mmol). The resulting mixture was stirred for 1 h at 50° C., after which it was cooled to room temperature. The resulting mixture was diluted with water and extracted with EtOAc (2×). The combined organic extracts were washed with brine (2×), dried over anhydrous $Na_2SO_{4(s)}$, filtered, and concentrated in vacuo to yield the title compound (84 mg, 80% yield) which was used in the next Step without purifications. MS (apci) m/z=520.2 (M+H).

Step 2: Preparation of 6-(1-(1-(azetidine-3-carbonyl)piperidin-4-yl)-1H-pyrazol-4-yl)-4-ethoxypyrazolo[1,5-a]pyridine-3-carbonitrile. A solution of tert-butyl 3-(4-(4-(3-cyano-4-ethoxypyrazolo[1,5-a]pyridin-6-yl)-1H-pyrazol-1-yl)piperidine-1-carbonyl)azetidine-1-carboxylate (step 1; 84 mg, 0.16 mmol) in 1:1 DCM:TFA (0.65 mL) was stirred for 30 min at room temperature. The resulting mixture was partitioned between 4:1 DCM:iPrOH and saturated $NaHCO_{3(aq)}$. The aqueous layer was extracted with 4:1 DCM:iPrOH. The combined organic extracts were washed successively with brine, dried over anhydrous $Na_2SO_{4(s)}$, filtered, and concentrated in vacuo to afford the title compound (68 mg, 100% yield). MS (apci) m/z=420.2 (M+H).

Intermediate P202

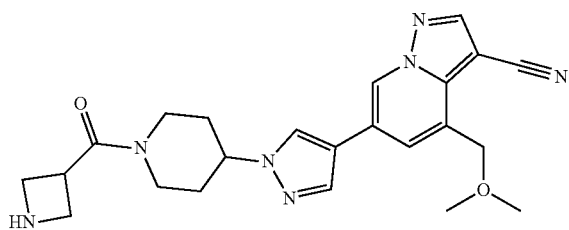

6-(1-(1-(azetidine-3-carbonyl)piperidin-4-yl)-1H-pyrazol-4-yl)-4-isopropoxypyrazolo[1,5-a]pyridine-3-carbonitrile Step 1: Preparation of tert-butyl 3-(4-(4-(3-cyano-4-isopropoxypyrazolo[1,5-a]pyridin-6-yl)-1H-pyrazol-1-yl)piperidine-1-carbonyl)azetidine-1-carboxylate. A solution of tert-butyl 3-(4-(4-(3-cyano-4-hydroxypyrazolo[1,5-a]pyridin-6-yl)-1H-pyrazol-1-yl) piperidine-1-carbonyl)azetidine-1-carboxylate (Intermediate P199; 100 mg, 0.203 mmol) and $K_2CO_{3(s)}$ (141 mg, 1.02 mmol) in DMF (2034 µL) was treated with 2-iodopropane (40.7 µL, 0.407 mmol). The reaction mixture was stirred for 3 h at 50° C., after which it was cooled to ambient temperature. The resulting mixture was diluted with water and extracted with EtOAc (2×). The combined organic extracts were washed with brine (2×), dried over anhydrous $Na_2SO_{4(s)}$, filtered, and concentrated in vacuo to yield the title compound (89 mg, 82% yield) which was used in the next Step without purifications. MS (apci) m/z=534.2 (M+H).

Step 2: Preparation of 6-(1-(1-(azetidine-3-carbonyl)piperidin-4-yl)-1H-pyrazol-4-yl)-4-isopropoxypyrazolo[1,5-a]pyridine-3-carbonitrile. A solution of tert-butyl 3-(4-(4-(3-cyano-4-isopropoxypyrazolo[1,5-a]pyridin-6-yl)-1H-pyrazol-1-yl)piperidine-1-carbonyl)azetidine-1-carboxylate (step 1; 89 mg, 0.17 mmol) in a 1:1 mix of DCM:TFA (0.67 µL) was stirred for 30 min at ambient temperature. The resulting mixture was partitioned between 4:1 DCM:iPrOH and saturated $NaHCO_{3(aq)}$. The aqueous layer was extracted with 4:1 DCM:iPrOH. The combined organic extracts were washed successively with brine, dried over anhydrous $Na_2SO_{4(s)}$, filtered, and concentrated in vacuo to afford the title compound (72 mg, 100% yield). MS (apci) m/z=434.2 (M+H).

Intermediate P203

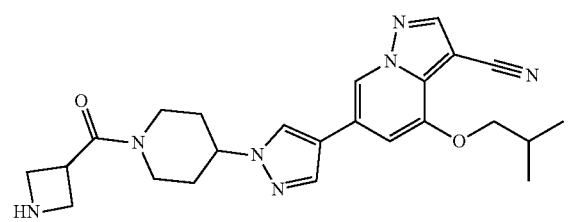 [SMILES: CC(C)COc1cc(-c2cnn(C3CCN(C(=O)C4CNC4)CC3)c2)cn2ncc(C#N)c12]

6-(1-(1-(azetidine-3-carbonyl)piperidin-4-yl)-1H-pyrazol-4-yl)-4-isobutoxypyrazolo[1,5-a]pyridine-3-carbonitrile Step 1: Preparation of tert-butyl 3-(4-(4-(3-cyano-4-isobutoxypyrazolo[1,5-a]pyridin-6-yl)-1H-pyrazol-1-yl)piperidine-1-carbonyl)azetidine-1-carboxylate. A mixture of tert-butyl 3-(4-(4-(3-cyano-4-hydroxypyrazolo[1,5-a]pyridin-6-yl)-1H-pyrazol-1-yl) piperidine-1-carbonyl)azetidine-1-carboxylate (Intermediate P199; 100 mg, 0.203 mmol) and $K_2CO_{3(s)}$ (140.6 mg, 1.017 mmol) in DMF (2034 µL) was treated with 1-iodo-2-methylpropane (46.83 µL, 0.4069 mmol), and stirred for 3 h at 50° C. After cooling to ambient temperature, the reaction mixture was diluted with water and extracted with EtOAc (2×). The combined organic extracts were washed with brine (2×), dried over anhydrous $Na_2SO_{4(s)}$, filtered, and concentrated in vacuo to afford the title compound (81 mg, 73% yield) which was used in the next Step without purifications. MS (apci) m/z=548.2 (M+H).

Step 2: Preparation of 6-(1-(1-(azetidine-3-carbonyl)piperidin-4-yl)-1H-pyrazol-4-yl)-4-isobutoxypyrazolo[1,5-a]pyridine-3-carbonitrile. A solution of tert-butyl 3-(4-(4-(3-cyano-4-isobutoxypyrazolo[1,5-a]pyridin-6-yl)-1H-pyrazol-1-yl)piperidine-1-carbonyl)azetidine-1-carboxylate (step 1; 81 mg, 0.15 mmol) in a 1:1 mix of DCM:TFA (0.6 mL) was stirred for 30 min at ambient temperature. The resulting mixture was partitioned between 4:1 DCM:iPrOH and saturated $NaHCO_{3(aq)}$. The aqueous layer was extracted with 4:1 DCM:iPrOH. The combined organic extracts were washed successively with brine, dried over anhydrous $Na_2SO_{4(s)}$, filtered, and concentrated in vacuo to afford the title compound (66 mg, 100% yield). MS (apci) m/z=448.2 (M+H).

Intermediate P204

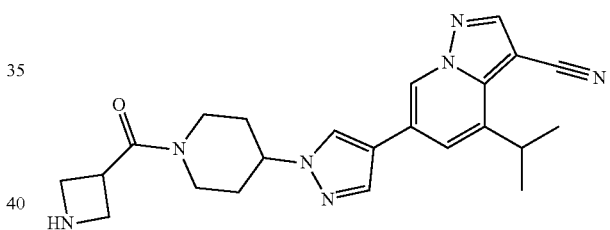

6-(1-(1-(azetidine-3-carbonyl)piperidin-4-yl)-1H-pyrazol-4-yl)-4-isopropylpyrazolo[1,5-a]pyridine-3-carbonitrile Step 1: Preparation of tert-butyl 3-(4-(4-(3-cyano-4-(((trifluoromethyl)sulfonyl)oxy)pyrazolo[1,5-a]pyridin-6-yl)-1Hpyrazol-1-yl)piperidine-1-carbonyl)azetidine-1-carboxylate. A solution of tert-butyl 3-(4-(4-(3-cyano-4-hydroxypyrazolo[1,5-a]pyridin-6-yl)-1H-pyrazol-1-yl) piperidine-1-carbonyl)azetidine-1-carboxylate (Intermediate P199; 1.60 g, 3.25 mmol) in DMA (33 mL, 0.1 M) was treated with DIEA (1.13 mL, 6.51 mmol), then cooled to 0° C. The resulting mixture was treated with $PhNTf_2$ (1.22 g, 3.42 mmol), and was stirred for 1.5 h at ambient temperature. Subsequently, the reaction mixture was diluted with water, and extracted with EtOAc (2×). The combined organic extracts were washed successively with water (3×) and brine (1×), dried over anhydrous $Na_2SO_{4(s)}$, filtered, and concentrated in vacuo to provide the title compound (2.03 g, 100% yield). MS (apci) m/z=624.1 (M+H).

Step 2: Preparation of tert-butyl 3-(4-(4-(3-cyano-4-(prop-1-en-2-yl)pyrazolo[1,5-a]pyridin-6-yl)-1H-pyrazol-1-yl)piperidine-1-carbonyl)azetidine-1-carboxylate. A suspension of tert-butyl 3-(4-(4-(3-cyano-4-(((trifluoromethyl)sulfonyl)oxy)pyrazolo[1,5-a]pyridin-6-yl)-1H-pyrazol-1-yl)piperidine-1-carbonyl)azetidine-1-carboxylate (step 1; 0.106 g, 0.170 mmol), potassium isopropenyltrifluoroborate (0.0377 g, 0.255 mmol), KOAc$_{(s)}$ (0.0500 g, 0.510 mmol) and Pd(PPh$_3$)$_4$ (0.0196 g, 0.0170 mmol) in 4:1 dioxanes-water (8 mL) was sparged with Ar$_{(g)}$ for 10 min. The reaction mixture then was stirred overnight at 90° C. under an atmosphere of Ar$_{(g)}$ (using an Ar$_{(g)}$ balloon). After cooling to ambient temperature, the reaction mixture was concentrated in vacuo, and the resulting residue was partition between EtOAc and water. The organic extracts were dried over anhydrous Na$_2$SO$_{4(s)}$, filtered, and concentrated in vacuo. The crude residue was purified by C18 reverse phase chromatography (using 5-95% MeCN-water with 0.1% TFA as gradient eluent) to afford the TFA salt of the title compound. The TFA salt was dissolved in 4:1 DCM:iPrOH and washed with saturated NaHCO$_{3(aq)}$. The organic extracts were dried over over anhydrous Na$_2$SO$_{4(s)}$, filtered, and concentrated in vacuo to afford the title compound (44 mg, 50% yield). MS (apci) m/z=516.2 (M+H).

Step 3: Preparation of tert-butyl 3-(4-(4-(3-cyano-4-isopropylpyrazolo[1,5-a]pyridin-6-yl)-1H-pyrazol-1-yl)piperidine-1-carbonyl)azetidine-1-carboxylate. A solution of tert-butyl 3-(4-(4-(3-cyano-4-(prop-1-en-2-yl)pyrazolo[1,5-a]pyridin-6-yl)-1H-pyrazol-1-yl)piperidine-1-carbonyl)azetidine-1-carboxylate (step 2; 0.044 g, 0.085 mmol) in EtOAc/MeOH (1:1, 8 mL) was treated with 10% Pd/C (0.0091 g, 0.0085 mmol). The reaction mixture was sparged with Ar$_{(g)}$ for 10 min, then evacuated and back filled with H$_{2(g)}$. The resulting mixture was stirred for 48 h at room temperature under an atmosphere of H$_{2(g)}$ (using a H$_{2(g)}$ balloon). Subsequently, the mixture was filtered through GF/F paper, and the filtrate was concentrated in vacuo to provide the title compound (44 mg, quantitative yield) which as used in the next Step without further purifications. MS (apci) m/z=518.2 (M+H).

Step 4: Preparation of 6-(1-(1-(azetidine-3-carbonyl)piperidin-4-yl)-1H-pyrazol-4-yl)-4-isopropylpyrazolo[1,5-a]pyridine-3-carbonitrile. A solution of tert-butyl 3-(4-(4-(3-cyano-4-isopropylpyrazolo[1,5-a]pyridin-6-yl)-1H-pyrazol-1-yl)piperidine-1-carbonyl)azetidine-1-carboxylate (step 3; 44 mg, 0.085 mmol) in DCM (4 mL) was treated with TFA (2 mL), and stirred for 30 min at room temperature. Subsequently, the reaction mixture was concentrated in vacuo. The resulting residue was purified by C18 reverse phase chromatography (using 5-95% MeCN-water with 0.1% TFA as gradient eluent) to afford the TFA salt of the title compound. The TFA salt was dissolved in 4:1 DCM:iPrOH and washed with saturated NaHCO$_{3(aq)}$, dried over anhydrous Na$_2$SO$_{4(s)}$, filtered, and concentrated in vacuo to afford the title compound (27 mg, 76% yield). MS (apci) m/z=418.2 (M+H).

Intermediate P205

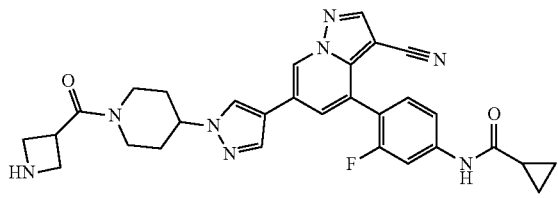 [SMILES: N#Cc1cnn2cc(-c3cnn(C4CCN(C(=O)C5CNC5)CC4)c3)cc(-c3ccc(NC(=O)C4CC4)cc3F)c12]

N-(4-(6-(1-(1-(azetidine-3-carbonyl)piperidin-4-yl)-1H-pyrazol-4-yl)-3-cyanopyrazolo[1,5-a]pyridin-4-yl)-3-fluorophenyl)cyclopropanecarboxamide Step 1: Preparation of tert-butyl 3-(4-(4-(3-cyano-4-(((trifluoromethyl)sulfonyl)oxy)pyrazolo[1,5-a]pyridin-6-yl)-1Hpyrazol-1-yl)piperidine-1-carbonyl)azetidine-1-carboxylate. A solution of tert-butyl 3-(4-(4-(3-cyano-4-hydroxypyrazolo[1,5-a]pyridin-6-yl)-1H-pyrazol-1-yl)piperidine-1-carbonyl)azetidine-1-carboxylate (Intermediate P199; 1.60 g, 3.25 mmol) in DMA (33 mL, 0.1 M) was treated with DIEA (1.13 mL, 6.51 mmol), then cooled to 0° C. The resulting mixture then was treated with PhNTf$_2$ (1.22 g, 3.42 mmol), and stirred for 1.5 h at ambient temperature. Subsequently, the reaction mixture was diluted with water and extracted with EtOAc (2×). The combined organic extracts were washed successively with water (3×) and brine (1×), dried over Na$_2$SO$_{4(s)}$, filtered, and concentrated in vacuo to provide the title compound (2.03 g, 100% yield). MS (apci) m/z=624.1 (M+H).

Step 2: Preparation of tert-butyl 3-(4-(4-(4-amino-2-fluorophenyl)-3-cyanopyrazolo[1,5-a]pyridin-6-yl)-1Hpyrazol-1-yl)piperidine-1-carbonyl)azetidine-1carboxylate.

A solution of tert-butyl 3-(4-(4-(3-cyano-4-(((trifluoromethyl)sulfonyl)oxy)pyrazolo[1,5-a]pyridin-6-yl)-1H-pyrazol-1-yl)piperidine-1-carbonyl)azetidine-1-carboxylate (step 1; 85.6 mg, 0.137 mmol) in 4:1 dioxane:water (1.4 mL) was treated with 4-amino-2-fluorophenylboronic acid pinacol ester (39.1 mg, 0.165 mmol), Pd(PPh$_3$)$_4$ (15.9 mg, 0.0137 mmol), and K$_2$CO$_{3(s)}$ (56.9 mg, 0.412 mmol). The reaction mixture was sparged with Ar$_{(g)}$, before sealing the reaction vessel. The resulting mixture was stirred for 16 h at 80° C. After cooling to room temperature, the reaction mixture was diluted with 4:1 DCM:iPrOH and washed with water (2×). The organic extracts were dried over anhydrous Na$_2$SO$_{4(s)}$, filtered, and concentrated in vacuo. The residue was purified by silica chromatography (using 5-95% DCM-Acetone as gradient eluent) to afford the title compound (50.4 mg, 63% yield). MS (apci) m/z=585.2 (M+H).

Step 3: Preparation of N-(4-(6-(1-(1-(azetidine-3-carbonyl)piperidin-4-yl)-1H-pyrazol-4-yl)-3-cyanopyrazolo[1,5-a]pyridin-4-yl)-3-fluorophenyl)cyclopropanecarboxamide. A solution of tert-butyl 3-(4-(4-(4-(4-amino-2-fluorophenyl)-3-cyanopyrazolo[1,5-a]pyridin-6-yl)-1H-pyrazol-1-yl)piperidine-1-carbonyl)azetidine-1-carboxylate (step 2; 50.4 mg, 0.0862 mmol) in DCM (0.9 mL) was treated sequentially with TEA (58.8 µL, 0.431 mmol) and cyclopropanecarbonyl chloride (15.7 µL, 0.172 mmol), then stirred at for 30 min at ambient temperature. Subsequently, the reaction mixture was treated with MeOH and concentrated in vacuo. The resulting residue was dissolved in 1:1 DCM:TFA (1.0 mL), and the solution was stirred for 15 min at ambient temperature. The reaction mixture was diluted with 4:1 DCM:iPrOH, washed with saturated NaHCO$_{3(aq)}$, dried over anhydrous Na$_2$SO$_{4(s)}$, filtered, and concentrated in vacuo to afford the title compound (assuming quantitative yield). MS (apci) m/z=553.3 (M+H).

Intermediate P206

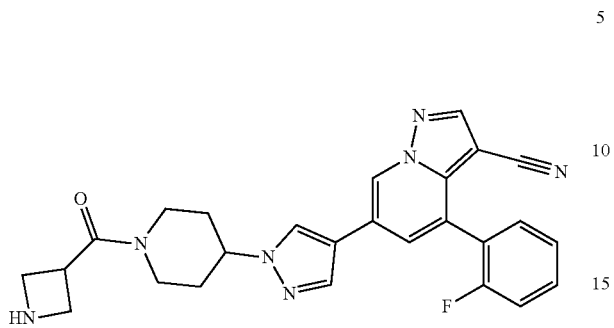

6-(1-(1-(azetidine-3-carbonyl)piperidin-4-yl)-1H-pyrazol-4-yl)-4-(2-fluorophenyl)pyrazolo[1,5-a]pyridine-3-carbonitrile Step 1: Preparation of tert-butyl 3-(4-(4-(3-cyano-4-(((trifluoromethyl)sulfonyl)oxy)pyrazolo[1,5-a]pyridin-6-yl)-1Hpyrazol-1-yl)piperidine-1-carbonyl)azetidine-1-carboxylate. A solution of tert-butyl 3-(4-(4-(3-cyano-4-hydroxypyrazolo[1,5-a]pyridin-6-yl)-1H-pyrazol-1-yl)piperidine-1-carbonyl)azetidine-1-carboxylate (Intermediate P199; 1.60 g, 3.25 mmol) in DMA (33 mL) was treated with DIEA (1.13 mL, 6.51 mmol), then cooled to 0° C. The resulting mixture then was treated with PhNTf$_2$ (1.22 g, 3.42 mmol), and stirred for 1.5 h at ambient temperature. Subsequently, the mixture was diluted with water, and extracted with EtOAc (2×). The combined organic extracts were washed successively with water (3×) and brine (1×), then dried over Na$_2$SO$_{4(s)}$, filtered, and concentrated in vacuo to provide the title compound (2.03 g, 100% yield). MS (apci) m/z=624.1 (M+H).

Step 2: Preparation of 6-(1-(1-(azetidine-3-carbonyl)piperidin-4-yl)-1H-pyrazol-4-yl)-4-(2-fluorophenyl)pyrazolo[1,5-a]pyridine-3-carbonitrile. A solution of tert-butyl 3-(4-(4-(3-cyano-4-(((trifluoromethyl)sulfonyl)oxy)pyrazolo[1,5-a]pyridin-6-yl)-1H-pyrazol-1-yl)piperidine-1-carbonyl)azetidine-1-carboxylate (98.9 mg, 0.159 mmol) in 4:1 dioxane:water (1.6 mL) was treated with 2-fluorophenyl boronic acid (24.4 mg, 0.174 mmol), Pd(PPh$_3$)$_4$ (18.3 mg, 0.0159 mmol), and KOAc$_{(s)}$ (46.7 mg, 0.476 mmol). The reaction mixture was sparged with Ar$_{(g)}$, before sealing the reaction vessel. The reaction mixture then was stirred for 16 h at 90° C. After cooling to room temperature, the resulting mixture was diluted with 4:1 DCM:iPrOH, washed with water (2×), dried over anhydrous Na$_2$SO$_{4(s)}$, filtered, and concentrated in vacuo. The resulting residue was dissolved in 1:1 DCM:TFA (2.0 mL), stirred for 15 min at ambient temperature, then concentrated in vacuo. The residue was purified by C18 reverse phase chromatography (using 5-95% water-ACN with 0.1% TFA as gradient eluent) to afford the TFA salt of the title compound. The TFA salt was dissolved in 4:1 DCM:iPrOH and washed with saturated NaHCO$_{3(aq)}$. The organic extracts were dried over anhydrous Na$_2$SO$_{4(s)}$, filtered, and concentrated in vacuo to afford the title compound (44.8 mg, 60% yield). MS (apci) m/z=470.2 (M+H).

Intermediate P207

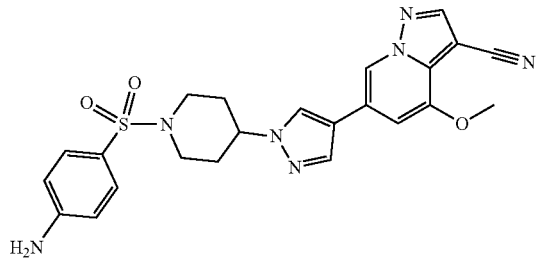 [SMILES: COc1cc(-c2cnn(C3CCN(S(=O)(=O)c4ccc(N)cc4)CC3)c2)cn2ncc(C#N)c12]

6-(1-(1-((4-aminophenyl)sulfonyl)piperidin-4-yl)-1H-pyrazol-4-yl)-4-methoxypyrazolo[1,5-a]pyridine-3-carbonitrile Step 1: Preparation of 4-methoxy-6-(1-(1-((4-nitrophenyl)sulfonyl)piperidin-4-yl)-1H-pyrazol-4-yl)pyrazolo[1,5-a]pyridine-3-carbonitrile. A solution of 4-methoxy-6-(1-(piperidin-4-yl)-1H-pyrazol-4-yl)pyrazolo[1,5-a]pyridine-3-carbonitrile (Intermediate P25; 105 mg, 0.326 mmol) and 4-nitrobenzenesulfonyl chloride (79.4 mg, 0.358 mmol) in DCM (6 mL) was treated with TEA (90.8 µL, 0.651 mmol), then stirred for 1 h at ambient temperature. The reaction mixture then was concentrated in vacuo. The crude solid was diluted with water, filtered and dried in vacuo to provide the title compound (145 mg, 88% yield), which was used without further purification in step 2.

Step 2: Preparation of 6-(1-(1-((4-aminophenyl)sulfonyl)piperidin-4-yl)-1H-pyrazol-4-yl)-4-methoxypyrazolo[1,5-a]pyridine-3-carbonitrile. A solution of 4-methoxy-6-(1-(1-((4-nitrophenyl)sulfonyl)piperidin-4-yl)-1H-pyrazol-4-yl)pyrazolo[1,5-a]pyridine-3-carbonitrile (Step 1; 145 mg, 0.286 mmol) in 1:1 EtOAc: MeOH (16 mL) was treated with 10% Pd/C (19.8 mg, 0.0186 mmol). The resulting mixture was sparged with Ar$_{(g)}$ for 10 min, evacuated then back filled with H$_{2(g)}$ at atmospheric pressure. The reaction mixture was stirred under a balloon of H$_{2(g)}$ overnight at ambient temperature, before filtering the mixture through Celite®. The filtrate was concentrated in vacuo, and the residue was purified by silica chromatography (using 50-100% EtOAc in Hexanes as the gradient eluent) to cleanly afford the title compound (17 mg, 13% yield). $^1$H NMR (400 MHz, d$^6$-DMSO) δ 8.83 (s, 1H), 8.50 (s, 1H), 8.46 (s, 1H), 8.07 (s, 1H), 7.37 (m, 2H), 7.25 (s, 1H), 6.63 (m, 2H), 6.04 (br s, 2H), 4.18 (m, 1H), 4.03 (s, 3H), 3.61 (m, 2H), 2.38 (m, 2H), 2.13 (m, 2H), 1.95 (m, 2H).

Intermediate P208

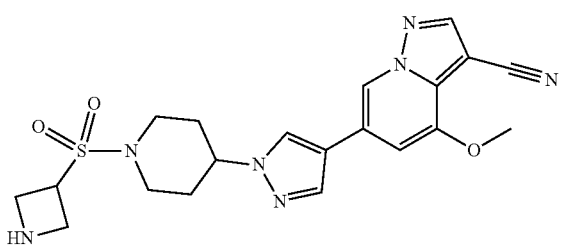 [SMILES: COc1cc(-c2cnn(C3CCN(S(=O)(=O)C4CNC4)CC3)c2)cn2ncc(C#N)c12]

6-(1-(1-(azetidin-3-ylsulfonyl)piperidin-4-yl)-1H-pyrazol-4-yl)-4-methoxypyrazolo[1,5-a]pyridine-3-carbonitrile Step 1: Preparation of tert-butyl 3-((4-(4-(3-cyano-4-methoxypyrazolo[1,5-a]pyridin-6-yl)-1H-pyrazol-1-yl)piperidin-1-yl)sulfonyl)azetidine-1-carboxylate. A solution of 4-methoxy-6-(1-(piperidin-4-yl)-1H-pyrazol-4-yl)pyrazolo[1,5-a]pyridine-3-carbonitrile (Intermediate P25; 80 mg, 0.25 mmol) in DCM (2.48 mL) was treated sequentially with TEA (173 µL, 1.24 mmol) and tert-butyl-3-(chlorosulfonyl)azetidine-1-carboxylate (76.1 mg, 0.298 mmol), then stirred overnight at ambient temperature. The reaction mixture then was concentrated in vacuo to provide the title compound in sufficient purity for use in Step 2 (134 mg, quantitative yield). MS (apci) m/z=542.1 (M+H).

Step 2: Preparation of 6-(1-(1-(azetidin-3-ylsulfonyl)piperidin-4-yl)-1H-pyrazol-4-yl)-4-methoxypyrazolo[1,5-a]pyridine-3-carbonitrile. A solution of tert-butyl 3-((4-(4-(3-cyano-4-methoxypyrazolo[1,5-a]pyridin-6-yl)-1H-pyrazol-1-yl)piperidin-1-yl)sulfonyl)azetidine-1-carboxylate (Step 1; 134 mg, 0.247 mmol) in 1:1 DCM:TFA (2 mL) was stirred for 30 min at ambient temperature. Subsequently, the reaction mixture was concentrated in vacuo. The crude residue was diluted with 4:1 DCM:iPrOH and saturated NaHCO₃ (aq). The organic extracts was washed with brine, dried over anhydrous Na₂SO₄(s), filtered, and concentrated in vacuo to cleanly afford the title compound (109 mg, quantitative yield). MS (apci) m/z=442.1 (M+H).

Reagents and Reagent Tables

Intermediate R1

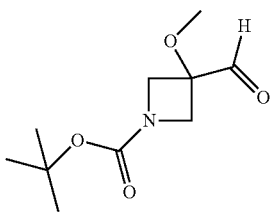

tert-butyl 3-formyl-3-methoxyazetidine-1-carboxylate

Step 1: Preparation of 1-(tert-butyl) 3-methyl 3-methoxyazetidine-1,3-dicarboxylate. A solution of 1-(tert-butyl) 3-methyl 3-hydroxyazetidine-1,3-dicarboxylate (2.04 g, 8.82 mmol) in DMF (30 mL) was treated sequentially with NaH (60 wt. % dispersion in mineral oil, 0.529 g, 13.2 mmol) and MeI (0.659 mL, 10.6 mmol), then stirred for 16 h at ambient temperature. The reaction mixture then was diluted with water and extracted with Et₂O (3×). The combined organic extracts were washed successively with water (3×) and brine (1×), dried over anhydrous Na₂SO₄(s), filtered, and concentrated in vacuo. The resulting residue was purified by silica chromatography (using 5-75% Hexanes-EtOAc as gradient eluent) to provide the title compound (1.07 g, 50% yield).

Step 2: Preparation of tert-butyl 3-(hydroxymethyl)-3-methoxyazetidine-1-carboxylate. A solution of 1-(tert-butyl) 3-methyl 3-methoxyazetidine-1,3-dicarboxylate (1.07 g, 4.362 mmol) in THF (44 mL) was treated LiBH₄ (0.3801 g, 17.45 mmol), and stirred for 1 h at room temperature. The resulting mixture was diluted with water and extracted with DCM (3×). The combined organic extracts were dried over anhydrous Na₂SO₄(s), filtered, and concentrated in vacuo to cleanly afford the title compound (755.0 mg, 80% yield).

Step 3: Preparation of tert-butyl 3-formyl-3-methoxyazetidine-1-carboxylate. A cold (−78° C.) solution of DMSO (987.3 µL, 13.90 mmol) in DCM (35 mL) was treated with oxalyl chloride (882.1 µL, 10.43 mmol). After stirring for 15 min at −78° C., the resulting mixture was treated with tert-butyl 3-(hydroxymethyl)-3-methoxyazetidine-1-carboxylate (755.0 mg, 3.475 mmol), stirred for an additional 15 min at −78° C., then treated with TEA (2906 µL, 20.85 mmol). Subsequently, the reaction mixture was stirred for 1 h at ambient temperature. The mixture then was diluted with additional DCM, and washed with water (2×). The organic extracts were dried over anhydrous Na₂SO₄(s), filtered, and concentrated in vacuo to provide cleanly the title compound (748.0 mg, quantitative yield).

Intermediate R2

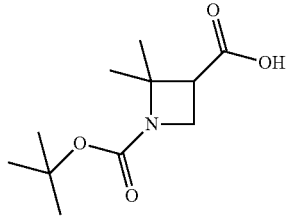 [SMILES: CC(C)(C)OC(=O)N1CC(C(=O)O)C1(C)C]

1-(tert-butoxycarbonyl)-2,2-dimethylazetidine-3-carboxylic Acid

Step 1: Preparation of 3-(benzhydrylamino)-3-methylbutan-2-one. A solution of benzhydrylamine (38.01 mL, 220.5 mmol) in MeOH (550 mL) was treated sequentially with TEA (74.76 mL, 551.1 mmol) and 3-bromo-3-methyl-2-butanone (67.37 mL, 551.1 mmol). The reaction mixture was stirred for 3 d at 70° C., after which it was cooled to ambient temperature and concentrated in vacuo. The resulting residue was diluted with DCM, washed with water (2×), dried over anhydrous Na₂SO₄(s), filtered, and concentrated in vacuo. The residue was purified by silica chromatography (using 5-75% Hexanes-MTBE as gradient eluent) to afford the title compound (34.6 g, 59% yield).

Step 2: Preparation of 3-(benzhydrylamino)-1-bromo-3-methylbutan-2-one. A cold solution of 3-(Benzhydrylamino)-3-methylbutan-2-one (Step 1; 34.6 g, 129 mmol) in 3:1 AcOH:conc. HCl (175 mL) was treated dropwise with bromine (6.65 mL, 129 mmol). The resulting mixture was stirred for 16 h at ambient temperature. After cooling to 0° C., the reaction mixture was quenched slowly with 10 M NaOH (300 mL) until the final pH was approximately 7. The resulting mixture was diluted with CHCl₃ and stirred for 15 min. The quenched mixture then was diluted with water and extracted with CHCl₃ (2×). The combined organic extracts were dried over anhydrous Na₂SO₄(s), filtered, and concentrated in vacuo to afford the title compound (14.4 g, 32% yield) which was used without further purification.

Step 3: Preparation of 1-benzhydryl-2,2-dimethylazetidin-3-one. 3-(Benzhydrylamino)-1-bromo-3-methylbutan- 2-one (Step 2; 14.2 g, 41.0 mmol) was dissolved in DMF (410 mL, 0.1 M), and the solution was treated with potassium carbonate (17.0 g, 123 mmol). The reaction was heated to 60° C. overnight (16 hrs), after which it was cooled to room temperature, diluted with water, and extracted with EtOAc. The combined organic extracts were washed successively with water (3×) and brine (1×), dried over anhydrous $Na_2SO_{4(s)}$, filtered, and concentrated to afford the title compound which was used in the next Step without further purification (10.9 g, quantitative yield). MS (apci) m/z=266.1 (M+H).

Step 4: Preparation of 1-benzhydryl-2,2-dimethylazetidin-3-ol. A solution of 1-benzhydryl-2,2-dimethylazetidin-3-one (Step 3; 10.9 g, 41.1 mmol) in MeOH (410 mL, 0.1 M) was treated with $NaBH_4$ (reagent grade, 98%, powder, 10.9 g, 288 mmol). The reaction mixture was stirred for 1 h at 70° C. After cooling to 0° C., the reaction mixture was treated with water. The resulting mixture was concentrated to remove most of the organic solvent, after which it was diluted with additional water and extracted with DCM (3×). The combined organic extracts were washed with water (1×), dried over anhydrous $Na_2SO_{4(s)}$, filtered, and concentrated in vacuo to afford the title compound (11.0 g, quantitative yield), which was used in the next Step without further purification.

Step 5: Preparation of 1-benzhydryl-2,2-dimethylazetidin-3-yl methanesulfonate. A cold (0° C.) solution of 1-benzhydryl-2,2-dimethylazetidin-3-ol (Step 4; 11.0 g, 41.1 mmol) in DCM (200 mL) was treated sequentially with TEA (11.2 mL, 82.3 mmol) and MSCl (3.82 mL, 49.4 mmol). The reaction was stirred for 1 h at 0° C. The reaction mixture then was diluted with additional DCM, washed with saturated $NaHCO_{3(aq)}$ (1×), dried over anhydrous $Na_2SO_{4(s)}$, filtered, and concentrated in vacuo to provide the title compound (14.2 g, quantitative yield).

Step 6: Preparation of 1-benzhydryl-2,2-dimethylazetidine-3-carbonitrile. A solution of 1-benzhydryl-2,2-dimethylazetidin-3-yl methanesulfonate (Step 5; 14.2 g, 41.1 mmol) in DMSO (165 mL, 0.25 M) was treated with KCN (4.01 g, 61.7 mmol). The mixture was stirred for 24 h and then cooled to ambient temperature. The resulting mixture was diluted with water, and extracted with EtOAc (3×). The combined organic extracts were washed successively with water (3×) and brine (1×), dried over anhydrous $Na_2SO_{4(s)}$, filtered, and concentrated in vacuo. The resulting residue was purified by silica chromatography (using 5-70% Hexanes-MTBE as gradient eluent) to provide the title compound (6.1 g, 54% yield).

Step 7: Preparation of potassium 1-benzhydryl-2,2-dimethylazetidine-3-carboxylate. A solution of 1-benzhydryl-2,2-dimethylazetidine-3-carbonitrile (Step 6; 6.1 g, 22.1 mmol) in EtOH (220 mL) was treated with 2 M $KOH_{(aq)}$ (110 mL, 221 mmol). The reaction mixture was stirred for 120 h at 85° C. After cooling to ambient temperature, the reaction mixture was concentrated in vacuo to provide the title compound (7.36 g, quantitative yield assumed), which as used in the next Step without further purification. MS (apci) m/z=296.2 (M+H, free acid).

Step 8: Preparation of methyl 1-benzhydryl-2,2-dimethylazetidine-3-carboxylate. A solution of potassium 1-benzhydryl-2,2-dimethylazetidine-3-carboxylate (Step 7; 7.36 g, 22.1 mmol) in DMF (88 mL) was treated sequentially with $K_2CO_{3(s)}$ (6.10 g, 44.1 mmol) and MeI (2.75 mL, 44.1 mmol), then stirred for 1 h at ambient temperature. The resulting mixture then was diluted with water, and extracted with EtOAc (2×). The combined organic extracts were washed with water (3×) and brine (1×), dried over anhydrous $Na_2SO_{4(s)}$, filtered, and concentrated in vacuo. The resulting residue was purified by silica chromatography (using 5-75% Hexanes-EtOAc as gradient eluent) to cleanly afford the title compound (4.20 g, 62% yield). MS (apci) m/z=310.1 (M+H).

Step 9: Preparation of 1-(tert-butyl) 3-methyl 2,2-dimethylazetidine-1,3-dicarboxylate. A solution of methyl 1-benzhydryl-2,2-dimethylazetidine-3-carboxylate (Step 8; 4.20 g, 13.6 mmol) in EtOAc (140 mL, 0.1 M) was treated with di-tert-butyl dicarbonate (3.56 g, 16.3 mmol) and palladium hydroxide (1.91 g, 1.36 mmol), then sequentially sparged with $N_{2(g)}$ for several min and with $H_{2(g)}$ for several additional min. The resulting mixture was stirred for 16 h at ambient temperature under an atmosphere of $H_{2(g)}$ (using a $H_{2(g)}$ balloon). The reaction then was filtered and concentrated in vacuo. The resulting residue was purified by silica chromatography (using 5-75% Hexanes-EtOAc as gradient eluent) to afford the title compound (2.96 g, 90% yield).

Step 10: Preparation of 1-(tert-butoxycarbonyl)-2,2-dimethylazetidine-3-carboxylic acid. A solution of 1-(tert-butyl) 3-methyl 2,2-dimethylazetidine-1,3-dicarboxylate (Step 9; 993.0 mg, 4.081 mmol) in MeOH (41 mL) was treated with 2 M $KOH_{(aq)}$ (6122 μL, 12.24 mmol), then stirred for 2 h at room temperature. The reaction mixture then was diluted with $Et_2O$ and washed with 1.0 M $NaOH_{(aq)}$ (2×).

The combined aqueous layers were then acidified to pH~4 using 2.0 M $HCl_{(aq)}$. The acidified aqueous layers then were extracted with 4:1 DCM:iPrOH (2×). The combined DCM:iPrOH extracts were dried over anhydrous $Na_2SO_{4(s)}$, filtered, and concentrated in vacuo to afford the title compound (889.8 mg, 95% yield). $^1H$ NMR (400 MHz, $d^6$-DMSO) δ 12.60 (br s, 1H), 3.71 (m, 2H), 3.03 (m, 1H), 1.42 (s, 3H), 1.30 (s, 9H), 1.23 (s, 3H).

Intermediate R3

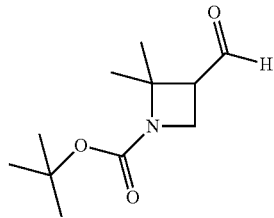

tert-butyl
3-formyl-2,2-dimethylazetidine-1-carboxylate

Step 1: Preparation of tert-butyl 3-(hydroxymethyl)-2,2-dimethylazetidine-1-carboxylate. A solution of 1-(tert-butyl) 3-methyl 2,2-dimethylazetidine-1,3-dicarboxylate (Step 9, Intermediate R2; 1.97 g, 8.10 mmol) in THF (76 mL) was treated with $LiBH_{4(s)}$ (882 mg, 40.5 mmol) then stirred for 1 h at 60° C. After cooling to ambient temperature, the reaction mixture was diluted with water and extracted with DCM (3×). The combined organic extracts were dried over anhydrous $Na_2SO_{4(s)}$, filtered, and concentrated in vacuo to cleanly provide the title compound (1.71 g, 98% yield).

Step 2: Preparation of tert-butyl 3-formyl-2,2-dimethylazetidine-1-carboxylate. A cold (−78° C.) solution of DMSO (2.26 mL, 31.8 mmol) in DCM (79 mL) was treated with oxalyl chloride (2.02 mL, 23.8 mmol). After stirring for 15 min at −78° C., the reaction mixture was treated with tert-butyl 3-(hydroxymethyl)-2,2-dimethylazetidine-1-carboxylate (Step 1; 1.71 g, 7.94 mmol). The reaction mixture was stirred for an additional 15 min at −78° C., then treated with TEA (6.64 ml, 47.7 mmol). The resulting mixture was stirred for 1 h at ambient temperature. Subsequently, the reaction mixture was diluted with DCM and washed with water (2×). The organic extracts were dried over anhydrous Na$_2$SO$_{4(s)}$, filtered, and concentrated in vacuo. The crude residue then was purified by silica chromatography (using 5-95% Hexanes-EtOAc as the gradient eluent) to afford the title compound (1.59 g, 94% yield).

Intermediate R4

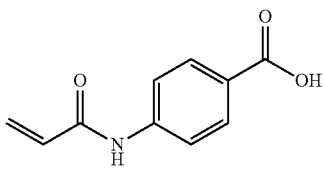

4-acrylamidobenzoic acid

Step 1: Preparation of tert-butyl 4-acrylamidobenzoate. A cold (0° C.) solution of tert-butyl 4-aminobenzoate (5.0 g, 25.87 mmol) and DIEA (9.038 mL, 51.75 mmol) in DCM (4 mL) was slowly treated with acryloyl chloride (2.102 mL, 25.87 mmol). The resulting mixture was stirred at ambient temperature until LCMS indicated complete consumption of the aminobenzoate. Subsequently, the reaction mixture was washed with brine (3×). The organic extracts were concentrated in vacuo, and the crude residue was purified by silica chromatography (using 0-100% Hexanes-EtOAc as the eluent) to cleanly afford the title compound (6.3 g, 98% yield).

Step 2: Preparation of 4-acrylamidobenzoic acid. A solution tert-butyl 4-acrylamidobenzoate (Step 1; 6.3 g, 25 mmol) in DCM (1.66 mL) was treated with TFA (2.0 mL, 25 mmol), then stirred 3 days at ambient temperature. Subsequently, the reaction mixture was concentrated in vacuo to afford the title compound (4.8 g, 99% yield).

Intermediate R5

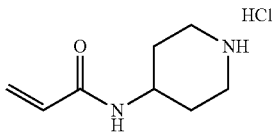

N-(piperidin-4-yl)acrylamide hydrochloride

Step 1: Preparation of tert-butyl 4-acrylamidopiperidine-1-carboxylate. A cold (0° C.) solution of 4-Amino-1-N-Boc-piperidine (510 mg, 2.55 mmol) in DCM (10 mL) treated sequentially with acryloyl chloride (220 μL, 2.67 mmol) and DIEA (489 μL, 2.80 mmol). After stirring for 3 h at ambient temperature, the reaction mixture was diluted with DCM (50 mL) and washed with water (50 mL). The organic extracts were dried over anhydrous MgSO$_{4(s)}$, filtered, and concentrated in vacuo to afford the title compound (585 mg, 90% yield).

Step 2: Preparation of N-(piperidin-4-yl)acrylamide hydrochloride. A solution tert-butyl 4-acrylamidopiperidine-1-carboxylate (Step 1; 483 mg, 1.90 mmol) in DCM (5 mL) was treated with TFA (3.0 mL, 37.5 mmol). After stirring for 4 h at ambient temperature, the reacting mixture was concentrated in vacuo. The residue then was dissolved in a mixture of 2:3 DCM: Dioxane (5 mL), treated dropwise with 4 N HCl$_{(aq)}$ (2 mL) and stirred for 1 h at ambient temperature. Subsequently, the reaction mixture was concentrated, azeotroping with toluene, and dried in vacuo for 12 h to afford the title compound (280 mg, 96% yield).

Intermediate R6

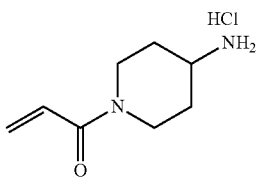

1-(4-aminopiperidin-1-yl)prop-2-en-1-one hydrochloride

The title compound (300 mg, 83% yield) was prepared, worked-up and purified using a similar 2 Step procedure to that described for the synthesis of N-(piperidin-4-yl)acrylamide hydrochloride (Intermediate R5), in Step 1 replacing the 4-amino-1-N-Boc-piperidine in Step 1 with 4-(N-Boc-amino)-piperidine and in Step 2 sonicating the HCl solution for 20 min in addition to stirring for 2 h at ambient temperature.

Intermediate R7

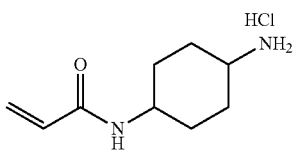

N-(4-aminocyclohexyl)acrylamide hydrochloride

The title compound (478 mg, 100% yield) was prepared, worked-up and purified using a similar 2 Step procedure to that described for the synthesis of N-(piperidin-4-yl)acrylamide hydrochloride (Intermediate R5), in Step 1 replacing the 4-Amino-1-N-Boc-piperidine in Step 1 with tert-butyl (4-aminocyclohexyl)carbamate and intermediate tert-butyl (4-acrylamidocyclohexyl)carbamate was isolated after trituration with Hexanes.

TABLE CA¹i

| CAS # | Structure | Chemical Name |
|---|---|---|
| 877399-74-1 | 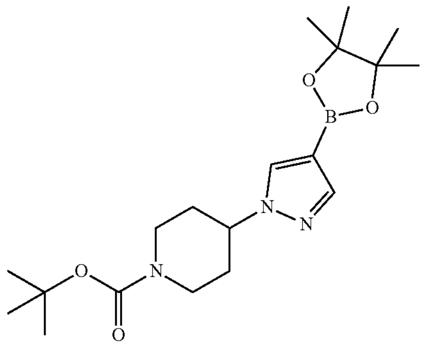 [SMILES: CC(C)(C)OC(=O)N1CCC(n2cc(B3OC(C)(C)C(C)(C)O3)cn2)CC1] | tert-Butyl 4-[4-(4,4,5,5-tetramethyl-1,3,2-dioxaborolan-2-yl)-1H-pyrazol-1-yl]piperidine-1-carboxylate |
| 99768-12-4 | 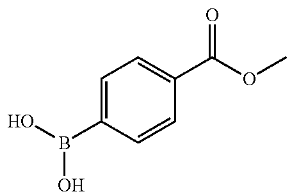 | (4-(methoxycarbonyl)phenyl)boronic acid |
| 470478-90-1 | 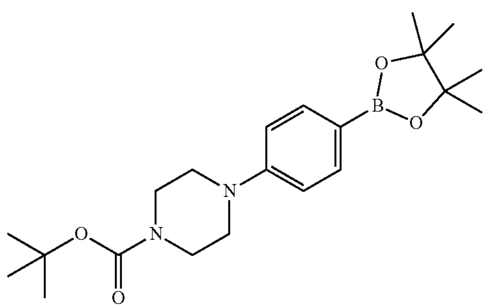 [SMILES: CC(C)(C)OC(=O)N1CCN(c2ccc(B3OC(C)(C)C(C)(C)O3)cc2)CC1] | Tert-butyl 4-(4-(4,4,5,5-tetramethyl-1,3,2-dioxaborolan-2-yl)phenyl)piperazine-1-carboxylate |
| 496786-98-2 | 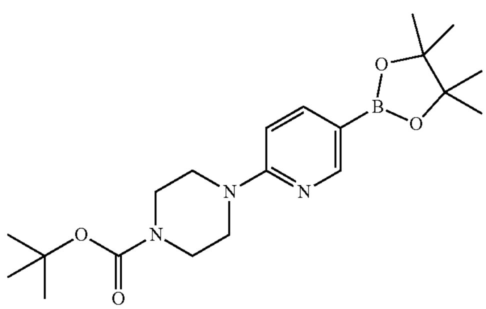 [SMILES: CC(C)(C)OC(=O)N1CCN(c2ccc(B3OC(C)(C)C(C)(C)O3)cn2)CC1] | Tert-butyl 4-(5-(4,4,5,5-tetramethyl-1,3,2-dioxaborolan-2-yl)pyridin-2-yl)piperazine-1-carboxylate |
| 1073354-54-7 | 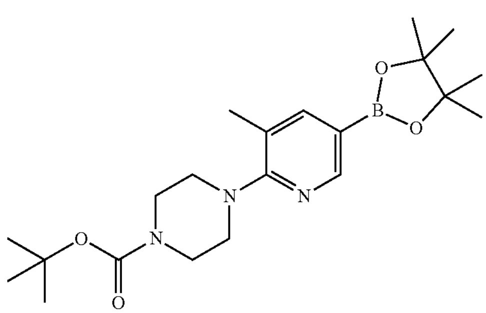 [SMILES: Cc1cc(B2OC(C)(C)C(C)(C)O2)cnc1N1CCN(C(=O)OC(C)(C)C)CC1] | Tert-Butyl 4-(3-methyl-5-(4,4,5,5-tetramethyl-1,3,2-dioxaborolan-2-yl)pyridin-2-yl)piperazine-1-carboxylate |

TABLE CA¹i-continued

| CAS # | Structure | Chemical Name |
|---|---|---|
| 940284-98-0 | 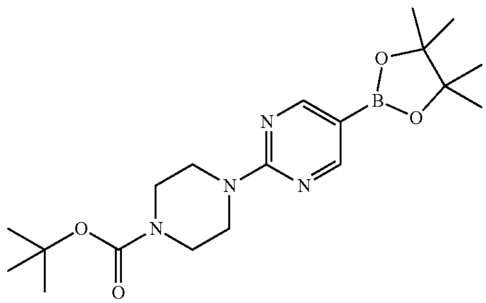 [SMILES: CC(C)(C)OC(=O)N1CCN(c2ncc(B3OC(C)(C)C(C)(C)O3)cn2)CC1] | 2-[4-(N-Boc)piperazin-1-yl]pyrimidine-5-boronic acid pinacol ester |
| 1401697-47-9 | 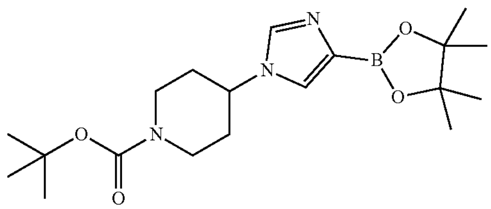 [SMILES: CC(C)(C)OC(=O)N1CCC(n2cnc(B3OC(C)(C)C(C)(C)O3)c2)CC1] | tert-butyl 4-(4-(4,4,5,5-tetramethyl-1,3,2-dioxaborolan-2-yl)-1H-imidazol-1-yl)piperidine-1-carboxylate |
| 877399-35-4 | 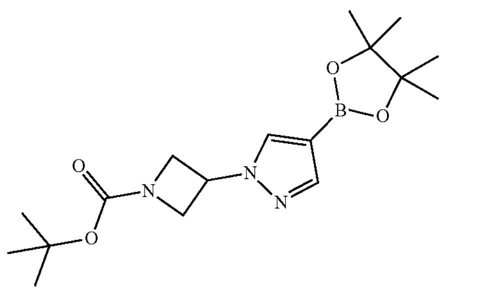 [SMILES: CC(C)(C)OC(=O)N1CC(n2cc(B3OC(C)(C)C(C)(C)O3)cn2)C1] | tert-butyl 3-(4-(4,4,5,5-tetramethyl-1,3,2-dioxaborolan-2-yl)-1H-pyrazol-1-yl)azetidine-1-carboxylate |

TABLE CA²i

| CAS #/ Intermediate # | Structure | Chemical Name |
|---|---|---|
| P18 | 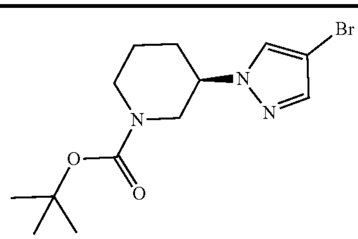 | tert-butyl (R)-3-(4-bromo-1H-pyrazol-1-yl)piperidine-1-carboxylate |
| P9 | 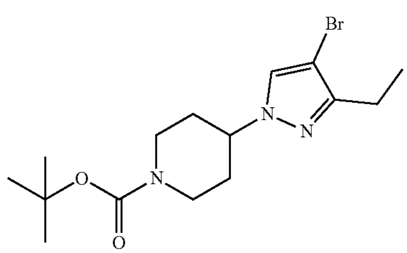 [SMILES: CCc1nn(C2CCN(C(=O)OC(C)(C)C)CC2)cc1Br] | tert-butyl 4-(4-bromo-3-ethyl-1H-pyrazol-1-yl)piperidine-1-carboxylate |

TABLE CA²i-continued

| CAS #/ Intermediate # | Structure | Chemical Name |
|---|---|---|
| P12 | 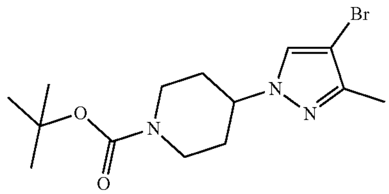 [SMILES: Cc1nn(C2CCN(C(=O)OC(C)(C)C)CC2)cc1Br] | tert-butyl 4-(4-bromo-3-methyl-1H-pyrazol-1-yl)piperidine-1-carboxylate |
| 492431-11-5 | 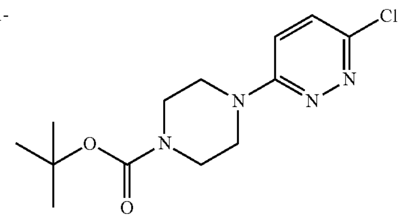 | tert-butyl 4-(6-chloropyridazin-3-yl)piperazine-1-carboxylate |
| P21 | 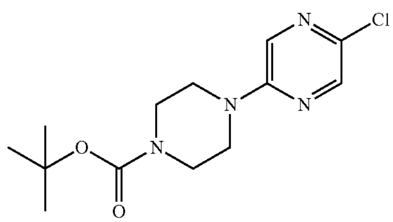 [SMILES: CC(C)(C)OC(=O)N1CCN(c2cnc(Cl)cn2)CC1] | tert-butyl 4-(5-chloropyrazin-2-yl)piperazine-1-carboxylate |
| 769944-78-7 | 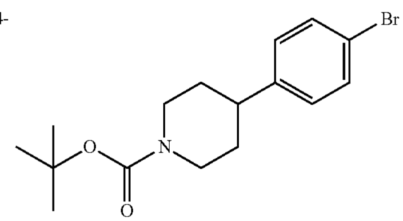 | 1-Boc-4-(4-Bromo-phenyl)-piperidine |
| P10 | 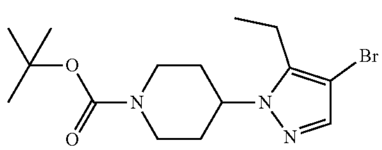 [SMILES: CCc1c(Br)cnn1C1CCN(C(=O)OC(C)(C)C)CC1] | tert-butyl 4-(4-bromo-5-ethyl-1H-pyrazol-1-yl)piperidine-1-carboxylate |
| P14 | 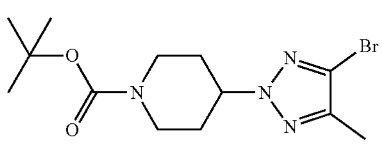 [SMILES: Cc1nn(C2CCN(C(=O)OC(C)(C)C)CC2)nc1Br] | tert-butyl 4-(4-bromo-5-methyl-2H-1,2,3-triazol-2-yl)piperidine-1-carboxylate |
| P15 | 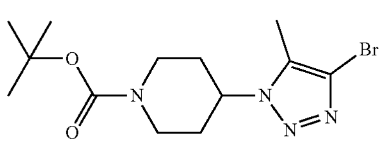 [SMILES: Cc1c(Br)nnn1C1CCN(C(=O)OC(C)(C)C)CC1] | tert-butyl 4-(4-bromo-5-methyl-1H-1,2,3-triazol-1-yl)piperidine-1-carboxylate |
| P16 | 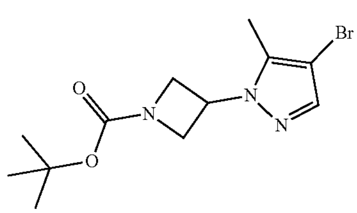 [SMILES: Cc1c(Br)cnn1C1CN(C(=O)OC(C)(C)C)C1] | tert-butyl 3-(4-bromo-5-methyl-1H-pyrazol-1-yl)azetidine-1-carboxylate |

TABLE CA²i-continued

| CAS #/ Intermediate # | Structure | Chemical Name |
|---|---|---|
| P13 | 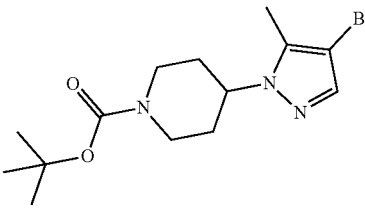 | tert-butyl 4-(4-bromo-5-methyl-1H-pyrazol-1-yl)piperidine-1-carboxylate |
| P22 | 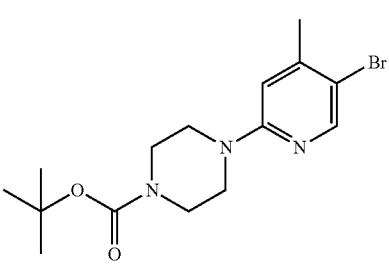 [SMILES: Cc1cc(N2CCN(C(=O)OC(C)(C)C)CC2)ncc1Br] | tert-butyl 4-(5-bromo-4-methylpyridin-2-yl)piperazine-1-carboxylate |
| P17 | 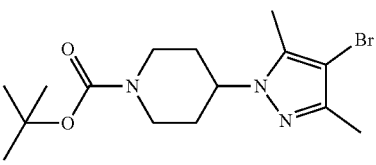 [SMILES: Cc1nn(C2CCN(C(=O)OC(C)(C)C)CC2)c(C)c1Br] | tert-butyl 4-(4-bromo-3,5-dimethyl-1H-pyrazol-1-yl)piperidine-1-carboxylate |
| P20 | 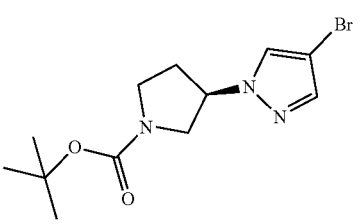 [SMILES: CC(C)(C)OC(=O)N1CC[C@@H](n2cc(Br)cn2)C1] | tert-butyl (R)-3-(4-bromo-1H-pyrazol-1-yl)pyrrolidine-1-carboxylate |
| P19 | 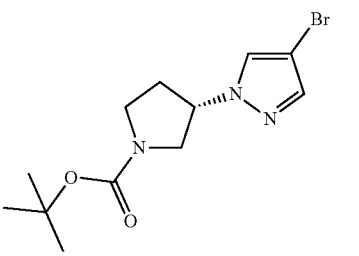 [SMILES: CC(C)(C)OC(=O)N1CC[C@H](n2cc(Br)cn2)C1] | tert-butyl (S)-3-(4-bromo-1H-pyrazol-1-yl)pyrrolidine-1-carboxylate |
| 352437-09-3 | 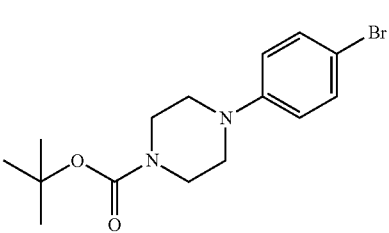 [SMILES: CC(C)(C)OC(=O)N1CCN(c2ccc(Br)cc2)CC1] | 1-Boc-4-(4-Bromophenyl)piperazine |

TABLE CA²i-continued

| CAS #/ Intermediate # | Structure | Chemical Name |
|---|---|---|
| P23 | 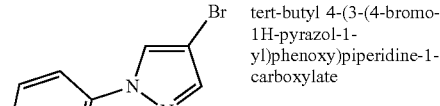 | tert-butyl 4-(3-(4-bromo-1H-pyrazol-1-yl)phenoxy)piperidine-1-carboxylate |
| P24 | 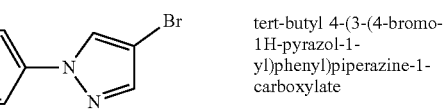 | tert-butyl 4-(3-(4-bromo-1H-pyrazol-1-yl)phenyl)piperazine-1-carboxylate |
| P11 | 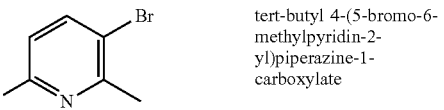 | tert-butyl 4-(5-bromo-6-methylpyridin-2-yl)piperazine-1-carboxylate |

TABLE CBi

SNAR COUPLING PARTNERS

| CAS #/ Intermediate # | Structure | Chemical Name |
|---|---|---|
| 149771-44-8 | 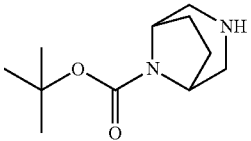 | tert-butyl 3,8-diazabicyclo[3.2.1]octane-8-carboxylate |
| 201162-53-0 | 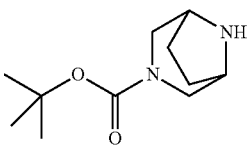 | tert-butyl 3,8-diazabicyclo[3.2.1]octane-3-carboxylate |
| 1251017-66-9 | 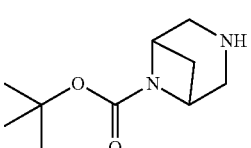 | Tert-butyl 3,6-diazabicyclo[3.1.1]heptane-3-carboxylate |
| 113451-59-5 | 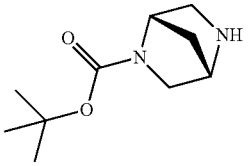 | tert-butyl (1S,4S)-2,5-diazabicyclo[2.2.1]heptane-2-carboxylate |
| 134003-84-2 | 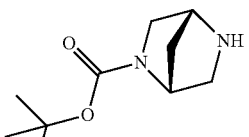 | (1R,4R)-2,5-diazabicyclo[2.2.1]heptane-2-carboxylic acid tert-butyl ester |

TABLE CBi-continued
SNAR COUPLING PARTNERS

| CAS #/Intermediate # | Chemical Name |
|---|---|
| 869494-16-6 | tert-Butyl 3,6-diazabicyclo[3.1.1]heptane-6-carboxylate |
| 896464-16-7 | tert-butyl 2,7-diazaspiro[3.5]nonane-7-carboxylate |
| 885270-86-0 | Tert-butyl 2,6-diazaspiro[3.4]octane-6-carboxylate |
| 1041026-70-3 | tert-butyl 2,6-diazaspiro[3.3]heptane-2-carboxylate |

TABLE CCi
UREA COUPLING PARTNERS

| CAS # | Chemical Name |
|---|---|
| 869494-16-6 | tert-Butyl 3,6-diazabicyclo[3.1.1]heptane-6-carboxylate |
| 799279-81-5 | tert-butyl (1R,5S)-3,6-diazabicyclo[3.2.0]heptane-6-carboxylate |
| 1251010-45-3 | tert-butyl 3-oxa-7,9-diazabicyclo[3.3.1]nonane-9-carboxylate |
| 236406-55-6 | tert-butyl 2,7-diazaspiro[3.5]nonane-2-carboxylate |
| 885270-84-8 | tert-butyl 2,6-diazaspiro[3.4]octane-2-carboxylate |

TABLE CCi-continued
UREA COUPLING PARTNERS

| CAS # | Chemical Name |
|---|---|
| 57260-71-6 | tert-butyl piperazine-1-carboxylate |
| 1251017-66-9 | Tert-butyl 3,6-diazabicyclo[3.1.1]heptane-3-carboxylate |
| 134003-84-2 | (1R,4R)-2,5-diazabicyclo[2.2.1]heptane-2-carboxylic acid tert-butyl ester |

TABLE CDi
REDUCTIVE AMINATION COUPLING PARTNERS

| CAS #/Intermediate # | Chemical Name |
|---|---|
| 177947-96-5 | tert-butyl 3-formylazetidine-1-carboxylate |
| 144072-30-0 | tert-butyl (4-formylphenyl)carbamate |
| 1205748-94-2 | tert-butyl 3-formyl-3-methylazetidine-1-carboxylate |
| R1 | tert-butyl 3-formyl-3-methoxyazetidine-1-carboxylate |
| R3 | tert-butyl 3-formyl-2,2-dimethylazetidine-1-carboxylate |

TABLE CEi

| AMIDATION (HATU/ACID) COUPLING PARTNERS | | |
|---|---|---|
| CAS #/ Intermediate # | Structure | Chemical Name |
| 84358-13-4 | | 1-(tert-butoxycarbonyl)piperidine-4-carboxylic acid |
| 53292-90-3 | | (1s,4s)-4-((tert-butoxycarbonyl)amino)cyclohexane-1-carboxylic acid |
| 53292-89-0 | | (1r,4r)-4-((tert-butoxycarbonyl)amino)cyclohexane-1-carboxylic acid |
| 614731-04-3 | | 1-(tert-butoxycarbonyl)-4-fluoropiperidine-4-carboxylic acid |
| 495415-34-4 | | 1-(tert-butoxycarbonyl)-4-cyanopiperidine-4-carboxylic acid |
| 1303972-81-7 | | 1-(tert-butoxycarbonyl)-3,3-difluoropiperidine-4-carboxylic acid |
| 88495-54-9 | | (S)-1-(tert-butoxycarbonyl)piperidine-3-carboxylic acid |
| 163438-09-3 | | (R)-1-(tert-butoxycarbonyl)piperidine-3-carboxylic acid |

TABLE CEi-continued

AMIDATION (HATU/ACID) COUPLING PARTNERS

| CAS #/ Intermediate # | Structure | Chemical Name |
|---|---|---|
| 222530-39-4 | 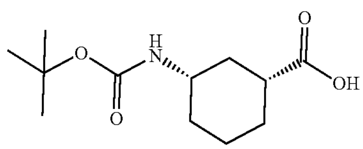 [SMILES: CC(C)(C)OC(=O)N[C@H]1CCC[C@@H](C(=O)O)C1] | (1R,3S)-3-((tert-butoxycarbonyl)amino)cyclohexane-1-carboxylic acid |
| 1363381-18-3 | 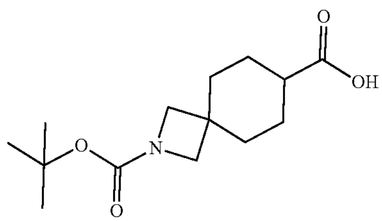 [SMILES: CC(C)(C)OC(=O)N1CC2(CCC(C(=O)O)CC2)C1] | 2-(tert-butoxycarbonyl)-2-azaspiro[3.5]nonane-7-carboxylic acid |
| 66493-39-8 | 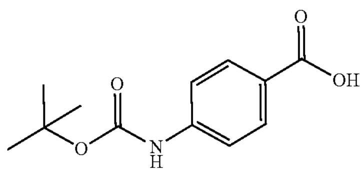 [SMILES: CC(C)(C)OC(=O)Nc1ccc(C(=O)O)cc1] | 4-((tert-butoxycarbonyl)amino)benzoic acid |
| 111331-82-9 | 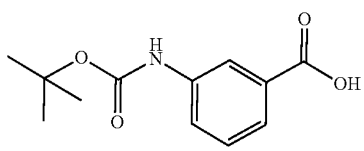 [SMILES: CC(C)(C)OC(=O)Nc1cccc(C(=O)O)c1] | 3-((tert-butoxycarbonyl)amino)benzoic acid |
| 140148-70-5 | 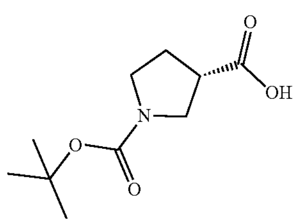 | (S)-1-(tert-butoxycarbonyl)pyrrolidine-3-carboxylic acid |
| 72925-16-7 | 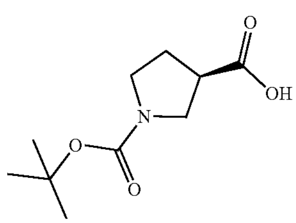 | (R)-1-(tert-butoxycarbonyl)pyrrolidine-3-carboxylic acid |
| 1001754-59-1 | 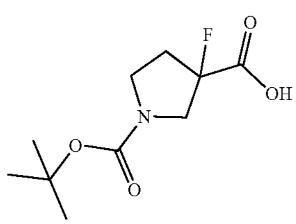 [SMILES: CC(C)(C)OC(=O)N1CCC(F)(C(=O)O)C1] | 1-(tert-butoxycarbonyl)-3-fluoropyrrolidine-3-carboxylic acid |

TABLE CEi-continued

AMIDATION (HATU/ACID) COUPLING PARTNERS

| CAS #/ Intermediate # | Structure | Chemical Name |
|---|---|---|
| 1158759-28-4 | 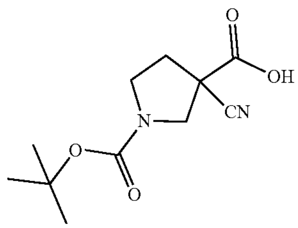 [SMILES: CC(C)(C)OC(=O)N1CCC(C#N)(C(=O)O)C1] | 1-(tert-butoxycarbonyl)-3-cyanopyrrolidine-3-carboxylic acid |
| 161601-29-2 | 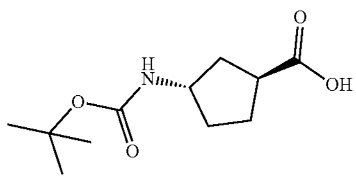 [SMILES: CC(C)(C)OC(=O)N[C@H]1CC[C@H](C(=O)O)C1] | (1S,3S)-3-((tert-butoxycarbonyl)amino)cyclopentane-1-carboxylic acid |
| 161660-94-2 | 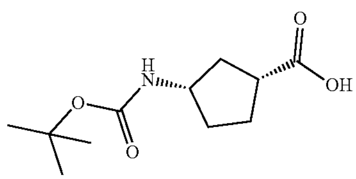 [SMILES: CC(C)(C)OC(=O)N[C@H]1CC[C@@H](C(=O)O)C1] | (1R,3S)-3-((tert-butoxycarbonyl)amino)cyclopentane-1-carboxylic acid |
| 489446-85-7 | 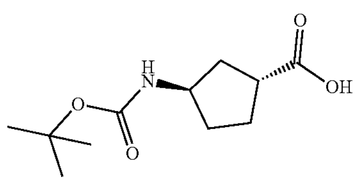 [SMILES: CC(C)(C)OC(=O)N[C@@H]1CC[C@@H](C(=O)O)C1] | (1R,3R)-3-((tert-butoxycarbonyl)amino)cyclopentane-1-carboxylic acid |
| 261165-05-3 | 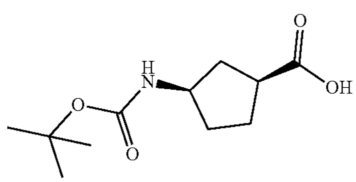 [SMILES: CC(C)(C)OC(=O)N[C@@H]1CC[C@H](C(=O)O)C1] | (1S,3R)-3-((tert-butoxycarbonyl)amino)cyclopentane-1-carboxylic acid |
| 142253-55-2 | 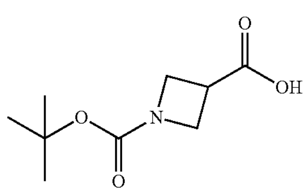 | 1-(tert-butoxycarbonyl)azetidine-3-carboxylic acid |
| 1126650-67-6 | 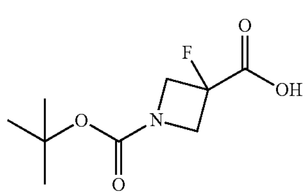 | 1-(tert-butoxycarbonyl)-3-fluoroazetidine-3-carboxylic acid |

TABLE CEi-continued

AMIDATION (HATU/ACID) COUPLING PARTNERS

| CAS #/Intermediate # | Structure | Chemical Name |
|---|---|---|
| 1158759-45-5 | 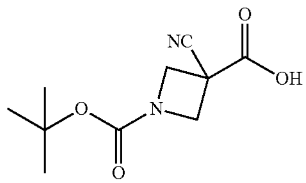 [SMILES: CC(C)(C)OC(=O)N1CC(C#N)(C(=O)O)C1] | 1-(tert-butoxycarbonyl)-3-cyanoazetidine-3-carboxylic acid |
| 887591-62-0 | 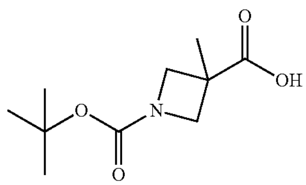 | 1-(tert-butoxycarbonyl)-3-methylazetidine-3-carboxylic acid |
| 1035351-06-4 | 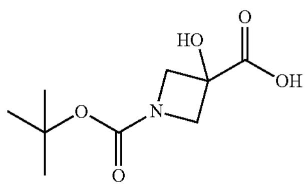 | 1-(tert-butoxycarbonyl)-3-hydroxyazetidine-3-carboxylic acid |
| 429669-07-8 | 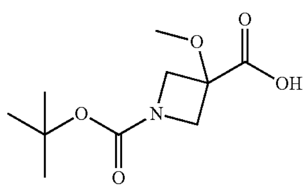 [SMILES: COC1(C(=O)O)CN(C(=O)OC(C)(C)C)C1] | 1-(tert-butoxycarbonyl)-3-methoxyazetidine-3-carboxylic acid |
| 610791-06-5 | 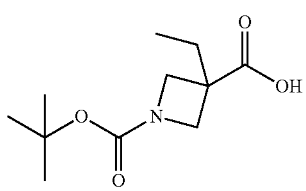 [SMILES: CCC1(C(=O)O)CN(C(=O)OC(C)(C)C)C1] | 1-(tert-butoxycarbonyl)-3-ethylazetidine-3-carboxylic acid |
| 1638760-82-3 | 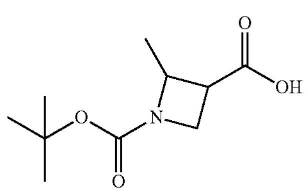 | 1-(tert-butoxycarbonyl)-2-methylazetidine-3-carboxylic acid |
| R2 | 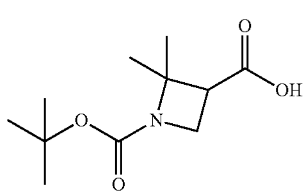 | 1-(tert-butoxycarbonyl)-2-methylazetidine-3-carboxylic acid |
| 1008773-79-2 | 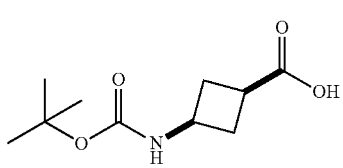 | Cis-3-[(tert-butoxycarbonyl)amino]cyclobutanecarboxylic acid |

TABLE CEi-continued

AMIDATION (HATU/ACID) COUPLING PARTNERS

| CAS #/Intermediate # | Structure | Chemical Name |
|---|---|---|
| 939400-34-7 | 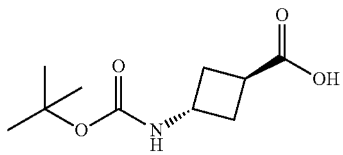 | (1r,3r)-3-((tert-butoxycarbonyl)amino)cyclobutane-1-carboxylic acid |
| 676371-64-5 | 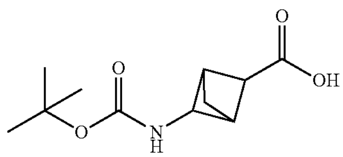 [SMILES: CC(C)(C)OC(=O)NC1C2CC1C2C(=O)O] | 4-((tert-butoxycarbonyl)amino)bicyclo[1.1.1]pentane-2-carboxylic acid |
| 1211526-53-2 | 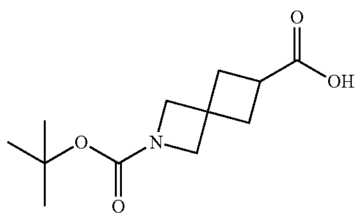 [SMILES: CC(C)(C)OC(=O)N1CC2(CC(C(=O)O)C2)C1] | 2-(tert-butoxycarbonyl)-2-azaspiro[3.3]heptane-6-carboxylic acid |
| 873624-12-0 | 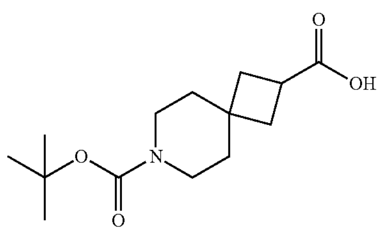 [SMILES: CC(C)(C)OC(=O)N1CCC2(CC1)CC(C(=O)O)C2] | 7-(tert-butoxycarbonyl)-7-azaspiro[3.5]nonane-2-carboxylic acid |
| 23519-90-6 | 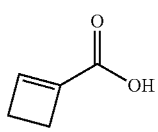 | cyclobut-1-ene-1-carboxylic acid |
| 471-25-0 | 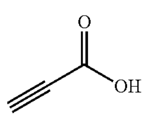 | propiolic acid |
| 590-93-2 | 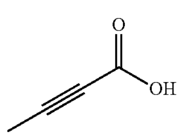 | but-2-ynoic acid |
| 430-99-9 | 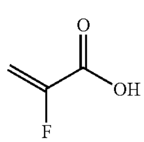 | 2-fluoroacrylic acid |
| 24587-49-3 | 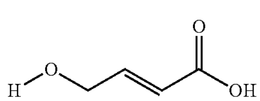 | (E)-4-hydroxybut-2-enoic acid |
| 98548-82-4 | 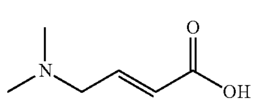 | (E)-4-(dimethylamino)but-2-enoic acid |

TABLE CEi-continued

AMIDATION (HATU/ACID) COUPLING PARTNERS

| CAS #/ Intermediate # | Structure | Chemical Name |
|---|---|---|
| 37759-72-1 | 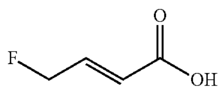 | (E)-4-fluorobut-2-enoic acid |
| 768341-84-0 | 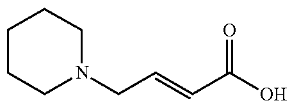 [SMILES: O=C(O)/C=C/CN1CCCCC1] | (E)-4-(piperidin-1-yl)but-2-enoic acid |
| 79-10-7 | 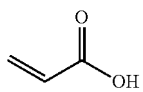 | acrylic acid |
| 59424-95-2 | 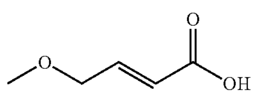 | (E)-4-methoxybut-2-enoic acid |
| 324769-07-5 | 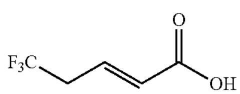 | (E)-5,5,5-trifluoropent-2-enoic acid |
| 16197-90-3 | 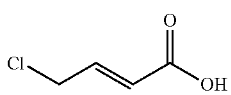 | (E)-4-chlorobut-2-enoic acid |
| 13991-36-1 | 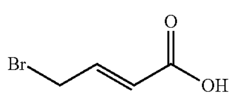 | (E)-4-bromobut-2-enoic acid |
| 848133-35-7 | 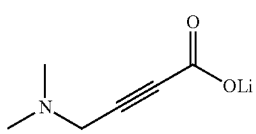 | lithium 4-(dimethylamino)but-2-ynoate |
| 102245-65-8 | 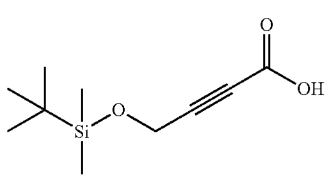 | 4-((tert-butyldimethylsilyl)oxy)but-2-ynoic acid |
| 15286-98-3 | 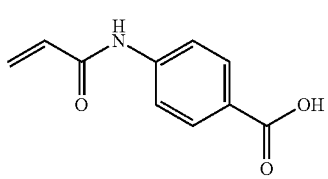 | 4-acrylamidobenzoic acid |

TABLE CE²i

AMIDATION (HATU/ACID)/REDUCTION COUPLING PARTNERS

| CAS # | Structure | Chemical Name |
|---|---|---|
| 121-92-6 | O₂N–C₆H₄–COOH (3-NO₂) | 3-nitrobenzoic acid |
| 552-16-9 | C₆H₄(NO₂)(COOH) (2-NO₂) | 2-nitrobenzoic acid |
| 1975-51-5 | O₂N–C₆H₃(CH₃)–COOH | 2-methyl-4-nitrobenzoic acid |
| 2597-56-0 | O₂N–C₆H₃(OCH₃)–COOH | 2-methoxy-4-nitrobenzoic acid |
| 3113-71-1 | O₂N–C₆H₃(CH₃)–COOH | 3-methyl-4-nitrobenzoic acid |
| 5081-36-7 | O₂N–C₆H₃(OCH₃)–COOH | 3-methoxy-4-nitrobenzoic acid |

TABLE CFi

SULFONYLATION COUPLING PARTNERS

| CAS # | Structure | Chemical Name |
|---|---|---|
| 98-74-8 | O₂N–C₆H₄–SO₂Cl | 4-nitrobenzenesulfonyl chloride |
| 1310732-18-3 | tert-butyl azetidine-SO₂Cl | tert-butyl 3-(chlorosulfonyl)azetidine-1-carboxylate |

TABLE CGi

TERMINAL AMINE COUPLING PARTNERS

| CAS # | Structure | Chemical Name |
|---|---|---|
| 679431-51-7 | (R)-3-fluoropyrrolidine | (R)-3-fluoropyrrolidine |
| 136725-54-7 | (S)-3-fluoropyrrolidine | (S)-3-fluoropyrrolidine |
| 110-91-8 | morpholine | morpholine |

PREPARATION OF SYNTHETIC EXAMPLES

Example 1

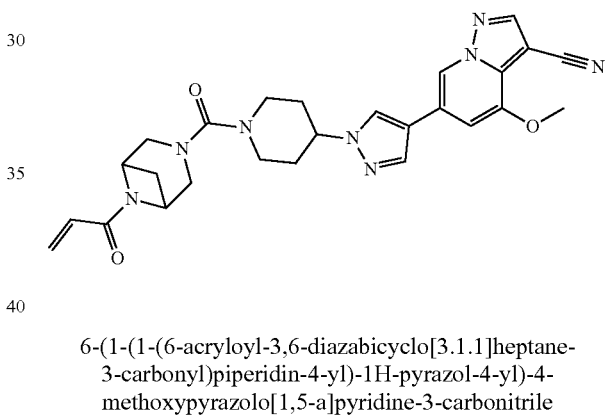

6-(1-(1-(6-acryloyl-3,6-diazabicyclo[3.1.1]heptane-3-carbonyl)piperidin-4-yl)-1H-pyrazol-4-yl)-4-methoxypyrazolo[1,5-a]pyridine-3-carbonitrile A solution of 6-(1-(1-(3,6-diazabicyclo[3.1.1]heptane-3-carbonyl)piperidin-4-yl)-1H-pyrazol-4-yl)-4-methoxypyrazolo[1,5-a]pyridine-3-carbonitrile (Intermediate P71; 21 mg, 0.047 mmol) in DCM (6 mL) was treated sequentially with TEA (33 µL, 0.24 mmol) and acryloyl chloride (7.6 µL, 0.094 mmol), then stirred overnight at ambient temperature. Subsequently, the reaction mixture was concentrated in vacuo. The crude residue was purified by C18 reverse phase chromatography (using 5-95% ACN in water with 0.1% TFA as the gradient eluent) to cleanly afford the title compound as the TFA salt. The TFA salt then was free based by dissolving in 4:1 DCM:iPrOH and extracting with saturated NaHCO$_{3(aq)}$. The organic extracts then were dried over anhydrous Na$_2$SO$_{4(s)}$, filtered, and concentrated in vacuo to cleanly afford the title compound (21 mg, 89% yield). MS (apci) m/z=501.2 (M+H).

The compounds in Table C1 were prepared using a similar method to that described in the synthesis of 6-(1-(1-(6-acryloyl-3,6-diazabicyclo[3.1.1]heptane-3-carbonyl)piperidin-4-yl)-1H-pyrazol-4-yl)-4-methoxypyrazolo[1,5-a]pyridine-3-carbonitrile (Example 1), employing the following modifications: replacing 6-(1-(1-(3,6-diazabicyclo[3.1.1]

heptane-3-carbonyl)piperidin-4-yl)-1H-pyrazol-4-yl)-4-methoxypyrazolo[1,5-a]pyridine-3-carbonitrile (Intermediate P71) with the appropriate amine (found in the synthetic intermediates section, e.g. Tables CA[1], CA[2], CB, CC, CD, CE, etc.), and using 0.01-0.1 M DCM, 2-20 equivalents of TEA along with 1-10 equivalents of acryloyl chloride (where noted * order of TEA and acryloyl chloride addition was inverted). Reactions were monitored for completion by LCMS, as such reaction durations were adjusted accordingly. When necessary, title compounds were isolated following chromatographic purification using an appropriate gradient eluent, and if necessary free based using a similar extraction procedure as found in Example 1.

TABLE C1

| Ex # | Structure | Chemical Name | MS apci (m/z) |
|---|---|---|---|
| 2 | 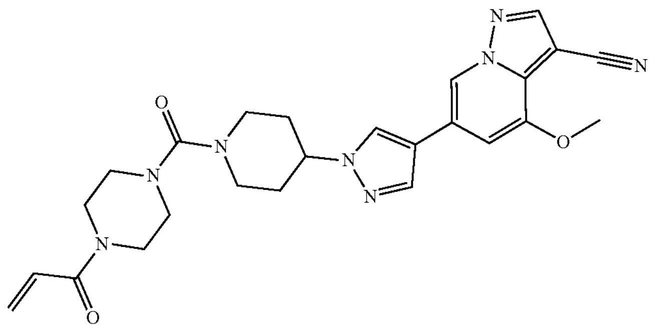 [SMILES: C=CC(=O)N1CCN(C(=O)N2CCC(n3cc(-c4cc(OC)c5c(C#N)cnn5c4)cn3)CC2)CC1] | 6-(1-(1-(4-acryloylpiperazine-1-carbonyl)piperidin-4-yl)-1H-pyrazol-4-yl)-4-methoxypyrazolo[1,5-a]pyridine-3-carbonitrile | 489.2 (M + H) |
| 3* | 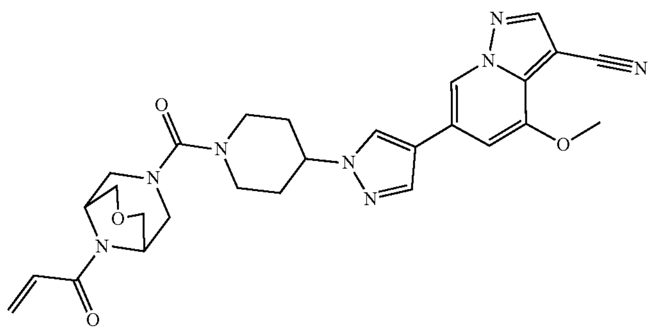 [SMILES: C=CC(=O)N1C2COCC1CN(C(=O)N1CCC(n3cc(-c4cc(OC)c5c(C#N)cnn5c4)cn3)CC1)C2] | 6-(1-(1-(9-acryloyl-3-oxa-7,9-diazabicyclo[3.3.1]nonane-7-carbonyl)piperidin-4-yl)-1H-pyrazol-4-yl)-4-methoxypyrazolo[1,5-a]pyridine-3-carbonitrile | 531.2 (M + H) |
| 4 | 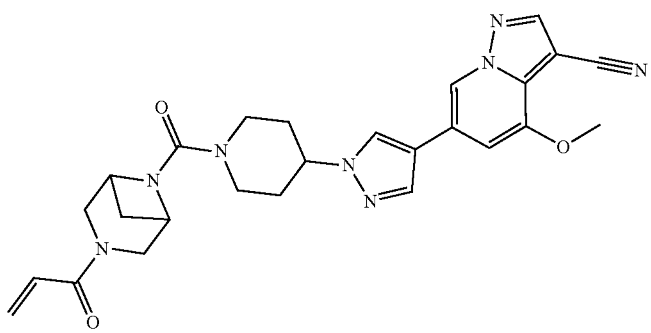 [SMILES: C=CC(=O)N1CC2CC(C1)N2C(=O)N1CCC(n2cc(-c3cc(OC)c4c(C#N)cnn4c3)cn2)CC1] | 6-(1-(1-(3-acryloyl-3,6-diazabicyclo[3.1.1]heptane-6-carbonyl)piperidin-4-yl)-1H-pyrazol-4-yl)-4-methoxypyrazolo[1,5-a]pyridine-3-carbonitrile | 501.2 (M + H) |
| 5 | 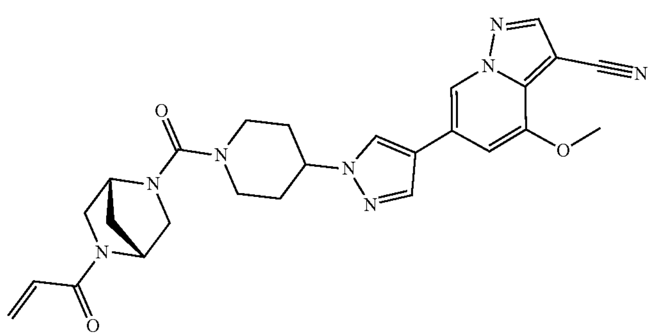 [SMILES: C=CC(=O)N1C[C@H]2C[C@@H]1CN2C(=O)N1CCC(n2cc(-c3cc(OC)c4c(C#N)cnn4c3)cn2)CC1] | 6-(1-(1-((1R,4R)-5-acryloyl-2,5-diazabicyclo[2.2.1]heptane-2-carbonyl)piperidin-4-yl)-1H-pyrazol-4-yl)-4-methoxypyrazolo[1,5-a]pyridine-3-carbonitrile | 501.2 (M + H) |

TABLE C1-continued

| Ex # | Structure | Chemical Name | MS apci (m/z) |
|---|---|---|---|
| 6* | 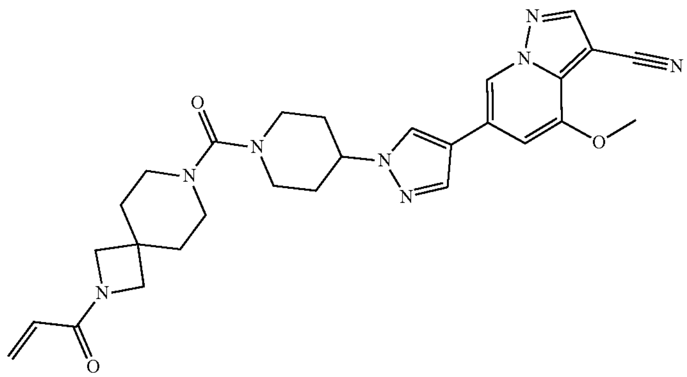 | 6-(1-(1-(2-acryloyl-2,7-diazaspiro[3.5]nonane-7-carbonyl)piperidin-4-yl)-1H-pyrazol-4-yl)-4-methoxypyrazolo[1,5-a]pyridine-3-carbonitrile | 529.3 (M + H) |
| 7 | 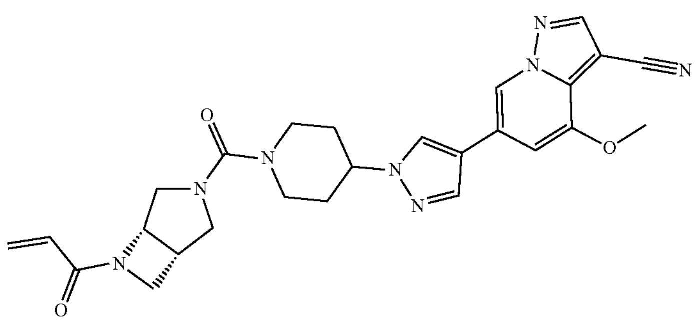 [SMILES: C=CC(=O)N1C[C@H]2CN(C(=O)N3CCC(n4cc(-c5cc(OC)c6c(C#N)cnn6c5)cn4)CC3)C[C@H]21] | 6-(1-(1-((1S,5S)-6-acryloyl-3,6-diazabicyclo[3.2.0]heptane-3-carbonyl)piperidin-4-yl)-1H-pyrazol-4-yl)-4-methoxypyrazolo[1,5-a]pyridine-3-carbonitrile | 501.2 (M + H) |
| 8* | 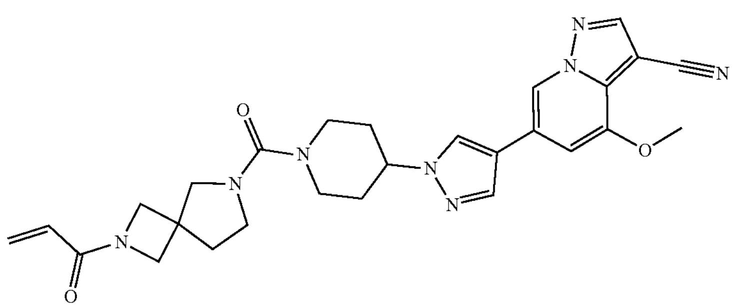 [SMILES: C=CC(=O)N1CC2(CCN(C(=O)N3CCC(n4cc(-c5cc(OC)c6c(C#N)cnn6c5)cn4)CC3)C2)C1] | 6-(1-(1-(2-acryloyl-2,6-diazaspiro[3.4]octane-6-carbonyl)piperidin-4-yl)-1H-pyrazol-4-yl)-4-methoxypyrazolo[1,5-a]pyridine-3-carbonitrile | 515.2 (M + H) |
| 9 | 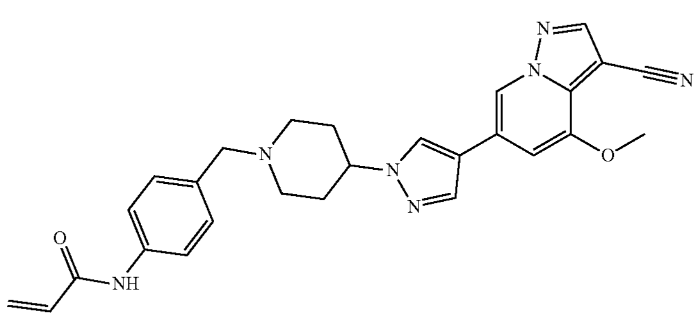 [SMILES: C=CC(=O)Nc1ccc(CN2CCC(n3cc(-c4cc(OC)c5c(C#N)cnn5c4)cn3)CC2)cc1] | N-(4-((4-(4-(3-cyano-4-methoxypyrazolo[1,5-a]pyridin-6-yl)-1H-pyrazol-1-yl)piperidin-1-yl)methyl)phenyl)acrylamide | 482.2 (M + H) |

TABLE C1-continued

| Ex # | Structure | Chemical Name | MS apci (m/z) |
|---|---|---|---|
| 10 | 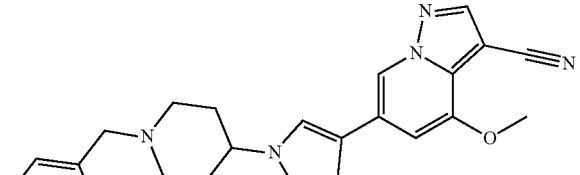 | N-(4-((4-(4-(3-cyano-4-methoxypyrazolo[1,5-a]pyridin-6-yl)-1H-pyrazol-1-yl)piperidin-1-yl)methyl)phenyl)-N-methylacrylamide | 496.2 (M + H) |
| 11 | 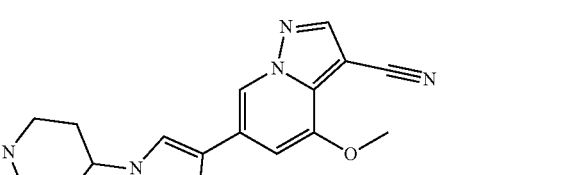 | 6-(1-(1-acryloylpiperidin-4-yl)-1H-pyrazol-4-yl)-4-methoxypyrazolo[1,5-a]pyridine-3-carbonitrile | 377.1 (M + H) |
| 12 | 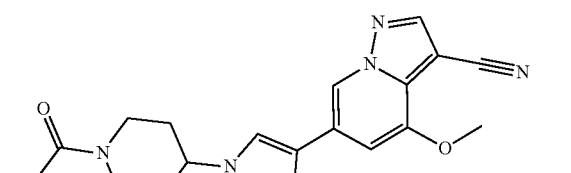 | 6-(1-(1-(1-acryloylpiperidine-4-carbonyl)piperidin-4-yl)-1H-pyrazol-4-yl)-4-methoxypyrazolo[1,5-a]pyridine-3-carbonitrile | 488.2 (M + H) |
| 13 | 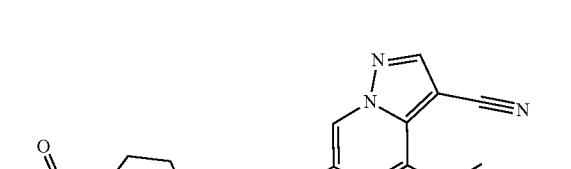 | 6-(1-(1-(1-acryloyl-4-fluoropiperidine-4-carbonyl)piperidin-4-yl)-1H-pyrazol-4-yl)-4-methoxypyrazolo[1,5-a]pyridine-3-carbonitrile | 506.2 (M + H) |
| 14 | 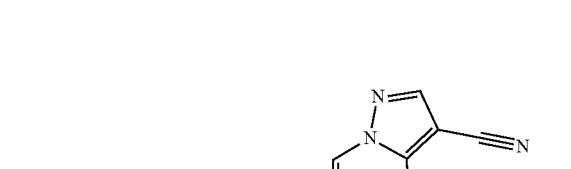 | 6-(1-(1-(1-acryloyl-4-cyanopiperidine-4-carbonyl)piperidin-4-yl)-1H-pyrazol-4-yl)-4-methoxypyrazolo[1,5-a]pyridine-3-carbonitrile | 513.2 (M + H) |

TABLE C1-continued

| Ex # | Structure | Chemical Name | MS apci (m/z) |
|---|---|---|---|
| 15 | 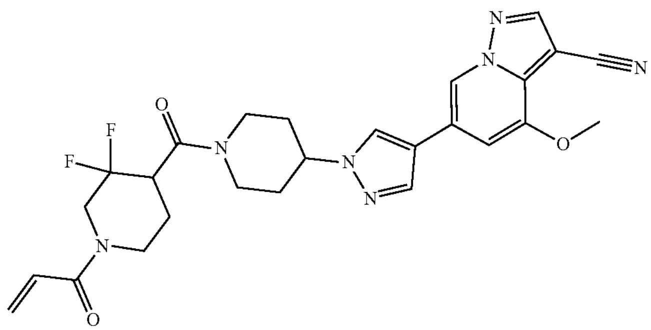 [SMILES: C=CC(=O)N1CCC(C(=O)N2CCC(n3cc(-c4cc(OC)c5c(C#N)cnn5c4)cn3)CC2)C(F)(F)C1] | 6-(1-(1-(1-acryloyl-3,3-difluoropiperidine-4-carbonyl)piperidin-4-yl)-1H-pyrazol-4-yl)-4-methoxypyrazolo[1,5-a]pyridine-3-carbonitrile | 524.2 (M + H) |
| 16 | 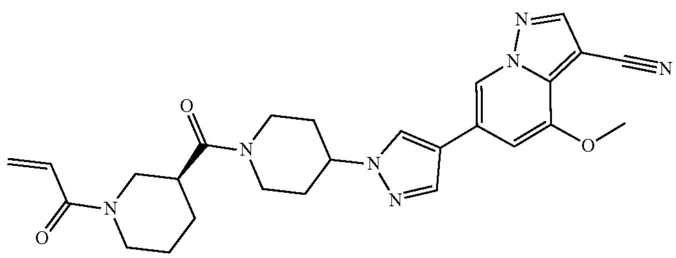 [SMILES: C=CC(=O)N1CCC[C@H](C(=O)N2CCC(n3cc(-c4cc(OC)c5c(C#N)cnn5c4)cn3)CC2)C1] | (S)-6-(1-(1-(1-acryloylpiperidine-3-carbonyl)piperidin-4-yl)-1H-pyrazol-4-yl)-4-methoxypyrazolo[1,5-a]pyridine-3-carbonitrile | 488.3 (M + H) |
| 17 | 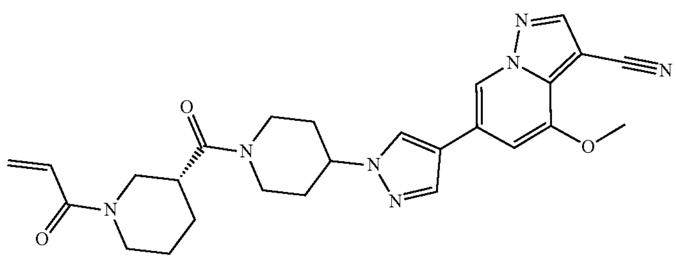 [SMILES: C=CC(=O)N1CCC[C@@H](C(=O)N2CCC(n3cc(-c4cc(OC)c5c(C#N)cnn5c4)cn3)CC2)C1] | (R)-6-(1-(1-(1-acryloylpiperidine-3-carbonyl)piperidin-4-yl)-1H-pyrazol-4-yl)-4-methoxypyrazolo[1,5-a]pyridine-3-carbonitrile | 488.3 (M + H) |
| 18 | 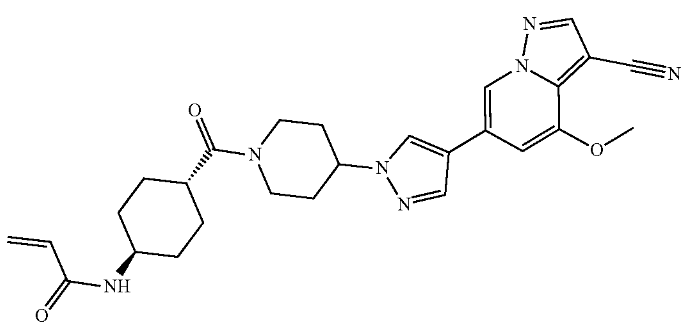 [SMILES: C=CC(=O)N[C@H]1CC[C@H](C(=O)N2CCC(n3cc(-c4cc(OC)c5c(C#N)cnn5c4)cn3)CC2)CC1] | N-((1r,4r)-4-(4-(4-(3-cyano-4-methoxypyrazolo[1,5-a]pyridin-6-yl)-1H-pyrazol-1-yl)piperidine-1-carbonyl)cyclohexyl)acrylamide | 502.3 (M + H) |
| 19 | 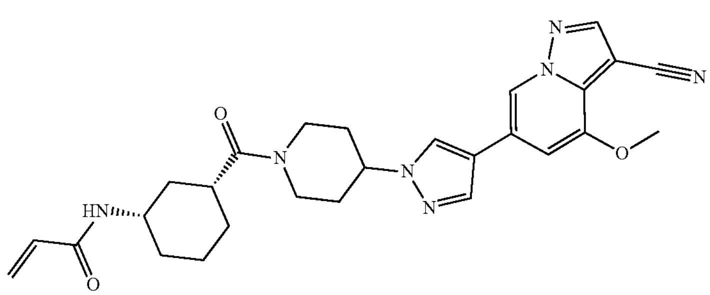 [SMILES: C=CC(=O)N[C@H]1CCC[C@@H](C(=O)N2CCC(n3cc(-c4cc(OC)c5c(C#N)cnn5c4)cn3)CC2)C1] | N-((1S,3R)-3-(4-(4-(3-cyano-4-methoxypyrazolo[1,5-a]pyridin-6-yl)-1H-pyrazol-1-yl)piperidine-1-carbonyl)cyclohexyl)acrylamide | 502.3 (M + H) |

TABLE C1-continued

| Ex # | Structure | Chemical Name | MS apci (m/z) |
|---|---|---|---|
| 20 | 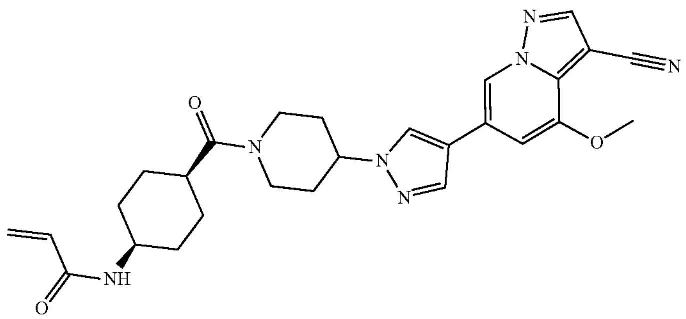 [SMILES: C=CC(=O)N[C@H]1CC[C@@H](C(=O)N2CCC(n3cc(-c4cc(OC)c5c(C#N)cnn5c4)cn3)CC2)CC1] | N-((1s,4s)-4-(4-(4-(3-cyano-4-methoxypyrazolo[1,5-a]pyridin-6-yl)-1H-pyrazol-1-yl)piperidine-1-carbonyl)cyclohexyl)acrylamide | 502.3 (M + H) |
| 21 | 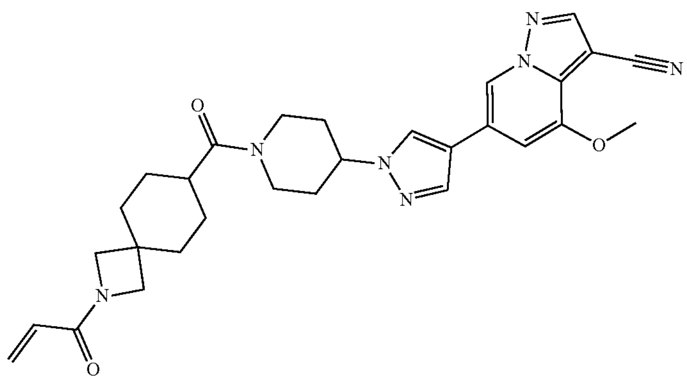 [SMILES: C=CC(=O)N1CC2(CCC(C(=O)N3CCC(n4cc(-c5cc(OC)c6c(C#N)cnn6c5)cn4)CC3)CC2)C1] | 6-(1-(1-(2-acryloyl-2-azaspiro[3.5]nonane-7-carbonyl)piperidin-4-yl)-1H-pyrazol-4-yl)-4-methoxypyrazolo[1,5-a]pyridine-3-carbonitrile | 528.2 (M + H) |
| 22 | 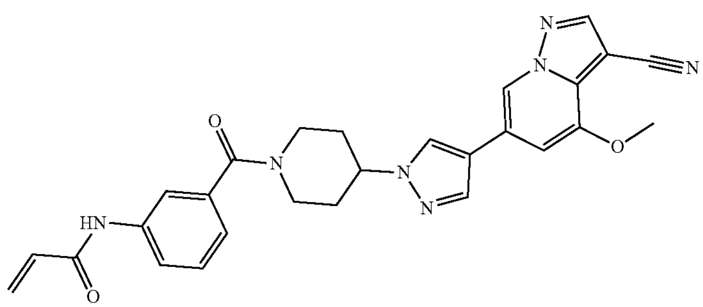 [SMILES: C=CC(=O)Nc1cccc(C(=O)N2CCC(n3cc(-c4cc(OC)c5c(C#N)cnn5c4)cn3)CC2)c1] | N-(3-(4-(4-(3-cyano-4-methoxypyrazolo[1,5-a]pyridin-6-yl)-1H-pyrazol-1-yl)piperidine-1-carbonyl)phenyl)acrylamide | 496.2 (M + H) |
| 23 | 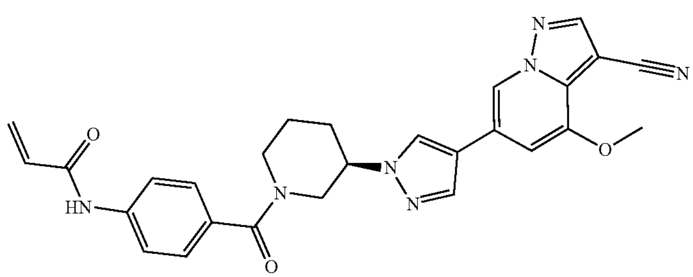 [SMILES: C=CC(=O)Nc1ccc(C(=O)N2CCC[C@@H](n3cc(-c4cc(OC)c5c(C#N)cnn5c4)cn3)C2)cc1] | (R)-N-(4-(3-(4-(3-cyano-4-methoxypyrazolo[1,5-a]pyridin-6-yl)-1H-pyrazol-1-yl)piperidine-1-carbonyl)phenyl)acrylamide | 496.2 (M + H) |
| 24 | 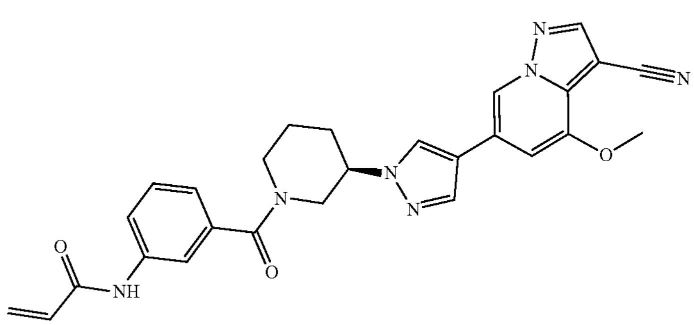 [SMILES: C=CC(=O)Nc1cccc(C(=O)N2CCC[C@@H](n3cc(-c4cc(OC)c5c(C#N)cnn5c4)cn3)C2)c1] | (R)-N-(3-(3-(4-(3-cyano-4-methoxypyrazolo[1,5-a]pyridin-6-yl)-1H-pyrazol-1-yl)piperidine-1-carbonyl)phenyl)acrylamide | 496.2 (M + H) |

TABLE C1-continued

| Ex # | Chemical Name | MS apci (m/z) |
|---|---|---|
| 25 | (R)-N-(2-(3-(4-(3-cyano-4-methoxypyrazolo[1,5-a]pyridin-6-yl)-1H-pyrazol-1-yl)piperidine-1-carbonyl)phenyl)acrylamide | 494.2 (M − H) |
| 26 | 6-(1-(3-((1-acryloylpiperidin-4-yl)oxy)phenyl)-1H-pyrazol-4-yl)-4-methoxypyrazolo[1,5-a]pyridine-3-carbonitrile | 469.1 (M + H) |
| 27 | 6-(1-(3-(4-acryloylpiperazin-1-yl)phenyl)-1H-pyrazol-4-yl)-4-methoxypyrazolo[1,5-a]pyridine-3-carbonitrile | 454.2 (M + H) |
| 28 | (S)-6-(1-(1-(1-acryloylpyrrolidine-3-carbonyl)piperidin-4-yl)-1H-pyrazol-4-yl)-4-methoxypyrazolo[1,5-a]pyridine-3-carbonitrile | 474.3 (M + H) |
| 29 | (R)-6-(1-(1-(1-acryloylpyrrolidine-3-carbonyl)piperidin-4-yl)-1H-pyrazol-4-yl)-4-methoxypyrazolo[1,5-a]pyridine-3-carbonitrile | 474.3 (M + H) |

TABLE C1-continued

| Ex # | Structure | Chemical Name | MS apci (m/z) |
|---|---|---|---|
| 30 | 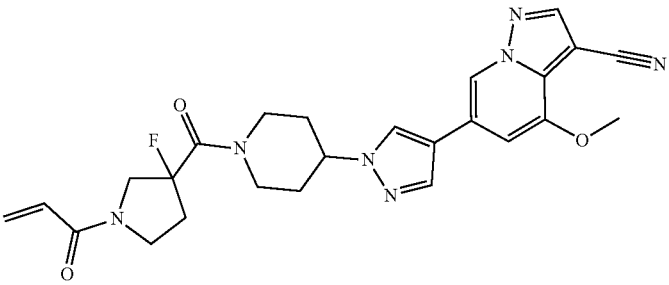 [SMILES: C=CC(=O)N1CCC(F)(C(=O)N2CCC(n3cc(-c4cc(OC)c5c(C#N)cnn5c4)cn3)CC2)C1] | 6-(1-(1-(1-acryloyl-3-fluoropyrrolidine-3-carbonyl)piperidin-4-yl)-1H-pyrazol-4-yl)-4-methoxypyrazolo[1,5-a]pyridine-3-carbonitrile | 492.2 (M + H) |
| 31 | 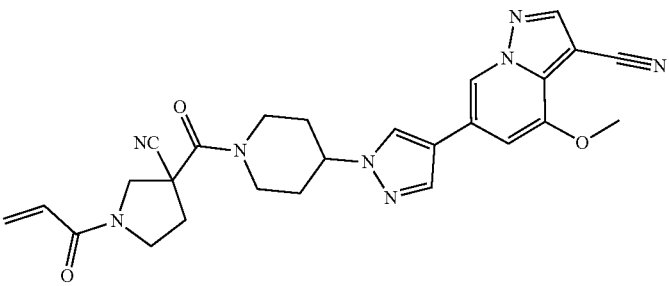 [SMILES: C=CC(=O)N1CCC(C#N)(C(=O)N2CCC(n3cc(-c4cc(OC)c5c(C#N)cnn5c4)cn3)CC2)C1] | 6-(1-(1-(1-acryloyl-3-cyanopyrrolidine-3-carbonyl)piperidin-4-yl)-1H-pyrazol-4-yl)-4-methoxypyrazolo[1,5-a]pyridine-3-carbonitrile | 499.2 (M + H) |
| 32 | 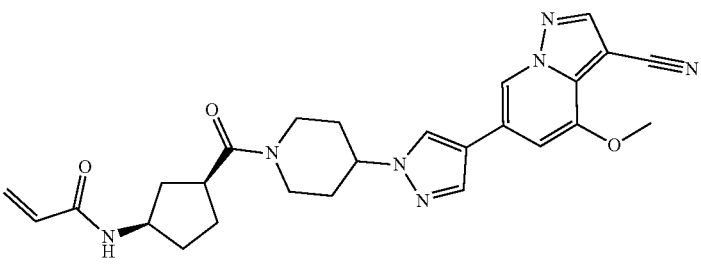 [SMILES: C=CC(=O)N[C@@H]1CC[C@H](C(=O)N2CCC(n3cc(-c4cc(OC)c5c(C#N)cnn5c4)cn3)CC2)C1] | N-((1R,3S)-3-(4-(4-(3-cyano-4-methoxypyrazolo[1,5-a]pyridin-6-yl)-1H-pyrazol-1-yl)piperidine-1-carbonyl)cyclopentyl)acrylamide | 488.3 (M + H) |
| 33 | 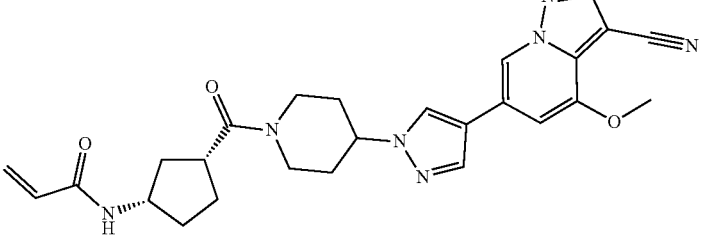 | N-((1S,3R)-3-(4-(4-(3-cyano-4-methoxypyrazolo[1,5-a]pyridin-6-yl)-1H-pyrazol-1-yl)piperidine-1-carbonyl)cyclopentyl)acrylamide | 488.2 (M + H) |
| 34 | 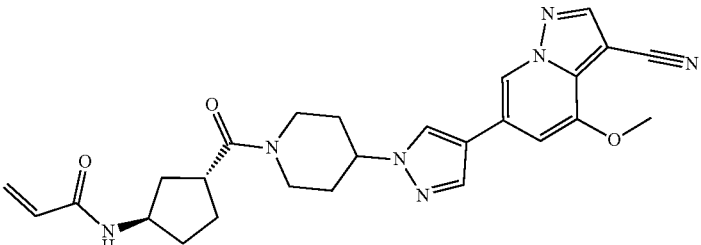 | N-((1R,3R)-3-(4-(4-(3-cyano-4-methoxypyrazolo[1,5-a]pyridin-6-yl)-1H-pyrazol-1-yl)piperidine-1-carbonyl)cyclopentyl)acrylamide | 488.2 (M + H) |

TABLE C1-continued

| Ex # | Structure | Chemical Name | MS apci (m/z) |
|---|---|---|---|
| 35 | 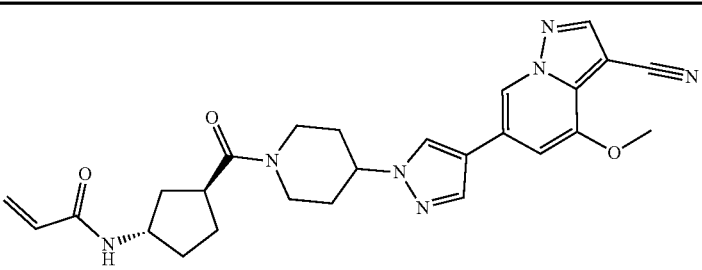 | N-((1S,3S)-3-(4-(4-(3-cyano-4-methoxypyrazolo[1,5-a]pyridin-6-yl)-1H-pyrazol-1-yl)piperidine-1-carbonyl)cyclopentyl)acrylamide | 488.3 (M + H) |
| 36 | 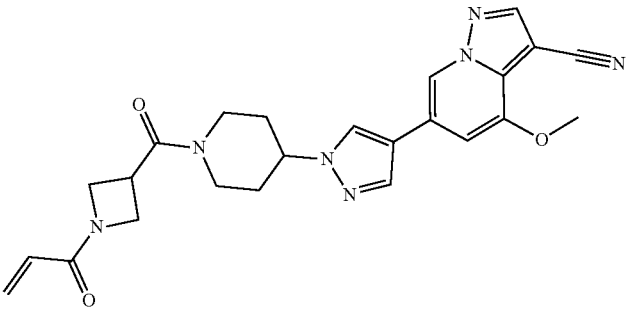 [SMILES: C=CC(=O)N1CC(C(=O)N2CCC(n3cc(-c4cc(OC)c5c(C#N)cnn5c4)cn3)CC2)C1] | 6-(1-(1-(1-acryloylazetidine-3-carbonyl)piperidin-4-yl)-1H-pyrazol-4-yl)-4-methoxypyrazolo[1,5-a]pyridine-3-carbonitrile | 460.2 (M + H) |
| 37 | 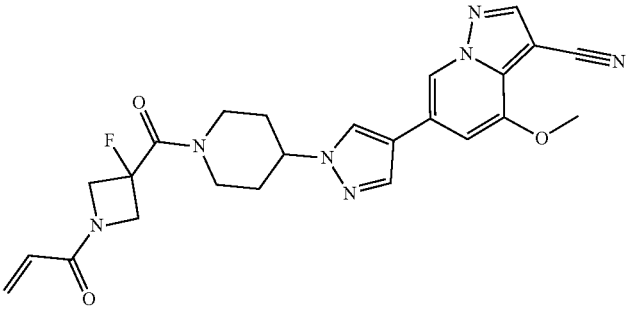 [SMILES: C=CC(=O)N1CC(F)(C(=O)N2CCC(n3cc(-c4cc(OC)c5c(C#N)cnn5c4)cn3)CC2)C1] | 6-(1-(1-(1-acryloyl-3-fluoroazetidine-3-carbonyl)piperidin-4-yl)-1H-pyrazol-4-yl)-4-methoxypyrazolo[1,5-a]pyridine-3-carbonitrile | 478.2 (M + H) |
| 38 | 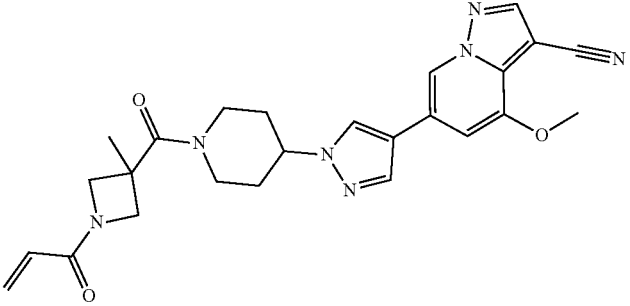 [SMILES: C=CC(=O)N1CC(C)(C(=O)N2CCC(n3cc(-c4cc(OC)c5c(C#N)cnn5c4)cn3)CC2)C1] | 6-(1-(1-(1-acryloyl-3-methylazetidine-3-carbonyl)piperidin-4-yl)-1H-pyrazol-4-yl)-4-methoxypyrazolo[1,5-a]pyridine-3-carbonitrile | 474.2 (M + H) |
| 39 | 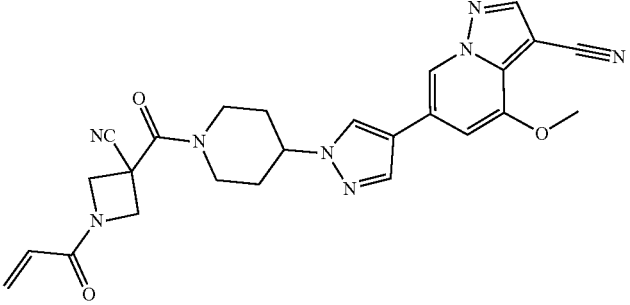 | 6-(1-(1-(1-acryloyl-3-cyanoazetidine-3-carbonyl)piperidin-4-yl)-1H-pyrazol-4-yl)-4-methoxypyrazolo[1,5-a]pyridine-3-carbonitrile | 485.2 (M + H) |

TABLE C1-continued

| Ex # | Structure | Chemical Name | MS apci (m/z) |
|---|---|---|---|
| 40 | 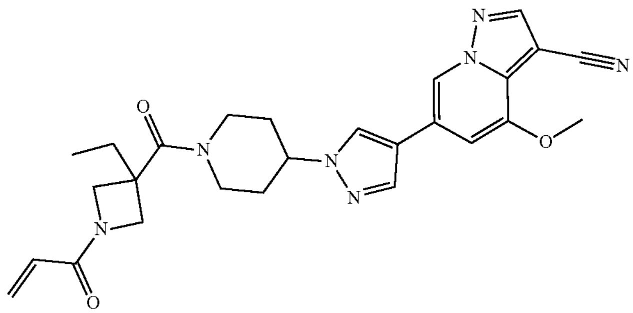 [SMILES: C=CC(=O)N1CC(CC)(C(=O)N2CCC(n3cc(-c4cc(OC)c5c(C#N)cnn5c4)cn3)CC2)C1] | 6-(1-(1-(1-acryloyl-3-ethylazetidine-3-carbonyl)piperidin-4-yl)-1H-pyrazol-4-yl)-4-methoxypyrazolo[1,5-a]pyridine-3-carbonitrile | 488.2 (M + H) |
| 41 | 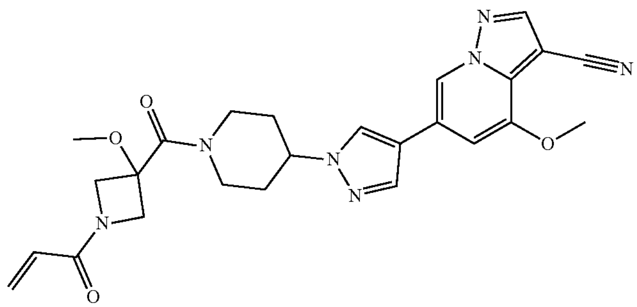 [SMILES: C=CC(=O)N1CC(OC)(C(=O)N2CCC(n3cc(-c4cc(OC)c5c(C#N)cnn5c4)cn3)CC2)C1] | 6-(1-(1-(1-acryloyl-3-methoxyazetidine-3-carbonyl)piperidin-4-yl)-1H-pyrazol-4-yl)-4-methoxypyrazolo[1,5-a]pyridine-3-carbonitrile | 490.2 (M + H) |
| 42 | 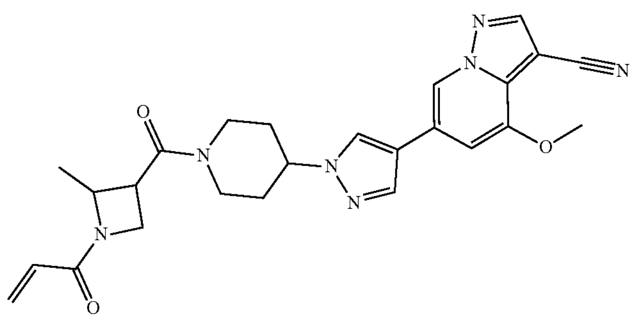 [SMILES: C=CC(=O)N1CC(C(=O)N2CCC(n3cc(-c4cc(OC)c5c(C#N)cnn5c4)cn3)CC2)C1C] | 6-(1-(1-(1-acryloyl-2-methylazetidine-3-carbonyl)piperidin-4-yl)-1H-pyrazol-4-yl)-4-methoxypyrazolo[1,5-a]pyridine-3-carbonitrile | 474.2 (M + H) |
| 43 | 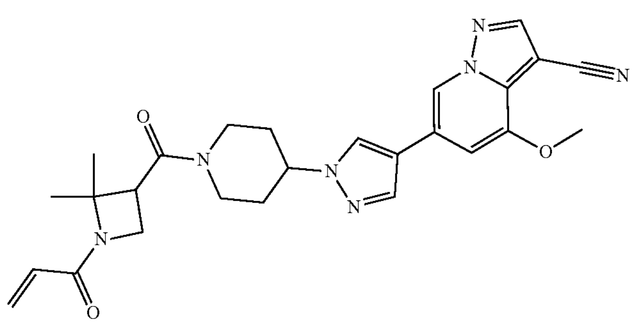 [SMILES: C=CC(=O)N1CC(C(=O)N2CCC(n3cc(-c4cc(OC)c5c(C#N)cnn5c4)cn3)CC2)C1(C)C] | 6-(1-(1-(1-acryloyl-2,2-dimethylazetidine-3-carbonyl)piperidin-4-yl)-1H-pyrazol-4-yl)-4-methoxypyrazolo[1,5-a]pyridine-3-carbonitrile | 488.2 (M + H) |
| 44 | 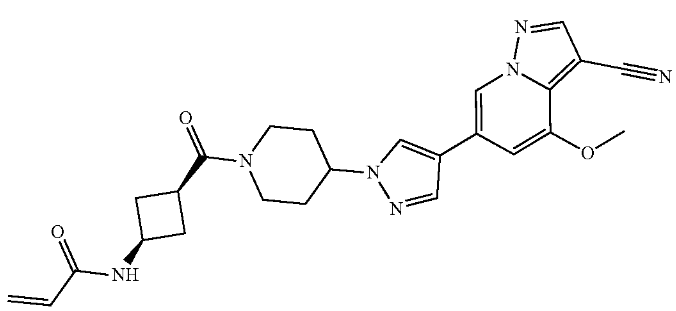 [SMILES: C=CC(=O)N[C@H]1C[C@@H](C(=O)N2CCC(n3cc(-c4cc(OC)c5c(C#N)cnn5c4)cn3)CC2)C1] | N-((1s,3s)-3-(4-(4-(3-cyano-4-methoxypyrazolo[1,5-a]pyridin-6-yl)-1H-pyrazol-1-yl)piperidine-1-carbonyl)cyclobutyl)acrylamide | 474.2 (M + H) |

TABLE C1-continued

| Ex # | Structure | Chemical Name | MS apci (m/z) |
|---|---|---|---|
| 45 | 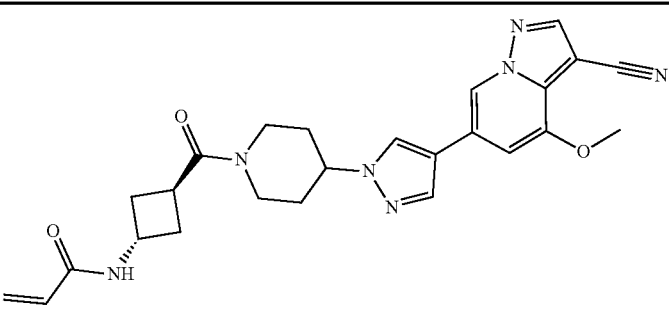 | N-((1r,3r)-3-(4-(4-(3-cyano-4-methoxypyrazolo[1,5-a]pyridin-6-yl)-1H-pyrazol-1-yl)piperidine-1-carbonyl)cyclobutyl)acrylamide | 474.3 (M + H) |
| 46 | 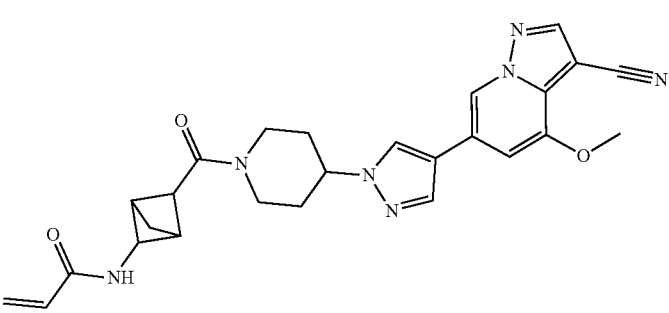 [SMILES: C=CC(=O)NC1C2CC1C2C(=O)N1CCC(n2cc(-c3cc(OC)c4c(C#N)cnn4c3)cn2)CC1] | N-(4-(4-(4-(3-cyano-4-methoxypyrazolo[1,5-a]pyridin-6-yl)-1H-pyrazol-1-yl)piperidine-1-carbonyl)bicyclo[1.1.1]pentan-2-yl)acrylamide | 486.1 (M + H) |
| 47 | 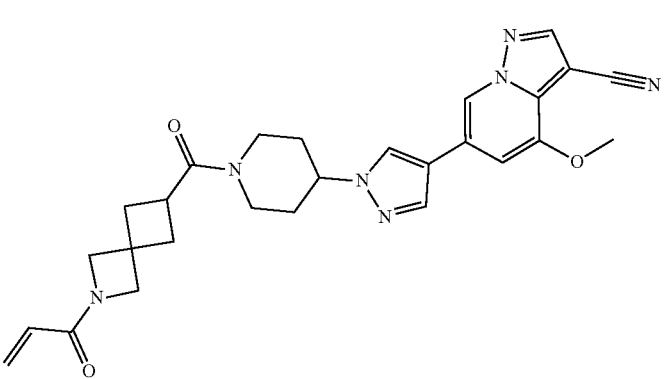 [SMILES: C=CC(=O)N1CC2(CC(C(=O)N3CCC(n4cc(-c5cc(OC)c6c(C#N)cnn6c5)cn4)CC3)C2)C1] | 6-(1-(1-(2-acryloyl-2-azaspiro[3.3]heptane-6-carbonyl)piperidin-4-yl)-1H-pyrazol-4-yl)-4-methoxypyrazolo[1,5-a]pyridine-3-carbonitrile | 500.2 (M + H) |
| 48 | 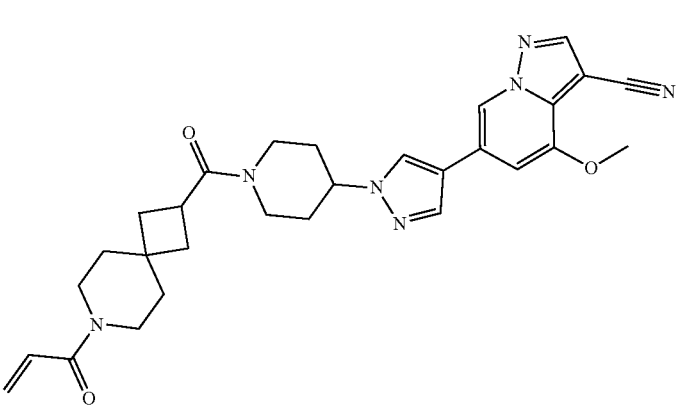 [SMILES: C=CC(=O)N1CCC2(CC1)CC(C(=O)N1CCC(n3cc(-c4cc(OC)c5c(C#N)cnn5c4)cn3)CC1)C2] | 6-(1-(1-(7-acryloyl-7-azaspiro[3.5]nonane-2-carbonyl)piperidin-4-yl)-1H-pyrazol-4-yl)-4-methoxypyrazolo[1,5-a]pyridine-3-carbonitrile | 528.3 (M + H) |

TABLE C1-continued

| Ex # | Structure | Chemical Name | MS apci (m/z) |
|---|---|---|---|
| 49 | 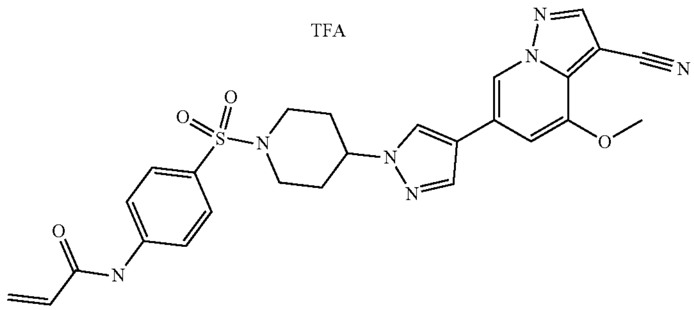 [SMILES: C=CC(=O)Nc1ccc(S(=O)(=O)N2CCC(n3cc(-c4cc(OC)c5c(C#N)cnn5c4)cn3)CC2)cc1] | N-(4-((4-(4-(3-cyano-4-methoxypyrazolo[1,5-a]pyridin-6-yl)-1H-pyrazol-1-yl)piperidin-1-yl)sulfonyl)phenyl)acrylamide (2,2,2-trifluoroacetate) | 530.2 (M − H) |
| 50 | 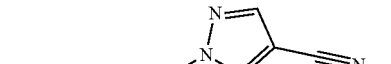 | 6-(6-(8-(1-acryloylazetidine-3-carbonyl)-3,8-diazabicyclo[3.2.1]octan-3-yl)pyridin-3-yl)-4-methoxypyrazolo[1,5-a]pyridine-3-carbonitrile | 498.2 (M + H) |
| 51 | 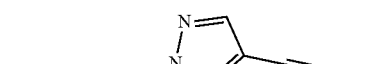 | 6-(6-(3-(1-acryloylazetidine-3-carbonyl)-3,8-diazabicyclo[3.2.1]octan-8-yl)pyridin-3-yl)-4-methoxypyrazolo[1,5-a]pyridine-3-carbonitrile | 498.2 (M + H) |
| 52 | 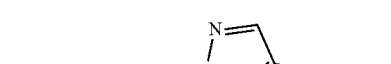 | 6-(6-(6-(1-acryloylazetidine-3-carbonyl)-3,6-diazabicyclo[3.1.1]heptan-3-yl)pyridin-3-yl)-4-methoxypyrazolo[1,5-a]pyridine-3-carbonitrile | 484.2 (M + H) |
| 53 | 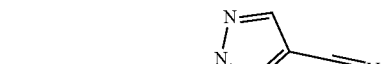 | (R)-6-(1-(1-(1-acryloylpiperidine-4-carbonyl)pyrrolidin-3-yl)-1H-pyrazol-4-yl)-4-methoxypyrazolo[1,5-a]pyridine-3-carbonitrile | 474.2 (M + H) |

| Ex # | Structure | Chemical Name | MS apci (m/z) |
|---|---|---|---|
| 54 | 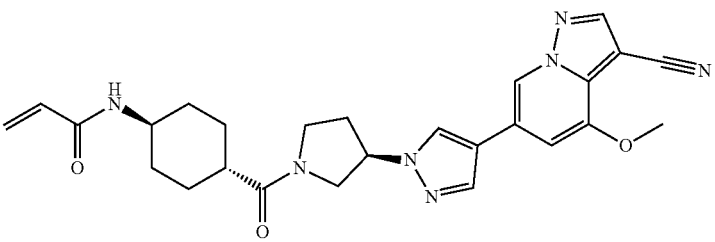 [SMILES: C=CC(=O)N[C@H]1CC[C@H](C(=O)N2CC[C@@H](n3cc(-c4cc(OC)c5c(C#N)cnn5c4)cn3)C2)CC1] | N-((1R,4r)-4-((R)-3-(4-(3-cyano-4-methoxypyrazolo[1,5-a]pyridin-6-yl)-1H-pyrazol-1-yl)pyrrolidine-1-carbonyl)cyclohexyl)acrylamide | 488.3 (M + H) |
| 55 | 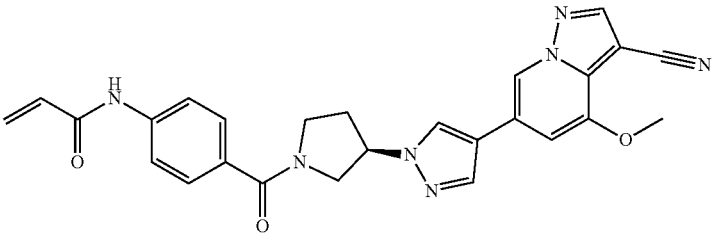 [SMILES: C=CC(=O)Nc1ccc(C(=O)N2CC[C@@H](n3cc(-c4cc(OC)c5c(C#N)cnn5c4)cn3)C2)cc1] | (R)-N-(4-(3-(4-(3-cyano-4-methoxypyrazolo[1,5-a]pyridin-6-yl)-1H-pyrazol-1-yl)pyrrolidine-1-carbonyl)phenyl)acrylamide | 482.2 (M + H) |
| 56 | 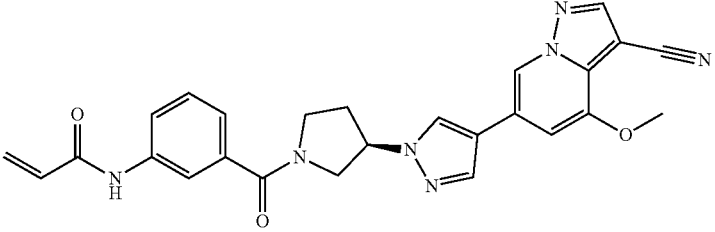 [SMILES: C=CC(=O)Nc1cccc(C(=O)N2CC[C@@H](n3cc(-c4cc(OC)c5c(C#N)cnn5c4)cn3)C2)c1] | (R)-N-(3-(3-(4-(3-cyano-4-methoxypyrazolo[1,5-a]pyridin-6-yl)-1H-pyrazol-1-yl)pyrrolidine-1-carbonyl)phenyl)acrylamide | 482.2 (M + H) |
| 57 | 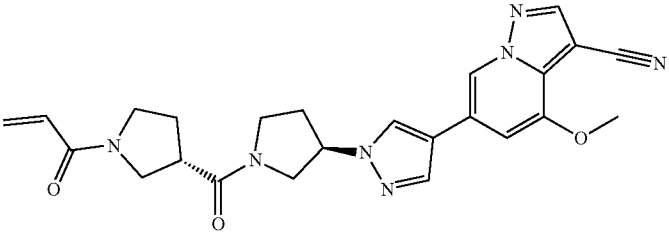 [SMILES: C=CC(=O)N1CC[C@H](C(=O)N2CC[C@@H](n3cc(-c4cc(OC)c5c(C#N)cnn5c4)cn3)C2)C1] | 6-(1-((R)-1-((S)-1-acryloylpyrrolidine-3-carbonyl)pyrrolidin-3-yl)-1H-pyrazol-4-yl)-4-methoxypyrazolo[1,5-a]pyridine-3-carbonitrile | 460.2 (M + H) |
| 58 | 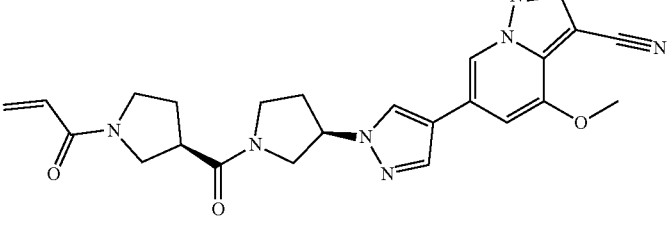 | 6-(1-((R)-1-((R)-1-acryloylpyrrolidine-3-carbonyl)pyrrolidin-3-yl)-1H-pyrazol-4-yl)-4-methoxypyrazolo[1,5-a]pyridine-3-carbonitrile | 460.2 (M + H) |
| 59 | 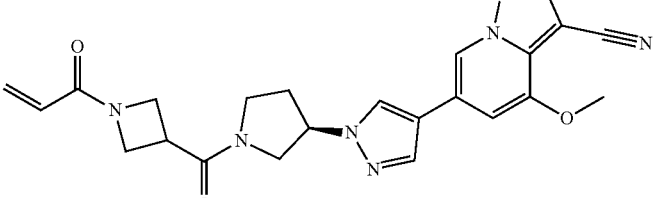 | (R)-6-(1-(1-(1-acryloylazetidine-3-carbonyl)pyrrolidin-3-yl)-1H-pyrazol-4-yl)-4-methoxypyrazolo[1,5-a]pyridine-3-carbonitrile | 446.2 (M + H) |

TABLE C1-continued

| Ex # | Structure | Chemical Name | MS apci (m/z) |
|---|---|---|---|
| 60 | 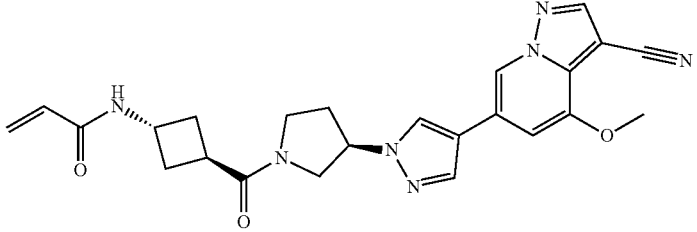 [SMILES: C=CC(=O)N[C@H]1C[C@H](C(=O)N2CC[C@@H](n3cc(-c4cc(OC)c5c(C#N)cnn5c4)cn3)C2)C1] | N-((1R,3r)-3-((R)-3-(4-(3-cyano-4-methoxypyrazolo[1,5-a]pyridin-6-yl)-1H-pyrazol-1-yl)pyrrolidine-1-carbonyl)cyclobutyl)acrylamide | 460.2 (M + H) |
| 61 | 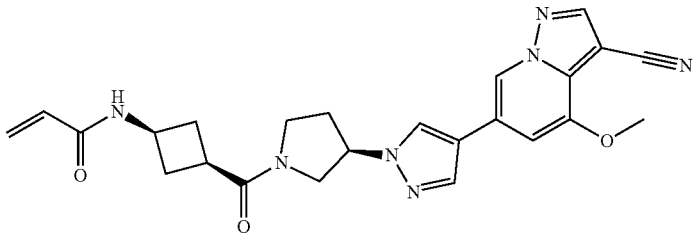 [SMILES: C=CC(=O)N[C@H]1C[C@@H](C(=O)N2CC[C@@H](n3cc(-c4cc(OC)c5c(C#N)cnn5c4)cn3)C2)C1] | N-((1S,3s)-3-((R)-3-(4-(3-cyano-4-methoxypyrazolo[1,5-a]pyridin-6-yl)-1H-pyrazol-1-yl)pyrrolidine-1-carbonyl)cyclobutyl)acrylamide | 460.2 (M + H) |
| 62 | 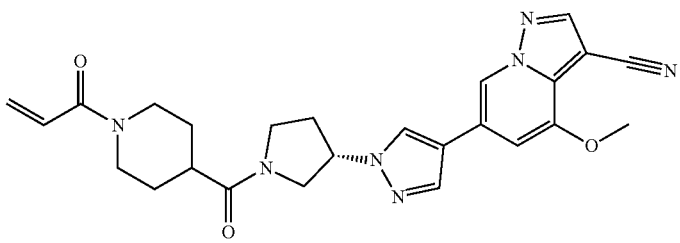 [SMILES: C=CC(=O)N1CCC(C(=O)N2CC[C@H](n3cc(-c4cc(OC)c5c(C#N)cnn5c4)cn3)C2)CC1] | (S)-6-(1-(1-(1-acryloylpiperidine-4-carbonyl)pyrrolidin-3-yl)-1H-pyrazol-4-yl)-4-methoxypyrazolo[1,5-a]pyridine-3-carbonitrile | 474.2 (M + H) |
| 63 | 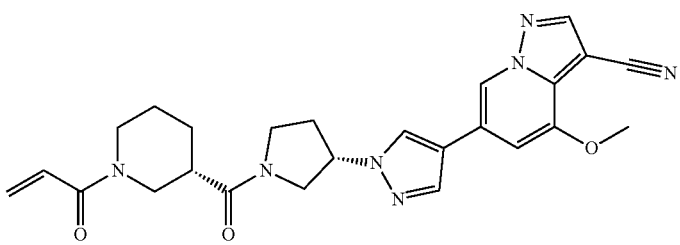 [SMILES: C=CC(=O)N1CCC[C@H](C(=O)N2CC[C@H](n3cc(-c4cc(OC)c5c(C#N)cnn5c4)cn3)C2)C1] | 6-(1-((S)-1-((S)-1-acryloylpiperidine-3-carbonyl)pyrrolidin-3-yl)-1H-pyrazol-4-yl)-4-methoxypyrazolo[1,5-a]pyridine-3-carbonitrile | 474.2 (M + H) |
| 64 | 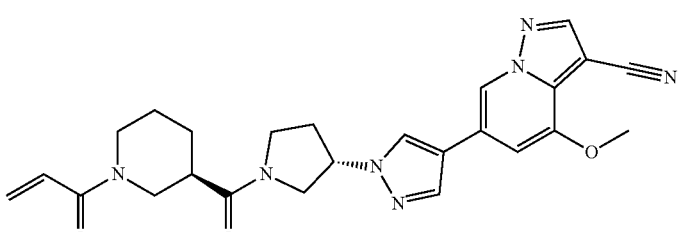 | 6-(1-((S)-1-((R)-1-acryloylpiperidine-3-carbonyl)pyrrolidin-3-yl)-1H-pyrazol-4-yl)-4-methoxypyrazolo[1,5-a]pyridine-3-carbonitrile | 474.2 (M + H) |
| 65 | 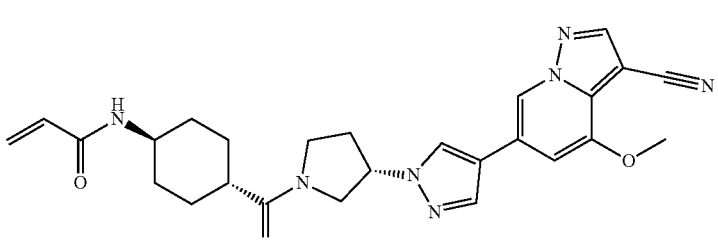 | N-((1S,4r)-4-((S)-3-(4-(3-cyano-4-methoxypyrazolo[1,5-a]pyridin-6-yl)-1H-pyrazol-1-yl)pyrrolidine-1-carbonyl)cyclohexyl)acrylamide | 488.3 (M + H) |

TABLE C1-continued

| Ex # | Structure | Chemical Name | MS apci (m/z) |
|---|---|---|---|
| 66 | 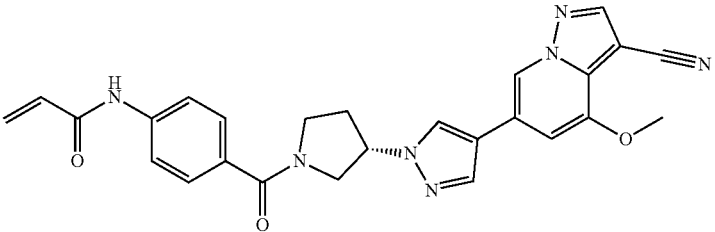 [SMILES: C=CC(=O)Nc1ccc(C(=O)N2CC[C@H](n3cc(-c4cc(OC)c5c(C#N)cnn5c4)cn3)C2)cc1] | (S)-N-(4-(3-(4-(3-cyano-4-methoxypyrazolo[1,5-a]pyridin-6-yl)-1H-pyrazol-1-yl)pyrrolidine-1-carbonyl)phenyl)acrylamide | 480.2 (M − H) |
| 67 | 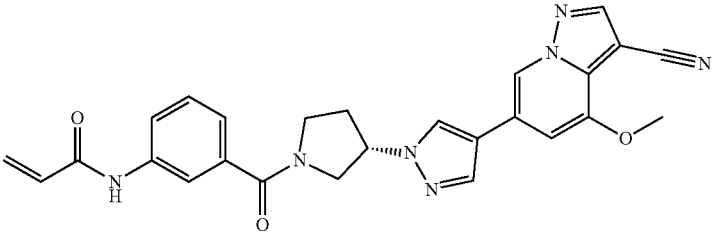 [SMILES: C=CC(=O)Nc1cccc(C(=O)N2CC[C@H](n3cc(-c4cc(OC)c5c(C#N)cnn5c4)cn3)C2)c1] | (S)-N-(3-(3-(4-(3-cyano-4-methoxypyrazolo[1,5-a]pyridin-6-yl)-1H-pyrazol-1-yl)pyrrolidine-1-carbonyl)phenyl)acrylamide | 482.2 (M + H) |
| 68 | 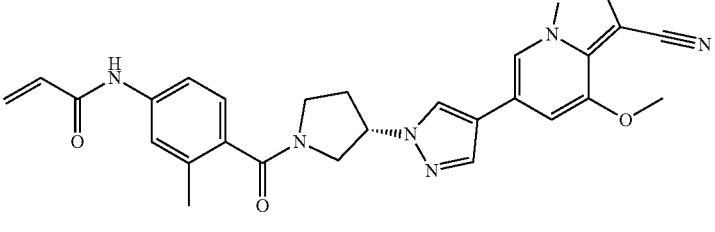 | (S)-N-(4-(3-(4-(3-cyano-4-methoxypyrazolo[1,5-a]pyridin-6-yl)-1H-pyrazol-1-yl)pyrrolidine-1-carbonyl)-3-methylphenyl)acrylamide | 496.2 (M + H) |
| 69 | 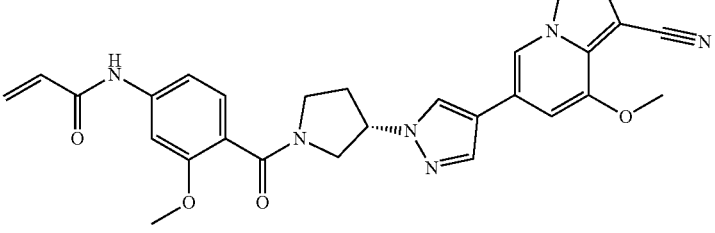 | (S)-N-(4-(3-(4-(3-cyano-4-methoxypyrazolo[1,5-a]pyridin-6-yl)-1H-pyrazol-1-yl)pyrrolidine-1-carbonyl)-3-methoxyphenyl)acrylamide | 512.2 (M + H) |
| 70 | 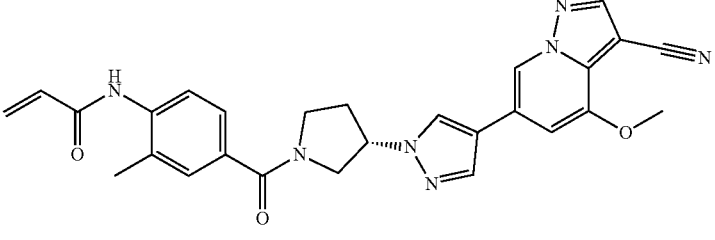 [SMILES: C=CC(=O)Nc1ccc(C(=O)N2CC[C@H](n3cc(-c4cc(OC)c5c(C#N)cnn5c4)cn3)C2)cc1C] | (S)-N-(4-(3-(4-(3-cyano-4-methoxypyrazolo[1,5-a]pyridin-6-yl)-1H-pyrazol-1-yl)pyrrolidine-1-carbonyl)-2-methylphenyl)acrylamide | 496.2 (M + H) |
| 71 | 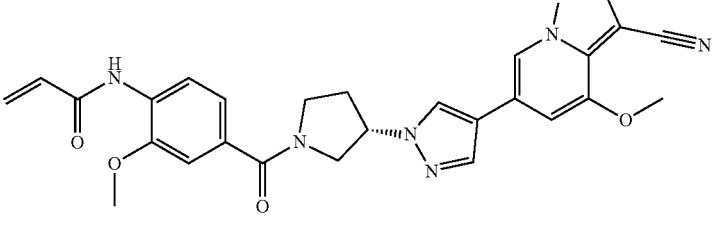 | (S)-N-(4-(3-(4-(3-cyano-4-methoxypyrazolo[1,5-a]pyridin-6-yl)-1H-pyrazol-1-yl)pyrrolidine-1-carbonyl)-2-methoxyphenyl)acrylamide | 512.2 (M + H) |

TABLE C1-continued

| Ex # | Chemical Name | MS apci (m/z) |
|---|---|---|
| 72 | 6-(1-((S)-1-((R)-1-acryloylpyrrolidine-3-carbonyl)pyrrolidin-3-yl)-1H-pyrazol-4-yl)-4-methoxypyrazolo[1,5-a]pyridine-3-carbonitrile | 460.2 (M + H) |
| 73 | (S)-6-(1-(1-(1-acryloylazetidine-3-carbonyl)pyrrolidin-3-yl)-1H-pyrazol-4-yl)-4-methoxypyrazolo[1,5-a]pyridine-3-carbonitrile | 446.2 (M + H) |
| 74 | N-((1S,3r)-3-((S)-3-(4-(3-cyano-4-methoxypyrazolo[1,5-a]pyridin-6-yl)-1H-pyrazol-1-yl)pyrrolidine-1-carbonyl)cyclobutyl)acrylamide | 460.2 (M + H) |
| 75 | 6-(1-(1-(1-acryloylpiperidine-4-carbonyl)azetidin-3-yl)-1H-pyrazol-4-yl)-4-methoxypyrazolo[1,5-a]pyridine-3-carbonitrile | 460.2 (M + H) |
| 76 | (S)-6-(1-(1-(1-acryloylpyrrolidine-3-carbonyl)azetidin-3-yl)-1H-pyrazol-4-yl)-4-methoxypyrazolo[1,5-a]pyridine-3-carbonitrile | 446.2 (M + H) |
| 77 | N-((1S,3S)-3-(3-(4-(3-cyano-4-methoxypyrazolo[1,5-a]pyridin-6-yl)-1H-pyrazol-1-yl)azetidine-1-carbonyl)cyclopentyl)acrylamide | 460.2 (M + H) |

TABLE C1-continued

| Ex # | Structure | Chemical Name | MS apci (m/z) |
|---|---|---|---|
| 78 | 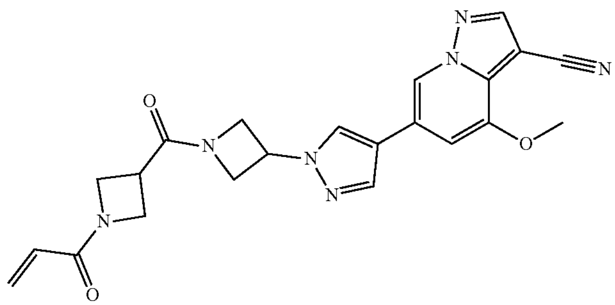 [SMILES: C=CC(=O)N1CC(C(=O)N2CC(n3cc(-c4cc(OC)c5c(C#N)cnn5c4)cn3)C2)C1] | 6-(1-(1-(1-acryloylazetidine-3-carbonyl)azetidin-3-yl)-1H-pyrazol-4-yl)-4-methoxypyrazolo[1,5-a]pyridine-3-carbonitrile | 432.2 (M + H) |
| 79 | 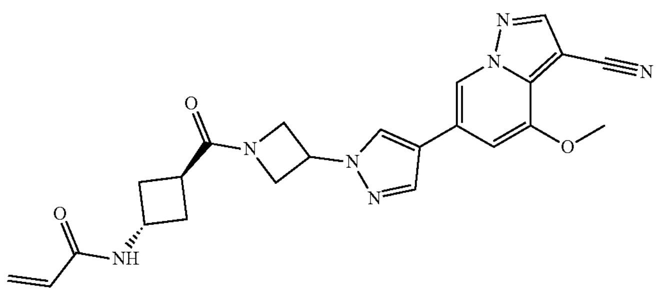 [SMILES: C=CC(=O)N[C@H]1C[C@H](C(=O)N2CC(n3cc(-c4cc(OC)c5c(C#N)cnn5c4)cn3)C2)C1] | N-((1r,3r)-3-(3-(4-(3-cyano-4-methoxypyrazolo[1,5-a]pyridin-6-yl)-1H-pyrazol-1-yl)azetidine-1-carbonyl)cyclobutyl)acrylamide | 446.2 (M + H) |
| 80 | 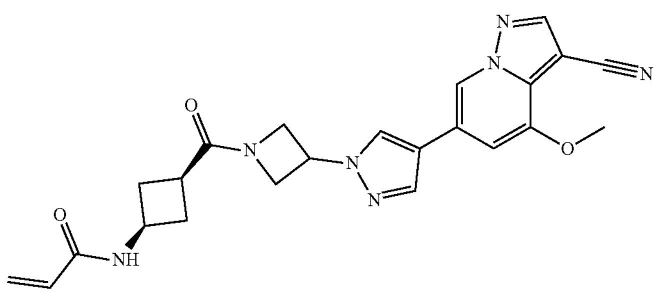 [SMILES: C=CC(=O)N[C@H]1C[C@@H](C(=O)N2CC(n3cc(-c4cc(OC)c5c(C#N)cnn5c4)cn3)C2)C1] | N-((1s,3s)-3-(3-(4-(3-cyano-4-methoxypyrazolo[1,5-a]pyridin-6-yl)-1H-pyrazol-1-yl)azetidine-1-carbonyl)cyclobutyl)acrylamide | 446.2 (M + H) |
| 81 | 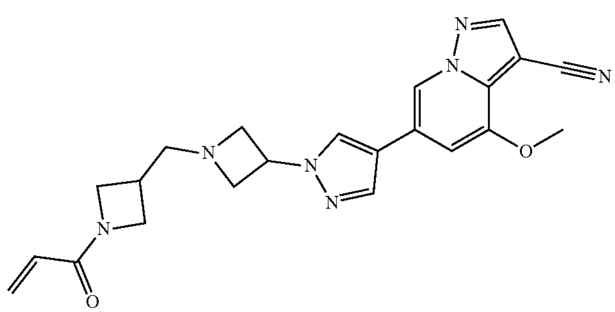 [SMILES: C=CC(=O)N1CC(CN2CC(n3cc(-c4cc(OC)c5c(C#N)cnn5c4)cn3)C2)C1] | 6-(1-(1-((1-acryloylazetidin-3-yl)methyl)azetidin-3-yl)-1H-pyrazol-4-yl)-4-methoxypyrazolo[1,5-a]pyridine-3-carbonitrile | 418.1 (M + H) |
| 82 | 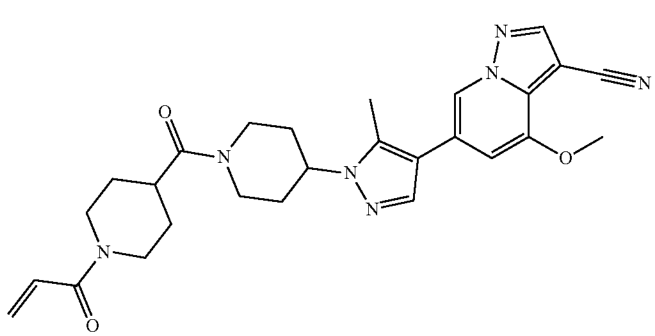 [SMILES: C=CC(=O)N1CCC(C(=O)N2CCC(n3ncc(-c4cc(OC)c5c(C#N)cnn5c4)c3C)CC2)CC1] | 6-(1-(1-(1-acryloylpiperidine-4-carbonyl)piperidin-4-yl)-5-methyl-1H-pyrazol-4-yl)-4-methoxypyrazolo[1,5-a]pyridine-3-carbonitrile | 502.2 (M + H) |

TABLE C1-continued

| Ex # | Chemical Name | MS apci (m/z) |
|---|---|---|
| 83 | (R)-6-(1-(1-(1-acryloylpyrrolidine-3-carbonyl)piperidin-4-yl)-5-methyl-1H-pyrazol-4-yl)-4-methoxypyrazolo[1,5-a]pyridine-3-carbonitrile | 488.3 (M + H) |
| 84 | 6-(1-(1-(1-acryloylazetidine-3-carbonyl)piperidin-4-yl)-5-methyl-1H-pyrazol-4-yl)-4-methoxypyrazolo[1,5-a]pyridine-3-carbonitrile | 474.2 (M + H) |
| 85 | 6-(1-(1-(1-acryloyl-3-fluoroazetidine-3-carbonyl)piperidin-4-yl)-5-methyl-1H-pyrazol-4-yl)-4-methoxypyrazolo[1,5-a]pyridine-3-carbonitrile | 492.2 (M + H) |
| 86 | 6-(1-(1-(1-acryloyl-3-methylazetidine-3-carbonyl)piperidin-4-yl)-5-methyl-1H-pyrazol-4-yl)-4-methoxypyrazolo[1,5-a]pyridine-3-carbonitrile | 488.2 (M + H) |
| 87 | 6-(1-(1-(1-acryloyl-2,2-dimethylazetidine-3-carbonyl)piperidin-4-yl)-5-methyl-1H-pyrazol-4-yl)-4-methoxypyrazolo[1,5-a]pyridine-3-carbonitrile | 502.3 (M + H) |

TABLE C1-continued

| Ex # | Structure | Chemical Name | MS apci (m/z) |
|---|---|---|---|
| 88 | 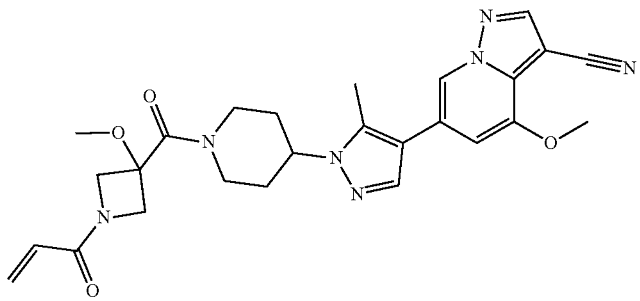 [SMILES: C=CC(=O)N1CC(OC)(C(=O)N2CCC(n3ncc(-c4cc(OC)c5c(C#N)cnn5c4)c3C)CC2)C1] | 6-(1-(1-(1-acryloyl-3-methoxyazetidine-3-carbonyl)piperidin-4-yl)-5-methyl-1H-pyrazol-4-yl)-4-methoxypyrazolo[1,5-a]pyridine-3-carbonitrile | 504.2 (M + H) |
| 89 | 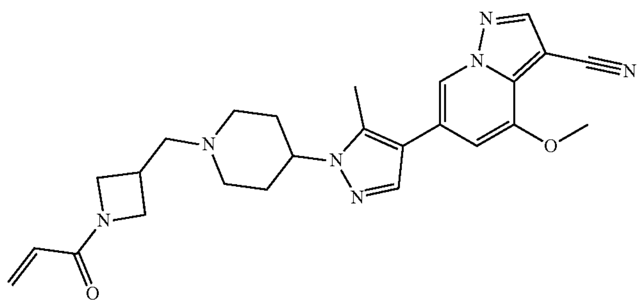 [SMILES: C=CC(=O)N1CC(CN2CCC(n3ncc(-c4cc(OC)c5c(C#N)cnn5c4)c3C)CC2)C1] | 6-(1-(1-((1-acryloylazetidin-3-yl)methyl)piperidin-4-yl)-5-methyl-1H-pyrazol-4-yl)-4-methoxypyrazolo[1,5-a]pyridine-3-carbonitrile | 460.2 (M + H) |
| 90 | 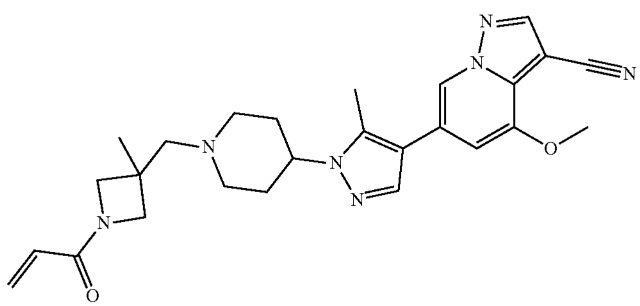 [SMILES: C=CC(=O)N1CC(C)(CN2CCC(n3ncc(-c4cc(OC)c5c(C#N)cnn5c4)c3C)CC2)C1] | 6-(1-(1-((1-acryloyl-3-methylazetidin-3-yl)methyl)piperidin-4-yl)-5-methyl-1H-pyrazol-4-yl)-4-methoxypyrazolo[1,5-a]pyridine-3-carbonitrile | 474.2 (M + H) |
| 91 | 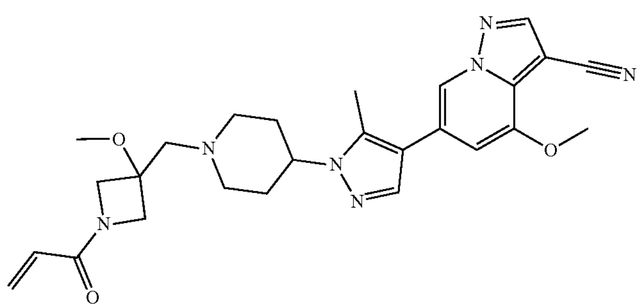 [SMILES: C=CC(=O)N1CC(CN2CCC(n3ncc(-c4cc(OC)c5c(C#N)cnn5c4)c3C)CC2)(OC)C1] | 6-(1-(1-((1-acryloyl-3-methoxyazetidin-3-yl)methyl)piperidin-4-yl)-5-methyl-1H-pyrazol-4-yl)-4-methoxypyrazolo[1,5-a]pyridine-3-carbonitrile | 490.2 (M + H) |
| 92 | 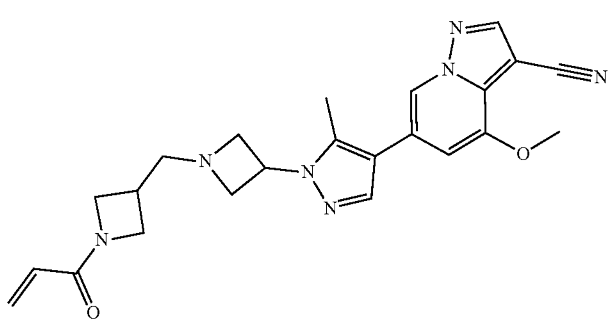 [SMILES: C=CC(=O)N1CC(CN2CC(n3ncc(-c4cc(OC)c5c(C#N)cnn5c4)c3C)C2)C1] | 6-(1-(1-((1-acryloylazetidin-3-yl)methyl)piperidin-4-yl)-5-methyl-1H-pyrazol-4-yl)-4-methoxypyrazolo[1,5-a]pyridine-3-carbonitrile | 432.2 (M + H) |

TABLE C1-continued

| Ex # | Structure | Chemical Name | MS apci (m/z) |
|---|---|---|---|
| 93 | 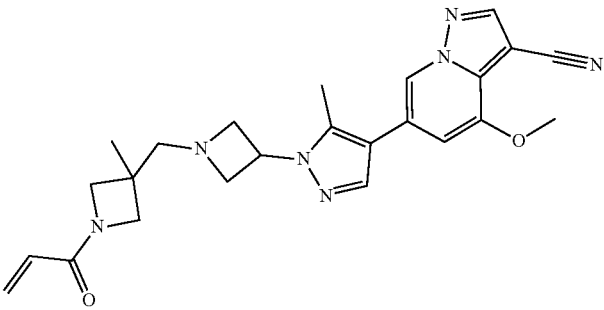 [SMILES: C=CC(=O)N1CC(C)(CN2CC(n3ncc(-c4cc(OC)c5c(C#N)cnn5c4)c3C)C2)C1] | 6-(1-(1-((1-acryloyl-3-methylazetidin-3-yl)methyl)azetidin-3-yl)-5-methyl-1H-pyrazol-4-yl)-4-methoxypyrazolo[1,5-a]pyridine-3-carbonitrile | 446.2 (M + H) |
| 94 | 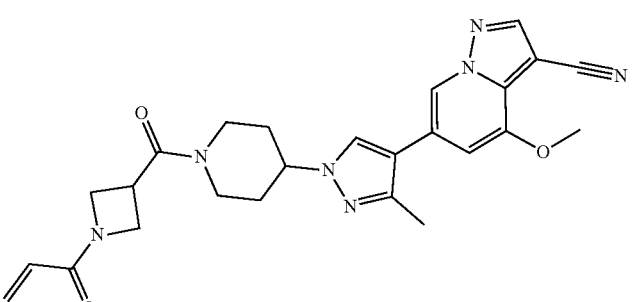 | 6-(1-(1-(1-acryloylazetidine-3-carbonyl)piperidin-4-yl)-3-methyl-1H-pyrazol-4-yl)-4-methoxypyrazolo[1,5-a]pyridine-3-carbonitrile | 474.2 (M + H) |
| 95 | 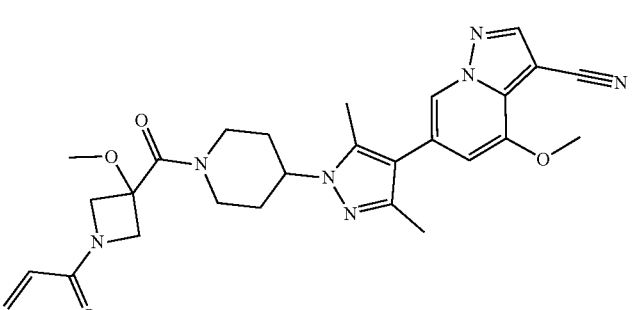 | 6-(1-(1-(1-acryloyl-3-methoxyazetidine-3-carbonyl)piperidin-4-yl)-3,5-dimethyl-1H-pyrazol-4-yl)-4-methoxypyrazolo[1,5-a]pyridine-3-carbonitrile | 518.2 (M + H) |
| 96 | 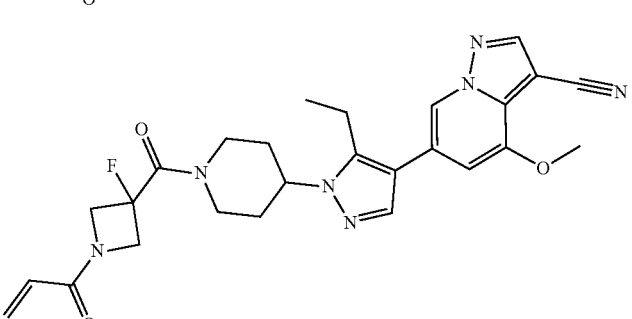 | 6-(1-(1-(1-acryloyl-3-fluoroazetidine-3-carbonyl)piperidin-4-yl)-5-ethyl-1H-pyrazol-4-yl)-4-methoxypyrazolo[1,5-a]pyridine-3-carbonitrile | 506.2 (M + H) |
| 97 | 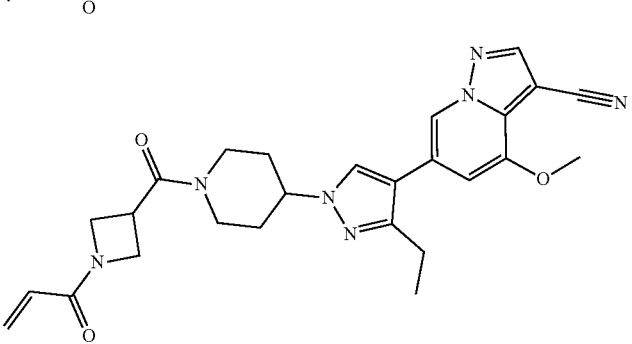 | 6-(1-(1-(1-acryloylazetidine-3-carbonyl)piperidin-4-yl)-3-ethyl-1H-pyrazol-4-yl)-4-methoxypyrazolo[1,5-a]pyridine-3-carbonitrile | 488.2 (M + H) |

TABLE C1-continued

| Ex # | Structure | Chemical Name | MS apci (m/z) |
|---|---|---|---|
| 98 | 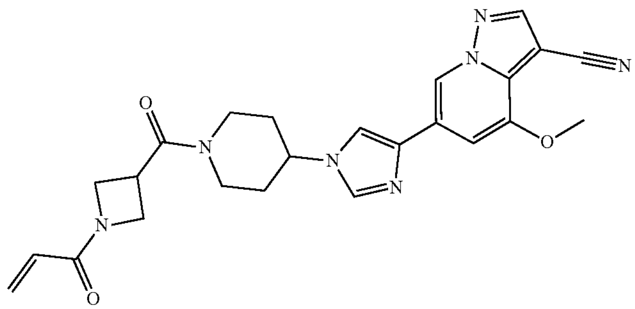 [SMILES: C=CC(=O)N1CC(C(=O)N2CCC(n3cnc(-c4cc(OC)c5c(C#N)cnn5c4)c3)CC2)C1] | 6-(1-(1-(1-acryloylazetidine-3-carbonyl)piperidin-4-yl)-1H-imidazol-4-yl)-4-methoxypyrazolo[1,5-a]pyridine-3-carbonitrile | 460.2 (M + H) |
| 99 | 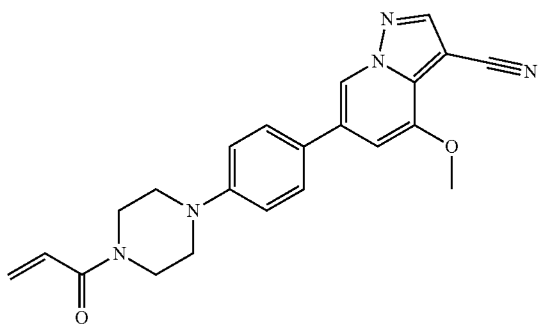 [SMILES: C=CC(=O)N1CCN(c2ccc(-c3cc(OC)c4c(C#N)cnn4c3)cc2)CC1] | 6-(4-(4-acryloylpiperazin-1-yl)phenyl)-4-methoxypyrazolo[1,5-a]pyridine-3-carbonitrile | 388.2 (M + H) |
| 100 | 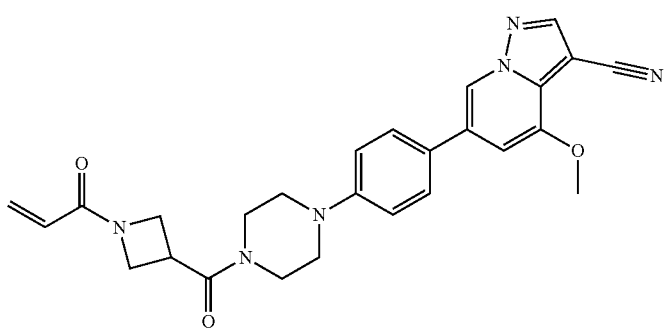 | 6-(4-(4-(1-acryloylazetidine-3-carbonyl)piperazin-1-yl)phenyl)-4-methoxypyrazolo[1,5-a]pyridine-3-carbonitrile | 471.2 (M + H) |
| 101 | 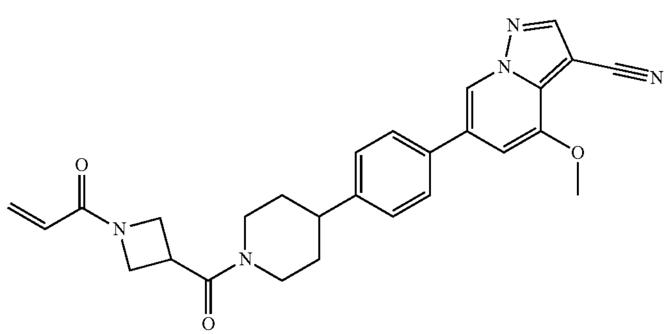 [SMILES: C=CC(=O)N1CC(C(=O)N2CCC(c3ccc(-c4cc(OC)c5c(C#N)cnn5c4)cc3)CC2)C1] | 6-(4-(1-(1-acryloylazetidine-3-carbonyl)piperidin-4-yl)phenyl)-4-methoxypyrazolo[1,5-a]pyridine-3-carbonitrile | 470.2 (M + H) |

TABLE C1-continued

| Ex # | Structure | Chemical Name | MS apci (m/z) |
|---|---|---|---|
| 102 | 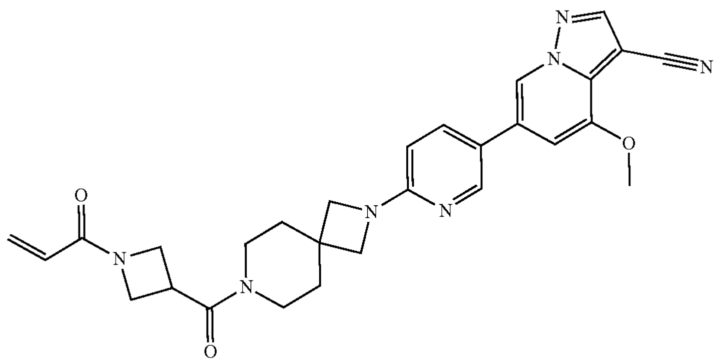 [SMILES: C=CC(=O)N1CC(C(=O)N2CCC3(CC2)CN(c2ccc(-c4cc(OC)c5c(C#N)cnn5c4)cn2)C3)C1] | 6-(6-(7-(1-acryloylazetidine-3-carbonyl)-2,7-diazaspiro[3.5]nonan-2-yl)pyridin-3-yl)-4-methoxypyrazolo[1,5-a]pyridine-3-carbonitrile | 512.3 (M + H) |
| 103 | 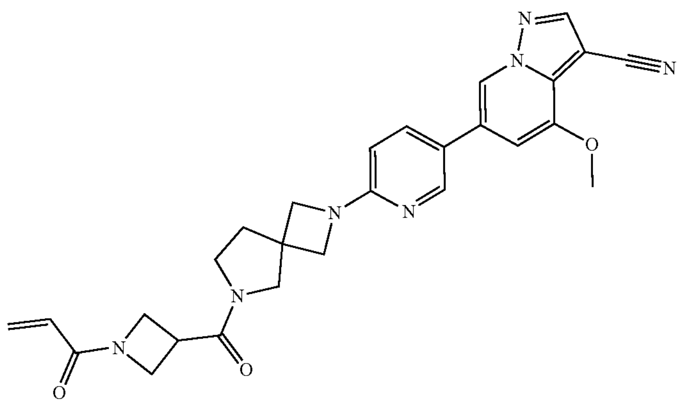 [SMILES: C=CC(=O)N1CC(C(=O)N2CCC3(C2)CN(c2ccc(-c4cc(OC)c5c(C#N)cnn5c4)cn2)C3)C1] | 6-(6-(6-(1-acryloylazetidine-3-carbonyl)-2,6-diazaspiro[3.4]octan-2-yl)pyridin-3-yl)-4-methoxypyrazolo[1,5-a]pyridine-3-carbonitrile | 498.2 (M + H) |
| 104 | 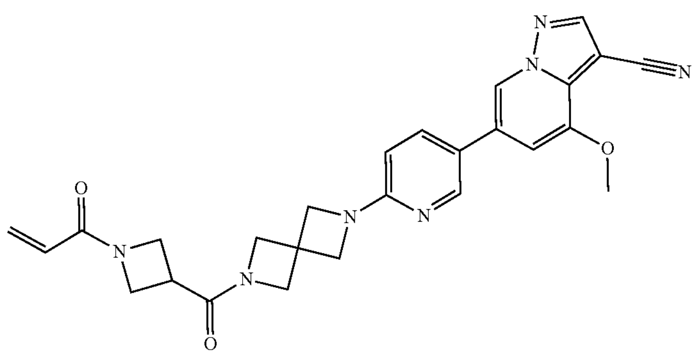 [SMILES: C=CC(=O)N1CC(C(=O)N2CC3(C2)CN(c2ccc(-c4cc(OC)c5c(C#N)cnn5c4)cn2)C3)C1] | 6-(6-(6-(1-acryloylazetidine-3-carbonyl)-2,6-diazaspiro[3.3]heptan-2-yl)pyridin-3-yl)-4-methoxypyrazolo[1,5-a]pyridine-3-carbonitrile | 484.2 (M + H) |
| 105 | 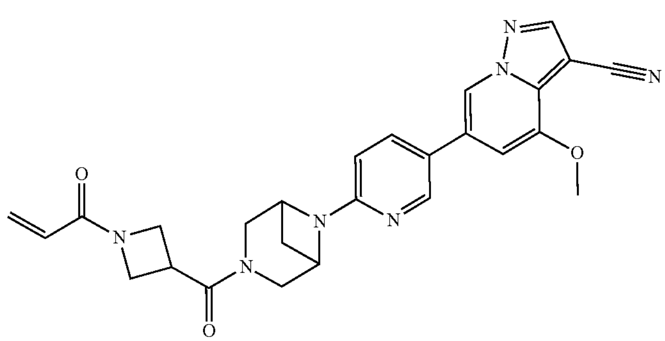 [SMILES: C=CC(=O)N1CC(C(=O)N2CC3CC(C2)N3c2ccc(-c3cc(OC)c4c(C#N)cnn4c3)cn2)C1] | 6-(6-(3-(1-acryloylazetidine-3-carbonyl)-3,6-diazabicyclo[3.1.1]heptan-6-yl)pyridin-3-yl)-4-methoxypyrazolo[1,5-a]pyridine-3-carbonitrile | 484.2 (M + H) |

TABLE C1-continued

| Ex # | Structure | Chemical Name | MS apci (m/z) |
|---|---|---|---|
| 106 | 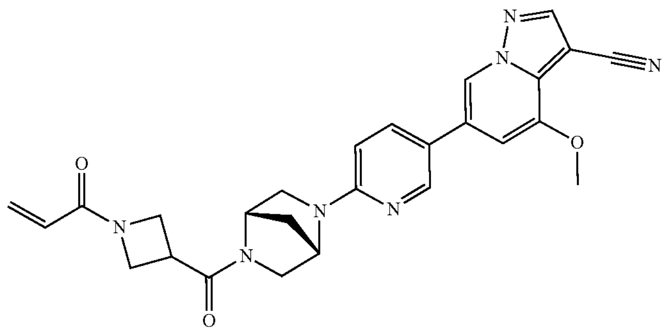 [SMILES: C=CC(=O)N1CC(C(=O)N2C[C@@H]3C[C@H]2CN3c2ccc(-c3cc(OC)c4c(C#N)cnn4c3)cn2)C1] | 6-(6-((1S,4S)-5-(1-acryloylazetidine-3-carbonyl)-2,5-diazabicyclo[2.2.1]heptan-2-yl)pyridin-3-yl)-4-methoxypyrazolo[1,5-a]pyridine-3-carbonitrile | 484.2 (M + H) |
| 107 | 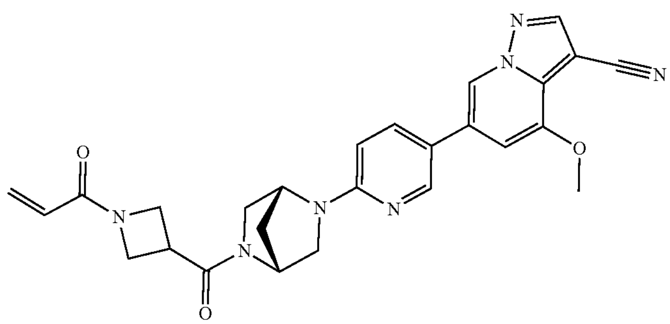 [SMILES: C=CC(=O)N1CC(C(=O)N2C[C@H]3C[C@@H]2CN3c2ccc(-c3cc(OC)c4c(C#N)cnn4c3)cn2)C1] | 6-(6-((1R,4R)-5-(1-acryloylazetidine-3-carbonyl)-2,5-diazabicyclo[2.2.1]heptan-2-yl)pyridin-3-yl)-4-methoxypyrazolo[1,5-a]pyridine-3-carbonitrile | 484.2 (M + H) |
| 108 | 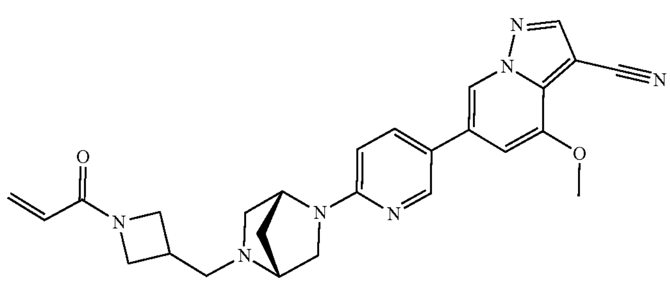 [SMILES: C=CC(=O)N1CC(CN2C[C@H]3C[C@@H]2CN3c2ccc(-c3cc(OC)c4c(C#N)cnn4c3)cn2)C1] | 6-(6-((1R,4R)-5-((1-acryloylazetidin-3-yl)methyl)-2,5-diazabicyclo[2.2.1]heptan-2-yl)pyridin-3-yl)-4-methoxypyrazolo[1,5-a]pyridine-3-carbonitrile | 470.2 (M + H) |
| 109 | 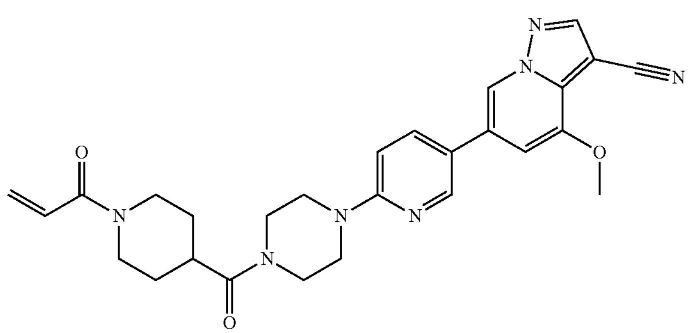 [SMILES: C=CC(=O)N1CCC(C(=O)N2CCN(c3ccc(-c4cc(OC)c5c(C#N)cnn5c4)cn3)CC2)CC1] | 6-(6-(4-(1-acryloylpiperidine-4-carbonyl)piperazin-1-yl)pyridin-3-yl)-4-methoxypyrazolo[1,5-a]pyridine-3-carbonitrile | 500.2 (M + H) |
| 110 | 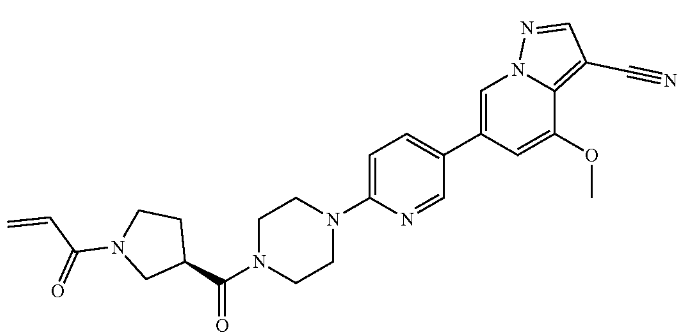 [SMILES: C=CC(=O)N1CC[C@@H](C(=O)N2CCN(c3ccc(-c4cc(OC)c5c(C#N)cnn5c4)cn3)CC2)C1] | (R)-6-(6-(4-(1-acryloylpyrrolidine-3-carbonyl)piperazin-1-yl)pyridin-3-yl)-4-methoxypyrazolo[1,5-a]pyridine-3-carbonitrile | 486.2 (M + H) |

TABLE C1-continued

| Ex # | Structure | Chemical Name | MS apci (m/z) |
|---|---|---|---|
| 111 | 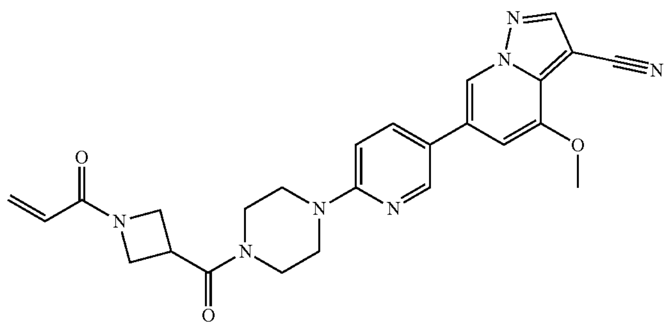 [SMILES: C=CC(=O)N1CC(C(=O)N2CCN(c3ccc(-c4cc(OC)c5c(C#N)cnn5c4)cn3)CC2)C1] | 6-(6-(4-(1-acryloylazetidine-3-carbonyl)piperazin-1-yl)pyridin-3-yl)-4-methoxypyrazolo[1,5-a]pyridine-3-carbonitrile | 472.2 (M + H) |
| 112 | 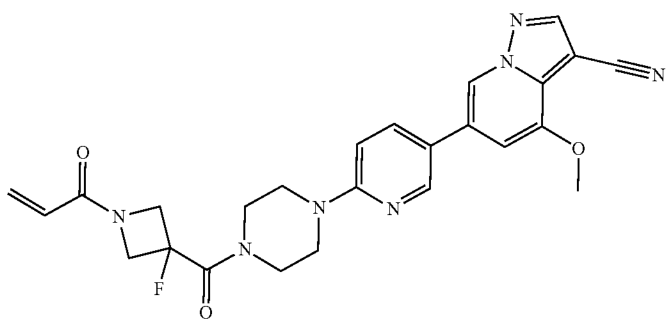 [SMILES: C=CC(=O)N1CC(F)(C(=O)N2CCN(c3ccc(-c4cc(OC)c5c(C#N)cnn5c4)cn3)CC2)C1] | 6-(6-(4-(1-acryloyl-3-fluoroazetidine-3-carbonyl)piperazin-1-yl)pyridin-3-yl)-4-methoxypyrazolo[1,5-a]pyridine-3-carbonitrile | 490.2 (M + H) |
| 113 | 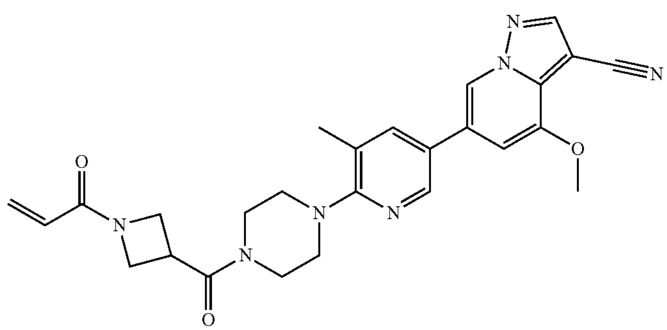 [SMILES: C=CC(=O)N1CC(C(=O)N2CCN(c3ncc(-c4cc(OC)c5c(C#N)cnn5c4)cc3C)CC2)C1] | 6-(6-(4-(1-acryloylazetidine-3-carbonyl)piperazin-1-yl)-5-methylpyridin-3-yl)-4-methoxypyrazolo[1,5-a]pyridine-3-carbonitrile | 486.2 (M + H) |
| 114 | 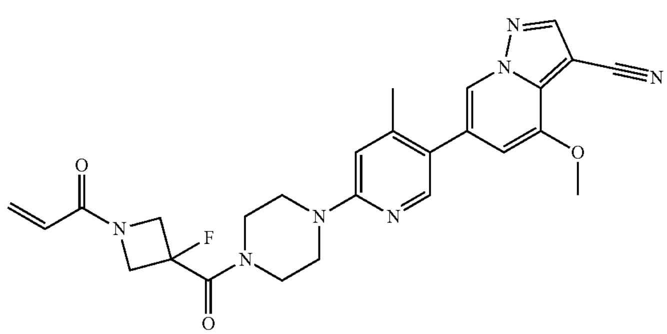 [SMILES: C=CC(=O)N1CC(F)(C(=O)N2CCN(c3cc(C)c(-c4cc(OC)c5c(C#N)cnn5c4)cn3)CC2)C1] | 6-(6-(4-(1-acryloyl-3-fluoroazetidine-3-carbonyl)piperazin-1-yl)-4-methylpyridin-3-yl)-4-methoxypyrazolo[1,5-a]pyridine-3-carbonitrile | 504.2 (M + H) |

TABLE C1-continued

| Ex # | Structure | Chemical Name | MS apci (m/z) |
|---|---|---|---|
| 115 | 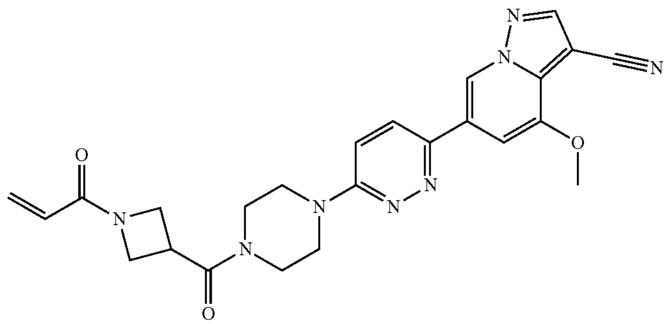 [SMILES: C=CC(=O)N1CC(C(=O)N2CCN(c3ccc(-c4cc(OC)c5c(C#N)cnn5c4)nn3)CC2)C1] | 6-(6-(4-(1-acryloylazetidine-3-carbonyl)piperazin-1-yl)pyridazin-3-yl)-4-methoxypyrazolo[1,5-a]pyridine-3-carbonitrile | 473.2 (M + H) |
| 116 | 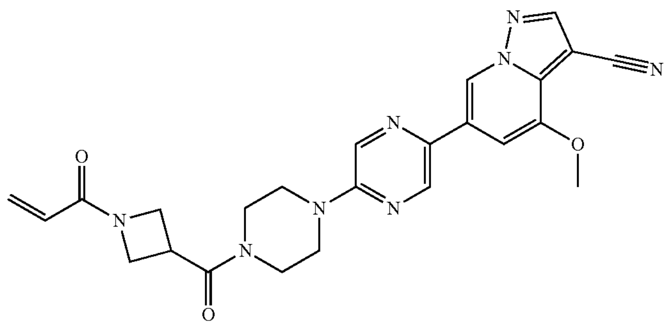 [SMILES: C=CC(=O)N1CC(C(=O)N2CCN(c3cnc(-c4cc(OC)c5c(C#N)cnn5c4)cn3)CC2)C1] | 6-(5-(4-(1-acryloylazetidine-3-carbonyl)piperazin-1-yl)pyrazin-2-yl)-4-methoxypyrazolo[1,5-a]pyridine-3-carbonitrile | 473.2 (M + H) |
| 117 | 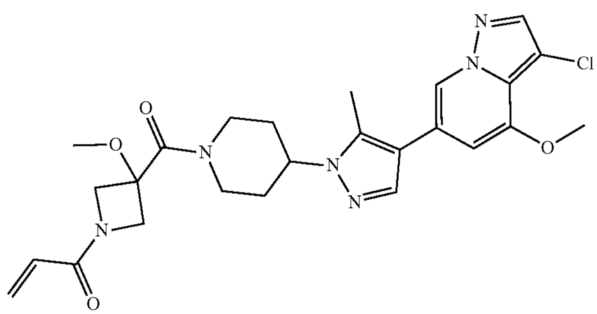 [SMILES: C=CC(=O)N1CC(OC)(C(=O)N2CCC(n3ncc(-c4cc(OC)c5c(Cl)cnn5c4)c3C)CC2)C1] | 1-(3-(4-(4-(3-chloro-4-methoxypyrazolo[1,5-a]pyridin-6-yl)-5-methyl-1H-pyrazol-1-yl)piperidine-1-carbonyl)-3-methoxyazetidin-1-yl)prop-2-en-1-one | 513.1 (M + H) |
| 118 | 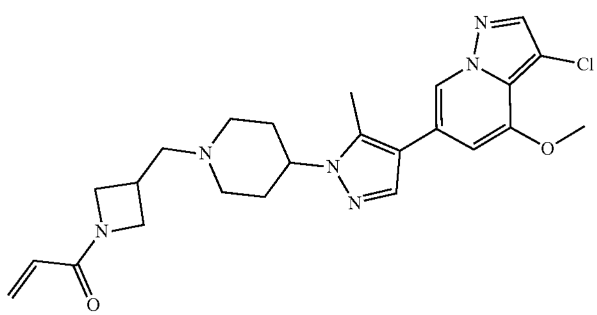 [SMILES: C=CC(=O)N1CC(CN2CCC(n3ncc(-c4cc(OC)c5c(Cl)cnn5c4)c3C)CC2)C1] | 1-(3-((4-(4-(3-chloro-4-methoxypyrazolo[1,5-a]pyridin-6-yl)-5-methyl-1H-pyrazol-1-yl)piperidin-1-yl)methyl)azetidin-1-yl)prop-2-en-1-one | 469.1 (M + H) |
| 119 | 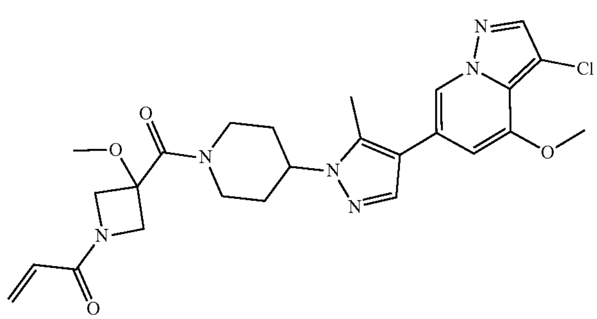 | 1-(3-((4-(4-(3-chloro-4-methoxypyrazolo[1,5-a]pyridin-6-yl)-5-methyl-1H-pyrazol-1-yl)piperidin-1-yl)methyl)-3-methoxyazetidin-1-yl)prop-2-en-1-one | 499.2 (M + H) |

TABLE C1-continued

| Ex # | Structure | Chemical Name | MS apci (m/z) |
|---|---|---|---|
| 120 | 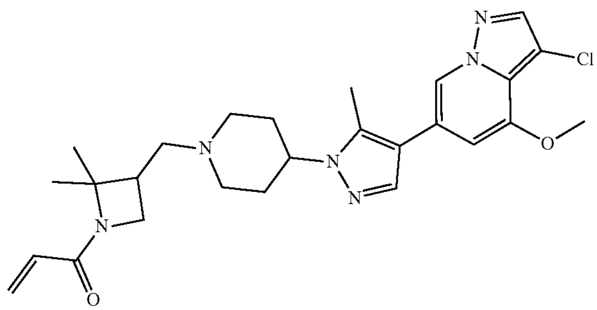 [SMILES: C=CC(=O)N1CC(CN2CCC(n3ncc(-c4cc(OC)c5c(Cl)cnn5c4)c3C)CC2)C1(C)C] | 1-(3-((4-(4-(3-chloro-4-methoxypyrazolo[1,5-a]pyridin-6-yl)-5-methyl-1H-pyrazol-1-yl)piperidin-1-yl)methyl)-2,2-dimethylazetidin-1-yl)prop-2-en-1-one | 497.2 (M + H) |
| 121 | 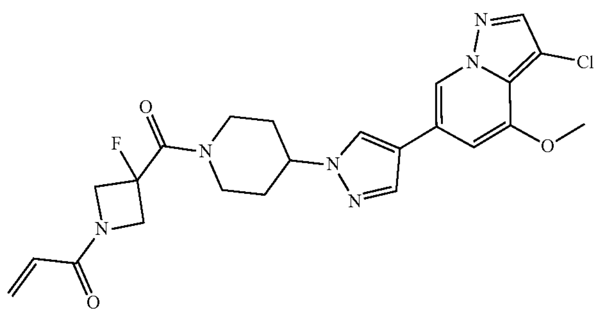 [SMILES: C=CC(=O)N1CC(F)(C(=O)N2CCC(n3cc(-c4cc(OC)c5c(Cl)cnn5c4)cn3)CC2)C1] | 1-(3-(4-(4-(3-chloro-4-methoxypyrazolo[1,5-a]pyridin-6-yl)-1H-pyrazol-1-yl)piperidine-1-carbonyl)-3-fluoroazetidin-1-yl)prop-2-en-1-one | 487.1 (M + H) |
| 122 | 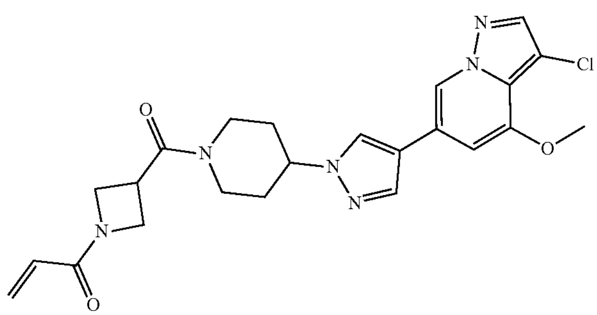 [SMILES: C=CC(=O)N1CC(C(=O)N2CCC(n3cc(-c4cc(OC)c5c(Cl)cnn5c4)cn3)CC2)C1] | 1-(3-(4-(4-(3-chloro-4-methoxypyrazolo[1,5-a]pyridin-6-yl)-1H-pyrazol-1-yl)piperidine-1-carbonyl)azetidin-1-yl)prop-2-en-1-one | 469.2 (M + H) |
| 123 | 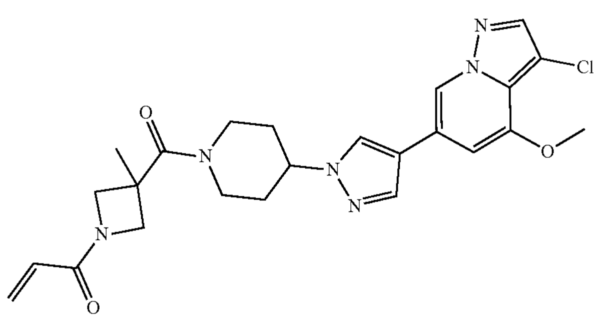 [SMILES: C=CC(=O)N1CC(C)(C(=O)N2CCC(n3cc(-c4cc(OC)c5c(Cl)cnn5c4)cn3)CC2)C1] | 1-(3-(4-(4-(3-chloro-4-methoxypyrazolo[1,5-a]pyridin-6-yl)-1H-pyrazol-1-yl)piperidine-1-carbonyl)-3-methylazetidin-1-yl)prop-2-en-1-one | 483.1 (M + H) |
| 124 | 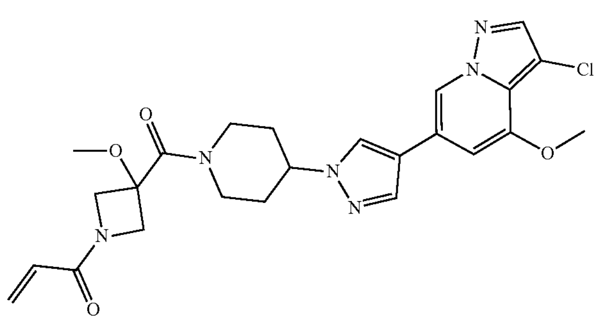 [SMILES: C=CC(=O)N1CC(OC)(C(=O)N2CCC(n3cc(-c4cc(OC)c5c(Cl)cnn5c4)cn3)CC2)C1] | 1-(3-(4-(4-(3-chloro-4-methoxypyrazolo[1,5-a]pyridin-6-yl)-1H-pyrazol-1-yl)piperidine-1-carbonyl)-3-methoxyazetidin-1-yl)prop-2-en-1-one | 499.1 (M + H) |

TABLE C1-continued

| Ex # | Structure | Chemical Name | MS apci (m/z) |
|---|---|---|---|
| 125 | 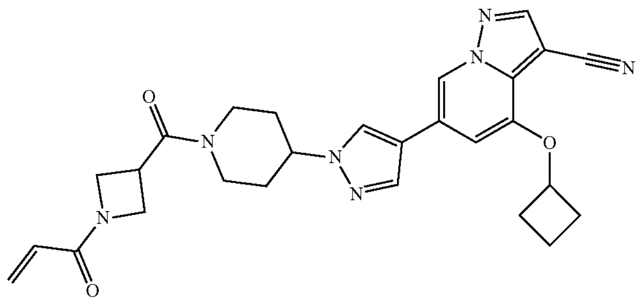 [SMILES: C=CC(=O)N1CC(C(=O)N2CCC(n3cc(-c4cc(OC5CCC5)c5c(C#N)cnn5c4)cn3)CC2)C1] | 6-(1-(1-(1-acryloylazetidine-3-carbonyl)piperidin-4-yl)-1H-pyrazol-4-yl)-4-cyclobutoxypyrazolo[1,5-a]pyridine-3-carbonitrile | 500.2 (M + H) |
| 126 | 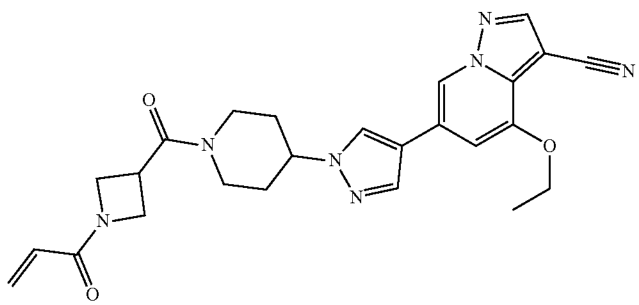 [SMILES: C=CC(=O)N1CC(C(=O)N2CCC(n3cc(-c4cc(OCC)c5c(C#N)cnn5c4)cn3)CC2)C1] | 6-(1-(1-(1-acryloylazetidine-3-carbonyl)piperidin-4-yl)-1H-pyrazol-4-yl)-4-ethoxypyrazolo[1,5-a]pyridine-3-carbonitrile | 474.2 (M + H) |
| 127 | 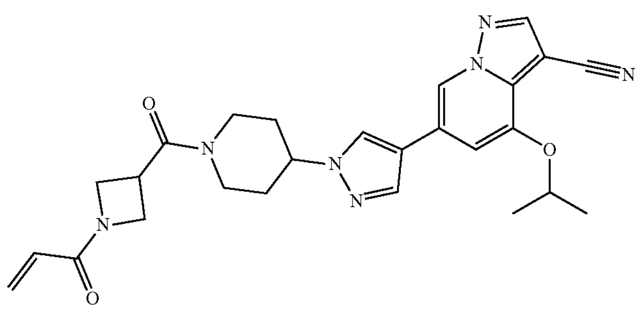 [SMILES: C=CC(=O)N1CC(C(=O)N2CCC(n3cc(-c4cc(OC(C)C)c5c(C#N)cnn5c4)cn3)CC2)C1] | 6-(1-(1-(1-acryloylazetidine-3-carbonyl)piperidin-4-yl)-1H-pyrazol-4-yl)-4-isopropoxypyrazolo[1,5-a]pyridine-3-carbonitrile | 488.2 (M + H) |
| 128 | 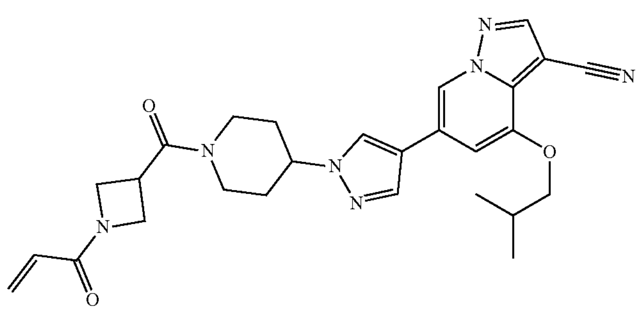 [SMILES: C=CC(=O)N1CC(C(=O)N2CCC(n3cc(-c4cc(OCC(C)C)c5c(C#N)cnn5c4)cn3)CC2)C1] | 6-(1-(1-(1-acryloylazetidine-3-carbonyl)piperidin-4-yl)-1H-pyrazol-4-yl)-4-isobutoxypyrazolo[1,5-a]pyridine-3-carbonitrile | 502.2 (M + H) |
| 129 | 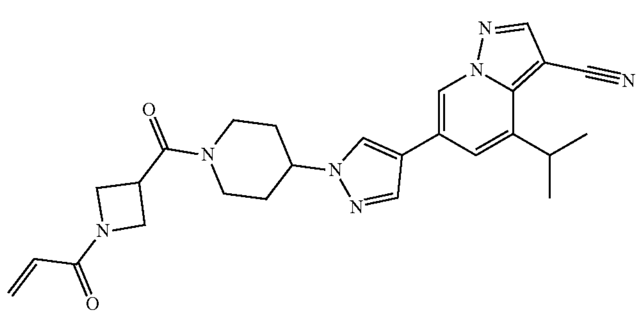 [SMILES: C=CC(=O)N1CC(C(=O)N2CCC(n3cc(-c4cc(C(C)C)c5c(C#N)cnn5c4)cn3)CC2)C1] | 6-(1-(1-(1-acryloylazetidine-3-carbonyl)piperidin-4-yl)-1H-pyrazol-4-yl)-4-isopropylpyrazolo[1,5-a]pyridine-3-carbonitrile | 472.2 (M + H) |

TABLE C1-continued

| Ex # | Structure | Chemical Name | MS apci (m/z) |
|---|---|---|---|
| 130 | 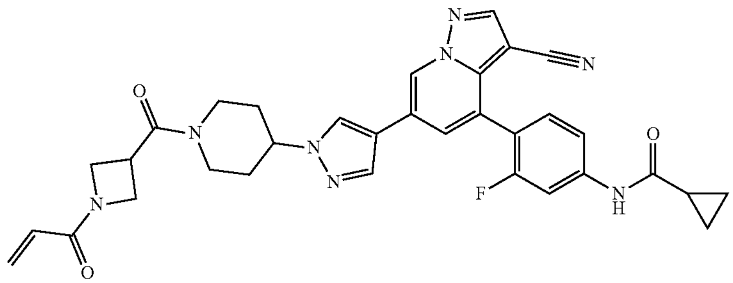 [SMILES: C=CC(=O)N1CC(C(=O)N2CCC(n3cc(-c4cc(-c5ccc(NC(=O)C6CC6)cc5F)c5c(C#N)cnn5c4)cn3)CC2)C1] | N-(4-(6-(1-(1-(1-acryloylazetidine-3-carbonyl)piperidin-4-yl)-1H-pyrazol-4-yl)-3-cyanopyrazolo[1,5-a]pyridin-4-yl)-3-fluorophenyl)cyclopropane-carboxamide | 607.3 (M + H) |
| 131 | 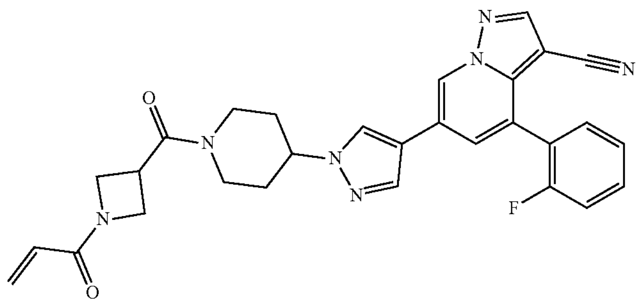 [SMILES: C=CC(=O)N1CC(C(=O)N2CCC(n3cc(-c4cc(-c5ccccc5F)c5c(C#N)cnn5c4)cn3)CC2)C1] | 6-(1-(1-(1-acryloylazetidine-3-carbonyl)piperidin-4-yl)-1H-pyrazol-4-yl)-4-(2-fluorophenyl)pyrazolo[1,5-a]pyridine-3-carbonitrile | 524.2 (M + H) |
| 132 | 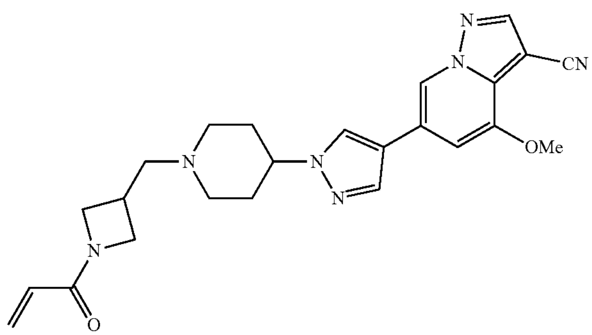 [SMILES: C=CC(=O)N1CC(CN2CCC(n3cc(-c4cc(OC)c5c(C#N)cnn5c4)cn3)CC2)C1] | 6-(1-(1-((1-acryloylazetidin-3-yl)methyl)piperidin-4-yl)-1H-pyrazol-4-yl)-4-methoxypyrazolo[1,5-a]pyridine-3-carbonitrile | 446.2 (M + H) |
| 133 | 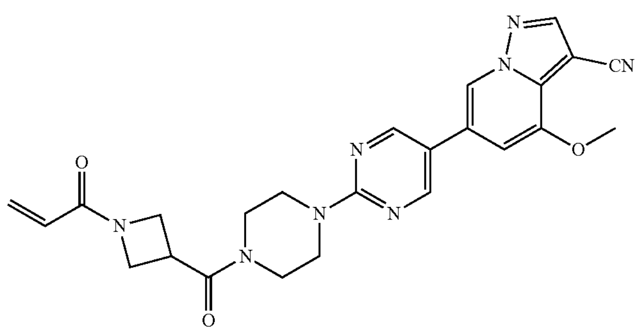 [SMILES: C=CC(=O)N1CC(C(=O)N2CCN(c3ncc(-c4cc(OC)c5c(C#N)cnn5c4)cn3)CC2)C1] | 6-(2-(4-(1-acryloylazetidine-3-carbonyl)piperazin-1-yl)pyrimidin-5-yl)-4-methoxypyrazolo[1,5-a]pyridine-3-carbonitrile | 473.2 (M + H) |
| 134 | 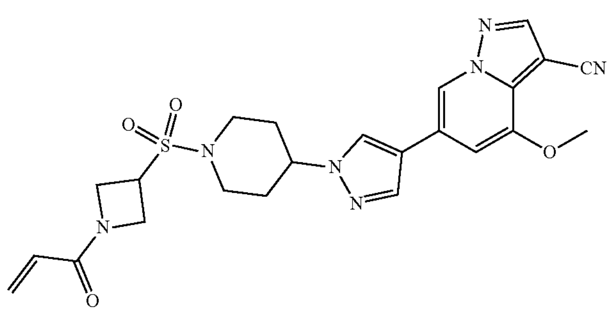 [SMILES: C=CC(=O)N1CC(S(=O)(=O)N2CCC(n3cc(-c4cc(OC)c5c(C#N)cnn5c4)cn3)CC2)C1] | 6-(1-(1-((1-acryloylazetidin-3-yl)sulfonyl)piperidin-4-yl)-1H-pyrazol-4-yl)-4-methoxypyrazolo[1,5-a]pyridine-3-carbonitrile | 496.1 (M + H) |

Example 135

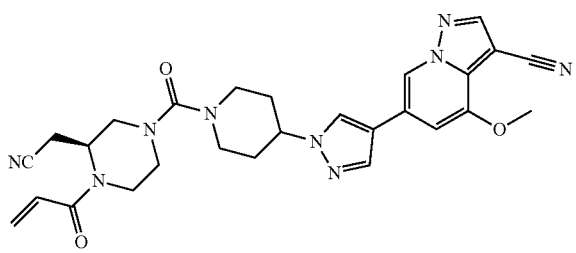 [SMILES: C=CC(=O)N1CCN(C(=O)N2CCC(n3cc(-c4cc(OC)c5c(C#N)cnn5c4)cn3)CC2)C[C@@H]1CC#N]

(S)-6-(1-(1-(4-acryloyl-3-(cyanomethyl)piperazine-1-carbonyl)piperidin-4-yl)-1H-pyrazol-4-yl)-4-methoxypyrazolo[1,5-a]pyridine-3-carbonitrile A solution of (S)-6-(1-(1-(3-(cyanomethyl)piperazine-1-carbonyl)piperidin-4-yl)-1H-pyrazol-4-yl)-4-methoxypyrazolo[1,5-a]pyridine-3-carbonitrile (Intermediate P73; 63 mg, 0.133 mmol) and acryloyl chloride (21.7 µL, 0.266 mmol) in DCM (4 mL) was treated with DIEA (116 µL, 0.665 mmol), then stirred for 1 h at ambient temperature. Subsequently, the reaction mixture was concentrated in vacuo. The crude residue was purified first by silica chromatography (using 10% MeOH in EtOAc as the gradient eluent) then by C18 reverse phase chromatography (5-95% ACN in water with 0.1% TFA as the gradient eluent) to cleanly afford the title compound as the TFA salt. The TFA salt then was free based by dissolving in 4:1 DCM:iPrOH and extracting with saturated NaHCO$_{3(aq)}$. The organic extracts then were dried over anhydrous Na$_2$SO$_{4(s)}$, filtered, and concentrated in vacuo to cleanly afford the title compound (29 mg, 41% yield). MS (apci) m/z=528.2 (M+H).

Example 137

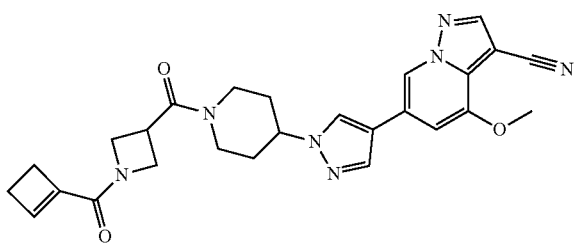 [SMILES: COc1cc(-c2cnn(C3CCN(C(=O)C4CN(C(=O)C5=CCC5)C4)CC3)c2)cn2ncc(C#N)c12]

6-(1-(1-(1-(cyclobut-1-ene-1-carbonyl)azetidine-3-carbonyl)piperidin-4-yl)-1H-pyrazol-4-yl)-4-methoxypyrazolo[1,5-a]pyridine-3-carbonitrile A suspension of 6-(1-(1-(azetidine-3-carbonyl)piperidin-4-yl)-1H-pyrazol-4-yl)-4-methoxypyrazolo[1,5-a]pyridine-3-carbonitrile (Intermediate P112; 30 mg, 0.0740 mmol), cyclobut-1-ene-1-carboxylic acid (7.98 mg, 0.0814 mmol) and HATU (70.3 mg, 0.185 mmol) in DCM (370 µL) was treated with DIEA (64.6 µL, 0.370 mmol). The resulting mixture was stirred overnight at ambient temperature. Subsequently, the reaction mixture was purified directly by C18 reverse phase chromatography (using 5-95% ACN in water with 0.1% TFA as the gradient eluent) to cleanly afford the title compound as the TFA salt. The TFA salt then was diluted with 4:1 DCM:iPrOH and extracted with saturated NaHCO$_{3(aq)}$ (2×). The organic extracts then were dried over anhydrous Na$_2$SO$_{4(s)}$, filtered, and concentrated in vacuo to cleanly afford the title compound (23.3 mg, 64% yield). MS (apci) m/z=486.2 (M+H).

The compounds in Table C2 were prepared using a similar method to that described in the synthesis of 6-(1-(1-(1-(cyclobut-1-ene-1-carbonyl)azetidine-3-carbonyl)piperidin-4-yl)-1H-pyrazol-4-yl)-4-methoxypyrazolo[1,5-a]pyridine-3-carbonitrile (Example 137), employing the following modifications: in Step 1, using 1.1-3.0 equivalents of HATU, 2-8 equivalents of DIEA, solvent (DCM or DMF*) concentration of 0.05-0.2 M and replacing the cyclobut-1-ene-1-carboxylic acid with 1.1-2.2 equivalents of the appropriate α,β-unsaturated carboxylic acid from Table CEi. Reactions were monitored for completion by LCMS, as such reaction durations were adjusted accordingly. When necessary, title compounds were isolated following chromatographic purification using an appropriate gradient eluent, and if necessary free based using a similar extraction procedure as found in Example 137.

TABLE C2

| Ex # | Structure | Chemical Name | MS apci (m/z) |
| --- | --- | --- | --- |
| 138 | 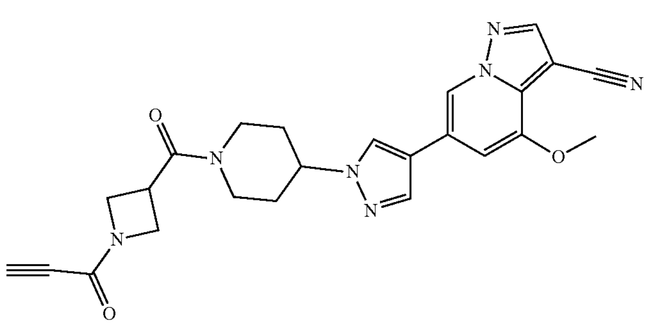 | 4-methoxy-6-(1-(1-(1-propioloylazetidine-3-carbonyl)piperidin-4-yl)-1H-pyrazol-4-yl)pyrazolo[1,5-a]pyridine-3-carbonitrile | 458.3 (M + H) |

TABLE C2-continued

| Ex # | Structure | Chemical Name | MS apci (m/z) |
|---|---|---|---|
| 139 | 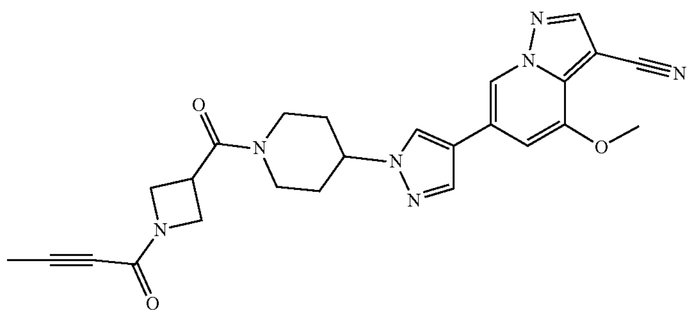 | 6-(1-(1-(1-(but-2-ynoyl)azetidine-3-carbonyl)piperidin-4-yl)-1H-pyrazol-4-yl)-4-methoxypyrazolo[1,5-a]pyridine-3-carbonitrile | 472.1 (M + H) |
| 140 | 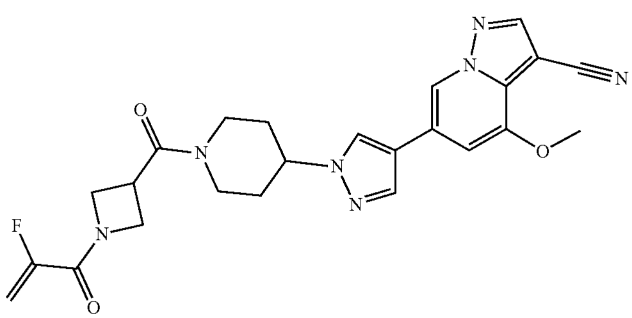 | 6-(1-(1-(1-(2-fluoroacryloyl)azetidine-3-carbonyl)piperidin-4-yl)-1H-pyrazol-4-yl)-4-methoxypyrazolo[1,5-a]pyridine-3-carbonitrile | 478.2 (M + H) |
| 141 | 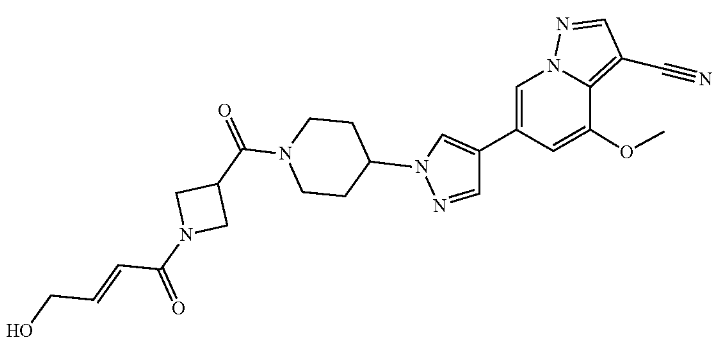 | (E)-6-(1-(1-(1-(4-hydroxybut-2-enoyl)azetidine-3-carbonyl)piperidin-4-yl)-1H-pyrazol-4-yl)-4-methoxypyrazolo[1,5-a]pyridine-3-carbonitrile | 490.2 (M + H) |
| 142 | 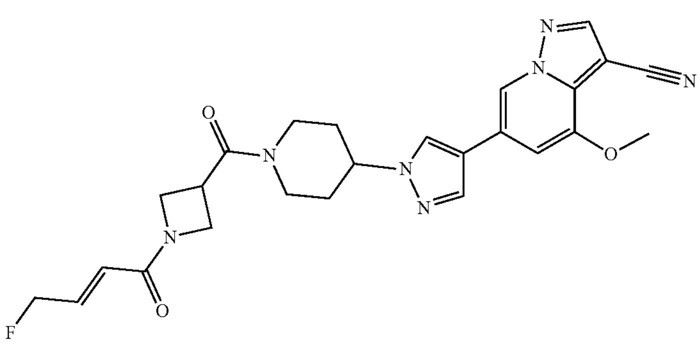 | (E)-6-(1-(1-(1-(4-fluorobut-2-enoyl)azetidine-3-carbonyl)piperidin-4-yl)-1H-pyrazol-methoxypyrazolo[1,5-a]pyridine-3-carbonitrile | 492.2 (M + H) |

TABLE C2-continued

| Ex # | Structure | Chemical Name | MS apci (m/z) |
|---|---|---|---|
| 143 | 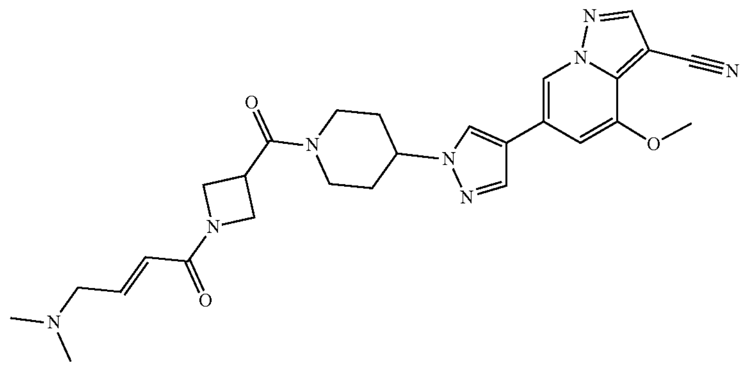 | (E)-6-(1-(1-(1-(4-(dimethylamino)but-2-enoyl)azetidine-3-carbonyl)piperidin-4-yl)-1H-pyrazol-4-yl)-4-methoxypyrazolo[1,5-a]pyridine-3-carbonitrile | 517.2 (M + H) |
| 144* | 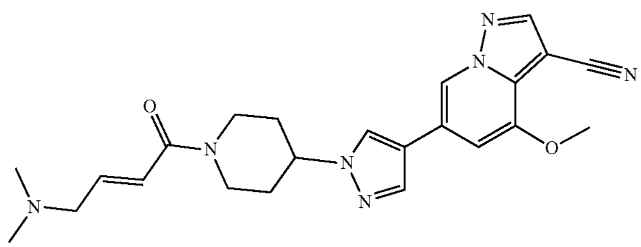 | (E)-6-(1-(1-(4-(dimethylamino)benzoyl)piperidin-4-yl)-1H-pyrazol-4-yl)-4-methoxypyrazol145o[1,5-a]pyridine-3-carbonitrile | 434.2 (M + H) |
| 145 | 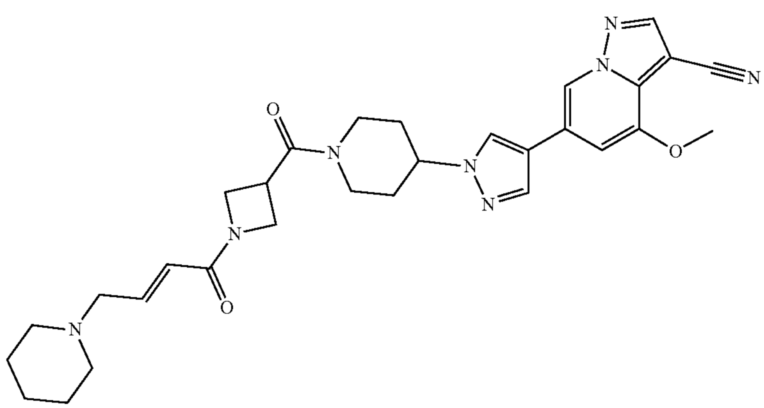 | (E)-4-methoxy-6-(1-(1-(1-(4-(piperidin-1-yl)but-2-enoyl)azetidine-3-carbonyl)piperidin-4-yl)-1H-pyrazol-4-yl)pyrazolo[1,5-a]pyridine-3-carbonitrile | 557.3 (M + H) |
| 146 | 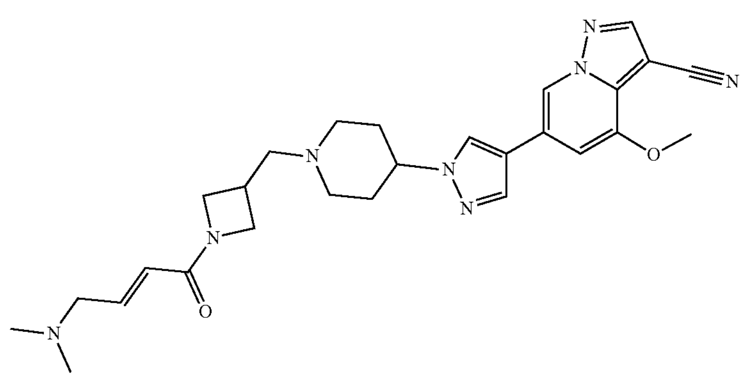 | (E)-6-(1-(1-((1-(4-(dimethylamino)but-2-enoyl)azetidin-3-yl)methyl)piperidin-4-yl)-1H-pyrazol-4-yl)-4-methoxypyrazolo[1,5-a]pyridine-3-carbonitrile | 503.3 (M + H) |

TABLE C2-continued

| Ex # | Structure | Chemical Name | MS apci (m/z) |
|---|---|---|---|
| 148 | 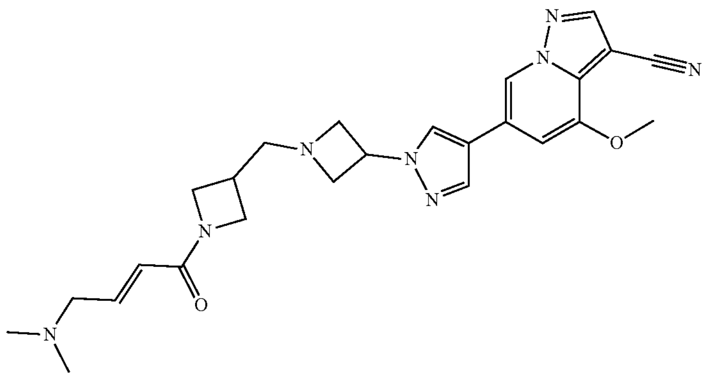 | (E)-6-(1-(1-((1-(4-(dimethylamino)but-2-enoyl)azetidin-3-yl)methyl)azetidin-3-yl)-1H-pyrazol-4-methoxypyrazolo[1,5-a]pyridine-3-carbonitrile | 475.2 (M + H) |
| 149 | 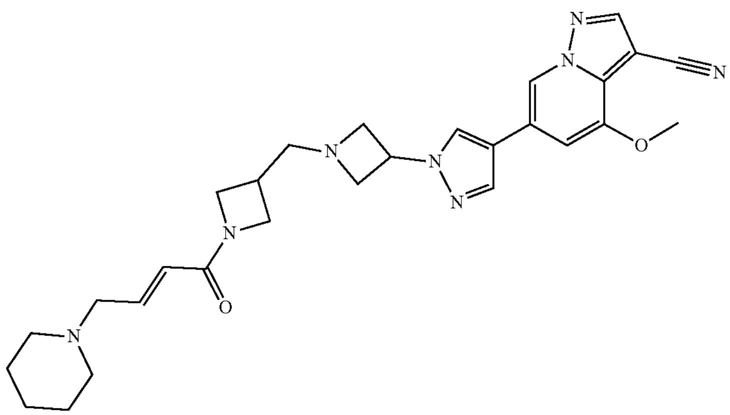 | (E)-4-methoxy-6-(1-(1-((1-(4-(piperidin-1-yl)but-2-enoyl)azetidin-3-yl)methyl)azetidin-3-yl)-1H-pyrazol-4-yl)pyrazolo[1,5-a]pyridine-3-carbonitrile | 515.3 (M + H) |
| 150 | 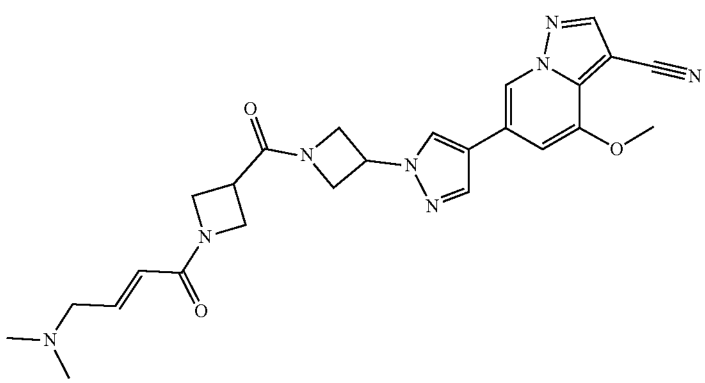 | (E)-6-(1-(1-(1-(4-(dimethylamino)but-2-enoyl)azetidine-3-carbonyl)azetidin-3-yl)-1H-pyrazol-4-methoxypyrazolo[1,5-a]pyridine-3-carbonitrile | 489.2 (M + H) |
| 151 | 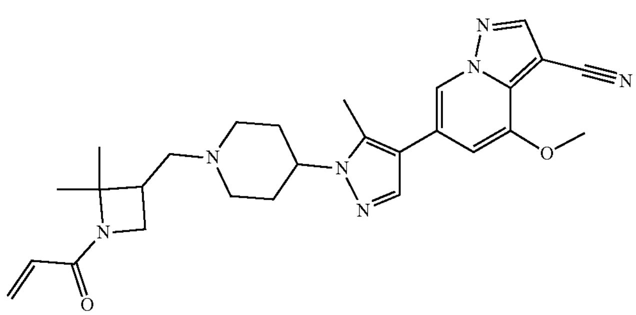 | 6-(1-(1-((1-acryloyl-2,2-dimethylazetidin-3-yl)methyl)piperidin-4-yl)-5-methyl-1H-pyrazol-4-yl)-4-methoxypyrazolo[1,5-a]pyridine-3-carbonitrile | 488.3 (M + H) |

TABLE C2-continued

| Ex # | Structure | Chemical Name | MS apci (m/z) |
|---|---|---|---|
| 152 | 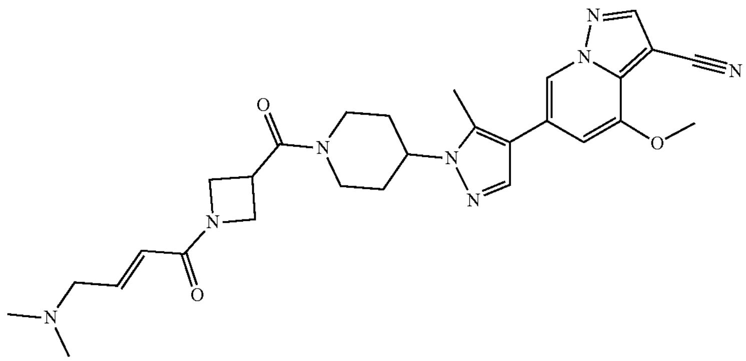 | (E)-6-(1-(1-(1-(4-(dimethylamino)but-2-enoyl)azetidine-3-carbonyl)piperidin-4-yl)-5-methyl-1H-pyrazol-4-yl)-4-methoxypyrazolo[1,5-a]pyridine-3-carbonitrile | 531.3 (M + H) |
| 153 | 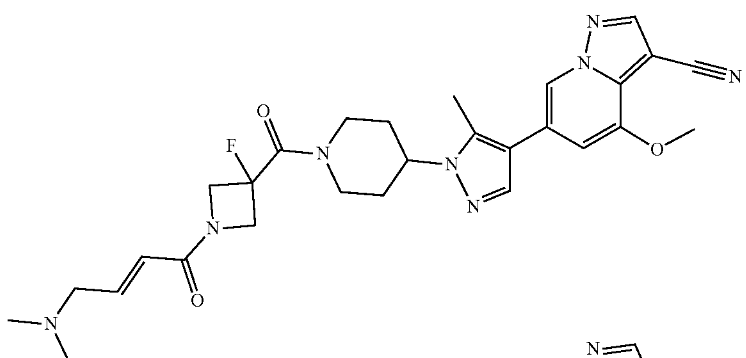 | (E)-6-(1-(1-(1-(4-(dimethylamino)but-2-enoyl)-3-fluoroazetidine-3-carbonyl)piperidin-4-yl)-5-methyl-1H-pyrazol-4-yl)-4-methoxypyrazolo[1,5-a]pyridine-3-carbonitrile | 549.3 (M + H) |
| 154 | 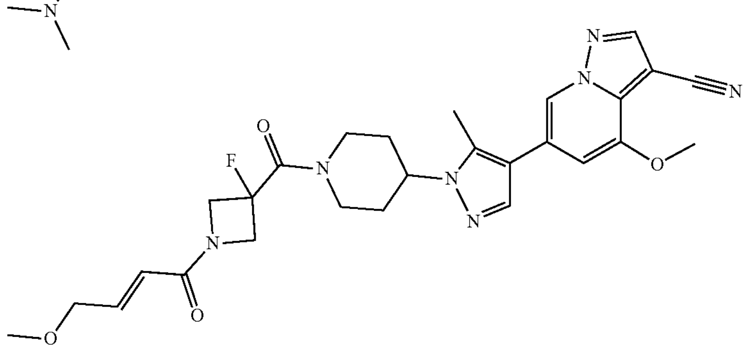 | (E)-6-(1-(1-(3-fluoro-1-(4-methoxybut-2-enoyl)azetidine-3-carbonyl)piperidin-4-yl)-5-methyl-1H-pyrazol-4-yl)-4-methoxypyrazolo[1,5-a]pyridine-3-carbonitrile | 536.2 (M + H) |
| 155 | 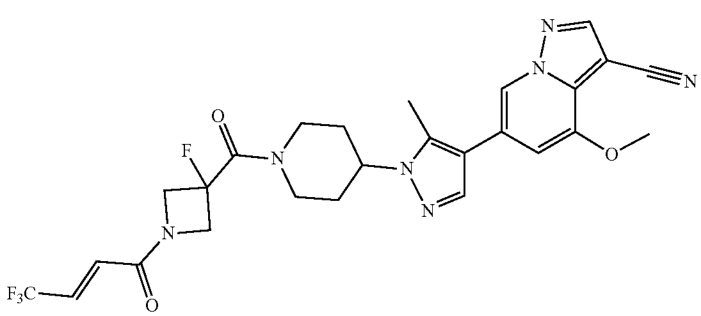 | (E)-6-(1-(1-(3-fluoro-1-(4,4,4-trifluorobut-2-enoyl)azetidine-3-carbonyl)piperidin-4-yl)-5-methyl-1H-pyrazol-4-yl)-4-methoxypyrazolo[1,5-a]pyridine-3-carbonitrile | 560.2 (M + H) |

TABLE C2-continued

| Ex # | Structure | Chemical Name | MS apci (m/z) |
|---|---|---|---|
| 156 | 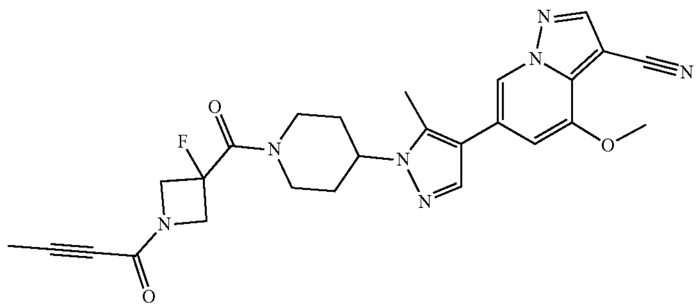 | 6-(1-(1-(1-(but-2-ynoyl)-3-fluoroazetidine-3-carbonyl)piperidin-4-yl)-5-methyl-1H-pyrazol-4-yl)-4-methoxypyrazolo[1,5-a]pyridine-3-carbonitrile | 504.2 (M + H) |
| 157 | 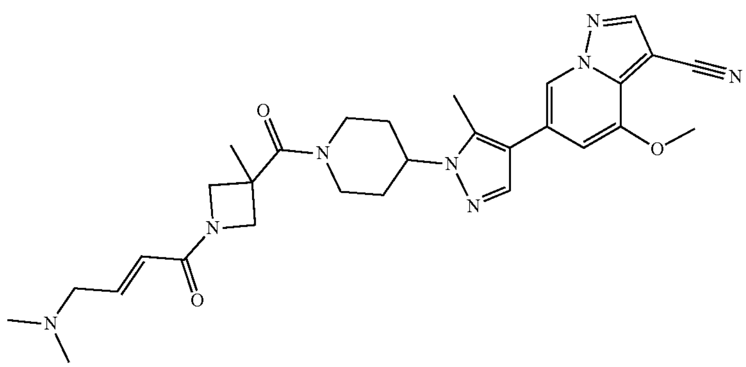 | (E)-6-(1-(1-(1-(4-(dimethylamino)but-2-enoyl)-3-methylazetidine-3-carbonyl)piperidin-4-yl)-5-methyl-1H-pyrazol-4-yl)-4-methoxypyrazolo[1,5-a]pyridine-3-carbonitrile | 545.3 (M + H) |
| 158 | 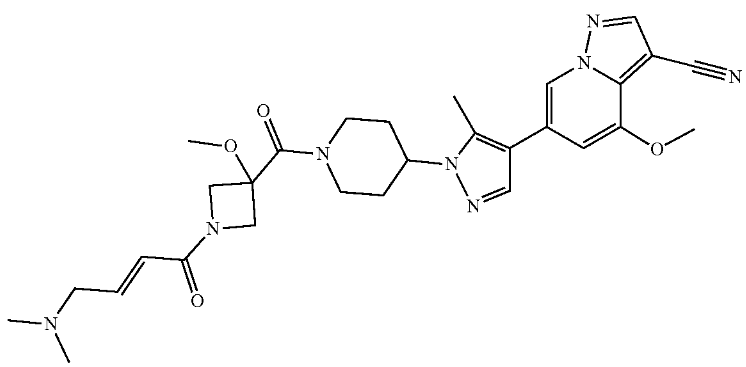 | (E)-6-(1-(1-(1-(4-(dimethylamino)but-2-enoyl)-3-methoxyazetidine-3-carbonyl)piperidin-4-yl)-5-methyl-1H-pyrazol-4-yl)-4-methoxypyrazolo[1,5-a]pyridine-3-carbonitrile | 561.3 (M + H) |
| 159 | 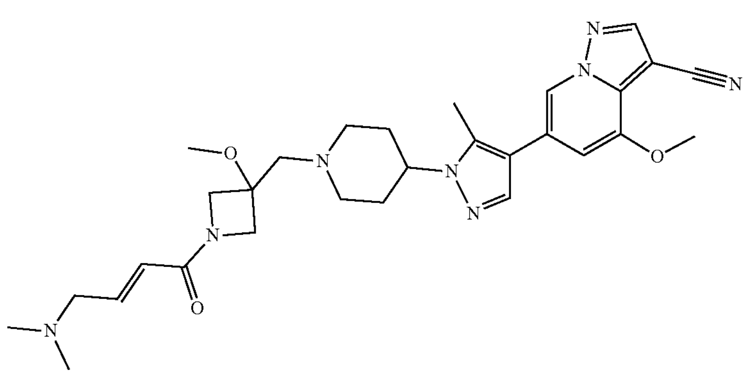 | (E)-6-(1-(1-((1-(4-(dimethylamino)but-2-enoyl)-3-methoxyazetidin-3-yl)methyl)piperidin-4-yl)-5-methyl-1H-pyrazol-4-yl)-4-methoxypyrazolo[1,5-a]pyridine-3-carbonitrile | 547.3 (M + H) |

TABLE C2-continued

| Ex # | Structure | Chemical Name | MS apci (m/z) |
|---|---|---|---|
| 160 | 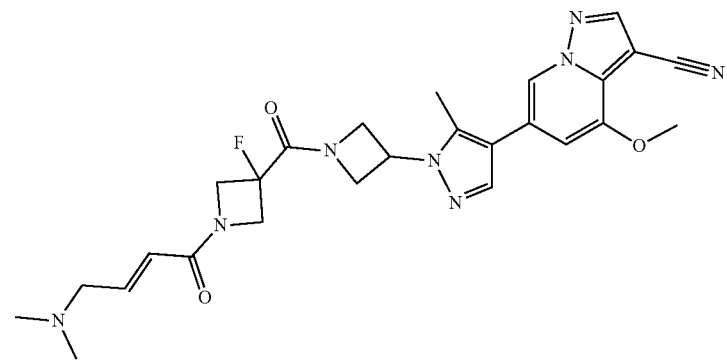 | (E)-6-(1-(1-(1-(4-(dimethylamino)but-2-enoyl)-3-fluoroazetidine-3-carbonyl)azetidin-3-yl)-5-methyl-1H-pyrazol-4-yl)-4-methoxypyrazolo[1,5-a]pyridine-3-carbonitrile | 521.2 (M + H) |
| 161 | 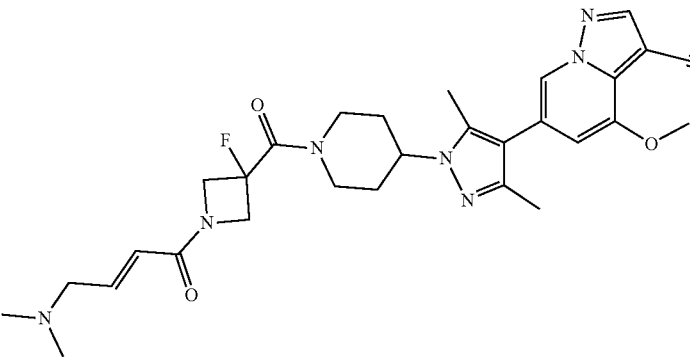 | (E)-6-(1-(1-(1-(4-(dimethylamino)but-2-enoyl)-3-fluoroazetidine-3-carbonyl)piperidin-4-yl)-3,5-dimethyl-1H-pyrazol-4-yl)-4-methoxypyrazolo[1,5-a]pyridine-3-carbonitrile | 563.3 (M + H) |
| 162 | 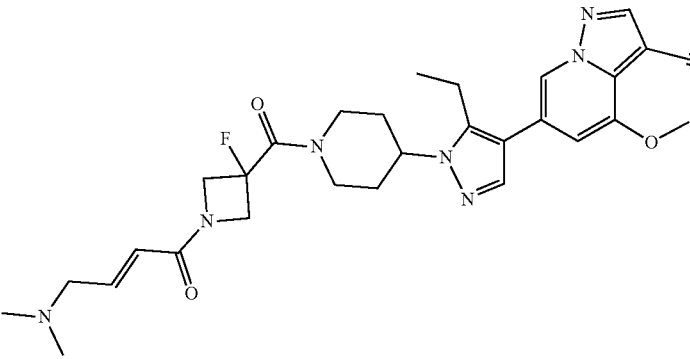 | (E)-6-(1-(1-(1-(4-(dimethylamino)but-2-enoyl)-3-fluoroazetidine-3-carbonyl)piperidin-4-yl)-5-ethyl-1H-pyrazol-4-yl)-4-methoxypyrazolo[1,5-a]pyridine-3-carbonitrile | 563.3 (M + H) |
| 163 | 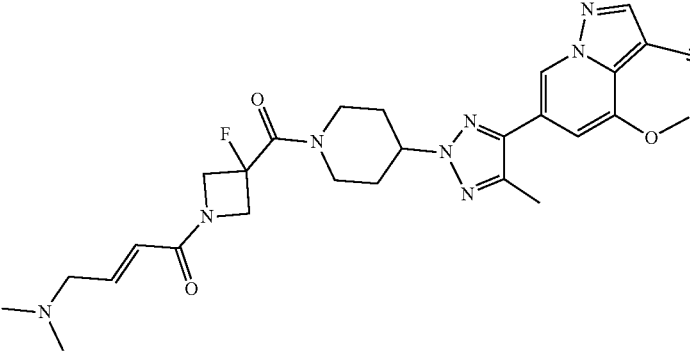 | (E)-6-(2-(1-(1-(4-(dimethylamino)but-2-enoyl)-3-fluoroazetidine-3-carbonyl)piperidin-4-yl)-5-methyl-2H-1,2,3-triazol-4-yl)-4-methoxypyrazolo[1,5-a]pyridine-3-carbonitrile | 550.2 (M + H) |

TABLE C2-continued

| Ex # | Structure | Chemical Name | MS apci (m/z) |
|---|---|---|---|
| 164 | 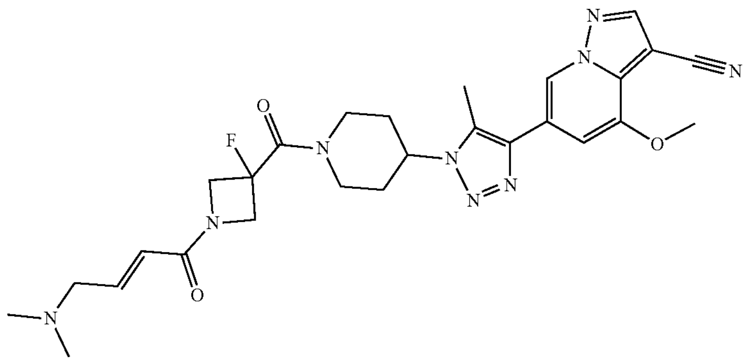 | (E)-6-(1-(1-(1-(4-(dimethylamino)but-2-enoyl)-3-fluoroazetidine-3-carbonyl)piperidin-4-yl)-5-methyl-1H-1,2,3-triazol-4-yl)-4-methoxypyrazolo[1,5-a]pyridine-3-carbonitrile | 550.2 (M + H) |
| 165 | 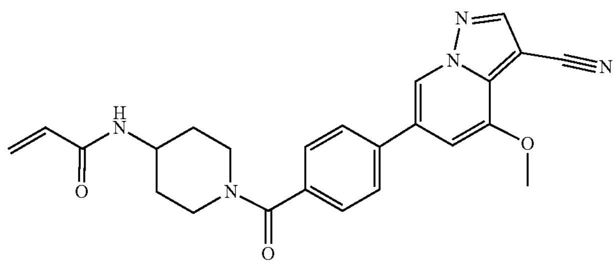 [SMILES: C=CC(=O)NC1CCN(C(=O)c2ccc(-c3cc(OC)c4c(C#N)cnn4c3)cc2)CC1] | N-(1-(4-(3-cyano-4-methoxypyrazolo[1,5-a]pyridin-6-yl)benzoyl)piperidin-4-yl)acrylamide | 430.2 (M + H) |
| 166 | 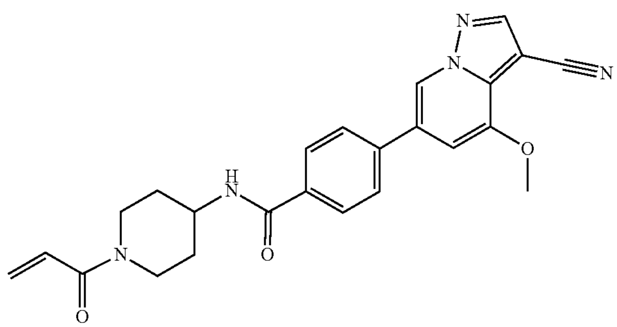 [SMILES: C=CC(=O)N1CCC(NC(=O)c2ccc(-c3cc(OC)c4c(C#N)cnn4c3)cc2)CC1] | N-(1-acryloylpiperidin-4-yl)-4-(3-cyano-4-methoxypyrazolo[1,5-a]pyridin-6-yl)benzamide | 430.2 (M + H) |
| 167 | 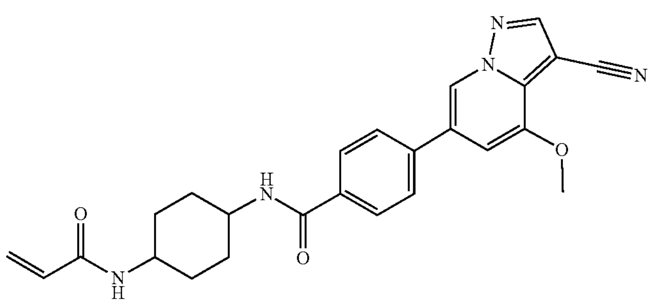 [SMILES: C=CC(=O)NC1CCC(NC(=O)c2ccc(-c3cc(OC)c4c(C#N)cnn4c3)cc2)CC1] | N-(4-acrylamido-cyclohexyl)-4-(3-cyano-4-methoxypyrazolo[1,5-a]pyridin-6-yl)benzamide | 442.1 (M − H) |
| 168 | 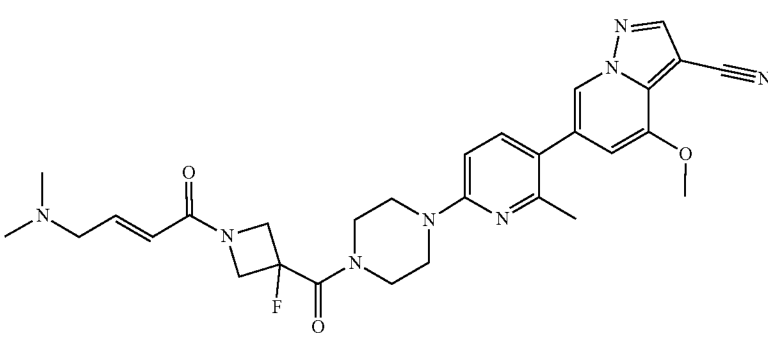 [SMILES: COc1cc(-c2ccc(N3CCN(C(=O)C4(F)CN(C(=O)/C=C/CN(C)C)C4)CC3)nc2C)cn2ncc(C#N)c12] | (E)-6-(6-(4-(1-(4-(dimethylamino)but-2-enoyl)-3-fluoroazetidine-3-carbonyl)piperazin-1-yl)-2-methylpyridin-3-yl)-4-methoxypyrazolo[1,5-a]pyridine-3-carbonitrile | 561.3 (M + H) |

TABLE C2-continued

| Ex # | Structure | Chemical Name | MS apci (m/z) |
|---|---|---|---|
| 169 | 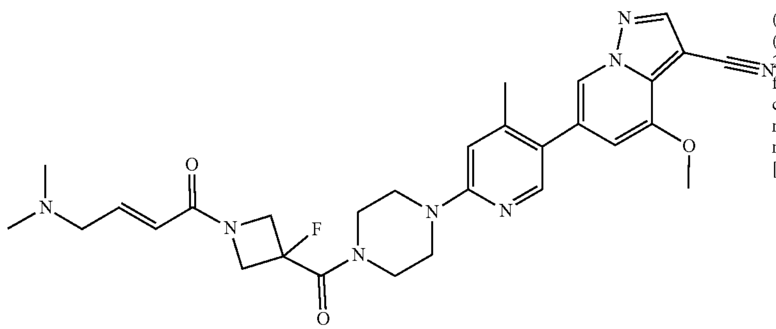 [SMILES: COc1cc(-c2cnc(N3CCN(C(=O)C4(F)CN(C(=O)/C=C/CN(C)C)C4)CC3)cc2C)cn2ncc(C#N)c12] | (E)-6-(6-(4-(1-(4-(dimethylamino)but-2-enoyl)-3-fluoroazetidine-3-carbonyl)piperazin-1-yl) -4-methylpyridin-3-yl)-4-methoxypyrazolo[1,5-a]pyridine-3-carbonitrile | 561.3 (M + H) |
| 170 | 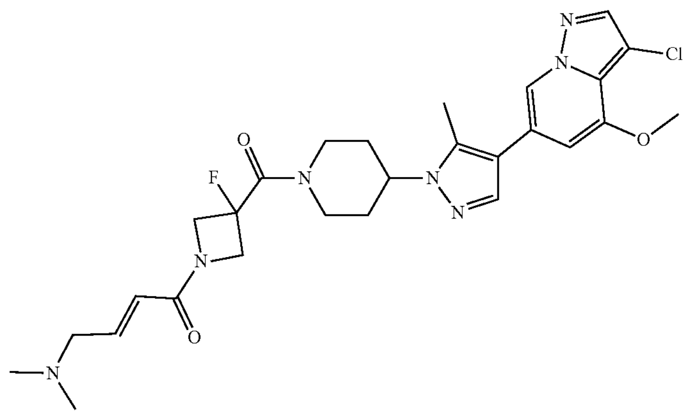 | (E)-1-(3-(4-(4-(3-chloro-4-methoxypyrazolo[1,5-a]pyridin-6-yl)-5-methyl-1H-pyrazol-1-yl)piperidine-1-carbonyl)-3-fluoroazetidin-1-yl)-4-(dimethylamino)but-2-en-1-one | 558.2 (M + H) |
| 171 | 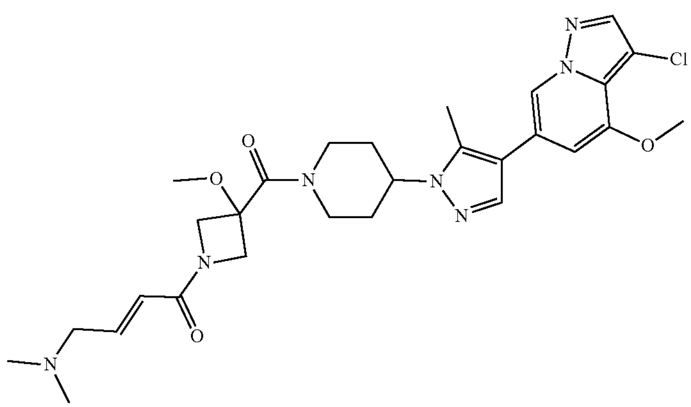 | (E)-1-(3-(4-(4-(3-chloro-4-methoxypyrazolo[1,5-a]pyridin-6-yl)-5-methyl-1H-pyrazol-1-yl)piperidine-1-carbonyl)-3-methoxyazetidin-1-yl)-4-(dimethylamino)but-2-en-1-one | 570.3 (M + H) |
| 172 | 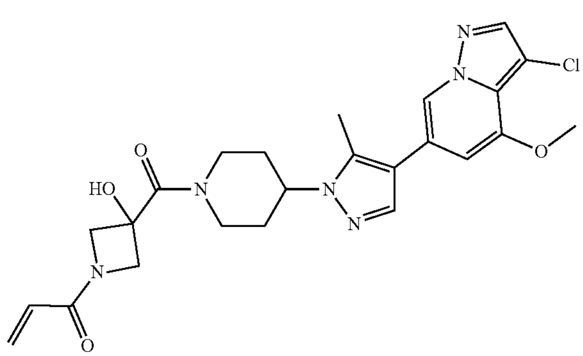 [SMILES: C=CC(=O)N1CC(O)(C(=O)N2CCC(n3ncc(-c4cc(OC)c5c(Cl)cnn5c4)c3C)CC2)C1] | 1-(3-(4-(4-(3-chloro-4-methoxypyrazolo[1,5-a]pyridin-6-yl)-5-methyl-1H-pyrazol-1-yl)piperidine-1-carbonyl)-3-hydroxyazetidin-1-yl)prop-2-en-1-one | 499.1 (M + H) |

TABLE C2-continued

| Ex # | Structure | Chemical Name | MS apci (m/z) |
|---|---|---|---|
| 173 | 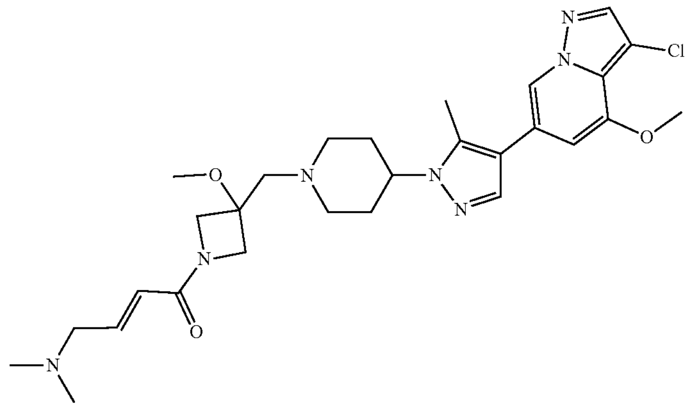 | (E)-1-(3-((4-(4-(3-chloro-4-methoxypyrazolo[1,5-a]pyridin-6-yl)-5-methyl-1H-pyrazol-1-yl)piperidin-1-yl)methyl)-3-methoxyazetidin-1-yl)-4-(dimethylamino)but-2-en-1-one | 556.3 (M + H) |
| 174 | 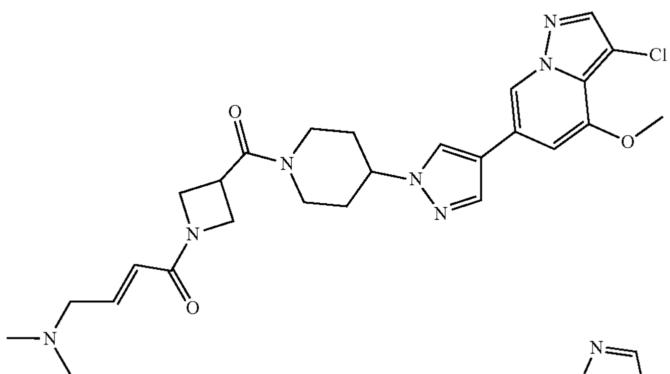 | (E)-1-(3-(4-(4-(3-chloro-4-methoxypyrazolo[1,5-a]pyridin-6-yl)-1H-pyrazol-1-yl)piperidine-1-carbonyl)azetidin-(dimethylamino)but-2-en-1-one | 526.2 (M + H) |
| 175 | 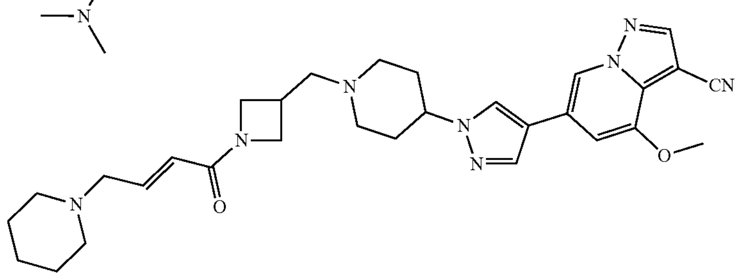 | (E)-4-methoxy-6-(1-(1-((1-(4-(piperidin-1-yl)but-2-enoyl)azetidin-3-yl)methyl)piperidin-4-yl)-1H-pyrazol-4-yl)pyrazolo[1,5-a]pyridine-3-carbonitrile | 543.3 (M + H) |

Example 176

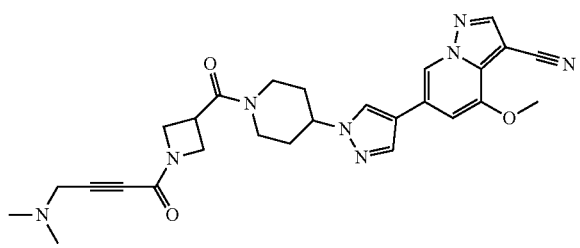 [SMILES: COc1cc(-c2cnn(C3CCN(C(=O)C4CN(C(=O)C#CCN(C)C)C4)CC3)c2)cn2ncc(C#N)c12]

6-(1-(1-(1-(4-(dimethylamino)but-2-ynoyl)azetidine-3-carbonyl)piperidin-4-yl)-1H-pyrazol-4-yl)-4-methoxypyrazolo[1,5-a]pyridine-3-carbonitrile A mixture of 6-(1-(1-(azetidine-3-carbonyl)piperidin-4-yl)-1H-pyrazol-4-yl)-4-methoxypyrazolo[1,5-a]pyridine-3-carbonitrile (Intermediate P112; 247 mg, 0.609 mmol), lithium 4-(dimethylamino)but-2-ynoate (7.98 mg, 0.0814 mmol) and HATU (97.3 mg, 0.731 mmol) in DCM (3046 µL) was stirred for 2 h at ambient temperature. Subsequently, the reaction mixture was concentrated in vacuo and purified three times first by silica chromatography (using 0-100% DCM: Acetone as the gradient eluent) then by C18 reverse phase chromatography (using 5-95% ACN in water with 0.1% TFA as the gradient eluent) and finally by silica chromatography again (using 10% MeOH in DCM as the eluent) to cleanly afford the title compound (3.2 mg, 1% yield). MS (apci) m/z=515.2 (M+H).

Example 177

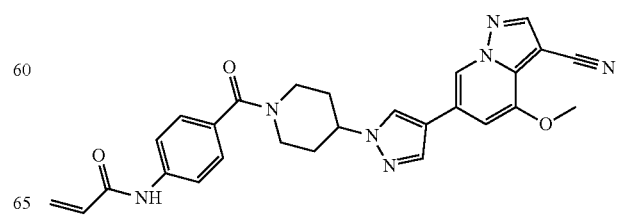

N-(4-(4-(4-(3-cyano-4-methoxypyrazolo[1,5-a]pyridin-6-yl)-1H-pyrazol-1-yl)piperidine-1-carbonyl)phenyl)acrylamide A solution of 4-methoxy-6-(1-(piperidin-4-yl)-1H-pyrazol-4-yl)pyrazolo[1,5-a]pyridine-3-carbonitrile hydrochloride (Intermediate P54; 307 mg, 0.952 mmol), 4-acrylamidobenzoic acid (Intermediate R4; 202 mg, 1.06 mmol) and DIEA (832 µL, 4.76 mmol) in DCM (4762 µL) was treated with HATU (398 mg, 1.05 mmol). The resulting mixture was stirred for 10 min at ambient temperature. Subsequently, the reaction mixture was diluted with DCM and washed with brine (3×). The organic extracts were dried over anhydrous $Na_2SO_{4(s)}$, filtered, and concentrated in vacuo. The crude product was purified by silica chromatography (using 0-100% EtOAc in Hexanes, then DCM/MeOH as the gradient eluent). The pure fractions were combined and concentrated in vacuo. The resulting residue was dissolved in DCM and MTBE was added. The solid precipitate was collected and dried in vacuo to cleanly afford the title compound (415 mg, 88% yield). MS (apci) m/z=496.1 (M+H).

Example 178

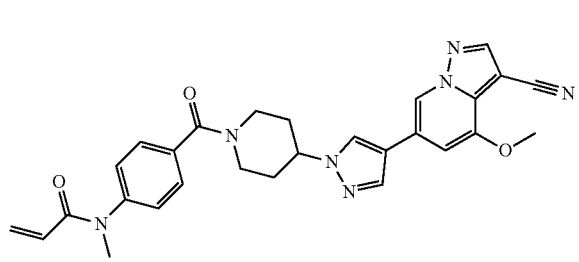 [SMILES: C=CC(=O)N(C)c1ccc(C(=O)N2CCC(n3cc(-c4cc(OC)c5c(C#N)cnn5c4)cn3)CC2)cc1]

N-(4-(4-(4-(3-cyano-4-methoxypyrazolo[1,5-a]pyridin-6-yl)-1H-pyrazol-1-yl)piperidine-1-carbonyl)phenyl)-N-methylacrylamide A solution of N-(4-(4-(4-(3-cyano-4-methoxypyrazolo[1,5-a]pyridin-6-yl)-1H-pyrazol-1-yl)piperidine-1-carbonyl)phenyl)acrylamide (Example 177; 150 mg, 0.303 mmol), NaH (60 wt. % mineral oil dispersion; 15.1 mg, 0.378 mmol) and MeI (18.9 µL, 0.303 mmol) in THF (1513 µL) was stirred for 3 days at ambient temperature. The resulting suspension was filtered through GF/F paper, the solids were discarded, and the filtrate was concentrated in vacuo. The crude residue was purified by silica chromatography (using 0-100% Hexanes:EtOAc, then 0-10% EtOAc:MeOH as the Stepped gradient eluent) to cleanly afford the title compound (57 mg, 37% yield). MS (apci) m/z=510.2 (M+H).

Example 179

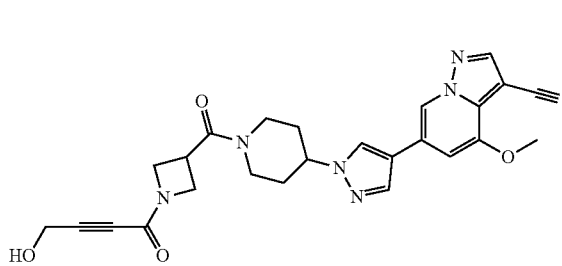

6-(1-(1-(1-(4-hydroxybut-2-ynoyl)azetidine-3-carbonyl)piperidin-4-yl)-1H-pyrazol-4-yl)-4-methoxypyrazolo[1,5-a]pyridine-3-carbonitrile A cold (0° C.) solution of 6-(1-(1-(azetidine-3-carbonyl)piperidin-4-yl)-1H-pyrazol-4-yl)-4-methoxypyrazolo[1,5-a]pyridine-3-carbonitrile (Intermediate P112; 50 mg, 0.1233 mmol), TEA (42.97 µL, 0.3083 mmol) in DMF (616.6 µL) was treated with 4-(tert-butyl-dimethyl-silanyloxy)-but-2-ynoic acid (39.65 mg, 0.1850 mmol), followed by slow addition of 1-Propanephosphonic acid cyclic anhydride (73.41 µL, 0.1233 mmol). The resulting mixture was stirred for 1 h at ambient temperature. Subsequently, the reaction mixture was diluted with water and extracted with EtOAc (3×). The organic extracts then were washed with brine (3×), dried over anhydrous $Na_2SO_{4(s)}$, filtered, and concentrated in vacuo. The crude product was purified by silica chromatography (using 0-30% DCM:MeOH with 2% $NH_4OH$ as the gradient eluent) to cleanly afford the title compound (5 mg, 8% yield). MS (apci) m/z=488.2 (M+H).

Example 180

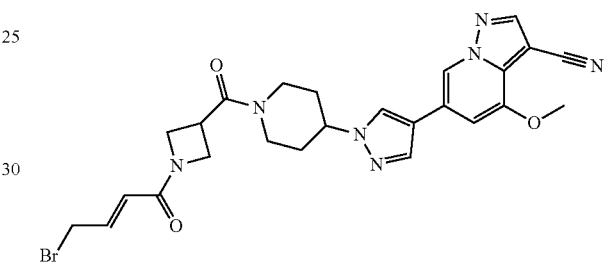

(E)-6-(1-(1-(1-(4-bromobut-2-enoyl)azetidine-3-carbonyl)piperidin-4-yl)-1H-pyrazol-4-yl)-4-methoxypyrazolo[1,5-a]pyridine-3-carbonitrile A mixture of gamma-bromocrotonic acid (122 mg, 0.740 mmol), HATU (281 mg, 0.740 mmol) and DIEA (258 µL, 1.48 mmol) in DCM (1480 µL) was stirred for 15 min at ambient temperature, then 6-(1-(1-(azetidine-3-carbonyl)piperidin-4-yl)-1H-pyrazol-4-yl)-4-methoxypyrazolo[1,5-a]pyridine-3-carbonitrile (Intermediate P112; 120 mg, 0.296 mmol) was introduced. The resulting mixture was stirred overnight at ambient temperature. The reaction mixture then was purified directly by silica chromatography (using 0-100% DCM: Acetone as the gradient eluent) to afford the title compound (128 mg, 71% yield). MS (apci) m/z=552.2 (M+H).

Example 181

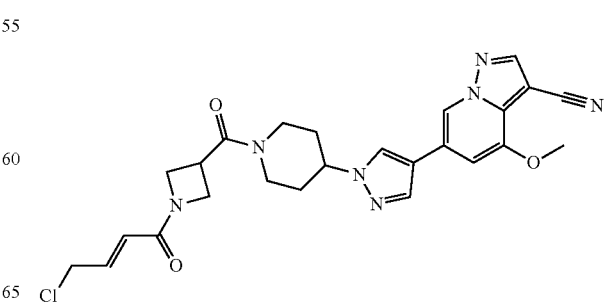

(E)-6-(1-(1-(1-(4-chlorobut-2-enoyl)azetidine-3-carbonyl)piperidin-4-yl)-1H-pyrazol-4-yl)-4-methoxypyrazolo[1,5-a]pyridine-3-carbonitrile The title compound (22.2 mg, 46% yield) was prepared and purified using a similar procedure to that described for the synthesis of (E)-6-(1-(1-(1-(4-bromobut-2-enoyl)azetidine-3-carbonyl)piperidin-4-yl)-1H-pyrazol-4-yl)-4-methoxypyrazolo[1,5-a]pyridine-3-carbonitrile (Example 180), replacing gamma-bromocrotonic acid with gamma-chlorocrotonic acid. MS (apci) m/z=508.2 (M+H).

Example 182

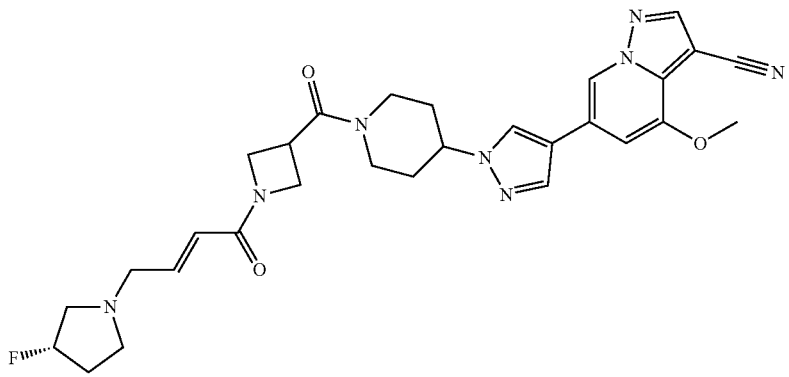 [SMILES: COc1cc(-c2cnn(C3CCN(C(=O)C4CN(C(=O)/C=C/CN5CC[C@H](F)C5)C4)CC3)c2)cn2ncc(C#N)c12]

(S,E)-6-(1-(1-(1-(4-(3-fluoropyrrolidin-1-yl)but-2-enoyl)azetidine-3-carbonyl)piperidin-4-yl)-1H-pyrazol-4-yl)-4-methoxypyrazolo[1,5-a]pyridine-3-carbonitrile A solution of (S)-3-fluoropyrrolidine (9.68 mg, 0.109 mmol) and DIEA (47.4 µL, 0.272 mmol) in DMF (543 µL, 0.0543 mmol) was treated with (E)-6-(1-(1-(1-(4-bromobut-2-enoyl)azetidine-3-carbonyl)piperidin-4-yl)-1H-pyrazol-4-yl)-4-methoxypyrazolo[1,5-a]pyridine-3-carbonitrile (Example 180; 30 mg, 0.0543 mmol), then stirred overnight at ambient temperature. Subsequently, the reaction mixture was purified directly by C18 reverse phase chromatography (using 5-95% ACN in water with 0.1% TFA as the gradient eluent) to cleanly afford the title compound as the TFA salt. The TFA salt then was diluted with 4:1 DCM:iPrOH and extracted with saturated NaHCO$_{3(aq)}$ (2×). The organic extracts then were dried over anhydrous Na$_2$SO$_{4(s)}$, filtered, and concentrated in vacuo to cleanly afford the title compound (23.1 mg, 76% yield). MS (apci) m/z=561.3 (M+H).

The compounds in Table C3 were prepared using a similar method to that described in the synthesis of (S,E)-6-(1-(1-(1-(4-(3-fluoropyrrolidin-1-yl)but-2-enoyl)azetidine-3-carbonyl)piperidin-4-yl)-1H-pyrazol-4-yl)-4-methoxypyrazolo[1,5-a]pyridine-3-carbonitrile (Example 182), replacing the (S)-3-fluoropyrrolidine with the appropriate amine (see Table CGi). Reactions were monitored for completion by LCMS, as such reaction durations were adjusted accordingly. When necessary, title compounds were purified by chromatographic purification using an appropriate gradient eluent, and if necessary free based using a similar extraction procedure as found in Example 182.

TABLE C3

| Ex # | Structure | Chemical Name | MS apci (m/z) |
|---|---|---|---|
| 183 | 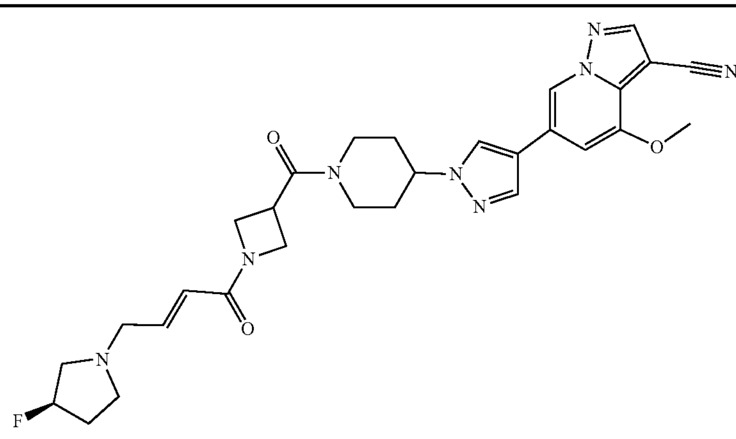 | (R,E)-6-(1-(1-(1-(4-(3-fluoropyrrolidin-1-yl)but-2-enoyl)azetidine-3-carbonyl)piperidin-4-yl)-1H-pyrazol-4-yl)-4-methoxypyrazolo[1,5-a]pyridine-3-carbonitrile | 561.3 (M + H) |

TABLE C3-continued

| Ex # | Structure | Chemical Name | MS apci (m/z) |
|---|---|---|---|
| 184 | 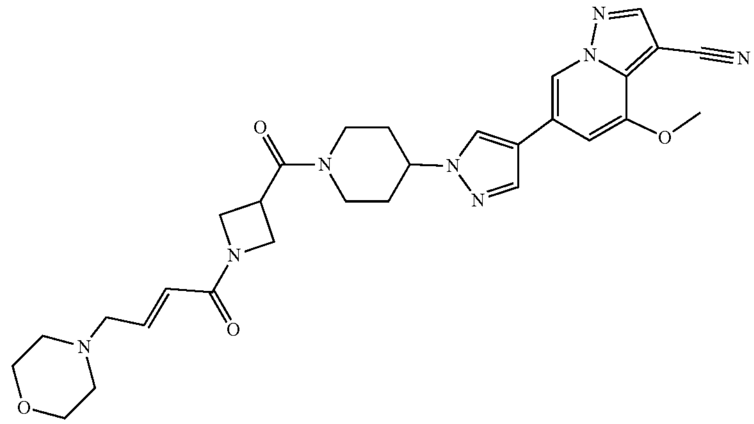 [SMILES: COc1cc(-c2cnn(C3CCN(C(=O)C4CN(C(=O)/C=C/CN5CCOCC5)C4)CC3)c2)cn2ncc(C#N)c12] | (E)-4-methoxy-6-(1-(1-(1-(4-morpholinobut-2-enoyl)azetidine-3-carbonyl)piperidin-4-yl)-1H-pyrazol-4-yl)pyrazolo[1,5-a]pyridine-3-carbonitrile | 559.3 (M + H) |

Example 185

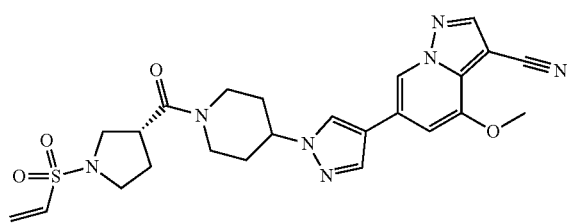 [SMILES: C=CS(=O)(=O)N1CC[C@@H](C(=O)N2CCC(n3cc(-c4cc(OC)c5c(C#N)cnn5c4)cn3)CC2)C1]

(R)-4-methoxy-6-(1-(1-(1-(vinylsulfonyl)pyrrolidine-3-carbonyl)piperidin-4-yl)-1H-pyrazol-4-4pyrazolo[1,5-a]pyridine-3-carbonitrile A solution of (R)-4-methoxy-6-(1-(1-(pyrrolidine-3-carbonyl)piperidin-4-yl)-1H-pyrazol-4-yl)pyrazolo[1,5-a]pyridine-3-carbonitrile (Intermediate P104, Table CE; 33 mg, 0.0787 mmol) in DCM (6 mL) was treated sequentially with TEA (54.8 µL, 0.383 mmol) and ethenesulfonyl chloride (13.4 µL, 0.157 mmol), then stirred for 2 h at ambient temperature. Subsequently, the reaction mixture was concentrated in vacuo and the resulting residue was purified by by C18 reverse phase chromatography (using 5-95% ACN in water with 0.1% TFA as the gradient eluent) to cleanly afford the title compound as the TFA salt. The TFA salt then was diluted with 4:1 DCM:iPrOH and extracted with saturated NaHCO$_{3(aq)}$. The organic extracts then were dried over anhydrous Na$_2$SO$_{4(s)}$, filtered, and concentrated in vacuo to cleanly afford the title compound (20 mg, 50% yield). MS (apci) m/z=510.2 (M+H).

The compounds in Table C4 were prepared using a similar method to that described in the synthesis of (R)-4-methoxy-6-(1-(1-(1-(vinylsulfonyl)pyrrolidine-3-carbonyl)piperidin-4-yl)-1H-pyrazol-4-yl)pyrazolo[1,5-a]pyridine-3-carbonitrile (Example 185), employing the following modifications: using 1.1-5 equivalents of ethenesulfonyl chloride, 1-10 equivalents of TEA, where noted (*) order of addition of TEA and vinyl sulfonyl chloride was inverted, solvent (DCM) concentration of 0.01-0.1 M, and replacing the (R)-4-methoxy-6-(1-(1-(pyrrolidine-3-carbonyl)piperidin-4-yl)-1H-pyrazol-4-yl)pyrazolo[1,5-a]pyridine-3-carbonitrile (Intermediate P104, Table CE) with the appropriate amine from the synthetic intermediates section (e.g. Table CA$^1$, CA$^2$, CB, CC, CD, CE, CF, etc.). Reactions were monitored for completion by LCMS, as such reaction durations were adjusted accordingly. When necessary, title compounds were purified chromatographically using an appropriate gradient eluent followed by an aqueous wash with a mild base (as in Example 185).

TABLE C4

| Ex # | Structure | Chemical Name | MS apci (m/z) |
|---|---|---|---|
| 186* | 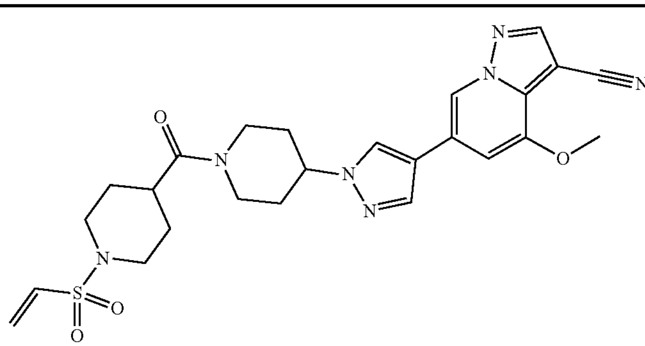 | 4-methoxy-6-(1-(1-(1-(vinylsulfonyl)piperidine-4-carbonyl)piperidin-4-yl)-1H-pyrazol-4-yl)pyrazolo[1,5-a]pyridine-3-carbonitrile | 524.2 (M + H) |

TABLE C4-continued

| Ex # | Structure | Chemical Name | MS apci (m/z) |
|---|---|---|---|
| 187* | 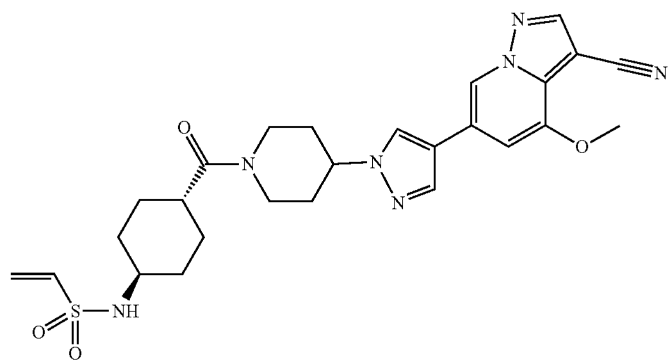 | N-((1r,4r)-4-(4-(4-(3-cyano-4-methoxypyrazolo[1,5-a]pyridin-6-yl)-1H-pyrazol-1-yl)piperidine-1-carbonyl)cyclohexyl)ethenesulfonamide | 536.1 (M − H) |
| 188 | 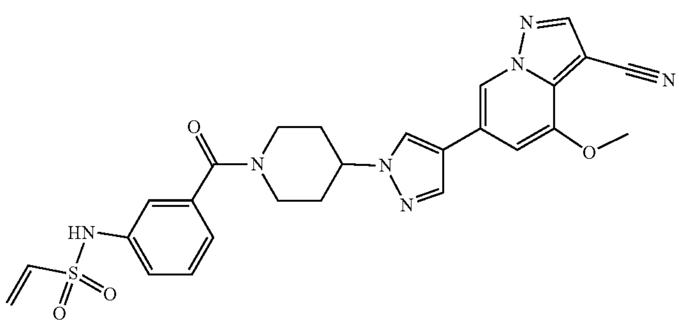 | N-(3-(4-(4-(3-cyano-4-methoxypyrazolo[1,5-a]pyridin-6-yl)-1H-pyrazol-1-yl)piperidine-1-carbonyl)phenyl)ethenesulfonamide | 530.2 (M − H) |
| 189 | 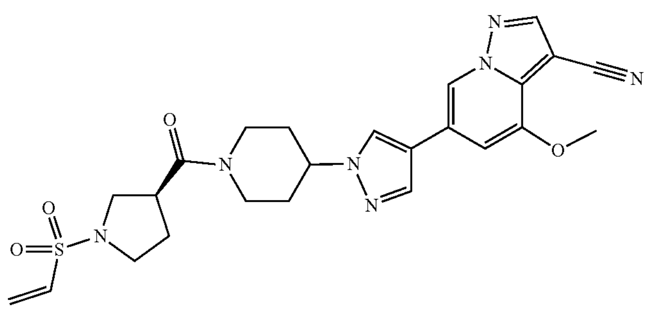 | (S)-4-methoxy-6-(1-(1-(1-(vinylsulfonyl)pyrrolidine-3-carbonyl)piperidin-4-yl)-1H-pyrazol-4-yl)pyrazolo[1,5-a]pyridine-3-carbonitrile | 510.2 (M + H) |
| 190 | 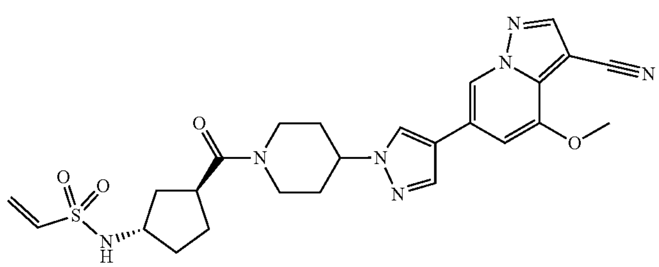 | N-((1S,3S)-3-(4-(4-(3-cyano-4-methoxypyrazolo[1,5-a]pyridin-6-yl)-1H-pyrazol-1-yl)piperidine-1-carbonyl)cyclopentyl)ethenesulfonamide | 524.4 (M + H) |
| 191* | 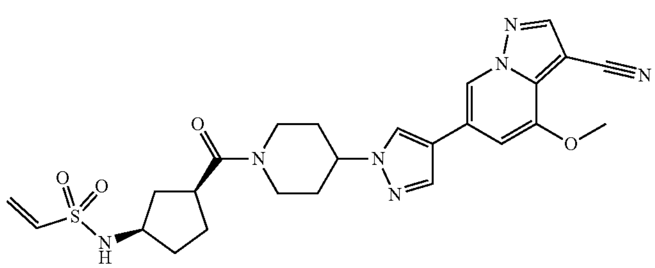 | N-((1R,3S)-3-(4-(4-(3-cyano-4-methoxypyrazolo[1,5-a]pyridin-6-yl)-1H-pyrazol-1-yl)piperidine-1-carbonyl)cyclopentyl)ethenesulfonamide | 524.2 (M + H) |

TABLE C4-continued

| Ex # | Structure | Chemical Name | MS apci (m/z) |
|---|---|---|---|
| 192* | 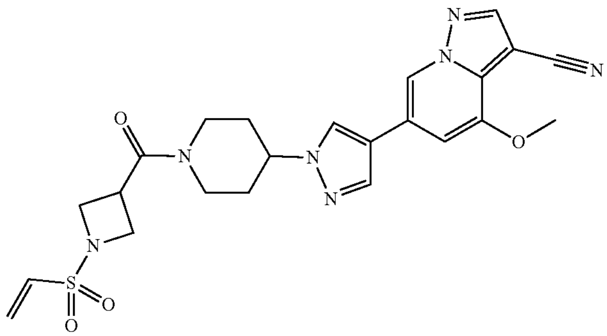 | 4-methoxy-6-(1-(1-(1-(vinylsulfonyl)azetidine-3-carbonyl)piperidin-4-yl)-1H-pyrazol-4-yl)pyrazolo[1,5-a]pyridine-3-carbonitrile | (1)H NMR data included below |
| 193 | 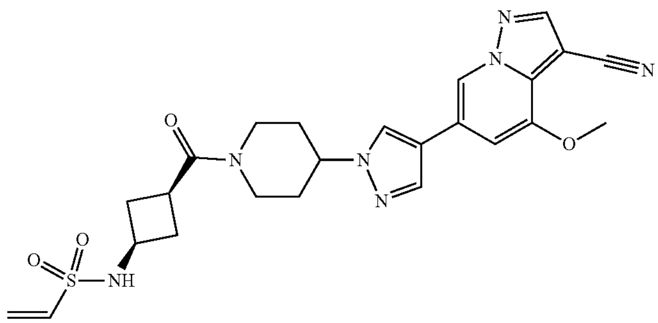 | N-((1s,3s)-3-(4-(4-(3-cyano-4-methoxypyrazolo[1,5-a]pyridin-6-yl)-1H-pyrazol-1-yl)piperidine-1-carbonyl)cyclobutyl)ethenesulfonamide | 510.2 (M + H) |
| 194* | 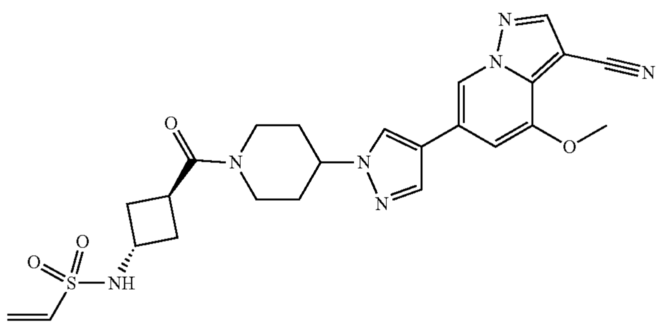 | N-((1r,3r)-3-(4-(4-(3-cyano-4-methoxypyrazolo[1,5-a]pyridin-6-yl)-1H-pyrazol-1-yl)piperidine-1-carbonyl)cyclobutyl)ethenesulfonamide | 508.1 (M − H) |
| 195* | 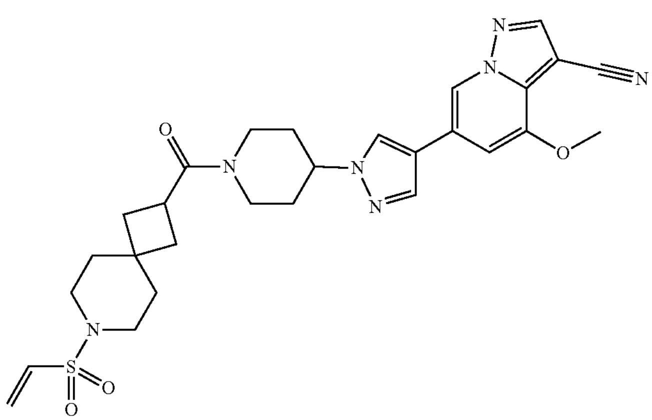 | 4-methoxy-6-(1-(1-(7-(vinylsulfonyl)-7-azaspiro[3.5]nonane-2-carbonyl)piperidin-4-yl)-1H-pyrazol-4-yl)pyrazolo[1,5-a]pyridine-3-carbonitrile | (1)H NMR data included below |

Example 192

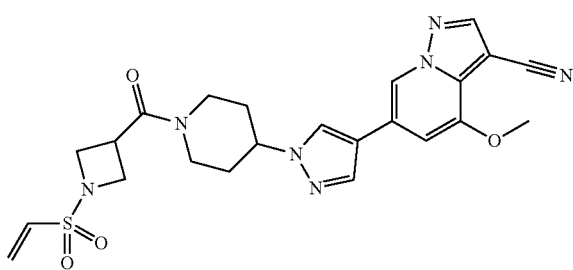 [SMILES: C=CS(=O)(=O)N1CC(C(=O)N2CCC(n3cc(-c4cc(OC)c5c(C#N)cnn5c4)cn3)CC2)C1]

4-methoxy-6-(1-(1-(1-(vinylsulfonyl)azetidine-3-carbonyl)piperidin-4-yl)-1H-pyrazol-4-yl)pyrazolo[1,5-a]pyridine-3-carbonitrile ¹H NMR (CDCl₃) δ 8.27 (s, 1H), 8.14 (s, 1H), 7.77 (s, 1H), 7.67 (s, 1H), 6.70 (s, 1H), 6.57 (m, 1H), 6.33 (m, 1H), 6.18 (m, 1H), 4.70 (m, 1H), 4.38 (m, 1H), 4.10 (m, 5H), 3.63 (m, 2H), 3.20 (m, 1H), 2.86 (m, 1H), 2.23 (m, 2H), 1.96 (m, 2H), 1.56 (m, 2H).

Example 195

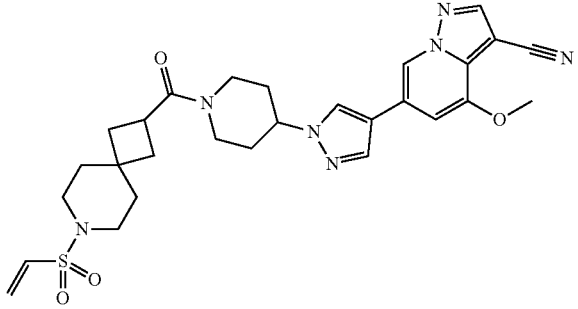 [SMILES: C=CS(=O)(=O)N1CCC2(CC1)CC(C(=O)N1CCC(n3cc(-c4cc(OC)c5c(C#N)cnn5c4)cn3)CC1)C2]

4-methoxy-6-(1-(1-(7-(vinylsulfonyl)-7-azaspiro[3.5]nonane-2-carbonyl)piperidin-4-yl)-1H-pyrazol-4-yl)pyrazolo[1,5-a]pyridine-3-carbonitrile ¹H NMR (CDCl₃) δ 8.27 (s, 1H), 8.13 (s, 1H), 7.76 (s, 1H), 7.67 (s, 1H), 6.71 (s, 1H), 6.38 (m, 1H), 6.20 (m, 1H), 5.99 (m, 1H), 4.73 (m, 1H), 4.37 (m, 1H), 4.06 (s, 3H), 3.83 (m, 1H), 3.17 (m, 4H), 2.80 (m, 1H), 2.17 (m, 4H), 1.96 (m, 4H), 1.74 (m, 2H), 1.65 (m, 2H), 1.38 (m, 2H).

Example 196

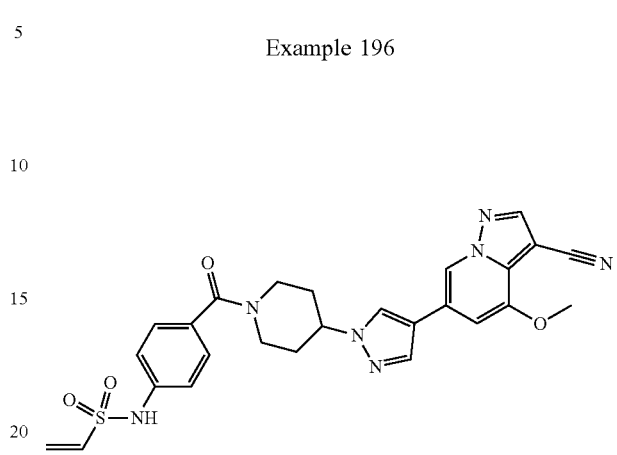

N-(4-(4-(4-(3-cyano-4-methoxypyrazolo[1,5-a]pyridin-6-yl)-1H-pyrazol-1-yl)piperidine-1-carbonyl)phenyl)ethenesulfonamide A solution of 6-(1-(1-(4-aminobenzoyl)piperidin-4-yl)-1H-pyrazol-4-yl)-4-methoxypyrazolo[1,5-a]pyridine-3-carbonitrile (Intermediate P101; 30 mg, 0.0680 mmol) and ethenesulfonyl chloride (6.97 μL, 0.0815 mmol) in DMSO (4.82 μL) was treated with pyridine (27.5 μL, 0.340 mmol), then stirred for 15 min at ambient temperature. Subsequently, the reaction mixture was diluted with water and allowed to stir for 15 min at ambient temperature. The resulting suspension was filtered, and the solids were collected. The solids were dissolved in DCM, and the solution was extracted sequentially with water (3×) and brine (2×). The organic extracts then were dried over anhydrous Na₂SO₄₍ₛ₎, filtered, and concentrated in vacuo. The crude residue was purified by silica chromatography (using 0-100% DCM:Acetone as the gradient eluent) to cleanly afford the title compound (5.2 mg, 14.4% yield). MS (apci) m/z=530.2 (M+H).

ABBREVIATIONS

| | |
|---|---|
| 10% Pd/C | Palladium 10 wt. % (dry basis), active carbon, wet, Degussa |
| 1-Boc-L-nipecotic acid | (S)-1-Boc-piperidine-3-carboxylic acid; or (S)-1-(tert-butoxycarbonyl)piperidine-3-carboxylic acid |
| ACN | Acetonitrile |
| AcOH | Acetic Acid |
| Bis(pinacolato)diboron | 4,4,4',4',5,5,5',5'-octamethyl-2,2'-bi(1,3,2-dioxaborolane) |
| Boc | tert-butyl carboxylate group |
| Boc-anhydride | di-tert-butyl dicarbonate |
| Boc-D-nipecotic acid | (R)-1-Boc-piperidine-3-carboxylic acid; or (R)-1-(tert-butoxycarbonyl)piperidine-3-carboxylic acid |
| Boc-Inp-OH | 1-Boc-piperidine-4-carboxylic acid, Boc-isonipecotic acid or 1-(tert-butoxycarbonyl)piperidine-4-carboxylic acid |
| Cu(OAc)₂ | Copper (II) diacetate; copper(II) acetate |
| CuI | Copper (I) Iodide |
| d | day, days |
| DCE | 1,2-Dichloroethane |
| DCM | Dichloromethane |
| DI water | Deionized water |
| DIAD | Diisopropyl azodicarboxylate |
| DIEA | N,N-Diisopropylethylamine |

| | |
|---|---|
| dioxane | 1,4-dioxane |
| DMA | N,N-Dimethylacetamide |
| DMAP | 4-Dimethylaminopyridine |
| DME | 1,2-Dimethoxyethane |
| DMF | N,N-Dimethylformamide |
| DMSO | Dimethylsulfoxide |
| EDC-HCl | 1-Ethyl-3-(3-dimethylaminopropyl)carbodiimide hydrochloride |
| eq | equivalent |
| $Et_2O$ | Diethyl Ether |
| EtOAc | Ethyl Acetate |
| EtOH | Ethanol |
| GF/F paper | GF/F glass microfiber filter paper |
| h | hour, hours |
| HATU | 1-[Bis(dimethylamino)methylene]-1H-1,2,3-triazolo[4,5-b]pyridinium 3-oxide hexafluorophosphate or 2-(7-Aza-1H-benzotriazole-1-yl)-1,1,3,3-tetramethyluronium hexafluorophosphate |
| HBTU | 3-[Bis(dimethylamino)methyliumyl]-3H-benzotriazol-1-oxide hexafluorophosphate or 2-(1H-benzotriazole-1-yl)-1,1,3,3-tetramethyluronium hexafluorophosphate |
| HOAc | Acetic Acid |
| i-PrMgCl | Isopropyl magnesium chloride |
| iPrOH | Isopropanol |
| $K_2HPO_4$ | Potassium Phosphate, Dibasic |
| KOAc | Potassium Acetate |
| LCMS | Liquid chromatography-mass spectrometry |
| $Me_4N(AcO)_3BH$ | Tetramethylammonium Triacetoxyborohydride |
| MeI | iodomethane |
| MeOH | Methanol |
| min | minute, minutes |
| MSH | o-(mesitylsulfonyl)hydroxylamine |
| MsCl | Methanesulfonyl chloride |
| MTBE | Methyl tert-Butyl Ether |
| $NaBH(OAc)_3$ | Sodium Triacetoxyborohydride |
| NBS | N-Bromosuccinimide |
| n-BuLi | n-butyllithium or 1-butyllithium |
| NCS | N-Chlorosuccinimide |
| $NH_4OAc$ | Ammonium Acetate |
| NIS | N-Iodosuccinimide |
| P1-HCO$_3$ resin | Stratospheres MP-HCO3 |
| $Pd(PPh_3)_4$ | Tetrakis(triphenylphosphine)palladium (0) |
| Pd/C | Palladium on Carbon |
| $Pd_2(dba)_3$ | tris(dibenzylideneacetone)dipalladium (0) |
| $Pd_2(dba)_3 \cdot CHCl_3$ | tris(dibenzylideneacetone)dipalladium (0) chloroform complex |
| $PdCl_2(dppf) \cdot CH_2Cl_2$ | 1,1-Bis(diphenylphosphino)ferrocene-palladium(II)dichloride dichloromethane complex |
| $PdCl_2(PPh_3)_2$ | Palladium(II)bis(triphenylphosphine) dichloride, |
| $PPh_3$ | Triphenylphosphine |
| $PhN(Tf)_2$ | 1,1,1-trifluoro-N-phenyl-N-((trifluoromethyl)sulfonyl)methanesulfonamide |
| PPTS | Pyridinium p-toluenesulfonate |
| PS frit | Biotage ® "Isolute Phase Separators" |
| PS paper | Whatman ® silicone treated Phase Separators filter paper |
| PVDF (0.45 μm) disc | polyvinylidene difluoride membrane with a 0.45-micron pore size |
| rt | Room temperature |
| s-BuOH | Sec-Butanol or 2-Butanol |
| TBAF | Tetra-n-butylammonium fluoride |
| t-BuOH | tert-Butanol or 2-Methylpropan-2-ol |
| TEA | Triethylamine |
| TFA | Trifluoroacetic acid |
| Tf-O-Tf | trifluoromethanesulfonic anhydride |
| THF | tetrahydrofuran |
| Triphosgene | (bis(trichloromethyl) carbonate |
| TsCl | 4-Toluenesulfonyl chloride |
| X-phos | dicyclohexyl(2',4',6'-triisopropyl-[1,1'-biphenyl]-2-yl)-phosphine |

Biological Activity

Example A

Enzyme Assay

The potency of compounds inhibiting human isoforms of FGFR kinase was determined using Life Technologies' Homogeneous Time Resolved Fluorescence (HTRF)-based binding assay technology. An incubation was conducted with either 5 nM dephosphorylated FGFR1 (Array Biopharma, p1702; SEQ ID NO: 1, amino acids 458 to 765, dephosphorylated by co-expression with PTP1b (protein tyrosine phosphatase 1B)), 5 nM dephosphorylated FGFR2 (Life Technologies, Cat. No. PV4106 that had been dephosphorylated with Lambda protein phosphatase (New England Biolabs, cat #P0753)) or 5 nM phosphorylated FGFR3 (Array Biopharma, p1836; SEQ ID NO: 5, amino acids 449 to 759), 50 nM Kinase Tracer 236 (Life Technologies Cat. No. PR9078A), 2 nM Biotin-anti-6HIS (Life Technologies Cat. No. PV6090) and 2 nM Europium-Streptavidin (Life Technologies Cat. No. PV6025) along with test compound in a buffer consisting of 50 mM HEPES ((4-(2-hydroxyethyl)-1-piperazineethanesulfonic acid, pH 7.5), 5 mM $MgCl_2$, 0.005% Triton X-100, 1 mM DTT, 1 mM $NaVO_4$ and 2% DMSO in a final volume of 12 µL. Compounds were typically prepared as a 3-fold or 4-fold serial dilution in DMSO and added to the assay to give the appropriate final concentration. After a 60 minute incubation at 22° C., the extent of tracer displacement was determined using a PerkinElmer EnVision multimode plate reader via HTRF dual wavelength detection, and the percent of control (POC) was calculated using a ratiometric emission factor. One hundred POC was determined using no test compound, and 0 POC was determined in the presence of 1 µM of an appropriate control inhibitor. A 4-parameter logistic curve was fit to the POC values as a function of the concentration of compound, and the $IC_{50}$ value was the point where the best-fit curve crossed 50 POC.

Table EA contains $IC_{50}$ values for compounds tested in this assay, presented as the average of multiple determinations if multiple determinations were made. ND=not determined.

TABLE EA

| | FGFR Enzyme Binding IC50 values | | |
|---|---|---|---|
| Example number | FGFR1 Binding $IC_{50}$ (nM) | FGFR2 Binding $IC_{50}$ (nM) | FGFR3 Binding $IC_{50}$ (nM) |
| 1 | 50 | ND | 4 |
| 2 | 45 | ND | 4 |
| 3 | 44 | ND | 3 |
| 4 | 42 | ND | 6 |
| 5 | 47 | ND | 5 |
| 6 | 157 | ND | 18 |
| 7 | 52 | ND | 9 |
| 8 | 73 | ND | 8 |
| 9 | 56 | ND | 5 |
| 10 | 56 | ND | 4 |
| 11 | 210 | ND | 25 |
| 12 | 214 | ND | 32 |
| 13 | 245 | ND | 39 |
| 14 | 84 | ND | 7 |
| 15 | 32 | ND | 2 |
| 16 | 31 | ND | 6 |
| 17 | 45 | ND | 8 |
| 18 | 131 | ND | 26 |
| 19 | 56 | ND | 11 |
| 20 | 93 | ND | 18 |
| 21 | 57 | ND | 5 |
| 22 | 112 | ND | 8 |
| 23 | 431 | ND | 54 |
| 24 | 310 | ND | 69 |
| 25 | 350 | ND | 52 |
| 26 | 552 | ND | 128 |
| 27 | 191 | ND | 44 |
| 28 | 105 | ND | 17 |
| 29 | 251 | ND | 43 |
| 30 | 51 | ND | 5 |
| 31 | 26 | ND | 2 |
| 32 | 113 | ND | 31 |
| 33 | 20 | ND | 3 |
| 34 | 231 | ND | 36 |
| 35 | 119 | ND | 23 |
| 36 | 59 | ND | 4 |
| 37 | 289 | 44 | 3 |
| 38 | 33 | ND | 2 |
| 39 | 26 | ND | 2 |
| 40 | 38 | ND | 5 |
| 41 | 61 | ND | 3 |
| 42 | 43 | ND | 3 |
| 43 | 54 | ND | 4 |
| 44 | 97 | ND | 20 |
| 45 | 164 | ND | 44 |
| 46 | 23 | ND | 4 |
| 47 | 177 | ND | 22 |
| 48 | 109 | ND | 25 |
| 49 | 113 | ND | 13 |
| 50 | 27 | 14 | 3 |
| 51 | 70 | 38 | 9 |
| 52 | 86 | 32 | 14 |
| 53 | 179 | ND | 31 |
| 54 | 142 | ND | 25 |
| 55 | 98 | ND | 7 |
| 56 | 135 | ND | 18 |
| 57 | 214 | ND | 25 |
| 58 | 290 | ND | 41 |
| 59 | 115 | ND | 16 |
| 60 | 203 | ND | 32 |
| 61 | 346 | ND | 61 |
| 62 | 328 | ND | 64 |
| 63 | 199 | ND | 62 |
| 64 | 94 | ND | 20 |
| 65 | 177 | ND | 56 |
| 66 | 72 | ND | 10 |
| 67 | 47 | ND | 12 |
| 68 | 94 | ND | 13 |
| 69 | 77 | ND | 11 |
| 70 | 199 | ND | 30 |
| 71 | 147 | ND | 18 |
| 72 | 36 | ND | 7 |
| 73 | 58 | ND | 7 |
| 74 | 18 | ND | 3 |
| 75 | 120 | ND | 22 |
| 76 | 409 | ND | 55 |
| 77 | 393 | ND | 118 |
| 78 | 98 | ND | 8 |
| 79 | 447 | ND | 79 |
| 80 | 174 | ND | 22 |
| 81 | 186 | ND | 60 |
| 82 | 374 | ND | 23 |
| 83 | 420 | 17 | 14 |
| 84 | 777 | 21 | 22 |
| 85 | 247 | 36 | 3 |
| 86 | 342 | 12 | 9 |
| 87 | 322 | 51 | 16 |
| 88 | 202 | 12 | 3 |
| 89 | 236 | 53 | 8 |
| 90 | 379 | 54 | 14 |
| 91 | 284 | 19 | 2 |
| 92 | 444 | ND | 49 |
| 93 | 482 | ND | 40 |
| 94 | 346 | ND | 18 |
| 95 | 675 | 155 | 26 |
| 96 | 1625 | ND | 73 |
| 97 | 572 | ND | 53 |
| 98 | 218 | ND | 19 |
| 99 | 47 | ND | 5 |
| 100 | 57 | ND | 5 |
| 101 | 42 | ND | 3 |
| 102 | 44 | 22 | 6 |
| 103 | 70 | 39 | 10 |
| 104 | 72 | 45 | 12 |
| 105 | 435 | 226 | 97 |
| 106 | 62 | 30 | 9 |
| 107 | 108 | 56 | 16 |
| 108 | 55 | 28 | 11 |
| 109 | 56 | ND | 8 |
| 110 | 58 | ND | 8 |
| 111 | 144 | ND | 11 |
| 112 | 82 | 16 | 4 |
| 113 | 388 | ND | 45 |
| 114 | 850 | ND | 63 |
| 115 | 90 | ND | 11 |
| 116 | 141 | ND | 19 |
| 117 | 814 | 103 | 19 |
| 118 | 455 | 56 | 9 |
| 119 | 565 | 60 | 8 |
| 120 | 400 | 84 | 33 |
| 121 | 114 | 12 | 3 |
| 122 | 120 | ND | 7 |

TABLE EA-continued

FGFR Enzyme Binding IC50 values

| Example number | FGFR1 Binding IC$_{50}$ (nM) | FGFR2 Binding IC$_{50}$ (nM) | FGFR3 Binding IC$_{50}$ (nM) |
|---|---|---|---|
| 123 | 221 | ND | 22 |
| 124 | 119 | ND | 9 |
| 125 | 13 | ND | 2 |
| 126 | 147 | ND | 11 |
| 127 | 59 | ND | 10 |
| 128 | 38 | ND | 6 |
| 129 | 271 | ND | 34 |
| 130 | 7 | ND | 3 |
| 131 | 7 | ND | 1 |
| 132 | 71 | ND | 7 |
| 133 | 2928 | ND | 160 |
| 134 | 35 | ND | 2 |
| 135 | 35 | 13 | 3 |
| 137 | 49 | 15 | 8 |
| 138 | 27 | ND | 2 |
| 139 | 104 | ND | 11 |
| 140 | 37 | 19 | 7 |
| 141 | 40 | 18 | 6 |
| 142 | 36 | 16 | 5 |
| 143 | 33 | ND | 2 |
| 144 | 276 | ND | 24 |
| 145 | 60 | ND | 4 |
| 146 | 51 | ND | 4 |
| 148 | 217 | ND | 14 |
| 149 | 229 | ND | 33 |
| 150 | 229 | ND | 22 |
| 151 | 171 | 38 | 11 |
| 152 | 320 | 49 | 7 |
| 153 | 210 | 11 | 2 |
| 154 | 430 | 69 | 19 |
| 155 | 426 | 51 | 10 |
| 156 | 598 | 26 | 18 |
| 157 | 274 | 6 | 6 |
| 158 | 168 | 8 | 2 |
| 159 | 144 | 24 | 3 |
| 160 | 571 | 33 | 16 |
| 161 | 589 | 44 | 5 |
| 162 | 1719 | 462 | 48 |
| 163 | 1138 | 125 | 34 |
| 164 | 350 | 14 | 3 |
| 165 | 800 | ND | 223 |
| 166 | 129 | ND | 48 |
| 167 | 1119 | ND | 192 |
| 168 | 608 | 219 | 34 |
| 169 | 788 | ND | 49 |
| 170 | 488 | 22 | 5 |
| 171 | 336 | 41 | 5 |
| 172 | 922 | 125 | 25 |
| 173 | 359 | 45 | 7 |
| 174 | 194 | ND | 12 |
| 175 | 90 | ND | 8 |
| 176 | 136 | ND | 15 |
| 177 | ND | ND | ND |
| 178 | 61 | ND | 8 |
| 179 | 22 | 6 | 1 |
| 180 | 14 | 4 | 2 |
| 181 | 32 | 12 | 3 |
| 182 | 40 | 15 | 2 |
| 183 | 46 | 19 | 4 |
| 184 | 52 | 20 | 6 |
| 185 | 40 | ND | 4 |
| 186 | 14 | ND | 2 |
| 187 | 31 | ND | 4 |
| 188 | 14 | ND | 1 |
| 189 | 27 | ND | 3 |
| 190 | 37 | ND | 3 |
| 191 | 103 | ND | 10 |
| 192 | 70 | ND | 12 |
| 193 | 36 | 3 | 2 |
| 194 | 93 | ND | 4 |
| 195 | 50 | ND | 4 |
| 196 | 31 | ND | 3 |

Example B

FGFR Enzyme Activity Assay

FGFR1 kinase activity was measured by the Invitrogen LanthaScreen™ Assay technology which directly measures the amount of substrate phosphorylation by Time-resolved fluorescence energy transfer (TR-FRET) using a fluorescently-labeled peptide and Europium-labeled antibody. Briefly, 200 µM His-tagged recombinant human FGFR1 catalytic domain (amino acids 308-731) (Life Technologies Cat. No. PR4660A) was incubated with 100 nM Alexa Fluor® 647-Poly-GT Peptide Substrate (Life Technologies Cat. No. PV5836) and 151.1M ATP along with test compound in a buffer consisting of 250 mM HEPES, 25 mM MgCl2, 0.05% TritonX-100, pH 7.5, and 2% DMSO. Compounds were typically prepared in a threefold serial dilution in DMSO and added to the assay to give the appropriate final concentration. After a 20 minutes incubation at 22° C., an equal volume of 2 nM LanthaScreen® Eu-PY20 Antibody (Life Technologies Cat. No. PV5691) and 10 mM EDTA was added to quench the kinase reaction and start the detection reaction. After an additional 60 minute incubation at 22° C., the reaction was measured using a PerkinElmer EnVision multimode plate reader via TR-FRET dual wavelength detection, and the percent of control (POC) calculated using a ratiometric emission factor. 100 POC was determined using no test compounds and 0 POC was determined using no enzyme. The POC values were fit to a 4-parameter logistic curve as a function of the concentration of the compound, and the IC50 value is the point where the curve crosses 50 POC.

FGFR2 kinase activity was measured by the Invitrogen LanthaScreen™ Assay technology which directly measures the amount of substrate phosphorylation by TR-FRET using a fluorescently-labeled peptide and Europium-labeled antibody. Briefly, 200 µM His-tagged recombinant human FGFR2 cytoplasmic domain (amino acids 403-822) (Life Technologies Cat. No. PR5332A) was incubated with 100 nM Alexa Fluor® 647-Poly-GT Peptide Substrate (Life Technologies Cat. No. PV5836) and 15 µM ATP along with test compound in a buffer consisting of 250 mM HEPES, 25 mM MgCl2, 0.05% TritonX-100, pH 7.5, and 2% DMSO. Compounds were typically prepared in a threefold serial dilution in DMSO and added to the assay to give the appropriate final concentration. After a 20 minute incubation at 22° C., an equal volume of 2 nM LanthaScreen® Eu-PY20 Antibody (Life Technologies Cat. No. PV5691) and 10 mM EDTA were added to quench the kinase reaction and start the detection reaction. After an additional 60 minute incubation at 22° C., the reaction was measured using a PerkinElmer EnVision multimode plate reader via TR-FRET dual wavelength detection, and the percent of control (POC) calculated using a ratiometric emission factor. 100 POC was determined using no test compounds and 0 POC was determined using no enzyme. The POC values were fit to a 4-parameter logistic curve as a function of the concentration of the compound, and the IC50 value is the point where the curve crosses 50 POC.

FGFR3 kinase activity was measured by the Invitrogen LanthaScreen™ Assay technology which directly measures the amount of substrate phosphorylation by TR-FRET using a fluorescently-labeled peptide and Europium-labeled antibody. Briefly, 750 µM N-terminal GST-HIS6 fusion protein with a 3C cleavage site recombinant human FGFR3 (amino acids R397-T806) (ProQinase Cat. No. 1068-0000-1) was incubated with 100 nM Alexa Fluor® 647-Poly-GT Peptide Substrate (Life Technologies Cat. No. PV5836) and 25 μM ATP along with test compound in a buffer consisting of 250 mM HEPES, 25 mM MgCl2, 0.05% TritonX-100, pH 7.5, and 2% DMSO. Compounds were typically prepared in a threefold serial dilution in DMSO and added to the assay to give the appropriate final concentration. After a 10 minute incubation at 22° C., an equal volume of 2 nM LanthaScreen® Eu-PY20 Antibody (Life Technologies Cat. No. PV5691) and 10 mM EDTA were added to quench the kinase reaction and start the detection reaction. After an additional 60 minute incubation at 22° C., the reaction was measured using a PerkinElmer EnVision multimode plate reader via TR-FRET dual wavelength detection, and the percent of control (POC) calculated using a ratiometric emission factor. 100 POC was determined using no test compounds and 0 POC was determined using no enzyme. The POC values were fit to a 4-parameter logistic curve as a function of the concentration of the compound, and the IC50 value is the point where the curve crosses 50 POC.

Table EB contains IC50 values for compounds tested in these assays, presented as the average of multiple determinations if multiple determinations were made. ND=Not determined.

TABLE EB

FGFR Enzyme Activity IC$_{50}$ values

| Example Number | FGFR1 Enz FRET IC$_{50}$ (nM) | FGFR2 Enz FRET IC$_{50}$ (nM) | FGFR3 Enz FRET IC$_{50}$ (nM) |
|---|---|---|---|
| 1 | 5 | 15 | 5 |
| 2 | 4 | 14 | 4 |
| 3 | 8 | 5 | 2 |
| 4 | 11 | 4 | 3 |
| 5 | 25 | 11 | 7 |
| 6 | 10 | 4 | 4 |
| 7 | 18 | 6 | 2 |
| 8 | 18 | 7 | 3 |
| 9 | 32 | 5 | 4 |
| 10 | 34 | 6 | 6 |
| 11 | 22 | 7 | 7 |
| 12 | 12 | 3 | 3 |
| 13 | 10 | 2 | 3 |
| 14 | 8 | 3 | 3 |
| 15 | 7 | 2 | 2 |
| 16 | 20 | 4 | 2 |
| 17 | 17 | 7 | 6 |
| 18 | 18 | 4 | 2 |
| 19 | 20 | 8 | 7 |
| 20 | 14 | 3 | 3 |
| 21 | 10 | 3 | 3 |
| 22 | 21 | 5 | 4 |
| 23 | 36 | 12 | 16 |
| 24 | 63 | 23 | 31 |
| 25 | 53 | 18 | 12 |
| 26 | 188 | 42 | 58 |
| 27 | 63 | 13 | 21 |
| 28 | 18 | 5 | 9 |
| 29 | 24 | 8 | 11 |
| 30 | 9 | 3 | 2 |
| 31 | 8 | 2 | 2 |
| 32 | 13 | 4 | 3 |
| 33 | 20 | 4 | 1 |
| 34 | 19 | 5 | 2 |
| 35 | 19 | 5 | 3 |
| 36 | 11 | 3 | 4 |
| 37 | 16 | 7 | 4 |
| 38 | 10 | 3 | 3 |
| 39 | 11 | 5 | 3 |
| 40 | 9 | 3 | 2 |
| 41 | 2 | 1 | 2 |
| 42 | 11 | 6 | 2 |
| 43 | 6 | 3 | 2 |
| 44 | 11 | 3 | 2 |
| 45 | 32 | 9 | 8 |
| 46 | 12 | 2 | 3 |
| 47 | 35 | 5 | 4 |
| 48 | 11 | 3 | 7 |
| 49 | 43 | 13 | 5 |
| 50 | 24 | 4 | 10 |
| 51 | 34 | 9 | 22 |
| 52 | 66 | 14 | 34 |
| 53 | 26 | 7 | 3 |
| 54 | 47 | 16 | 16 |
| 55 | 19 | 5 | 9 |
| 56 | 28 | 8 | 10 |
| 57 | 34 | 7 | 6 |
| 58 | 55 | 8 | 8 |
| 59 | 47 | 16 | 16 |
| 60 | 31 | 7 | 7 |
| 61 | 28 | 6 | 5 |
| 62 | 18 | 5 | 2 |
| 63 | 26 | 7 | 3 |
| 64 | 23 | 5 | 2 |
| 65 | 26 | 6 | 3 |
| 66 | 16 | 5 | 7 |
| 67 | 8 | 3 | 5 |
| 68 | 6 | 4 | 5 |
| 69 | 12 | 6 | 6 |
| 70 | 16 | 4 | 6 |
| 71 | 18 | 4 | 6 |
| 72 | 25 | 5 | 3 |
| 73 | 20 | 4 | 4 |
| 74 | 19 | 6 | 2 |
| 75 | 39 | 14 | 13 |
| 76 | 52 | 17 | 13 |
| 77 | 35 | 12 | 11 |
| 78 | 17 | 23 | 12 |
| 79 | 36 | 11 | 10 |
| 80 | 26 | 7 | 7 |
| 81 | 31 | 8 | 9 |
| 82 | 73 | 9 | 10 |
| 83 | 77 | 9 | 7 |
| 84 | 100 | 15 | 6 |
| 85 | 77 | 13 | 7 |
| 86 | 617 | 96 | 11 |
| 87 | 240 | 18 | 32 |
| 88 | 152 | 69 | 29 |
| 89 | 108 | 50 | 15 |
| 90 | 165 | 56 | 21 |
| 91 | 197 | 99 | 19 |
| 92 | 285 | 131 | 39 |
| 93 | 376 | 127 | 41 |
| 94 | 73 | 22 | 8 |
| 95 | 842 | 324 | 103 |
| 96 | 384 | 155 | 291 |
| 97 | 117 | 38 | 72 |
| 98 | 22 | 6 | 9 |
| 99 | 13 | 5 | 3 |
| 100 | 9 | 5 | 2 |
| 101 | 13 | 3 | 4 |
| 102 | 38 | 11 | 22 |
| 103 | 49 | 10 | 20 |
| 104 | 63 | 20 | 20 |
| 105 | 193 | 42 | 125 |
| 106 | 61 | 11 | 25 |
| 107 | 68 | 9 | 27 |
| 108 | 20 | 7 | 10 |
| 109 | 12 | 4 | 6 |
| 110 | 16 | 5 | 6 |
| 111 | 12 | 4 | 3 |
| 112 | 21 | 9 | 20 |
| 113 | 107 | 42 | 105 |
| 114 | 308 | 150 | 258 |
| 115 | 85 | 25 | 18 |
| 116 | 54 | 19 | 27 |
| 117 | 789 | 359 | 43 |
| 118 | 551 | 239 | 41 |

TABLE EB-continued

FGFR Enzyme Activity IC$_{50}$ values

| Example Number | FGFR1 Enz FRET IC$_{50}$ (nM) | FGFR2 Enz FRET IC$_{50}$ (nM) | FGFR3 Enz FRET IC$_{50}$ (nM) |
|---|---|---|---|
| 119 | 334 | 219 | 39 |
| 120 | 338 | 39 | 72 |
| 121 | 28 | 13 | 9 |
| 122 | 28 | 12 | 9 |
| 123 | 40 | 13 | 8 |
| 124 | 38 | 17 | 8 |
| 125 | 4 | 3 | 3 |
| 126 | 13 | 6 | 5 |
| 127 | 7 | 5 | 3 |
| 128 | 7 | 5 | 3 |
| 129 | 14 | 9 | 6 |
| 130 | 3 | 3 | 2 |
| 131 | 9 | 10 | 4 |
| 132 | 14 | 13 | 8 |
| 133 | 119 | 63 | 264 |
| 134 | 5 | 16 | 6 |
| 135 | 20 | 4 | 6 |
| 137 | 12 | 4 | 5 |
| 138 | 7 | 3 | 2 |
| 139 | 13 | 3 | 4 |
| 140 | 21 | 2 | 4 |
| 141 | 43 | 5 | 6 |
| 142 | 20 | 3 | 5 |
| 143 | 10 | 2 | 2 |
| 144 | 11 | 5 | 4 |
| 145 | 4 | 3 | 3 |
| 146 | 12 | 2 | 2 |
| 148 | 47 | 6 | 4 |
| 149 | 39 | 6 | 4 |
| 150 | 8 | 6 | 7 |
| 151 | 86 | 9 | 17 |
| 152 | 99 | 35 | 16 |
| 153 | 39 | 4 | 5 |
| 154 | 335 | 16 | 19 |
| 155 | 255 | 114 | 11 |
| 156 | 375 | 84 | 24 |
| 157 | 90 | 30 | 18 |
| 158 | 77 | 30 | 8 |
| 159 | 70 | 7 | 10 |
| 160 | 248 | 179 | 34 |
| 161 | 154 | 31 | 20 |
| 162 | 311 | 69 | 99 |
| 163 | 2210 | 1169 | 229 |
| 164 | 102 | 15 | 8 |
| 165 | 62 | 18 | 15 |
| 166 | 61 | 15 | 14 |
| 167 | 68 | 18 | 17 |
| 168 | 148 | 50 | 72 |
| 169 | 156 | 80 | 83 |
| 170 | 903 | 239 | 17 |
| 171 | 111 | 19 | 24 |
| 172 | 856 | 454 | 101 |
| 173 | 281 | 28 | 41 |
| 174 | 16 | 6 | 4 |
| 175 | 4 | 10 | 5 |
| 176 | 1197 | 732 | 1163 |
| 177 | 11 | 4 | 8 |
| 178 | 14 | 5 | 12 |
| 179 | 15 | 3 | 3 |
| 180 | 19 | 5 | 6 |
| 181 | 9 | 2 | 2 |
| 182 | 12 | 3 | 3 |
| 183 | 16 | 4 | 5 |
| 184 | 15 | 4 | 6 |
| 185 | 16 | 5 | 3 |
| 186 | 5 | 8 | 5 |
| 187 | 17 | 5 | 4 |
| 188 | 11 | 5 | 3 |
| 189 | 8 | 3 | 4 |
| 190 | 9 | 3 | 1 |
| 191 | 19 | 5 | 4 |
| 192 | 14 | 9 | 3 |
| 193 | 7 | 3 | 2 |
| 194 | 13 | 4 | 7 |
| 195 | 19 | 7 | 5 |
| 196 | 10 | 8 | 2 |

Example C

FGFR k$_{obs}$ Assay

The LC/MS FGFR1 and FGFR3 k$_{obs}$ assays were conducted as follows. 500 nM FGFR1 (Array BioPharma construct p1702; SEQ ID NO: 1, amino acids 458-765) or FGFR3 (Array BioPharma construct p1700; SEQ ID NO: 5, amino acids 449-759) were incubated with 3 μM compound in 25 mM HEPES (4-(2-hydroxyethyl)-1-piperazineethanesulfonic acid), pH 7.4, 5 mM MgCl2, 150 mM NaCl, 0.5 mM TCEP (tris(2-carboxyethyl) phosphine), and 2% DMSO in a total volume of 20 μL. At each time point, the reaction was quenched with 20 μL of 0.4% formic acid. The extent of protein modification by each compound was determined by LC/MS on an Agilent Technologies 6520 Q-TOF LC/MS. Protein signals were then automatically deconvoluted using Agilent Masshunter software. Deconvoluted mass signals were exported to Tibco Spotfire data analysis program for further processing and normalization.

Data analysis included five steps. First, the signals for the "DMSO Controls" were analyzed to determine the percent of signal associated with unmodified FGFR1 or FGFR3 at each time point. Next, the percent of the signal associated with the covalent modification was determined. Third, the average nonmodified "DMSO Control" signal was used to normalize the modified protein signals at each time point. The percent of unmodified protein was fit to an exponential decay model where A$_0$ is the Percent Unmodified at the start of the reaction, and kobs is the observed rate constant over the time period.

Table EC contains k$_{obs}$ values for compounds tested in these assays, presented as the average of multiple determinations if multiple determinations were made. ND=not determined.

TABLE EC k$_{obs}$ values

| Example Number | FGFR1 Enz k$_{obs}$ (min$^{-1}$) | FGFR3 Enz k$_{obs}$ (min$^{-1}$) |
|---|---|---|
| 1 | 0.00122 | 0.01496 |
| 2 | 0.00076 | 0.00444 |
| 3 | 0.00172 | 0.01875 |
| 4 | 0.00052 | 0.00283 |
| 5 | 0.00047 | 0.00287 |
| 6 | 0.00093 | 0.00902 |
| 7 | 0.00042 | 0.00305 |
| 8 | 0.00124 | 0.01122 |
| 9 | 0.00590 | 0.02298 |
| 10 | 0.00340 | 0.01566 |
| 11 | 0.00020 | 0.00206 |
| 12 | 0.00029 | 0.00231 |
| 13 | 0.00056 | 0.00418 |
| 14 | 0.00069 | 0.00997 |
| 15 | 0.00168 | 0.01716 |
| 16 | 0.00054 | 0.00124 |
| 17 | 0.00041 | 0.00163 |

TABLE EC-continued $k_{obs}$ values

| Example Number | FGFR1 Enz $k_{obs}$ (min$^{-1}$) | FGFR3 Enz $k_{obs}$ (min$^{-1}$) |
|---|---|---|
| 18 | ND | 0.00040 |
| 19 | ND | 0.00045 |
| 20 | ND | 0.00051 |
| 21 | 0.00085 | 0.00661 |
| 22 | 0.00187 | 0.01080 |
| 23 | 0.00247 | 0.01176 |
| 24 | 0.00250 | 0.00708 |
| 25 | 0.00103 | 0.00672 |
| 26 | ND | 0.00070 |
| 27 | 0.00017 | 0.00184 |
| 28 | 0.00075 | 0.00294 |
| 29 | 0.00075 | 0.00297 |
| 30 | 0.00104 | 0.01214 |
| 31 | 0.00146 | 0.02377 |
| 32 | ND | 0.00043 |
| 33 | ND | 0.00053 |
| 34 | ND | 0.00040 |
| 35 | ND | 0.00043 |
| 36 | 0.00127 | 0.01426 |
| 37 | 0.00447 | 0.07092 |
| 38 | 0.00134 | 0.01168 |
| 39 | 0.01019 | 0.20195 |
| 40 | 0.00138 | 0.01133 |
| 41 | 0.00254 | 0.02709 |
| 42 | 0.00113 | 0.01575 |
| 43 | 0.00050 | 0.00410 |
| 44 | 0.00014 | 0.00100 |
| 45 | 0.00016 | 0.00116 |
| 46 | ND | 0.00153 |
| 47 | 0.00093 | 0.00501 |
| 48 | 0.00071 | 0.00114 |
| 49 | 0.00143 | 0.01768 |
| 50 | 0.00381 | 0.04375 |
| 51 | 0.00338 | 0.01769 |
| 52 | 0.00086 | 0.00929 |
| 53 | 0.00038 | 0.00112 |
| 54 | ND | 0.00025 |
| 55 | 0.00277 | 0.02050 |
| 56 | 0.00181 | 0.01264 |
| 57 | 0.00051 | 0.00150 |
| 58 | 0.00058 | 0.00158 |
| 59 | 0.00106 | 0.00665 |
| 60 | ND | 0.00083 |
| 61 | ND | 0.00064 |
| 62 | 0.00033 | 0.00106 |
| 63 | 0.00050 | 0.00130 |
| 64 | ND | 0.00074 |
| 65 | ND | 0.00020 |
| 66 | 0.00332 | 0.02230 |
| 67 | 0.00146 | 0.00341 |
| 68 | 0.00181 | 0.00950 |
| 69 | 0.00422 | 0.01649 |
| 70 | 0.00278 | 0.01140 |
| 71 | 0.00457 | 0.02545 |
| 72 | 0.00049 | 0.00117 |
| 73 | 0.00108 | 0.00908 |
| 74 | ND | 0.00063 |
| 75 | 0.00081 | 0.00200 |
| 76 | 0.00070 | 0.00317 |
| 77 | ND | 0.00028 |
| 78 | 0.00146 | 0.01629 |
| 79 | ND | 0.00116 |
| 80 | 0.00024 | 0.00111 |
| 81 | 0.00086 | 0.00615 |
| 82 | 0.00034 | 0.00319 |
| 83 | 0.00058 | 0.00547 |
| 84 | 0.00183 | 0.02394 |
| 85 | 0.00492 | 0.10605 |
| 86 | 0.00258 | 0.02116 |
| 87 | 0.00052 | 0.00502 |
| 88 | 0.00646 | 0.05581 |
| 89 | 0.00364 | 0.02499 |
| 90 | 0.00243 | 0.01468 |
| 91 | 0.00431 | 0.04322 |
| 92 | 0.00191 | 0.00836 |
| 93 | 0.00120 | 0.00896 |
| 94 | 0.00145 | 0.01518 |
| 95 | 0.00409 | 0.04202 |
| 96 | 0.00363 | 0.03335 |
| 97 | 0.00276 | 0.01865 |
| 98 | 0.00167 | 0.01995 |
| 99 | 0.00044 | 0.00353 |
| 100 | 0.00250 | 0.02324 |
| 101 | 0.00223 | 0.01185 |
| 102 | 0.00313 | 0.02912 |
| 103 | 0.00388 | 0.02186 |
| 104 | 0.00386 | 0.03006 |
| 105 | 0.00042 | 0.00147 |
| 106 | 0.00246 | 0.01259 |
| 107 | 0.00291 | 0.01688 |
| 108 | 0.00291 | 0.01344 |
| 109 | 0.00060 | 0.00352 |
| 110 | 0.00068 | 0.00626 |
| 111 | 0.00263 | 0.04009 |
| 112 | 0.00852 | 0.11082 |
| 113 | 0.00304 | 0.02175 |
| 114 | 0.00369 | 0.03264 |
| 115 | 0.00160 | 0.01937 |
| 116 | 0.00277 | 0.02585 |
| 117 | 0.00318 | 0.03885 |
| 118 | 0.00303 | 0.02502 |
| 119 | 0.00359 | 0.04536 |
| 120 | 0.00068 | 0.00758 |
| 121 | 0.00369 | 0.06393 |
| 122 | 0.00127 | 0.01396 |
| 123 | 0.00126 | 0.01169 |
| 124 | 0.00241 | 0.02484 |
| 125 | 0.00246 | 0.01842 |
| 126 | 0.00280 | 0.01992 |
| 127 | 0.00133 | 0.01654 |
| 128 | 0.00134 | 0.01702 |
| 129 | 0.00148 | 0.01646 |
| 130 | 0.00132 | 0.01127 |
| 131 | 0.00146 | 0.01762 |
| 132 | 0.00146 | 0.01300 |
| 133 | 0.00274 | 0.02206 |
| 134 | 0.00288 | 0.02537 |
| 135 | 0.00290 | 0.02201 |
| 137 | ND | 0.00097 |
| 138 | 0.01359 | 0.34459 |
| 139 | 0.00047 | 0.00281 |
| 140 | 0.00008 | ND |
| 141 | 0.00014 | 0.00171 |
| 142 | 0.00091 | 0.00708 |
| 143 | 0.00278 | 0.02052 |
| 144 | ND | 0.00271 |
| 145 | 0.00179 | 0.01811 |
| 146 | 0.00306 | 0.01542 |
| 148 | 0.00184 | 0.00827 |
| 149 | 0.00121 | 0.00455 |
| 150 | 0.00266 | 0.02533 |
| 151 | 0.00080 | 0.00820 |
| 152 | 0.00338 | 0.03526 |
| 153 | 0.00975 | 0.15777 |
| 154 | 0.00081 | 0.00747 |
| 155 | 0.03227 | ND |
| 156 | 0.00080 | 0.00585 |
| 157 | 0.00250 | 0.03267 |
| 158 | 0.00588 | 0.10081 |
| 159 | 0.00408 | 0.06050 |
| 160 | 0.00659 | 0.08254 |
| 161 | 0.00744 | 0.11288 |
| 162 | 0.00455 | 0.07862 |
| 163 | 0.00486 | 0.03573 |
| 164 | 0.00713 | 0.17048 |
| 165 | 0.00005 | 0.00020 |
| 166 | 0.00032 | 0.00177 |
| 167 | 0.00004 | 0.00039 |
| 168 | 0.00847 | 0.06456 |
| 169 | 0.00576 | 0.08000 |

TABLE EC-continued k$_{obs}$ values

| Example Number | FGFR1 Enz k$_{obs}$ (min$^{-1}$) | FGFR3 Enz k$_{obs}$ (min$^{-1}$) |
|---|---|---|
| 170 | 0.00774 | 0.13879 |
| 171 | 0.00471 | 0.08040 |
| 172 | 0.00191 | 0.02599 |
| 173 | 0.00434 | 0.06559 |
| 174 | 0.00242 | 0.02588 |
| 175 | 0.00204 | 0.01233 |
| 176 | 0.04970 | ND |
| 177 | 0.00324 | 0.01958 |
| 178 | 0.00131 | 0.01469 |
| 179 | 0.01248 | 0.18905 |
| 180 | 0.04552 | 0.13290 |
| 181 | 0.00249 | 0.02709 |
| 182 | 0.00202 | 0.01781 |
| 183 | 0.00259 | 0.02414 |
| 184 | 0.00043 | 0.00475 |
| 185 | 0.00917 | 0.06081 |
| 186 | 0.01483 | 0.08793 |
| 187 | 0.00383 | 0.01828 |
| 188 | ND | 0.08524 |
| 189 | 0.01182 | 0.07280 |
| 190 | 0.00423 | 0.02714 |
| 191 | 0.00583 | 0.02236 |
| 192 | ND | 0.10084 |
| 193 | 0.00275 | 0.02874 |
| 194 | 0.00596 | 0.03375 |
| 195 | ND | 0.02572 |
| 196 | ND | 0.14256 |

Example D

FGFR pERK Assay

FGFR1 pERK Cell Assay:

HEK-293 cells transfected with doxycycline(dox)-inducible human wild type FGFR1 (SEQ ID NO: 1) were plated in a collagen or poly-D-lysine coated 96 well flat bottom plates at 4×10$^5$ cells/well in complete Dulbecco's Modified Eagle Medium (DMEM) containing 10% FBS and 1 µg/ml doxycycline and allowed to attach for 24 h at 37° C., 5% CO$_2$. Cells were treated with compound using 1:3 serial dilutions with a maximum final concentration of 5 µM. Compound was incubated on cells for 1 hour at 37° C., 5% CO$_2$. Cells were then stimulated with a final concentration of 100 ng/ml human FGF-acidic (R&D Systems Cat number 232-FA/CF) for 5 minutes at 37° C., 5% CO$_2$. Medium was removed, and cells were lysed with lysis buffer containing phosphatase and protease inhibitors. Phospho ERK1/2 was measured using the Meso Scale Discovery sandwich assay (Meso Scale Discovery cat. no. K151DWD). The assay captures phospho ERK1/2 and detects with a sulfo-tagged total ERK1/2 antibody. The chemiluminescent signal was read on the Sector Imager Plate reader. 100 POC was determined using no test compound and 0 POC was determined using a control compound. The POC values were fit to a 4-parameter logistic curve as a function of the concentration of the compound, and the IC$_{50}$ value is the point where the curve crosses 50 POC.

FGFR2 pERK Cell Assay:

HEK-293 cells transfected with dox-inducible human wild type FGFR2 (SEQ ID NO: 3) are plated in a collagen or poly-D-lysine coated 96 well flat bottom plates at 4×10$^5$ cells/well in complete DMEM medium containing 10% FBS and 1 µg/ml doxycycline and allowed to attach for 24 h at 37° C., 5% CO$_2$. Cells are treated with compound using 1:3 serial dilutions with a maximum final concentration of 5 µM. Compound is incubated on cells for 1 hour at 37° C., 5% CO$_2$. Cells are then stimulated with a final concentration of 30 ng/ml human FGF-acidic (R&D Systems Cat number 232-FA/CF) for 5 minutes at 37° C., 5% CO$_2$. Medium is removed, and cells are lysed with lysis buffer containing phosphatase and protease inhibitors. Phospho ERK1/2 is measured using the Meso Scale Discovery sandwich assay (Meso Scale Discovery cat. no. K151DWD). The assay captures phospho ERK1/2 and detects with a sulfo-tagged total ERK1/2 antibody. The chemiluminescent signal is read on the Sector Imager Plate reader. 100 POC is determined using no test compounds and 0 POC is determined using a control compound. The POC values are fit to a 4-parameter logistic curve as a function of the concentration of the compound, and the IC$_{50}$ value is the point where the curve crosses 50 POC.

FGFR3 pERK Cell Assay:

HEK-293 cells transfected with dox-inducible human wild type FGFR3 (SEQ ID NO: 5) were plated in a collagen or poly-D-lysine coated 96 well flat bottom plates at 4×10$^5$ cells/well in complete DMEM medium containing 10% FBS and 1 µg/ml doxycycline and allowed to attach for 24 h at 37° C., 5% CO$_2$. Cells were treated with compound using 1:3 serial dilutions with a maximum final concentration of 5 µM. Compound was incubated on cells for 1 hour at 37° C., 5% CO$_2$. Cells were then stimulated with a final concentration of 100 ng/ml human FGF-acidic (R&D Systems Cat number 232-FA/CF) for 5 minutes at 37° C., 5% CO$_2$. Medium was removed, and cells were lysed with lysis buffer containing phosphatase and protease inhibitors. Phospho ERK1/2 was measured using the Meso Scale Discovery sandwich assay (Meso Scale Discovery cat. no. K151DWD). The assay captures phospho ERK1/2 and detects with a sulfo-tagged total ERK1/2 antibody. The chemiluminescent signal was read on the Sector Imager Plate reader. 100 POC was determined using no test compounds and 0 POC was determined using a control compound. The POC values were fit to a 4-parameter logistic curve as a function of the concentration of the compound, and the IC$_{50}$ value is the point where the curve crosses 50 POC.

Table ED contains IC$_{50}$ values for compounds tested in these assays, presented as the average of multiple determinations if multiple determinations were made. ND=not determined.

TABLE ED pERK cell IC$_{50}$ values

| Example Number | FGFR1 Cell pERK IC$_{50}$ (nM) | FGFR3 Cell pERK IC$_{50}$ (nM) |
|---|---|---|
| 1 | 525 | 86 |
| 3 | 870 | 108 |
| 31 | 247 | 26 |
| 36 | 363 | 43 |
| 37 | 59 | 8 |
| 39 | 52 | 8 |
| 41 | 91 | 12 |
| 42 | 631 | 77 |
| 43 | 428 | 90 |
| 50 | 103 | 25 |
| 51 | 198 | 61 |

TABLE ED-continued pERK cell IC$_{50}$ values

| Example Number | FGFR1 Cell pERK IC$_{50}$ (nM) | FGFR3 Cell pERK IC$_{50}$ (nM) |
|---|---|---|
| 52 | 759 | 262 |
| 55 | 381 | 71 |
| 82 | 3360 | 853 |
| 83 | 5000 | 549 |
| 84 | 2531 | 108 |
| 85 | 462 | 19 |
| 86 | 2374 | 159 |
| 87 | 2352 | 520 |
| 88 | 605 | 34 |
| 89 | 541 | 22 |
| 90 | 2241 | 43 |
| 91 | 341 | 15 |
| 92 | 2527 | 205 |
| 93 | 1911 | 174 |
| 94 | 4505 | 450 |
| 95 | 1071 | 98 |
| 96 | 2101 | 351 |
| 97 | ND | 384 |
| 100 | 180 | 21 |
| 102 | 239 | 44 |
| 103 | 573 | 137 |
| 104 | 1115 | 146 |
| 105 | 3960 | 2658 |
| 106 | 955 | 244 |
| 107 | 1351 | 355 |
| 108 | 116 | 47 |
| 111 | 288 | 34 |
| 112 | 122 | 21 |
| 113 | 1573 | 186 |
| 114 | 1309 | 248 |
| 115 | 5000 | 1241 |
| 116 | 1226 | 164 |
| 117 | 1203 | 36 |
| 118 | 674 | 62 |
| 119 | 591 | 50 |
| 120 | 523 | 142 |
| 121 | 169 | 25 |
| 122 | 492 | 52 |
| 134 | 96 | 13 |
| 135 | 342 | 40 |
| 137 | 989 | 318 |
| 138 | 116 | 16 |
| 140 | 206 | 105 |
| 141 | 5000 | 3906 |
| 142 | 769 | 119 |
| 146 | 496 | 96 |
| 151 | 1964 | 592 |
| 152 | 5000 | 849 |
| 153 | 2 | 25 |
| 154 | 2633 | 122 |
| 155 | 157 | 31 |
| 156 | 3106 | 91 |
| 157 | 5000 | 1154 |
| 158 | 1833 | 108 |
| 159 | 737 | 30 |
| 160 | 3277 | 481 |
| 161 | 1619 | 133 |
| 162 | 1440 | 357 |
| 163 | 1652 | 207 |
| 164 | 5000 | 188 |
| 168 | 502 | 99 |
| 169 | 751 | 175 |
| 170 | 915 | 55 |
| 171 | 888 | 50 |
| 172 | 3288 | 171 |
| 173 | 1282 | 164 |
| 179 | 1600 | 236 |
| 180 | 130 | 45 |
| 181 | 196 | 34 |
| 182 | 3634 | 348 |
| 183 | 4566 | 592 |
| 184 | 5000 | 2832 |
| 186 | 35 | 6 |
| 188 | 134 | 19 |
| 193 | 328 | 47 |
| 194 | 401 | 58 |

Example E pFGFR Assay

FGFR1 pFGFR Cell Assay:

HEK-293 cells transfected with dox-inducible human wild type FGFR1 (SEQ ID NO: 1) were plated in a collagen or poly-D-lysine coated 96 well flat bottom plates at 4×10$^5$ cells/well in complete DMEM medium containing 10% FBS and 1 µg/ml doxycycline and allowed to attach for 24 h at 37° C., 5% CO$_2$. Cells were treated with compound using 1:3 serial dilutions with a maximum final concentration of 5 µM. Compound was incubated on cells for 1 hour at 37° C., 5% CO$_2$. Medium was removed, and cells were lysed with lysis buffer containing phosphatase and protease inhibitors. Phospho FGFR1 was measured by ELISA (R&D Systems cat. no. DYC5079 or Cell Signaling Technology cat. no. 12909). The ELISA captures total FGFR1 and detects total phospho tyrosine. Optical density was measured for each well using a Versamax reader at a wavelength of 450 nm. 100 POC was determined using no test compounds and 0 POC was determined using a control compound. The POC values were fit to a 4-parameter logistic curve as a function of the concentration of the compound, and the IC$_{50}$ value is the point where the curve crosses 50 POC.

FGFR2 pFGFR Cell Assay:

HEK-293 cells transfected with dox-inducible human wild type FGFR2 (SEQ ID NO: 3) were plated in a collagen or poly-D-lysine coated 96 well flat bottom plates at 4×10$^5$ cells/well in complete DMEM medium containing 10% FBS and 1 µg/ml doxycycline and allowed to attach for 24 h at 37° C., 5% CO$_2$. Cells were treated with compound using 1:3 serial dilutions with a maximum final concentration of 5 µM. Compound was incubated on cells for 1 hour at 37° C., 5% CO$_2$. Cells were then stimulated with a final concentration of 30 ng/ml human FGF-acidic (R&D Systems Cat number 232-FA/CF) for 5 minutes at 37° C., 5% CO$_2$. Medium was removed and cells were lysed with lysis buffer containing phosphatase and protease inhibitors. Phospho FGFR2 was measured by ELISA (R&D Systems cat. no. DYC684). The ELISA captures total FGFR2 and detects total phospho tyrosine. Optical density was measured for each well using a Versamax reader at a wavelength of 450 nm. 100 POC was determined using no test compounds and 0 POC was determined using a control compound. The POC values were fit to a 4-parameter logistic curve as a function of the concentration of the compound, and the IC$_{50}$ value is the point where the curve crosses 50 POC.

FGFR3 pFGFR Cell Assay:

HEK-293 cells transfected with dox-inducible human wild type FGFR3 (SEQ ID NO: 5) were plated in a collagen or poly-D-lysine coated 96 well flat bottom plates at $4\times10^5$ cells/well in complete DMEM medium containing 10% FBS and 1 µg/ml doxycycline and allowed to attach for 24 h at 37° C., 5% $CO_2$. Cells were treated with compound using 1:3 serial dilutions with a top final concentration of 5 µM. Compound was incubated on cells for 1 hour at 37° C., 5% $CO_2$. Cells were then stimulated with a final concentration of 100 ng/ml human FGF-acidic for 5 minutes at 37° C., 5% $CO_2$. Medium was removed and cells were lysed with lysis buffer containing phosphatase and protease inhibitors. Phospho FGFR3 was measured by ELISA (R&D Systems cat DYC2719). The ELISA captures total FGFR3 and detects total phospho tyrosine. Optical density was measured for each well using a Versamax reader at a wavelength of 450 nm. 100 POC was determined using no test compounds and 0 POC was determined using a control compound. The POC values were fit to a 4-parameter logistic curve as a function of the concentration of the compound, and the $IC_{50}$ value is the point where the curve crosses 50 POC.

Table EE contains $IC_{50}$ values for compounds tested in these assays, presented as the average of multiple determinations if multiple determinations were made. ND=not determined.

TABLE EE pFGFR cell $IC_{50}$ values

| Example number | FGFR1 Cell pFGFR $IC_{50}$ (nM) | FGFR2 Cell pFGFR $IC_{50}$ (nM) | FGFR3 Cell pFGFR $IC_{50}$ (nM) |
|---|---|---|---|
| 1 | ND | ND | 26 |
| 3 | ND | ND | 41 |
| 6 | ND | ND | 72 |
| 7 | ND | ND | 110 |
| 8 | ND | ND | 149 |
| 9 | ND | 37 | 28 |
| 10 | ND | 36 | 38 |
| 11 | ND | 14 | ND |
| 12 | ND | ND | 242 |
| 13 | ND | ND | 39 |
| 14 | ND | ND | 25 |
| 15 | ND | ND | 10 |
| 21 | ND | ND | 40 |
| 22 | ND | ND | 87 |
| 23 | ND | ND | 90 |
| 24 | ND | ND | 435 |
| 25 | ND | ND | 83 |
| 28 | ND | ND | 285 |
| 29 | ND | ND | 359 |
| 30 | ND | ND | 23 |
| 31 | ND | ND | 15 |
| 36 | ND | 197 | 37 |
| 37 | ND | ND | 12 |
| 38 | ND | ND | 9 |
| 39 | ND | ND | 101 |
| 40 | ND | ND | 16 |
| 41 | ND | ND | 10 |
| 42 | ND | ND | 31 |
| 43 | ND | 79 | 64 |
| 49 | ND | ND | 20 |
| 50 | ND | 178 | ND |
| 51 | ND | 433 | ND |
| 52 | ND | 766 | ND |
| 55 | ND | ND | 64 |
| 56 | ND | ND | 182 |
| 59 | ND | ND | 667 |
| 66 | ND | ND | 82 |
| 68 | ND | ND | 187 |
| 69 | ND | ND | 311 |
| 70 | ND | ND | 104 |
| 71 | ND | ND | 35 |
| 73 | ND | ND | 313 |
| 76 | ND | ND | 1900 |
| 78 | ND | ND | 536 |
| 81 | ND | ND | 117 |
| 82 | ND | ND | 814 |
| 83 | ND | ND | 546 |
| 84 | ND | ND | 77 |
| 85 | ND | 61 | 16 |
| 88 | ND | 143 | ND |
| 89 | ND | 96 | ND |
| 90 | ND | 109 | ND |
| 91 | ND | 108 | ND |
| 94 | ND | ND | 336 |
| 98 | ND | ND | 1134 |
| 100 | ND | ND | 21 |
| 101 | ND | ND | 69 |
| 102 | ND | 129 | ND |
| 106 | ND | 1198 | ND |
| 108 | ND | 236 | ND |
| 111 | ND | 348 | 43 |
| 117 | ND | 283 | ND |
| 118 | ND | 267 | ND |
| 119 | ND | 322 | ND |
| 121 | ND | ND | 31 |
| 122 | ND | ND | 71 |
| 123 | ND | ND | 57 |
| 124 | ND | ND | 24 |
| 125 | ND | ND | 9 |
| 126 | ND | ND | 20 |
| 127 | ND | ND | 18 |
| 128 | ND | ND | 28 |
| 129 | ND | ND | 23 |
| 130 | ND | ND | 295 |
| 131 | ND | ND | 15 |
| 132 | ND | ND | 31 |
| 134 | ND | ND | 12 |
| 135 | ND | 83 | ND |
| 138 | ND | ND | 17 |
| 142 | ND | 424 | ND |
| 143 | ND | ND | 527 |
| 144 | ND | 34 | ND |
| 145 | ND | ND | 257 |
| 146 | ND | ND | 80 |
| 148 | ND | ND | 351 |
| 150 | ND | ND | 2323 |
| 153 | ND | 188 | ND |
| 154 | ND | 327 | ND |
| 156 | ND | 244 | ND |
| 158 | ND | 1547 | ND |
| 159 | ND | 451 | ND |
| 161 | ND | 537 | ND |
| 164 | ND | 1178 | ND |
| 170 | ND | 171 | ND |
| 171 | ND | 263 | ND |
| 174 | ND | ND | 139 |
| 175 | ND | ND | 52 |
| 176 | ND | ND | 18 |
| 177 | 123 | ND | 57 |
| 178 | ND | ND | 44 |
| 179 | ND | 1684 | ND |
| 181 | ND | 292 | ND |
| 185 | ND | ND | 12 |
| 186 | ND | 42 | 6 |
| 187 | ND | ND | 74 |
| 188 | ND | 160 | 24 |
| 189 | ND | ND | 9 |
| 190 | ND | ND | 32 |
| 191 | ND | ND | 20 |
| 192 | ND | ND | 12 |
| 193 | ND | ND | 53 |
| 194 | ND | ND | 43 |
| 195 | ND | ND | 14 |
| 196 | ND | ND | 26 |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound of Formula I

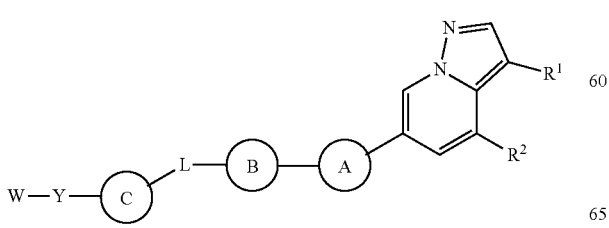

wherein:

$R^1$ is CN or Cl;

$R^2$ is C1-C6 alkoxy, C1-C6 alkyl, C3-C6 cycloalkoxy, or phenyl optionally substituted with 1-2 groups independently selected from halogen and (C3-C6 cycloalkyl)C(=O)NH—;

Ring A is $Ar^1$ or $hetAr^1$;

$Ar^1$ is phenyl optionally substituted with 1-2 groups independently selected from halogen, C1-C6 alkyl, fluoroC1-C6 alkyl, and C1-C6 alkoxy;

$hetAr^1$ is a 5-6 membered heteroaryl ring having 1-3 ring nitrogen atoms and optionally substituted with 1-2 independently selected halogen, C1-C6 alkyl, fluoroC1-C6 alkyl, or C1-C6 alkoxy substituents;

Ring B is a 4-8 membered monocyclic heterocyclic ring having 1-2 ring nitrogen atoms, a 7-11 membered bridged heterocyclic ring having 1-2 ring nitrogen atoms, a 7-12 membered spiroheterocyclic ring having 2 ring nitrogen atoms, or absent;

L is —C(=O)—, —CH$_2$—, —SO$_2$—, —C(=O)NH*, or absent, wherein the asterisk indicates the point of attachment to Ring C;

Ring C is Cyc$^1$, Cyc$^2$, hetCyc$^1$, hetCyc$^2$, hetCyc$^3$, Ar$^3$, or absent;

Cyc$^1$ is 4-8 membered cycloalkyl ring optionally substituted with halo, CN, OH, C1-C6 alkyl, fluoroC1-C6 alkoxy, and C1-C6 alkoxy;

Cyc$^2$ is a 5-11 membered bridged cycloalkyl ring;

hetCyc$^1$ is a 4-6 membered heterocyclic ring having 1-2 ring nitrogen atoms and optionally substituted with 1-4 substituents independently selected from halogen, CN, OH, C1-C6 alkyl, C1-C6 alkoxy, and cyanoC1-C6 alkyl;

hetCyc$^2$ is a 7-11 membered bridged heterocyclic ring having 1-3 ring heteroatoms independently selected from N and O;

hetCyc$^3$ is a 7-12 membered spiroheterocyclic ring having 1-2 ring nitrogen atoms;

Ar$^3$ is phenyl optionally substituted with C1-C6 alkyl or C1-C6 alkoxy;

Y is —NH—, —N(C1-C3 alkyl)-, or absent;

W is R$^3$R$^4$C=CR$^5$C(=O)—, R$^6$R$^7$NCH$_2$CH=CHC(=O)—, H$_2$C=CHSO$_2$— or R$^8$C=C≡C(=O)—;

R$^3$ is hydrogen;

R$^4$ is hydrogen, CF$_3$ or Z (C1-C6 alkyl)-wherein Z is H, F, Cl, Br, HO—, or C1-C6 alkoxy, and R$^5$ is hydrogen, C1-C3 alkyl, or halogen, or R$^4$ and R$^5$ together with the carbon atoms to which they are attached form a 4-8-membered carbocyclic ring;

each of R$^6$ and R$^7$ is independently C1-C6 alkyl, or R$^6$ and R$^7$ together with the nitrogen atom to which they are attached form a 5-6 membered heterocyclic ring optionally having an additional ring heteroatom which is O, wherein said ring is optionally substituted with halogen;

R$^8$ is hydrogen, C1-C3 alkyl, HO-C1-C3 alkyl or R'R"NCH$_2$—; and

R' and R" are each independently hydrogen or C1-C6 alkyl, or a pharmaceutically acceptable salt thereof.

2. The compound according to claim 1, wherein Ring A is

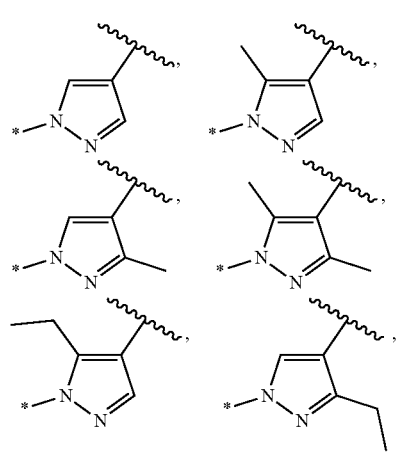

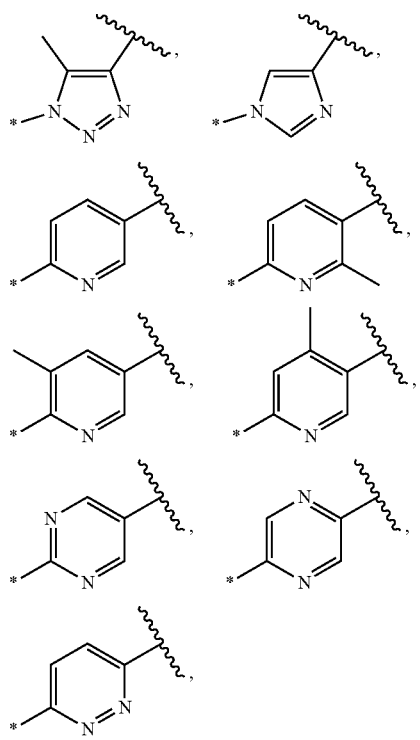

or unsubstituted phenyl, wherein the asterisk indicates point of attachment to Ring B, and pharmaceutically acceptable salts thereof.

3. The compound according to claim 1, wherein Ring B is

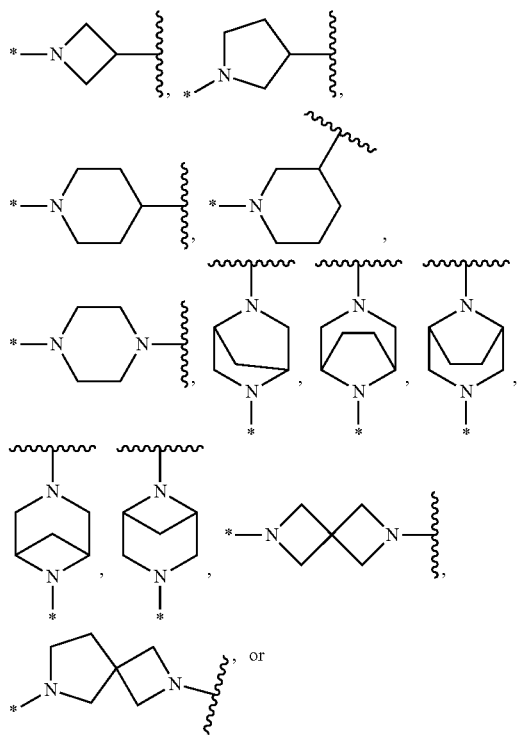

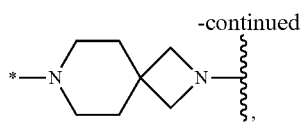

wherein the asterisk indicates point of attachment to L, and pharmaceutically acceptable salts thereof.

4. The compound of claim 1, wherein L is —C(=O)— or —CH$_2$—.

5. The compound according to claim 1, wherein Ring C is

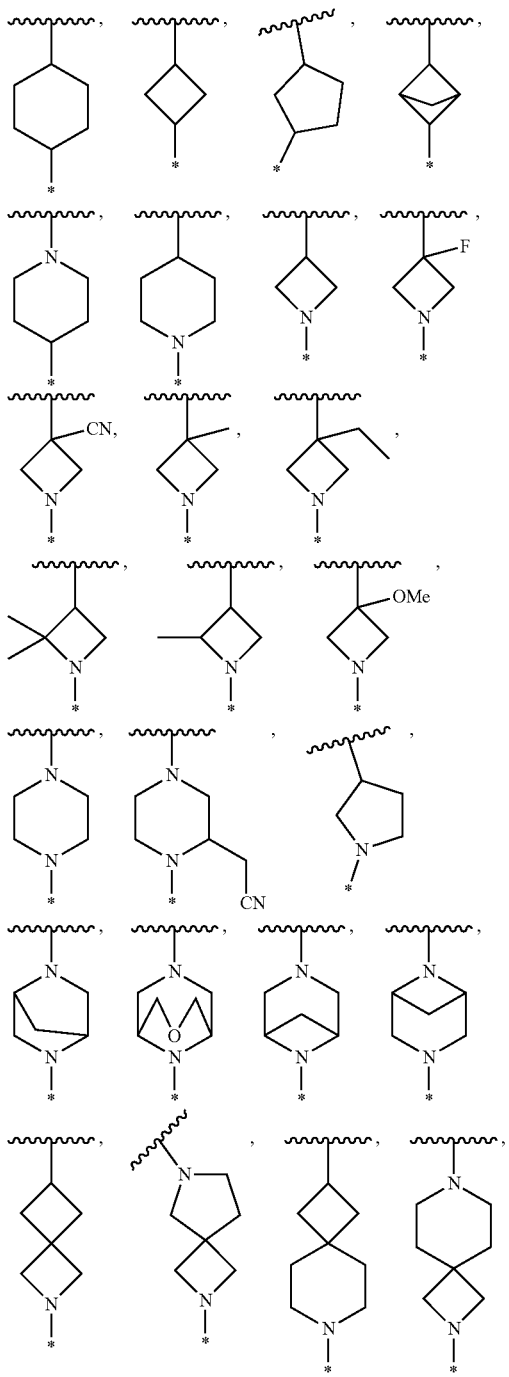

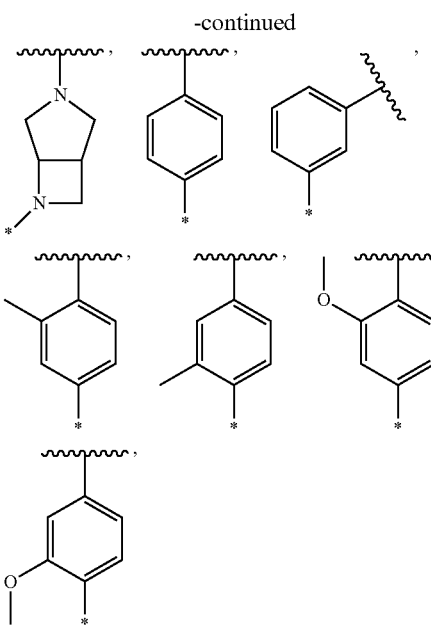

wherein the asterisk indicates point of attachment to —Y—W, and pharmaceutically acceptable salts thereof.

6. The compound of claim 1, wherein the compound is at least about 3-fold more selective for FGFR3 than FGFR1, and wherein the compound forms a covalent bond with a cysteine in a FGFR protein.

7. The compound of claim 1, wherein the compound is at least about 3-fold more selective for FGFR2 than FGFR1, and wherein the compound forms a covalent bond with a cysteine in a FGFR protein.

8. A pharmaceutical composition, comprising a compound according to claim 1 in admixture with a pharmaceutically acceptable diluent or carrier.

9. A method for treating an FGFR-associated cancer in a subject in need thereof, the method comprising administering to the subject a pharmaceutical composition comprising a therapeutically effective amount of a compound according to claim 1 or a pharmaceutically acceptable salt thereof.

10. The method of claim 9, wherein the FGFR-associated cancer is selected from the group consisting of: bladder cancer, brain cancer, breast cancer, cholangiocarcinoma, head and neck cancer, lung cancer, multiple myeloma, rhabdomyosarcoma, urethral cancer, and uterine cancer.

11. The method of claim 9, wherein the FGFR-associated cancer is a FGFR fusion lung cancer, a FGFR fusion breast cancer, a FGFR fusion bladder cancer, a FGFR fusion biliary tract cancer, a FGFR fusion urethral cancer, a FGFR fusion head and neck cancer, or a FGFR fusion multiple myeloma.

12. The method of claim 9, wherein the FGFR-associated cancer is lung cancer, and the lung cancer is small cell lung carcinoma, non-small cell lung cancer, squamous cell lung cancer, or lung adenocarcinoma.

13. The method of claim 9, wherein the compound or a pharmaceutically acceptable salt thereof is orally administered.

14. The method of claim 9, wherein the method further comprises administering an additional therapy or therapeutic agent to the subject.

* * * * *

SEQUENCE LISTING

```
<160> NUMBER OF SEQ ID NOS: 8

<210> SEQ ID NO 1
<211> LENGTH: 822
<212> TYPE: PRT
<213> ORGANISM: Artificial Sequence
<220> FEATURE:
<223> OTHER INFORMATION: synthetic construct

<400> SEQUENCE: 1

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300
```

-continued

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Ile Tyr Cys Thr Gly Ala
            370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
            645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys

```
                        725                 730                 735
Trp His Ala Val Pro Ser Gln Arg Pro Thr Phe Lys Gln Leu Val Glu
                740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
        770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820

<210> SEQ ID NO 2
<211> LENGTH: 820
<212> TYPE: PRT
<213> ORGANISM: Artificial Sequence
<220> FEATURE:
<223> OTHER INFORMATION: synthetic construct

<400> SEQUENCE: 2

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
            115                 120                 125

Asp Asp Asp Asp Asp Ser Ser Ser Glu Glu Lys Glu Thr Asp Asn Thr
        130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
```

```
                260                 265                 270
Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Ile Tyr Cys Thr Gly Ala
            370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Ser Ala Asp Ser Ser
            420                 425                 430

Ala Ser Met Asn Ser Gly Val Leu Leu Val Arg Pro Ser Arg Leu Ser
            435                 440                 445

Ser Ser Gly Thr Pro Met Leu Ala Gly Val Ser Glu Tyr Glu Leu Pro
        450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
            485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
            515                 520                 525

Glu Met Glu Met Met Lys Met Ile Gly Lys His Lys Asn Ile Ile Asn
            530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
            565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
            595                 600                 605

Met Glu Tyr Leu Ala Ser Lys Lys Cys Ile His Arg Asp Leu Ala Ala
            610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
            645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
            675                 680                 685
```

```
Trp Glu Ile Phe Thr Leu Gly Gly Ser Pro Tyr Pro Gly Val Pro Val
    690             695                 700

Glu Glu Leu Phe Lys Leu Leu Lys Glu Gly His Arg Met Asp Lys Pro
705             710                 715                 720

Ser Asn Cys Thr Asn Glu Leu Tyr Met Met Arg Asp Cys Trp His
            725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 3
<211> LENGTH: 821
<212> TYPE: PRT
<213> ORGANISM: Artificial Sequence
<220> FEATURE:
<223> OTHER INFORMATION: synthetic construct

<400> SEQUENCE: 3

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220
```

-continued

```
Asp Lys Gly Asn Tyr Thr Cys Val Val Glu Asn Gly Ser Ile
225                 230                 235                 240

Asn His Thr Tyr His Leu Asp Val Val Glu Arg Ser Pro His Arg Pro
            245                 250                 255

Ile Leu Gln Ala Gly Leu Pro Ala Asn Ala Ser Thr Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
            290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
            325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
            370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
            405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
            450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
            485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
            515                 520                 525

Ser Asp Leu Val Ser Glu Met Glu Met Met Lys Met Ile Gly Lys His
            530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
            565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
            610                 615                 620

Arg Asp Leu Ala Ala Arg Asn Val Leu Val Thr Glu Asn Asn Val Met
625                 630                 635                 640
```

```
Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
            675                 680                 685

Phe Gly Val Leu Met Trp Glu Ile Phe Thr Leu Gly Gly Ser Pro Tyr
690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 4
<211> LENGTH: 822
<212> TYPE: PRT
<213> ORGANISM: Artificial Sequence
<220> FEATURE:
<223> OTHER INFORMATION: synthetic construct

<400> SEQUENCE: 4

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175
```

```
Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
```

```
                        595                 600                 605
Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820

<210> SEQ ID NO 5
<211> LENGTH: 806
<212> TYPE: PRT
<213> ORGANISM: Artificial Sequence
<220> FEATURE:
<223> OTHER INFORMATION: synthetic construct

<400> SEQUENCE: 5

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
```

-continued

```
            130                 135                 140
Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Ile Lys Leu Arg His
                195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560
```

Gly Asn Leu Arg Glu Phe Leu Arg Ala Arg Pro Pro Gly Leu Asp
            565                 570                 575

Tyr Ser Phe Asp Thr Cys Lys Pro Pro Glu Glu Leu Thr Phe Lys
            580                 585                 590

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
            610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
            645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
            690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
            725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
            755                 760                 765

Gln Tyr Ser Pro Gly Gly Gln Asp Thr Pro Ser Ser Ser Ser Ser Gly
            770                 775                 780

Asp Asp Ser Val Phe Ala His Asp Leu Leu Pro Pro Ala Pro Pro Ser
785                 790                 795                 800

Ser Gly Gly Ser Arg Thr
            805

<210> SEQ ID NO 6
<211> LENGTH: 808
<212> TYPE: PRT
<213> ORGANISM: Artificial Sequence
<220> FEATURE:
<223> OTHER INFORMATION: synthetic construct

<400> SEQUENCE: 6

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
            50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
            85                  90                  95

Leu Asn Ala Ser His Glu Asp Ser Gly Ala Tyr Ser Cys Arg Gln Arg
            100                 105                 110

```
Leu Thr Gln Arg Val Leu Cys His Phe Ser Val Arg Val Thr Asp Ala
        115                 120                 125

Pro Ser Ser Gly Asp Asp Glu Asp Gly Glu Asp Ala Glu Asp Thr
130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Leu Val Glu Ala
        355                 360                 365

Asp Glu Ala Gly Ser Val Tyr Ala Gly Ile Leu Ser Tyr Gly Val Gly
370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525
```

```
Glu Met Met Lys Met Ile Gly Lys His Lys Asn Ile Ile Asn Leu Leu
    530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Arg Pro Pro Gly
                565                 570                 575
Leu Asp Tyr Ser Phe Asp Thr Cys Lys Pro Pro Glu Glu Gln Leu Thr
                580                 585                 590
Phe Lys Asp Leu Val Ser Cys Ala Tyr Gln Val Ala Arg Gly Met Glu
                595                 600                 605
Tyr Leu Ala Ser Gln Lys Cys Ile His Arg Asp Leu Ala Ala Arg Asn
            610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
                660                 665                 670
Tyr Thr His Gln Ser Asp Val Trp Ser Phe Gly Val Leu Leu Trp Glu
            675                 680                 685
Ile Phe Thr Leu Gly Gly Ser Pro Tyr Pro Gly Ile Pro Val Glu Glu
            690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Glu Asp Leu Asp Arg
                740                 745                 750
Val Leu Thr Val Thr Ser Thr Asp Glu Tyr Leu Asp Leu Ser Ala Pro
            755                 760                 765
Phe Glu Gln Tyr Ser Pro Gly Gly Gln Asp Thr Pro Ser Ser Ser Ser
    770                 775                 780
Ser Gly Asp Asp Ser Val Phe Ala His Asp Leu Leu Pro Pro Ala Pro
785                 790                 795                 800
Pro Ser Ser Gly Gly Ser Arg Thr
                805

<210> SEQ ID NO 7
<211> LENGTH: 802
<212> TYPE: PRT
<213> ORGANISM: Artificial Sequence
<220> FEATURE:
<223> OTHER INFORMATION: synthetic construct

<400> SEQUENCE: 7

Met Arg Leu Leu Leu Ala Leu Leu Gly Val Leu Leu Ser Val Pro Gly
1               5                   10                  15
Pro Pro Val Leu Ser Leu Glu Ala Ser Glu Glu Val Glu Leu Glu Pro
                20                  25                  30
Cys Leu Ala Pro Ser Leu Glu Gln Gln Glu Gln Glu Leu Thr Val Ala
            35                  40                  45
Leu Gly Gln Pro Val Arg Leu Cys Cys Gly Arg Ala Glu Arg Gly Gly
        50                  55                  60
His Trp Tyr Lys Glu Gly Ser Arg Leu Ala Pro Ala Gly Arg Val Arg
65                  70                  75                  80
```

```
Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
    275                 280                 285

Ile Asn Gly Ser Ser Phe Gly Ala Asp Gly Phe Pro Tyr Val Gln Val
290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Ala Pro Glu Ala Arg Tyr Thr
        355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Gly Pro Ala Leu Leu Ala Gly
    435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
```

```
            500                 505                 510
Asp Leu Ala Asp Leu Val Ser Glu Met Glu Val Met Lys Leu Ile Gly
            515                 520                 525

Arg His Lys Asn Ile Ile Asn Leu Leu Gly Val Cys Thr Gln Glu Gly
            530                 535                 540

Pro Leu Tyr Val Ile Val Glu Cys Ala Ala Lys Gly Asn Leu Arg Glu
545                 550                 555                 560

Phe Leu Arg Ala Arg Pro Pro Gly Pro Asp Leu Ser Pro Asp Gly
            565                 570                 575

Pro Arg Ser Ser Glu Gly Pro Leu Ser Phe Pro Val Leu Val Ser Cys
            580                 585                 590

Ala Tyr Gln Val Ala Arg Gly Met Gln Tyr Leu Glu Ser Arg Lys Cys
            595                 600                 605

Ile His Arg Asp Leu Ala Ala Arg Asn Val Leu Val Thr Glu Asp Asn
            610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
            645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
            690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
            725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
            755                 760                 765

Gly Asp Ala Ser Ser Thr Cys Ser Ser Ser Asp Ser Val Phe Ser His
770                 775                 780

Asp Pro Leu Pro Leu Gly Ser Ser Phe Pro Phe Gly Ser Gly Val
785                 790                 795                 800

Gln Thr

<210> SEQ ID NO 8
<211> LENGTH: 762
<212> TYPE: PRT
<213> ORGANISM: Artificial Sequence
<220> FEATURE:
<223> OTHER INFORMATION: synthetic construct

<400> SEQUENCE: 8

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60
```

```
His Trp Tyr Lys Glu Gly Ser Arg Leu Ala Pro Ala Gly Arg Val Arg
 65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
    275                 280                 285

Ile Asn Gly Ser Ser Phe Gly Ala Asp Gly Phe Pro Tyr Val Gln Val
290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Gly Thr Gly Arg Ile Pro His Leu Thr Cys Asp Ser Leu Thr Pro Ala
        355                 360                 365

Gly Arg Thr Lys Ser Pro Thr Leu Gln Phe Ser Leu Glu Ser Gly Ser
    370                 375                 380

Ser Gly Lys Ser Ser Ser Leu Val Arg Gly Val Arg Leu Ser Ser
385                 390                 395                 400

Ser Gly Pro Ala Leu Leu Ala Gly Leu Val Ser Leu Asp Leu Pro Leu
                405                 410                 415

Asp Pro Leu Trp Glu Phe Pro Arg Asp Arg Leu Val Leu Gly Lys Pro
            420                 425                 430

Leu Gly Glu Gly Cys Phe Gly Gln Val Val Arg Ala Glu Ala Phe Gly
        435                 440                 445
```

```
Met Asp Pro Ala Arg Pro Asp Gln Ala Ser Thr Val Ala Val Lys Met
    450             455                 460
Leu Lys Asp Asn Ala Ser Asp Lys Asp Leu Ala Asp Leu Val Ser Glu
465             470                 475                 480
Met Glu Val Met Lys Leu Ile Gly Arg His Lys Asn Ile Ile Asn Leu
                485                 490                 495
Leu Gly Val Cys Thr Gln Glu Gly Pro Leu Tyr Val Ile Val Glu Cys
                500                 505                 510
Ala Ala Lys Gly Asn Leu Arg Glu Phe Leu Arg Ala Arg Arg Pro Pro
            515                 520                 525
Gly Pro Asp Leu Ser Pro Asp Gly Pro Arg Ser Ser Glu Gly Pro Leu
    530                 535                 540
Ser Phe Pro Val Leu Val Ser Cys Ala Tyr Gln Val Ala Arg Gly Met
545                 550                 555                 560
Gln Tyr Leu Glu Ser Arg Lys Cys Ile His Arg Asp Leu Ala Ala Arg
                565                 570                 575
Asn Val Leu Val Thr Glu Asp Asn Val Met Lys Ile Ala Asp Phe Gly
                580                 585                 590
Leu Ala Arg Gly Val His His Ile Asp Tyr Tyr Lys Lys Thr Ser Asn
            595                 600                 605
Gly Arg Leu Pro Val Lys Trp Met Ala Pro Glu Ala Leu Phe Asp Arg
    610                 615                 620
Val Tyr Thr His Gln Ser Asp Val Trp Ser Phe Gly Ile Leu Leu Trp
625                 630                 635                 640
Glu Ile Phe Thr Leu Gly Gly Ser Pro Tyr Pro Gly Ile Pro Val Glu
                645                 650                 655
Glu Leu Phe Ser Leu Leu Arg Glu Gly His Arg Met Asp Arg Pro Pro
                660                 665                 670
His Cys Pro Pro Glu Leu Tyr Gly Leu Met Arg Glu Cys Trp His Ala
            675                 680                 685
Ala Pro Ser Gln Arg Pro Thr Phe Lys Gln Leu Val Glu Ala Leu Asp
    690                 695                 700
Lys Val Leu Leu Ala Val Ser Glu Glu Tyr Leu Asp Leu Arg Leu Thr
705                 710                 715                 720
Phe Gly Pro Tyr Ser Pro Ser Gly Gly Asp Ala Ser Ser Thr Cys Ser
                725                 730                 735
Ser Ser Asp Ser Val Phe Ser His Asp Pro Leu Pro Leu Gly Ser Ser
            740                 745                 750
Ser Phe Pro Phe Gly Ser Gly Val Gln Thr
    755                 760
```